(12) United States Patent
Bosanac et al.

(10) Patent No.: US 8,815,857 B2
(45) Date of Patent: Aug. 26, 2014

(54) SOLUBLE GUANYLATE CYCLASE ACTIVATORS

(75) Inventors: Todd Bosanac, New Milford, CT (US);
Angela Berry, Gaylordsville, CT (US);
John David Ginn, New Milford, CT (US); Tamara Denise Hopkins, Danbury, CT (US); Sabine Schlyer, New Milford, CT (US); Fariba Soleymanzadeh, Danbury, CT (US); John Westbrook, Woodbridge, CT (US); Maolin Yu, Brookfield, CT (US); Zhonghua Zhang, Ridgefield, CT (US)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 156 days.

(21) Appl. No.: 13/570,432

(22) Filed: Aug. 9, 2012

(65) Prior Publication Data
US 2013/0203729 A1   Aug. 8, 2013

Related U.S. Application Data

(60) Provisional application No. 61/522,851, filed on Aug. 12, 2011.

(51) Int. Cl.
| | |
|---|---|
| *A61K 31/5377* | (2006.01) |
| *A61K 31/454* | (2006.01) |
| *A61K 31/4545* | (2006.01) |
| *C07D 401/14* | (2006.01) |
| *C07D 401/04* | (2006.01) |
| *C07D 401/12* | (2006.01) |
| *C07D 413/14* | (2006.01) |
| *C07D 413/12* | (2006.01) |
| *C07D 417/12* | (2006.01) |
| *C07D 417/04* | (2006.01) |
| *C07D 417/14* | (2006.01) |

(52) U.S. Cl.
CPC ........... *C07D 417/14* (2013.01); *C07D 417/12* (2013.01); *C07D 417/04* (2013.01)
USPC ............. 514/236.8; 514/233.5; 514/316; 514/326; 544/124; 544/133; 546/316; 546/326

(58) Field of Classification Search
USPC ............ 544/124, 133; 514/236.8, 233.5, 316, 514/326; 546/187, 209
See application file for complete search history.

(56) References Cited

U.S. PATENT DOCUMENTS

| | | |
|---|---|---|
| 2009/0209556 A1 | 8/2009 | Bittner et al. |
| 2010/0016305 A1 | 1/2010 | Krahn et al. |
| 2010/0216764 A1 | 8/2010 | Kim et al. |
| 2013/0065918 A1 | 3/2013 | Brenneman et al. |

FOREIGN PATENT DOCUMENTS

| | | |
|---|---|---|
| WO | 0226712 A2 | 4/2002 |
| WO | 2008021339 A2 | 2/2008 |
| WO | 2008138483 A1 | 11/2008 |
| WO | 2009032249 A1 | 3/2009 |
| WO | 2009068652 A1 | 6/2009 |
| WO | 2009071504 A1 | 6/2009 |
| WO | 2010015652 A2 | 2/2010 |
| WO | 2010015653 A1 | 2/2010 |
| WO | 2010065275 A1 | 6/2010 |
| WO | 2010099054 A2 | 9/2010 |
| WO | 2012058132 A1 | 5/2012 |
| WO | 2012122340 A1 | 9/2012 |
| WO | 2013025425 A1 | 2/2013 |

OTHER PUBLICATIONS

Evgenov, Oleg, V. et al, "NO-Independent Stimulators and Activators of Soluble Guanylate Cyclase: Discovery and Therapeutic Potential" Nature Reviews/Drug Discovery (2006) vol. 5 pp. 755-768.
International Search Report and Written Opinion for PCT/US2012/028205 mailed Jul. 4, 2012.
International Search Report for PCT/US2012/050052 mailed Oct. 22, 2012.
Schindler, Ursula., "Biochemistry and Pharmacology of Novel Anthranilic Acid Derivates Activating Heme-Oxidized Soluble Guanylyl Cyclase" Molecular Pharmacology (2006) vol. 69', No. 4 pp. 1260-1268.
Stasch, Johannes-Peter, et al., "NO- and HAEM-Independent Activation of Soluble Guanylyl Cyclase: Molecular Basis and Cardiovascular Implications of a New Pharmacological Principle" British Journal of Pharmacology (2002) vol. 136 pp. 773-783.
U.S. Appl. No. 61/697,899, filed Sep. 7, 2012.

*Primary Examiner* — Rebecca Anderson
(74) *Attorney, Agent, or Firm* — Michael P. Morris; Edward S. Lazer

(57) ABSTRACT

The present invention relates to compounds of formula (I):

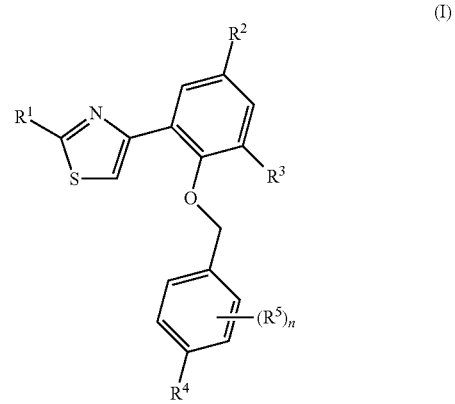

and pharmaceutically acceptable salts thereof, wherein $R^1$-$R^5$ and n are as defined herein. The invention also relates to pharmaceutical compositions comprising these compounds, methods of using these compounds in the treatment of various diseases and disorders, processes for preparing these compounds and intermediates useful in these processes.

15 Claims, No Drawings

SOLUBLE GUANYLATE CYCLASE ACTIVATORS

FIELD OF THE INVENTION

This invention relates to heterocyclic compounds which are useful as activators of soluble guanylate cyclase and are thus useful for treating a variety of diseases that are mediated or sustained by decreased or diminished soluble guanylate cyclase activity, including cardiovascular diseases, renal disease, diabetes, fibrotic disorders, urologic disorders, neurological disorders and inflammatory disorders. This invention also relates to pharmaceutical compositions comprising these compounds, methods of using these compounds in the treatment of various diseases and disorders, processes for preparing these compounds and intermediates useful in these processes.

BACKGROUND

Soluble guanylate cyclase (sGC) is a receptor for nitric oxide (NO) which is found in the cytoplasm of many cell types. In humans, functional sGC is a heterodimer composed of either an alpha 1 or alpha 2 subunit combined with the beta 1 subunit which has a heme prosthetic group. Under non-pathophysiological conditions, NO binding to the heme of sGC activates the enzyme to catalyze the conversion of guanosine-5'-triphosphate (GTP) to cyclic guanosine monophosphate (cGMP). cGMP is a second messenger which exerts effects by modulating cGMP dependent protein kinase (PKG) isoforms, phosphodiesterases, and cGMP gated ion channels. In doing so, sGC has been demonstrated to modulate numerous pathways associated with diseases including arterial hypertension, pulmonary hypertension, atherosclerosis, heart failure, liver cirrhosis, renal fibrosis, and erectile dysfunction (O. Evgenov et al., Nature Reviews, 2006, 5, 755-768 and Y. Wang-Rosenke et al., Curr. Med. Chem., 2008, 15, 1396-1406).

Under normal conditions, the iron in sGC exists in the ferrous state which is capable of binding to NO and carbon monoxide (CO). However, under conditions of oxidative stress which can occur in various diseases, published reports indicate that the heme iron becomes oxidized to the ferric state which is incapable of being activated by NO or CO. The inability of NO to signal through sGC with an oxidized heme iron has been hypothesized to contribute to disease processes. Recently, two novel classes of compounds have been described which potentiate sGC activity in a heme dependent (sGC stimulators) and heme independent (sGC activators) manner. The activity of sGC stimulators synergizes with NO to increase cGMP production while sGC activators are only additive with NO to augment cGMP levels (O. Evgenov et al., Nature Reviews, 2006, 5, 755-768). Both stimulators and activators of sGC have demonstrated benefit in animal models of disease. Activators of sGC provide the advantage of being able to preferentially target the diseased, non-functional form of the enzyme. sGC activators include BAY 58-2667 (cinaciguat) (J-P Stasch et al., Brit J. Pharmacol., 2002, 136, 773-783) and HMR-1766 (ataciguat) (U. Schindler et al., 2006, Mol. Pharmacol., 69, 1260-1268).

NO has an important role in maintaining normal cellular and tissue function. However, adequate signaling in the NO pathway can be disrupted at a number of steps. NO signaling can be impaired by reduced levels of nitric oxide synthase (NOS) enzymes, NOS activity, NO bioavailability, sGC levels, and sGC activity. sGC activators have the potential to bypass the functional impediment produced by all of these impairments. Since sGC activation occurs downstream of NO synthesis or NO availability, these deficiencies will not impact the activity of sGC activators. As described above, the activity of sGC in which function is disrupted by heme iron oxidation will be corrected by sGC activators. Thus, sGC activators have the potential to provide benefit in many diseases caused by defective signaling in the NO pathway.

Activation of sGC has the potential to provide therapeutic benefit for atherosclerosis and arteriosclerosis. Cinaciguat treatment has been demonstrated to prevent neointimal hyperplasia after endothelial denudation by wire injury of the carotid artery in rats (K. Hirschberg et al., Cardiovasc. Res., 2010, 87, Suppl. 1, S100, Abstract 343). Ataciguat inhibited atherosclerotic plaque formation in ApoE−/− mice feed a high fat diet (M. van Eickels, BMC Pharmacology, 2007, 7, Suppl. 1, S4). Decreased NO production in endothelial nitric oxide synthase (eNOS) deficient mice increased vascular inflammation and insulin resistance in response to nutrient excess. In the same study, the phosphodiesterase 5 (PDE5) inhibitor sildenafil reduced vascular inflammation and insulin resistance in mice fed a high-fat diet (N. Rizzo et al., Arterioscler. Thromb. Vasc. Biol., 2010, 30, 758-765). Lastly, after balloon-injury of rat carotid arteries in vivo, a sGC stimulator (YC-1) inhibited neotima formation (C. Wu, J. Pharmacol. Sci., 2004, 94, 252-260

The complications of diabetes may be reduced by sGC activation. Glucose induced suppression of glucagon release is lost in pancreatic islets that lack PKG, thus suggesting a role of sGC mediated cGMP production in glucose regulation (V. Leiss et al., BMC Pharmacology, 2009, 9, Suppl. 1, P40).

It is well established clinically that elevation of cGMP by treatment with PDE5 inhibitors is efficacious for the treatment of erectile dysfunction (ED). However, 30% of ED patients are resistant to PDE5 inhibitor treatment (S. Gur et al., Curr Pharm. Des., 2010, 16, 1619-1633). The sGC stimulator BAY-41-2272 is able to relax corpus cavernosum muscle in a sGC dependent manner, thus suggesting that increased sGC activity could provide benefit in ED patients (C. Teixeira et al., J. Pharmacol. & Exp. Ther., 2007, 322, 1093-1102). Furthermore, sGC stimulators and sGC activators used individually or either in combination with PDE5 inhibitor was able to treat ED in animal models (WO 10/081,647).

There is evidence that sGC activation may be useful in preventing tissue fibrosis, including that of the lung, liver, and kidney. The processes of epithelial to mesenchyal transition (EMT) and fibroblast to myofibroblast conversion are believed to contribute to tissue fibrosis. When either cinaciguat or BAY 41-2272 was combined with sildenafil, lung fibroblast to myofibroblast conversion was inhibited (T. Dunkern et al., Eur. J. Pharm., 2007, 572, 12-22). NO is capable of inhibiting EMT of alveolar epithelial cells (S. Vyas-Read et al., Am. J. Physiol. Lung Cell Mol. Physiol., 2007, 293, 1212-1221), suggesting that sGC activation is involved in this process. NO has also been shown to inhibit glomerular TGF beta signaling (E. Dreieicher et al., J. Am. Soc. Nephrol., 2009, 20, 1963-1974) which indicates that sGC activation may be able to inhibit glomerular sclerosis. In a pig serum model and carbon tetrachloride model of liver fibrosis, an sGC activator (BAY 60-2260) was effective at inhibiting fibrosis (A. Knorr et al., Arzneimittel-Forschung, 2008, 58, 71-80).

Clinical studies have demonstrated efficacy using the sGC activator cinaciguat for the treatment of acute decompensated heart failure (H. Lapp et al., Circulation, 2009, 119, 2781-2788). This is consistent with results from a canine tachypacing-induced heart failure model in which acute intravenous infusion of cinaciguat was able to produce cardiac unloading (G. Boerrigter et al., Hypertension, 2007, 49, 1128-1133). In a rat myocardial infarction induced chronic heart failure model, HMR 1766 improved cardiac function and reduced cardiac fibrosis which was further potentiated by ramipril (F. Daniela, Circulation, 2009, 120, Suppl. 2, S852-S853).

Activators of sGC can be used to treat hypertension. This has been clearly demonstrated in clinical studies in which the dose of cinaciguat is titrated based on the magnitude of blood pressure reduction achieved (H. Lapp et al., Circulation, 2009, 119, 2781-2788). Preclinical studies using cinaciguat had previously shown the ability of sGC activation to reduce blood pressure (J.-P. Stasch et al., 2006, J. Clin. Invest., 116, 2552-2561). Similar findings have been reported using the sGC activator HMR 1766 as well (U. Schindler et al., 2006, Mol. Pharmacol., 69, 1260-1268).

The activation of sGC has the potential to reduce inflammation by effects on the endothelium. BAY 41-2272 and a NO donor inhibited leukocyte rolling and adhesion in eNOS deficient mice. This was demonstrated to be mediated by down-regulation of expression of the adhesion molecule P-selectin (A. Ahluwalla et al., Proc. Natl. Acad. Sci. USA, 2004, 101, 1386-1391). Inhibitors of NOS and sGC were shown to increase endotoxin (LPS) induced ICAM expression on mesenteric microcirculation vessels. This was reduced by an NO donor in a cGMP dependent manner. Treatment of mice with NOS or sGC inhibitors increased neutrophil migration, rolling, and adhesion induced by LPS or carrageenen (D. Dal Secco, Nitric Oxide, 2006, 15, 77-86). Activation of sGC has been shown to produce protection from ischemia-reperfusion injury using BAY 58-2667 in both in vivo and in an isolated heart model (T. Krieg et al., Eur. Heart J., 2009, 30, 1607-6013). Similar results were obtained using the same compound in a canine model of cardioplegic arrest and extracorporeal circulation (T. Radovits et al., Eur J. Cardiothorac. Surg., 2010).

Some studies have indicated the potential of sGC activation to have antinociceptive effects. In streptozotocin-induced diabetes models of nociception in mice (writhing assay) and rats (paw hyperalgesia), elevation of cGMP levels by administration of sildenafil blocked the pain response, which in turn was abrogated by a NOS or sGC inhibitor (C. Patil et al., Pharm., 2004, 72, 190-195). The sGC inhibitor 1H-1,2,4.-oxadiazolo-4,2-a.quinoxalin-1-one (ODQ) has been demonstrated to block the antinociceptive effects of various agents including meloxicam and diphenyl diselenide in a formalin induced pain model (P. Aguirre-Banuelos et al., Eur. J. Pharmacol., 2000, 395, 9-13 and L. Savegnago et al., J. Pharmacy Pharmacol., 2008, 60, 1679-1686) and xylazine in a paw pressure model (T. Romero et al., Eur. J. Pharmacol., 2009, 613, 64-67). Furthermore, ataciguat was antinociceptive in the carrageenan model of inflammatory triggered thermal hyperalgesia and the spared nerve injury model of neuropathic pain in mice (WO 09/043,495).

Inhibition of PDE9, a phosphodiesterase specific for cGMP expressed in the brain, has been shown to improve long-term potentiation (F. van der Staay et al., Neuropharmacol. 2008, 55, 908-918). In the central nervous system, sGC is the primary enzyme which catalyzes the formation of cGMP (K. Domek-Lopacinska et al., Mol. Neurobiol., 2010, 41, 129-137). Thus, sGC activation may be beneficial in treating Alzheimer's and Parkinson's disease. In a phase II clinical study, the sGC stimulator riociguat, was efficacious in treating chronic thromboembolic pulmonary hypertension and pulmonary arterial hypertension (H. Ghofrani et al., Eur. Respir. J., 2010, 36, 792-799). These findings extend the preclinical studies in which BAY 41-2272 and cinaciguat reduced pulmonary hypertension in mouse (R. Dumitrascu et al., Circulation, 2006, 113, 286-295) and lamb (O. Evgenov et al., 2007, Am. J. Respir. Crit. Care Med., 176, 1138-1145) models. Similar results were obtained using HMR 1766 in a mouse model of pulmonary hypertension (N. Weissmann et al., 2009, Am. J. Physiol. Lung Cell. Mol. 297, L658-665).

Activation of sGC has the potential to treat chronic kidney disease. Both BAY 58-2667 and HMR 1766 improved renal function and structure in a rat subtotal nephrectomy model of kidney disease (P. Kalk et al., 2006, Brit. J. Pharmacol., 148, 853-859 and K. Benz et al., 2007, Kidney Blood Press. Res., 30, 224-233). Improved kidney function and survival was provided by BAY 58-2667 treatment in hypertensive renin transgenic rats (TG(mRen2)27 rats) treated with a NOS inhibitor (J.-P. Stasch et al., 2006, J. Clin. Invest., 116, 2552-2561). BAY 41-2272 treatment preserved kidney function and structure in a chronic model of kidney disease in rats induced by uninephrectomy and anti-thyl antibody treatment (Y. Wang et al., 2005, Kidney Intl., 68, 47-61). Diseases caused by excessive blood clotting may be treated with sGC activators. Activation of sGC using BAY 58-2667 was capable of inhibiting platelet aggregation induced by various stimuli ex vivo. Additionally, this compound inhibited thrombus formation in vivo in mice and prolonged bleeding time (J.-P. Stasch et al., 2002, Brit. J. Pharmacol., 136, 773-783). In another study using HMR 1766, in vivo platelet activation was inhibited in streptozotocin treated rats (A. Schafer et al., 2006, Arterioscler. Thromb. Vasc. Biol., 2006, 26, 2813-2818).

sGC activation may also be beneficial in the treatment of urologic disorders (WO/08138483). This is supported by clinical studies using the PDE5 inhibitor vardenafil (C. Stief et al., 2008, Eur. Urol., 53, 1236-1244). The soluble guanylate cyclase stimulator BAY 41-8543 was able to inhibit prostatic, urethra, and bladder smooth muscle cell proliferation using patient samples (B. Fibbi et al., 2010, J. Sex. Med., 7, 59-69), thus providing further evidence supporting the utility of treating urologic disorders with sGC activators.

The above studies provide evidence for the use of sGC activators to treat cardiovascular diseases including hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina, thromboembolic disorders. Additionally, sGC activators have the potential to treat renal disease, diabetes, fibrotic disorders including those of the liver, kidney and lungs, urologic disorders including overactive bladder, benign pro static hyperplasia, and erectile dysfunction, and neurological disorders including Alzheimer's disease, Parkinson's disease, as well as neuropathic pain. Treatment with sGC activators may also provide benefits in inflammatory disorders such as psoriasis, multiple sclerosis, arthritis, asthma, and chronic obstructive pulmonary disease.

BRIEF SUMMARY OF THE INVENTION

The present invention provides novel compounds which activate or potentiate sGC and are thus useful for treating a variety of diseases and disorders that can be alleviated by sGC activation or potentiation including cardiovascular, inflammatory and renal diseases. This invention also relates to pharmaceutical compositions comprising these compounds, methods of using these compounds in the treatment of various diseases and disorders, processes for preparing these compounds and intermediates useful in these processes.

In a further aspect, the present invention provides activators of soluble guanylate cyclase having solubility properties consistent with acceptable pharmacokinetic properties. As is known in the art, poorly soluble compounds may suffer from poor human exposure. The compounds of the present invention would be expected to have exposure properties consistent with being a suitable drug.

DETAILED DESCRIPTION OF THE INVENTION

In an embodiment, there are provided compounds of the formula I

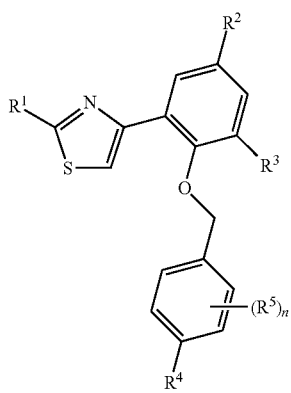

I wherein:
$R^1$ is selected from pyrrolidin-1-yl, piperidin-1-yl, azetidin-1-yl, 5-azaspiro[2.3]hexan-5-yl, azepan-1-yl, 3-azabicyclo[3.1.0.]hexan-3-yl, cyclohexyl, cyclohexen-1-yl, cyclohexylamino and cyclopentylamino, wherein each $R^1$ is substituted with —$CO_2H$ or —$CH_2CO_2H$ and optionally further substituted by a group selected from $C_{1-3}$alkyl, OH, —$CH_2OMe$, —$CF_3$ and —F, and wherein two different carbons in said pyrrolidin-1-yl, piperidin-1-yl, azetidin-1-yl or azepan-1-yl may optionally be joined by a $C_{1-3}$alkylene bridge;
or $R^1$ is —$N(R^6)(CH_2)_{2-3}CO_2H$;
$R^2$ and $R^3$ are independently selected from H, $C_{1-6}$alkyl, halogen, —CN and —$CF_3$, provided that at least one of $R^2$ or $R^3$ is H;
$R^4$ is selected from —$C(O)N(R^6)(R^7)$, —$C(O)R^8$ and —$CH(R^6)R^9$;
$R^5$ is selected from H, $C_{1-4}$alkyl, halogen, —$CF_3$, —$OC_{1-4}$alkyl, —$OCF_3$ and —CN;
$R^6$ is H, —$CH_3$ or —$CH_2CH_3$;
$R^7$ is selected from —$CH_3$, —$CH_2CH_3$, —$(CH_2)_{2-3}OCH_3$, —$(CH_2)_2N(CH_3)_2$, $C_{1-3}$alkyl, —$(CH_2)_{1-2}CN$, —$(CH_2)_{2-3}OH$, —$CH_2C(O)NHCH_3$, —$CH_2C(O)N(CH_3)_2$, —$CH_2$-tetrahydrofuranyl, —$CH_2$-1-methylpyrrazol-3-yl, —$CH_2$-1-methylpyrrazol-4-yl, —$CH_2$-1-methylpyrrazol-5-yl, —$CH_2$-imidazol-2-yl and —$(CH_2)_{0-1}$cyclohexyl;
$R^8$ is selected from azepan-1-yl, azetidin-1-yl, 1,1-dioxothiomorpholin-4-yl, morpholin-4-yl, piperidin-1-yl, piperazin-1-yl, pyrrolidin-1-yl, [1,4]oxazepan-4-yl, 5,6,7,8-tetrahydro[1,2,4]triazolo[1,5-a]pyrazin-7-yl and 5,6,7,8-[1,2,4]triazolo[4,3-a]pyrazine-7-yl and is optionally substituted with one to three groups independently selected from $C_{1-3}$alkyl, —$CH_2OH$, —$OCH_3$, —$N(CH_3)_2$, —OH, oxo, —CN and halogen;
$R^9$ is a heterocyclyl selected from morpholin-4-yl, 1,1-dioxothiomorpholin-4-yl, pyrrolidin-1-yl, piperidin-1-yl, octahydropyrrolo[1,2-a]pyrazin-2-yl and piperazin-1-yl, wherein said heterocyclyl is optionally substituted with one to three groups independently selected from $C_{1-3}$alkyl, —$CH_2OH$, —$CH_2OCH_3$, halogen, —CN, oxo, —OH, —$SO_2C_{1-6}$alkyl, —$SO_2N(C_{1-6}$alkyl$)_2$, —$C(O)NH_2$, —$C(O)NHCH_3$, —$C(O)N(CH_3)_2$, $C(O)C_{1-6}$alkyl, —$C(O)C_{3-6}$cycloalkyl, and —$C(O)$tetrahydrofuran-3-yl; or
$R^9$ is —$N(R^6)(R^{10})$;
$R^{10}$ is selected from tetrahydropyran-4-ylmethyl, $C_{3-6}$cycloalkyl, $C_{3-6}$cycloalkylmethyl, 1,1-dioxotetrahydrothiophen-3-yl, —$CH_2C(CH_3)_2OH$, —$CH_2C(CH_3)_2CH_2OH$, —$C(CH_3)_2CH_2OH$, —$CH_2(CH_2)_{1-2}OCH_3$ and —$CH_2CH_2CO_2H$; and
n is 1 or 2;
or a salt thereof.

In another embodiment, there are provided compounds as described above, wherein $R^1$ is selected from the group consisting of

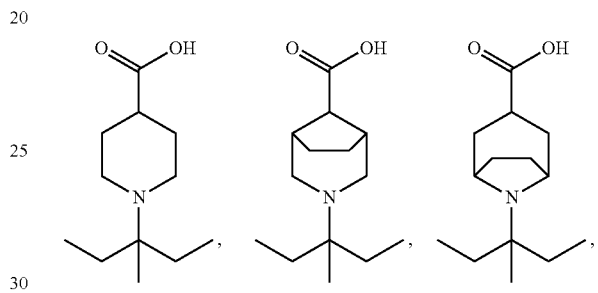

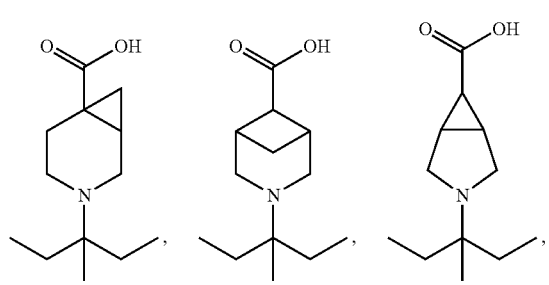

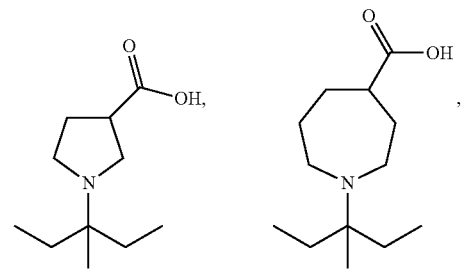

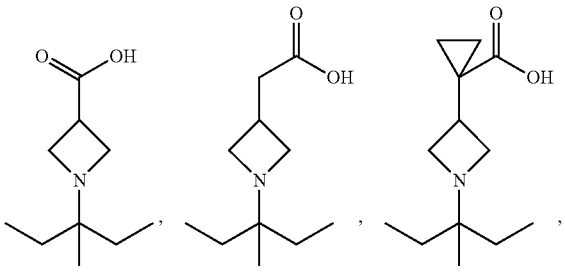

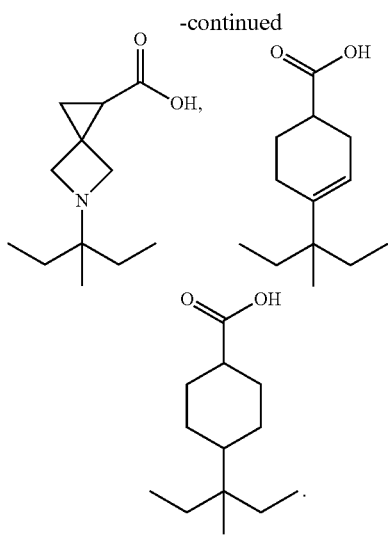

and wherein each $R^1$ is optionally substituted by a group selected from $C_{1-3}$alkyl, OH, —CH$_2$OMe, —CF$_3$ and —F;
or a salt thereof.

In another embodiment, there are provided compounds as described in the first embodiment, wherein
$R^1$ is selected from pyrrolidin-1-yl, piperidin-1-yl, azepan-1-yl, 3-azabicyclo[3.1.0.]hexan-3-yl, cyclohexyl, cyclohexen-1-yl, cyclohexylamino and cyclopentylamino, wherein each $R^1$ is substituted with —CO$_2$H or —CH$_2$CO$_2$H and optionally further substituted by a group selected from —CH$_3$, —CF$_3$ and —F, and wherein two different carbons in said piperidin-1-yl may optionally be joined by a $C_{1-3}$alkylene bridge;
or $R^1$ is —N($R^6$)(CH$_2$)$_{2-3}$CO$_2$H;
n is 1;
$R^2$ and $R^3$ are independently selected from H, $C_{1-6}$alkyl, halogen, —CN and —CF$_3$, provided that at least one of $R^2$ or $R^3$ is H;
$R^4$ is selected from —C(O)N($R^6$)($R^7$), —C(O)$R^8$ and —CH$_2R^9$;
$R^5$ is selected from H, $C_{1-4}$alkyl, halogen, —CF$_3$, —O$C_{1-4}$alkyl, and —CN and is bonded to a position on the phenyl ring meta to $R^4$;
$R^6$ is H or —CH$_3$;
$R^7$ is selected from —(CH$_2$)$_{2-3}$OCH$_3$, —(CH$_2$)$_2$N(CH$_3$)$_2$ and —(CH$_2$)$_{0-1}$cyclohexyl;
$R^8$ is selected from morpholin-4-yl, 1,1-dioxothiomorpholin-4-yl, pyrrolidin-1-yl, and piperidin-1-yl, and is optionally substituted with —OH or 1 to two halogens;
$R^9$ is a heterocyclyl selected from morpholin-4-yl, 1,1-dioxothiomorpholin-4-yl, pyrrolidin-1-yl, piperidin-1-yl and piperazin-1-yl, wherein said heterocyclyl is optionally substituted with one to two groups selected from halogen, —OH, —SO$_2C_{1-6}$alkyl, —SO$_2$N($C_{1-6}$alkyl)$_2$, —C(O)NH$_2$, —C(O)NHCH$_3$, —C(O)N(CH$_3$)$_2$, C(O)$C_{1-6}$alkyl, —C(O)$C_{3-6}$cycloalkyl, and —C(O)tetrahydrofuran-3-yl; or
$R^9$ is —N($R^6$)($R^{10}$); and
$R^{10}$ is selected from tetrahydropyran-4-ylmethyl, $C_{3-6}$cycloalkyl, $C_{3-6}$cycloalkylmethyl, 1,1-dioxotetrahydrothiophen-3-yl, —CH$_2$C(CH$_3$)$_2$OH, —CH$_2$C(CH$_3$)$_2$CH$_2$OH, —C(CH$_3$)$_2$CH$_2$OH, —CH$_2$(CH$_2$)$_{1-2}$OCH$_3$ and —CH$_2$CH$_2$CO$_2$H;
or a salt thereof.

In another embodiment, there are provided compounds as described in any embodiment above, wherein $R^1$ is selected from the group consisting of

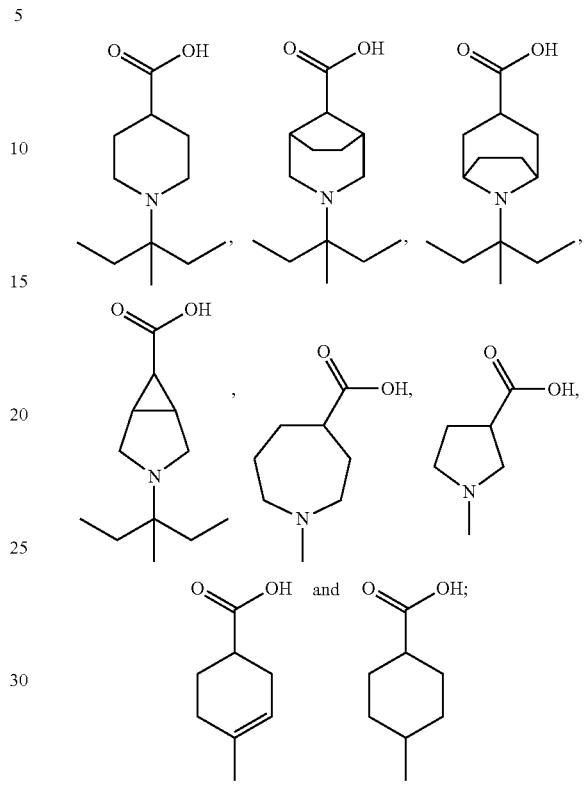

and wherein each $R^1$ is optionally substituted by a group selected from —CH$_3$, —CF$_3$ and —F,
or a salt thereof.

In another embodiment, there are provided compounds as described in any embodiment above wherein $R^1$ is selected from the group consisting of

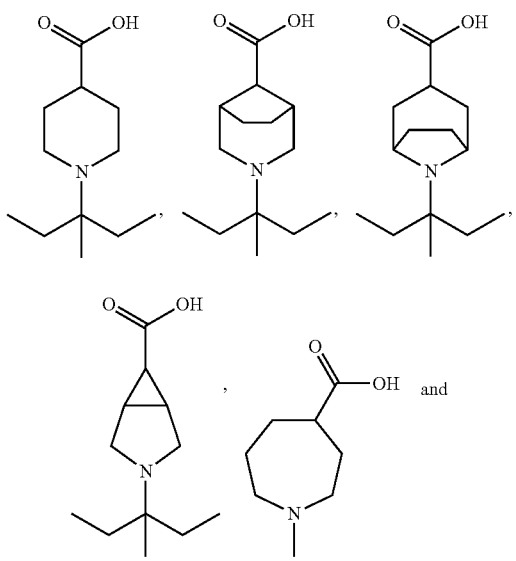

-continued

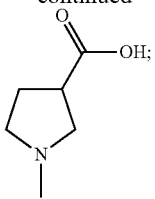

and wherein each $R^1$ is optionally substituted by a group selected from —$CH_3$, —$CF_3$ and —F,
or a salt thereof.

In another embodiment, there are provided compounds as described in any embodiment above wherein $R^1$ is selected from the group consisting of

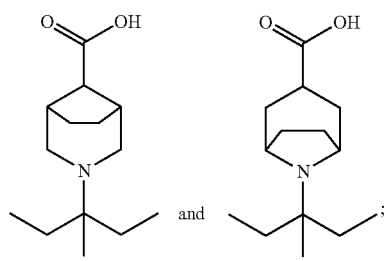 [SMILES: CCC(C)(CC)N1CC2CCC(C1)C2C(=O)O ; CCC(C)(CC)N1C2CCC1CC(C(=O)O)C2]

or a salt thereof.

In another embodiment, there are provided compounds as described in any embodiment above wherein $R^1$ is

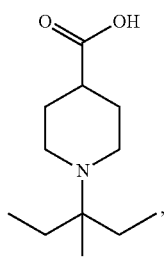

or a salt thereof.

In another embodiment, there are provided compounds as described in the first embodiment wherein $R^1$ is selected from the group consisting of

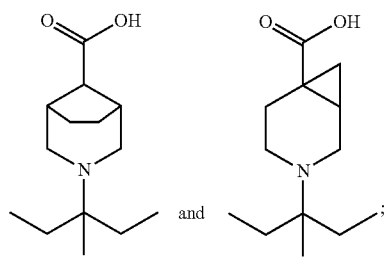 [SMILES: CCC(C)(CC)N1CC2CCC(C1)C2C(=O)O ; CCC(C)(CC)N1CCC2(C(=O)O)CC2C1]

or a salt thereof.

In another embodiment, there are provided compounds as described in the first embodiment wherein $R^1$ is selected from the group consisting of

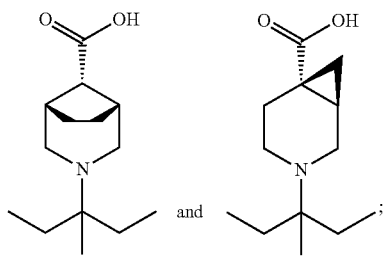 [SMILES: CCC(C)(CC)N1C[C@H]2CC[C@@H](C1)[C@H]2C(=O)O ; CCC(C)(CC)N1CC[C@@]2(C(=O)O)C[C@H]2C1]

or a salt thereof.

In another embodiment there are compounds as described in any of the embodiments above, wherein:

n is 1;

$R^2$ and $R^3$ are independently selected from H, —$CH_3$, —Cl, —F, —CN and —$CF_3$, provided that at least one of $R^2$ or $R^3$ is H;

$R^5$ is selected from —$CH_3$, —$CH_2CH_3$, —$OCF_3$ and —CN and is bonded to a position on the phenyl ring meta to $R^4$;

$R^8$ is selected from azepan-1-yl, azetidin-1-yl, morpholin-4-yl, 1,1-dioxothiomorpholin-4-yl, pyrrolidin-1-yl, piperazin-1-yl, [1,4]oxazepan-4-yl, and piperidin-1-yl, wherein each $R^8$ is optionally substituted with one to three groups independently selected from —$CH_3$, —$OCH_3$, —$CH_2OH$, —$OCH_3$, —$N(CH_3)_2$, —OH, oxo, —CN and halogen;

$R^9$ is a heterocyclyl selected from morpholin-4-yl, 1,1-dioxothiomorpholin-4-yl, pyrrolidin-1-yl, piperidin-1-yl and piperazin-1-yl, wherein said heterocyclyl is optionally substituted with one to three groups independently selected from —$CH_3$, —$CH_2CH_3$, Cl, F, oxo, —OH, —$C(O)CH_3$, —C(O)cyclopropyl and —C(O)tetrahydrofuran-3-yl;

or a salt thereof.

In another embodiment, there are provided compounds as described in any of the embodiments above wherein:

$R^4$ is selected from —$C(O)R^8$ and —$CH_2R^9$;

$R^8$ is selected from morpholin-4-yl, 1,1-dioxothiomorpholin-4-yl, pyrrolidin-1-yl, and piperidin-1-yl; and $R^9$ is a heterocyclyl selected from morpholin-4-yl, 1,1-dioxothiomorpholin-4-yl, pyrrolidin-1-yl, piperidin-1-yl and 4-acylpiperazin-1-yl;

or a salt thereof.

In another embodiment, there are provided compounds as described in any of the embodiments above wherein:

$R^4$ is —$C(O)R^8$;

or a salt thereof.

In another embodiment, there are provided compounds as described in any of the embodiments above wherein:

$R^4$ is —$CH_2R^9$;

or a salt thereof.

The following are representative compounds of the invention which can be made by the general synthetic methods and synthetic examples described herein and methods known in the art.

TABLE 1
| Cpd No. | |
|---|---|
| 1 | 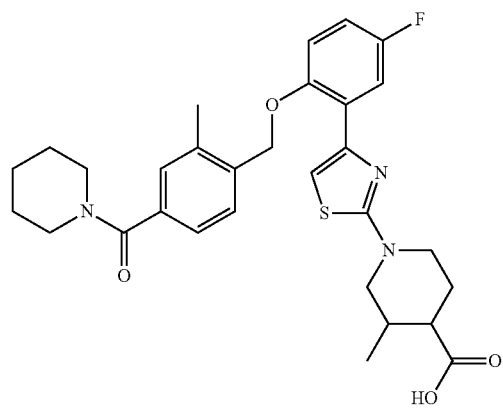 |
| 2 | 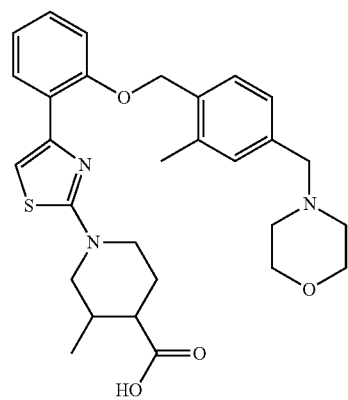 [SMILES: Cc1cc(CN2CCOCC2)ccc1COc1ccccc1-c1csc(N2CCC(C(=O)O)C(C)C2)n1] |
| 3 | 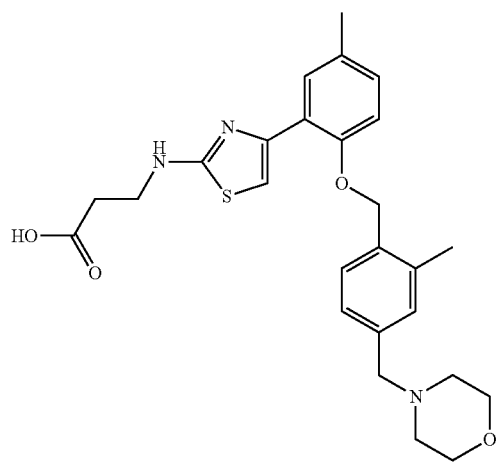 [SMILES: Cc1ccc(OCc2ccc(CN3CCOCC3)cc2C)c(-c2csc(NCCC(=O)O)n2)c1] |

TABLE 1-continued
| Cpd No. | |
|---|---|
| 4 | 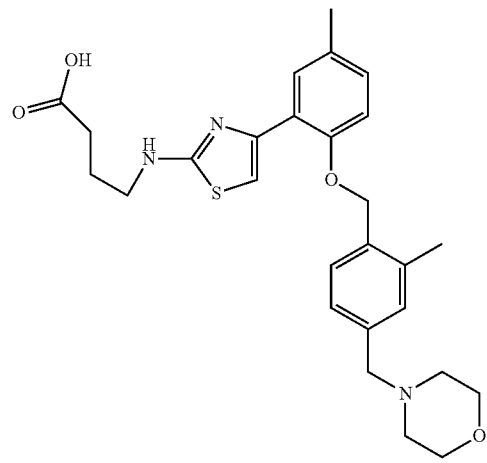 [SMILES: Cc1ccc(OCc2ccc(CN3CCOCC3)cc2C)c(-c2csc(NCCCC(=O)O)n2)c1] |
| 5 | 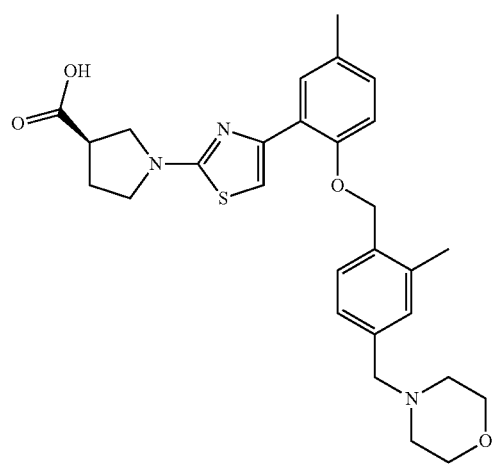 [SMILES: Cc1ccc(OCc2ccc(CN3CCOCC3)cc2C)c(-c2csc(N3CC[C@@H](C(=O)O)C3)n2)c1] |
| 6 | 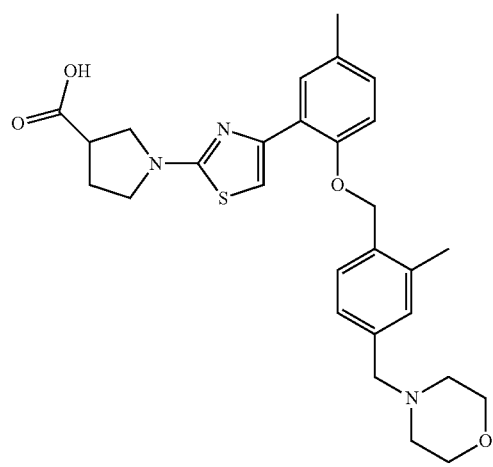 [SMILES: Cc1ccc(OCc2ccc(CN3CCOCC3)cc2C)c(-c2csc(N3CCC(C(=O)O)C3)n2)c1] |

TABLE 1-continued
| Cpd No. | |
|---|---|
| 7 | 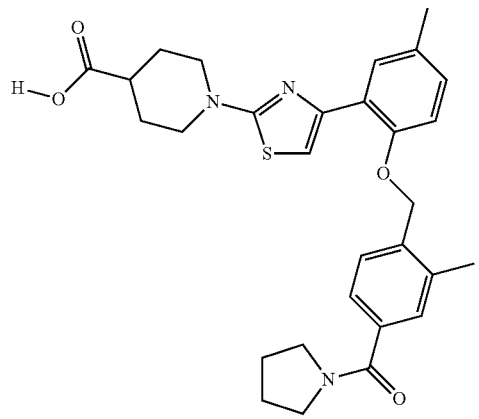 [SMILES: Cc1ccc(OCc2ccc(C(=O)N3CCCC3)cc2C)c(-c2csc(N3CCC(C(=O)O)CC3)n2)c1] |
| 8 | 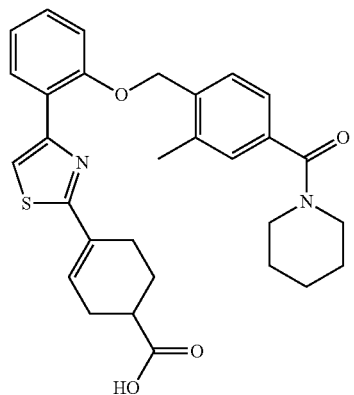 [SMILES: Cc1cc(C(=O)N2CCCCC2)ccc1COc1ccccc1-c1csc(C2=CCC(C(=O)O)CC2)n1] |
| 9 | 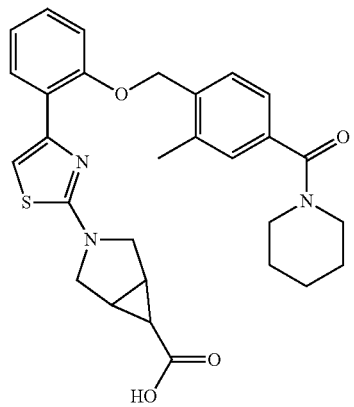 [SMILES: Cc1cc(C(=O)N2CCCCC2)ccc1COc1ccccc1-c1csc(N2CC3C(C2)C3C(=O)O)n1] |

TABLE 1-continued
| Cpd No. |
| --- |
| 10 |
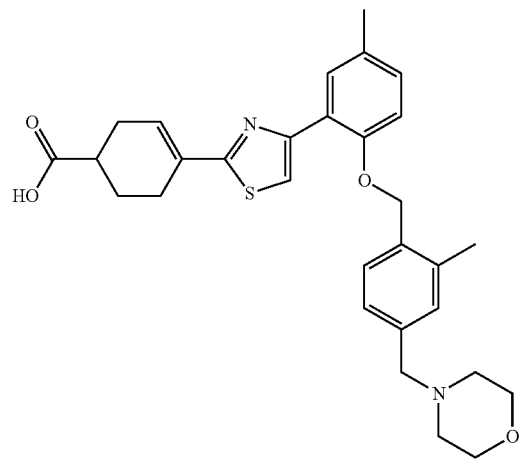 [SMILES: Cc1ccc(OCc2ccc(CN3CCOCC3)cc2C)c(-c2csc(C3=CCC(C(=O)O)CC3)n2)c1]
| 11 |
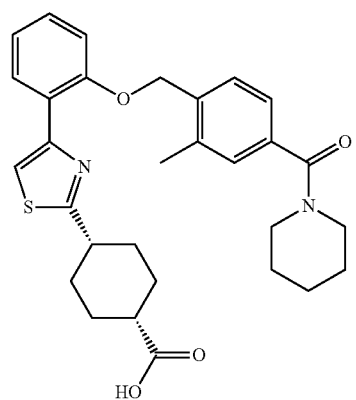
| 12 |
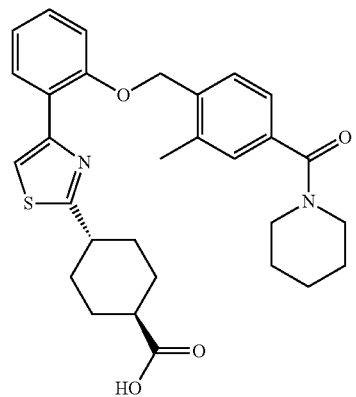 [SMILES: Cc1cc(C(=O)N2CCCCC2)ccc1COc1ccccc1-c1csc([C@H]2CC[C@H](C(=O)O)CC2)n1]

TABLE 1-continued
| Cpd No. | |
|---|---|
| 13 | 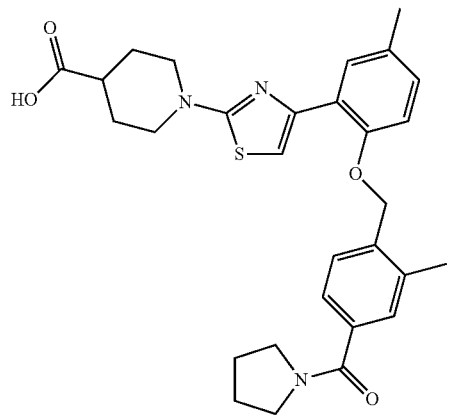 [SMILES: Cc1ccc(OCc2ccc(C(=O)N3CCCC3)cc2C)c(-c2csc(N3CCC(C(=O)O)CC3)n2)c1] |
| 14 | 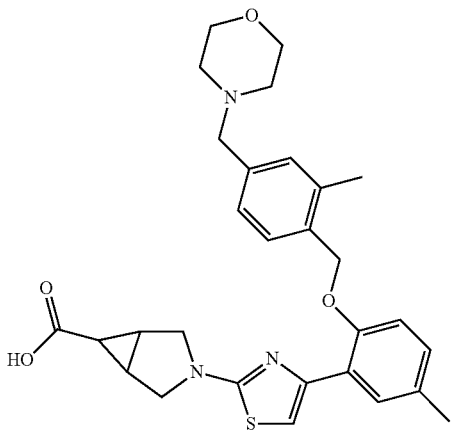 [SMILES: Cc1ccc(OCc2ccc(CN3CCOCC3)cc2C)c(-c2csc(N3CC4C(C3)C4C(=O)O)n2)c1] |
| 15 | 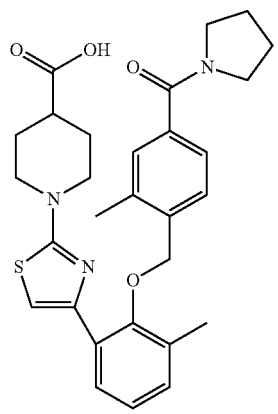 [SMILES: Cc1cc(C(=O)N2CCCC2)ccc1COc1c(C)cccc1-c1csc(N2CCC(C(=O)O)CC2)n1] |

TABLE 1-continued
| Cpd No. | |
|---|---|
| 16 | 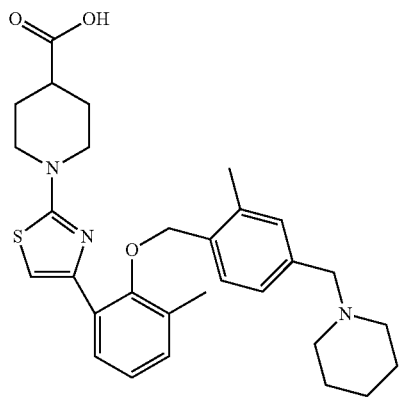 [SMILES: Cc1cc(CN2CCCCC2)ccc1COc1c(C)cccc1-c1csc(N2CCC(C(=O)O)CC2)n1] |
| 17 | 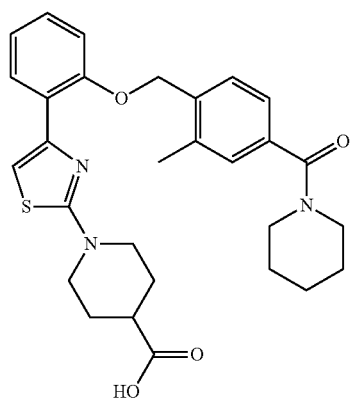 [SMILES: Cc1cc(C(=O)N2CCCCC2)ccc1COc1ccccc1-c1csc(N2CCC(C(=O)O)CC2)n1] |
| 18 | 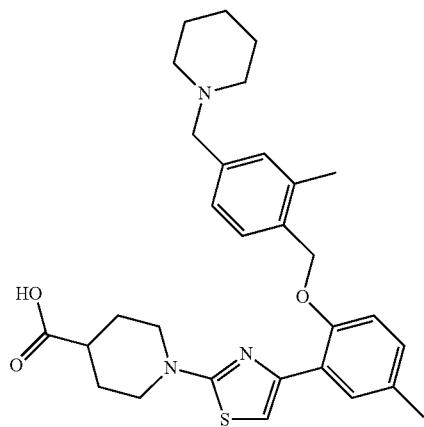 [SMILES: Cc1ccc(OCc2ccc(CN3CCCCC3)cc2C)c(-c2csc(N3CCC(C(=O)O)CC3)n2)c1] |

TABLE 1-continued
| Cpd No. | |
|---|---|
| 19 | 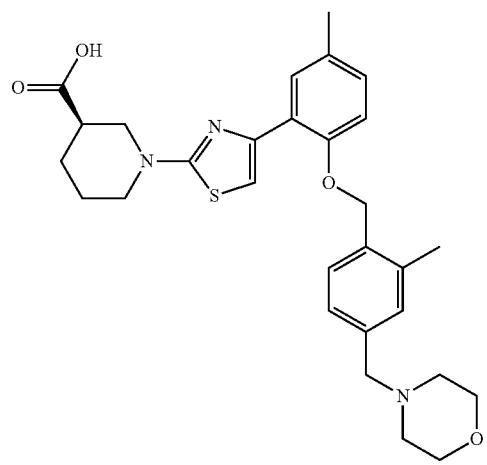 [SMILES: Cc1ccc(OCc2ccc(CN3CCOCC3)cc2C)c(-c2csc(N3CCC[C@@H](C(=O)O)C3)n2)c1] |
| 20 | 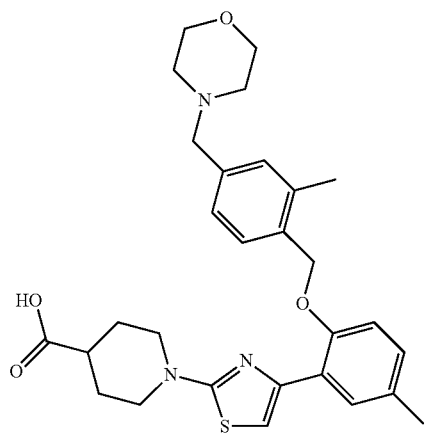 [SMILES: Cc1ccc(OCc2ccc(CN3CCOCC3)cc2C)c(-c2csc(N3CCC(C(=O)O)CC3)n2)c1] |
| 21 | 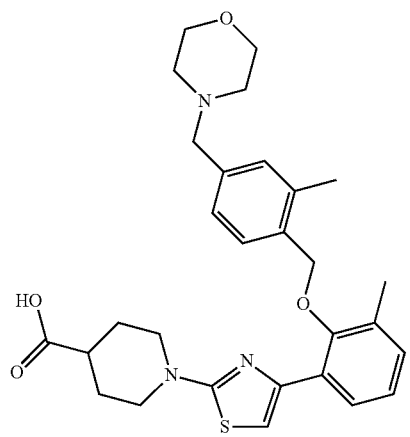 [SMILES: Cc1cc(CN2CCOCC2)ccc1COc1c(C)cccc1-c1csc(N2CCC(C(=O)O)CC2)n1] |

TABLE 1-continued
| Cpd No. | |
|---|---|
| 22 | 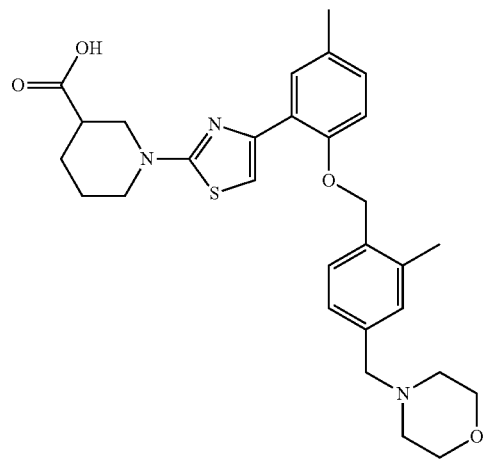 [SMILES: Cc1ccc(OCc2ccc(CN3CCOCC3)cc2C)c(-c2csc(N3CCCC(C(=O)O)C3)n2)c1] |
| 23 | 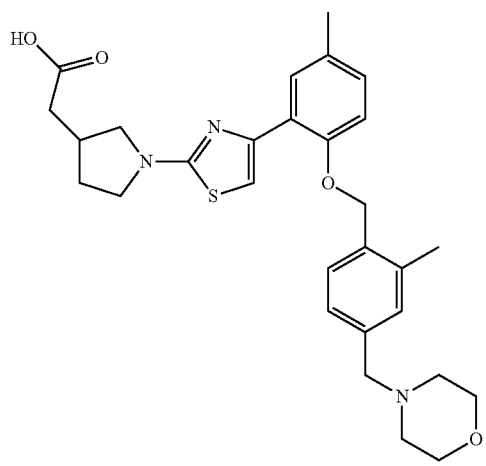 [SMILES: Cc1ccc(OCc2ccc(CN3CCOCC3)cc2C)c(-c2csc(N3CCC(CC(=O)O)C3)n2)c1] |
| 24 | 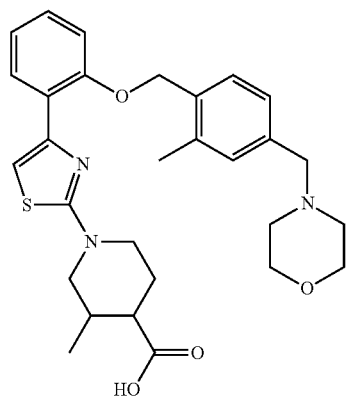 [SMILES: Cc1cc(CN2CCOCC2)ccc1COc1ccccc1-c1csc(N2CCC(C(=O)O)C(C)C2)n1] |

TABLE 1-continued
| Cpd No. | |
|---|---|
| 25 | 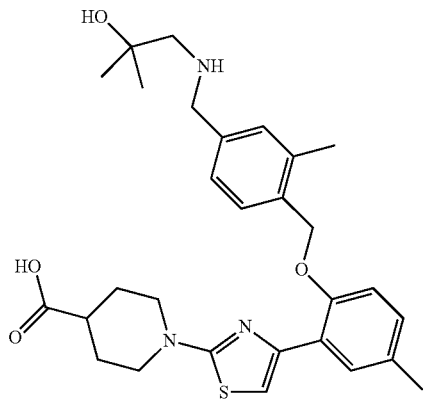 [SMILES: Cc1ccc(OCc2ccc(CNCC(C)(C)O)cc2C)c(-c2csc(N3CCC(C(=O)O)CC3)n2)c1] |
| 26 | 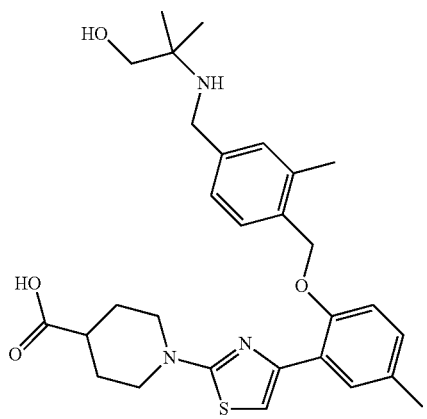 [SMILES: Cc1ccc(OCc2ccc(CNC(C)(C)CO)cc2C)c(-c2csc(N3CCC(C(=O)O)CC3)n2)c1] |
| 27 | 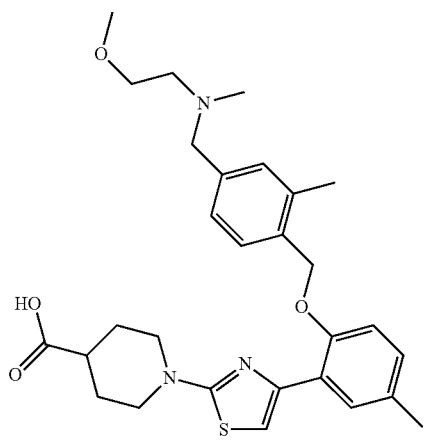 [SMILES: COCCN(C)Cc1ccc(COc2ccc(C)cc2-c2csc(N3CCC(C(=O)O)CC3)n2)c(C)c1] |

TABLE 1-continued
| Cpd No. | |
|---|---|
| 28 | 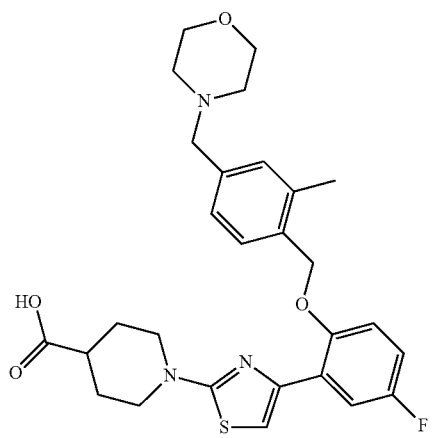 [SMILES: Cc1cc(CN2CCOCC2)ccc1COc1ccc(F)cc1-c1csc(N2CCC(C(=O)O)CC2)n1] |
| 29 | 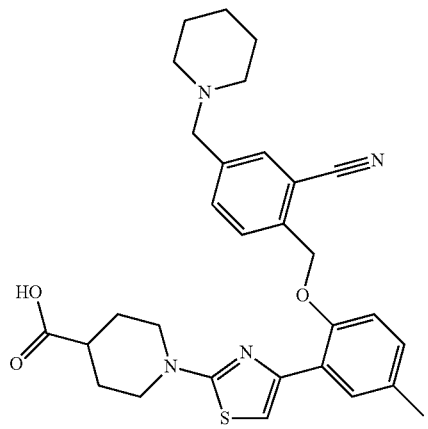 [SMILES: Cc1ccc(OCc2ccc(CN3CCCCC3)cc2C#N)c(-c2csc(N3CCC(C(=O)O)CC3)n2)c1] |
| 30 | 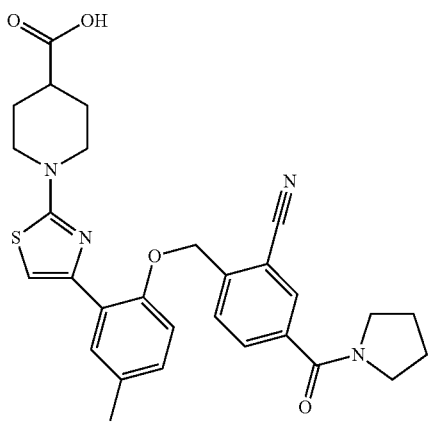 [SMILES: Cc1ccc(OCc2ccc(C(=O)N3CCCC3)cc2C#N)c(-c2csc(N3CCC(C(=O)O)CC3)n2)c1] |

TABLE 1-continued
| Cpd No. | |
|---|---|
| 31 | 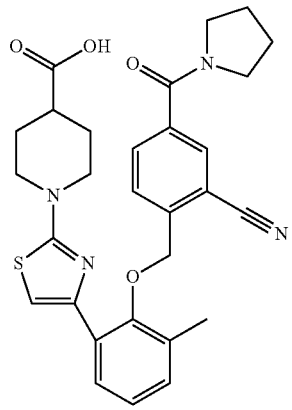 [SMILES: Cc1cccc(-c2csc(N3CCC(C(=O)O)CC3)n2)c1OCc1ccc(C(=O)N2CCCC2)cc1C#N] |
| 32 | 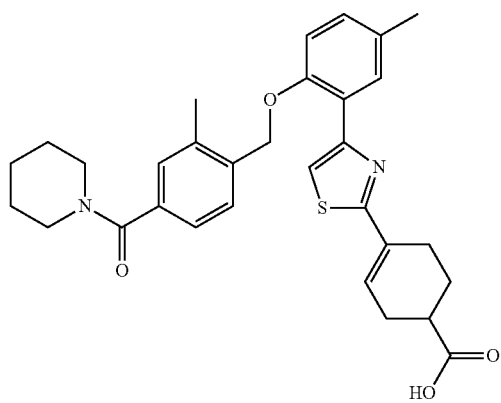 [SMILES: Cc1ccc(OCc2ccc(C(=O)N3CCCCC3)cc2C)c(-c2csc(C3=CCC(C(=O)O)CC3)n2)c1] |
| 33 | 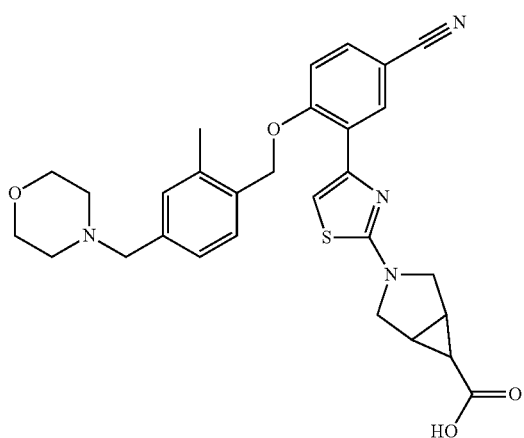 [SMILES: Cc1cc(CN2CCOCC2)ccc1COc1ccc(C#N)cc1-c1csc(N2CC3C(C2)C3C(=O)O)n1] |

TABLE 1-continued
| Cpd No. | |
|---|---|
| 34 | 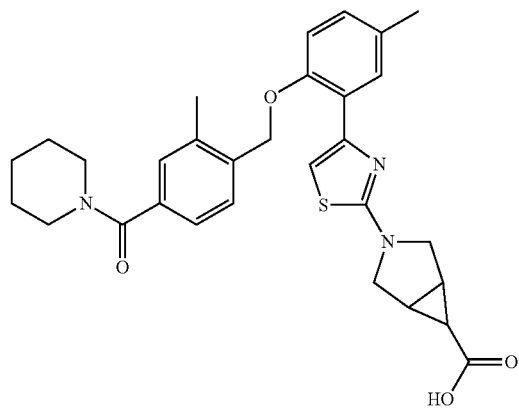 [SMILES: Cc1ccc(OCc2ccc(C(=O)N3CCCCC3)cc2C)c(-c2csc(N3CC4C(C3)C4C(=O)O)n2)c1] |
| 35 | 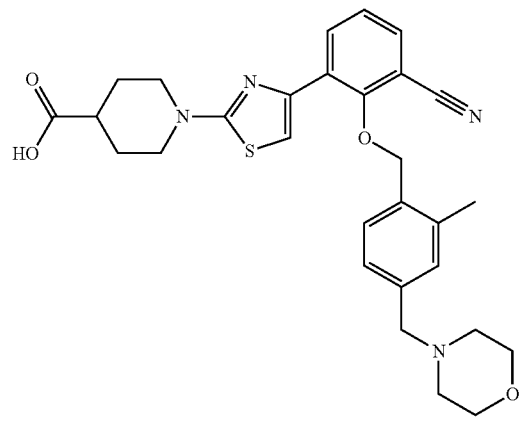 [SMILES: Cc1cc(CN2CCOCC2)ccc1COc1c(C#N)cccc1-c1csc(N2CCC(C(=O)O)CC2)n1] |
| 36 | 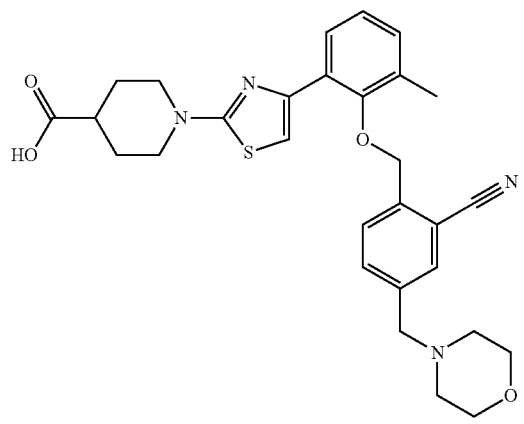 [SMILES: Cc1cccc(-c2csc(N3CCC(C(=O)O)CC3)n2)c1OCc1ccc(CN2CCOCC2)cc1C#N] |

TABLE 1-continued
| Cpd No. | |
|---|---|
| 37 | 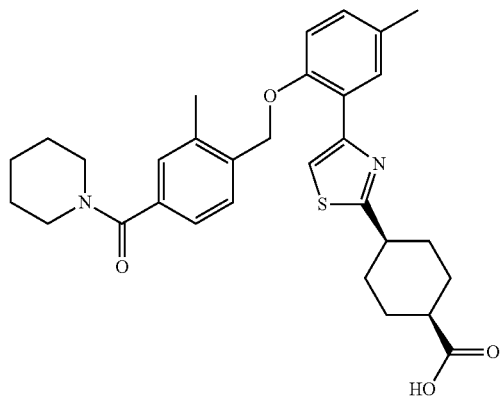 [SMILES: Cc1ccc(OCc2ccc(C(=O)N3CCCCC3)cc2C)c(-c2csc([C@H]3CC[C@@H](C(=O)O)CC3)n2)c1] |
| 38 | 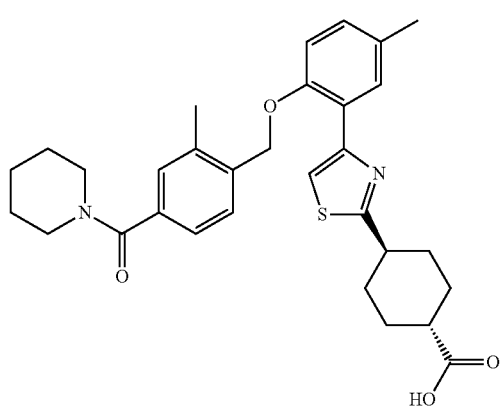 [SMILES: Cc1ccc(OCc2ccc(C(=O)N3CCCCC3)cc2C)c(-c2csc([C@H]3CC[C@H](C(=O)O)CC3)n2)c1] |
| 39 | 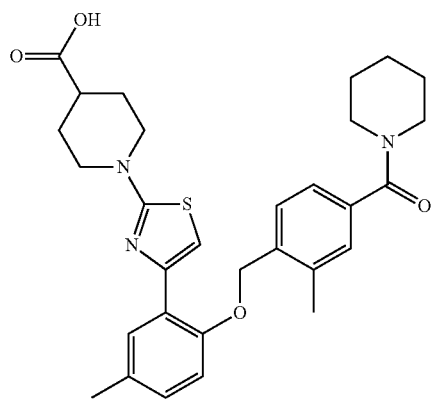 [SMILES: Cc1ccc(OCc2ccc(C(=O)N3CCCCC3)cc2C)c(-c2csc(N3CCC(C(=O)O)CC3)n2)c1] |
| 40 | 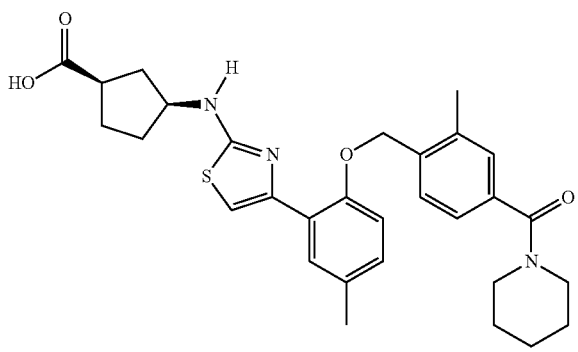 [SMILES: Cc1ccc(OCc2ccc(C(=O)N3CCCCC3)cc2C)c(-c2csc(N[C@H]3CC[C@@H](C(=O)O)C3)n2)c1] |

TABLE 1-continued
| Cpd No. | |
|---|---|
| 41 | 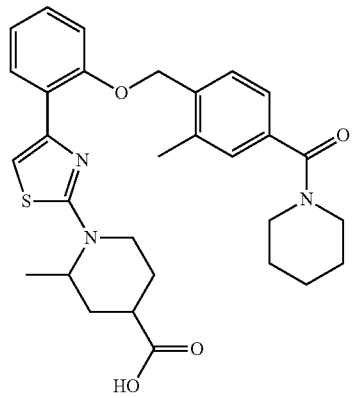 [SMILES: Cc1cc(C(=O)N2CCCCC2)ccc1COc1ccccc1-c1csc(N2CCC(C(=O)O)CC2C)n1] |
| 42 | 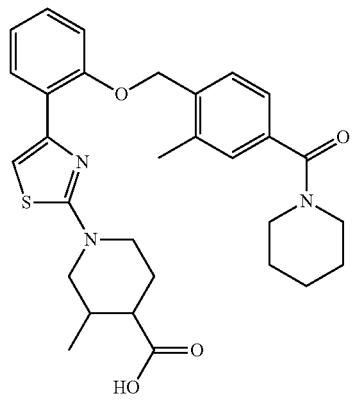 [SMILES: Cc1cc(C(=O)N2CCCCC2)ccc1COc1ccccc1-c1csc(N2CCC(C(=O)O)C(C)C2)n1] |
| 43 | 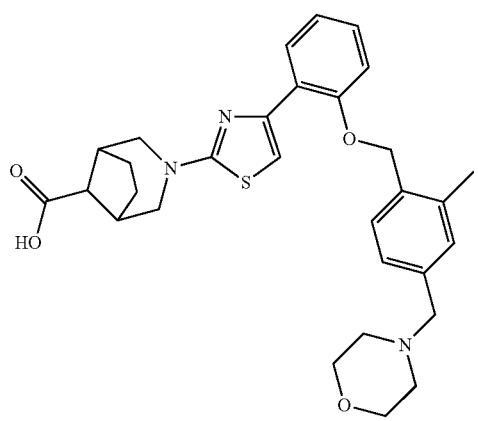 [SMILES: Cc1cc(CN2CCOCC2)ccc1COc1ccccc1-c1csc(N2CC3CCC(C2)C3C(=O)O)n1] |

TABLE 1-continued
| Cpd No. |
|---|
| 44 |
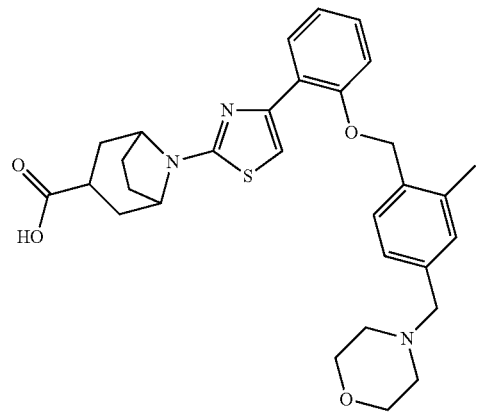 [SMILES: Cc1cc(CN2CCOCC2)ccc1COc1ccccc1-c1csc(N2C3CCC2CC(C(=O)O)C3)n1]
| 45 |
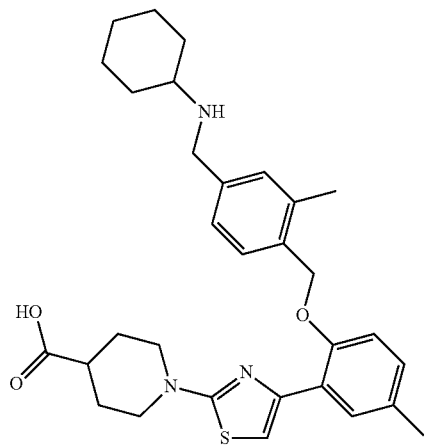 [SMILES: Cc1ccc(OCc2ccc(CNC3CCCCC3)cc2C)c(-c2csc(N3CCC(C(=O)O)CC3)n2)c1]
| 46 |
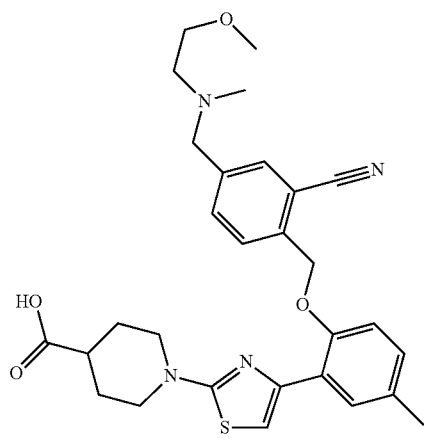 [SMILES: COCCN(C)Cc1ccc(COc2ccc(C)cc2-c2csc(N3CCC(C(=O)O)CC3)n2)c(C#N)c1]

TABLE 1-continued
| Cpd No. | |
|---|---|
| 47 | 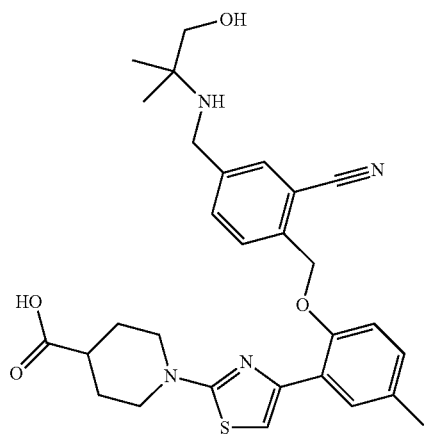 [SMILES: Cc1ccc(OCc2ccc(CNC(C)(C)CO)cc2C#N)c(-c2csc(N3CCC(C(=O)O)CC3)n2)c1] |
| 48 | 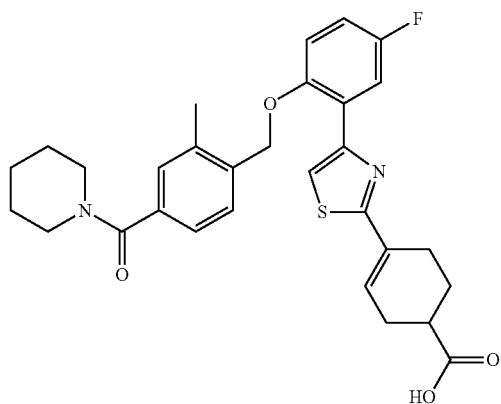 [SMILES: Cc1cc(C(=O)N2CCCCC2)ccc1COc1ccc(F)cc1-c1csc(C2=CCC(C(=O)O)CC2)n1] |
| 49 | 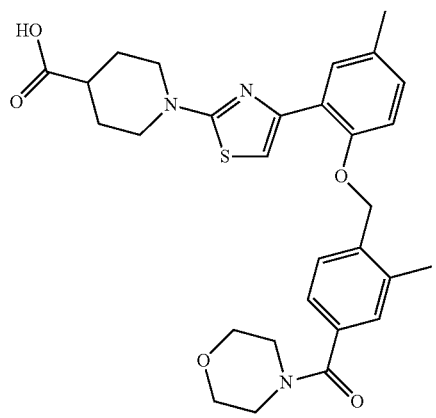 [SMILES: Cc1ccc(OCc2ccc(C(=O)N3CCOCC3)cc2C)c(-c2csc(N3CCC(C(=O)O)CC3)n2)c1] |

TABLE 1-continued
| Cpd No. | |
|---|---|
| 50 | 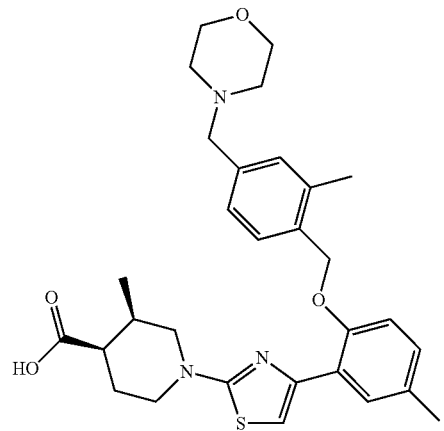 [SMILES: Cc1ccc(OCc2ccc(CN3CCOCC3)cc2C)c(-c2csc(N3CC[C@@H](C(=O)O)[C@@H](C)C3)n2)c1] |
| 51 | 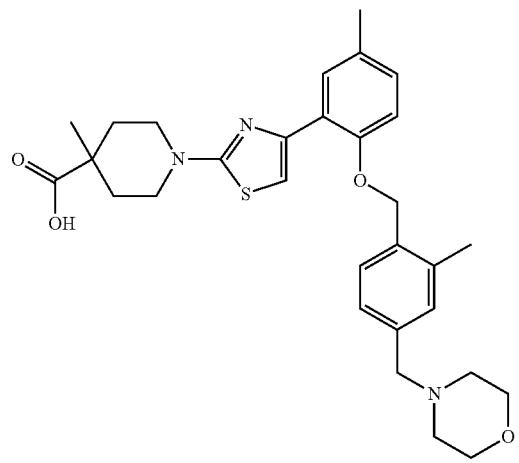 [SMILES: Cc1ccc(OCc2ccc(CN3CCOCC3)cc2C)c(-c2csc(N3CCC(C)(C(=O)O)CC3)n2)c1] |
| 52 | 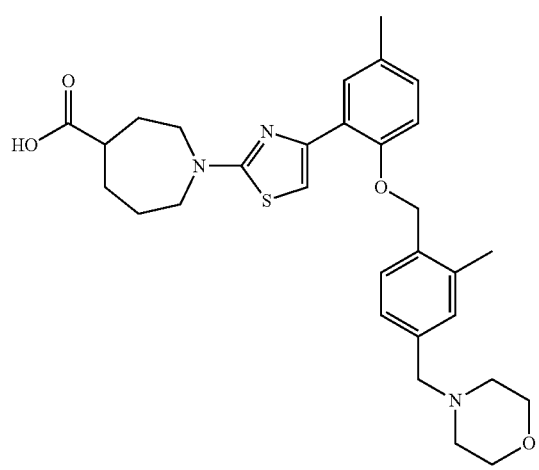 [SMILES: Cc1ccc(OCc2ccc(CN3CCOCC3)cc2C)c(-c2csc(N3CCCC(C(=O)O)CC3)n2)c1] |

TABLE 1-continued
| Cpd No. | |
|---|---|
| 53 | 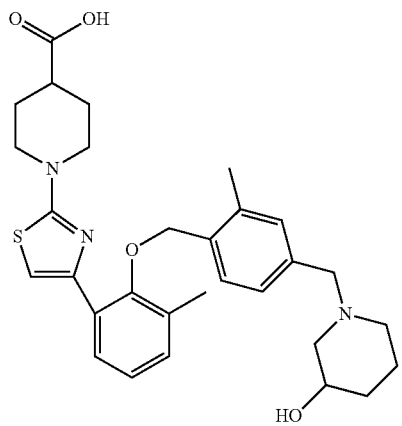 [SMILES: Cc1cc(CN2CCCC(O)C2)ccc1COc1c(C)cccc1-c1csc(N2CCC(C(=O)O)CC2)n1] |
| 54 | 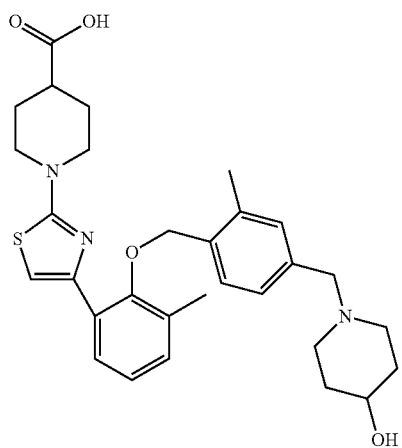 [SMILES: Cc1cc(CN2CCC(O)CC2)ccc1COc1c(C)cccc1-c1csc(N2CCC(C(=O)O)CC2)n1] |
| 55 | 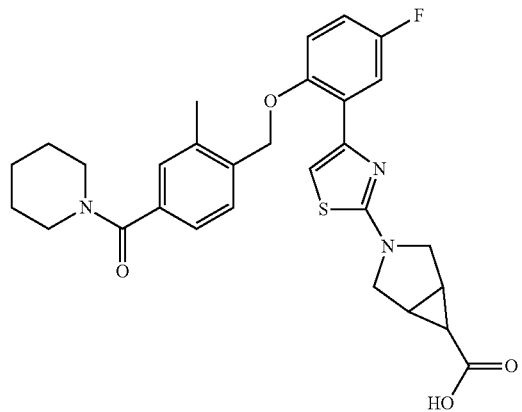 [SMILES: Cc1cc(C(=O)N2CCCCC2)ccc1COc1ccc(F)cc1-c1csc(N2CC3C(C2)C3C(=O)O)n1] |

TABLE 1-continued
| Cpd No. | |
|---|---|
| 56 | 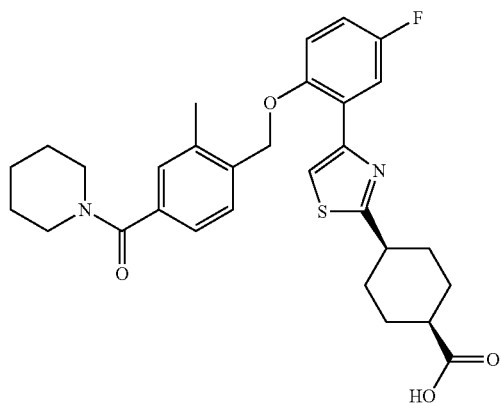 [SMILES: Cc1cc(C(=O)N2CCCCC2)ccc1COc1ccc(F)cc1-c1csc([C@H]2CC[C@@H](C(=O)O)CC2)n1] |
| 57 | 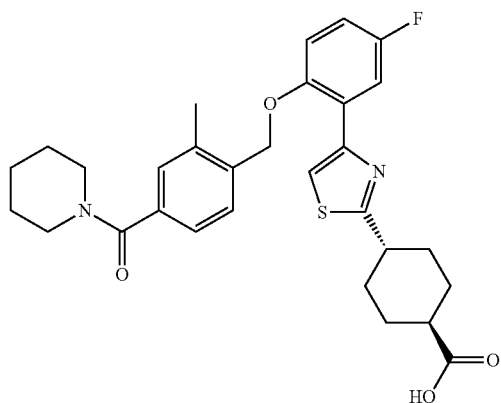 [SMILES: Cc1cc(C(=O)N2CCCCC2)ccc1COc1ccc(F)cc1-c1csc([C@H]2CC[C@H](C(=O)O)CC2)n1] |
| 58 | 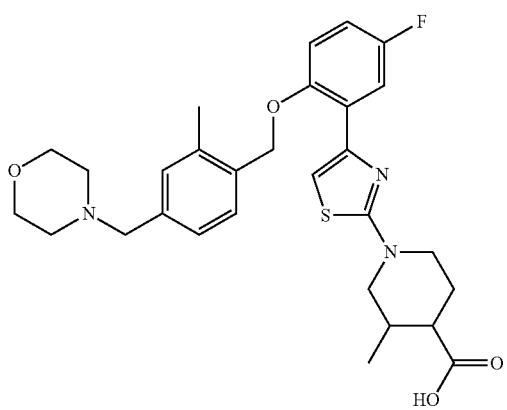 [SMILES: Cc1cc(CN2CCOCC2)ccc1COc1ccc(F)cc1-c1csc(N2CCC(C(=O)O)C(C)C2)n1] |

TABLE 1-continued
| Cpd No. | |
|---|---|
| 59 | 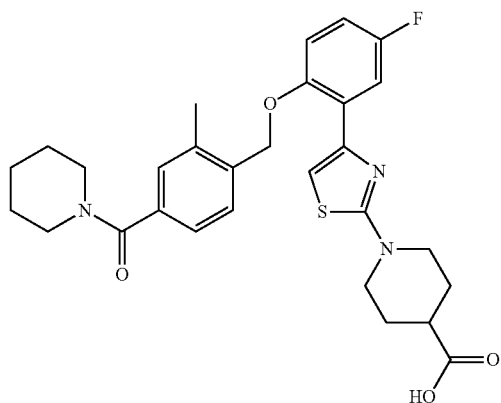 [SMILES: Cc1cc(C(=O)N2CCCCC2)ccc1COc1ccc(F)cc1-c1csc(N2CCC(C(=O)O)CC2)n1] |
| 60 | 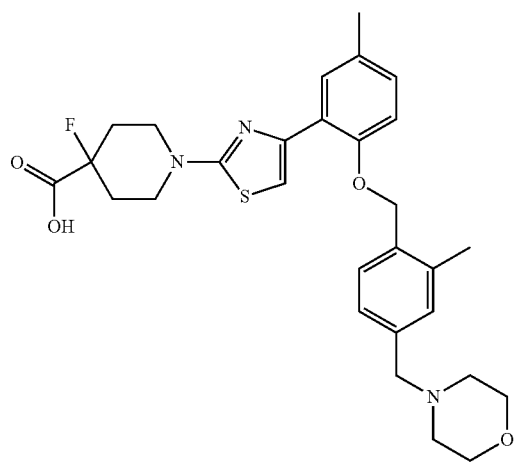 [SMILES: Cc1ccc(OCc2ccc(CN3CCOCC3)cc2C)c(-c2csc(N3CCC(F)(C(=O)O)CC3)n2)c1] |
| 61 | 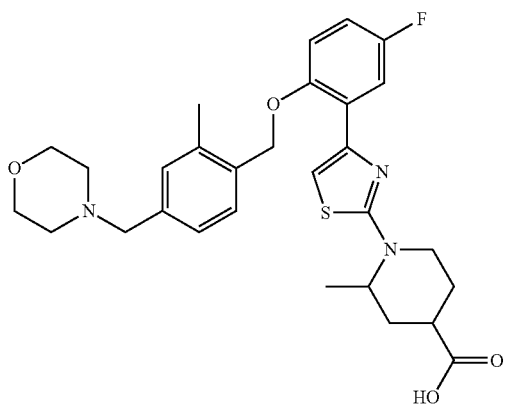 [SMILES: Cc1cc(CN2CCOCC2)ccc1COc1ccc(F)cc1-c1csc(N2CCC(C(=O)O)CC2C)n1] |

TABLE 1-continued
| Cpd No. | |
|---|---|
| 62 | 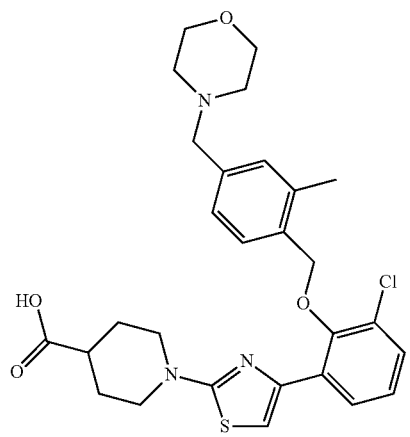 [SMILES: Cc1cc(CN2CCOCC2)ccc1COc1c(Cl)cccc1-c1csc(N2CCC(C(=O)O)CC2)n1] |
| 63 | 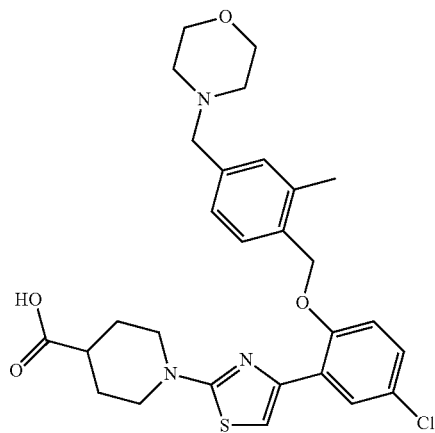 [SMILES: Cc1cc(CN2CCOCC2)ccc1COc1ccc(Cl)cc1-c1csc(N2CCC(C(=O)O)CC2)n1] |
| 64 | 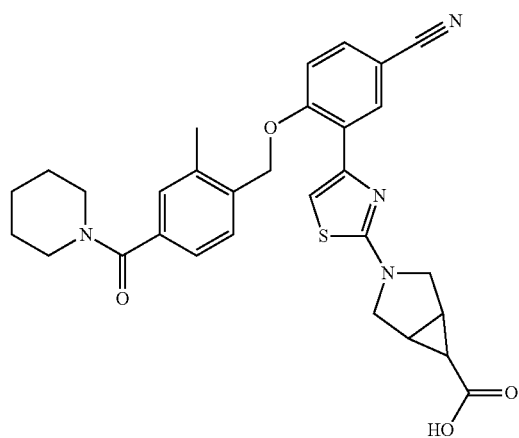 [SMILES: Cc1cc(C(=O)N2CCCCC2)ccc1COc1ccc(C#N)cc1-c1csc(N2CC3C(C2)C3C(=O)O)n1] |

TABLE 1-continued
| Cpd No. | |
|---|---|
| 65 | 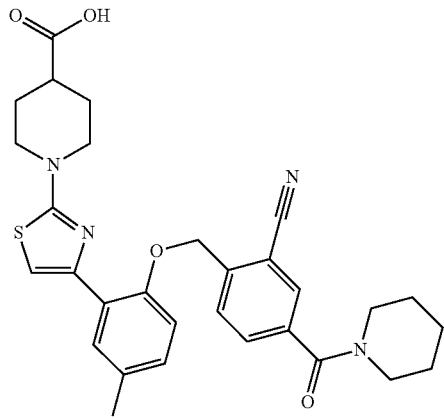 [SMILES: Cc1ccc(OCc2ccc(C(=O)N3CCCCC3)cc2C#N)c(-c2csc(N3CCC(C(=O)O)CC3)n2)c1] |
| 66 | 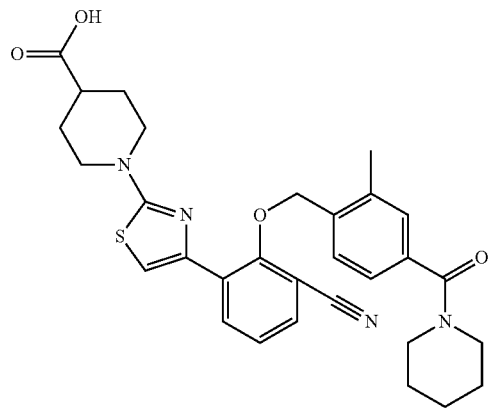 [SMILES: Cc1cc(C(=O)N2CCCCC2)ccc1COc1c(C#N)cccc1-c1csc(N2CCC(C(=O)O)CC2)n1] |
| 67 | 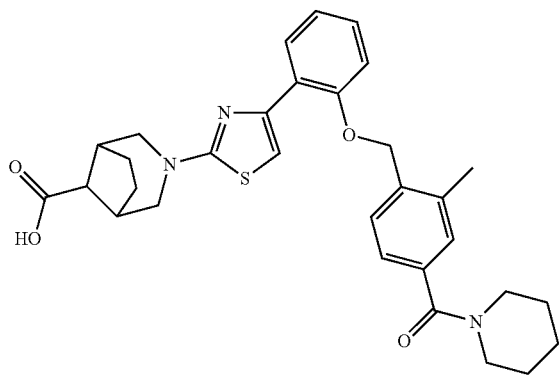 [SMILES: Cc1cc(C(=O)N2CCCCC2)ccc1COc1ccccc1-c1csc(N2CC3CCC(C2)C3C(=O)O)n1] |

TABLE 1-continued
| Cpd No. | |
|---|---|
| 68 | 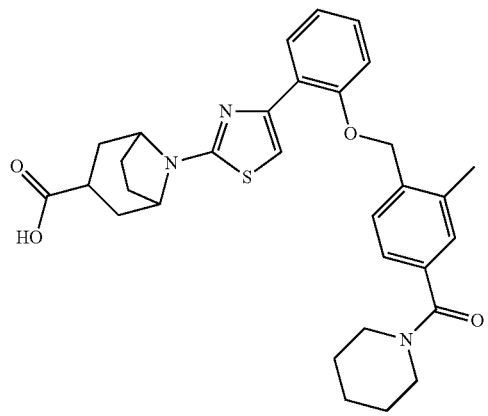 [SMILES: Cc1cc(C(=O)N2CCCCC2)ccc1COc1ccccc1-c1csc(N2C3CCC2CC(C(=O)O)C3)n1] |
| 69 | 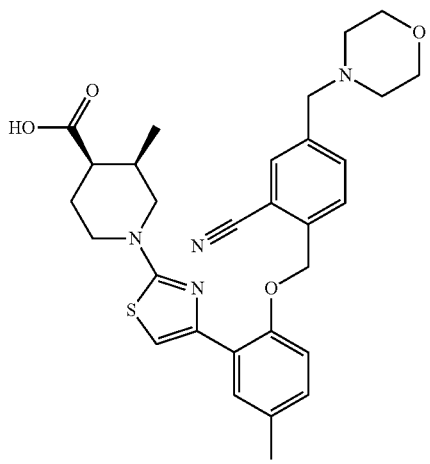 [SMILES: Cc1ccc(OCc2ccc(CN3CCOCC3)cc2C#N)c(-c2csc(N3CC[C@@H](C(=O)O)[C@@H](C)C3)n2)c1] |
| 70 | 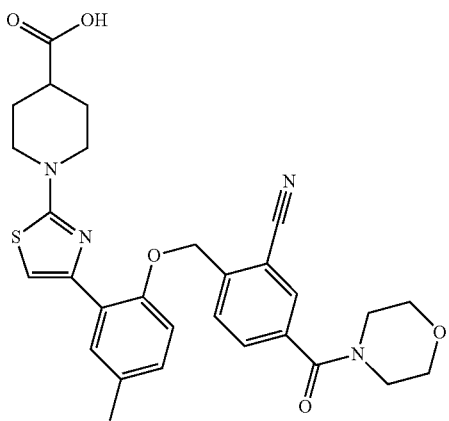 [SMILES: Cc1ccc(OCc2ccc(C(=O)N3CCOCC3)cc2C#N)c(-c2csc(N3CCC(C(=O)O)CC3)n2)c1] |

TABLE 1-continued
| Cpd No. | |
|---|---|
| 71 | 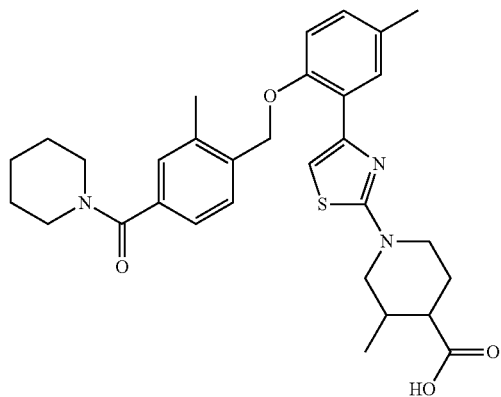 [SMILES: Cc1ccc(OCc2ccc(C(=O)N3CCCCC3)cc2C)c(-c2csc(N3CCC(C(=O)O)C(C)C3)n2)c1] |
| 72 | 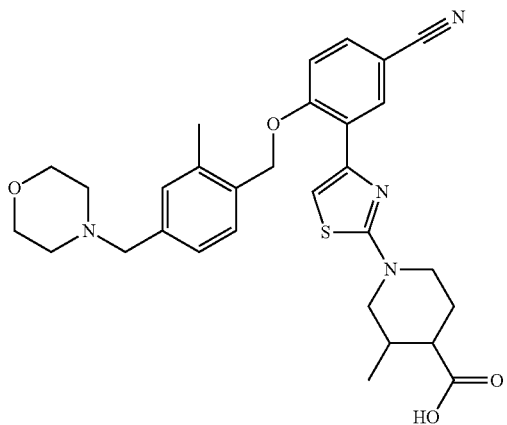 [SMILES: Cc1cc(CN2CCOCC2)ccc1COc1ccc(C#N)cc1-c1csc(N2CCC(C(=O)O)C(C)C2)n1] |
| 73 | 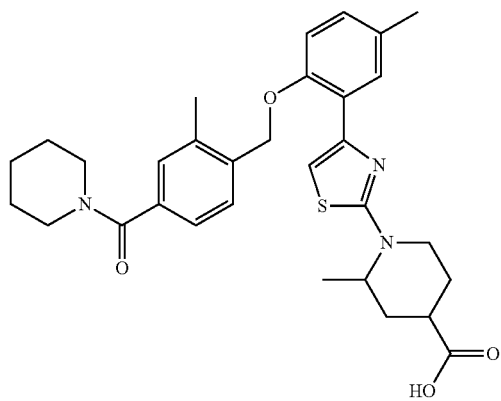 [SMILES: Cc1ccc(OCc2ccc(C(=O)N3CCCCC3)cc2C)c(-c2csc(N3CCC(C(=O)O)CC3C)n2)c1] |

TABLE 1-continued
| Cpd No. | |
|---|---|
| 74 | 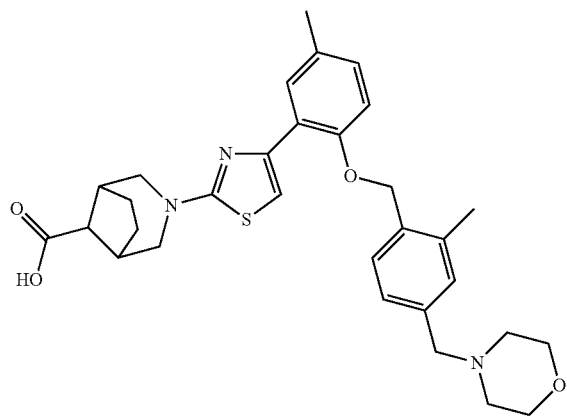 [SMILES: Cc1ccc(OCc2ccc(CN3CCOCC3)cc2C)c(-c2csc(N3CC4CCC(C3)C4C(=O)O)n2)c1] |
| 75 | 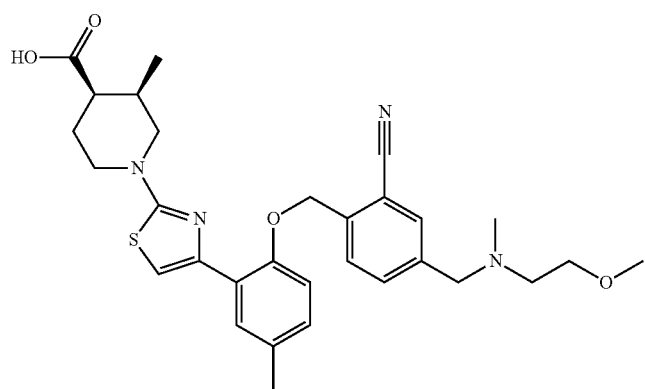 [SMILES: COCCN(C)Cc1ccc(COc2ccc(C)cc2-c2csc(N3CC[C@@H](C(=O)O)[C@@H](C)C3)n2)c(C#N)c1] |
| 76 | 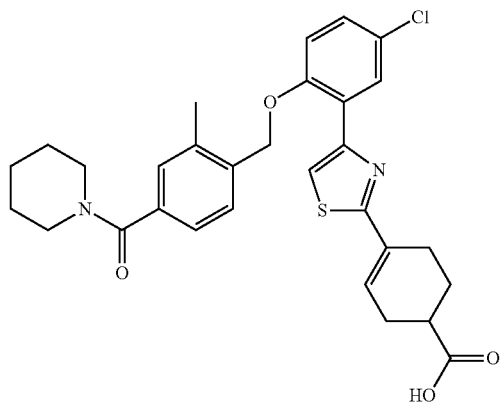 [SMILES: Cc1cc(C(=O)N2CCCCC2)ccc1COc1ccc(Cl)cc1-c1csc(C2=CCC(C(=O)O)CC2)n1] |

TABLE 1-continued
| Cpd No. |
|---|
| 77 |
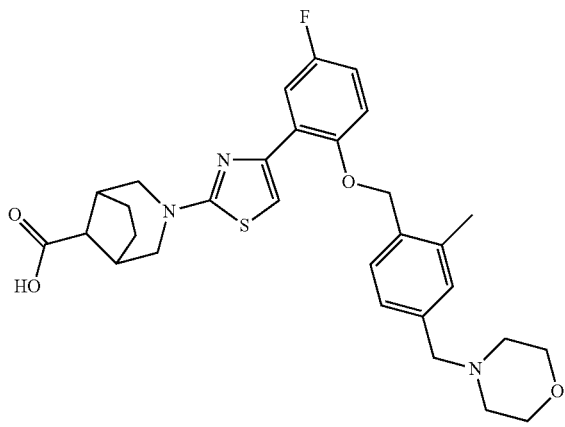 [SMILES: Cc1cc(CN2CCOCC2)ccc1COc1ccc(F)cc1-c1csc(N2CC3CCC(C2)C3C(=O)O)n1]
| 78 |
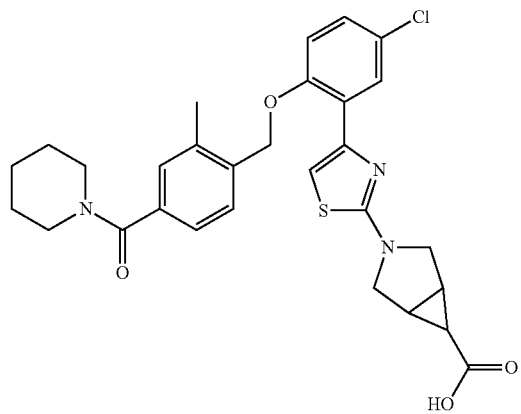 [SMILES: Cc1cc(C(=O)N2CCCCC2)ccc1COc1ccc(Cl)cc1-c1csc(N2CC3C(C2)C3C(=O)O)n1]
| 79 |
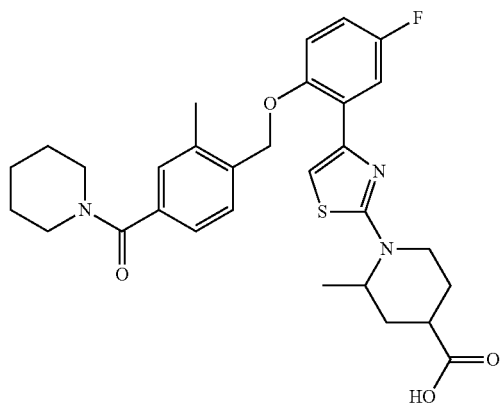 [SMILES: Cc1cc(C(=O)N2CCCCC2)ccc1COc1ccc(F)cc1-c1csc(N2CCC(C(=O)O)CC2C)n1]

TABLE 1-continued
| Cpd No. | |
|---|---|
| 80 | 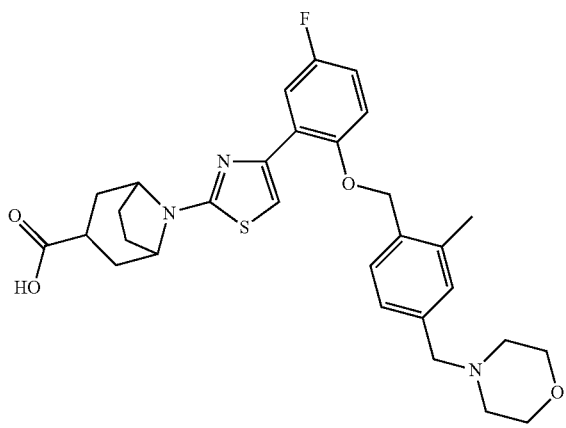 [SMILES: Cc1cc(CN2CCOCC2)ccc1COc1ccc(F)cc1-c1csc(N2C3CCC2CC(C(=O)O)C3)n1] |
| 81 | 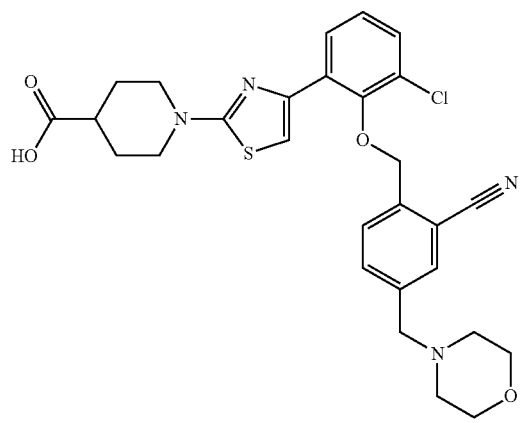 |
| 82 | 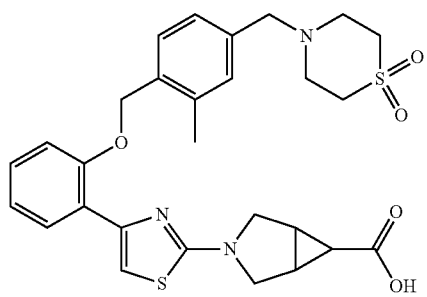 [SMILES: Cc1cc(CN2CCS(=O)(=O)CC2)ccc1COc1ccccc1-c1csc(N2CC3C(C2)C3C(=O)O)n1] |
| 83 | 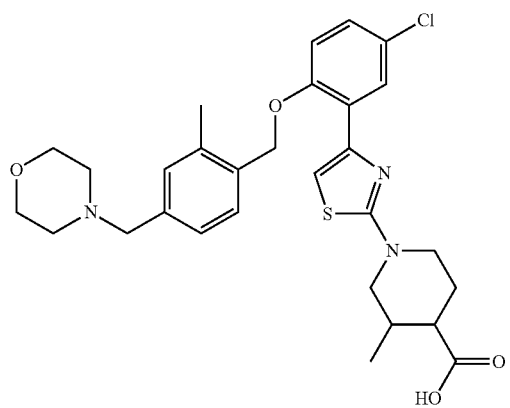 [SMILES: Cc1cc(CN2CCOCC2)ccc1COc1ccc(Cl)cc1-c1csc(N2CCC(C(=O)O)C(C)C2)n1] |

TABLE 1-continued
| Cpd No. | |
|---|---|
| 84 | 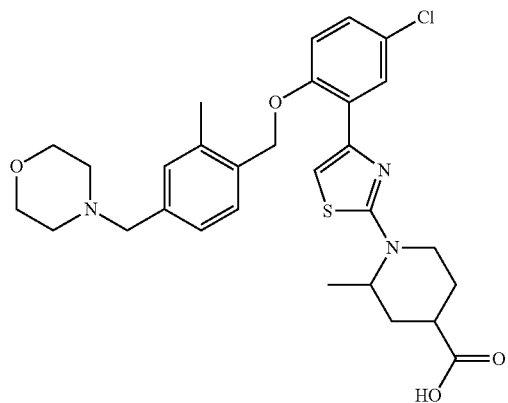 [SMILES: Cc1cc(CN2CCOCC2)ccc1COc1ccc(Cl)cc1-c1csc(N2CCC(C(=O)O)CC2C)n1] |
| 85 | 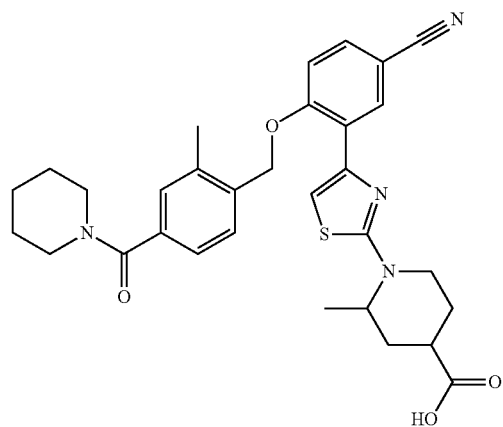 [SMILES: Cc1cc(C(=O)N2CCCCC2)ccc1COc1ccc(C#N)cc1-c1csc(N2CCC(C(=O)O)CC2C)n1] |
| 86 | 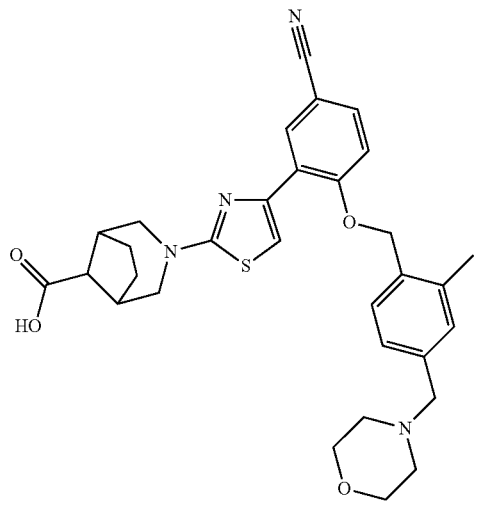 [SMILES: Cc1cc(CN2CCOCC2)ccc1COc1ccc(C#N)cc1-c1csc(N2CC3CCC(C2)C3C(=O)O)n1] |

TABLE 1-continued
| Cpd No. |
|---|
| 87 |
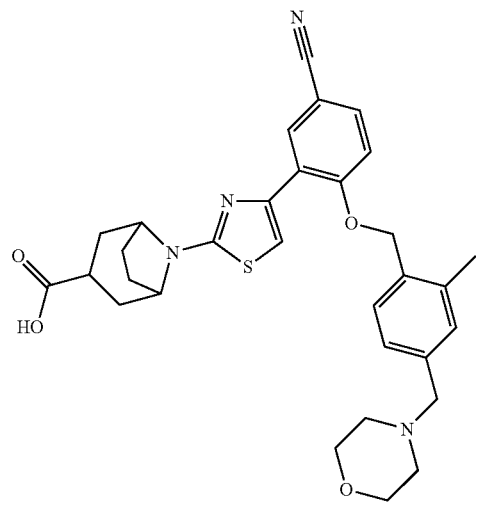 [SMILES: Cc1cc(CN2CCOCC2)ccc1COc1ccc(C#N)cc1-c1csc(N2C3CCC2CC(C(=O)O)C3)n1]
| 88 |
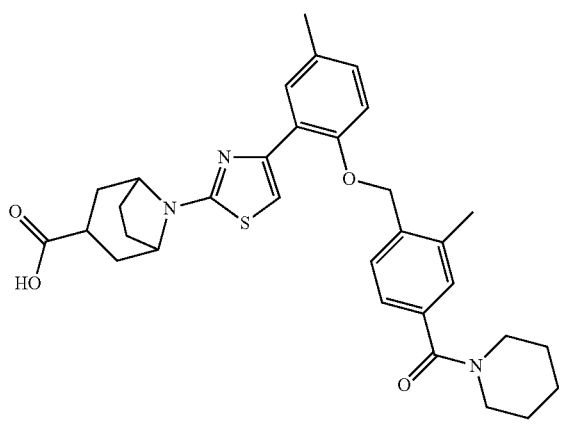 [SMILES: Cc1ccc(OCc2ccc(C(=O)N3CCCCC3)cc2C)c(-c2csc(N3C4CCC3CC(C(=O)O)C4)n2)c1]
| 89 |
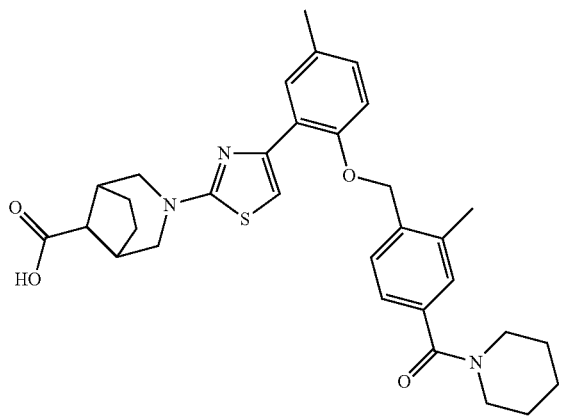 [SMILES: Cc1ccc(OCc2ccc(C(=O)N3CCCCC3)cc2C)c(-c2csc(N3CC4CCC(C3)C4C(=O)O)n2)c1]

TABLE 1-continued
| Cpd No. | |
|---|---|
| 90 | 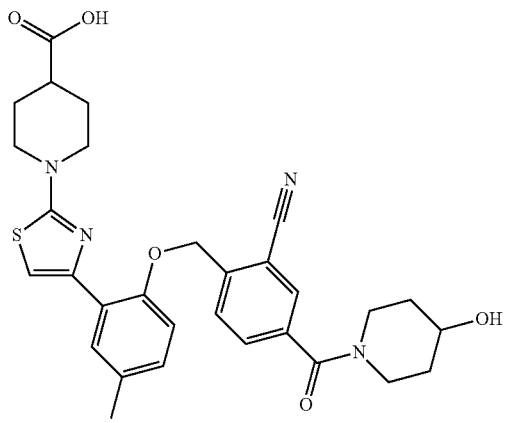 [SMILES: Cc1ccc(OCc2ccc(C(=O)N3CCC(O)CC3)cc2C#N)c(-c2csc(N3CCC(C(=O)O)CC3)n2)c1] |
| 91 | 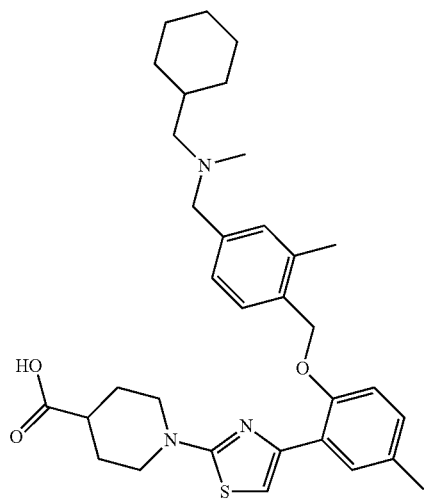 [SMILES: Cc1ccc(OCc2ccc(CN(C)CC3CCCCC3)cc2C)c(-c2csc(N3CCC(C(=O)O)CC3)n2)c1] |
| 92 | 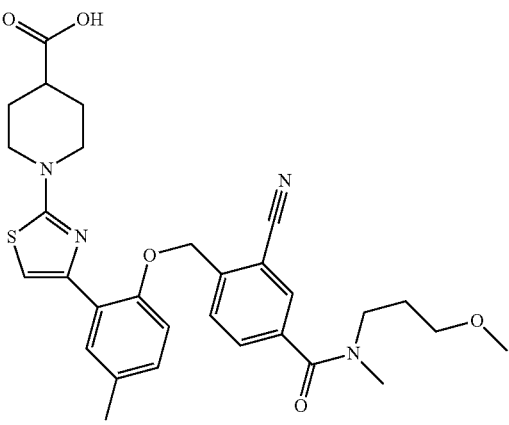 [SMILES: COCCCN(C)C(=O)c1ccc(COc2ccc(C)cc2-c2csc(N3CCC(C(=O)O)CC3)n2)c(C#N)c1] |

TABLE 1-continued
| Cpd No. | |
|---|---|
| 93 | 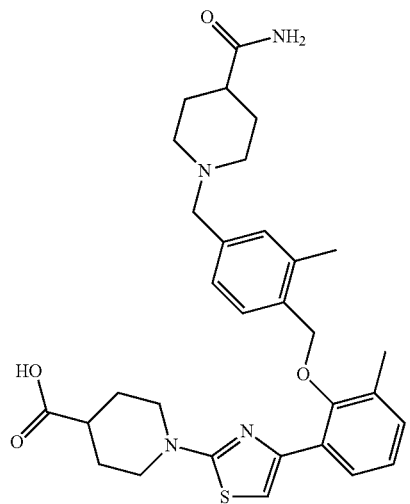 [SMILES: Cc1cc(CN2CCC(C(N)=O)CC2)ccc1COc1c(C)cccc1-c1csc(N2CCC(C(=O)O)CC2)n1] |
| 94 | 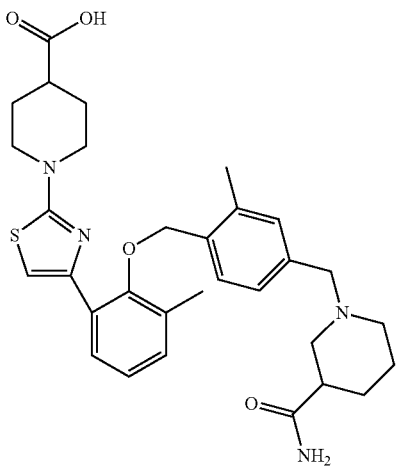 [SMILES: Cc1cc(CN2CCCC(C(N)=O)C2)ccc1COc1c(C)cccc1-c1csc(N2CCC(C(=O)O)CC2)n1] |
| 95 | 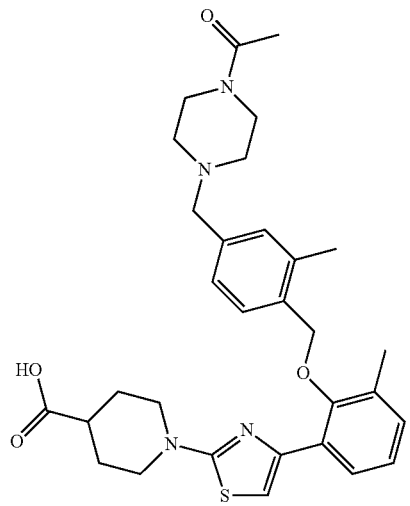 [SMILES: CC(=O)N1CCN(Cc2ccc(COc3c(C)cccc3-c3csc(N4CCC(C(=O)O)CC4)n3)c(C)c2)CC1] |

TABLE 1-continued
| Cpd No. | |
|---|---|
| 96 | 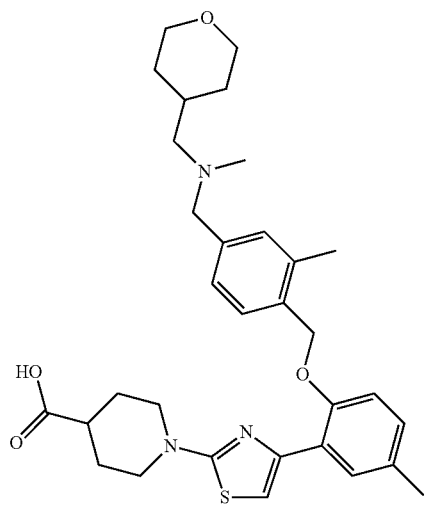 [SMILES: Cc1ccc(OCc2ccc(CN(C)CC3CCOCC3)cc2C)c(-c2csc(N3CCC(C(=O)O)CC3)n2)c1] |
| 97 | 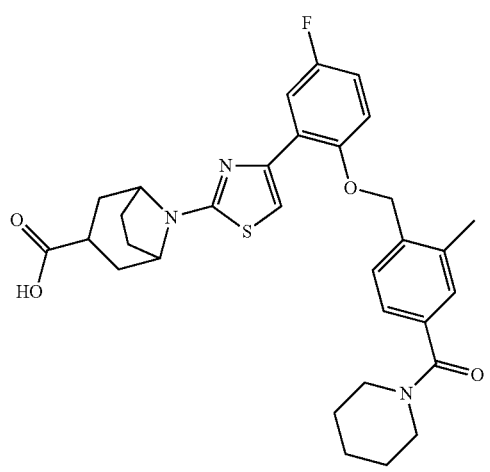 [SMILES: Cc1cc(C(=O)N2CCCCC2)ccc1COc1ccc(F)cc1-c1csc(N2C3CCC2CC(C(=O)O)C3)n1] |
| 98 | 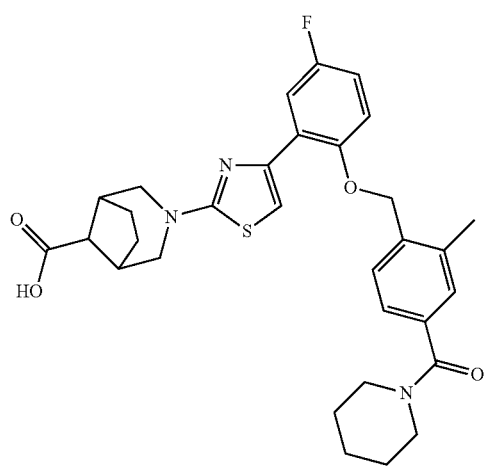 [SMILES: Cc1cc(C(=O)N2CCCCC2)ccc1COc1ccc(F)cc1-c1csc(N2CC3CCC(C2)C3C(=O)O)n1] |

TABLE 1-continued
| Cpd No. |
| --- |
99
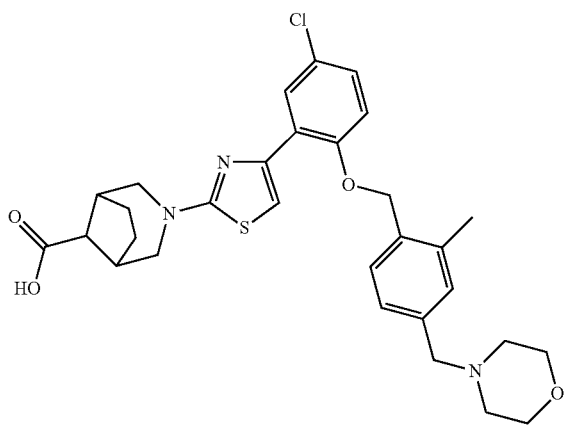 [SMILES: Cc1cc(CN2CCOCC2)ccc1COc1ccc(Cl)cc1-c1csc(N2CC3CCC(C2)C3C(=O)O)n1]
100
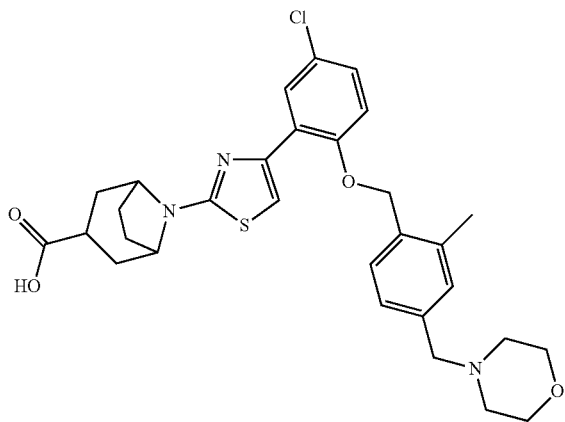
101
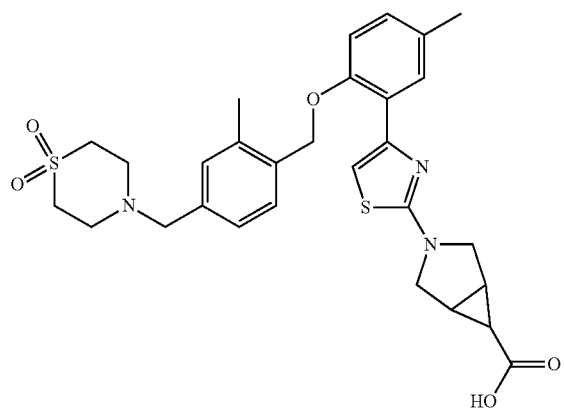 [SMILES: Cc1ccc(OCc2ccc(CN3CCS(=O)(=O)CC3)cc2C)c(-c2csc(N3CC4C(C3)C4C(=O)O)n2)c1]

TABLE 1-continued
| Cpd No. | |
|---|---|
| 102 | 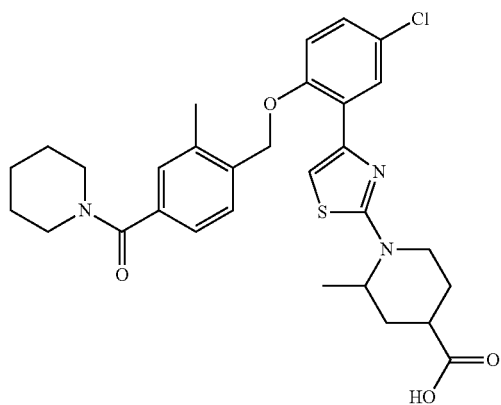 |
| 103 | 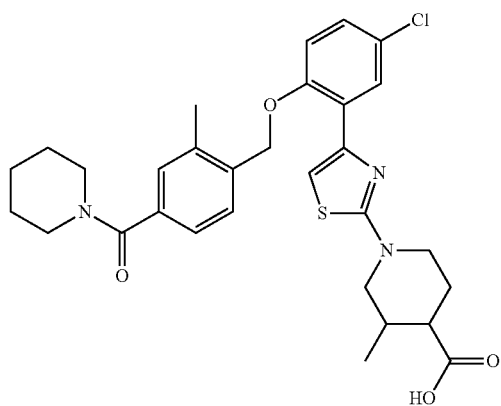 [SMILES: Cc1cc(C(=O)N2CCCCC2)ccc1COc1ccc(Cl)cc1-c1csc(N2CCC(C(=O)O)C(C)C2)n1] |
| 104 | 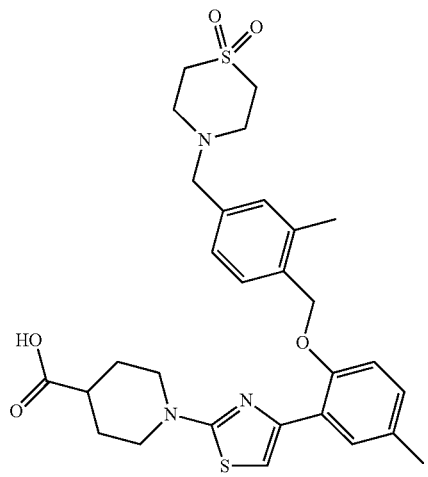 [SMILES: Cc1ccc(OCc2ccc(CN3CCS(=O)(=O)CC3)cc2C)c(-c2csc(N3CCC(C(=O)O)CC3)n2)c1] |

TABLE 1-continued
| Cpd No. | |
|---|---|
| 105 | 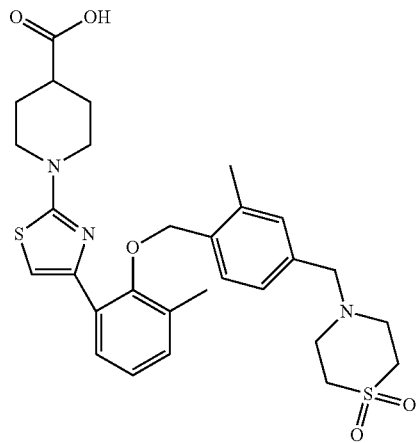 [SMILES: Cc1cc(CN2CCS(=O)(=O)CC2)ccc1COc1c(C)cccc1-c1csc(N2CCC(C(=O)O)CC2)n1] |
| 106 | 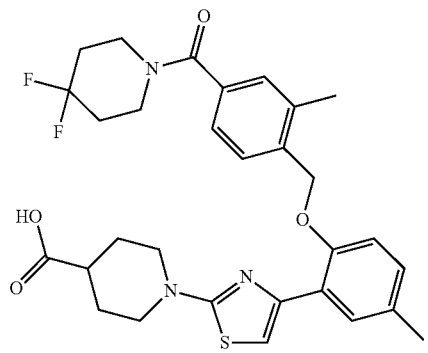 [SMILES: Cc1ccc(OCc2ccc(C(=O)N3CCC(F)(F)CC3)cc2C)c(-c2csc(N3CCC(C(=O)O)CC3)n2)c1] |
| 107 | 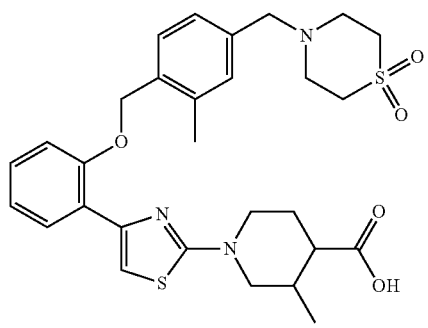 [SMILES: Cc1cc(CN2CCS(=O)(=O)CC2)ccc1COc1ccccc1-c1csc(N2CCC(C(=O)O)C(C)C2)n1] |
| 108 | 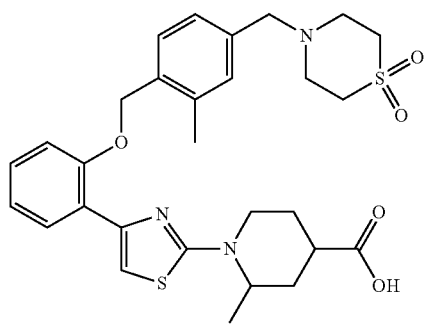 [SMILES: Cc1cc(CN2CCS(=O)(=O)CC2)ccc1COc1ccccc1-c1csc(N2CCC(C(=O)O)CC2C)n1] |

TABLE 1-continued
Cpd No.
109
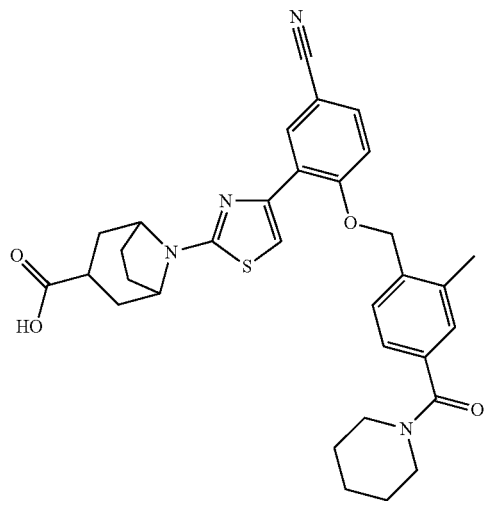 [SMILES: Cc1cc(C(=O)N2CCCCC2)ccc1COc1ccc(C#N)cc1-c1csc(N2C3CCC2CC(C(=O)O)C3)n1]
110
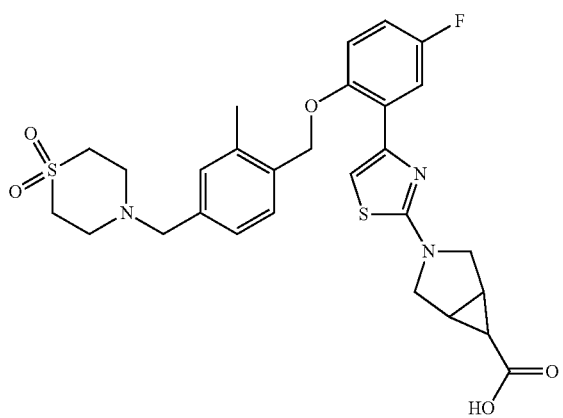 [SMILES: Cc1cc(CN2CCS(=O)(=O)CC2)ccc1COc1ccc(F)cc1-c1csc(N2CC3C(C2)C3C(=O)O)n1]
111
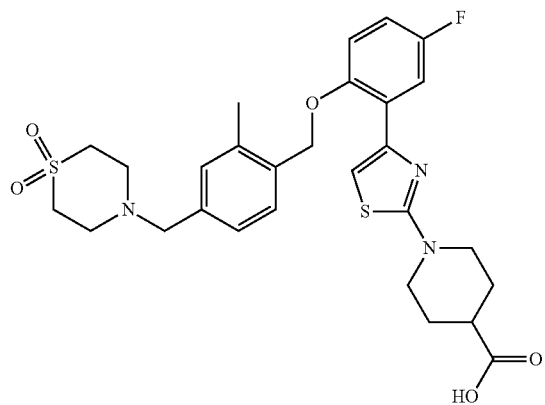 [SMILES: Cc1cc(CN2CCS(=O)(=O)CC2)ccc1COc1ccc(F)cc1-c1csc(N2CCC(C(=O)O)CC2)n1]

| Cpd No. | |
|---|---|
| 112 | 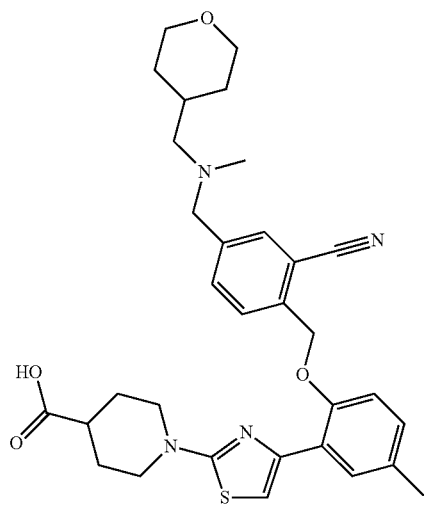 [SMILES: Cc1ccc(OCc2ccc(CN(C)CC3CCOCC3)cc2C#N)c(-c2csc(N3CCC(C(=O)O)CC3)n2)c1] |
| 113 | 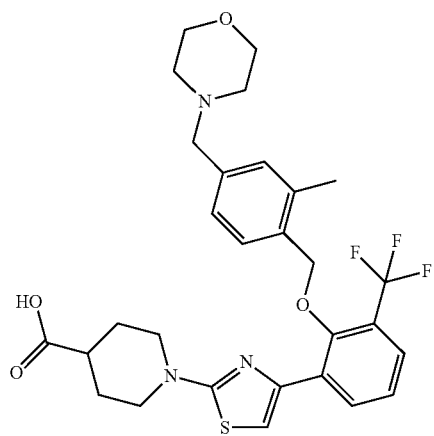 [SMILES: Cc1cc(CN2CCOCC2)ccc1COc1c(-c2csc(N3CCC(C(=O)O)CC3)n2)cccc1C(F)(F)F] |
| 114 | 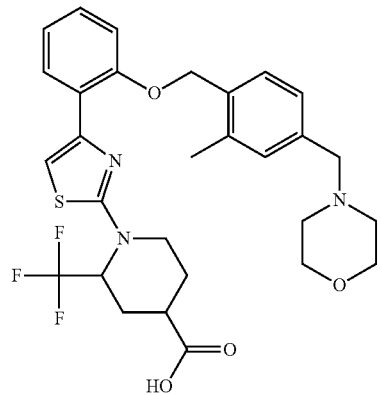 [SMILES: Cc1cc(CN2CCOCC2)ccc1COc1ccccc1-c1csc(N2CCC(C(=O)O)CC2C(F)(F)F)n1] |

TABLE 1-continued
| Cpd No. | |
|---|---|
| 115 | 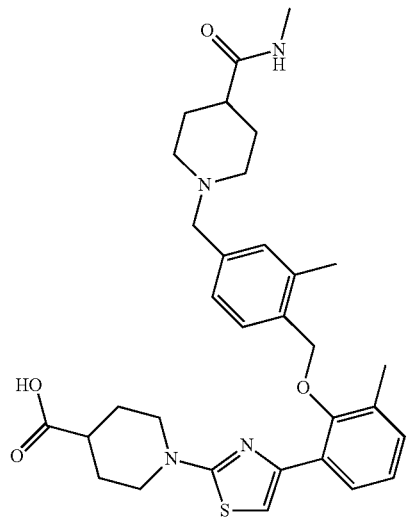 [SMILES: CNC(=O)C1CCN(Cc2ccc(COc3c(C)cccc3-c3csc(N4CCC(C(=O)O)CC4)n3)c(C)c2)CC1] |
| 116 | 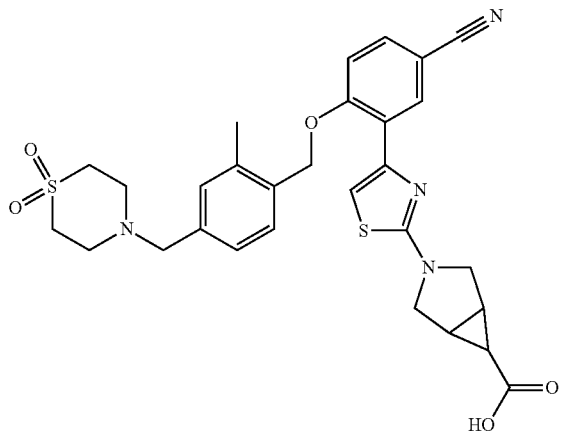 [SMILES: Cc1cc(CN2CCS(=O)(=O)CC2)ccc1COc1ccc(C#N)cc1-c1csc(N2CC3C(C2)C3C(=O)O)n1] |
| 117 | 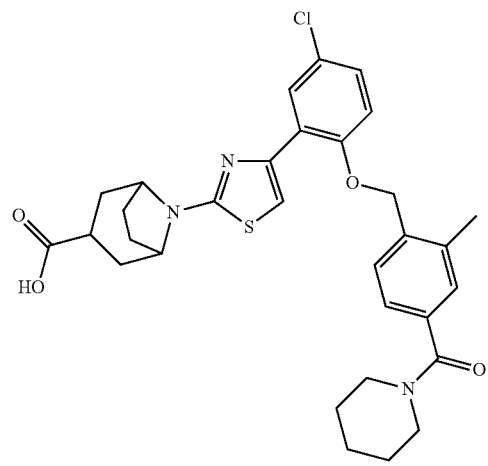 |

TABLE 1-continued
| Cpd No. |
|---|
| 118 |
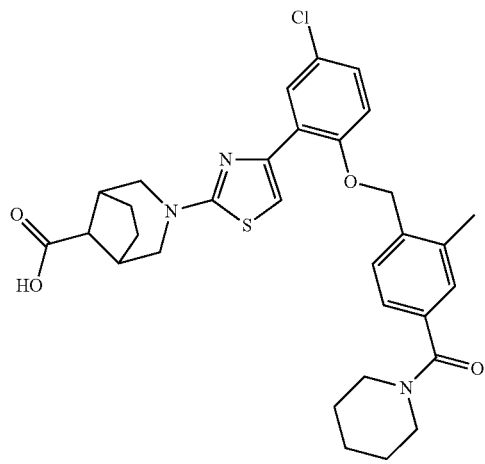
119
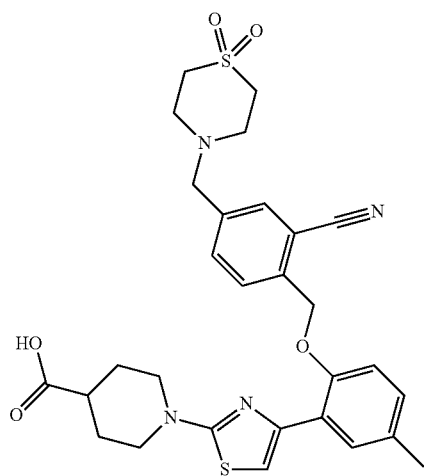 [SMILES: Cc1ccc(OCc2ccc(CN3CCS(=O)(=O)CC3)cc2C#N)c(-c2csc(N3CCC(C(=O)O)CC3)n2)c1]
120
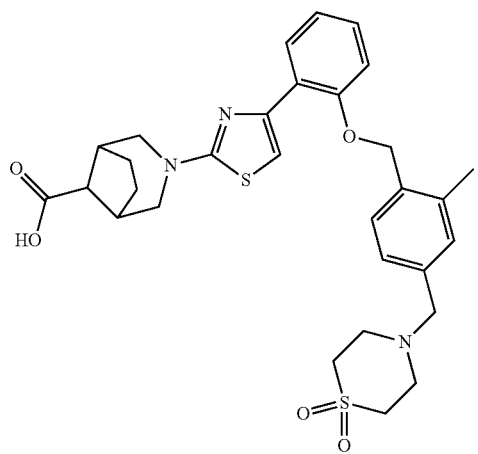 [SMILES: Cc1cc(CN2CCS(=O)(=O)CC2)ccc1COc1ccccc1-c1csc(N2CC3CCC(C2)C3C(=O)O)n1]

TABLE 1-continued
| Cpd No. |
| --- |
| 121 |
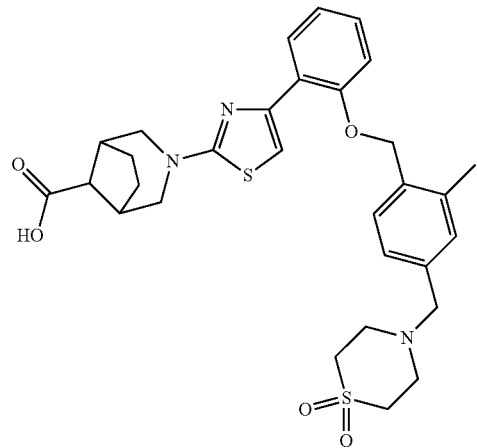 [SMILES: Cc1cc(CN2CCS(=O)(=O)CC2)ccc1COc1ccccc1-c1csc(N2CC3CCC(C2)C3C(=O)O)n1]
122
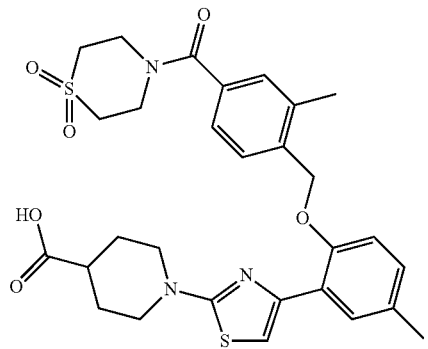 [SMILES: Cc1ccc(OCc2ccc(C(=O)N3CCS(=O)(=O)CC3)cc2C)c(-c2csc(N3CCC(C(=O)O)CC3)n2)c1]
123
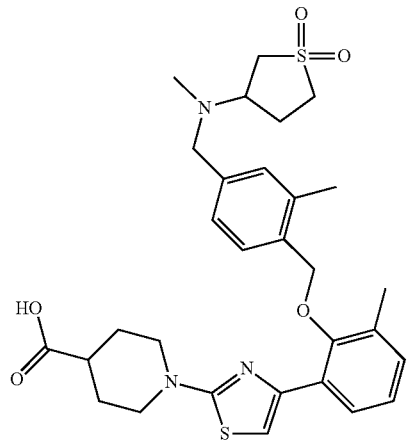 [SMILES: Cc1cc(CN(C)C2CCS(=O)(=O)C2)ccc1COc1c(C)cccc1-c1csc(N2CCC(C(=O)O)CC2)n1]

TABLE 1-continued
| Cpd No. | |
|---|---|
| 124 | 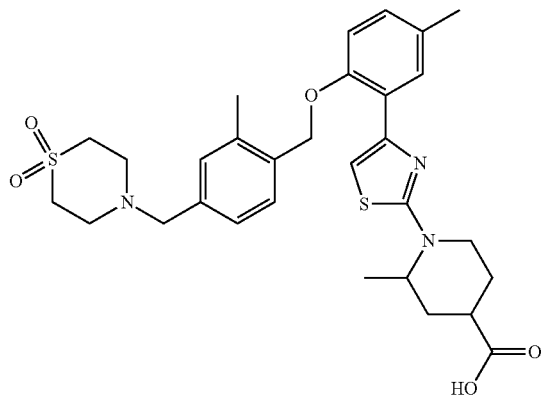 [SMILES: Cc1ccc(OCc2ccc(CN3CCS(=O)(=O)CC3)cc2C)c(-c2csc(N3CCC(C(=O)O)CC3C)n2)c1] |
| 125 | 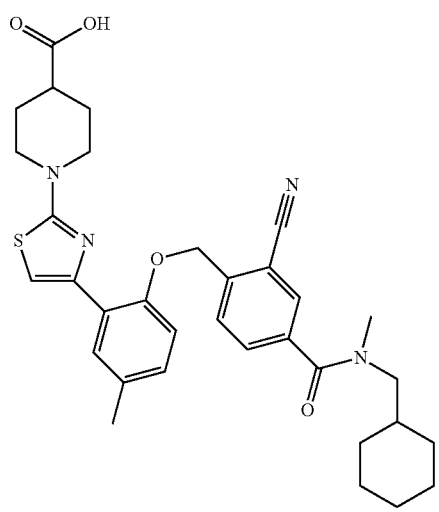 [SMILES: Cc1ccc(OCc2ccc(C(=O)N(C)CC3CCCCC3)cc2C#N)c(-c2csc(N3CCC(C(=O)O)CC3)n2)c1] |
| 126 | 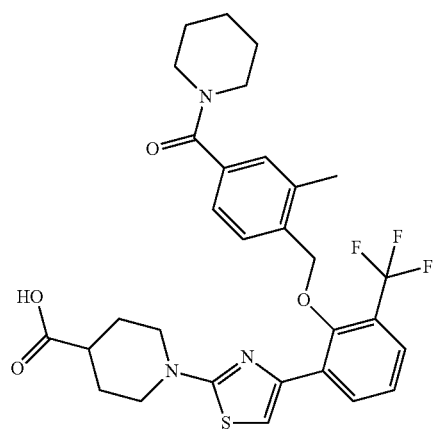 [SMILES: Cc1cc(C(=O)N2CCCCC2)ccc1COc1c(-c2csc(N3CCC(C(=O)O)CC3)n2)cccc1C(F)(F)F] |

TABLE 1-continued
| Cpd No. | |
|---|---|
| 127 | 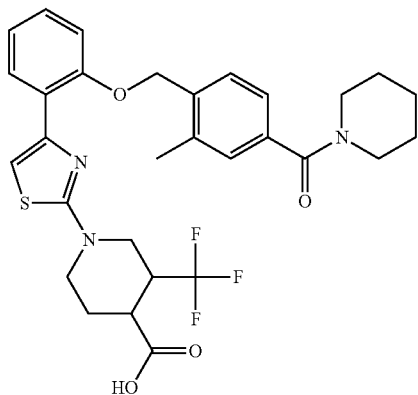 [SMILES: Cc1cc(C(=O)N2CCCCC2)ccc1COc1ccccc1-c1csc(N2CCC(C(=O)O)C(C(F)(F)F)C2)n1] |
| 128 | 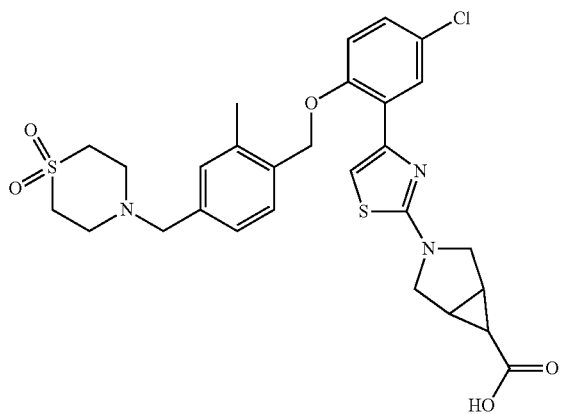 [SMILES: Cc1cc(CN2CCS(=O)(=O)CC2)ccc1COc1ccc(Cl)cc1-c1csc(N2CC3C(C2)C3C(=O)O)n1] |
| 129 | 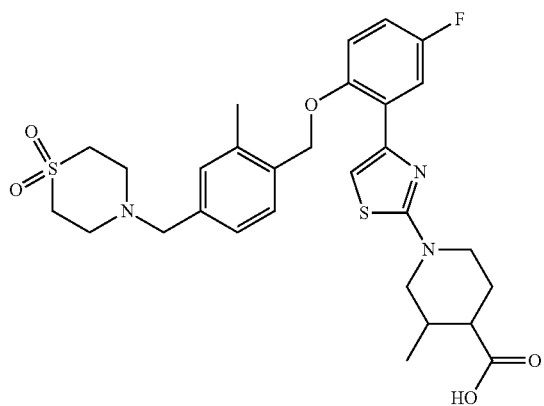 |

TABLE 1-continued
| Cpd No. | |
|---|---|
| 130 | 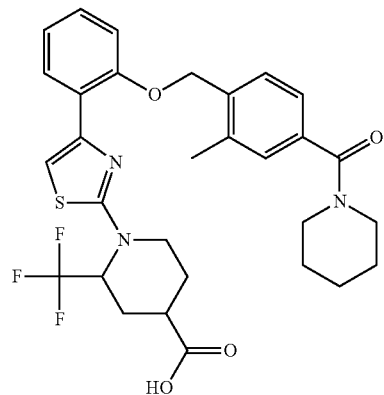 [SMILES: Cc1cc(C(=O)N2CCCCC2)ccc1COc1ccccc1-c1csc(N2CCC(C(=O)O)CC2C(F)(F)F)n1] |
| 131 | 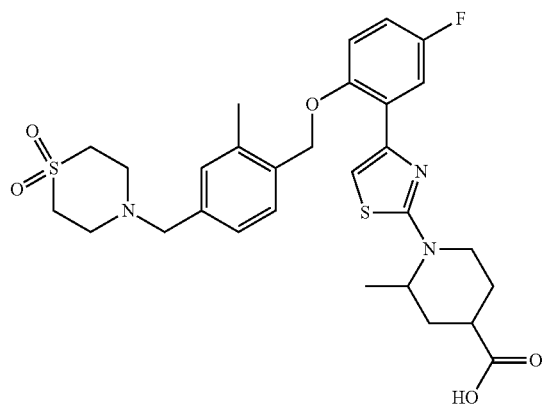 [SMILES: Cc1cc(CN2CCS(=O)(=O)CC2)ccc1COc1ccc(F)cc1-c1csc(N2CCC(C(=O)O)CC2C)n1] |
| 132 | 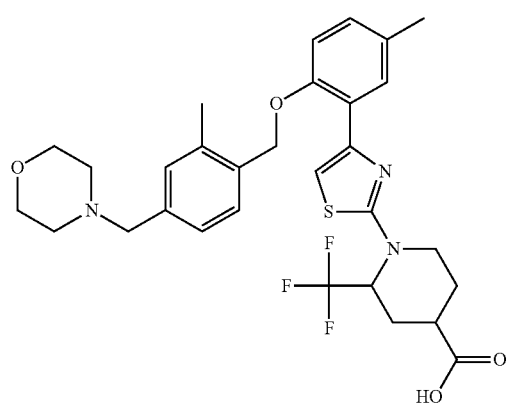 [SMILES: Cc1ccc(OCc2ccc(CN3CCOCC3)cc2C)c(-c2csc(N3CCC(C(=O)O)CC3C(F)(F)F)n2)c1] |

TABLE 1-continued
| Cpd No. | |
|---|---|
| 133 | 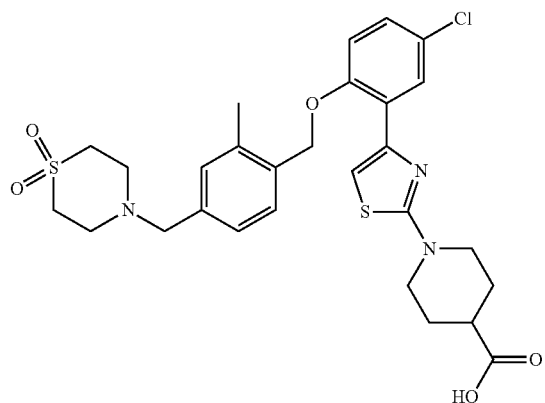 |
| 134 | 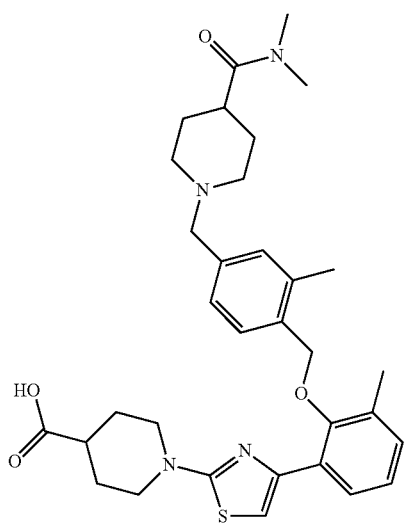 [SMILES: Cc1cc(CN2CCC(C(=O)N(C)C)CC2)ccc1COc1c(C)cccc1-c1csc(N2CCC(C(=O)O)CC2)n1] |
| 135 | 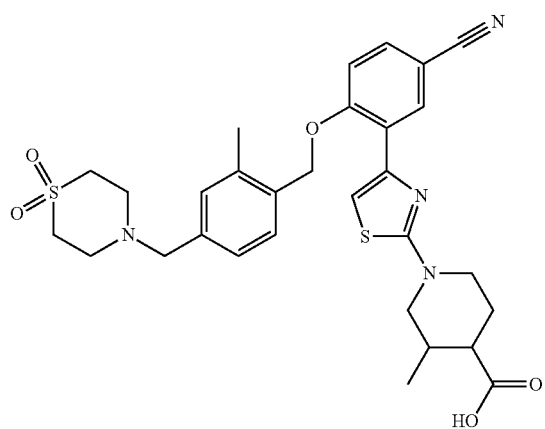 [SMILES: Cc1cc(CN2CCS(=O)(=O)CC2)ccc1COc1ccc(C#N)cc1-c1csc(N2CCC(C(=O)O)C(C)C2)n1] |

TABLE 1-continued
| Cpd No. | |
|---|---|
| 136 | 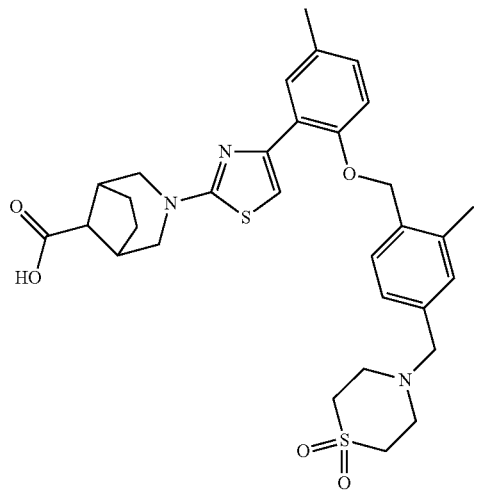 [SMILES: Cc1ccc(OCc2ccc(CN3CCS(=O)(=O)CC3)cc2C)c(-c2csc(N3CC4CCC(C3)C4C(=O)O)n2)c1] |
| 137 | 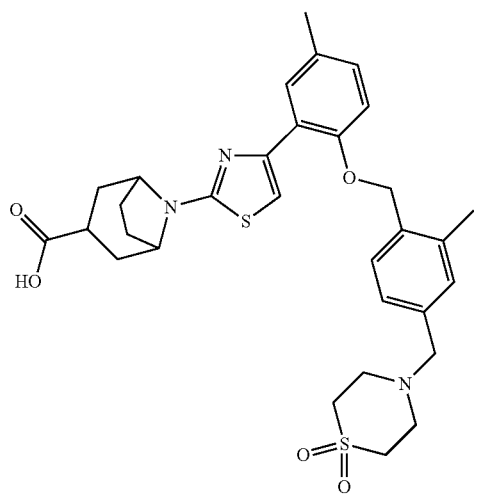 [SMILES: Cc1ccc(OCc2ccc(CN3CCS(=O)(=O)CC3)cc2C)c(-c2csc(N3C4CCC3CC(C(=O)O)C4)n2)c1] |
| 138 | 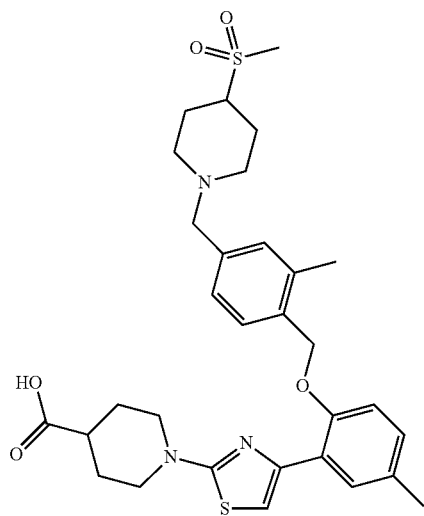 [SMILES: Cc1ccc(OCc2ccc(CN3CCC(S(C)(=O)=O)CC3)cc2C)c(-c2csc(N3CCC(C(=O)O)CC3)n2)c1] |

TABLE 1-continued
| Cpd No. | |
|---|---|
| 139 | 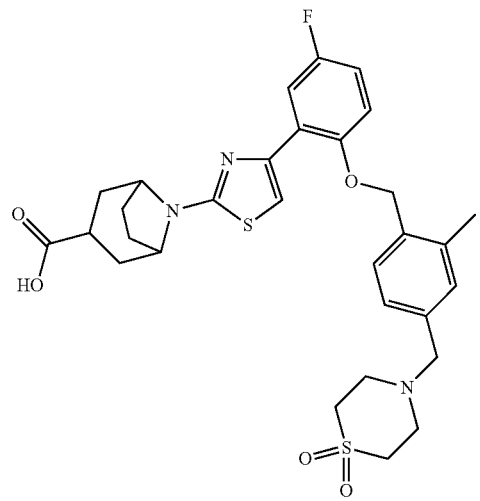 |
| 140 | 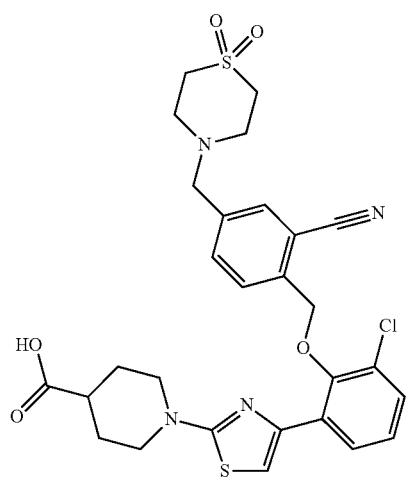 [SMILES: N#Cc1cc(CN2CCS(=O)(=O)CC2)ccc1COc1c(Cl)cccc1-c1csc(N2CCC(C(=O)O)CC2)n1] |
| 141 | 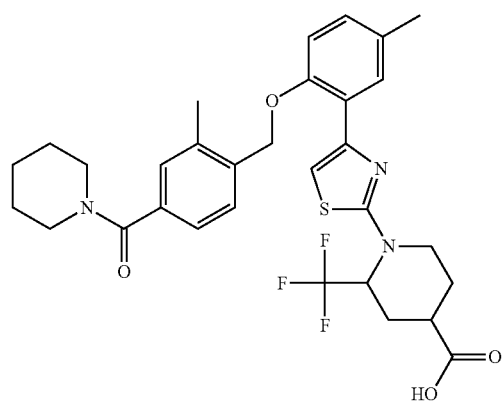 [SMILES: Cc1ccc(OCc2ccc(C(=O)N3CCCCC3)cc2C)c(-c2csc(N3CCC(C(=O)O)CC3C(F)(F)F)n2)c1] |

TABLE 1-continued
| Cpd No. | |
|---|---|
| 142 | 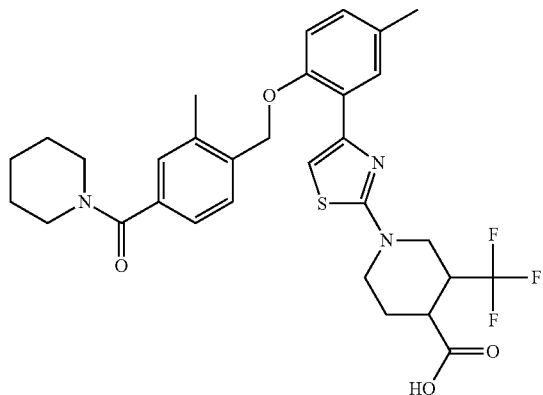 [SMILES: Cc1ccc(OCc2ccc(C(=O)N3CCCCC3)cc2C)c(-c2csc(N3CCC(C(=O)O)C(C(F)(F)F)C3)n2)c1] |
| 143 | 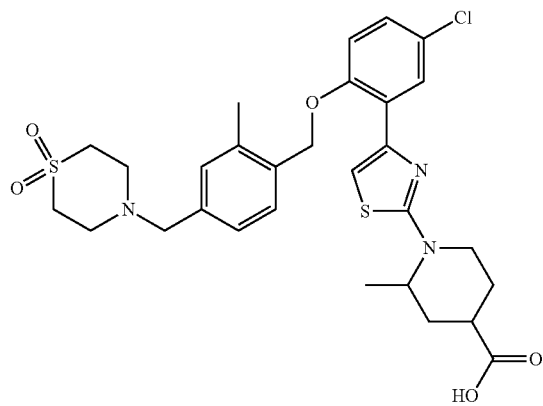 |
| 144 | 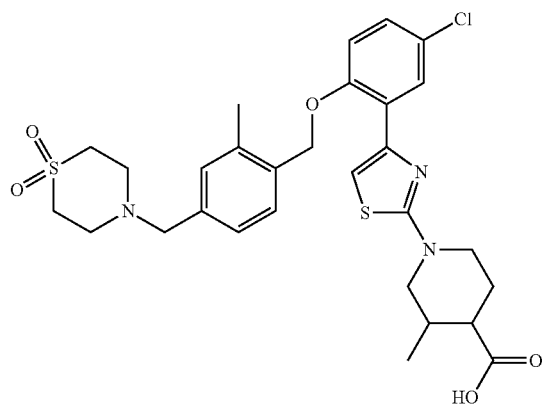 [SMILES: Cc1cc(CN2CCS(=O)(=O)CC2)ccc1COc1ccc(Cl)cc1-c1csc(N2CCC(C(=O)O)C(C)C2)n1] |

TABLE 1-continued
| Cpd No. | |
|---|---|
| 145 | 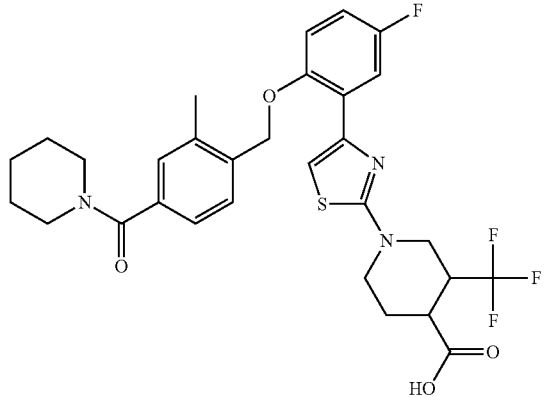 [SMILES: Cc1cc(C(=O)N2CCCCC2)ccc1COc1ccc(F)cc1-c1csc(N2CCC(C(=O)O)C(C(F)(F)F)C2)n1] |
| 146 | 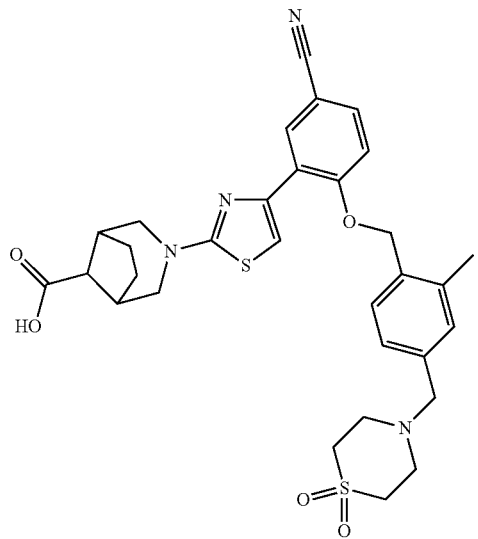 [SMILES: Cc1cc(CN2CCS(=O)(=O)CC2)ccc1COc1ccc(C#N)cc1-c1csc(N2CC3CCC(C2)C3C(=O)O)n1] |
| 147 | 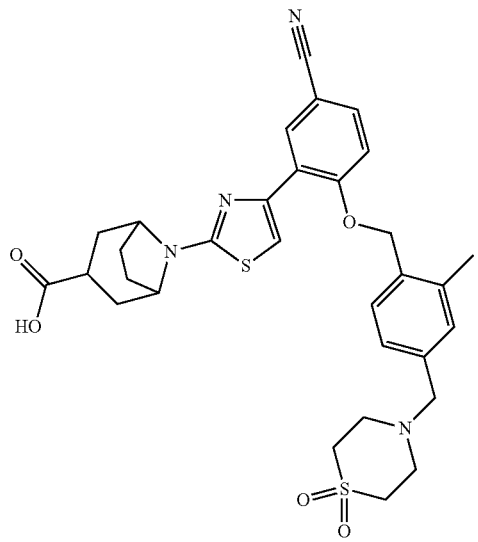 [SMILES: Cc1cc(CN2CCS(=O)(=O)CC2)ccc1COc1ccc(C#N)cc1-c1csc(N2C3CCC2CC(C(=O)O)C3)n1] |

TABLE 1-continued
| Cpd No. | |
|---|---|
| 148 | 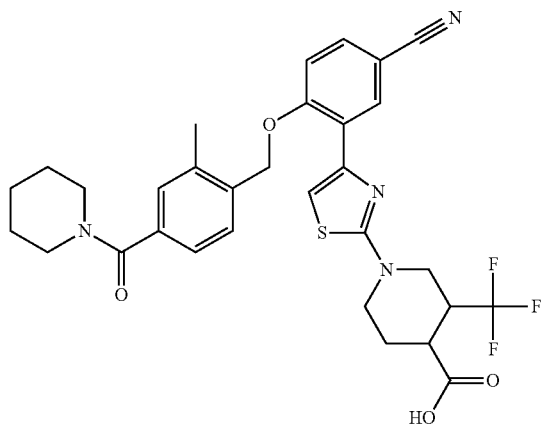 [SMILES: Cc1cc(C(=O)N2CCCCC2)ccc1COc1ccc(C#N)cc1-c1csc(N2CCC(C(=O)O)C(C(F)(F)F)C2)n1] |
| 149 | 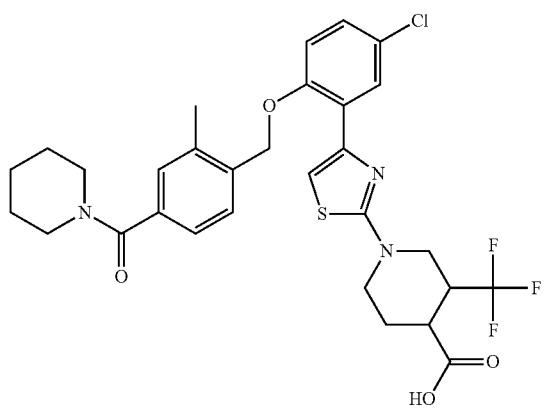 [SMILES: Cc1cc(C(=O)N2CCCCC2)ccc1COc1ccc(Cl)cc1-c1csc(N2CCC(C(=O)O)C(C(F)(F)F)C2)n1] |
| 150 | 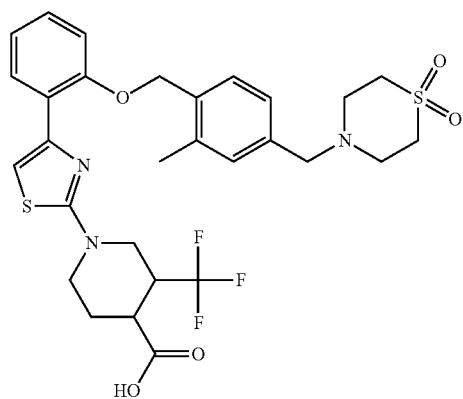 [SMILES: Cc1cc(CN2CCS(=O)(=O)CC2)ccc1COc1ccccc1-c1csc(N2CCC(C(=O)O)C(C(F)(F)F)C2)n1] |

TABLE 1-continued
Cpd No.
151
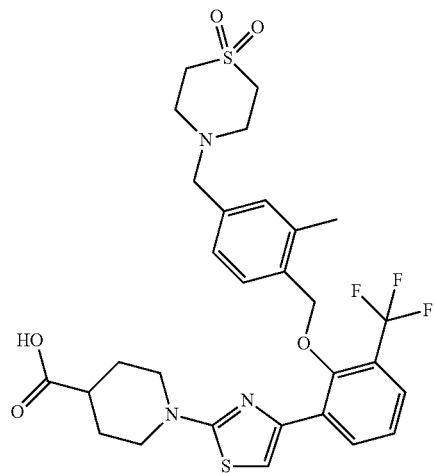 [SMILES: Cc1cc(CN2CCS(=O)(=O)CC2)ccc1COc1c(-c2csc(N3CCC(C(=O)O)CC3)n2)cccc1C(F)(F)F]
152
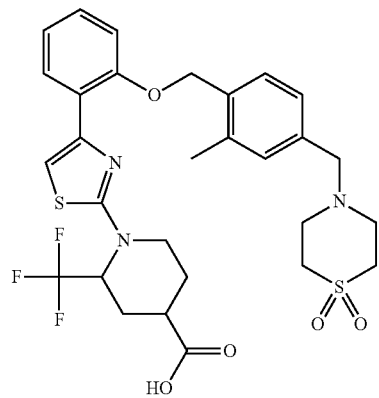 [SMILES: Cc1cc(CN2CCS(=O)(=O)CC2)ccc1COc1ccccc1-c1csc(N2CCC(C(=O)O)CC2C(F)(F)F)n1]
153
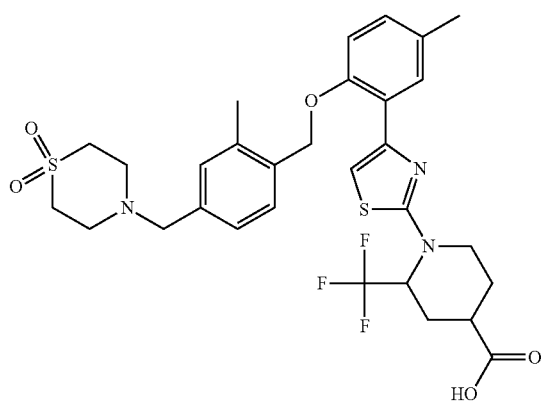 [SMILES: Cc1ccc(OCc2ccc(CN3CCS(=O)(=O)CC3)cc2C)c(-c2csc(N3CCC(C(=O)O)CC3C(F)(F)F)n2)c1]

TABLE 1-continued
| Cpd No. | |
|---|---|
| 154 | 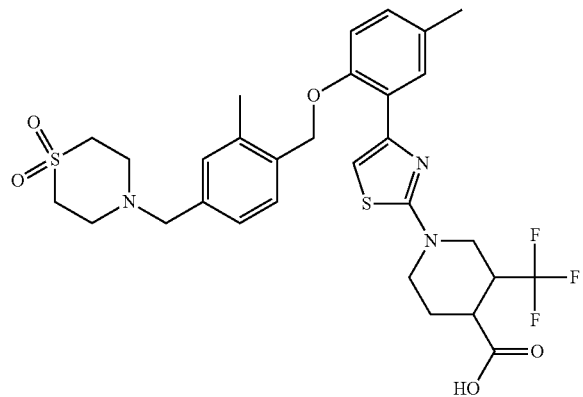 [SMILES: Cc1ccc(OCc2ccc(CN3CCS(=O)(=O)CC3)cc2C)c(-c2csc(N3CCC(C(=O)O)C(C(F)(F)F)C3)n2)c1] |
| 155 | 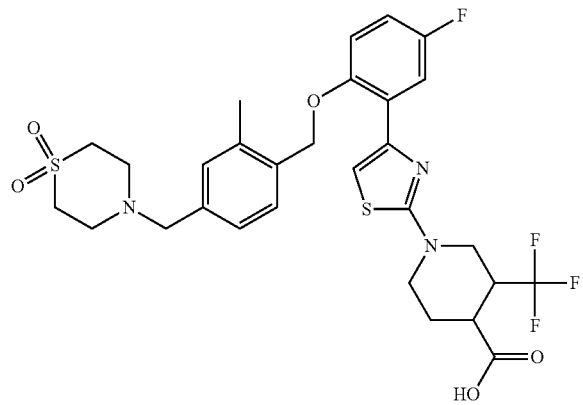 [SMILES: Cc1cc(CN2CCS(=O)(=O)CC2)ccc1COc1ccc(F)cc1-c1csc(N2CCC(C(=O)O)C(C(F)(F)F)C2)n1] |
| 156 | 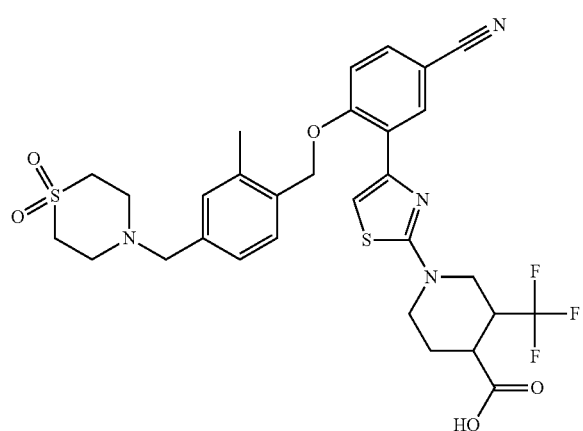 [SMILES: Cc1cc(CN2CCS(=O)(=O)CC2)ccc1COc1ccc(C#N)cc1-c1csc(N2CCC(C(=O)O)C(C(F)(F)F)C2)n1] |

TABLE 1-continued
Cpd No.
157
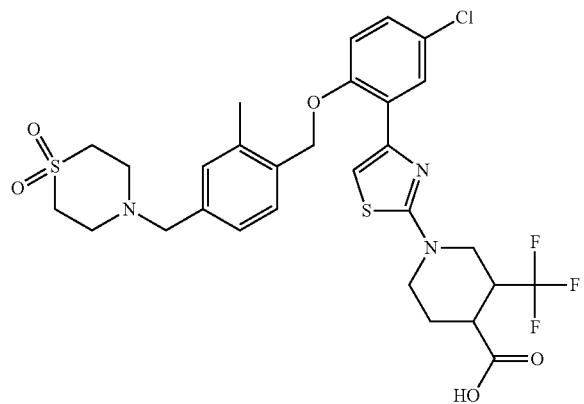
158
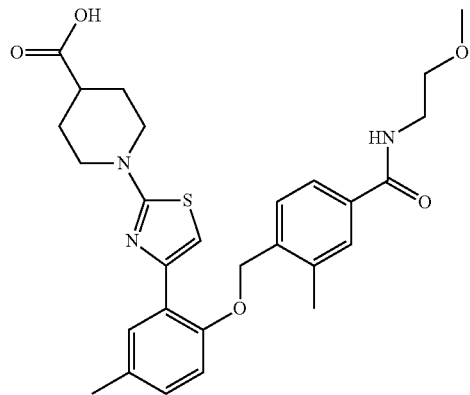 [SMILES: COCCNC(=O)c1ccc(COc2ccc(C)cc2-c2csc(N3CCC(C(=O)O)CC3)n2)c(C)c1]
159
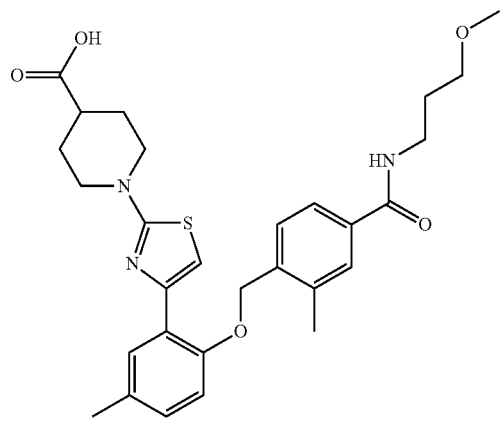

TABLE 1-continued
| Cpd No. | |
|---|---|
| 160 | 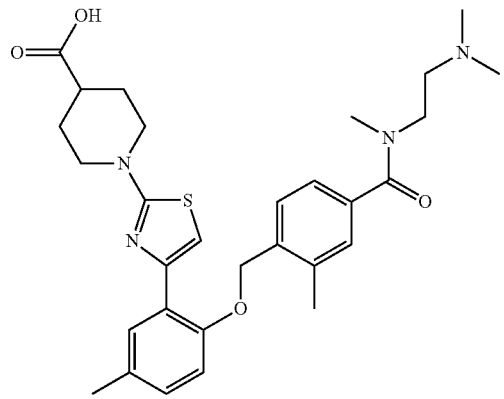 [SMILES: Cc1ccc(OCc2ccc(C(=O)N(C)CCN(C)C)cc2C)c(-c2csc(N3CCC(C(=O)O)CC3)n2)c1] |
| 161 | 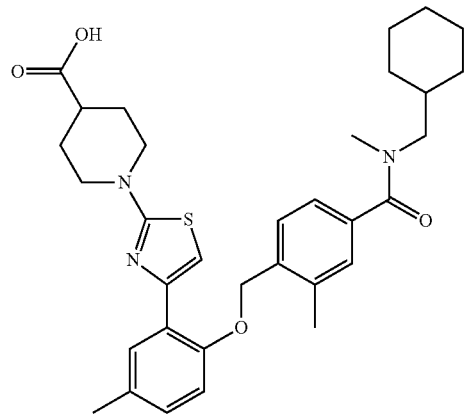 [SMILES: Cc1ccc(OCc2ccc(C(=O)N(C)CC3CCCCC3)cc2C)c(-c2csc(N3CCC(C(=O)O)CC3)n2)c1] |
| 162 | 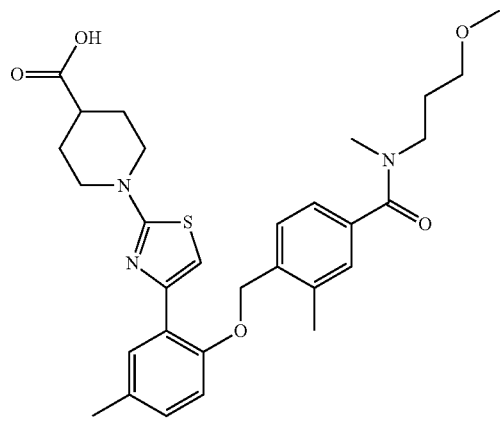 [SMILES: COCCCN(C)C(=O)c1ccc(COc2ccc(C)cc2-c2csc(N3CCC(C(=O)O)CC3)n2)c(C)c1] |

TABLE 1-continued
| Cpd No. | |
|---|---|
| 163 | 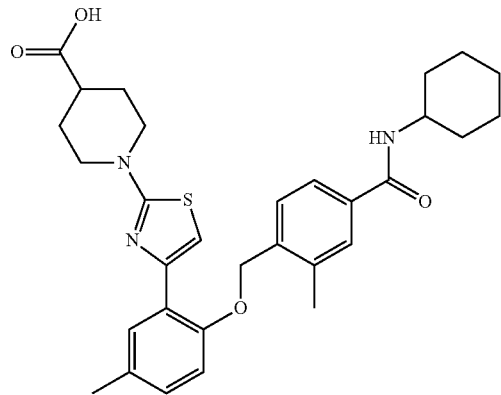 [SMILES: Cc1ccc(OCc2ccc(C(=O)NC3CCCCC3)cc2C)c(-c2csc(N3CCC(C(=O)O)CC3)n2)c1] |
| 164 | 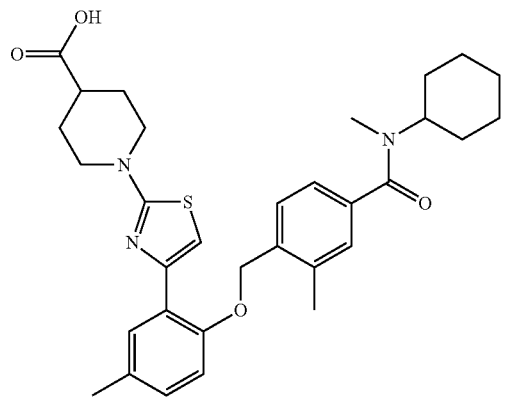 [SMILES: Cc1ccc(OCc2ccc(C(=O)N(C)C3CCCCC3)cc2C)c(-c2csc(N3CCC(C(=O)O)CC3)n2)c1] |
| 165 | 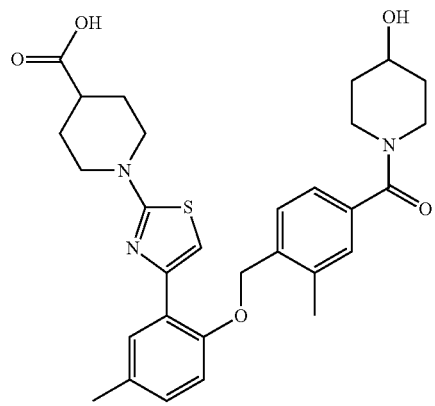 [SMILES: Cc1ccc(OCc2ccc(C(=O)N3CCC(O)CC3)cc2C)c(-c2csc(N3CCC(C(=O)O)CC3)n2)c1] |

TABLE 1-continued
| Cpd No. | |
|---|---|
| 166 | 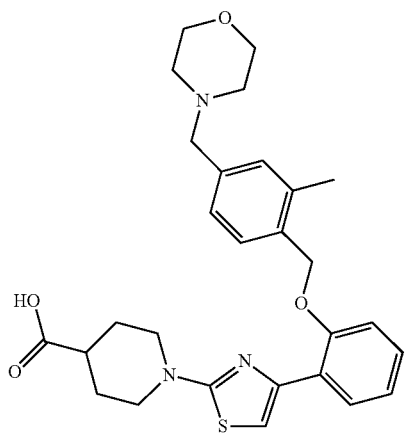 [SMILES: Cc1cc(CN2CCOCC2)ccc1COc1ccccc1-c1csc(N2CCC(C(=O)O)CC2)n1] |
| 167 | 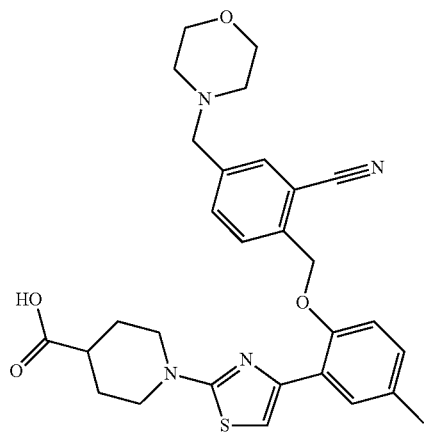 [SMILES: Cc1ccc(OCc2ccc(CN3CCOCC3)cc2C#N)c(-c2csc(N3CCC(C(=O)O)CC3)n2)c1] |
| 168 | 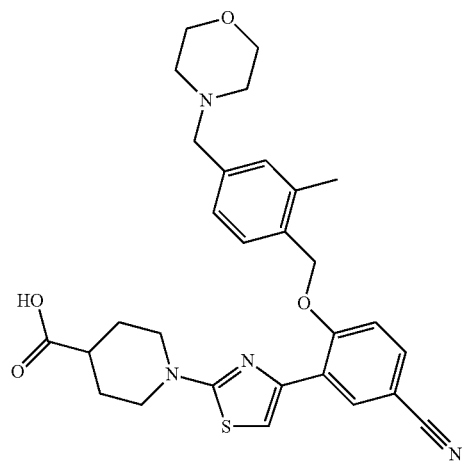 [SMILES: Cc1cc(CN2CCOCC2)ccc1COc1ccc(C#N)cc1-c1csc(N2CCC(C(=O)O)CC2)n1] |

TABLE 1-continued
| Cpd No. | |
|---|---|
| 169 | 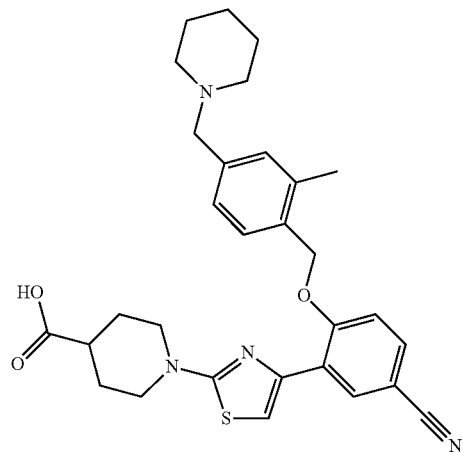 [SMILES: Cc1cc(CN2CCCCC2)ccc1COc1ccc(C#N)cc1-c1csc(N2CCC(C(=O)O)CC2)n1] |
| 170 | 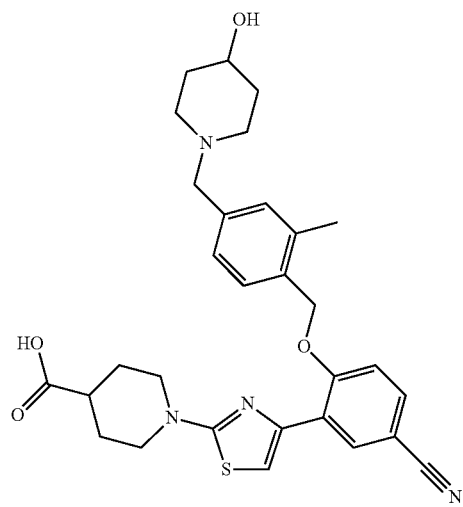 [SMILES: Cc1cc(CN2CCC(O)CC2)ccc1COc1ccc(C#N)cc1-c1csc(N2CCC(C(=O)O)CC2)n1] |
| 171 | 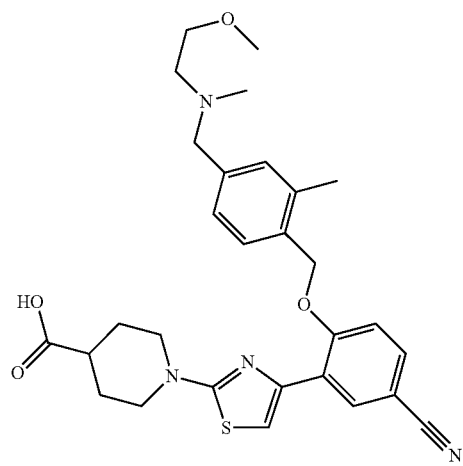 [SMILES: COCCN(C)Cc1ccc(COc2ccc(C#N)cc2-c2csc(N3CCC(C(=O)O)CC3)n2)c(C)c1] |

TABLE 1-continued
| Cpd No. | |
|---|---|
| 172 | 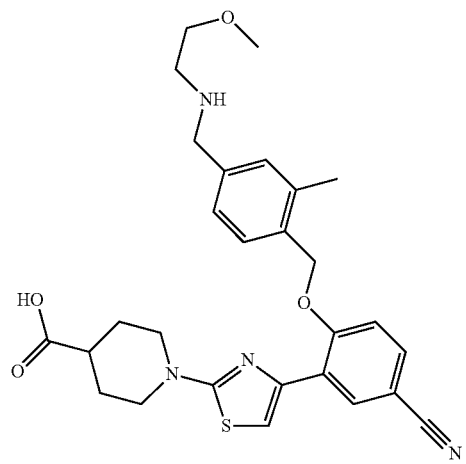 |
| 173 | 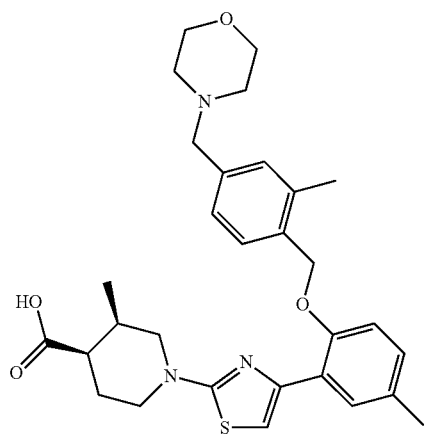 [SMILES: Cc1ccc(OCc2ccc(CN3CCOCC3)cc2C)c(-c2csc(N3CC[C@@H](C(=O)O)[C@@H](C)C3)n2)c1] |
| 174 | 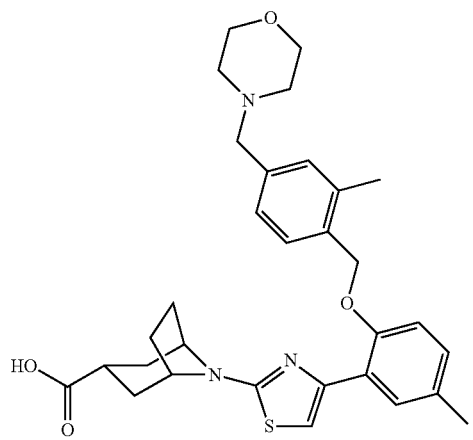 [SMILES: Cc1ccc(OCc2ccc(CN3CCOCC3)cc2C)c(-c2csc(N3C4CCC3CC(C(=O)O)C4)n2)c1] |

TABLE 1-continued
| Cpd No. |
| --- |
| 175 |
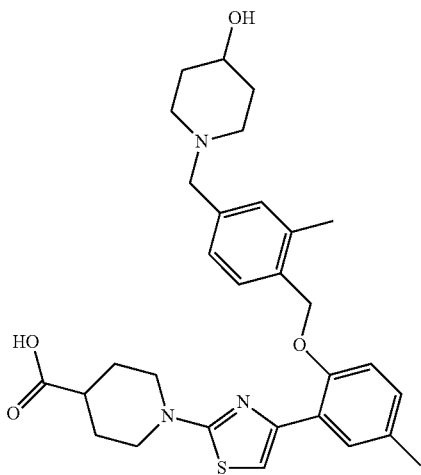 [SMILES: Cc1ccc(OCc2ccc(CN3CCC(O)CC3)cc2C)c(-c2csc(N3CCC(C(=O)O)CC3)n2)c1]
| 176 |
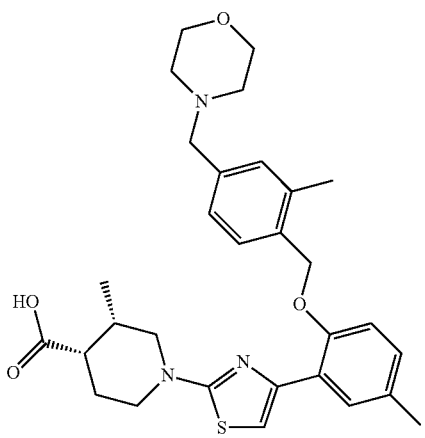 [SMILES: Cc1ccc(OCc2ccc(CN3CCOCC3)cc2C)c(-c2csc(N3CC[C@H](C(=O)O)[C@H](C)C3)n2)c1]
| 177 |
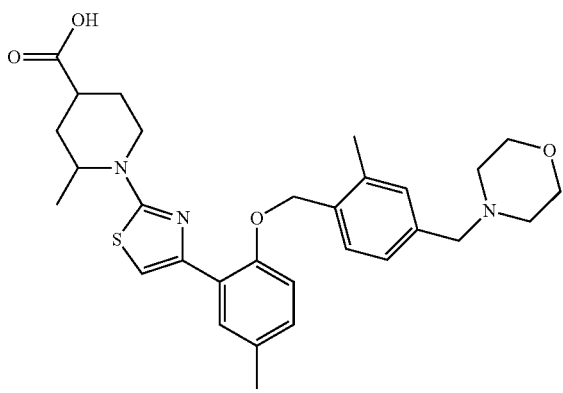 [SMILES: Cc1ccc(OCc2ccc(CN3CCOCC3)cc2C)c(-c2csc(N3CCC(C(=O)O)CC3C)n2)c1]

TABLE 1-continued
| Cpd No. |
| --- |
178
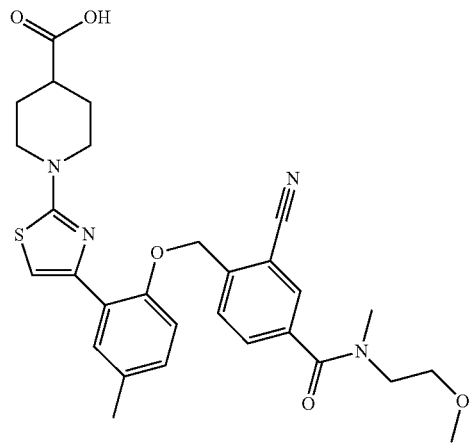 [SMILES: COCCN(C)C(=O)c1ccc(COc2ccc(C)cc2-c2csc(N3CCC(C(=O)O)CC3)n2)c(C#N)c1]
179
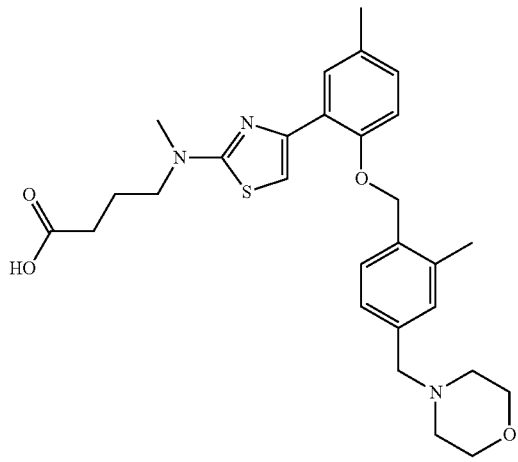 [SMILES: Cc1ccc(OCc2ccc(CN3CCOCC3)cc2C)c(-c2csc(N(C)CCCC(=O)O)n2)c1]
180
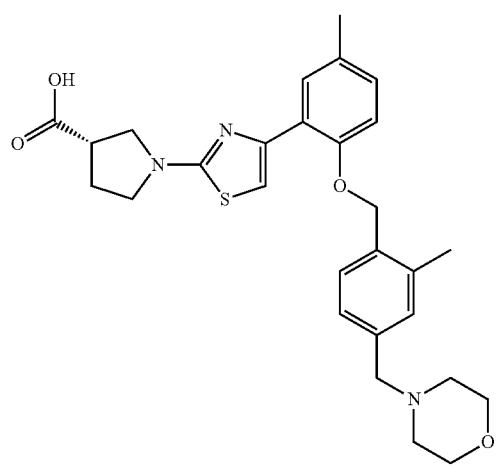 [SMILES: Cc1ccc(OCc2ccc(CN3CCOCC3)cc2C)c(-c2csc(N3CC[C@H](C(=O)O)C3)n2)c1]

TABLE 1-continued
| Cpd No. |
| --- |
| 181 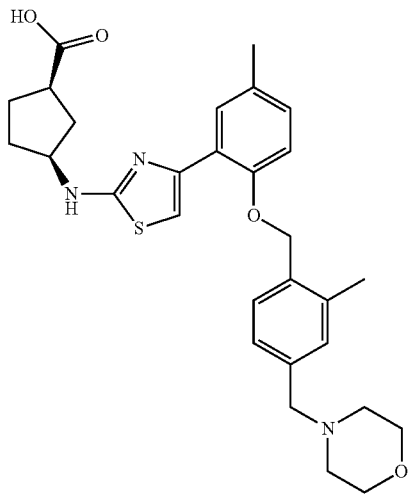 [SMILES: Cc1ccc(OCc2ccc(CN3CCOCC3)cc2C)c(-c2csc(N[C@H]3CC[C@@H](C(=O)O)C3)n2)c1] |
| 182 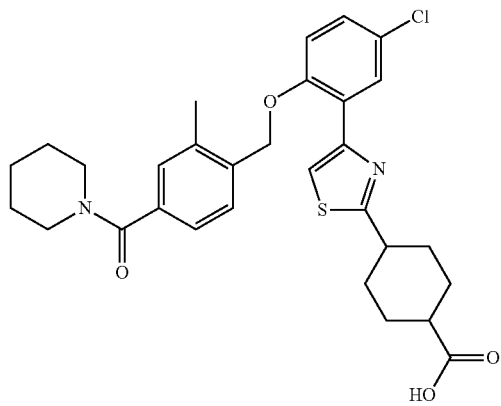 |
| 183 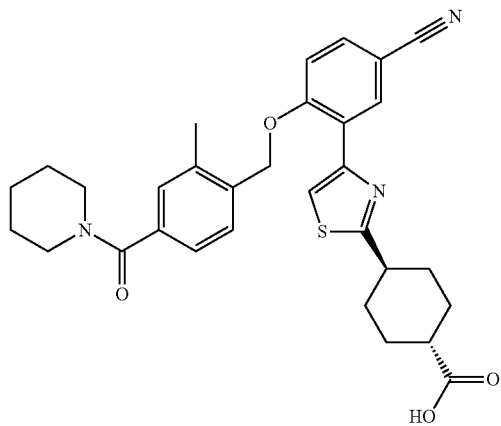 [SMILES: Cc1cc(C(=O)N2CCCCC2)ccc1COc1ccc(C#N)cc1-c1csc([C@H]2CC[C@H](C(=O)O)CC2)n1] |

TABLE 1-continued
| Cpd No. |
| --- |
184
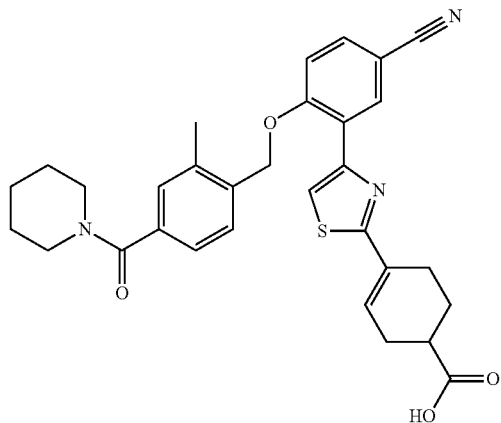 [SMILES: Cc1cc(C(=O)N2CCCCC2)ccc1COc1ccc(C#N)cc1-c1csc(C2=CCC(C(=O)O)CC2)n1]
185
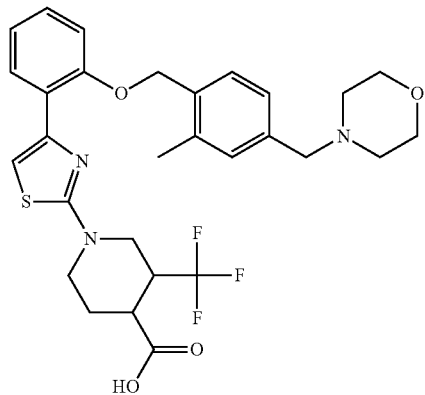 [SMILES: Cc1cc(CN2CCOCC2)ccc1COc1ccccc1-c1csc(N2CCC(C(=O)O)C(C(F)(F)F)C2)n1]
186
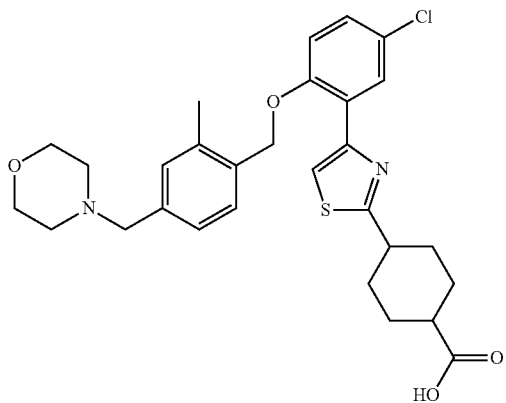

TABLE 1-continued
| Cpd No. |
| --- |
| 187 |
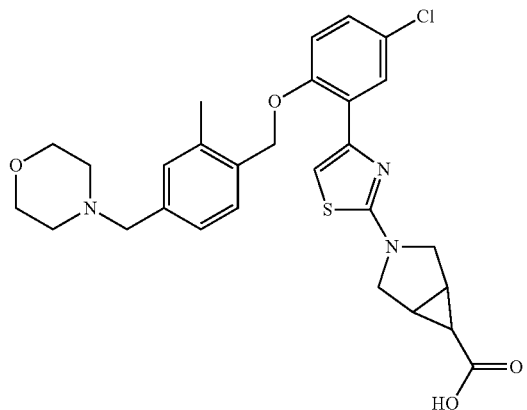 [SMILES: Cc1cc(CN2CCOCC2)ccc1COc1ccc(Cl)cc1-c1csc(N2CC3C(C2)C3C(=O)O)n1]
188
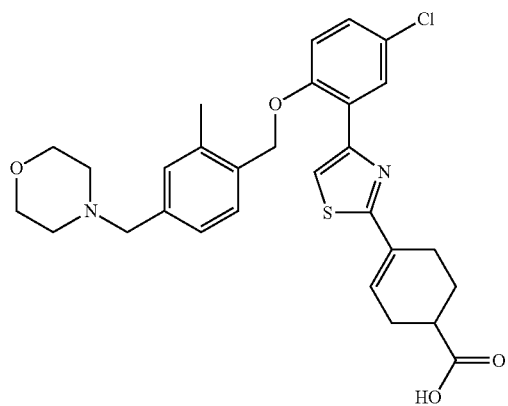
189
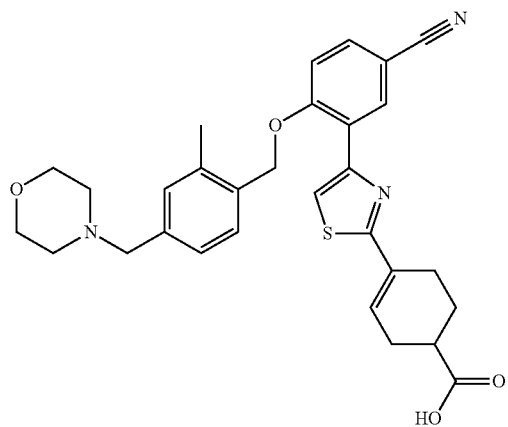 [SMILES: Cc1cc(CN2CCOCC2)ccc1COc1ccc(C#N)cc1-c1csc(C2=CCC(C(=O)O)CC2)n1]

TABLE 1-continued
| Cpd No. | |
|---|---|
| 190 | 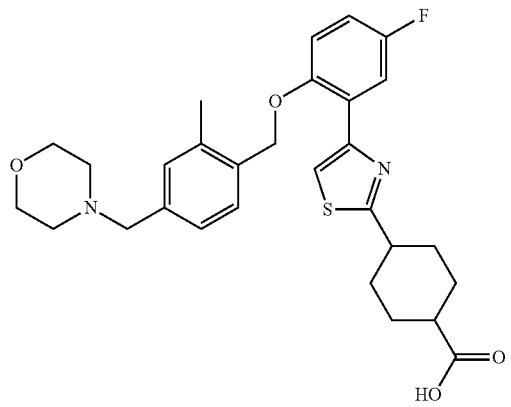 [SMILES: Cc1cc(CN2CCOCC2)ccc1COc1ccc(F)cc1-c1csc(C2CCC(C(=O)O)CC2)n1] |
| 191 | 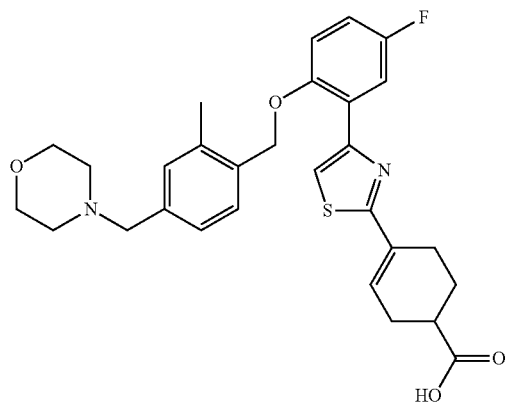 [SMILES: Cc1cc(CN2CCOCC2)ccc1COc1ccc(F)cc1-c1csc(C2=CCC(C(=O)O)CC2)n1] |
| 192 | 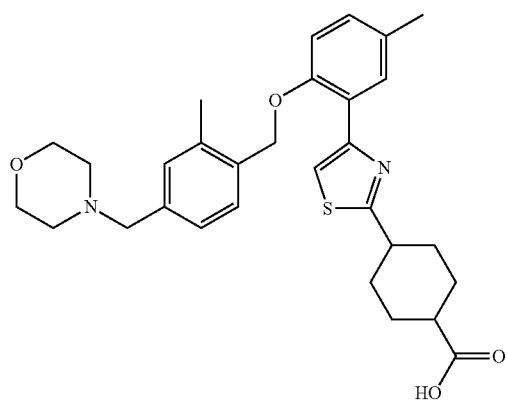 [SMILES: Cc1ccc(OCc2ccc(CN3CCOCC3)cc2C)c(-c2csc(C3CCC(C(=O)O)CC3)n2)c1] |
| 193 | 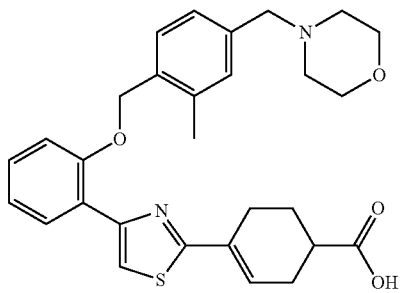 [SMILES: Cc1cc(CN2CCOCC2)ccc1COc1ccccc1-c1csc(C2=CCC(C(=O)O)CC2)n1] |

TABLE 1-continued
| Cpd No. |
| --- |
| 194 |
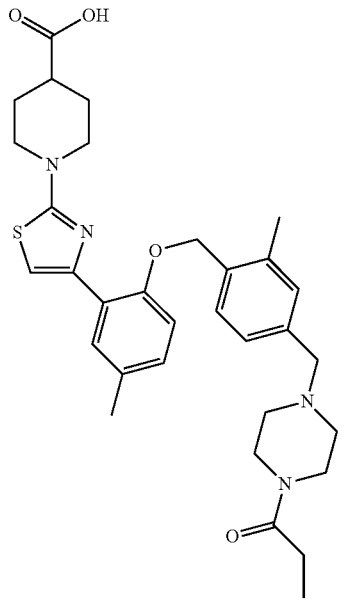 [SMILES: CCC(=O)N1CCN(Cc2ccc(COc3ccc(C)cc3-c3csc(N4CCC(C(=O)O)CC4)n3)c(C)c2)CC1]
| 195 |
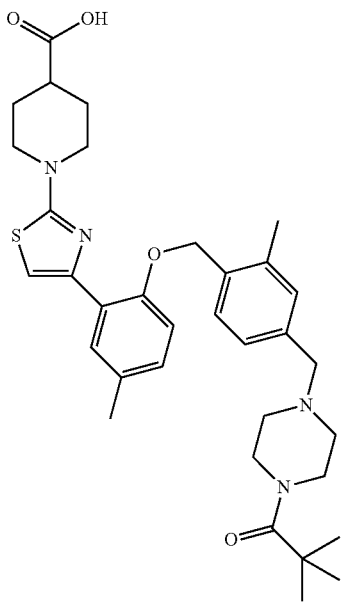 [SMILES: Cc1ccc(OCc2ccc(CN3CCN(C(=O)C(C)(C)C)CC3)cc2C)c(-c2csc(N3CCC(C(=O)O)CC3)n2)c1]

TABLE 1-continued
| Cpd No. |
| --- |
| 196 |
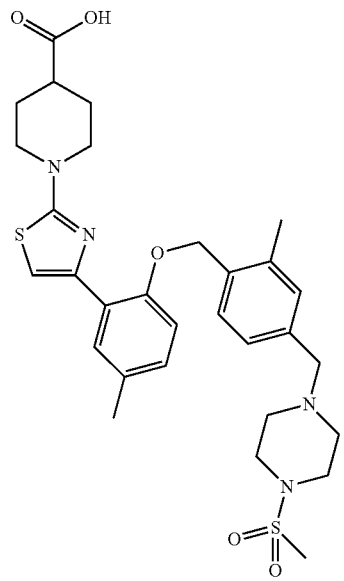 [SMILES: Cc1ccc(OCc2ccc(CN3CCN(S(C)(=O)=O)CC3)cc2C)c(-c2csc(N3CCC(C(=O)O)CC3)n2)c1]
197
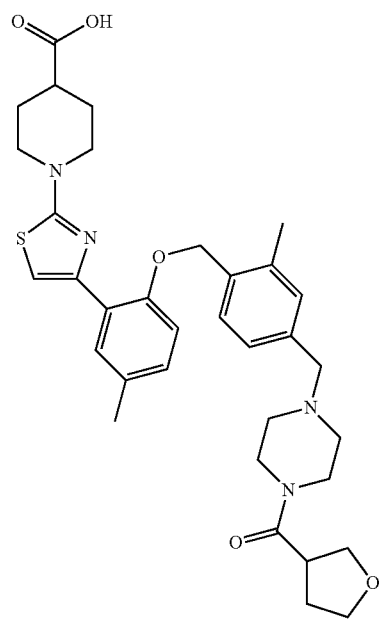 [SMILES: Cc1ccc(OCc2ccc(CN3CCN(C(=O)C4CCOC4)CC3)cc2C)c(-c2csc(N3CCC(C(=O)O)CC3)n2)c1]

TABLE 1-continued
Cpd No.
198
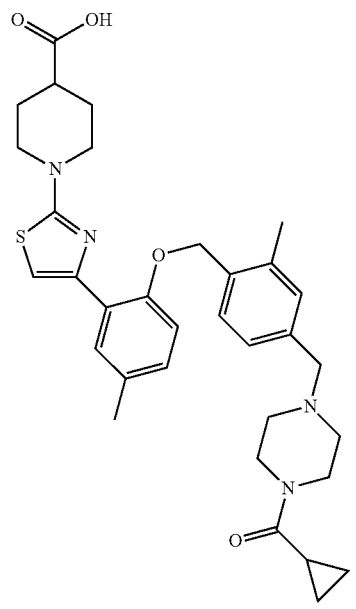 [SMILES: Cc1ccc(OCc2ccc(CN3CCN(C(=O)C4CC4)CC3)cc2C)c(-c2csc(N3CCC(C(=O)O)CC3)n2)c1]
199
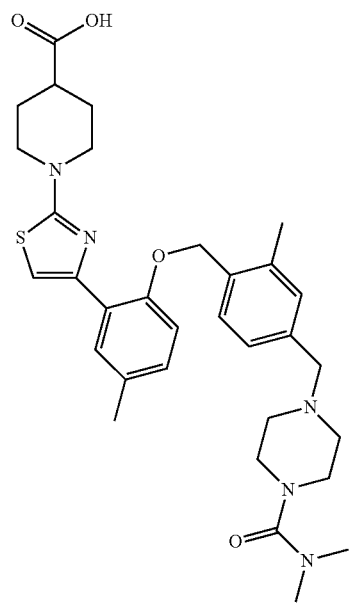 [SMILES: Cc1ccc(OCc2ccc(CN3CCN(C(=O)N(C)C)CC3)cc2C)c(-c2csc(N3CCC(C(=O)O)CC3)n2)c1]

TABLE 1-continued
| Cpd No. | |
|---|---|
| 200 | 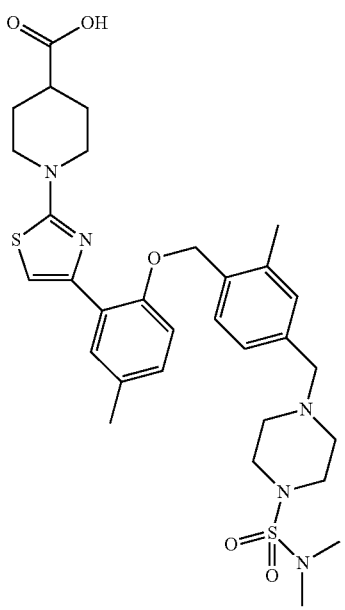 [SMILES: Cc1ccc(OCc2ccc(CN3CCN(S(=O)(=O)N(C)C)CC3)cc2C)c(-c2csc(N3CCC(C(=O)O)CC3)n2)c1] |
| 201 | 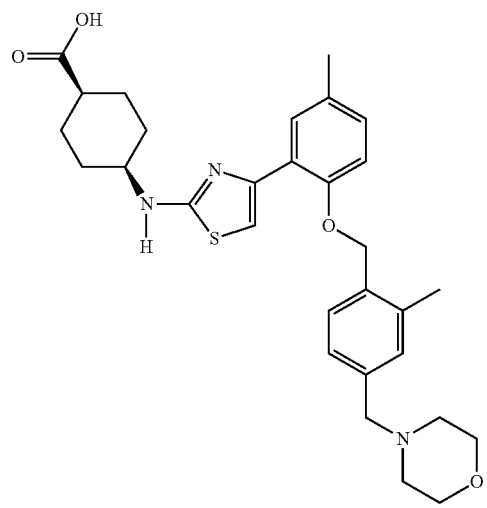 [SMILES: Cc1ccc(OCc2ccc(CN3CCOCC3)cc2C)c(-c2csc(N[C@H]3CC[C@@H](C(=O)O)CC3)n2)c1] |
| 202 | 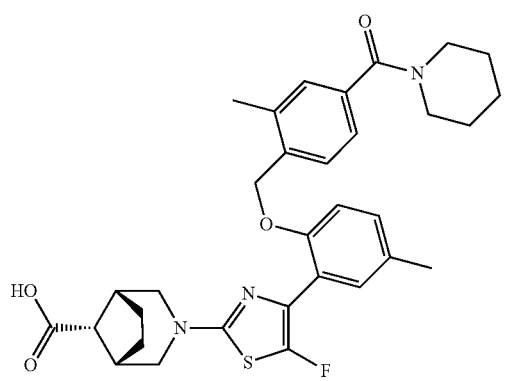 [SMILES: Cc1ccc(OCc2ccc(C(=O)N3CCCCC3)cc2C)c(-c2nc(N3C[C@H]4CC[C@@H](C3)[C@H]4C(=O)O)sc2F)c1] |

TABLE 1-continued
| Cpd No. | |
|---|---|
| 203 | 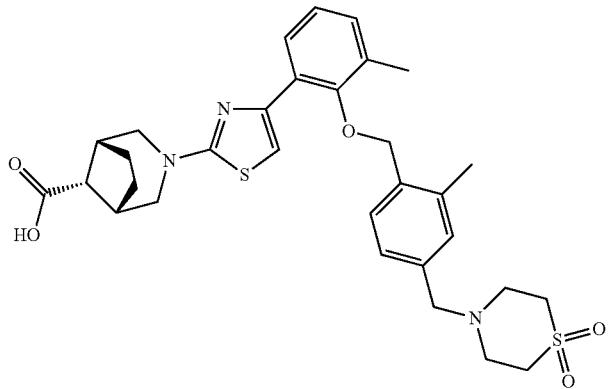 [SMILES: Cc1cc(CN2CCS(=O)(=O)CC2)ccc1COc1c(C)cccc1-c1csc(N2C[C@H]3CC[C@@H](C2)[C@H]3C(=O)O)n1] |
| 204 | 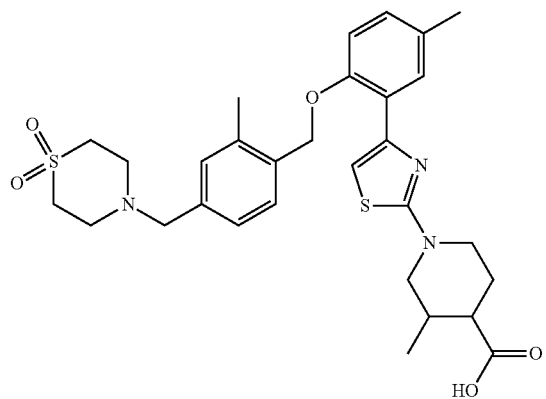 [SMILES: Cc1ccc(OCc2ccc(CN3CCS(=O)(=O)CC3)cc2C)c(-c2csc(N3CCC(C(=O)O)C(C)C3)n2)c1] |
| 205 | 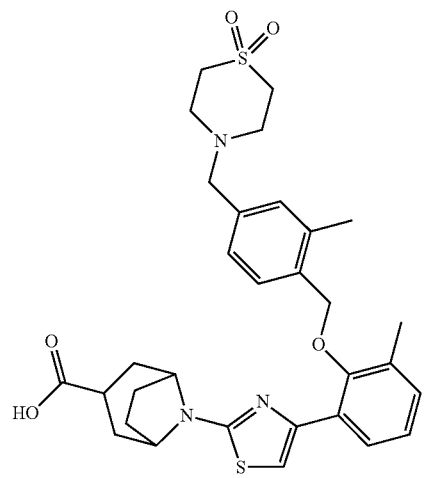 [SMILES: Cc1cc(CN2CCS(=O)(=O)CC2)ccc1COc1c(C)cccc1-c1csc(N2C3CCC2CC(C(=O)O)C3)n1] |

TABLE 1-continued
| Cpd No. |
|---|
| 206 |
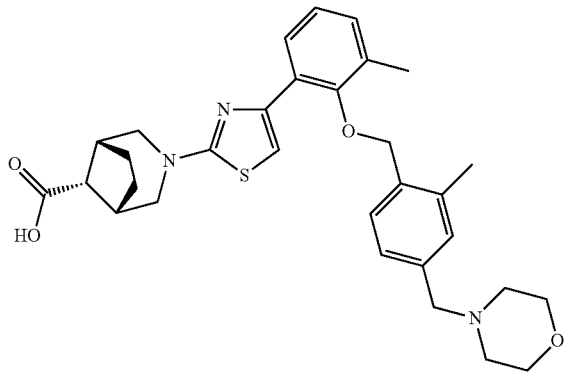 [SMILES: Cc1cc(CN2CCOCC2)ccc1COc1c(C)cccc1-c1csc(N2C[C@H]3CC[C@@H](C2)[C@H]3C(=O)O)n1]
| 207 |
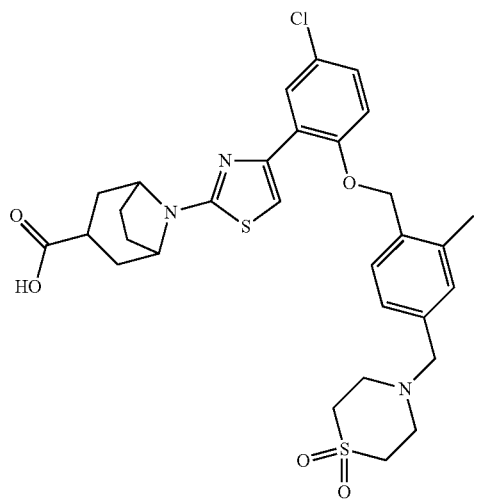 [SMILES: Cc1cc(CN2CCS(=O)(=O)CC2)ccc1COc1ccc(Cl)cc1-c1csc(N2C3CCC2CC(C(=O)O)C3)n1]
| 208 |
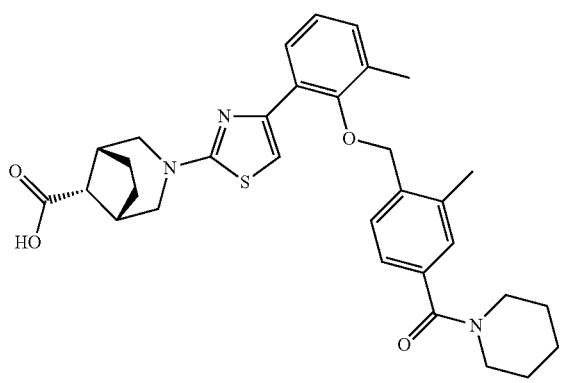 [SMILES: Cc1cc(C(=O)N2CCCCC2)ccc1COc1c(C)cccc1-c1csc(N2C[C@H]3CC[C@@H](C2)[C@H]3C(=O)O)n1]

TABLE 1-continued
| Cpd No. | |
|---|---|
| 209 | 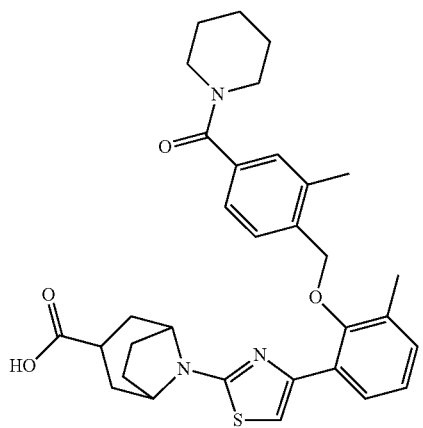 [SMILES: Cc1cc(C(=O)N2CCCCC2)ccc1COc1c(C)cccc1-c1csc(N2C3CCC2CC(C(=O)O)C3)n1] |
| 210 | 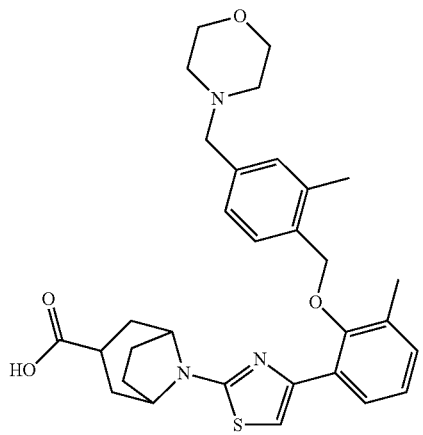 [SMILES: Cc1cc(CN2CCOCC2)ccc1COc1c(C)cccc1-c1csc(N2C3CCC2CC(C(=O)O)C3)n1] |
| 211 | 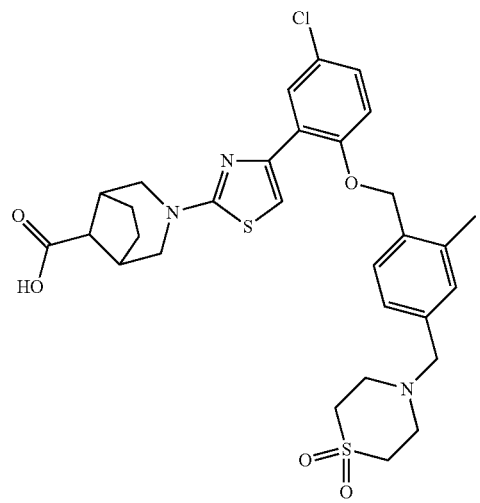 [SMILES: Cc1cc(CN2CCS(=O)(=O)CC2)ccc1COc1ccc(Cl)cc1-c1csc(N2CC3CCC(C2)C3C(=O)O)n1] |

TABLE 1-continued
| Cpd No. | |
|---|---|
| 212 | 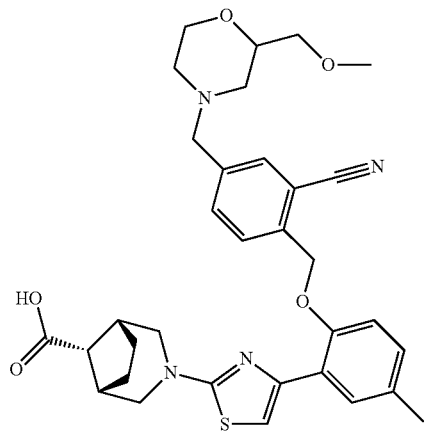 [SMILES: COCC1CN(Cc2ccc(COc3ccc(C)cc3-c3csc(N4C[C@H]5CC[C@@H](C4)[C@H]5C(=O)O)n3)c(C#N)c2)CCO1] |
| 213 | 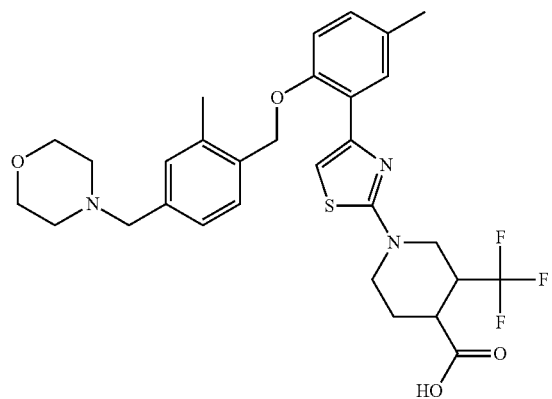 [SMILES: Cc1ccc(OCc2ccc(CN3CCOCC3)cc2C)c(-c2csc(N3CCC(C(=O)O)C(C(F)(F)F)C3)n2)c1] |
| 214 | 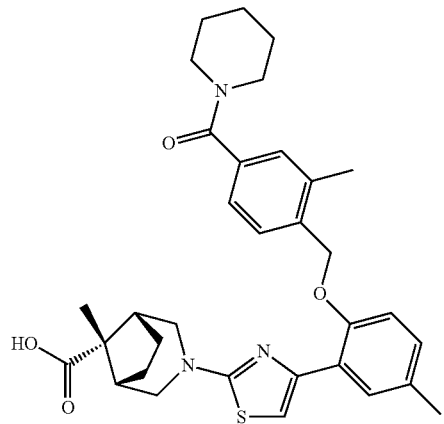 [SMILES: Cc1ccc(OCc2ccc(C(=O)N3CCCCC3)cc2C)c(-c2csc(N3C[C@H]4CC[C@@H](C3)[C@@]4(C)C(=O)O)n2)c1] |

TABLE 1-continued
| Cpd No. |
| --- |
215
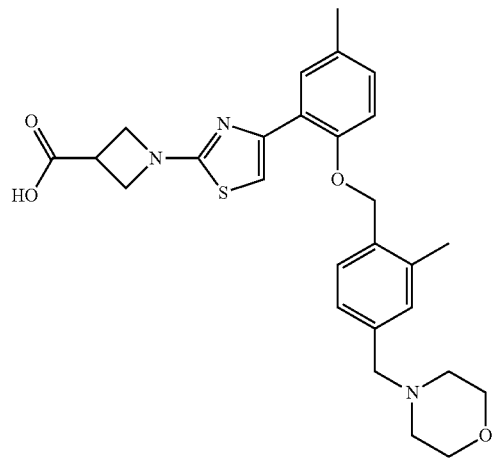 [SMILES: Cc1ccc(OCc2ccc(CN3CCOCC3)cc2C)c(-c2csc(N3CC(C(=O)O)C3)n2)c1]
216
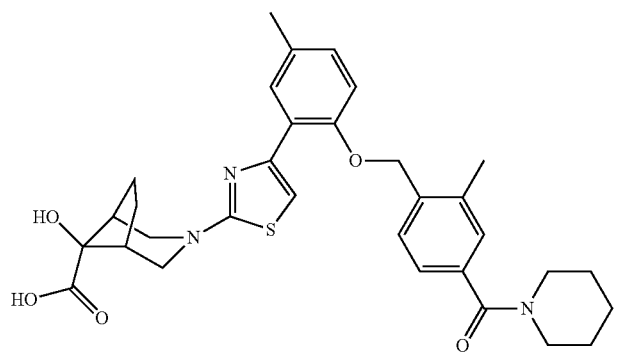 [SMILES: Cc1ccc(OCc2ccc(C(=O)N3CCCCC3)cc2C)c(-c2csc(N3CC4CCC(C3)C4(O)C(=O)O)n2)c1]
217
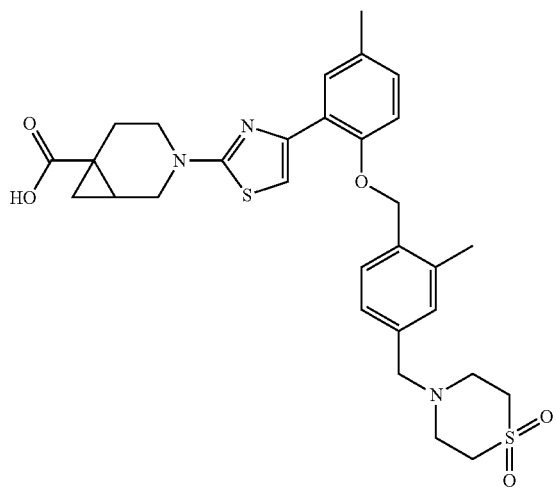 [SMILES: Cc1ccc(OCc2ccc(CN3CCS(=O)(=O)CC3)cc2C)c(-c2csc(N3CCC4(C(=O)O)CC4C3)n2)c1]

TABLE 1-continued
| Cpd No. | |
|---|---|
| 218 | 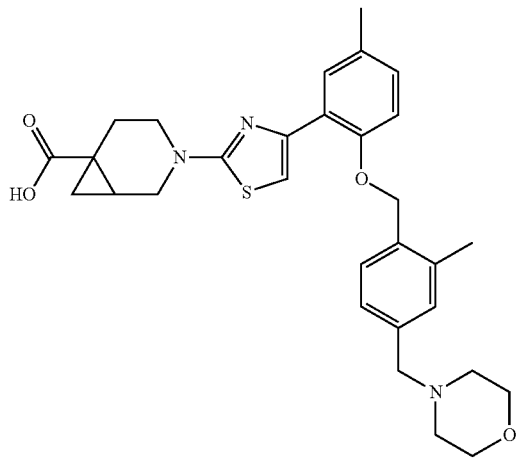 [SMILES: Cc1ccc(OCc2ccc(CN3CCOCC3)cc2C)c(-c2csc(N3CCC4(C(=O)O)CC4C3)n2)c1] |
| 219 | 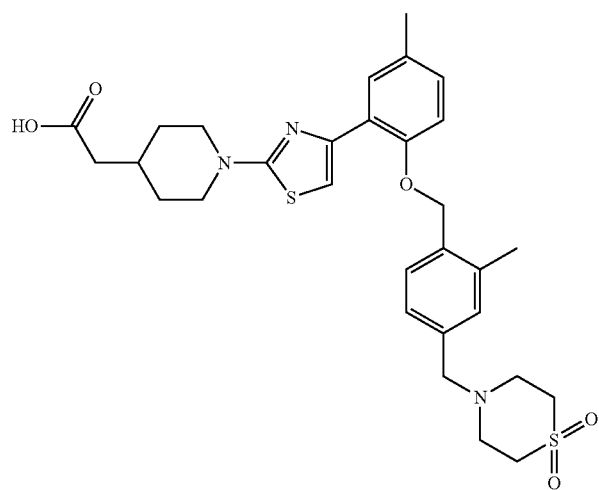 [SMILES: Cc1ccc(OCc2ccc(CN3CCS(=O)(=O)CC3)cc2C)c(-c2csc(N3CCC(CC(=O)O)CC3)n2)c1] |
| 220 | 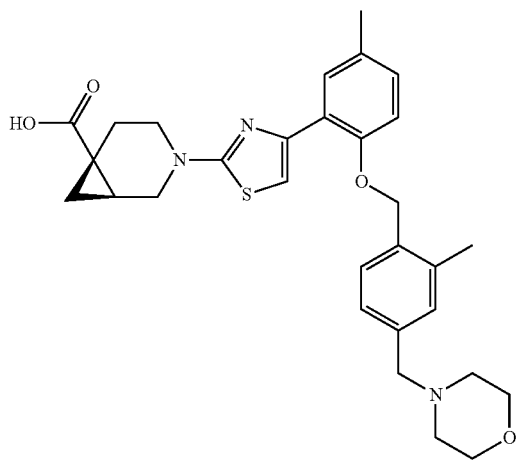 [SMILES: Cc1ccc(OCc2ccc(CN3CCOCC3)cc2C)c(-c2csc(N3CC[C@]4(C(=O)O)C[C@@H]4C3)n2)c1] |

TABLE 1-continued
| Cpd No. |
|---|
| 221 |
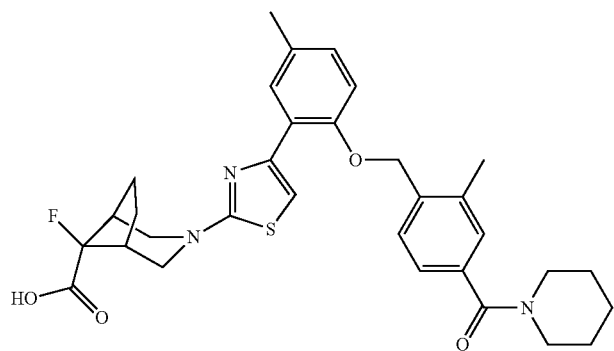 [SMILES: Cc1ccc(OCc2ccc(C(=O)N3CCCCC3)cc2C)c(-c2csc(N3CC4CCC(C3)C4(F)C(=O)O)n2)c1]
| 222 |
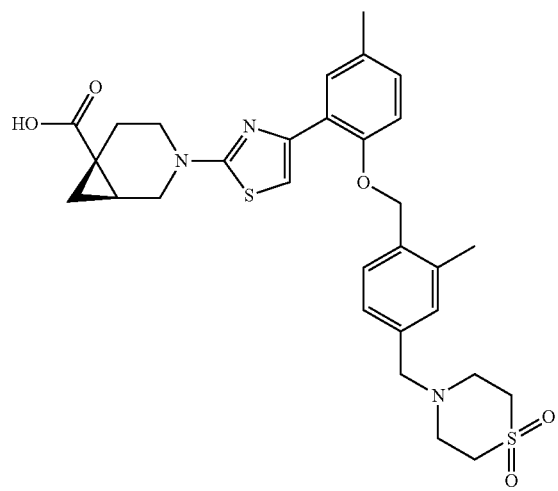 [SMILES: Cc1ccc(OCc2ccc(CN3CCS(=O)(=O)CC3)cc2C)c(-c2csc(N3CC[C@]4(C(=O)O)C[C@@H]4C3)n2)c1]
| 223 |
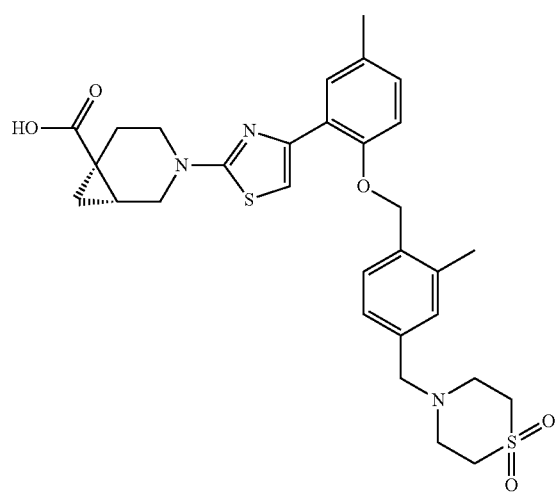 [SMILES: Cc1ccc(OCc2ccc(CN3CCS(=O)(=O)CC3)cc2C)c(-c2csc(N3CC[C@@]4(C(=O)O)C[C@H]4C3)n2)c1]

TABLE 1-continued
| Cpd No. |
|---|
| 224 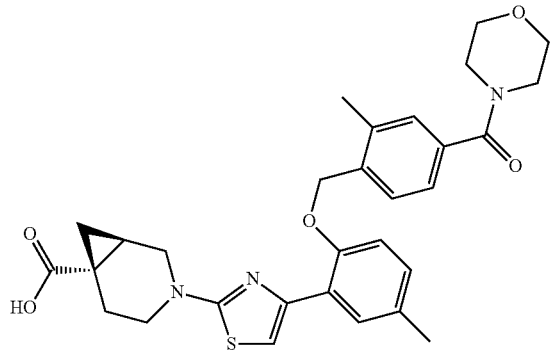 [SMILES: Cc1ccc(OCc2ccc(C(=O)N3CCOCC3)cc2C)c(-c2csc(N3CC[C@@]4(C(=O)O)C[C@H]4C3)n2)c1] |
| 225 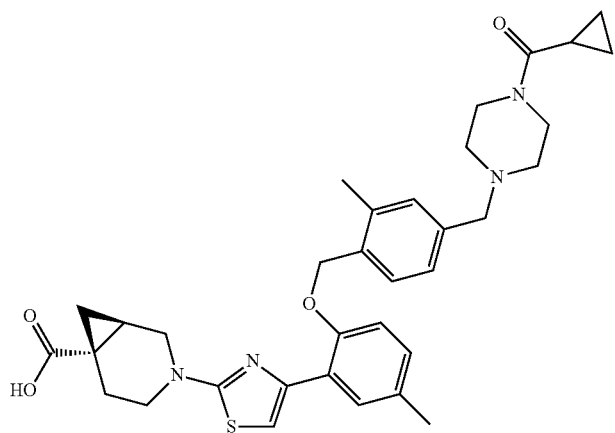 [SMILES: Cc1ccc(OCc2ccc(CN3CCN(C(=O)C4CC4)CC3)cc2C)c(-c2csc(N3CC[C@@]4(C(=O)O)C[C@H]4C3)n2)c1] |
| 226 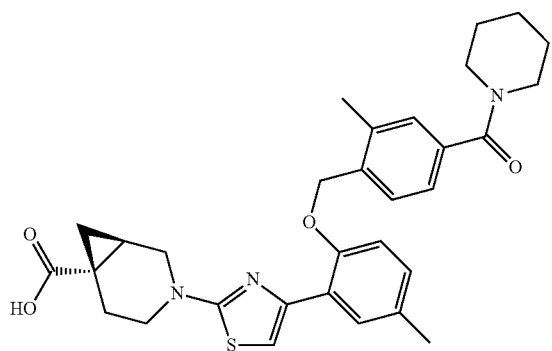 [SMILES: Cc1ccc(OCc2ccc(C(=O)N3CCCCC3)cc2C)c(-c2csc(N3CC[C@@]4(C(=O)O)C[C@H]4C3)n2)c1] |
| 227 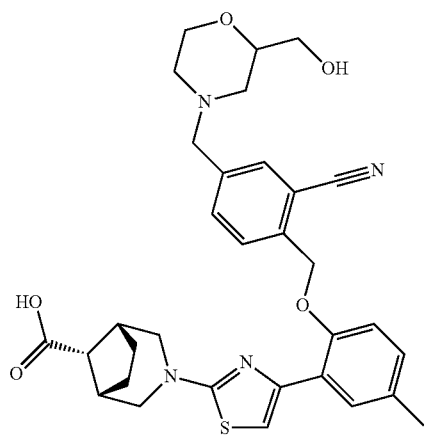 [SMILES: Cc1ccc(OCc2ccc(CN3CCOC(CO)C3)cc2C#N)c(-c2csc(N3C[C@H]4CC[C@@H](C3)[C@H]4C(=O)O)n2)c1] |

| Cpd No. | |
|---|---|
| 228 | 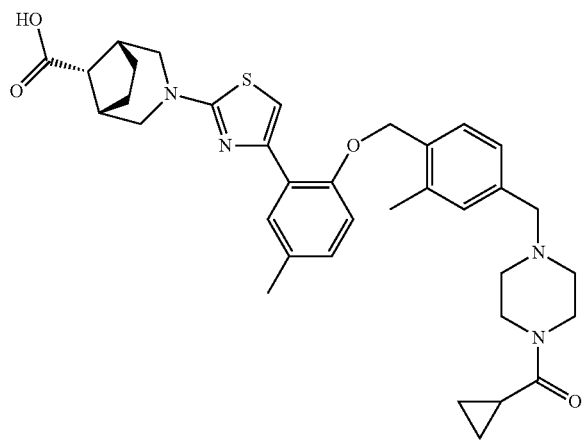 [SMILES: Cc1ccc(OCc2ccc(CN3CCN(C(=O)C4CC4)CC3)cc2C)c(-c2csc(N3C[C@H]4CC[C@@H](C3)[C@H]4C(=O)O)n2)c1] |
| 229 | 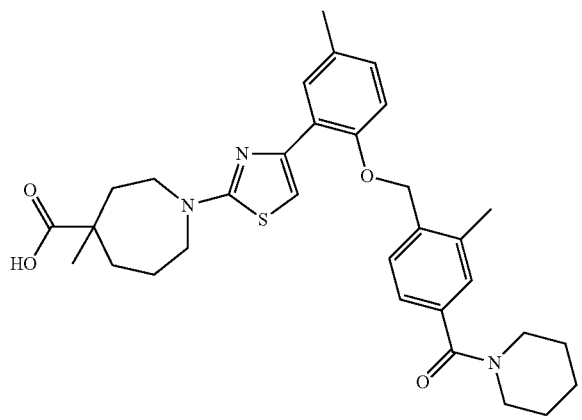 [SMILES: Cc1ccc(OCc2ccc(C(=O)N3CCCCC3)cc2C)c(-c2csc(N3CCCC(C)(C(=O)O)CC3)n2)c1] |
| 230 | 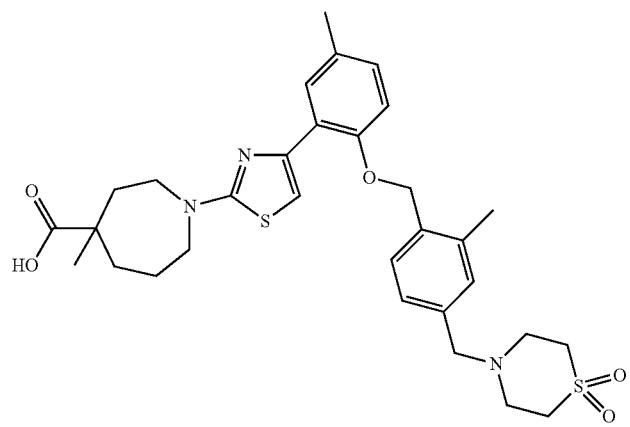 [SMILES: Cc1ccc(OCc2ccc(CN3CCS(=O)(=O)CC3)cc2C)c(-c2csc(N3CCCC(C)(C(=O)O)CC3)n2)c1] |

TABLE 1-continued
| Cpd No. | |
|---|---|
| 231 | 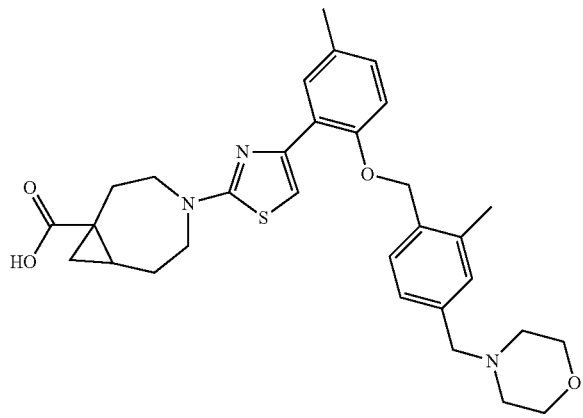 [SMILES: Cc1ccc(OCc2ccc(CN3CCOCC3)cc2C)c(-c2csc(N3CCC4CC4(C(=O)O)CC3)n2)c1] |
| 232 | 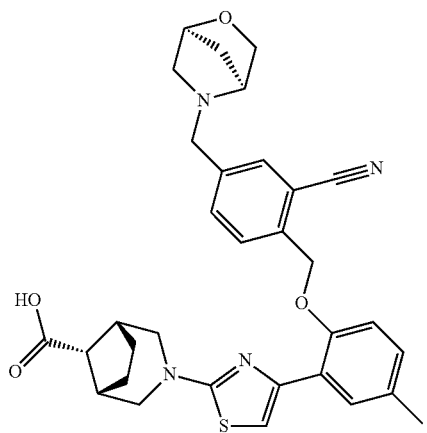 [SMILES: Cc1ccc(OCc2ccc(CN3C[C@@H]4C[C@H]3CO4)cc2C#N)c(-c2csc(N3C[C@H]4CC[C@@H](C3)[C@H]4C(=O)O)n2)c1] |
| 233 | 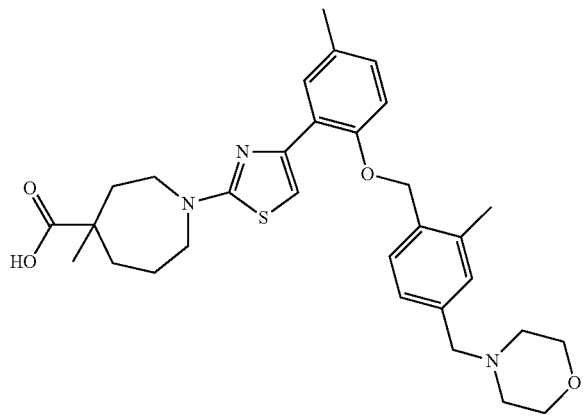 [SMILES: Cc1ccc(OCc2ccc(CN3CCOCC3)cc2C)c(-c2csc(N3CCCC(C)(C(=O)O)CC3)n2)c1] |

TABLE 1-continued
| Cpd No. | |
|---|---|
| 234 | 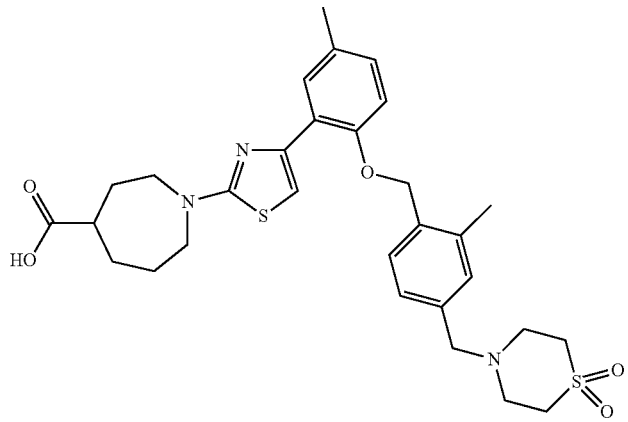 [SMILES: Cc1ccc(OCc2ccc(CN3CCS(=O)(=O)CC3)cc2C)c(-c2csc(N3CCCC(C(=O)O)CC3)n2)c1] |
| 235 | 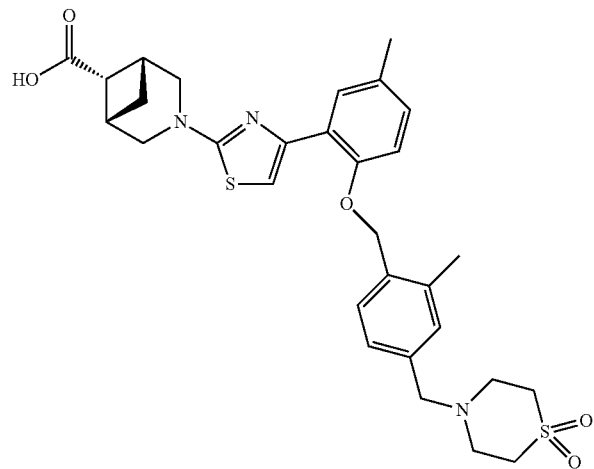 [SMILES: Cc1ccc(OCc2ccc(CN3CCS(=O)(=O)CC3)cc2C)c(-c2csc(N3C[C@H]4C[C@@H](C3)[C@H]4C(=O)O)n2)c1] |
| 236 | 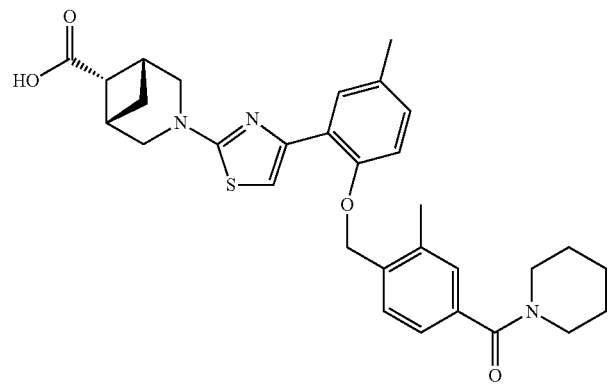 [SMILES: Cc1ccc(OCc2ccc(C(=O)N3CCCCC3)cc2C)c(-c2csc(N3C[C@H]4C[C@@H](C3)[C@H]4C(=O)O)n2)c1] |

TABLE 1-continued
| Cpd No. | |
|---|---|
| 237 | 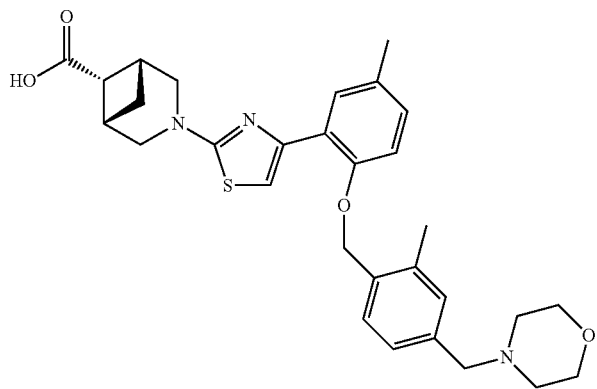 [SMILES: Cc1ccc(OCc2ccc(CN3CCOCC3)cc2C)c(-c2csc(N3C[C@H]4C[C@@H](C3)[C@H]4C(=O)O)n2)c1] |
| 238 | 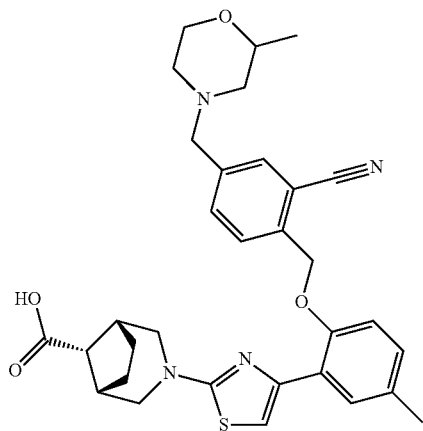 [SMILES: Cc1ccc(OCc2ccc(CN3CCOC(C)C3)cc2C#N)c(-c2csc(N3C[C@H]4CC[C@@H](C3)[C@H]4C(=O)O)n2)c1] |
| 239 | 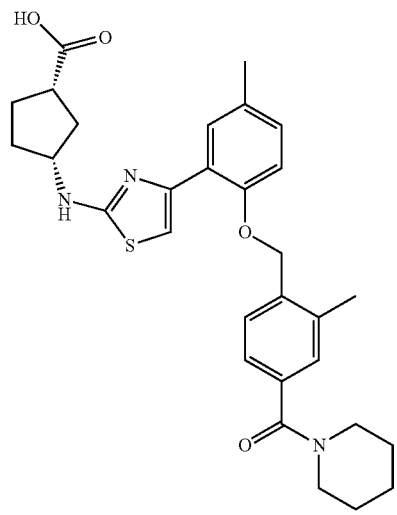 [SMILES: Cc1ccc(OCc2ccc(C(=O)N3CCCCC3)cc2C)c(-c2csc(N[C@@H]3CC[C@H](C(=O)O)C3)n2)c1] |

TABLE 1-continued
| Cpd No. |
| --- |
240
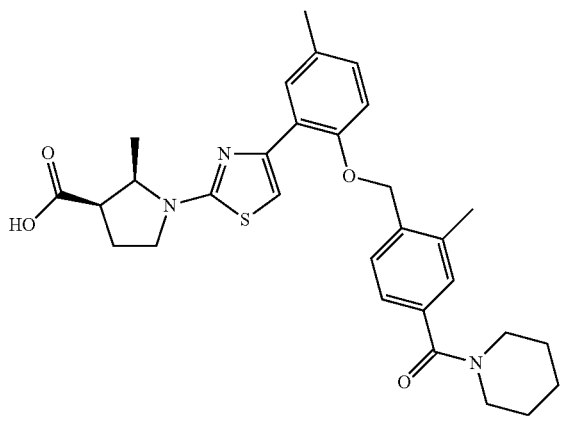 [SMILES: Cc1ccc(OCc2ccc(C(=O)N3CCCCC3)cc2C)c(-c2csc(N3CC[C@@H](C(=O)O)[C@H]3C)n2)c1]
241
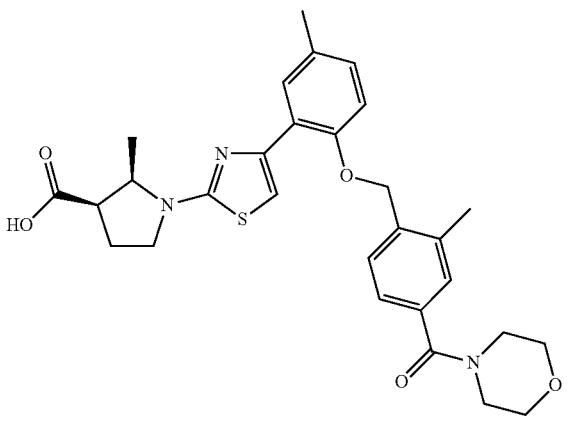 [SMILES: Cc1ccc(OCc2ccc(C(=O)N3CCOCC3)cc2C)c(-c2csc(N3CC[C@@H](C(=O)O)[C@H]3C)n2)c1]
242
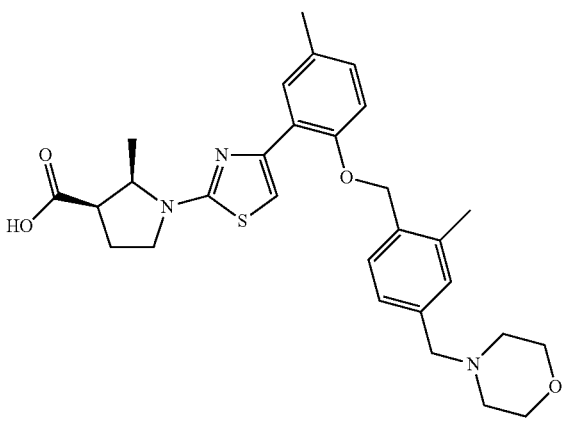 [SMILES: Cc1ccc(OCc2ccc(CN3CCOCC3)cc2C)c(-c2csc(N3CC[C@@H](C(=O)O)[C@H]3C)n2)c1]

TABLE 1-continued
| Cpd No. | |
|---|---|
| 243 | 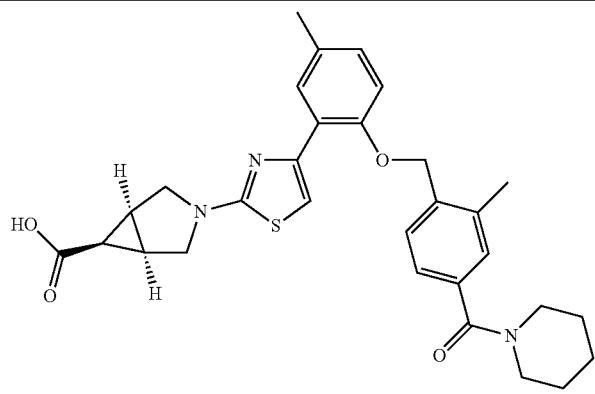 |
| 244 | 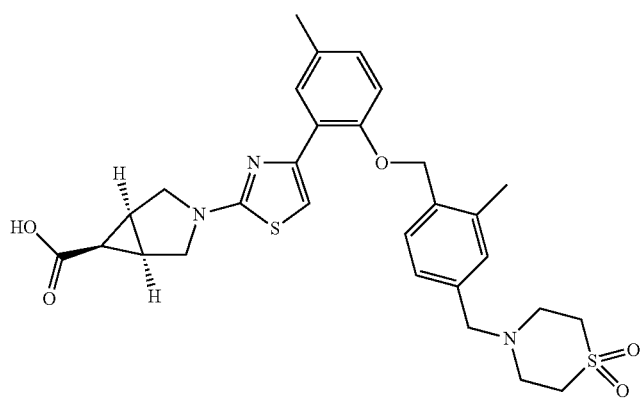 [SMILES: Cc1ccc(OCc2ccc(CN3CCS(=O)(=O)CC3)cc2C)c(-c2csc(N3C[C@@H]4[C@H](C3)[C@@H]4C(=O)O)n2)c1] |
| 245 | 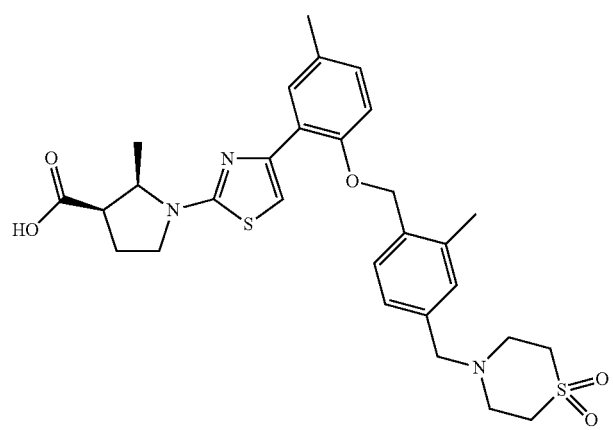 [SMILES: Cc1ccc(OCc2ccc(CN3CCS(=O)(=O)CC3)cc2C)c(-c2csc(N3CC[C@@H](C(=O)O)[C@H]3C)n2)c1] |
| 246 | 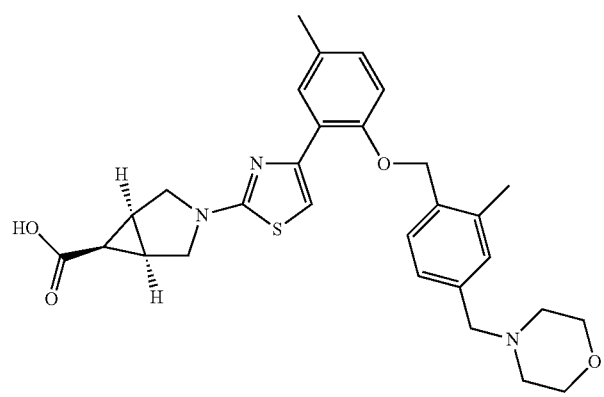 [SMILES: Cc1ccc(OCc2ccc(CN3CCOCC3)cc2C)c(-c2csc(N3C[C@@H]4[C@H](C3)[C@@H]4C(=O)O)n2)c1] |

TABLE 1-continued
Cpd No.
247
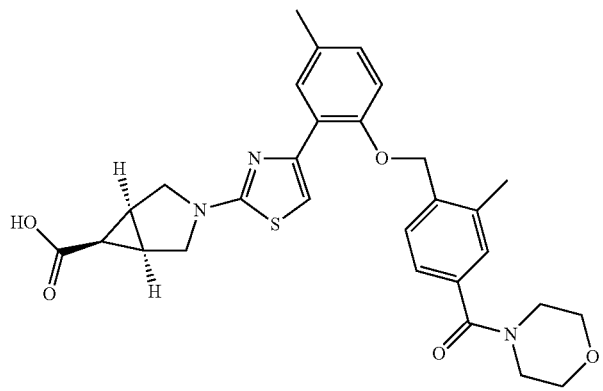 [SMILES: Cc1ccc(OCc2ccc(C(=O)N3CCOCC3)cc2C)c(-c2csc(N3C[C@@H]4[C@H](C3)[C@@H]4C(=O)O)n2)c1]
248
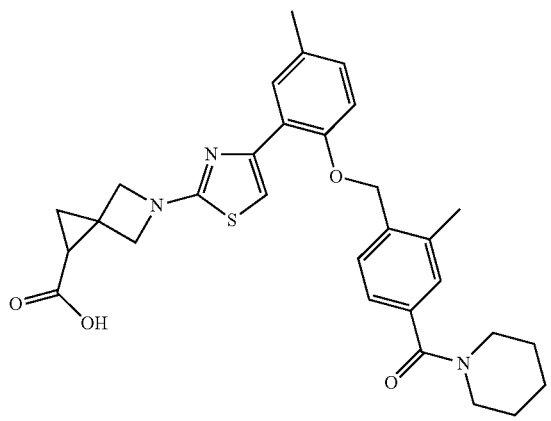 [SMILES: Cc1ccc(OCc2ccc(C(=O)N3CCCCC3)cc2C)c(-c2csc(N3CC4(CC4C(=O)O)C3)n2)c1]
249
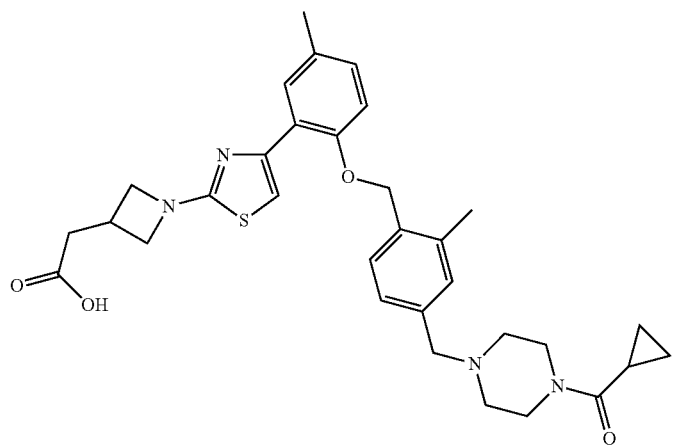 [SMILES: Cc1ccc(OCc2ccc(CN3CCN(C(=O)C4CC4)CC3)cc2C)c(-c2csc(N3CC(CC(=O)O)C3)n2)c1]

TABLE 1-continued
Cpd No.
250
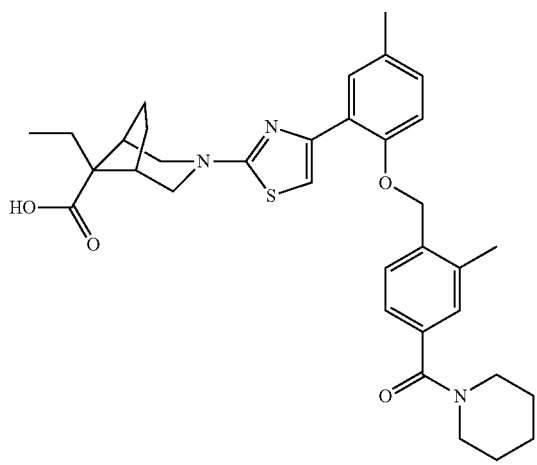 [SMILES: CCC1(C(=O)O)C2CCC1CN(c1nc(-c3cc(C)ccc3OCc3ccc(C(=O)N4CCCCC4)cc3C)cs1)C2]
251
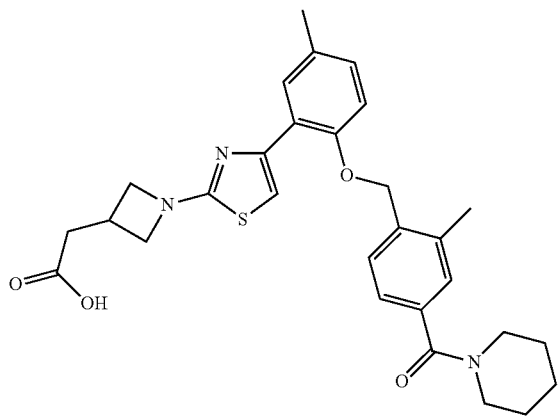 [SMILES: Cc1ccc(OCc2ccc(C(=O)N3CCCCC3)cc2C)c(-c2csc(N3CC(CC(=O)O)C3)n2)c1]
252
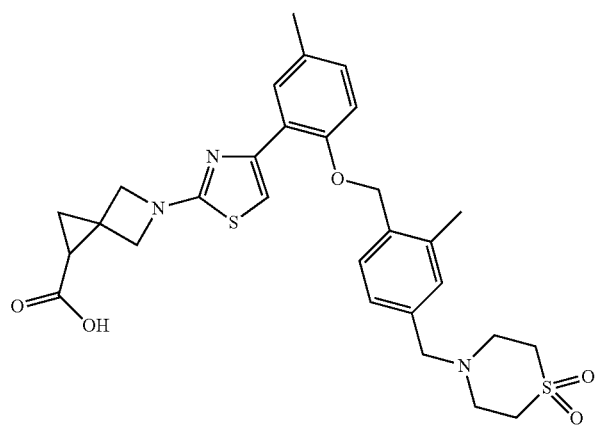 [SMILES: Cc1ccc(OCc2ccc(CN3CCS(=O)(=O)CC3)cc2C)c(-c2csc(N3CC4(CC4C(=O)O)C3)n2)c1]

TABLE 1-continued
Cpd No.
253
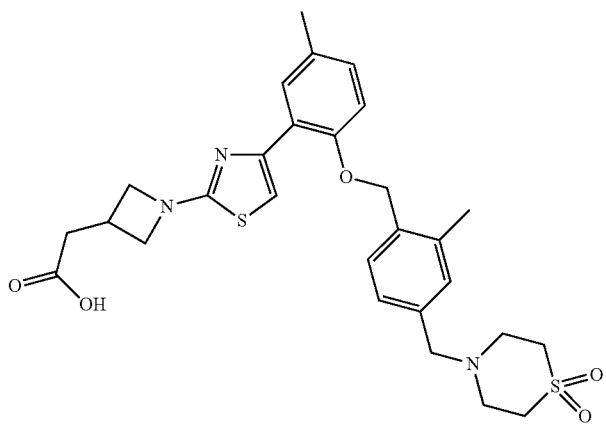 [SMILES: Cc1ccc(OCc2ccc(CN3CCS(=O)(=O)CC3)cc2C)c(-c2csc(N3CC(CC(=O)O)C3)n2)c1]
254
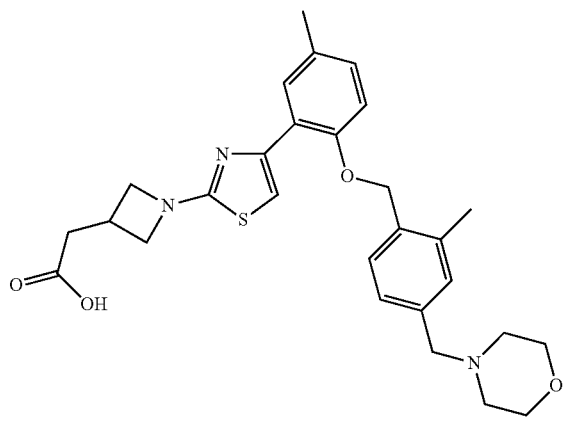 [SMILES: Cc1ccc(OCc2ccc(CN3CCOCC3)cc2C)c(-c2csc(N3CC(CC(=O)O)C3)n2)c1]
255
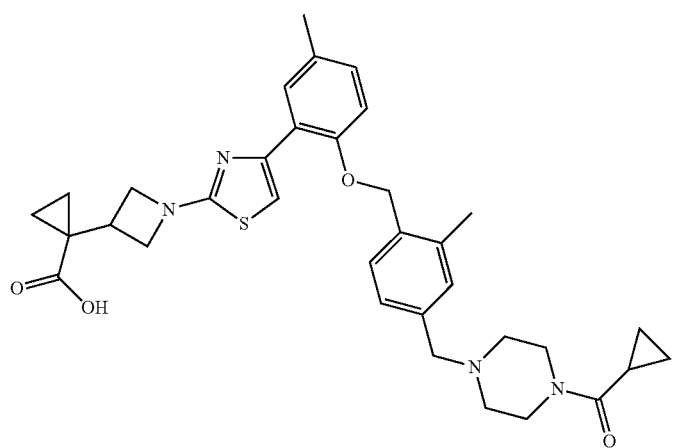 [SMILES: Cc1ccc(OCc2ccc(CN3CCN(C(=O)C4CC4)CC3)cc2C)c(-c2csc(N3CC(C4(C(=O)O)CC4)C3)n2)c1]

TABLE 1-continued
Cpd No.
256
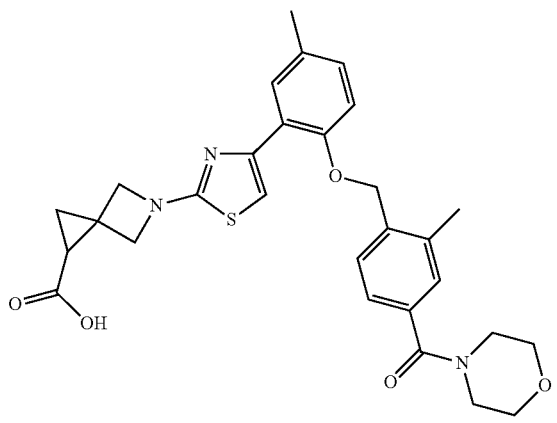 [SMILES: Cc1ccc(OCc2ccc(C(=O)N3CCOCC3)cc2C)c(-c2csc(N3CC4(CC4C(=O)O)C3)n2)c1]
257
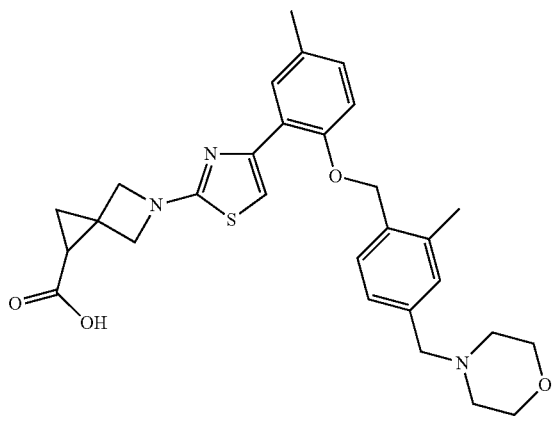 [SMILES: Cc1ccc(OCc2ccc(CN3CCOCC3)cc2C)c(-c2csc(N3CC4(CC4C(=O)O)C3)n2)c1]
258
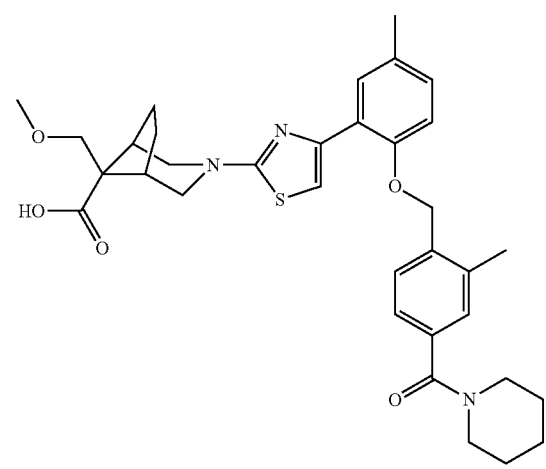 [SMILES: COCC1(C(=O)O)C2CCC1CN(c1nc(-c3cc(C)ccc3OCc3ccc(C(=O)N4CCCCC4)cc3C)cs1)C2]

TABLE 1-continued
| Cpd No. | |
|---|---|
| 259 | 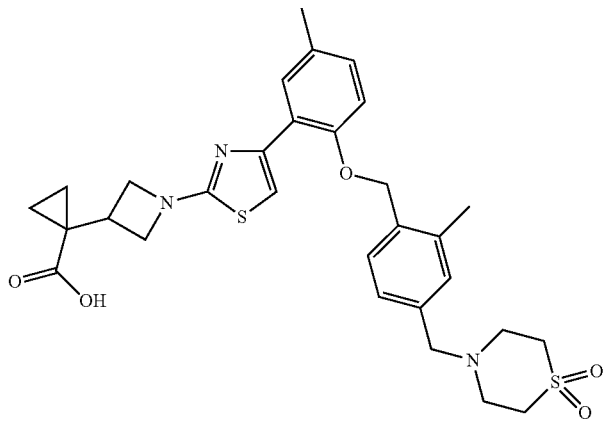 [SMILES: Cc1ccc(OCc2ccc(CN3CCS(=O)(=O)CC3)cc2C)c(-c2csc(N3CC(C4(C(=O)O)CC4)C3)n2)c1] |
| 260 | 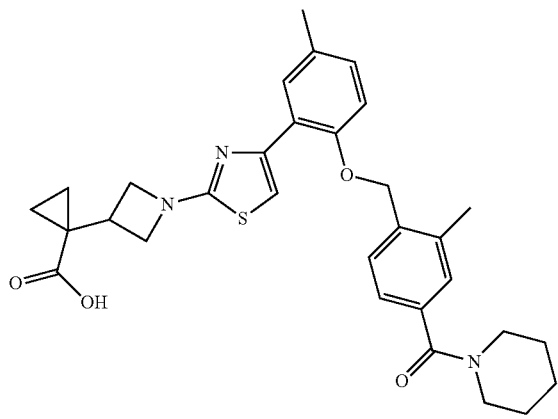 [SMILES: Cc1ccc(OCc2ccc(C(=O)N3CCCCC3)cc2C)c(-c2csc(N3CC(C4(C(=O)O)CC4)C3)n2)c1] |
| 261 | 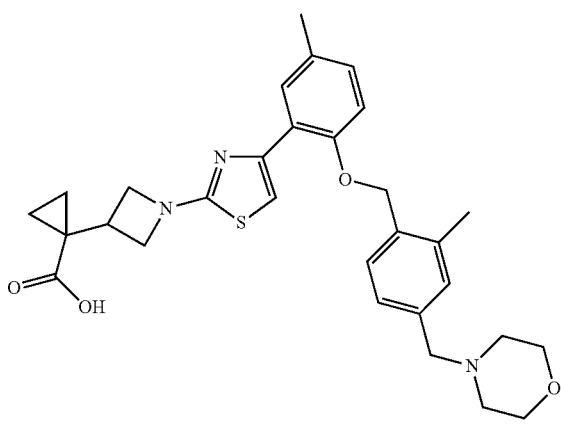 [SMILES: Cc1ccc(OCc2ccc(CN3CCOCC3)cc2C)c(-c2csc(N3CC(C4(C(=O)O)CC4)C3)n2)c1] |

| Cpd No. | |
|---|---|
| 262 | 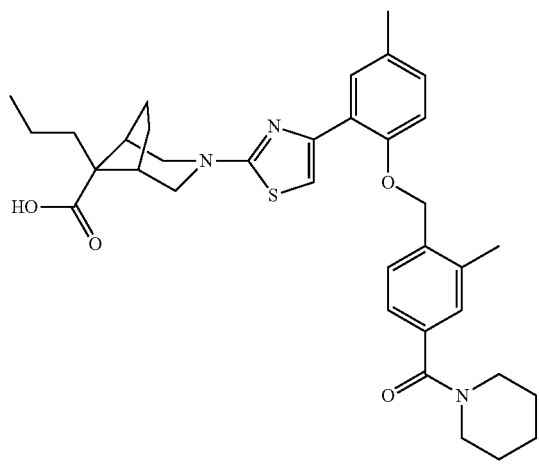 |
| 263 | 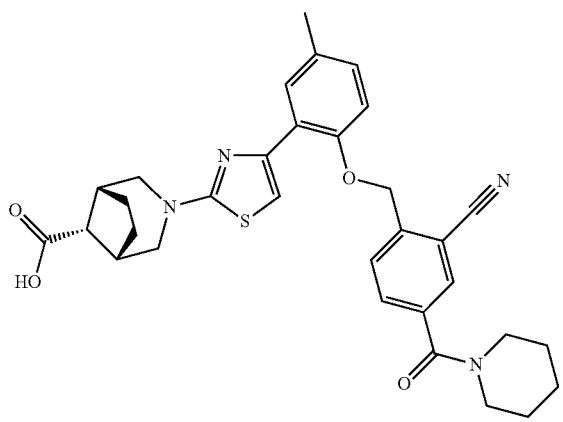 [SMILES: Cc1ccc(OCc2ccc(C(=O)N3CCCCC3)cc2C#N)c(-c2csc(N3C[C@H]4CC[C@@H](C3)[C@H]4C(=O)O)n2)c1] |
| 264 | 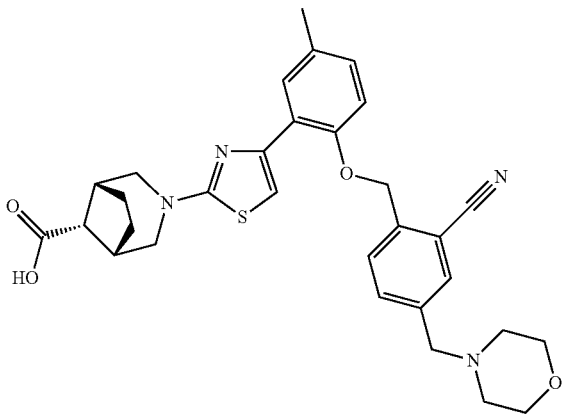 [SMILES: Cc1ccc(OCc2ccc(CN3CCOCC3)cc2C#N)c(-c2csc(N3C[C@H]4CC[C@@H](C3)[C@H]4C(=O)O)n2)c1] |

| Cpd No. | |
|---|---|
| 265 | 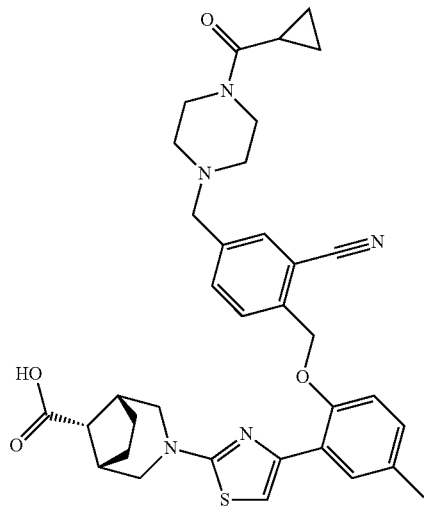 [SMILES: Cc1ccc(OCc2ccc(CN3CCN(C(=O)C4CC4)CC3)cc2C#N)c(-c2csc(N3C[C@H]4CC[C@@H](C3)[C@H]4C(=O)O)n2)c1] |
| 266 | 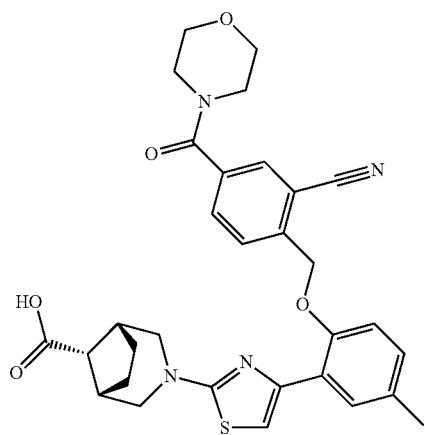 [SMILES: Cc1ccc(OCc2ccc(C(=O)N3CCOCC3)cc2C#N)c(-c2csc(N3C[C@H]4CC[C@@H](C3)[C@H]4C(=O)O)n2)c1] |
| 267 | 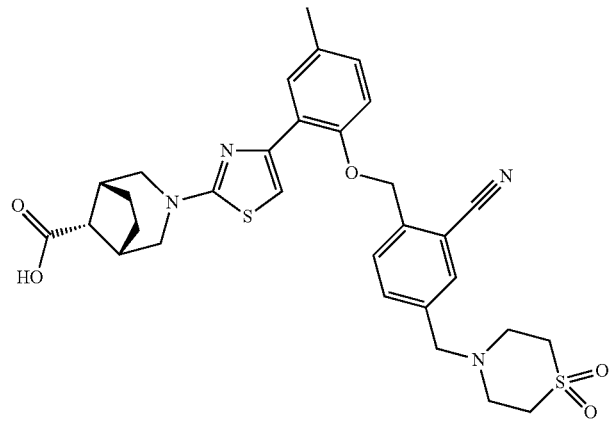 [SMILES: Cc1ccc(OCc2ccc(CN3CCS(=O)(=O)CC3)cc2C#N)c(-c2csc(N3C[C@H]4CC[C@@H](C3)[C@H]4C(=O)O)n2)c1] |

| Cpd No. | |
|---|---|
| 268 | 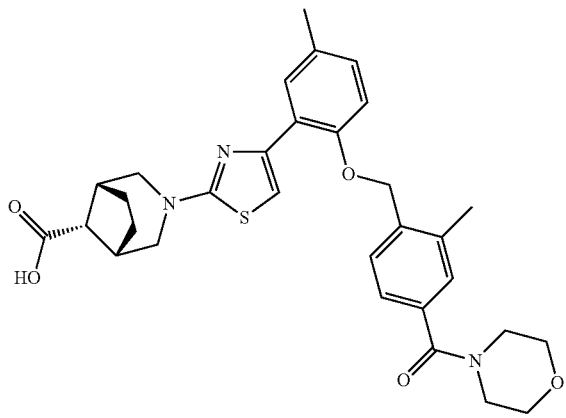 [SMILES: Cc1ccc(OCc2ccc(C(=O)N3CCOCC3)cc2C)c(-c2csc(N3C[C@H]4CC[C@@H](C3)[C@H]4C(=O)O)n2)c1] |
| 269 | 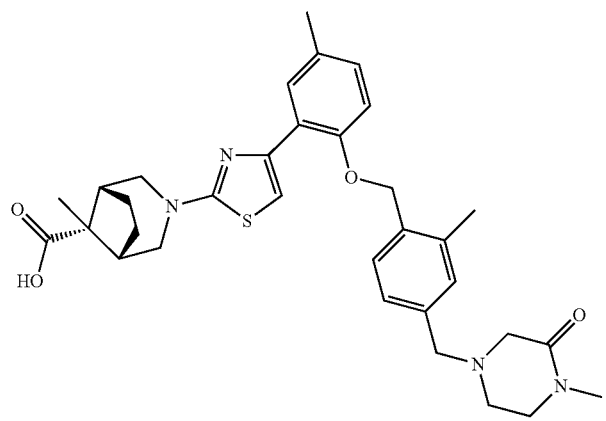 [SMILES: Cc1ccc(OCc2ccc(CN3CCN(C)C(=O)C3)cc2C)c(-c2csc(N3C[C@H]4CC[C@@H](C3)[C@@]4(C)C(=O)O)n2)c1] |
| 270 | 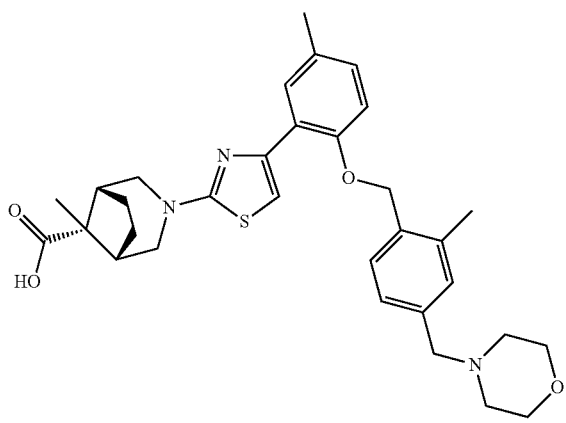 [SMILES: Cc1ccc(OCc2ccc(CN3CCOCC3)cc2C)c(-c2csc(N3C[C@H]4CC[C@@H](C3)[C@@]4(C)C(=O)O)n2)c1] |

TABLE 1-continued
| Cpd No. | |
|---|---|
| 271 | 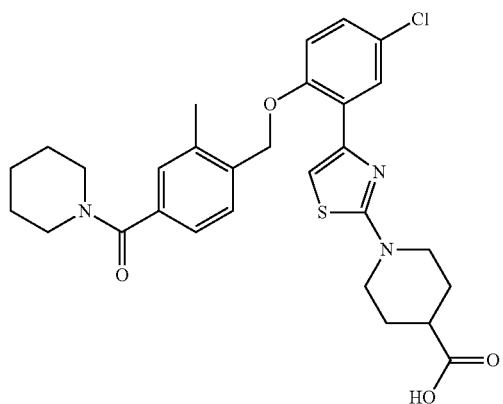 |
| 272 | 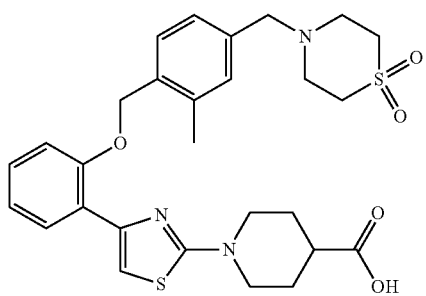 [SMILES: Cc1cc(CN2CCS(=O)(=O)CC2)ccc1COc1ccccc1-c1csc(N2CCC(C(=O)O)CC2)n1] |
| 273 | 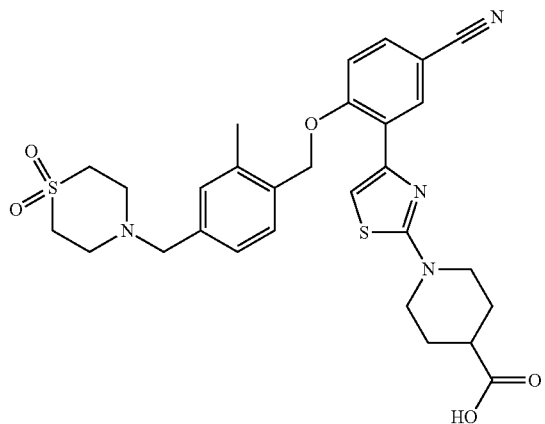 [SMILES: Cc1cc(CN2CCS(=O)(=O)CC2)ccc1COc1ccc(C#N)cc1-c1csc(N2CCC(C(=O)O)CC2)n1] |
| 274 | 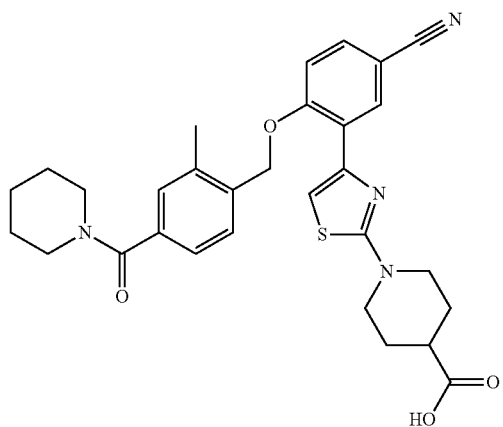 [SMILES: Cc1cc(C(=O)N2CCCCC2)ccc1COc1ccc(C#N)cc1-c1csc(N2CCC(C(=O)O)CC2)n1] |

TABLE 1-continued
| Cpd No. | |
|---|---|
| 275 | 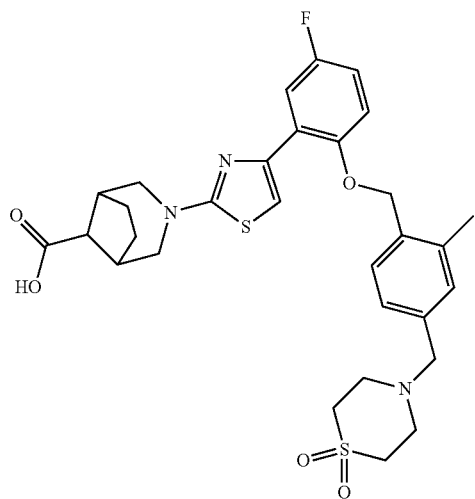 [SMILES: Cc1cc(CN2CCS(=O)(=O)CC2)ccc1COc1ccc(F)cc1-c1csc(N2CC3CCC(C2)C3C(=O)O)n1] |
| 276 | 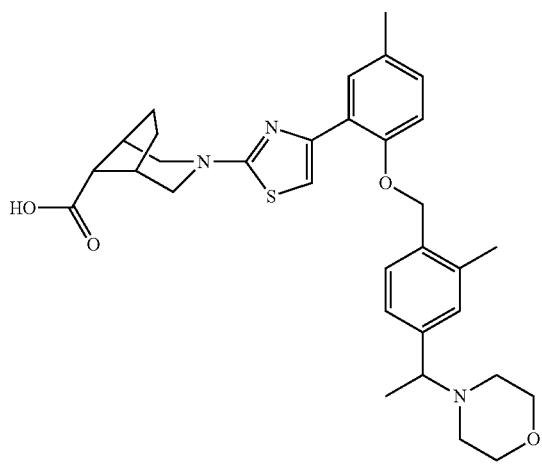 [SMILES: Cc1ccc(OCc2ccc(C(C)N3CCOCC3)cc2C)c(-c2csc(N3CC4CCC(C3)C4C(=O)O)n2)c1] |
| 277 | 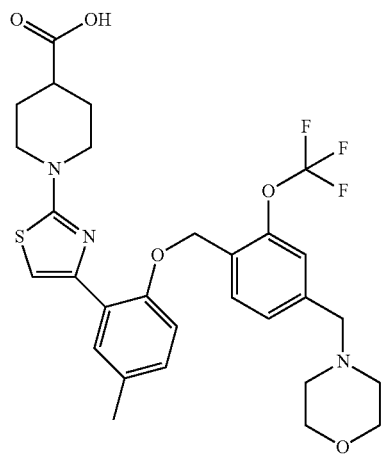 [SMILES: Cc1ccc(OCc2ccc(CN3CCOCC3)cc2OC(F)(F)F)c(-c2csc(N3CCC(C(=O)O)CC3)n2)c1] |

US 8,815,857 B2
193 194
TABLE 1-continued
| Cpd No. | |
|---|---|
| 278 | 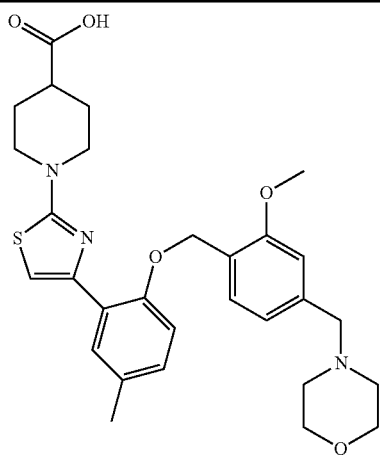 |
| 279 | 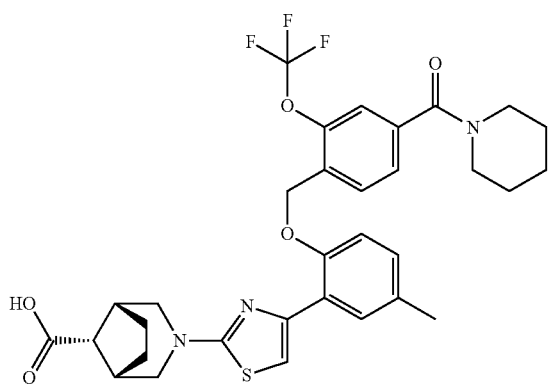 [SMILES: Cc1ccc(OCc2ccc(C(=O)N3CCCCC3)cc2OC(F)(F)F)c(-c2csc(N3C[C@H]4CC[C@@H](C3)[C@H]4C(=O)O)n2)c1] |
| 280 | 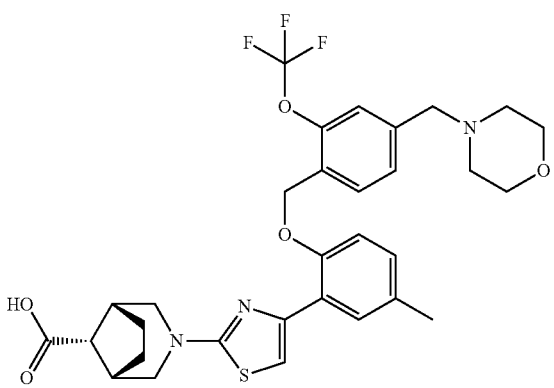 [SMILES: Cc1ccc(OCc2ccc(CN3CCOCC3)cc2OC(F)(F)F)c(-c2csc(N3C[C@H]4CC[C@@H](C3)[C@H]4C(=O)O)n2)c1] |
| 281 | 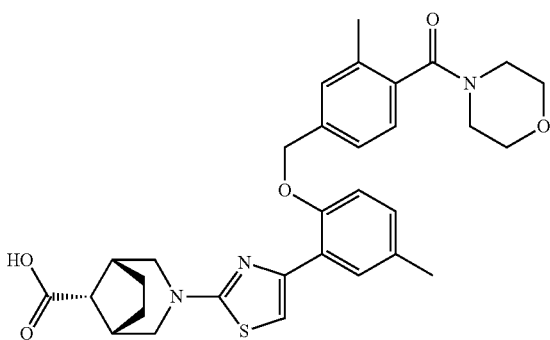 [SMILES: Cc1ccc(OCc2ccc(C(=O)N3CCOCC3)c(C)c2)c(-c2csc(N3C[C@H]4CC[C@@H](C3)[C@H]4C(=O)O)n2)c1] |

TABLE 1-continued
| Cpd No. | |
|---|---|
| 282 | 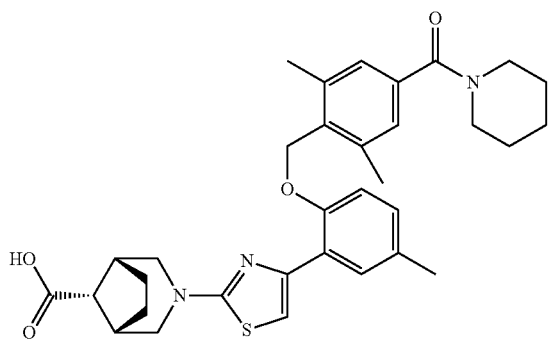 [SMILES: Cc1ccc(OCc2c(C)cc(C(=O)N3CCCCC3)cc2C)c(-c2csc(N3C[C@H]4CC[C@@H](C3)[C@H]4C(=O)O)n2)c1] |
| 283 | 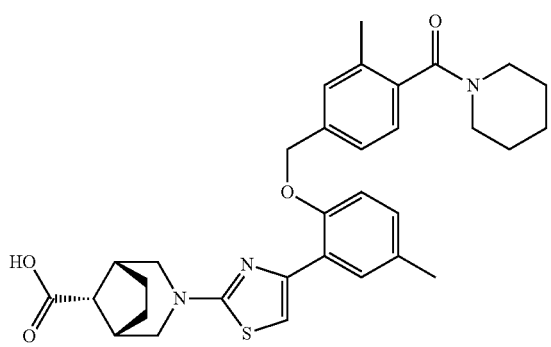 [SMILES: Cc1ccc(OCc2ccc(C(=O)N3CCCCC3)c(C)c2)c(-c2csc(N3C[C@H]4CC[C@@H](C3)[C@H]4C(=O)O)n2)c1] |
| 284 | 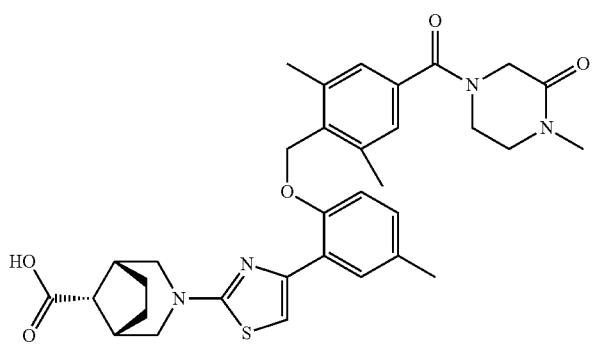 [SMILES: Cc1ccc(OCc2c(C)cc(C(=O)N3CCN(C)C(=O)C3)cc2C)c(-c2csc(N3C[C@H]4CC[C@@H](C3)[C@H]4C(=O)O)n2)c1] |
| 285 | 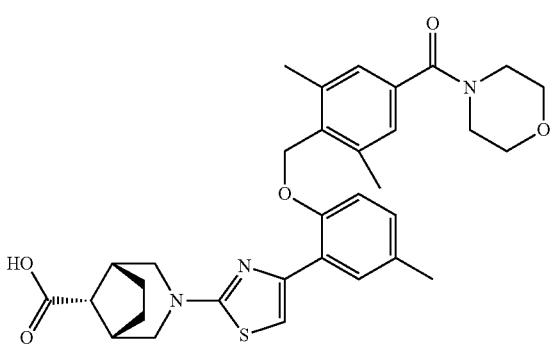 [SMILES: Cc1ccc(OCc2c(C)cc(C(=O)N3CCOCC3)cc2C)c(-c2csc(N3C[C@H]4CC[C@@H](C3)[C@H]4C(=O)O)n2)c1] |

TABLE 1-continued
Cpd No.
286
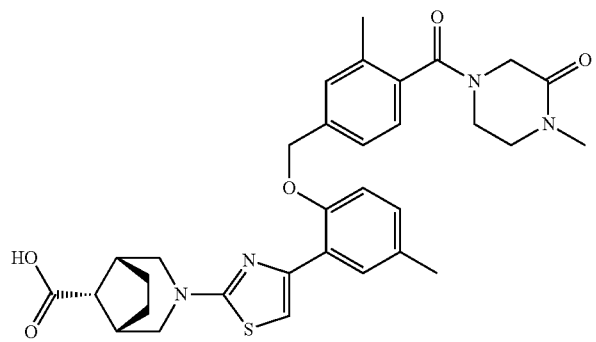 [SMILES: Cc1ccc(OCc2ccc(C(=O)N3CCN(C)C(=O)C3)c(C)c2)c(-c2csc(N3C[C@H]4CC[C@@H](C3)[C@H]4C(=O)O)n2)c1]
287
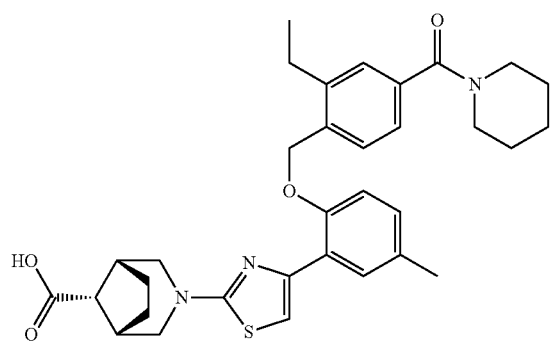 [SMILES: CCc1cc(C(=O)N2CCCCC2)ccc1COc1ccc(C)cc1-c1csc(N2C[C@H]3CC[C@@H](C2)[C@H]3C(=O)O)n1]
288
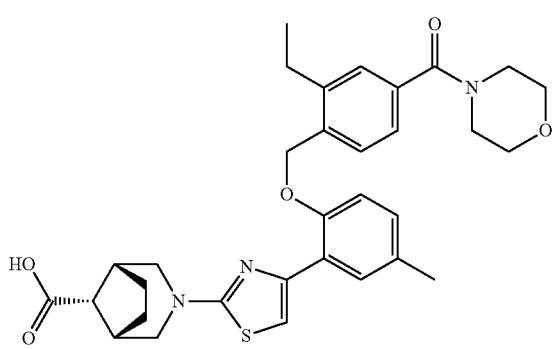 [SMILES: CCc1cc(C(=O)N2CCOCC2)ccc1COc1ccc(C)cc1-c1csc(N2C[C@H]3CC[C@@H](C2)[C@H]3C(=O)O)n1]
289
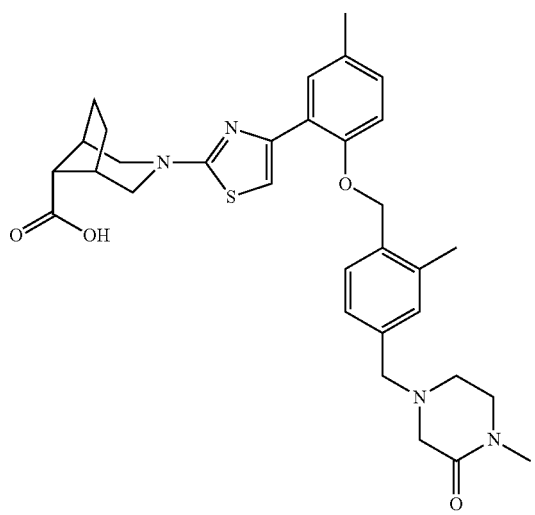 [SMILES: Cc1ccc(OCc2ccc(CN3CCN(C)C(=O)C3)cc2C)c(-c2csc(N3CC4CCC(C3)C4C(=O)O)n2)c1]

TABLE 1-continued
| Cpd No. | |
|---|---|
| 290 | 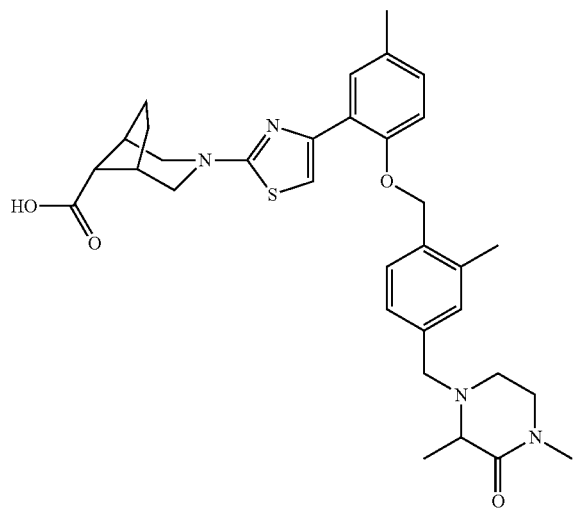 [SMILES: Cc1ccc(OCc2ccc(CN3CCN(C)C(=O)C3C)cc2C)c(-c2csc(N3CC4CCC(C3)C4C(=O)O)n2)c1] |
| 291 | 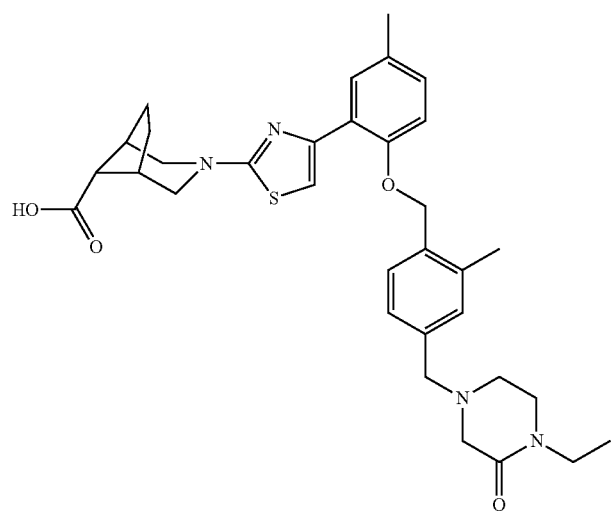 [SMILES: CCN1CCN(Cc2ccc(COc3ccc(C)cc3-c3csc(N4CC5CCC(C4)C5C(=O)O)n3)c(C)c2)CC1=O] |
| 292 | 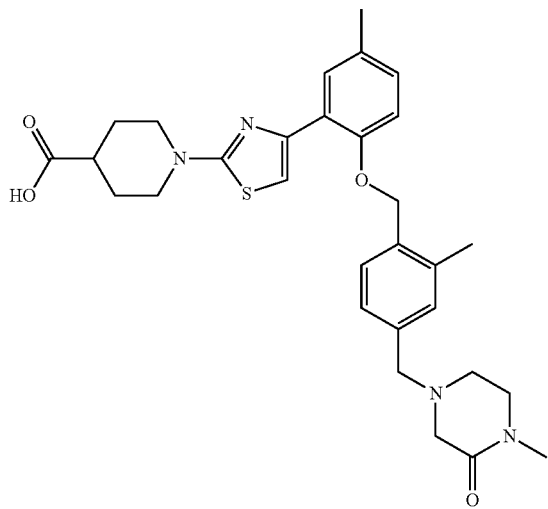 [SMILES: Cc1ccc(OCc2ccc(CN3CCN(C)C(=O)C3)cc2C)c(-c2csc(N3CCC(C(=O)O)CC3)n2)c1] |

TABLE 1-continued
| Cpd No. | |
|---|---|
| 293 | 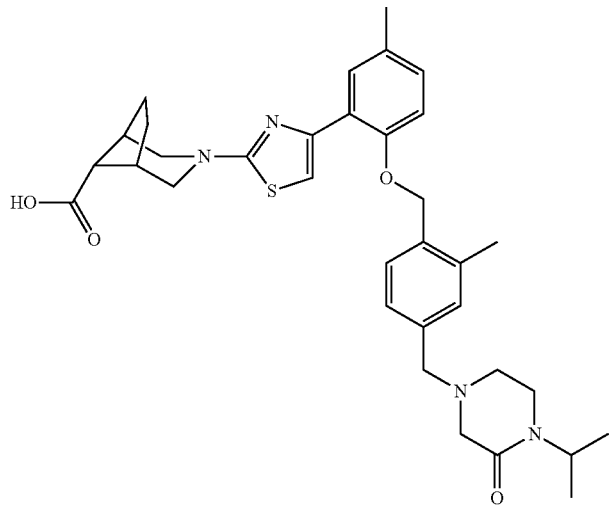 [SMILES: Cc1ccc(OCc2ccc(CN3CCN(C(C)C)C(=O)C3)cc2C)c(-c2csc(N3CC4CCC(C3)C4C(=O)O)n2)c1] |
| 294 | 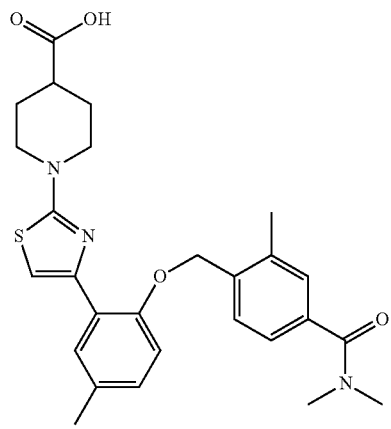 [SMILES: Cc1ccc(OCc2ccc(C(=O)N(C)C)cc2C)c(-c2csc(N3CCC(C(=O)O)CC3)n2)c1] |
| 295 | 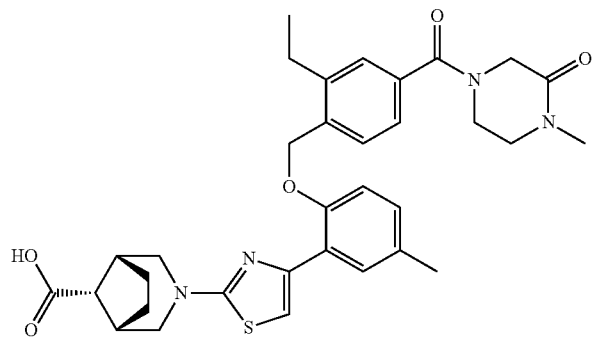 [SMILES: CCc1cc(C(=O)N2CCN(C)C(=O)C2)ccc1COc1ccc(C)cc1-c1csc(N2C[C@H]3CC[C@@H](C2)[C@H]3C(=O)O)n1] |

TABLE 1-continued
| Cpd No. | |
|---|---|
| 296 | 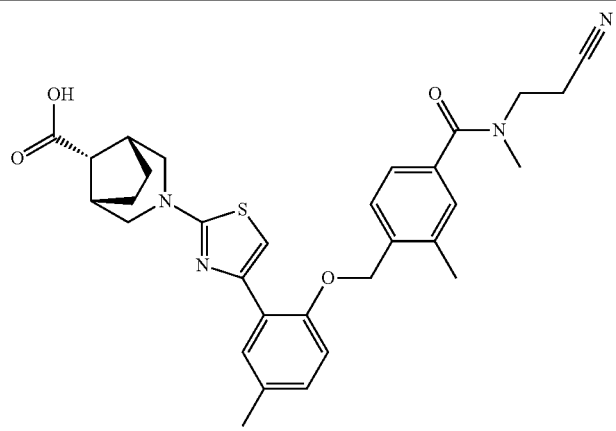 |
| 297 | 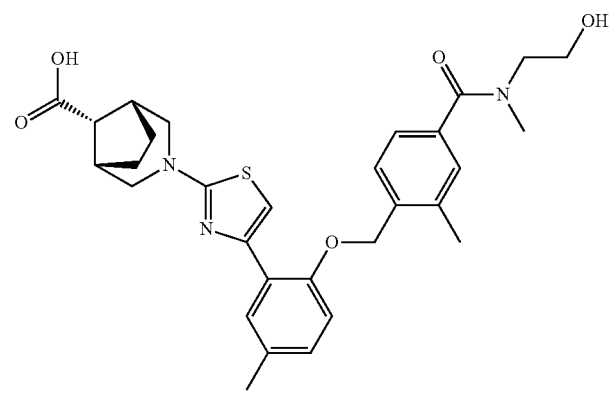 [SMILES: Cc1ccc(OCc2ccc(C(=O)N(C)CCO)cc2C)c(-c2csc(N3C[C@H]4CC[C@@H](C3)[C@H]4C(=O)O)n2)c1] |
| 298 | 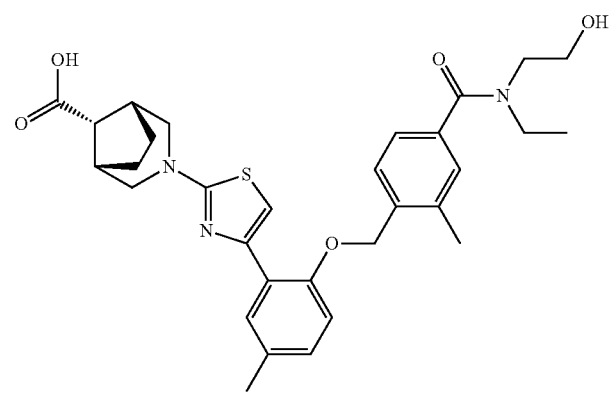 |
| 299 | 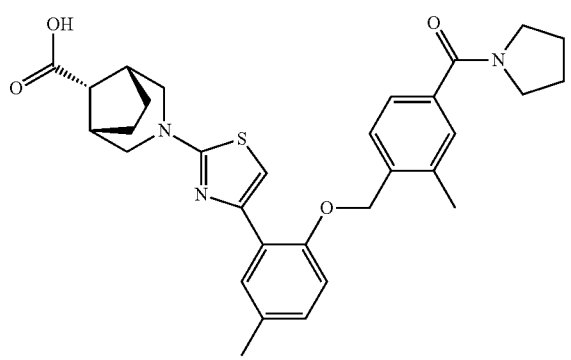 [SMILES: Cc1ccc(OCc2ccc(C(=O)N3CCCC3)cc2C)c(-c2csc(N3C[C@H]4CC[C@@H](C3)[C@H]4C(=O)O)n2)c1] |

TABLE 1-continued
| Cpd No. | |
|---|---|
| 300 | 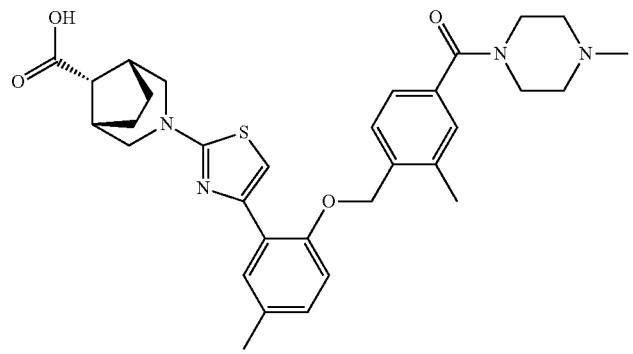 [SMILES: Cc1ccc(OCc2ccc(C(=O)N3CCN(C)CC3)cc2C)c(-c2csc(N3C[C@H]4CC[C@@H](C3)[C@H]4C(=O)O)n2)c1] |
| 301 | 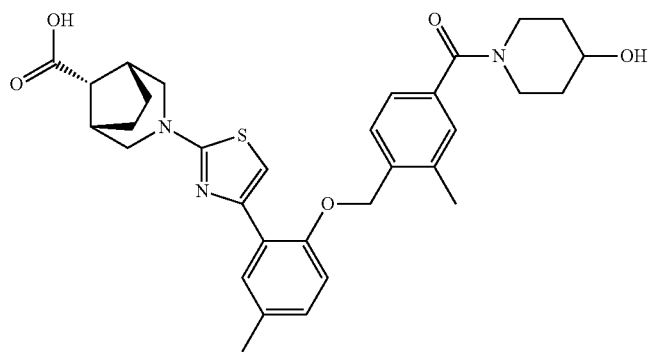 [SMILES: Cc1ccc(OCc2ccc(C(=O)N3CCC(O)CC3)cc2C)c(-c2csc(N3C[C@H]4CC[C@@H](C3)[C@H]4C(=O)O)n2)c1] |
| 302 | 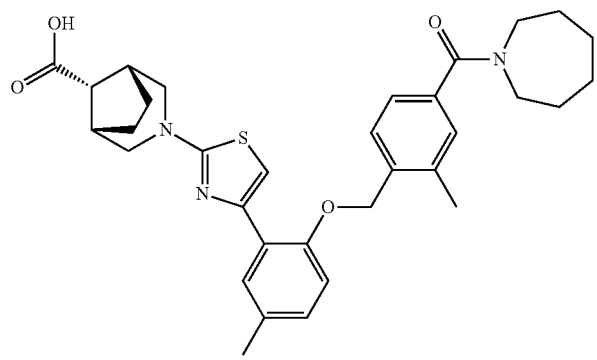 [SMILES: Cc1ccc(OCc2ccc(C(=O)N3CCCCCC3)cc2C)c(-c2csc(N3C[C@H]4CC[C@@H](C3)[C@H]4C(=O)O)n2)c1] |
| 303 | 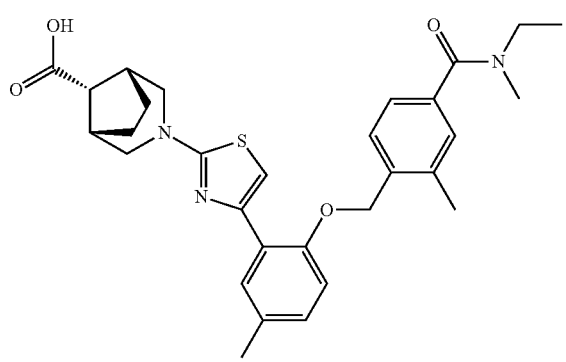 [SMILES: CCN(C)C(=O)c1ccc(COc2ccc(C)cc2-c2csc(N3C[C@H]4CC[C@@H](C3)[C@H]4C(=O)O)n2)c(C)c1] |

TABLE 1-continued
| Cpd No. | |
|---|---|
| 304 | 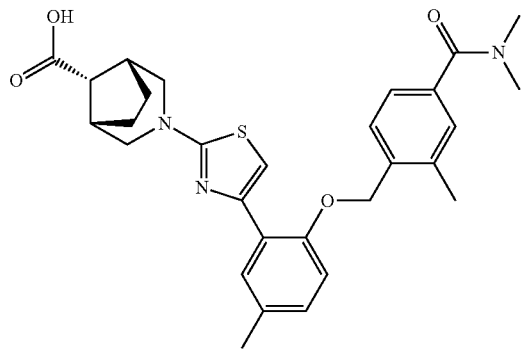 [SMILES: Cc1ccc(OCc2ccc(C(=O)N(C)C)cc2C)c(-c2csc(N3C[C@H]4CC[C@@H](C3)[C@H]4C(=O)O)n2)c1] |
| 305 | 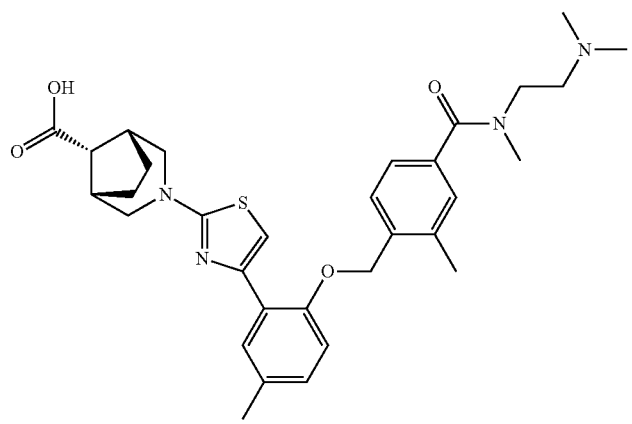 [SMILES: Cc1ccc(OCc2ccc(C(=O)N(C)CCN(C)C)cc2C)c(-c2csc(N3C[C@H]4CC[C@@H](C3)[C@H]4C(=O)O)n2)c1] |
| 306 | 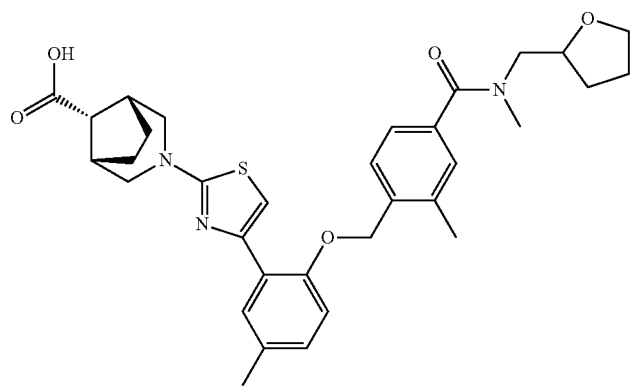 [SMILES: Cc1ccc(OCc2ccc(C(=O)N(C)CC3CCCO3)cc2C)c(-c2csc(N3C[C@H]4CC[C@@H](C3)[C@H]4C(=O)O)n2)c1] |
| 307 | 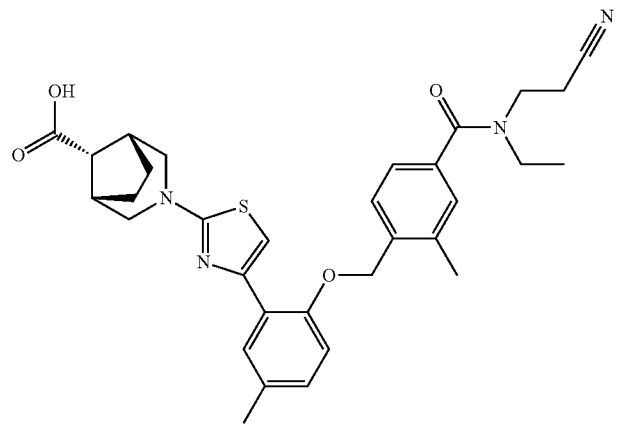 [SMILES: CCN(CCC#N)C(=O)c1ccc(COc2ccc(C)cc2-c2csc(N3C[C@H]4CC[C@@H](C3)[C@H]4C(=O)O)n2)c(C)c1] |

TABLE 1-continued
| Cpd No. | |
|---|---|
| 308 | 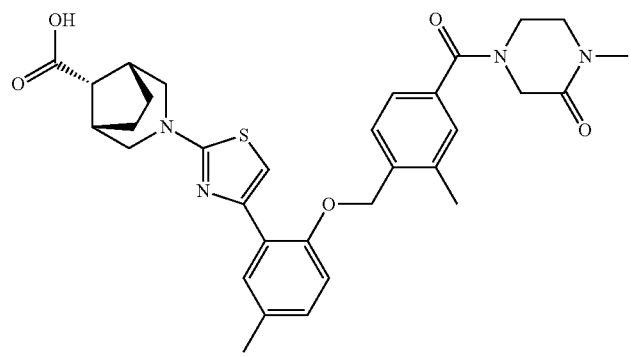 [SMILES: Cc1ccc(OCc2ccc(C(=O)N3CCN(C)C(=O)C3)cc2C)c(-c2csc(N3C[C@H]4CC[C@@H](C3)[C@H]4C(=O)O)n2)c1] |
| 309 | 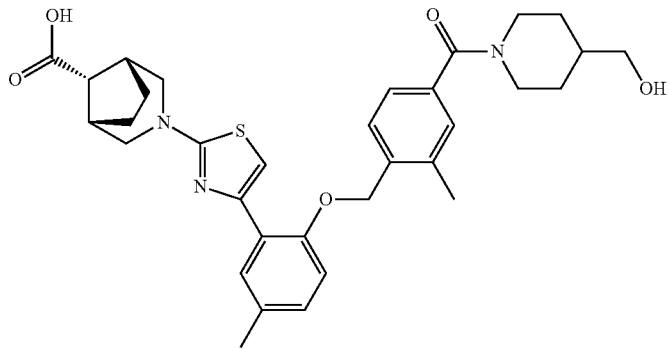 [SMILES: Cc1ccc(OCc2ccc(C(=O)N3CCC(CO)CC3)cc2C)c(-c2csc(N3C[C@H]4CC[C@@H](C3)[C@H]4C(=O)O)n2)c1] |
| 310 | 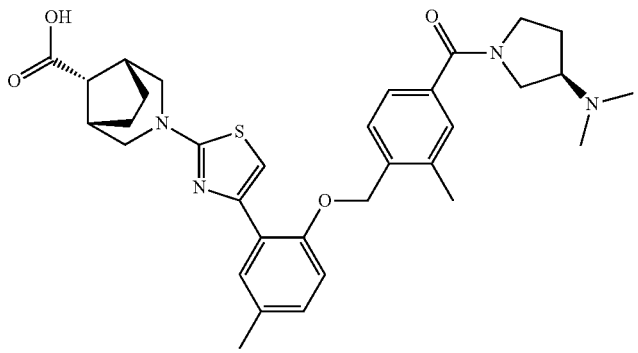 [SMILES: Cc1ccc(OCc2ccc(C(=O)N3CC[C@@H](N(C)C)C3)cc2C)c(-c2csc(N3C[C@H]4CC[C@@H](C3)[C@H]4C(=O)O)n2)c1] |
| 311 | 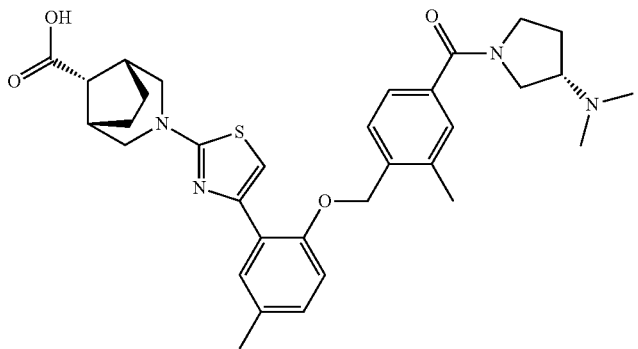 [SMILES: Cc1ccc(OCc2ccc(C(=O)N3CC[C@H](N(C)C)C3)cc2C)c(-c2csc(N3C[C@H]4CC[C@@H](C3)[C@H]4C(=O)O)n2)c1] |

TABLE 1-continued
Cpd No.
312
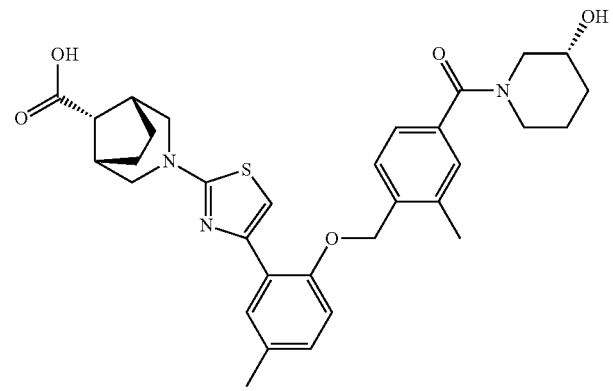 [SMILES: Cc1ccc(OCc2ccc(C(=O)N3CCC[C@@H](O)C3)cc2C)c(-c2csc(N3C[C@H]4CC[C@@H](C3)[C@H]4C(=O)O)n2)c1]
313
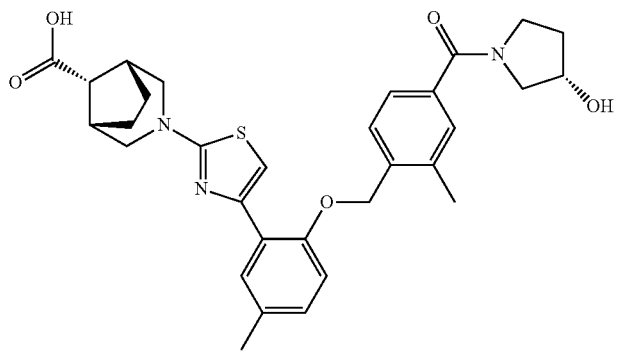 [SMILES: Cc1ccc(OCc2ccc(C(=O)N3CC[C@H](O)C3)cc2C)c(-c2csc(N3C[C@H]4CC[C@@H](C3)[C@H]4C(=O)O)n2)c1]
314
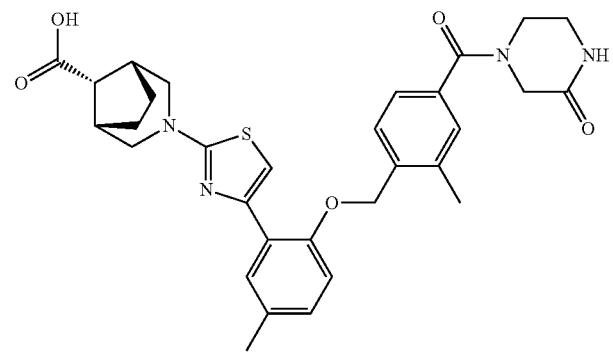 [SMILES: Cc1ccc(OCc2ccc(C(=O)N3CCNC(=O)C3)cc2C)c(-c2csc(N3C[C@H]4CC[C@@H](C3)[C@H]4C(=O)O)n2)c1]
315
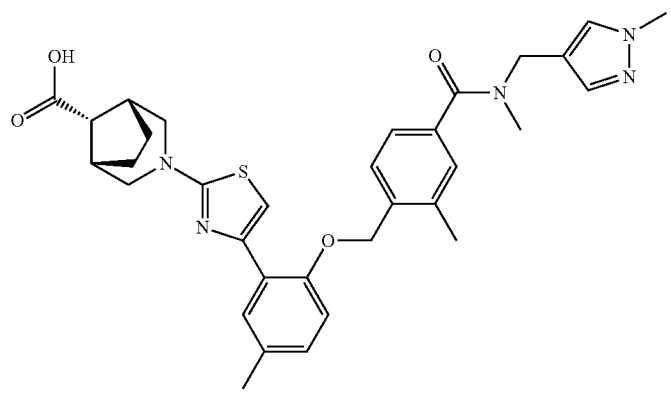

TABLE 1-continued
| Cpd No. | |
|---|---|
| 316 | 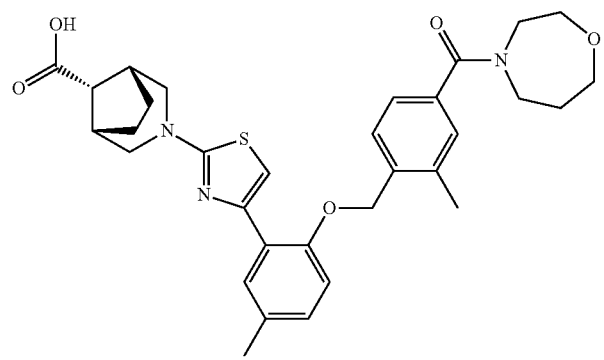 [SMILES: Cc1ccc(OCc2ccc(C(=O)N3CCCOCC3)cc2C)c(-c2csc(N3C[C@H]4CC[C@@H](C3)[C@H]4C(=O)O)n2)c1] |
| 317 | 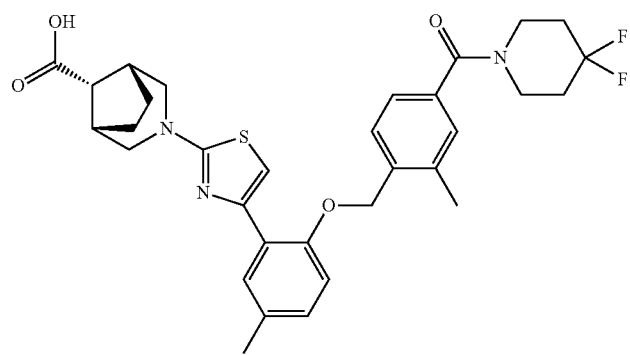 [SMILES: Cc1ccc(OCc2ccc(C(=O)N3CCC(F)(F)CC3)cc2C)c(-c2csc(N3C[C@H]4CC[C@@H](C3)[C@H]4C(=O)O)n2)c1] |
| 318 | 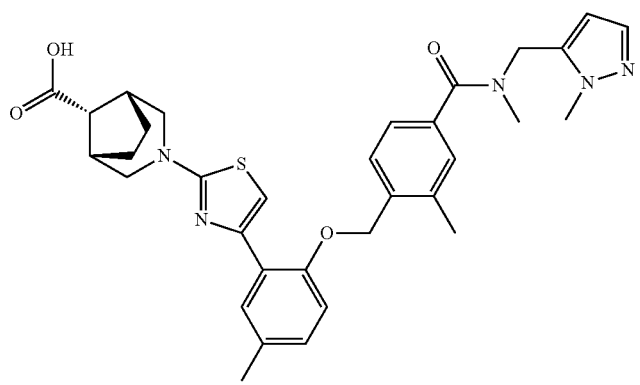 [SMILES: Cc1ccc(OCc2ccc(C(=O)N(C)Cc3ccnn3C)cc2C)c(-c2csc(N3C[C@H]4CC[C@@H](C3)[C@H]4C(=O)O)n2)c1] |
| 319 | 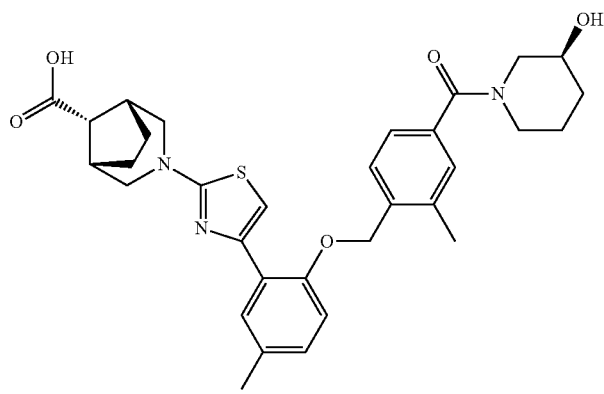 [SMILES: Cc1ccc(OCc2ccc(C(=O)N3CCC[C@H](O)C3)cc2C)c(-c2csc(N3C[C@H]4CC[C@@H](C3)[C@H]4C(=O)O)n2)c1] |

TABLE 1-continued
| Cpd No. | |
|---|---|
| 320 | 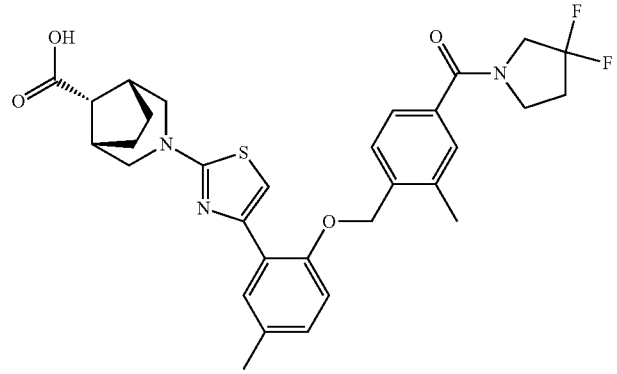 [SMILES: Cc1ccc(OCc2ccc(C(=O)N3CCC(F)(F)C3)cc2C)c(-c2csc(N3C[C@H]4CC[C@@H](C3)[C@H]4C(=O)O)n2)c1] |
| 321 | 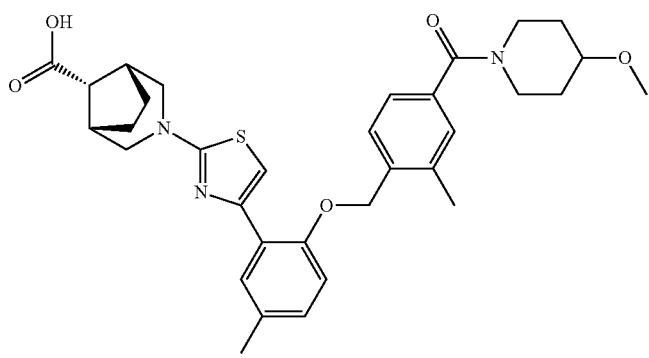 [SMILES: COC1CCN(C(=O)c2ccc(COc3ccc(C)cc3-c3csc(N4C[C@H]5CC[C@@H](C4)[C@H]5C(=O)O)n3)c(C)c2)CC1] |
| 322 | 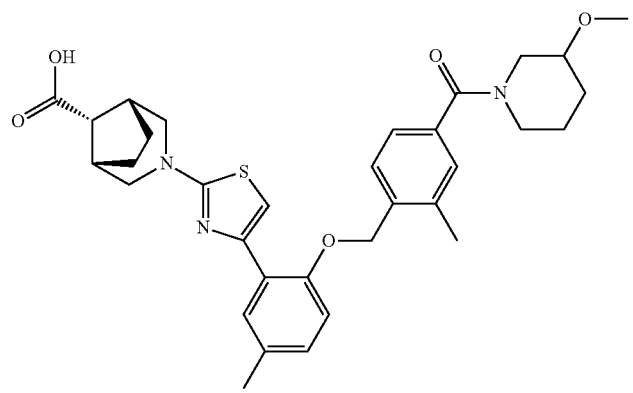 [SMILES: COC1CCCN(C(=O)c2ccc(COc3ccc(C)cc3-c3csc(N4C[C@H]5CC[C@@H](C4)[C@H]5C(=O)O)n3)c(C)c2)C1] |
| 323 | 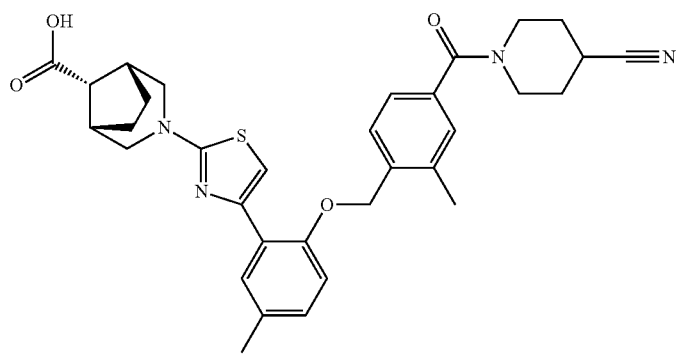 [SMILES: Cc1ccc(OCc2ccc(C(=O)N3CCC(C#N)CC3)cc2C)c(-c2csc(N3C[C@H]4CC[C@@H](C3)[C@H]4C(=O)O)n2)c1] |

TABLE 1-continued
| Cpd No. | |
|---|---|
| 324 | 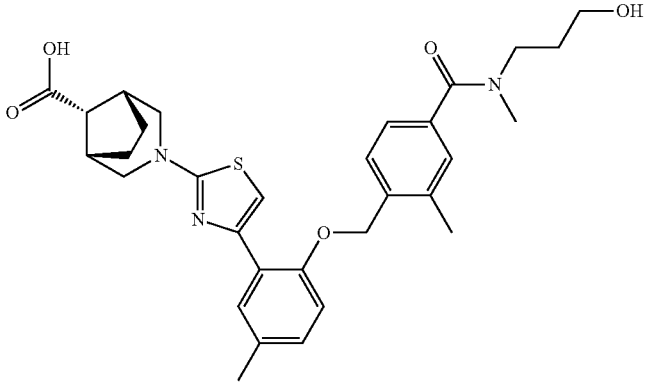 [SMILES: Cc1ccc(OCc2ccc(C(=O)N(C)CCCO)cc2C)c(-c2csc(N3C[C@H]4CC[C@@H](C3)[C@H]4C(=O)O)n2)c1] |
| 325 | 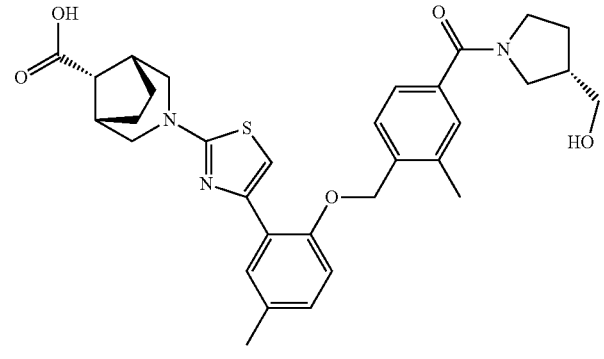 [SMILES: Cc1ccc(OCc2ccc(C(=O)N3CC[C@H](CO)C3)cc2C)c(-c2csc(N3C[C@H]4CC[C@@H](C3)[C@H]4C(=O)O)n2)c1] |
| 326 | 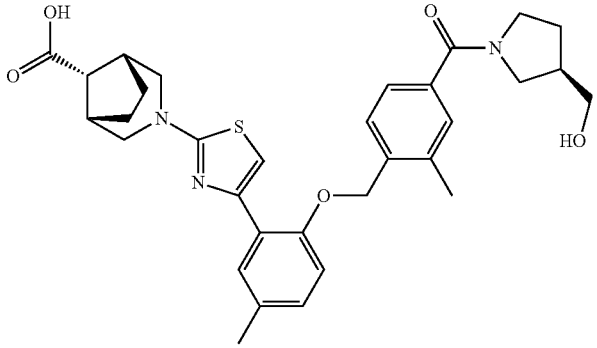 [SMILES: Cc1ccc(OCc2ccc(C(=O)N3CC[C@@H](CO)C3)cc2C)c(-c2csc(N3C[C@H]4CC[C@@H](C3)[C@H]4C(=O)O)n2)c1] |
| 327 | 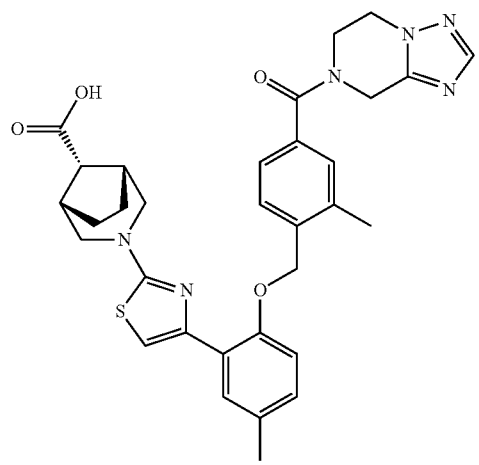 [SMILES: Cc1ccc(OCc2ccc(C(=O)N3CCn4ncnc4C3)cc2C)c(-c2csc(N3C[C@H]4CC[C@@H](C3)[C@H]4C(=O)O)n2)c1] |

TABLE 1-continued
| Cpd No. | |
|---|---|
| 328 | 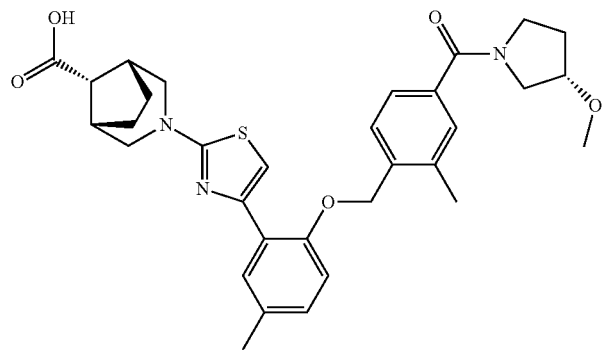 [SMILES: CO[C@H]1CCN(C(=O)c2ccc(COc3ccc(C)cc3-c3csc(N4C[C@H]5CC[C@@H](C4)[C@H]5C(=O)O)n3)c(C)c2)C1] |
| 329 | 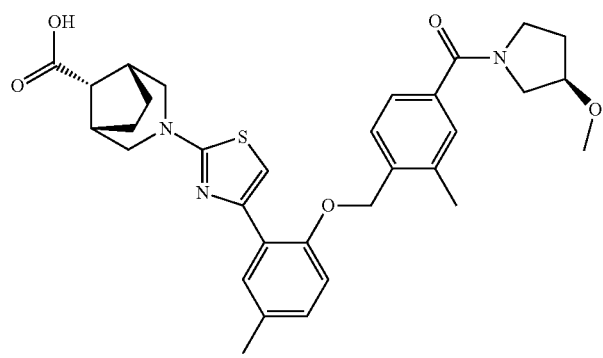 [SMILES: CO[C@@H]1CCN(C(=O)c2ccc(COc3ccc(C)cc3-c3csc(N4C[C@H]5CC[C@@H](C4)[C@H]5C(=O)O)n3)c(C)c2)C1] |
| 330 | 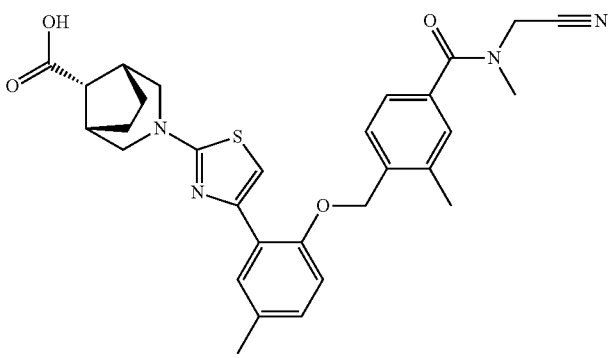 [SMILES: Cc1ccc(OCc2ccc(C(=O)N(C)CC#N)cc2C)c(-c2csc(N3C[C@H]4CC[C@@H](C3)[C@H]4C(=O)O)n2)c1] |
| 331 | 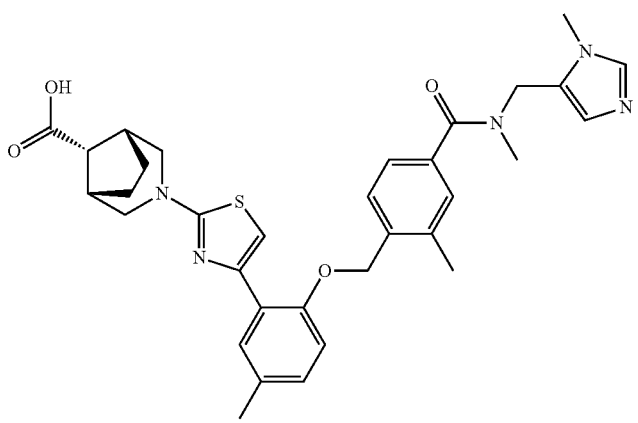 [SMILES: Cc1ccc(OCc2ccc(C(=O)N(C)Cc3cncn3C)cc2C)c(-c2csc(N3C[C@H]4CC[C@@H](C3)[C@H]4C(=O)O)n2)c1] |

| Cpd No. | |
|---|---|
| 332 | 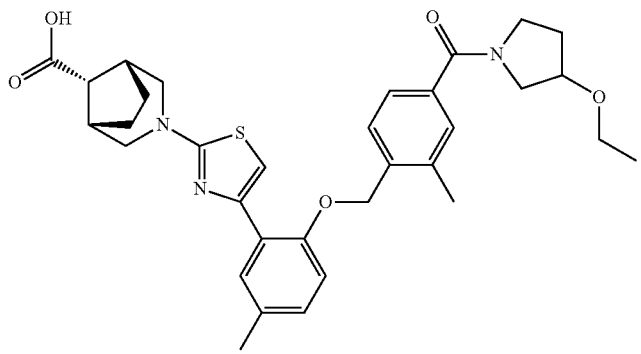 [SMILES: CCOC1CCN(C(=O)c2ccc(COc3ccc(C)cc3-c3csc(N4C[C@H]5CC[C@@H](C4)[C@H]5C(=O)O)n3)c(C)c2)C1] |
| 333 | 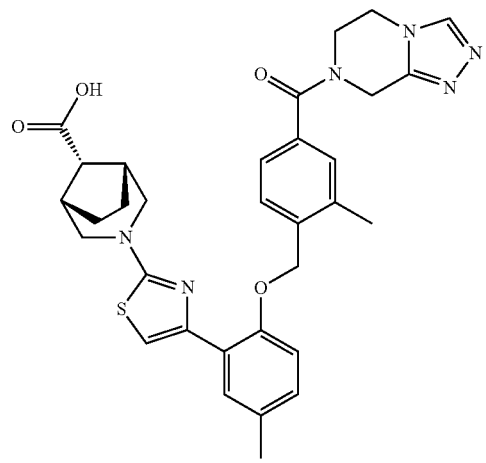 [SMILES: Cc1ccc(OCc2ccc(C(=O)N3CCn4cnnc4C3)cc2C)c(-c2csc(N3C[C@H]4CC[C@@H](C3)[C@H]4C(=O)O)n2)c1] |
| 334 | 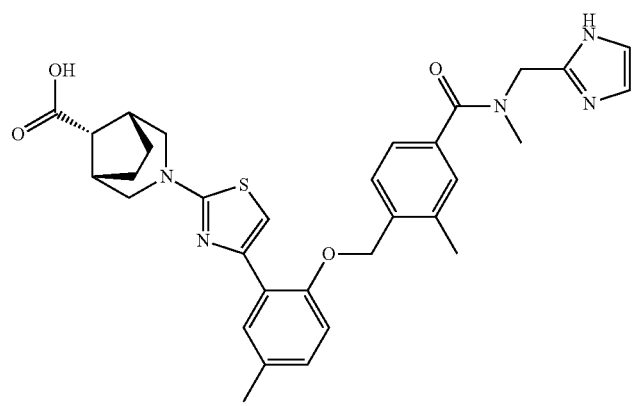 [SMILES: Cc1ccc(OCc2ccc(C(=O)N(C)Cc3ncc[nH]3)cc2C)c(-c2csc(N3C[C@H]4CC[C@@H](C3)[C@H]4C(=O)O)n2)c1] |

TABLE 1-continued
Cpd No.
335
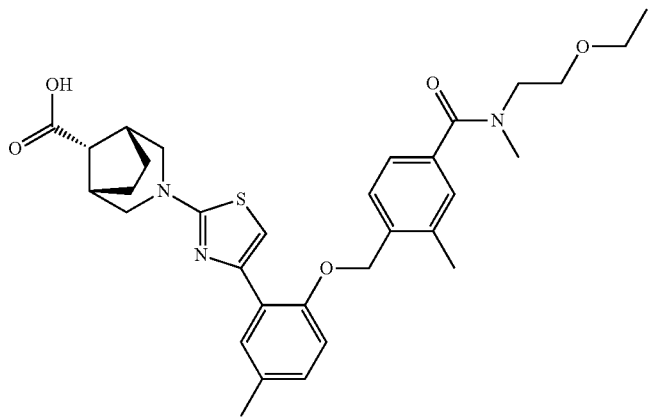
336
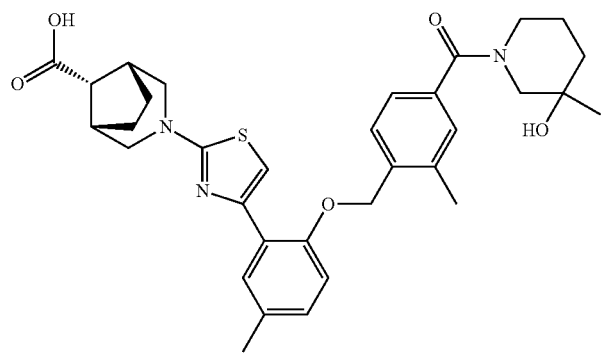 [SMILES: Cc1ccc(OCc2ccc(C(=O)N3CCCC(C)(O)C3)cc2C)c(-c2csc(N3C[C@H]4CC[C@@H](C3)[C@H]4C(=O)O)n2)c1]
337
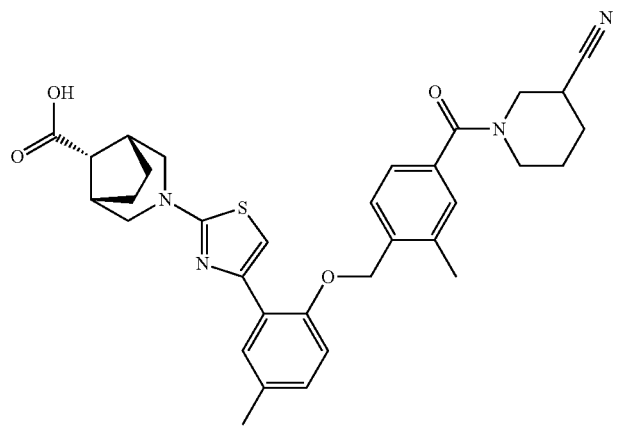 [SMILES: Cc1ccc(OCc2ccc(C(=O)N3CCCC(C#N)C3)cc2C)c(-c2csc(N3C[C@H]4CC[C@@H](C3)[C@H]4C(=O)O)n2)c1]

TABLE 1-continued
| Cpd No. | |
|---|---|
| 338 | 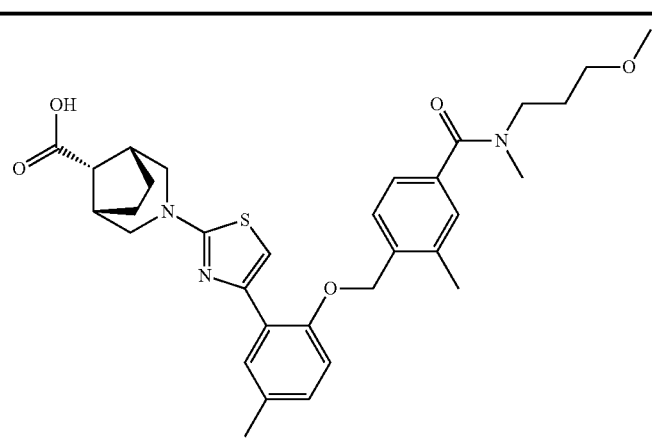 |
| 339 | 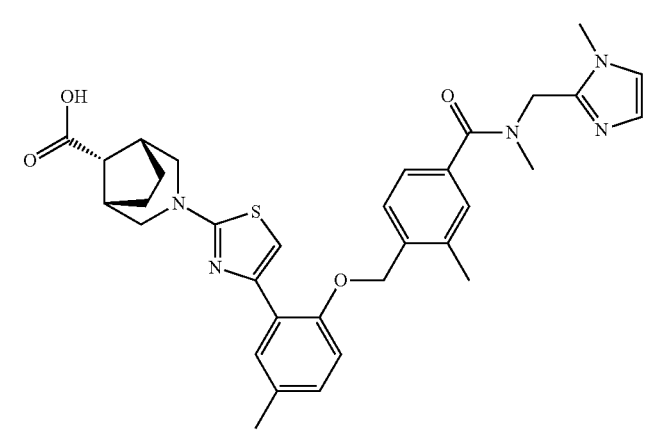 [SMILES: Cc1ccc(OCc2ccc(C(=O)N(C)Cc3nccn3C)cc2C)c(-c2csc(N3C[C@H]4CC[C@@H](C3)[C@H]4C(=O)O)n2)c1] |
| 340 | 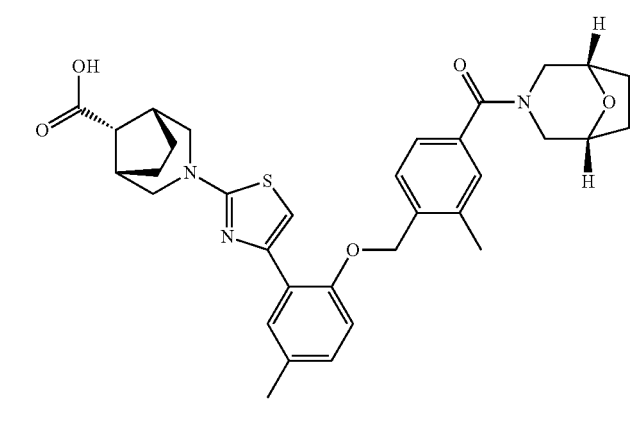 [SMILES: Cc1ccc(OCc2ccc(C(=O)N3C[C@H]4CC[C@@H](C3)O4)cc2C)c(-c2csc(N3C[C@H]4CC[C@@H](C3)[C@H]4C(=O)O)n2)c1] |
| 341 | 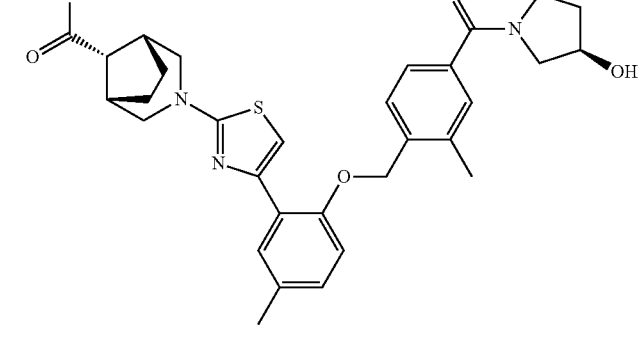 |

TABLE 1-continued
| Cpd No. | |
|---|---|
| 342 | 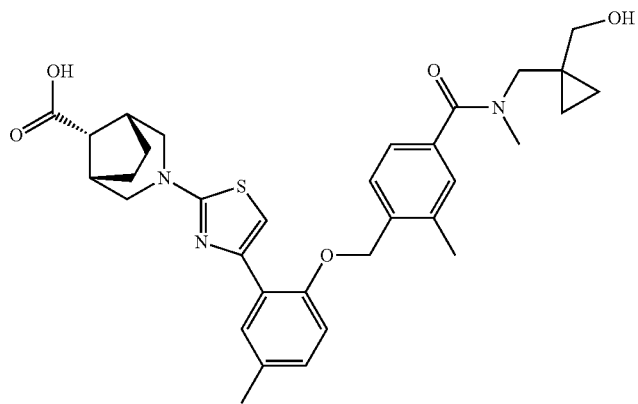 [SMILES: Cc1ccc(OCc2ccc(C(=O)N(C)CC3(CO)CC3)cc2C)c(-c2csc(N3C[C@H]4CC[C@@H](C3)[C@H]4C(=O)O)n2)c1] |
| 343 | 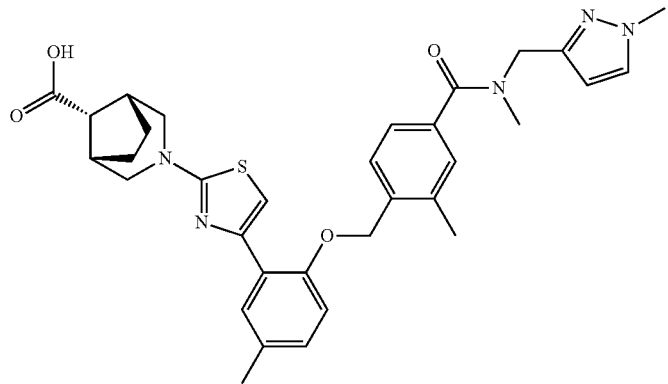 [SMILES: Cc1ccc(OCc2ccc(C(=O)N(C)Cc3ccn(C)n3)cc2C)c(-c2csc(N3C[C@H]4CC[C@@H](C3)[C@H]4C(=O)O)n2)c1] |
| 344 | 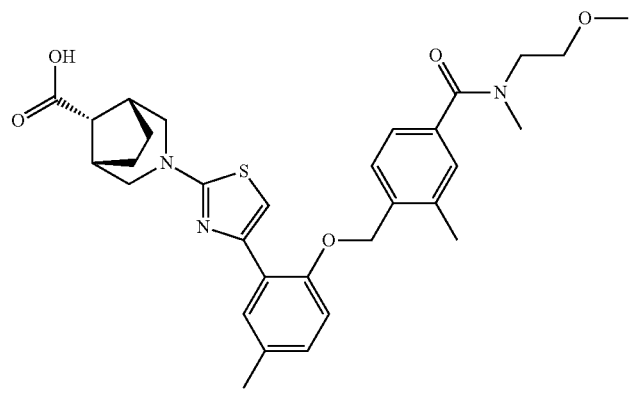 [SMILES: COCCN(C)C(=O)c1ccc(COc2ccc(C)cc2-c2csc(N3C[C@H]4CC[C@@H](C3)[C@H]4C(=O)O)n2)c(C)c1] |

TABLE 1-continued
| Cpd No. |
| --- |
345
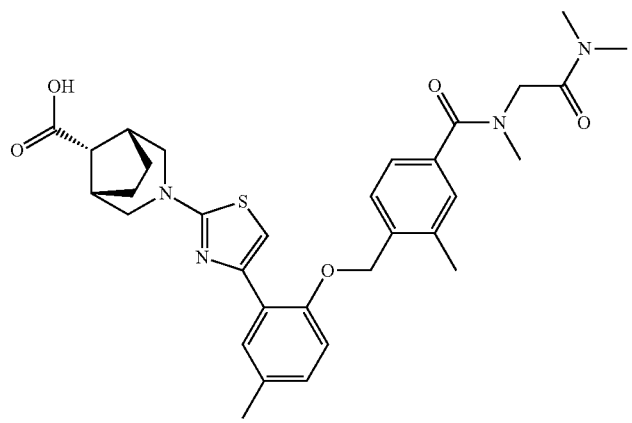 [SMILES: Cc1ccc(OCc2ccc(C(=O)N(C)CC(=O)N(C)C)cc2C)c(-c2csc(N3C[C@H]4CC[C@@H](C3)[C@H]4C(=O)O)n2)c1]
346
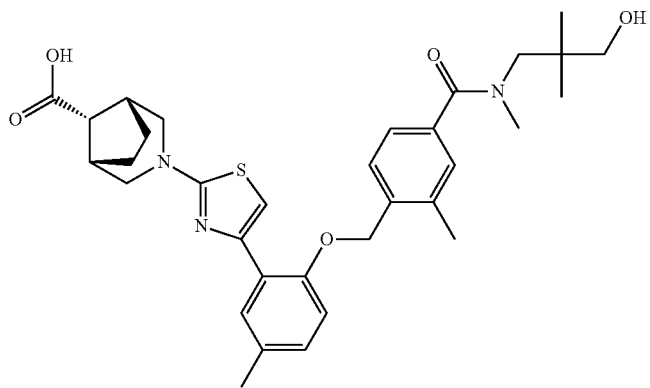 [SMILES: Cc1ccc(OCc2ccc(C(=O)N(C)CC(C)(C)CO)cc2C)c(-c2csc(N3C[C@H]4CC[C@@H](C3)[C@H]4C(=O)O)n2)c1]
347
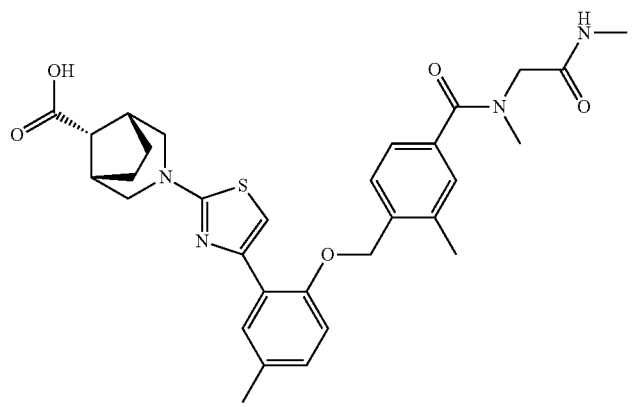 [SMILES: CNC(=O)CN(C)C(=O)c1ccc(COc2ccc(C)cc2-c2csc(N3C[C@H]4CC[C@@H](C3)[C@H]4C(=O)O)n2)c(C)c1]

| Cpd No. | |
|---|---|
| 348 | 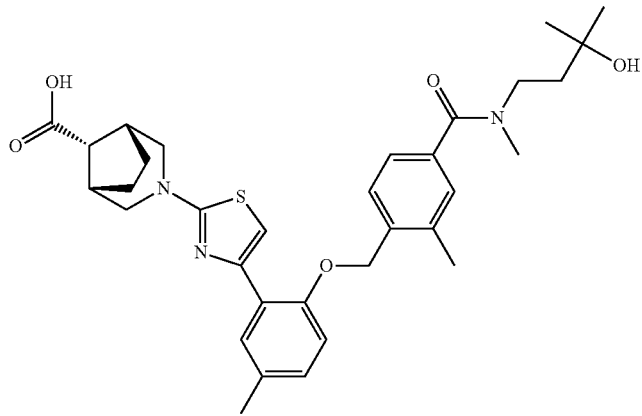 [SMILES: Cc1ccc(OCc2ccc(C(=O)N(C)CCC(C)(C)O)cc2C)c(-c2csc(N3C[C@H]4CC[C@@H](C3)[C@H]4C(=O)O)n2)c1] |
| 349 | 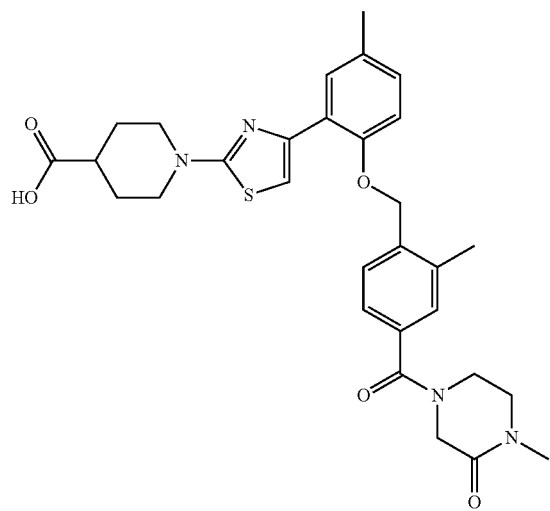 [SMILES: Cc1ccc(OCc2ccc(C(=O)N3CCN(C)C(=O)C3)cc2C)c(-c2csc(N3CCC(C(=O)O)CC3)n2)c1] |
| 350 | 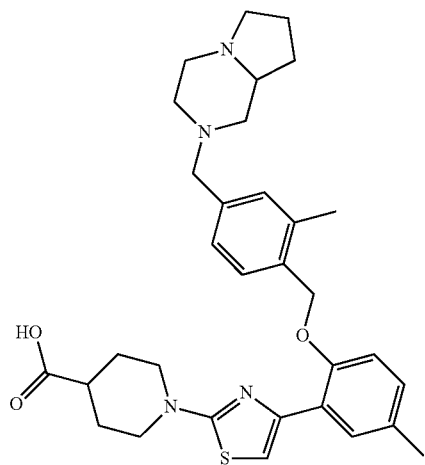 [SMILES: Cc1ccc(OCc2ccc(CN3CCN4CCCC4C3)cc2C)c(-c2csc(N3CCC(C(=O)O)CC3)n2)c1] |

TABLE 1-continued
Cpd No.
351
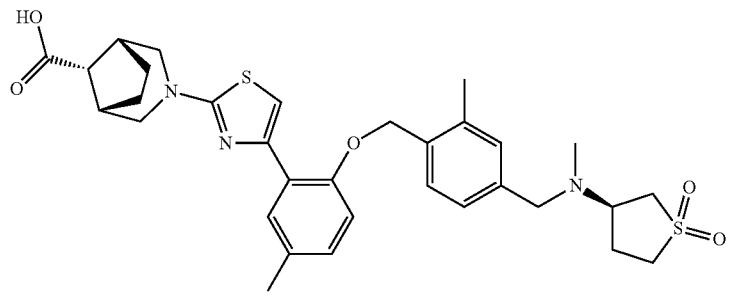 [SMILES: Cc1ccc(OCc2ccc(CN(C)[C@@H]3CCS(=O)(=O)C3)cc2C)c(-c2csc(N3C[C@H]4CC[C@@H](C3)[C@H]4C(=O)O)n2)c1]
352
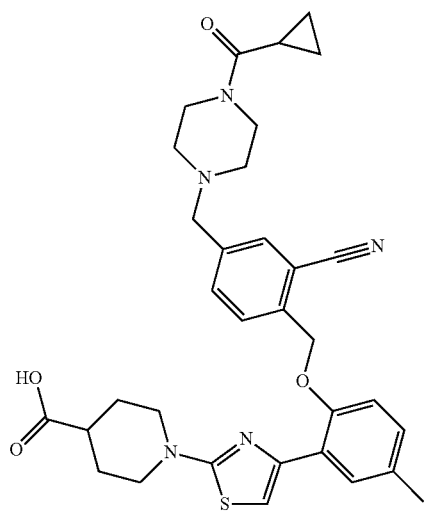 [SMILES: Cc1ccc(OCc2ccc(CN3CCN(C(=O)C4CC4)CC3)cc2C#N)c(-c2csc(N3CCC(C(=O)O)CC3)n2)c1]
353
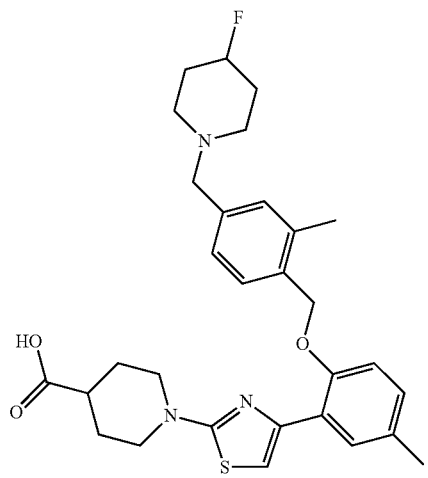 [SMILES: Cc1ccc(OCc2ccc(CN3CCC(F)CC3)cc2C)c(-c2csc(N3CCC(C(=O)O)CC3)n2)c1]

| Cpd No. | |
|---|---|
| 354 | 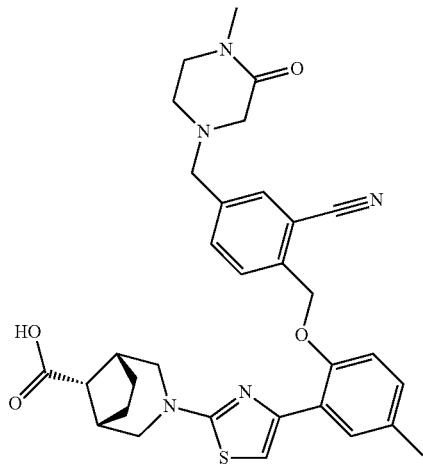 [SMILES: Cc1ccc(OCc2ccc(CN3CCN(C)C(=O)C3)cc2C#N)c(-c2csc(N3C[C@H]4CC[C@@H](C3)[C@H]4C(=O)O)n2)c1] |
| 355 | 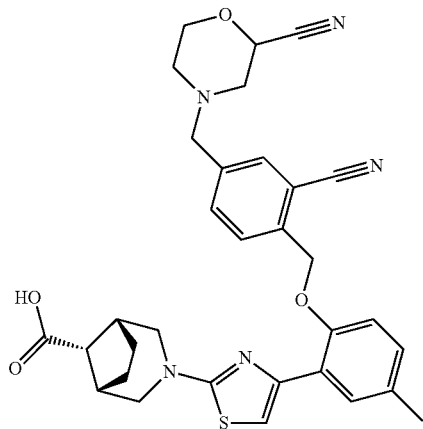 [SMILES: Cc1ccc(OCc2ccc(CN3CCOC(C#N)C3)cc2C#N)c(-c2csc(N3C[C@H]4CC[C@@H](C3)[C@H]4C(=O)O)n2)c1] |
| 356 | 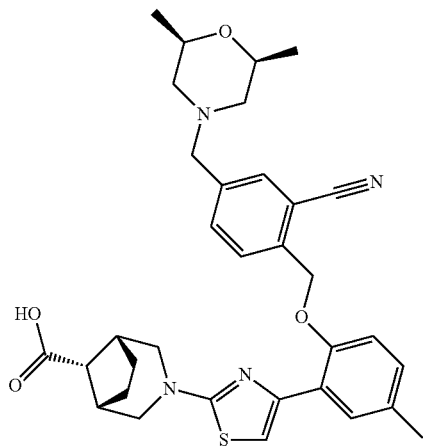 [SMILES: Cc1ccc(OCc2ccc(CN3C[C@@H](C)O[C@@H](C)C3)cc2C#N)c(-c2csc(N3C[C@H]4CC[C@@H](C3)[C@H]4C(=O)O)n2)c1] |

TABLE 1-continued
| Cpd No. | |
|---|---|
| 357 | 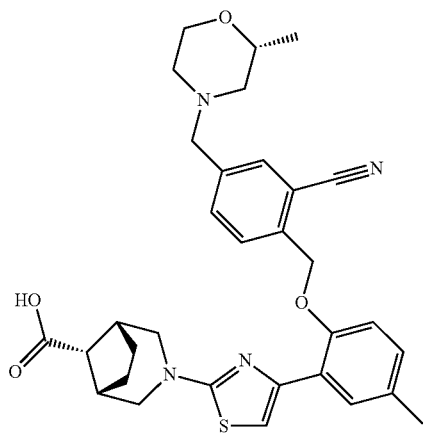 [SMILES: Cc1ccc(OCc2ccc(CN3CCO[C@H](C)C3)cc2C#N)c(-c2csc(N3C[C@H]4CC[C@@H](C3)[C@H]4C(=O)O)n2)c1] |
| 358 | 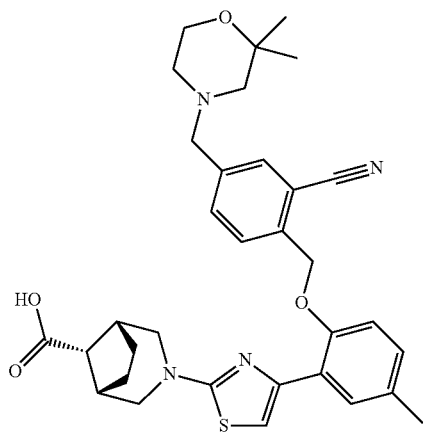 [SMILES: Cc1ccc(OCc2ccc(CN3CCOC(C)(C)C3)cc2C#N)c(-c2csc(N3C[C@H]4CC[C@@H](C3)[C@H]4C(=O)O)n2)c1] |
| 359 | 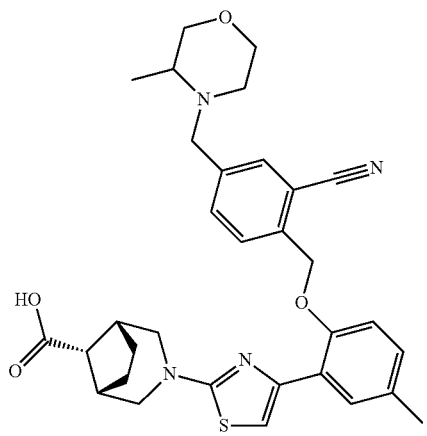 [SMILES: Cc1ccc(OCc2ccc(CN3CCOCC3C)cc2C#N)c(-c2csc(N3C[C@H]4CC[C@@H](C3)[C@H]4C(=O)O)n2)c1] |

TABLE 1-continued

| Cpd No. | |
|---|---|
| 360 | |
| 361 | |

In one embodiment, the invention relates to any of the compounds depicted in Table 1 above and the pharmaceutically acceptable salts thereof.

In another embodiment, the invention relates to the group consisting of compounds 1, 13, 15, 17, 20, 21, 28, 30, 36, 39, 41-43, 49, 52, 59, 62, 63, 65, 67-70, 72-74, 79, 81, 84, 88-90, 92, 95, 97, 102-108, 111, 113, 117-120, 122-126, 129-133, 136-138, 140-144, 151-153, 161, 162, 164, 167, 173, 176, 177, 194-196, 198-200, 203-209, 211, 212, 214, 217, 218, 220-232, 234-238, 240-244, 248, 249, 250, 263-272, 276-293, 296-346, and 348-361 from Table 1 above and the pharmaceutically acceptable salts thereof.

In another embodiment, the invention relates to the group consisting of compounds 7, 13, 20, 30, 39, 43, 65, 74, 89, 95, 136, 167, 194, 198, 208, 214, 217, 218, 220-226, 228, 232, 238, 263-270, 276, 277, 279, 280, 287, 288-293, 295, 299, 300, 302-304, 306-309, 311, 312, 316, 317, 320-323, 325, 327-329, 332, 336, 337, 340, 344, 349, 351 and 354-361 from Table 1 above and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl(isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $-(CH_2)-$, $-(CH_2-CH_2)-$, $-(CH(CH_3))-$, $-(CH_2-CH_2-CH_2)-$, $-(C(CH_3)_2)-$, $-(CH(CH_2CH_3))-$, $-(CH(CH_3)-CH_2)-$, $-(CH_2-CH(CH_3))-$, $-(CH_2-CH_2-CH_2-CH_2)-$, $-(CH_2-CH_2-CH(CH_3))-$, $-(CH(CH_3)-CH_2-CH_2)-$, $-(CH_2-CH(CH_3)-CH_2)-$, $-(CH_2-C(CH_3)_2)-$, $-(C(CH_3)_2-CH_2)-$, $-(CH(CH_3)-CH(CH_3))-$, $-(CH_2-CH(CH_2CH_3))-$, $-(CH(CH_2CH_3)-CH_2)-$, $-(CH(CH_2CH_3)-CH_2)-$, $-(CH(CH_2CH_2CH_3))-$, $-(CHCH(CH_3)_2)-$ and $-C(CH_3)(CH_2CH_3)-$.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 4 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]

heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —$S(O)_2$—$C_{1-6}$ alkyl, likewise, —S—$R_a$ may be represented as phenyl-$S(O)_m$— when $R_a$ is phenyl and where m is 0, 1 or 2.

General Synthetic Methods

The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Starting materials and reagents used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization. Flash chromatography purification methods used anywhere from 0-100% EtOAc in heptane or 0-10% MeOH in $CH_2Cl_2$. HPLC purification methods used anywhere from 0-100% acetonitrile in water and may contain 0.1% formic acid or 0.1% TFA and one of the following columns:

a) Waters Sunfire OBD C18 5 µM 30×150 mm column
b) Waters XBridge OBD C18 5 µM 30×150 mm column
c) Waters OBD C8 5 µM 19×150 mm column.
d) Waters Atlantis OBD DC18 5 µM 19×250 mm column.
e) Waters Atlantis T3 OBD 5 µM 30×150 mm column
f) Phenomenex Gemini Axia C18 5 µM 30×100 mm column
g) Waters SunFire C18 Prep OBD 5 µM 19×150 mm
h) Waters XBridge Prep C18 5 µM 19×100 mm The methods described below and in the Synthetic Examples section may be used to prepare the compounds of formula I. In the Schemes below, compounds of formula I and intermediate structures are shown having n=1 and $R^5$ in a position on the phenyl ring meta with respect to $R^4$. The methods may also be used to prepare compounds of formula I having n=2 and $R^5$ in any available position.

Compounds of formula I may be prepared by Method 1 as described in Scheme 1.

Scheme 1 (Method 1)

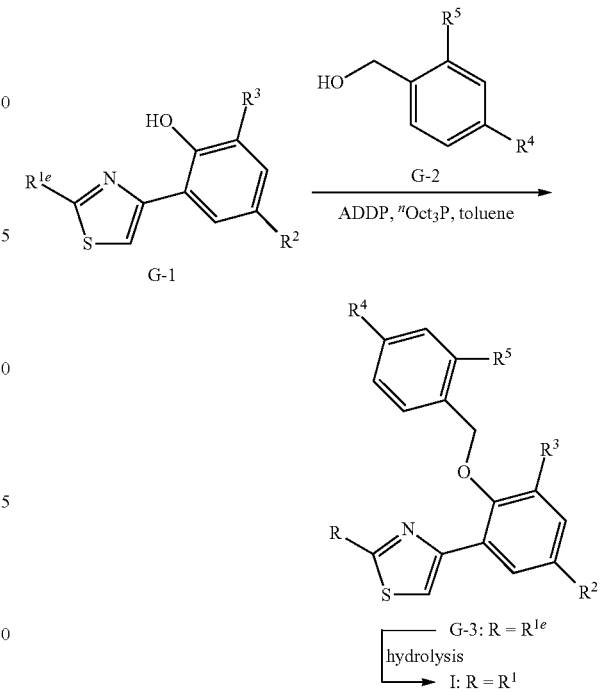

$R^{1e}$ = ester of $R^1$

As described in Scheme 1, intermediate G-1 is reacted with G-2 under suitable coupling conditions such as reacting in the presence of trioctylphosphine 1,1'-(azodicarbonyl)dipiperidine to provide the ester G-3. Hydrolysis of the ester, for example by treatment with aqueous base provides the desired compound of formula I.

Compounds of formula I having $R^4$=—$CH_2R^9$ may be prepared by Method 2 as described in Scheme 2.

Scheme 2 (Method 2)

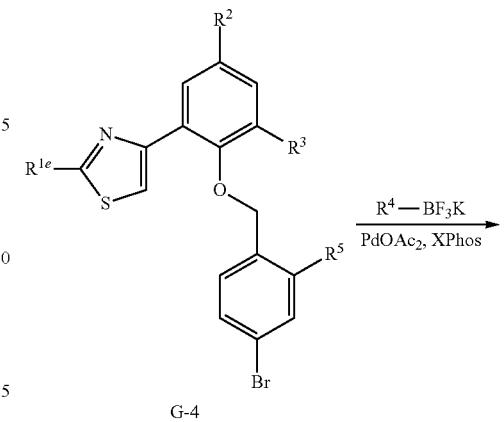

-continued

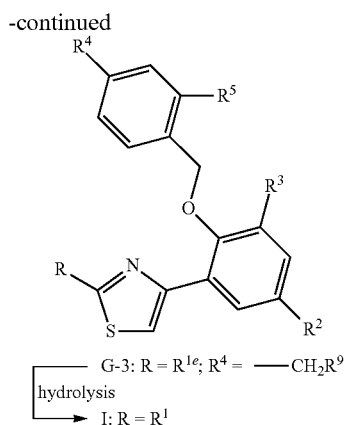

G-3: R = R$^{1e}$; R$^4$ = —CH$_2$R$^9$
hydrolysis
I: R = R$^1$

As described in Scheme 2, intermediate G-4 is reacted with R$^4$BF$_3$K, in the presence of a suitable Pd catalyst such as Pd(OAc)$_2$ and a suitable phosphorous ligand such as dicyclohexyl-[2-(2,4,6-triisopropylphenyl)phenyl]phosphane and a suitable base such as cesium carbonate to provide the desired intermediate, G-3. Hydrolysis of the ester, for example by treatment with aqueous base provides the desired compound of formula I.

Compounds of formula I having R$^4$=—C(O)R$^8$ may be prepared from intermediate G-4 by Method 3 as described in Scheme 3.

Scheme 3 (Method 3)

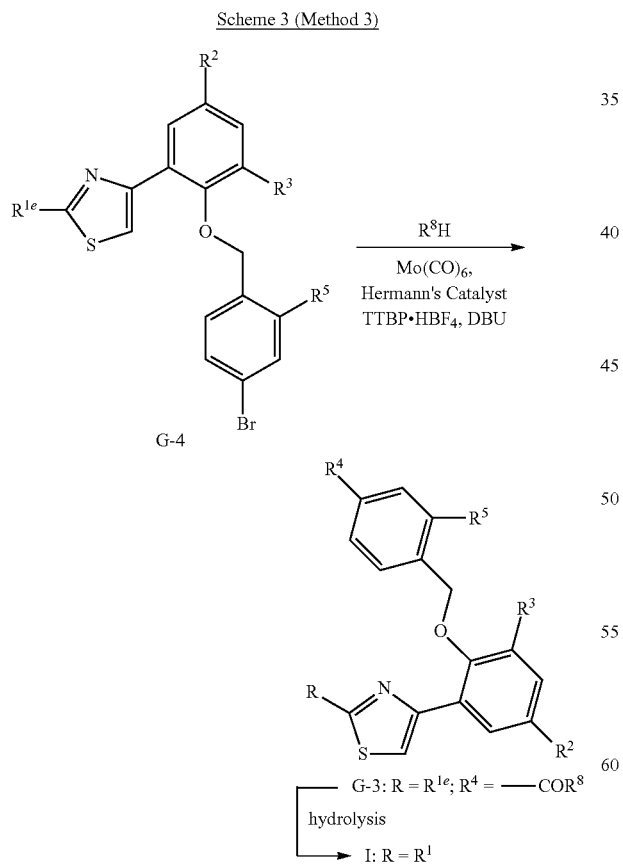

G-4

R$^8$H
————→
Mo(CO)$_6$,
Hermann's Catalyst
TTBP·HBF$_4$, DBU

G-3: R = R$^{1e}$; R$^4$ = —COR$^8$
hydrolysis
I: R = R$^1$

As described in Scheme 3, intermediate G-4 is reacted with molybdenum hexacarbonyl, a palladium catalyst such as acetoxy-[[2-(bis-o-tolylphosphanyl)phenyl]methyl]palladium, a phosphorous ligand such as tri-tert-butyl-phosphonium tetrafluoroborate and a suitable base such as piperidine and DBU (1,8-diazabicyclo[5.4.0]undec-7-ene) to provide the ester G-3. Preferably, the reaction is carried out in a sealed tube, in a microwave reactor. Hydrolysis of the ester, for example by treatment with aqueous base provides the desired compound of formula I.

Scheme 4 (Method 4) describes another method by which compounds of formula I having R$^4$=—CH$_2$R$^9$ may be prepared.

Scheme 4 (Method 4)

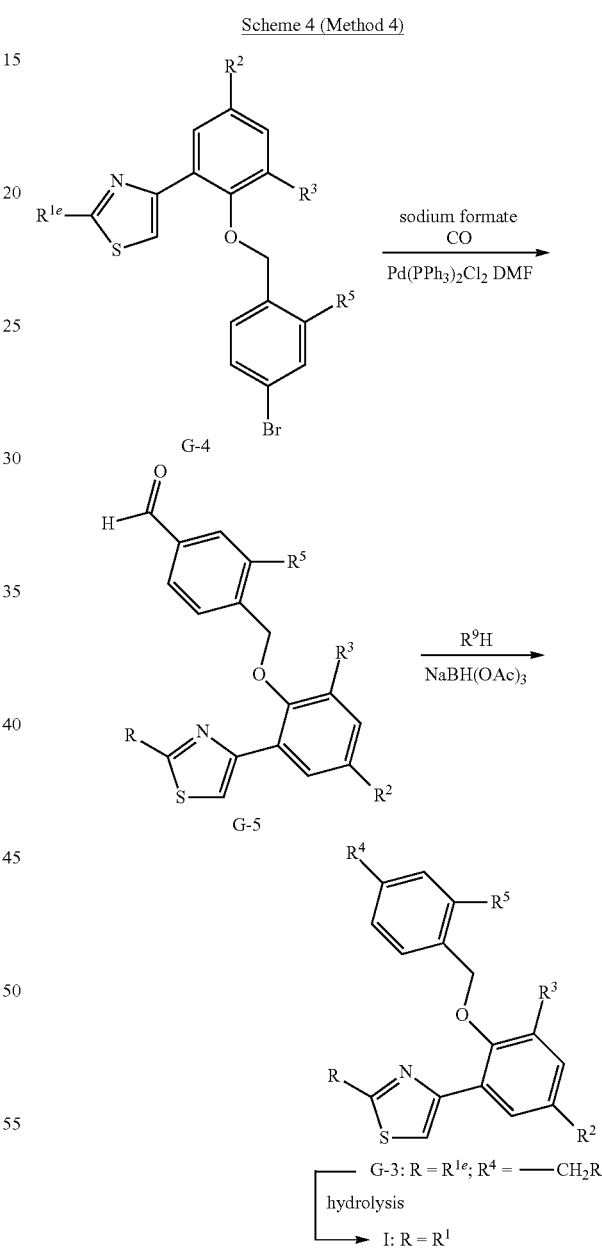

G-3: R = R$^{1e}$; R$^4$ = —CH$_2$R$^9$
hydrolysis
I: R = R$^1$

As described in Scheme 4, intermediate G-4 is reacted with sodium formate in the presence of CO and a Pd catalyst such as palladium(II) bis-triphenylphosphine chloride in a suitable solvent such as DMF to provide the aldehyde intermediate G-5. Reductive amination with R$^9$H in the presence of a suitable reducing agent such as NaBH(OAc)$_3$ provides G-3, with $R^4$=—$CH_2R^9$. Hydrolysis of the ester on $R^1$ provides the desired compound of formula I.

Scheme 5 (Method 5) shows an alternate method by which compounds of formula I having $R^4$=—$C(O)R^8$ may be prepared.

base such as diisopropylethylamine provides G-3, $R^4$=—C(O)$R^8$. Hydrolysis of the ester on $R^1$ provides the desired compound of formula I.

Compounds having $R^4$=—$C(O)N(R^6)(R^7)$ may be prepared as described below in Scheme 6 (Method 6)

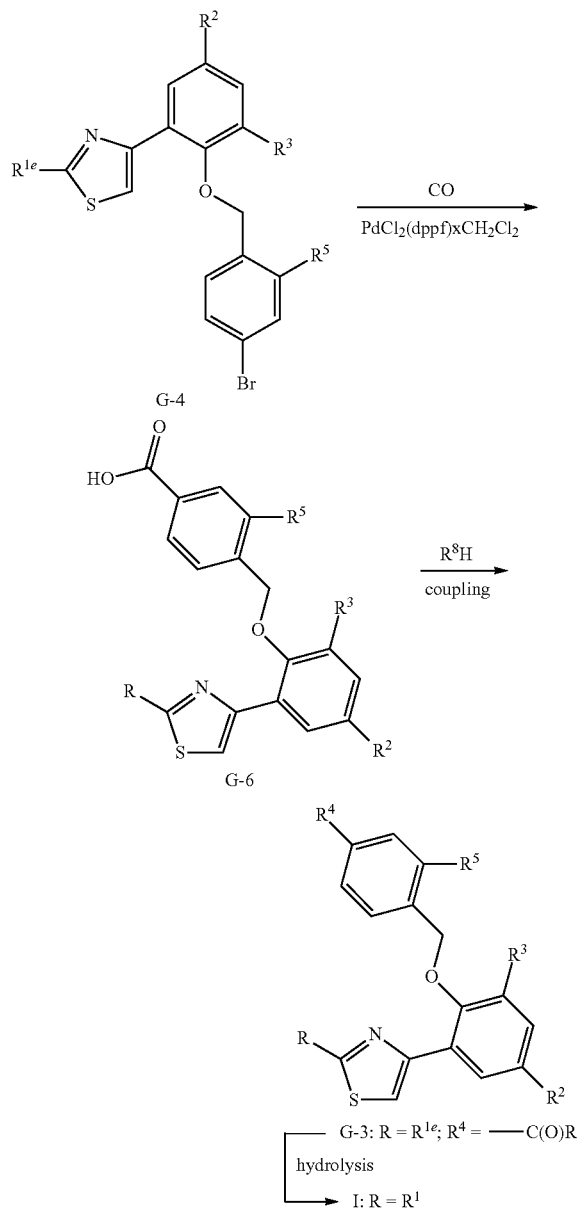

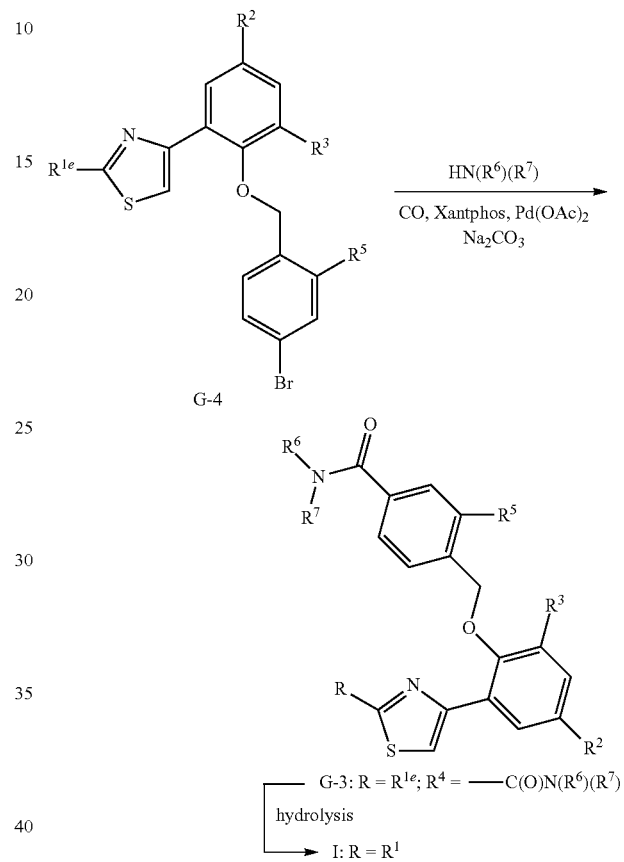

As described above in Scheme 6, intermediate G-4 is reacted with $HN(R^6)(R^7)$ in the presence of CO, 4,5-bis(diphenylphosphino)-9,9-dimethylxanthene (Xantphos), a suitable Pd source such as Pd(OAc)$_2$ and a base such as sodium carbonate to provide intermediate G-3, $R^4$=—C(O)N$(R^6)(R^7)$. Hydrolysis of the ester on $R^1$ provides the desired compound of formula I.

Compounds of formula I prepared by the above methods may be reacted further by methods known in the art or described in the synthetic examples below to prepare additional compounds of formula I.

Analytical Methods

LCMS retention time and observed m/z data for the final compounds in the Synthetic Examples section are obtained by the following methods. The data are shown in Table 2, at the end of the Synthetic Examples section.

LC-MS Method A

| Column | Waters BEH C18 2.1 × 50 mm, 1.7 μm column |
|---|---|
| Mobile phase | A - 0.05% Formic acid (95:5 acetonitrile:water) |
| | B - 0.05% Formic acid (acetonitrile) |

As illustrated in Scheme 5, intermediate G-4 is reacted with CO, preferably under pressure while heating in a closed reactor, in the presence of a suitable Pd catalyst such as [1,1'-bis(diphenylphosphino)ferrocene]dichloro palladium(II) dichloromethane adduct, water and a suitable base such as triethylamine, in a suitable solvent such as dioxane to provide carboxylic acid intermediate G-6. Coupling of the carboxylic acid with $R^8H$ in the presence of a suitable coupling reagent such as TBTU (O-(Benzotriazol-1-yl)-N,N,N',N'-tetramethyluronium tetrafluoroborate) in the presence of a suitable

| | |
|---|---|
| Flow rate | 0.8 ml/min @ 60° C. |
| Injection volume | 1 μL |
| Detector | 210-400 nm (PDA) |
| Gradient | |

| Time (mins) | % B |
|---|---|
| 0 | 10 |
| 1.19 | 100 |
| 1.7 | 100 |

LC-MS Method B

| | |
|---|---|
| Column | Thermo Scientific, Aquasil C18, 2.1 × 50 mm, 5 μm column |
| Mobile phase | A - 0.1% Formic acid (water) <br> B - 0.1% Formic acid (acetonitrile) |
| Flow rate | 0.5 ml/min @ 35° C. |
| Injection volume | 10 μL |
| Detector | AB Sciex API5000 Triple Quadrupole Mass Spectrometer |
| Gradient | |

| Time (mins) | % B |
|---|---|
| 0 | 10.0 |
| 0.5 | 10.0 |
| 1.5 | 99.0 |
| 2.5 | 99.0 |
| 3.3 | 10.0 |
| 3.85 | 10.0 |

SYNTHETIC EXAMPLES

Final compounds are designated by compound numbers corresponding to the compound numbers in Table 1. Intermediates are given hyphenated numbers corresponding to the figures and numbers shown in the scheme for each example. All of the compounds in Table I are prepared by the methods illustrated in the General Synthesis section, above and in the Synthetic Examples section below.

Synthesis of Intermediates

Synthesis of 2-Bromo-1-[2-(4-bromo-2-methyl-benzyloxy)-5-methyl-phenyl]-ethanone (I-1)

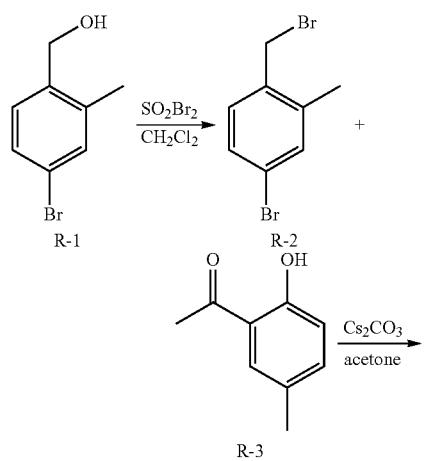

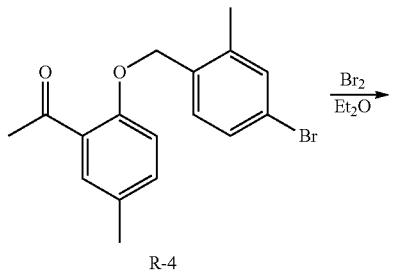

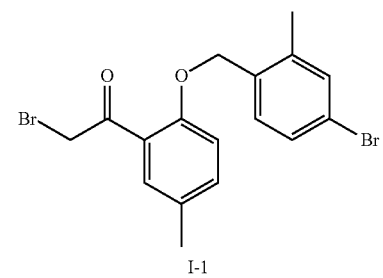

To a solution of R-1 (50 mmol, 10.00 g) in CH$_2$Cl$_2$ (200 mL) is added thionyl bromide (75 mmol, 6 mL). The mixture is stirred at ambient temperature for 2 min then treated with saturated aqueous NaHCO$_3$. The mixture is then passed through a hydrophobic frit and concentrated to give R-2. R-2 (10 mmol, 1.50 g), R-3 (12 mmol, 3.20 g) and cesium carbonate (20 mmol, 6.50 g) are dissolved in acetone (25 mL) and stirred at ambient temperature for 3 d. The mixture is filtered then concentrated to give R-4. R-4 (3 mmol, 1.00 g) is dissolved in Et$_2$O (20 mL), bromine (3 mmol, 0.52 mL) is added and the reaction is stirred at ambient temperature for 5 min. The reaction is then diluted with 1:1 (v/v) water:saturated aqueous NaHCO$_3$ (20 mL) and ethyl acetate (40 mL). Combined organics are washed with brine, dried over sodium sulfate and concentrated to give title intermediate in quantitative yield.

Synthesis of [4-(hydroxymethyl)-3-methyl-phenyl]-(1-piperidyl)methanone (I-2)

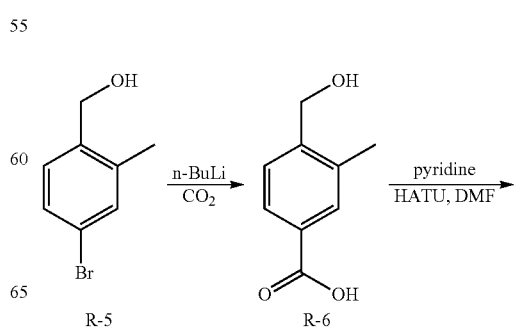

251
-continued

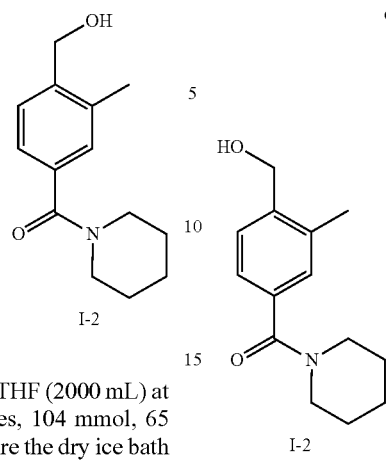

I-2

To a solution of R-5 (47 mmol, 9.5 g) in THF (2000 mL) at −78° C. is added n-BuLi (1.6M in hexanes, 104 mmol, 65 mL). The mixture is stirred for 15 min before the dry ice bath is removed. After 5 min dry ice is added. Water is added and the pH adjusted to 3 with 1N HCl. The mixture is saturated with NaCl and extracted with ethyl acetate (3×20 mL). Organics are combined and dried over MgSO₄ and concentrated in vacuo. The crude is purified by flash chromatography to give R-6 (7.6 g, 97%). R-6 (7.2 mmol, 1.2 g) is dissolved in DMF (30 mL) followed by piperidine (36 mmol, 3.00 g) then HATU (2-(7-Aza-1H-benzotriazole-1-yl)-1,1,3,3-tetramethyluronium hexafluorophosphate) (8.7 mmol, 3.3 g). The mixture is stirred at ambient temperature for 3 h. Water is added and the mixture extracted with ethyl acetate. Organics are combined, washed with brine, dried over MgSO₄ and concentrated in vacuo. The residue is purified by HPLC to yield the title intermediate (1.10 g, 65%).

The following intermediates are synthesized in a similar fashion from the appropriate reagents:

I-3

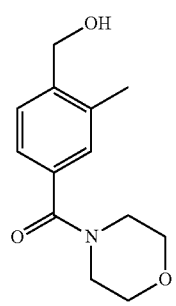 [SMILES: Cc1cc(C(=O)N2CCOCC2)ccc1CO]

I-4

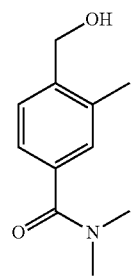

252

Synthesis (4-Bromomethyl-3-methyl-phenyl)-piperidin-1-yl-methanone (I-5)

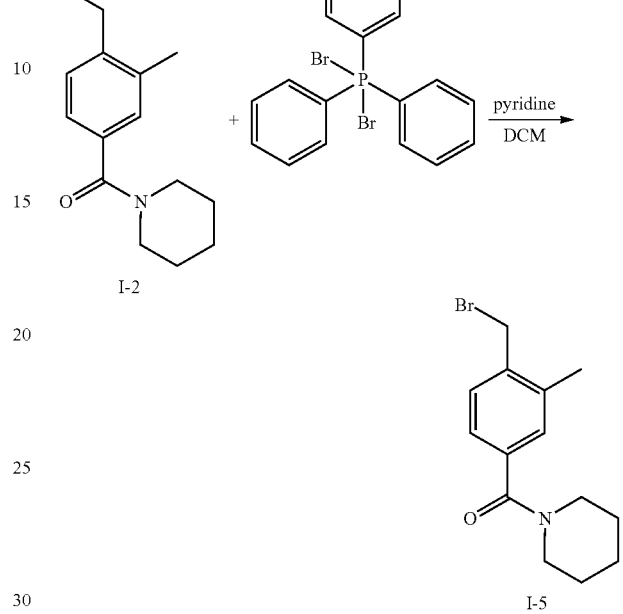

To a solution of I-2 (2.1 mmol, 0.50 g) in DCM (20 mL), cooled to 0° C., is added pyridine (3.2 mmol, 0.34 mL) followed by dibromotriphenylphosphorane (2.8 mmol, 1.2 g). The mixture is allowed to slowly warm to ambient temperature and stirred overnight. The mixture is concentrated under reduced pressure and the residue purified by flash silica gel chromatography to provide 1-5 (0.47 g, 74%) as a white powder.

Synthesis of methanesulfonic acid 2-methyl-4-(piperidine-1-carbonyl)-benzyl ester (I-6)

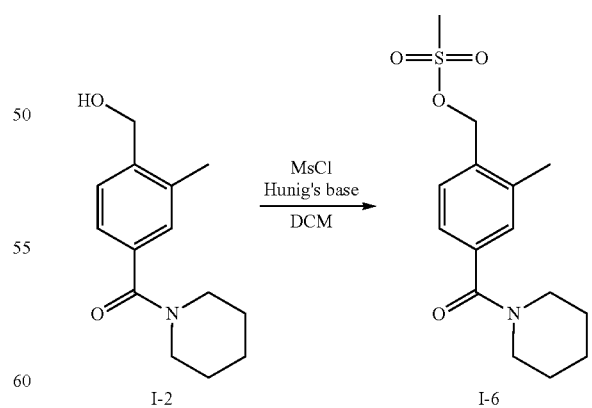

To a solution of I-2 (42.9 mmol, 10 g) in DCM (430 mL), cooled to 0° C., is added Hunig's base (64 mmol, 11 mL) followed by methanesulfonyl chloride (55 mmol, 4.3 mL). The mixture is stirred at 0° C. for 1 h then washed with a 1N solution of HCl followed by saturated NaHCO₃. The mixture

253 is dried over anhydrous Na$_2$SO$_4$ and concentrated under reduced pressure to provide the title compound (13.3 g, 100%) as a yellow oil.

The following intermediates are synthesized in a similar fashion from the appropriate reagents:

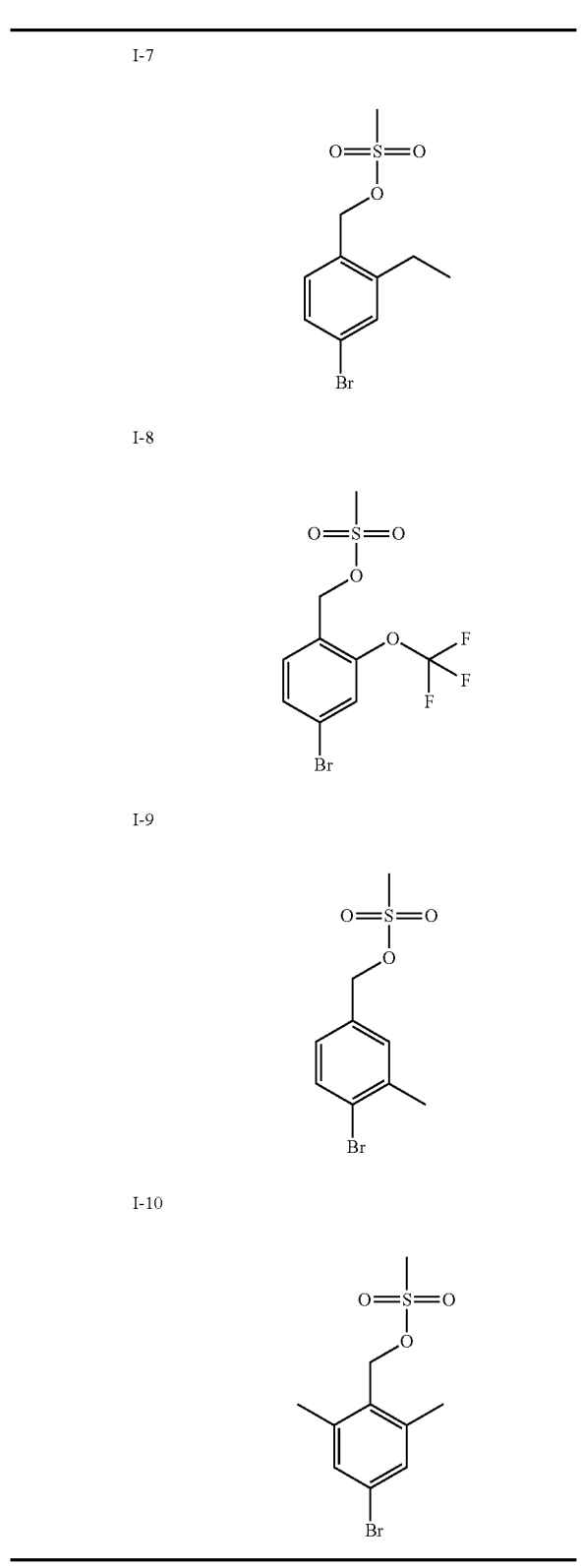

254

Synthesis of
[2-methyl-4-(morpholinomethyl)phenyl]methanol
(I-11)

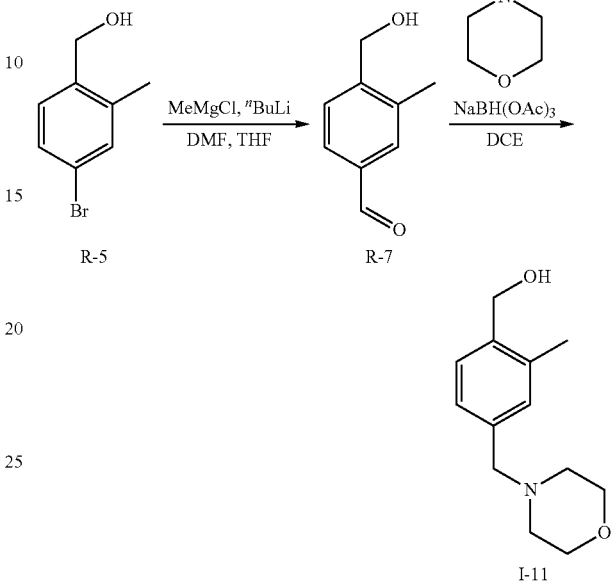

To a 0° C. solution of R-5 (15 mmol, 3.0 g) in THF (50 mL) is added methylmagnesium chloride (1.5M in THF, 18 mmol, 12 mL). The solution is stirred for 5 min then treated with a solution of n-BuLi (2.6M in hexanes, 45 mmol, 18 mL). The solution is stirred for 5 min then treated with DMF (150 mmol, 11.0 g). The cold bath is removed and the mixture is stirred for 10 min then treated with water, extracted with CH$_2$Cl$_2$ and filtered through a phase separator. The filtrate is concentrated in vacuo to give R-7 (2.20 g, 99%). To a solution of R-7 (14.5 mmol, 2.20 g) and morpholine (44 mmol, 38.00 g) in DCE (dichloroethane) (150 mL) is added sodium triacetoxyborohydride (73 mmol, 15.50 g). The mixture is stirred at 60° C. for 24 h then cooled to ambient temperature and poured into 20% (w/w) aqueous Na$_2$CO$_3$ and extracted with 10% methanol in CH$_2$Cl$_2$. The organics are collected, dried over MgSO$_4$, filtered, and concentrated in vacuo. The residue is purified by flash chromatography to give the title intermediate (2.50 g, 76%).

The following intermediates are synthesized in similar fashion from the appropriate reagents:

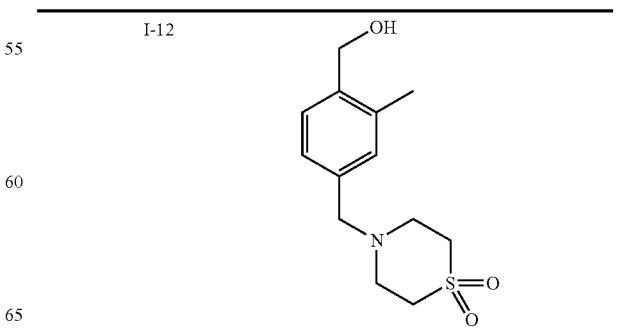

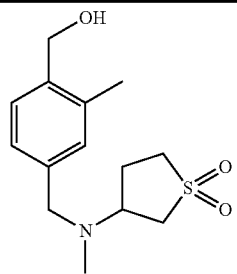

I-13

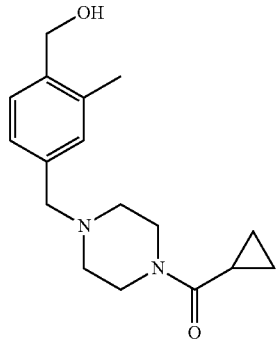 [SMILES: Cc1cc(CN2CCN(C(=O)C3CC3)CC2)ccc1CO]

I-14

Synthesis of (4-morpholin-4-ylmethyl-2-trifluoromethoxy-phenyl)-methanol (I-15)

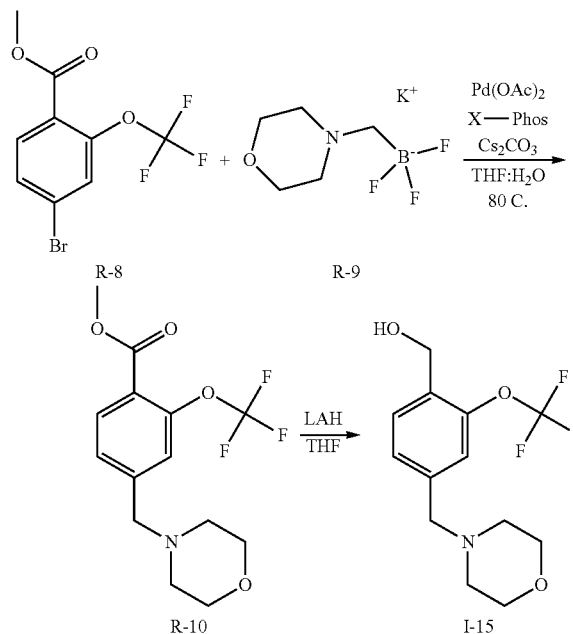

To a vial is added R-8 (0.78 mmol, 0.23 g), R-9 (1.2 mmol, 0.24 g), palladium(II)acetate (0.078 mmol, 0.017 g), Xphos (0.14 mmol, 0.067 g) and cesium carbonate (2.3 mmol, 0.76 g) and a 10:1 mixture of THF:water (2 mL). The vial is sealed then heated to 80° C. for 72 h. The reaction mixture is cooled to ambient temperature and concentrated under reduced pressure, and purified by flash silica gel chromatography to provide R-10 (0.28 g, 100%). A solution of R-10 (0.98 mmol, 0.39 g) in THF (15 ml) is treated with LAH (1.7 mmol, 0.066 g). The mixture is heated to 65° C. for 3 h then cooled to ambient temperature. Excess reactants are consumed by the addition of a saturated aqueous solution of $Na_2SO_4$. The slurry is diluted with DCM and water. The mixture is stirred vigorously for 1 h then the organic layer is separated, dried and concentrated under reduced pressure to provide the title compound (0.28 g, 100%).

Synthesis of [2-methyl-4-(1-morpholin-4-yl-ethyl)-phenyl]-methanol (I-16)

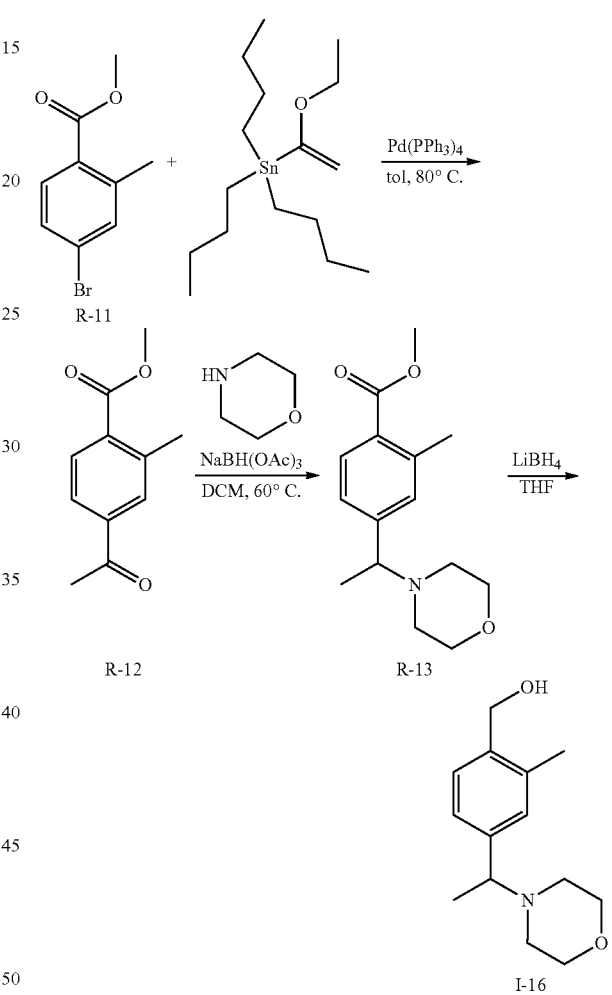

To a solution of R-11 (2.2 mmol, 0.50 g) in toluene (10 mL) is added tributyl-(1-ethoxy-vinyl)-stannane (2.6 mmol, 0.85 g) followed by of $Pd(PPh_3)_4$ (0.22 mmol, 0.25 g). The mixture is heated overnight at 80° C. then cooled to ambient temperature, diluted with water, and extracted with ethyl acetate. The combined organic phase is concentrated under reduced pressure and the residue is stirred overnight in 2 N hydrochloric acid. The mixture is extracted with ethyl acetate and the combined organic phase is dried over anhydrous sodium sulfate then concentrated under reduced pressure. The residue is purified by flash silica gel chromatography to provide R-12 (0.15 g, 35%) as a clear oil. To a solution of R-12 (0.78 mmol, 0.15 g) in DCM (8 mL) is added morpholine (1.6 mmol, 0.14 mL) followed by $NaBH(OAc)_3$ (2.4 mmol, 0.50 g). The mixture is stirred at room temperature for 4 days then heated for 2 days at 60° C. The mixture is cooled to ambient temperature, concentrated under reduced pressure, and the residue is purified by C18 reverse phase flash chromatography to provide R-13 (0.33 g, 110%) as a clear oil. To a solution of R-13 (0.87 mmol, 0.33 g) in THF (10 mL) was added a solution of LiBH₄ in THF (2M, 4.4 mmol, 2.2 mL). The mixture is stirred at room temperature for 3 days then diluted with water and extracted with ethyl acetate. The combined organic phase is dried over anhydrous sodium sulfate and concentrated under reduced pressure to provide the title compound (0.067 g, 32%) as a clear oil.

Synthesis of 4-methyl-azepane-4-carboxylic acid methyl ester hydrochloride (I-17)

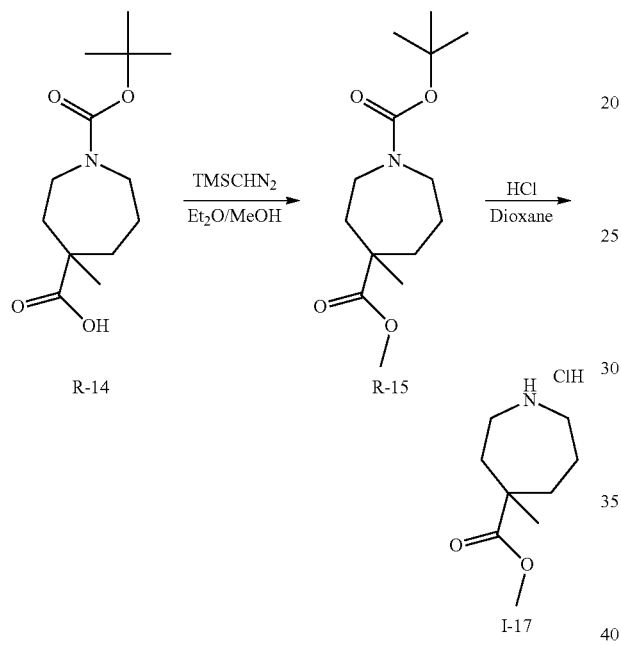

To a solution of R-14 (2.3 mmol, 0.60 g) in a 10:1 mixture of diethylether:methanol (22 mL) is added, dropwise, trimethylsilyldiazomethane (7.4 mmol, 3.7 mL). The mixture is stirred at room temperature for 1 h then concentrated under reduced pressure to provide R-15 which is not purified but used directly. The crude reaction product containing R-15 is taken up in a solution of HCl in 1,4-dioxane (4N, 12 mmol, 3 mL) and stirred at ambient temperature for 1 h. The mixture is concentrated under reduced pressure to provide the title compound (0.55 g, 110%).

Synthesis of aza-bicyclo[5.1.0]octane-1-carboxylic acid ethyl ester hydrochloride (I-18)

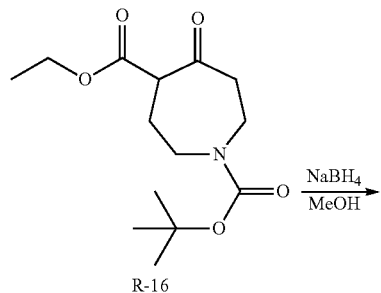

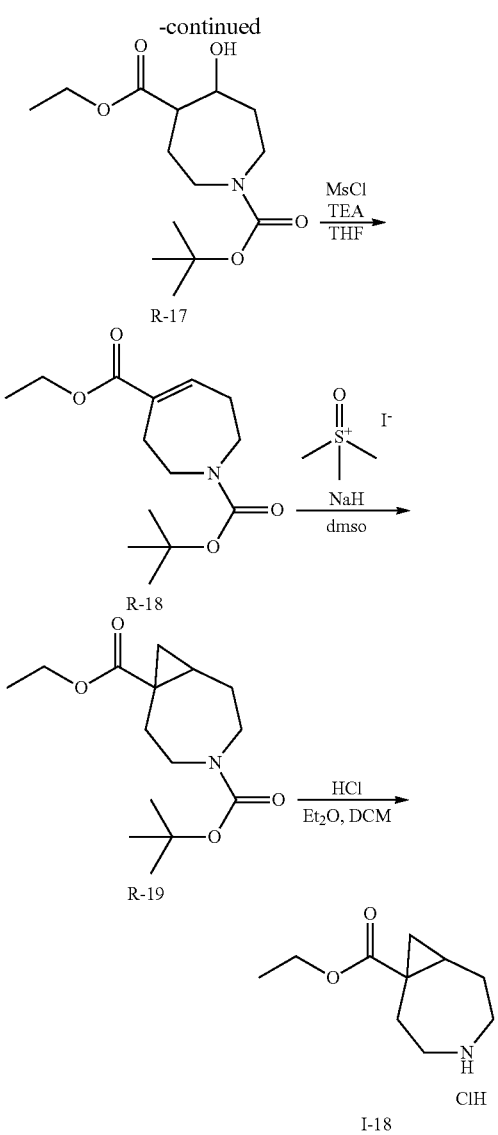

A solution of R-16 (9.0 mmol, 2.6 g) is dissolved in MeOH (24 mL) and cooled to 0° C. Sodium borohydride (9.0 mmol, 0.34 g) is added slowly to the mixture and the reaction is stirred at room temperature for 3 h. The mixture is concentrated under reduced pressure and the residue is diluted with DCM and water. The organic layer is separated, washed with brine, dried over Na₂SO₄, and concentrated under reduced pressure. The residue is purified using flash silica gel chromatography to provide R-17 (0.26 g, 100%). To a solution of R-17 (0.91 mmol, 0.26 g) in THF (5 mL) is added TEA (0.14 ml, 1.0 mmol) followed by methanesulfonyl chloride (1.0 mmol, 0.078 ml). The reaction mixture is allowed to stir at room temperature for 16 h. To the mixture is added DBU (1.8 mmol, 0.27 m) and the reaction is allowed to stir at room temperature for 2 h. The mixture is diluted with EtOAc and washed sequentially with a saturated aqueous solution of NH₄Cl followed by a 1M solution of HCl. The organic phase is dried over anhydrous Na₂SO₄ and concentrated under reduced pressure. The residue is purified by flash silica gel chromatography to provide R-18 (0.26 g, 100%). To a solution of trimethylsulfoxonium iodide (1.0 mmol, 0.23 g) in DMSO (24 mL) is slowly added NaH (60% dispersion in mineral oil, 1.0 mmol, 0.042 g). The mixture is stirred at room temperature for 1 h and then a solution of R-18 (0.950 mmol, 0.26 g) in DMSO (0.5 mL) is rapidly added. The reaction mixture is heated to 50° C. for 2 h and then cooled to ambient temperature and stirred for 16 h. The reaction mixture is diluted with water and extracted with ethyl acetate. The combined organic phase is washed with brine then dried over anhydrous sodium sulfate and concentrated under reduced pressure to provide R-19 (0.17 g, 63%). To a solution of R-19 (0.60 mmol, 0.17 g) in a 3:1 mixture of Et$_2$O:DCM (4 ml) is added a solution of HCl in 1,4-dioxane (4M, 4 mmol, 1.0 mL). The mixture is stirred at 45° C. for 3 h then concentrated under reduced pressure. The residue is washed with Et$_2$O and dried to provide the title compound (0.099 g, 75%).

Synthesis of 5-aza-spiro[2.3]hexane-1-carbocylic acid ethyl ester (I-19)

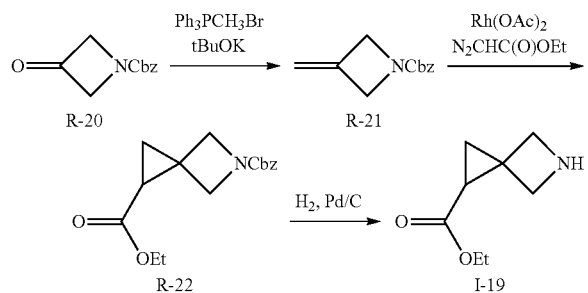

A suspension of methyl triphenylphosphonium bromide (97 mmol, 35 g) and KOtBu (97 mmol, 11 g) in Et$_2$O (200 mL) is stirred for 1 h at 35° C. under Ar. To this is added, dropwise, a solution of R-20 (24 mmol, 5.0 g) in Et$_2$O (20 mL). The mixture is heated to reflux and stirred for 12 h. After cooling down to ambient temperature, the resulting suspension is filtered through a pad of diatomaceous earth and the filter pad is rinsed with Et$_2$O. The filtrate is concentrated under reduced pressure and the residue is purified by flash silica gel chromatography to provide R-21 (2.9 g, 59%). To the stirred solution of R-21 (14 mmol, 2.8 g) and Rh(OAc)$_2$ catalyst (0.7 mmol, 0.3 g) in DCM (35 mL) is slowly added a solution of diazoethyl acetate (28 mmol, 3.1 g) in DCM (15 mL) over a 12 h period. The solution is diluted with ethyl acetate and washed with an aqueous solution of NaHCO$_3$ and brine. The organic phase is concentrated under reduced pressure and the residue is purified by flash silica gel chromatography to provide R-22 (2.1 g, 53%). A suspension of R-22 (7.3 mmol, 2.1 g) and 5% Pd/C (0.400 g) in MeOH (20 mL) is stirred overnight at ambient temperature under an atmosphere of hydrogen. The mixture is filtered through diatomaceous earth and the filter pad rinsed with a 10% solution of MeOH in DCM. The filtrate is concentrated under reduced pressure to provide the title compound (1.1 g, 98%).

Synthesis of 1-azetidin-3-yl-cyclopropyanecarboxylic acid tert-butyl ester (I-20)

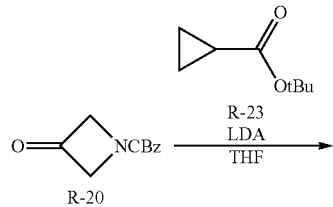

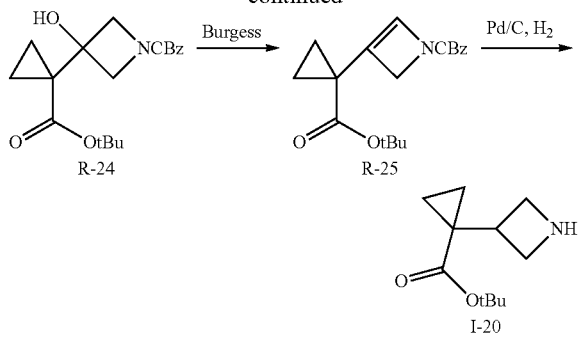

To a solution of diisopropylamine (17 mmol, 2.4 mL) in THF (20 mL), cooled to 0° C., is added a solution of n-BuLi in pentane (2.5 N, 17 mmol, 6.8 mL). The solution is warmed to room temperature, stirred for 30 min, and then cooled to −78° C. To this is added a solution of R-23 (14 mmol, 2.0 g) in THF (4 mL). The mixture is stirred at −78° C. for 3 h then a solution of R-20 (17 mmol, 3.5 g) in THF (4 mL) is added. The reaction mixture is stirred at −78° C. for 1 h then warmed to ambient temperature and stirred for an additional 2 h. The reaction is diluted with water and extracted with ethyl acetate. The combined organic phase is concentrated under reduced pressure and the residue purified by flash silica gel chromatography to provide R-24 (2.7 g, 55%). To a solution of R-24 (7.2 mmol, 2.5 g) in toluene (40 mL) is added Burgess reagent (8.7 mmol, 2.1 g). The mixture is heated to 90° C. for 1 h then cooled to ambient temperature and concentrated under reduced pressure. The residue is purified by flash silica gel chromatography to provide R-25 (0.44 g, 19%). A mixture of R-25 (0.49 mmol, 0.16 g) and 5% Pd/C (0.050 g) in methanol (5 mL) is stirred overnight at ambient temperature under an atmosphere of hydrogen. The mixture is filtered through diatomaceous earth and the filter pad rinsed with a 10% solution of MeOH in DCM. The filtrate is concentrated under reduced pressure to provide the title compound (0.091 g, 95%).

Synthesis of (6-S,1-R)-3-aza-bicyclo[4.1.0]heptane-3,6-dicarboxylic acid 3-benzyl ester 6-ethyl ester (I-21) and (6-R, 1-S)-3-aza-bicyclo[4.1.0]heptane-3,6-dicarboxylic acid 3-benzyl ester 6-ethyl ester (I-22)

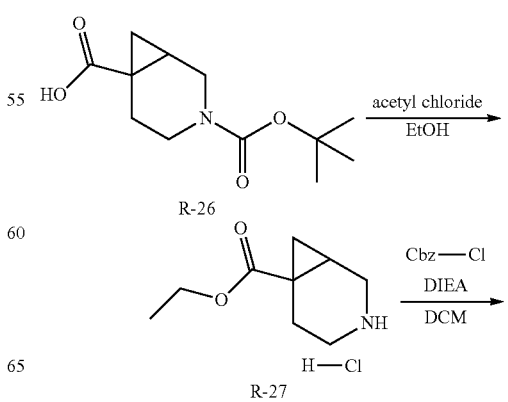

-continued

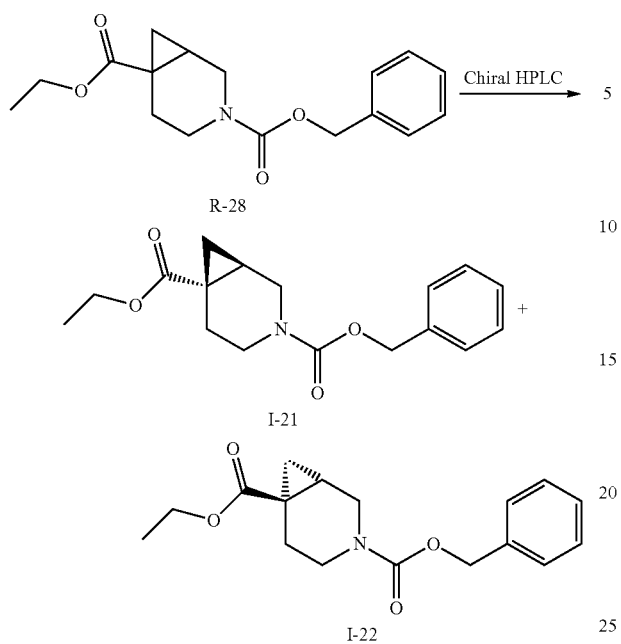

A flask is charged with EtOH (60 mL) and cooled to 0° C. To this is added acetyl chloride (28 mmol, 2.0 mL). The mixture is stirred at 0° C. for 15 min then R-26 (10 mmol, 2.5 g) is added. The mixture is warmed to room temperature for 30 min then heated to 60° C. for 2 h. The mixture is cooled to room temperature, concentrated under reduced pressure, and the residue was taken up in toluene and concentrated under reduced pressure again to provide R-27 (2.2 g, 100%) as a white powder. To a solution of R-27 (4.7 mmol, 0.80 g) in methylene chloride (50 mL) is added benzylchloroformate (7.0 mmol, 1.0 mL) followed by Hunig's base (11 mmol, 2.0 mL). The mixture is shaken overnight at ambient temperature then washed with a saturated solution of ammonium chloride. The organic phase is separated then dried over anhydrous sodium sulfate and concentrated under reduced pressure. The residue is purified by flash silica gel chromatography to provide R-28 (1.2 g, 84%) as a clear oil. A sample of R-28 (3.9 mmol, 1.2 g) was separated by chiral HPLC. The eluent was removed under reduced pressure to provide I-21 (0.40 g, 34%, 99% ee) and I-22 (0.51 g, 43%, >99% ee). The absolute configuration of I-21 and I-22 is determined using experimental vibrational circular dichroism (VCD) and density functional theory (DFT) calculation. VCD measurements are performed on a ChiralIR spectrometer (BioTools, FL, USA). Both samples are dissolved in $CDCl_3$ solution at the concentration of 50 mg/mL. Spectra are collected for 4 h in a 100 μm path length cell. The final VCD spectra are corrected by subtracting the solvent spectra ($CDCl_3$) measured in the same conditions. A conformer search of the 1S,3R enantiomer was performed using Hyperchem 7 software at molecular mechanic level (MM+). Four obtained conformers with the lowest energies were further applied for VCD calculation using Gaussian09 software at DFT level with B3LYP/6-31G (d) basis sets and functionals. The final spectra were constructed by averaging the four conformers based on Boltzmann distribution. The absolute configuration of I-21 and I-22 is assigned from the agreement of the VCD bands between experimental spectra and calculated spectra.

Synthesis of ethyl 1-[4-(2-hydroxy-5-methyl-phenyl)thiazol-2-yl]pyrrolidine-3-carboxylate (I-23)

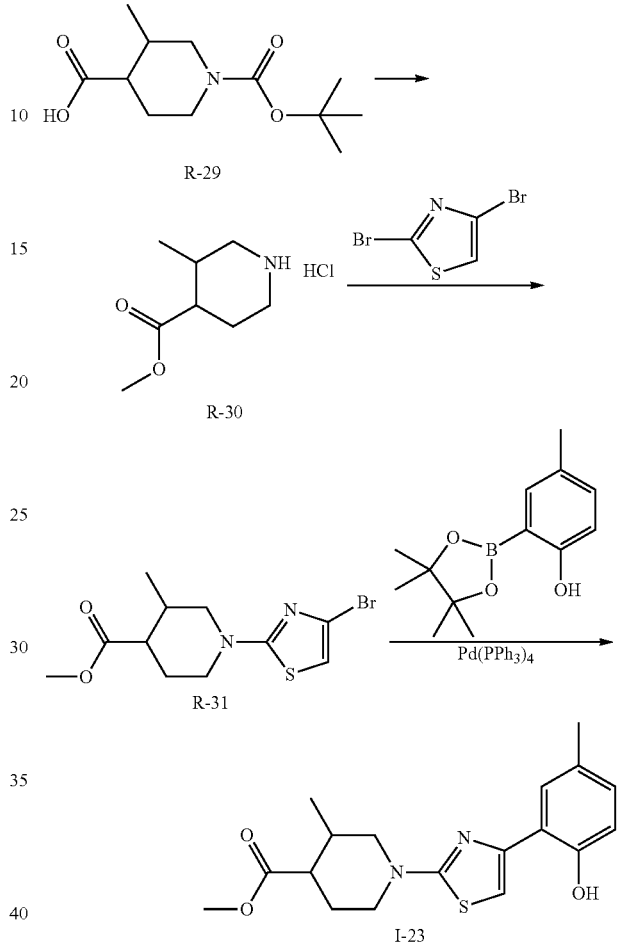

To a solution of R-29 (3.5 mmol, 1.00 g) dissolved in 10:1 (V:V) $Et_2O$:MeOH (40 mL) is added TMS diazomethane (0.5M in THF, 13 mmol, 6.4 mL). The mixture is stirred at ambient temperature for 4 h. The reaction is concentrated in vacuo and the residue is dissolved in 4 N HCl in dioxane (5 mL) and stirred at ambient temperature for 4 h then concentrated in vacuo to give R-30. To a solution of R-30 (4.0 mmol, 0.78 g) and dibromothiazole (2.7 mmol, 0.65 g) in DMF (10 mL) is added triethylamine (10 mmol, 1.5 mL). The solution is heated at 80° C. for 16 h. The reaction is concentrated in vacuo and the residue is purified by flash chromatography to give R-31 (0.66 g, 60%). A solution of R-31 (2.4 mmol, 0.76 g), 4-methyl-2-(4,4,5,5-tetramethyl-1,3,2-dioxaborolan-2-yl)phenol (2.9 mmol, 0.67 g) in THF (20 mL) and 2 M aqueous $Na_2CO_3$ (9 mmol, 4.5 mL) is sparged with argon. Tetrakistriphenylphosphinepalladium(0) (0.24 mmol, 0.28 g) is added and the mixture is heated at 80° C. for 16 h. The mixture is cooled then diluted with DCM and passed through a hydrophobic frit. The organics are concentrated in vacuo and the residue is purified by flash chromatography to give the title intermediate (0.68 g, 82%).

The following intermediates are synthesized in similar fashion from the appropriate reagents:

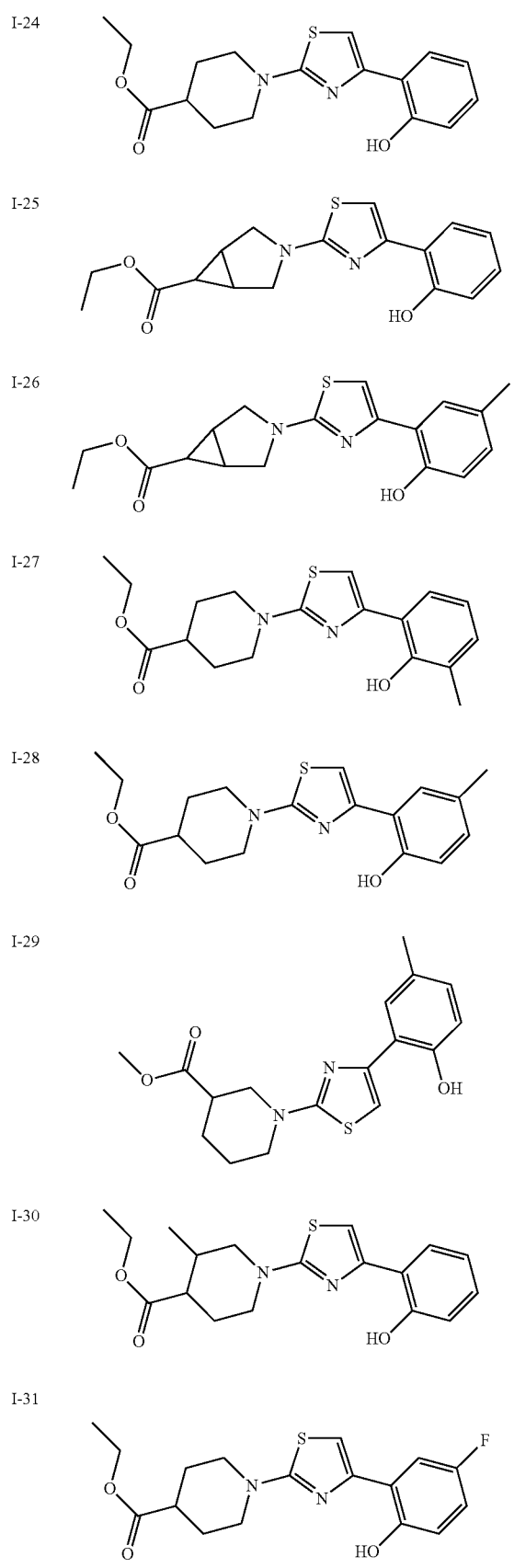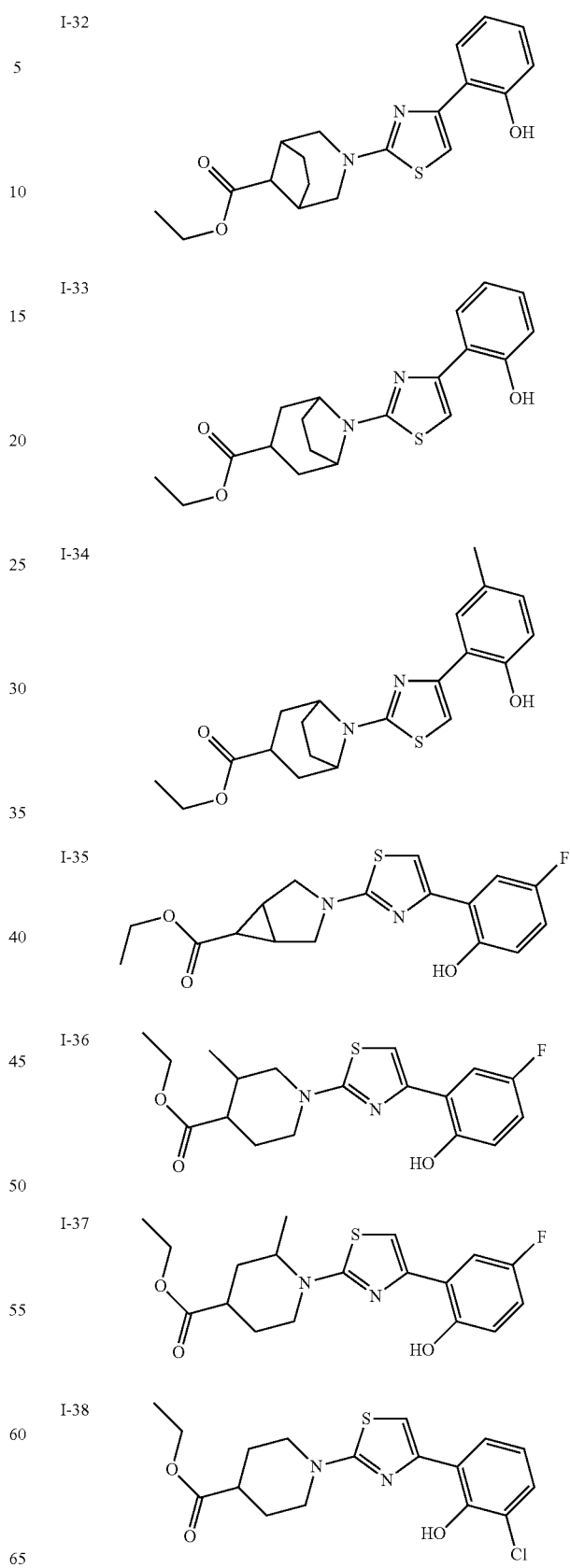

-continued
I-39 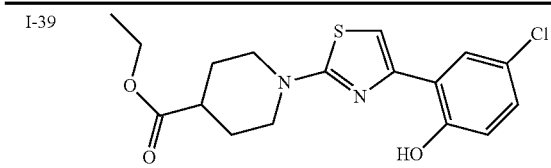
I-40 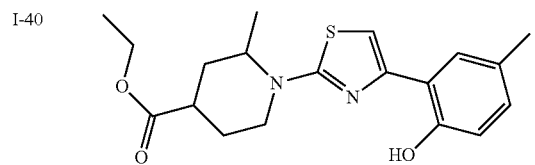
I-41 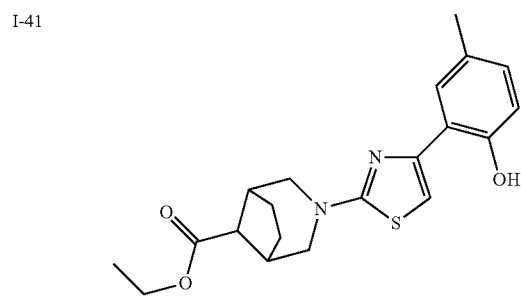
I-42 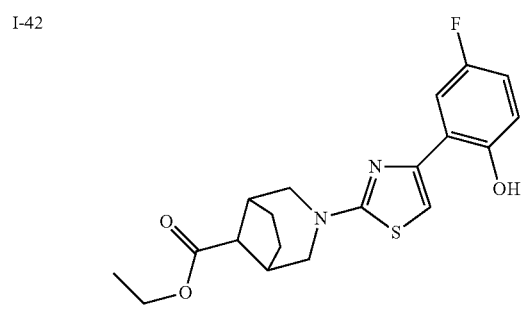
I-43 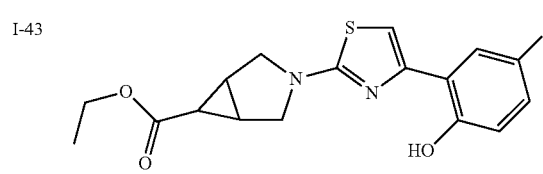
I-44 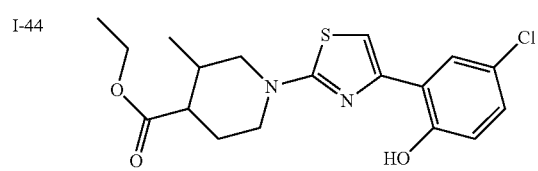
I-45 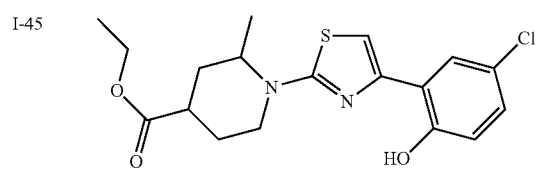
I-46 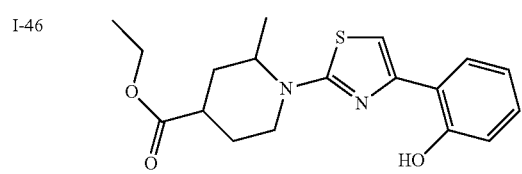
-continued
I-47 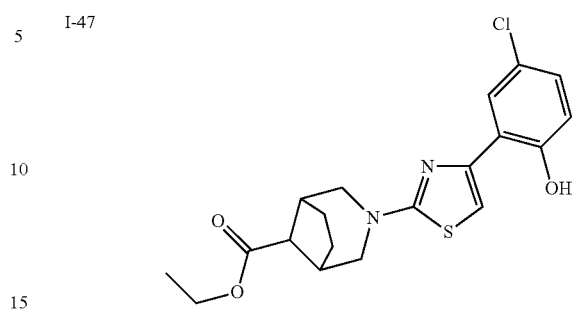
I-48 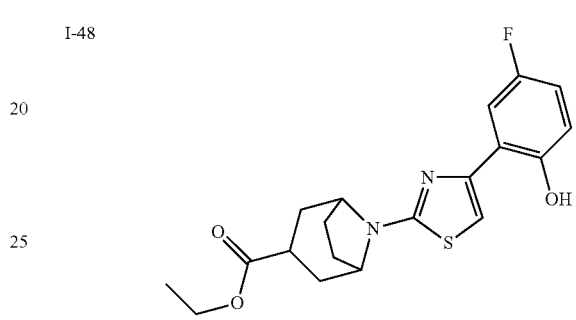
I-49 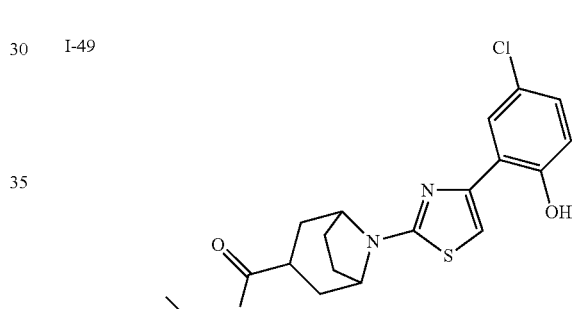
I-50 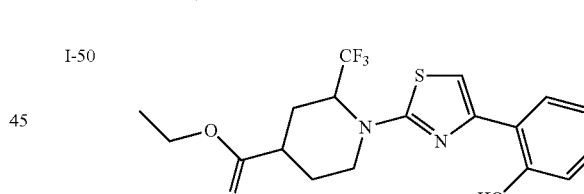
I-51 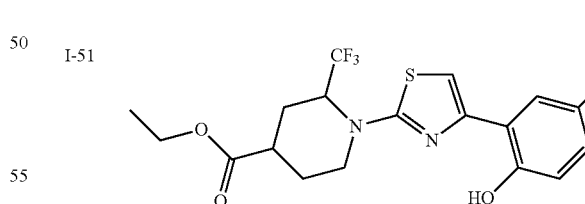
I-52 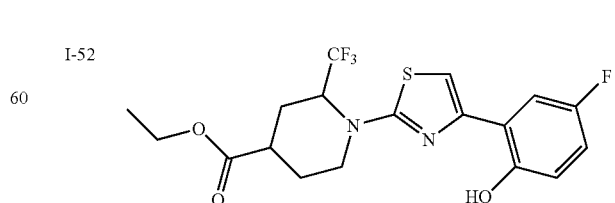

267
-continued
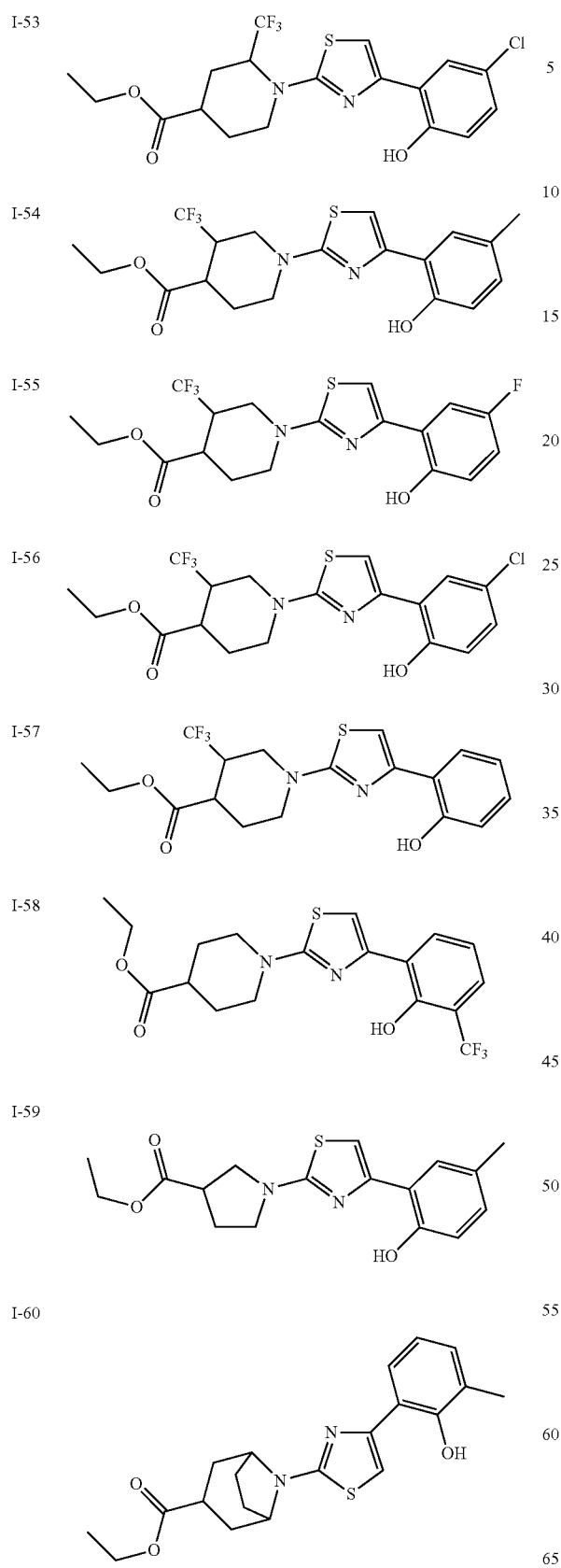
268
-continued
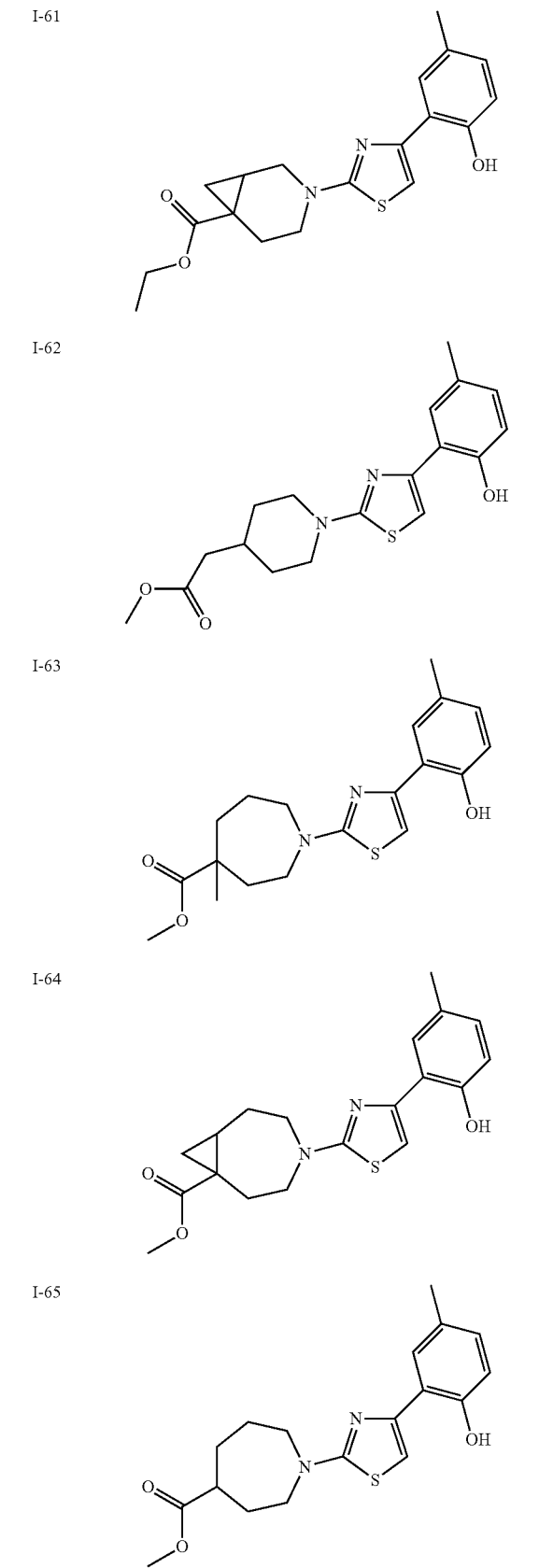

I-66
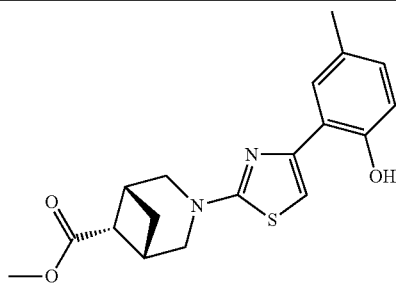
I-67
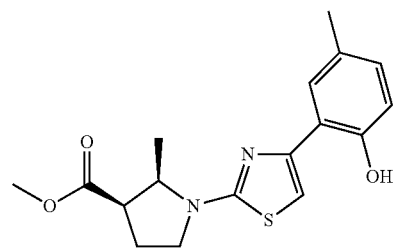 [SMILES: COC(=O)[C@@H]1CCN(c2nc(-c3cc(C)ccc3O)cs2)[C@@H]1C]
I-68
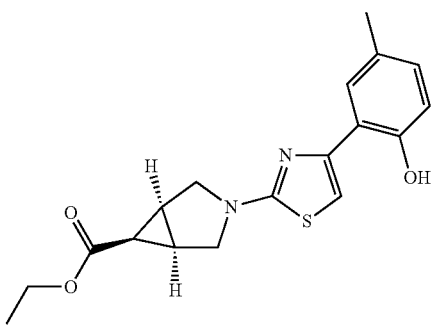 [SMILES: CCOC(=O)[C@@H]1[C@@H]2CN(c3nc(-c4cc(C)ccc4O)cs3)C[C@@H]21]
I-69
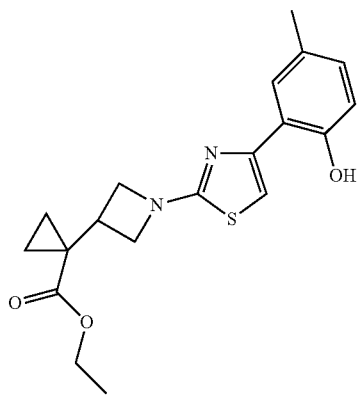 [SMILES: CCOC(=O)C1(C2CN(c3nc(-c4cc(C)ccc4O)cs3)C2)CC1]
I-70
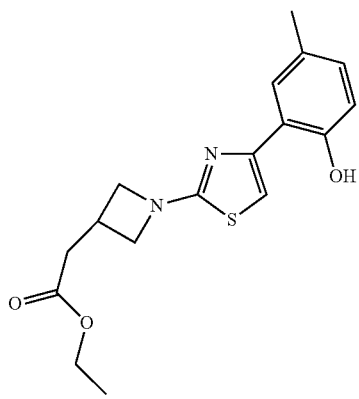 [SMILES: CCOC(=O)CC1CN(c2nc(-c3cc(C)ccc3O)cs2)C1]
I-71
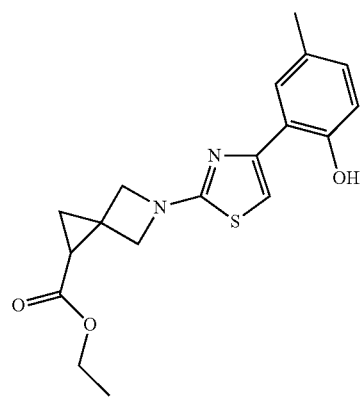 [SMILES: CCOC(=O)C1CC12CN(c1nc(-c3cc(C)ccc3O)cs1)C2]
Synthesis of ethyl 4-[4-(2-hydroxy-5-methyl-phenyl)thiazol-2-yl]cyclohex-3-ene-1-carboxylate (I-72) and ethyl 4-[4-(2-hydroxy-5-methyl-phenyl)thiazol-2-yl]cyclohexanecarboxylate (I-73)
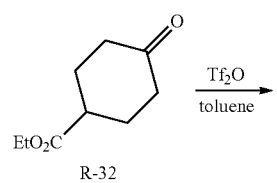
R-32
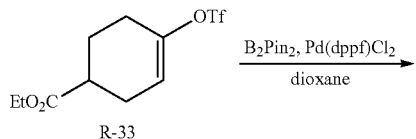
R-33
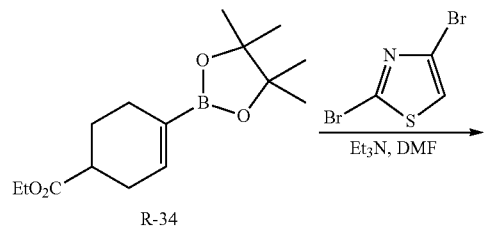
R-34
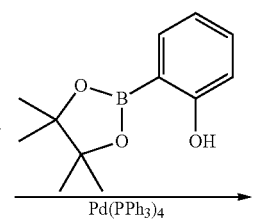
R-35

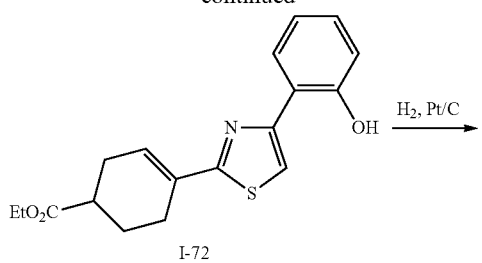

I-72

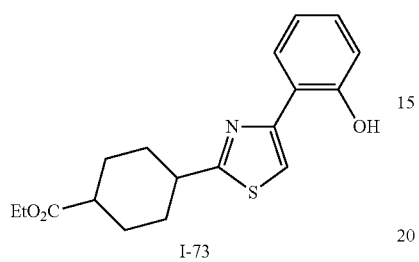

I-73

Pyridine (2.60 g) is dissolved in toluene (5.0 mL), and then trifluoroacetic anhydride (10 g) is added to the mixture. The solution is stirred at room temperature for 30 min. R-32 (14 g) is added and the solution stirred for 12 h. The mixture is extracted with ethyl acetate and water. The organic layer is washed with brine, dried over $Na_2SO_4$ and concentrated in vacuo. The residue is purified by flash chromatography to give R-33 (8 g, 82%). The mixture of R-33 (8 g), $Pin_2B_2$ (7.4 g), dppf (1 g), $Pd(dppf)_2Cl_2$ (1 g) and $K_2CO_3$ (11 g) in dioxane (100 mL) is stirred at 100° C. for 1 h. The solvent is removed in vacuo. The mixture is extracted with ethyl acetate and water. The organic layer is washed with brine, dried over $Na_2SO_4$ and concentrated in vacuo. The residue is purified by flash chromatography to give R-34 (5 g, 68%). A mixture of dibromothiazole (1.3 eq), R-34 (1.0 eq) and $Et_3N$ (6.0 eq) in DMF is stirred at 90° C. for 5 h. The mixture is extracted with ethyl acetate and water. The organic layer is washed with brine, dried over $Na_2SO_4$ and concentrated in vacuo. The residue is purified by flash chromatography to give compound R-35. A mixture of compound R-35 (735 mg), 4-methyl-2-(4,4,5,5-tetramethyl-1,3,2-dioxaborolan-2-yl)phenol (768 mg), $Pd(PPh_3)_4$ (268 mg) and $Cs_2CO_3$ (2.3 g) in DME (dimethoxyethane) and $H_2O$ is stirred at 100° C. for 4 h. The mixture is extracted with ethyl acetate and water. The organic layer is washed with brine, dried over $Na_2SO_4$ and concentrated in vacuo. The residue is purified by flash chromatography to give compound I-72 (766 mg, 93%). A mixture of compound I-72 (660 mg) and $PtO_2$ (46 mg) in EtOH is stirred at 20° C. under $H_2$ at a pressure of 50 psi for 4 h. The mixture is concentrated in vacuo. The crude product is purified by flash chromatography to give compound I-73 (680 mg, 95%).

The following intermediates are synthesized in similar fashion from the appropriate reagents:

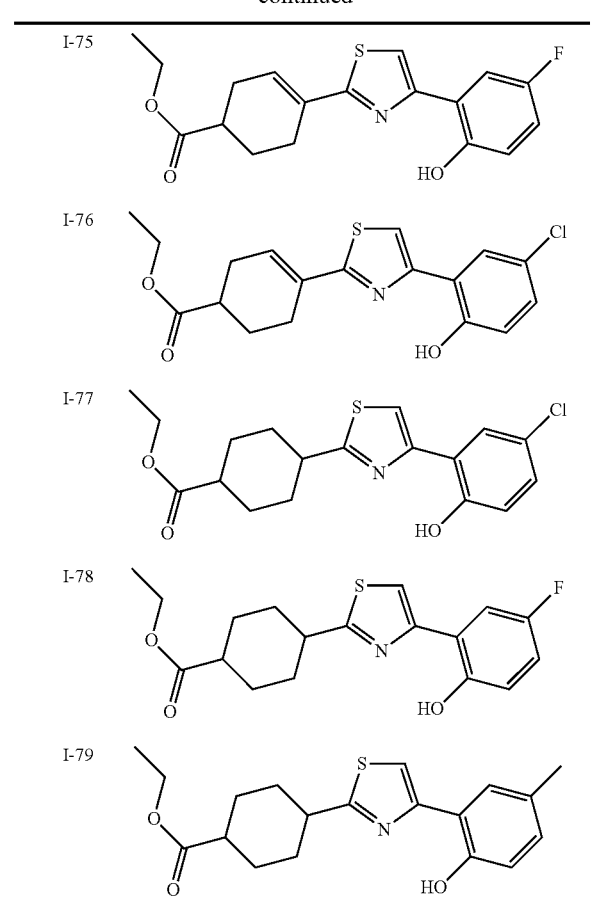

Synthesis of ethyl 1-[4-(2-hydroxy-5-methyl-phenyl)thiazol-2-yl]pyrrolidine-3-carboxylate (I-80)

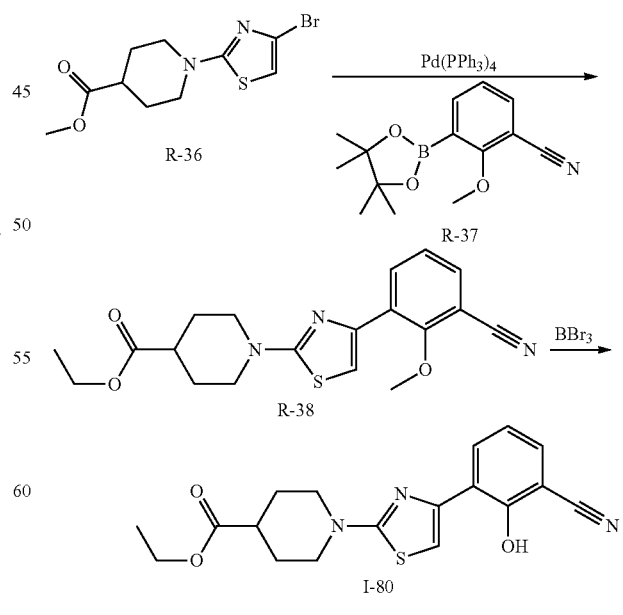

A solution of R-36 (2.7 mmol, 0.85 g), R-37 (3.5 mmol, 0.90 g), and tetrakistriphenylphosphinepalladium(0) (0.27 mmol, 0.31 g) in THF (6 mL) and 20% (w/w) aqueous Na₂CO₃ (3 mL) is heated at reflux for 3 h. The mixture is cooled and then partitioned between CH₂Cl₂ and brine. The organics were collected, dried with MgSO₄, filtered, and concentrated in vacuo. The crude was purified by flash chromatography to give R-38 (0.67 g, 68%). A solution of R-38 (1.8 mmol, 0.67 g) in CH₂Cl₂ (10 mL) is cooled to 0° C. then treated with a solution of BBr₃ in DCM (1.0 M, 9 mmol, 9 mL). The mixture is stirred at 0° C. for 1 h then treated with saturated aqueous NaHCO₃. The mixture was diluted with DCM and organics were collected, dried with MgSO₄, filtered, and concentrated in vacuo. The crude was purified by flash silica gel chromatography to give the title intermediate (0.44 g, 67%).

The following intermediates are synthesized in similar fashion from the appropriate reagents:

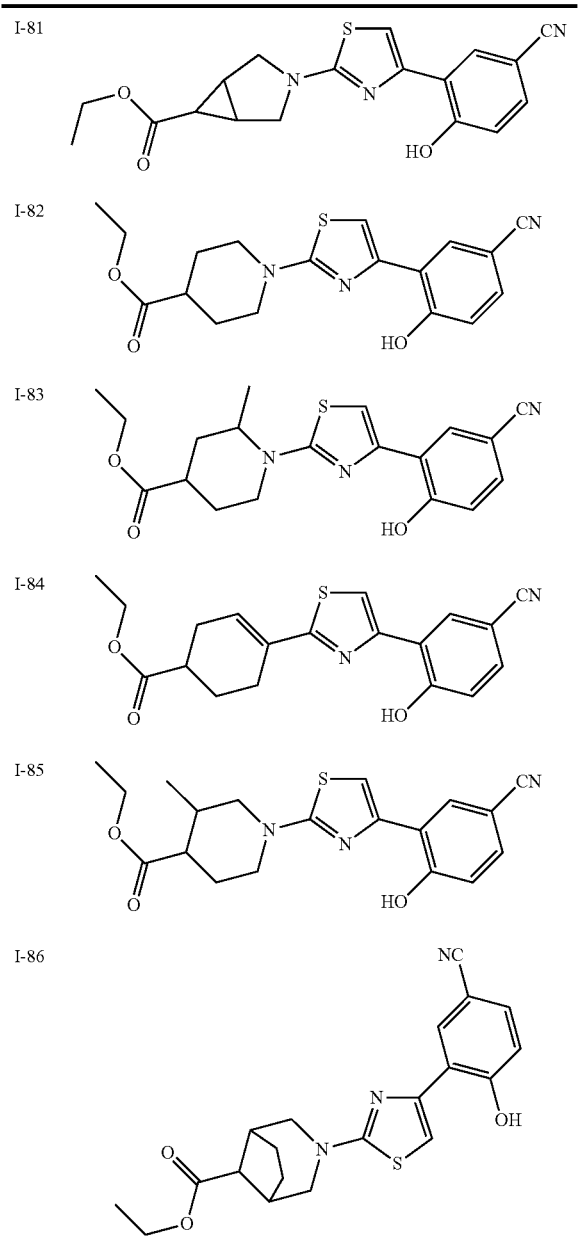

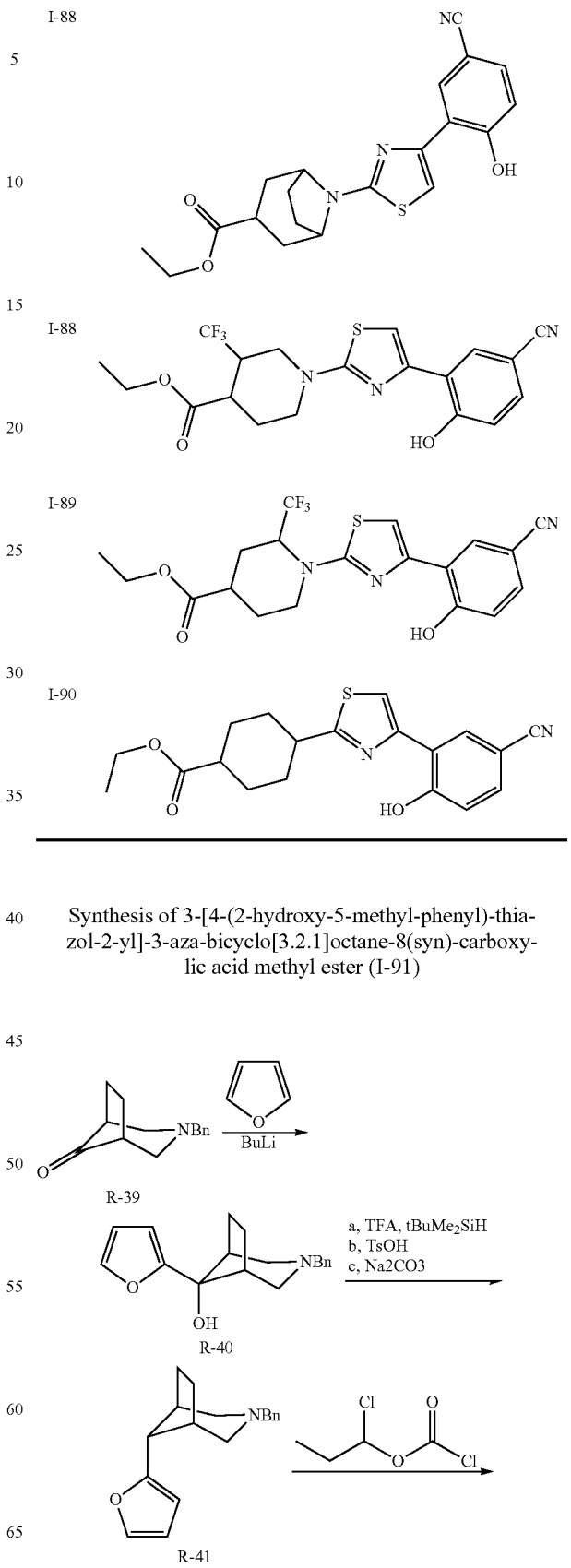

Synthesis of 3-[4-(2-hydroxy-5-methyl-phenyl)-thiazol-2-yl]-3-aza-bicyclo[3.2.1]octane-8(syn)-carboxylic acid methyl ester (I-91)

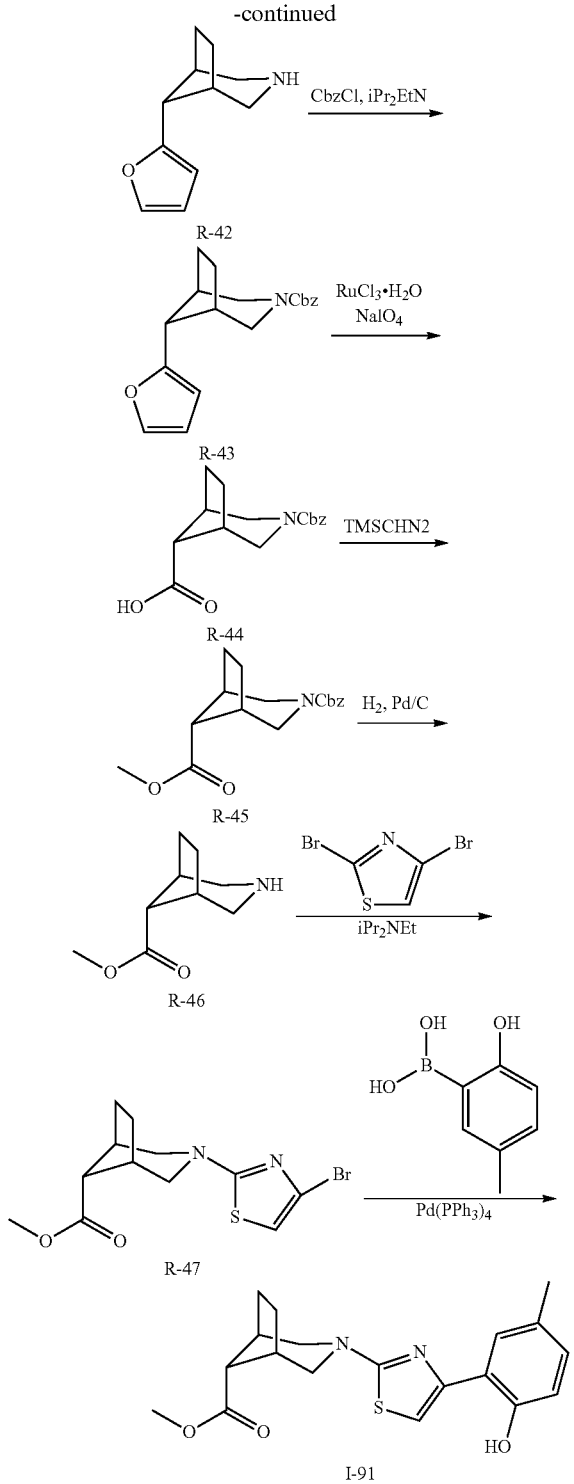

To a stirred solution of furan (63 mmol, 4.5 mL) in THF (30 mL), under argon and cooled to −20° C., is added a solution of n-BuLi in pentane (2.0 N, 69 mmol, 34.5 mL). The mixture is warmed up to ambient temperature and stirred for 1 h. The mixture is then cooled to 0° C. and a solution of R-39 (13 mmol, 2.7 g) in THF (5 mL) is added. The mixture is warmed to ambient temperature and stirred overnight. The mixture is diluted with water, extracted with ethyl acetate, washed with brine, and then concentrated to afford R-40 (3.5 g, 100%). To a solution of R-40 (8.8 mmol, 2.5 g) in DCM (30 mL) is added TFA (88 mmol, 6.7 mL) and t-butyldimethylethylsilane (44 mmol, 7.3 mL). The mixture is stirred at 35° C. overnight. The reaction mixture is concentrated under reduced pressure and the residue is dissolved in ethyl acetate, washed successively with aqueous NaHCO₃, water, and brine then concentrated under reduced pressure. The residue is dissolved in DCM (30 mL) then TsOH (8.8 mmol, 1.7 g) is added. After a clear solution is obtained the solvent is concentrated under reduced pressure. The residue is recrystallized from an isopropanol: heptanes mixture and collected by filtration. The isolated solid is dissolved in methylene chloride then washed with an aqueous sodium carbonate solution followed by brine then dried over anhydrous sodium sulfate and concentrated to give R-41 (1.7 g, 68%). To the stirred solution of R-41 (3.2 mmol, 0.85 g) in DCE is added 1-chloroethyl chloroformate (9.6 mmol, 1.0 mL), the resulting solution is stirred at ambient temperature for 10 min, then heated to 80° C. for 3 h. The solution is then cooled down to ambient temperature and concentrated under reduced pressure. Methanol is added to the residue and the mixture is heated to reflux for 1 h then cooled to ambient temperature and concentrated under reduced pressure to afford R-42 which is used directly. The above crude R-42 is dissolved in DCM then Hunig's base (13 mmol, 2.4 mL) and benzylchloroformate (6.4 mmol, 0.9 mL) are added successively. The resulting solution is stirred at ambient temperature for 2 h and then concentrated under reduced pressure. The residue is dried in a vacuum oven at 40° C. overnight to afford R-43 (quantitative yield). To a solution of R-43 (3.8 mmol, 1.2 g) in a 2:2:3 mixture of acetonitrile:carbon tetrachloride:water mixture (50 mL) is added sodium periodate (38 mmol, 8.2 g). After 10 min, ruthenium trichloride (0.2 mmol, 43 mg) is added. The mixture is stirred for 20 min then diluted with water, extracted with ethyl acetate, washed with brine, dried over anhydrous sodium sulfate, and concentrated under reduced pressure to provide R-44 which is used directly. The isolated R-44 is dissolved in MeOH and the solution is cooled to 0° C. To this mixture is added trimethylsilyldiazomethane (2.0 N in ether, ca. 12 mL), dropwise, until a yellowish color is persistent. Stirring is continued for 30 min then excess reactants are consumed by the addition of acetic acid. The solution is concentrated under reduced pressure and the residue is purified by flash silica gel chromatography to afford the R-45 (0.81 g, 70%). A suspension of R-45 (2.2 mmol, 0.66 g) and 5% palladium on carbon (0.10 g) in MeOH (5 mL) is stirred under a hydrogen atmosphere for 3 h. The mixture is filtered through a pad of diatomaceous earth, rinsed with a 10% MeOH in DCM mixture and the filtrate concentrated under reduced pressure R-46 (0.34 g, 92%). A mixture of R-46 (0.62 mmol, 0.10 g), 2,4-dibromothiazole (0.62 mmol, 0.15 g) and Hunig's base (2.5 mmol, 0.44 ml) in DMF (3 mL) are heated to 85° C. overnight. The mixture is cooled to ambient temperature and the mixture is concentrated under reduced pressure. The residue is purified by flash silica gel chromatography to afford R-47 (0.16 g, 76%). A mixture of R-47 (0.47 mmol, 0.054 g), 4-methyl-2-boronic acid-phenol (0.56 mmol, 0.085 g), tetrakis(triphenylphosphine)palladium (0) (0.047 mmol, 0.31 g, and aqueous sodium carbonate (2 N, 1.9 mmol, 0.9 mL) in THF (3 mL) is heated to reflux overnight. The mixture is cooled to ambient temperature then diluted with water and extracted with ethyl acetate. The combined organic phase is washed with brine then dried over anhydrous sodium sulfate and concentrated under reduced pressure. The residue is purified by flash silica gel chromatography to provide the title compound (0.14 g, 84.7%).

The following intermediate is synthesized in similar fashion from the appropriate reagents:

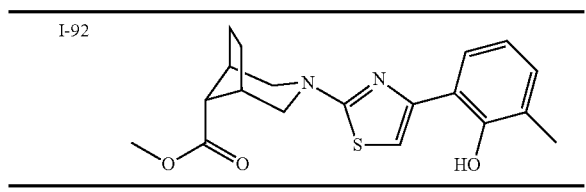

I-92

Synthesis of 3-[4-(2-hydroxy-5-methyl-phenyl)-thiazol-2-yl]-3-aza-bicyclo[3.2.1]octane-8(syn)-carboxylic acid tert-butyl ester (I-93)

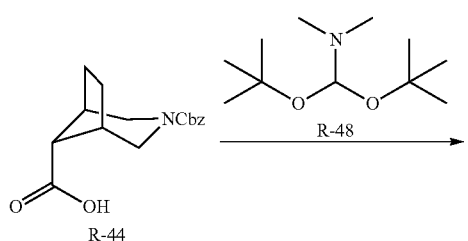

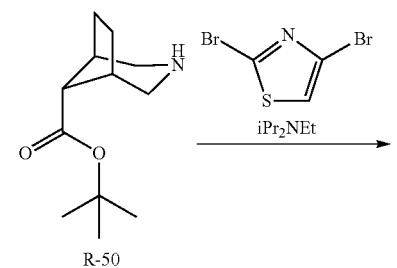

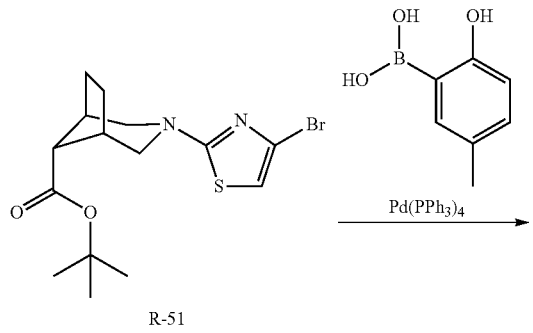

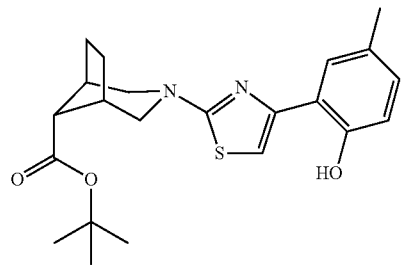

I-93

A suspension of R-44 (28 mmol, 8.0 g) in toluene (40 mL) is heated to 110° C. To this R-48 (166 mmol, 40 mL) is added dropwise. After the addition is complete the solution is stirred at 110° C. for 1 h then cooled to ambient temperature. The solvent is removed under reduced pressure and the residue purified by flash silica gel chromatography to provide R-49 (7.1 g, 74%). A mixture of R-49 (11.6 mmol, 4.0 g) and 5% Pd/C (0.50 g) in MeOH (30 mL) is stirred for 3 h at ambient temperature under an atmosphere of hydrogen. The mixture is filtered through a pad of diatomaceous earth and the filter pad is rinsed with a 10% solution of MeOH in DCM.

The filtrate is concentrated under reduced pressure to provide R-50 (2.4 g, 100%). A mixture of R-50 (11 mmol, 2.7 g), 2,4-dibromothiazole (11 mmol, 2.3 g) and Hunig's base (44 mmol, 7.9 ml) in DMF (12 mL) is heated to 85° C. overnight. The mixture is cooled to ambient temperature and concentrated under reduced pressure. The residue is purified by flash silica gel chromatography to provide R-51 (4.0 g, 96.4%). A mixture of R-51 (11 mmol, 4.4 g), 4-methyl-2-boronic acid-phenol (13 mmol, 1.9 g), tetrakis(triphenylphosphine)palladium(0) (1.1 mmol, 1.2 g) and aqueous $Na_2CO_3$ (2 N, 42 mmol, 21 mL) in THF (20 mL) is heated at reflux overnight. The reaction mixture is cooled to ambient temperature and diluted with water. The mixture is extracted with EtOAc and the combined extracts are washed with brine then dried over anhydrous $Na_2SO_4$ and concentrated under reduced pressure. The residue is purified by flash silica gel chromatography to provide the title compound (3.1 g, 72.2%).

Synthesis of (3-[4-(2-hydroxy-5-methyl-phenyl)-thiazol-2-yl]-8-methyl-3-aza-bicyclo[3.2.1]octane-8(syn)-carboxylic acid methyl ester (I-94)

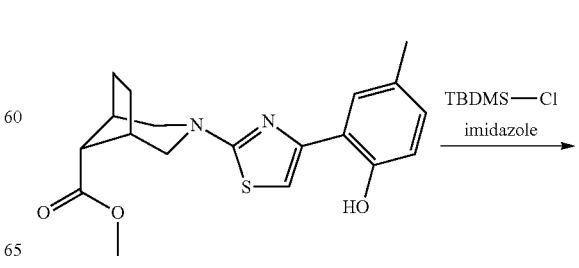

I-91

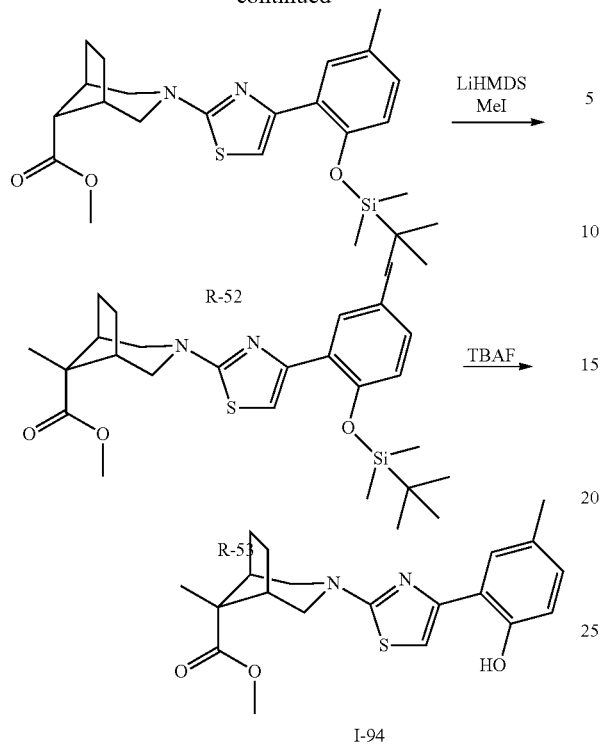

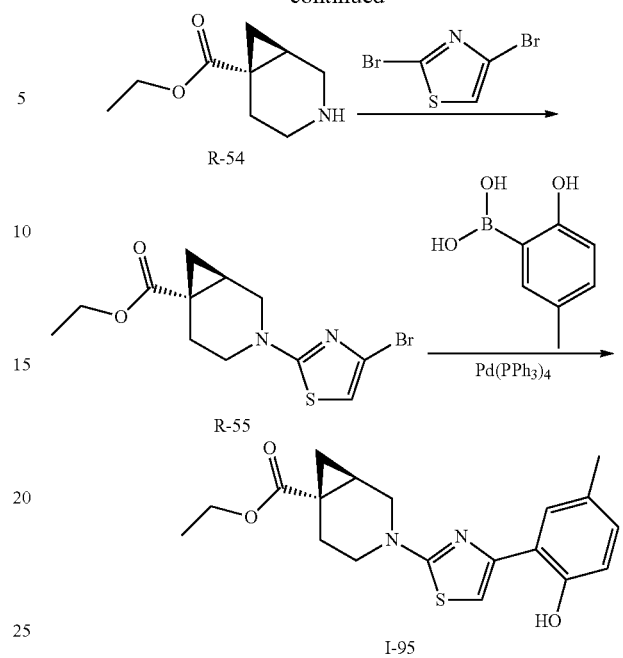

To a solution of I-91 (1.7 mmol, 0.63 g) in DMF (9 mL) is added imidazole (4.2 mmol, 0.29 g), followed by tert-butyldimethyl chlorosilane (2.1 mmol, 0.32 g). The mixture is stirred at ambient temperature for three days then diluted with water and extracted with EtOAc. The combined organic layers are washed with water followed by brine and then concentrated under reduced pressure. The residue is purified by flash silica gel chromatography to provide R-52 (0.72 g, 86%). To a solution of R-52 (1.4 mmol, 0.65 g) in THF (10 mL), cooled to −78° C., is added a solution of LiHMDS in THF (1M, 2.7 mmol, 2.7 mL). The resulting solution is stirred at −78° C. for 30 min then MeI (0.017 mL, 2.7 mmol) is added. The reaction mixture is warmed to ambient temperature and stirred overnight. The mixture is diluted with DCM and excess reactants are consumed by the addition of a saturated aqueous solution of $NH_4Cl$. The organic layer is washed with brine then concentrated under reduced pressure and the residue purified by flash silica gel chromatography to provide R-53 (0.49 g, 75%). To a solution of R-53 (1.0 mmol, 0.49 g) in THF (5 mL) is added a solution of TBAF in THF (1M, 2.5 mmol, 2.5 mL). The mixture is stirred at room temperature for 1 h then concentrated under reduced pressure and the residue purified by flash silica gel chromatography to give the title compound (0.29 g, 77%).

Synthesis of (1R,6S)-3-[4-(2-Hydroxy-5-methyl-phenyl)-thiazol-2-yl]-3-aza-bicyclo-[4.1.0]-heptane-6-carboxylic acid ethyl ester (I-95)

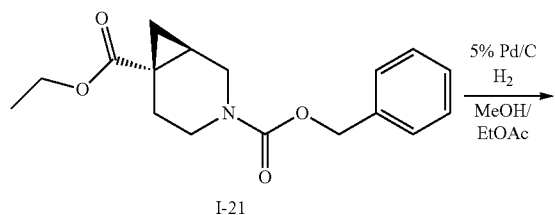

A mixture of I-21 (1.1 mmol, 0.35 g) and 5% Pd/C (0.09 mmol, 0.2 g) in 1:1 mixture of MeOH:EtOAc (12 mL) is stirred at ambient temperature for 3 h under an atmosphere of hydrogen. The mixture is filtered through a pad of diatomaceous earth and concentrated under reduced pressure to provide R-54 (0.24 g, 106%). To a solution of R-54 (1.4 mmol, 0.24 g) in DMF (14 mL) is added 2,4-dibromothiazole (1.6 mmol, 0.40 g) followed by diisopropylethylamine (2.9 mmol, 0.50 mL). The resultant reaction mixture is heated at 80° C. for 3 days then cooled to ambient temperature. The mixture is diluted with water and extracted with EtOAc. The combined organic extracts are washed with brine, dried over anhydrous sodium sulfate and concentrated under reduced pressure. The residue is purified by flash silica gel chromatography to provide R-55 (0.15 g, 35%). To a solution of R-55 (0.49 mmol, 0.15 g) in 1,4-dioxane (5 mL) is added 4-methyl-2-boronic acid-phenol (0.049 mmol, 0.075 g) and a solution of $Na_2CO_3$ (1.8 mmol, 2M, 0.90 mL). The mixture is sparged with $N_2$ for 10 min then $Pd(PPh_3)_4$ (0.043 mmol, 0.050 g) is added and the mixture is heated to 80° C. and stirred overnight. The reaction mixture is cooled to ambient temperature, diluted water, and extracted with EtOAc. The combined organic extracts are washed with brine, dried over anhydrous sodium sulfate, and concentrated under reduced pressure. The residue is purified by flash silica gel chromatography to provide the title compound (0.072 g, 41%).

The following intermediate is synthesized in similar fashion from the appropriate reagents:

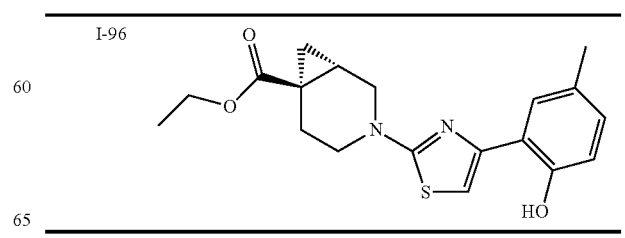

Preparation of ethyl 4-[[4-[2-[(4-bromo-2-methyl-phenyl)methoxy]-5-methyl-phenyl]thiazol-2-yl]amino]butanoate (I-97)

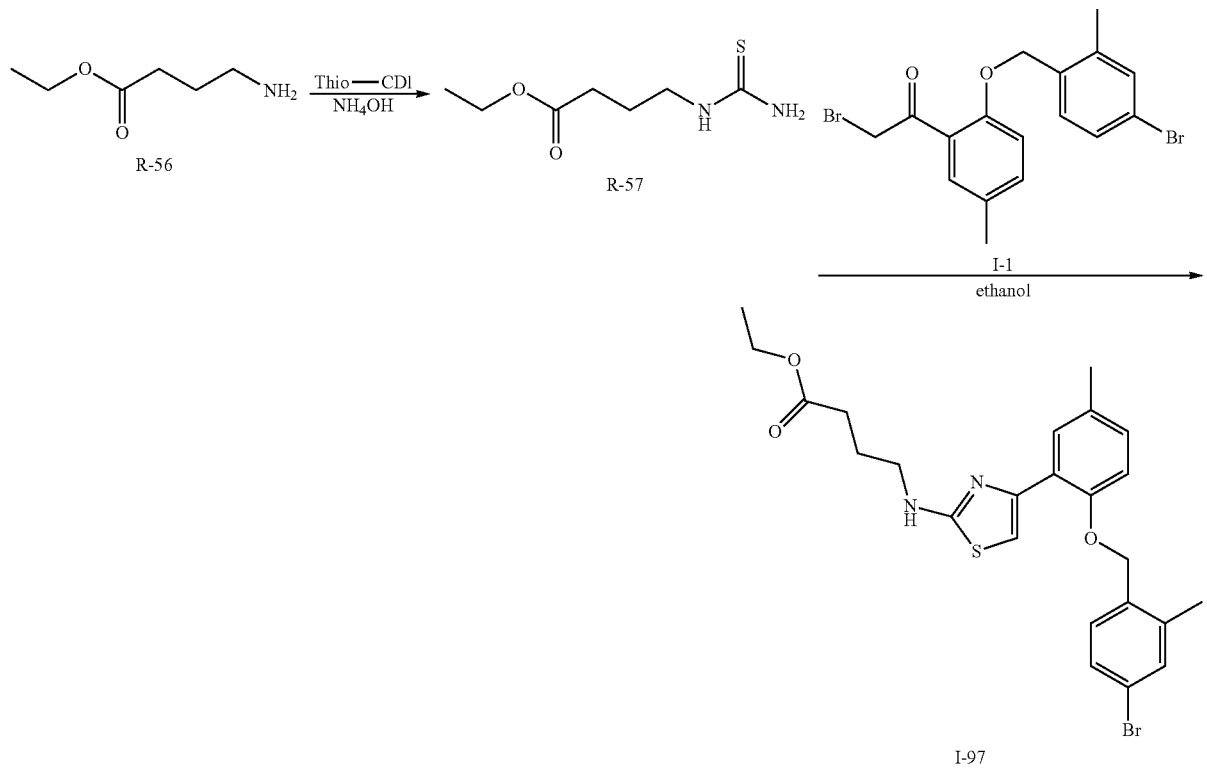

A mixture of R-56 (4.5 mmol, 0.75 g) and di-imidazol-1-yl-methanethione (7.5 mmol, 1.30 g) are dissolved in THF (20 mL) and triethylamine (13.4 mmol, 2 mL) is added. The mixture is stirred at ambient temperature for 16 h. Then it is concentrated under reduced pressure and the residue is dissolved in a mixture of $CH_3CN$ (10 mL) and $NH_4OH$ (5 mL). The resulting solution is heated to 60° C. for 3 h then cooled to ambient temperature and concentrated in vacuo to give R-57. A mixture of R-57 (0.36 mmol, 0.070 g) and I-1 (0.36 mmol, 0.15 g) are dissolved in EtOH (10 mL) and heated to 65° C. for 6 h. The reaction is concentrated in vacuo and the residue is purified by flash silica gel chromatography to give title intermediate (0.12 g, 66%).

The following intermediates are synthesized in similar fashion from the appropriate reagents:

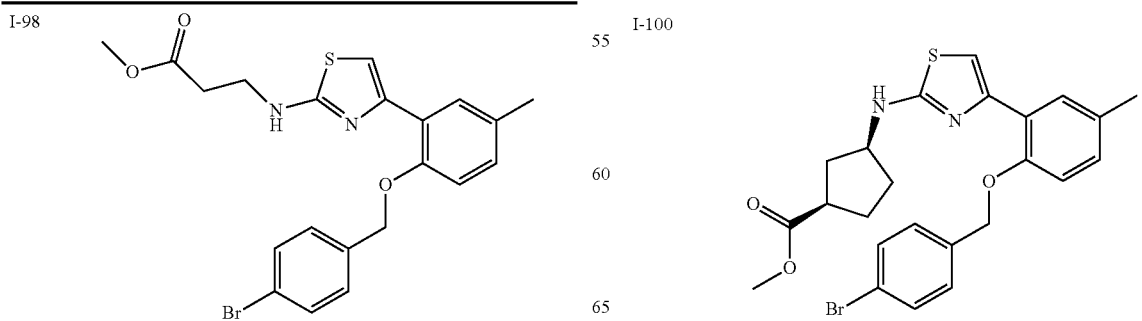

I-101 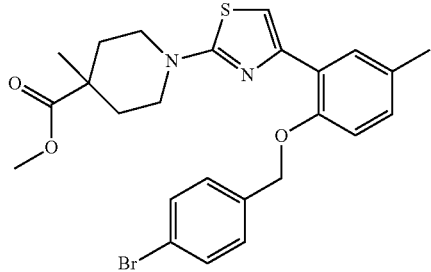 [SMILES: COC(=O)C1(C)CCN(c2nc(-c3cc(C)ccc3OCc3ccc(Br)cc3)cs2)CC1]

I-102 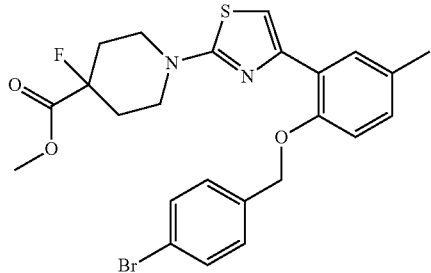 [SMILES: COC(=O)C1(F)CCN(c2nc(-c3cc(C)ccc3OCc3ccc(Br)cc3)cs2)CC1]

I-103 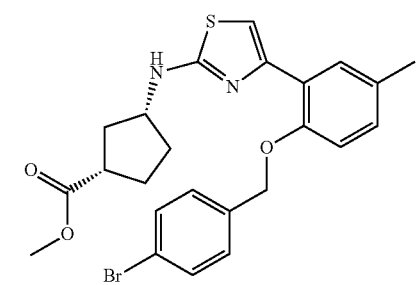 [SMILES: COC(=O)[C@H]1CC[C@@H](Nc2nc(-c3cc(C)ccc3OCc3ccc(Br)cc3)cs2)C1]

I-104 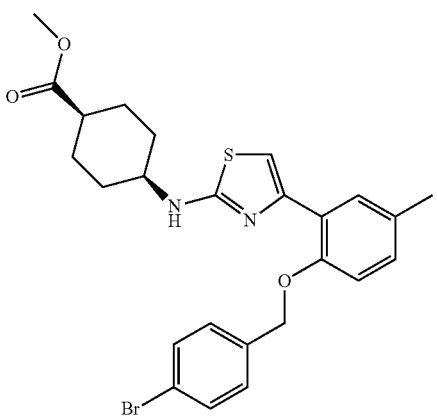 [SMILES: COC(=O)[C@H]1CC[C@@H](Nc2nc(-c3cc(C)ccc3OCc3ccc(Br)cc3)cs2)CC1]

I-105 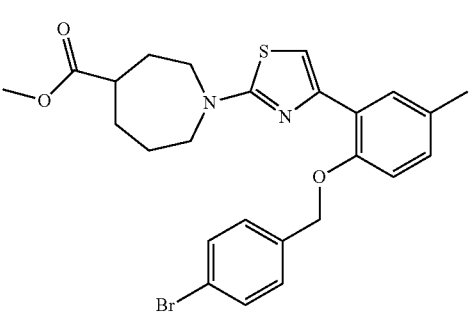

I-106 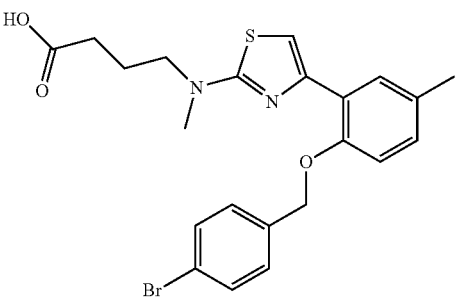 [SMILES: Cc1ccc(OCc2ccc(Br)cc2)c(-c2csc(N(C)CCCC(=O)O)n2)c1]

Preparation of ethyl 1-[4-[2-[(4-bromo-2-methyl-phenyl)methoxy]-5-methyl-phenyl]thiazol-2-yl]pyrrolidine-3-carboxylate (I-107)

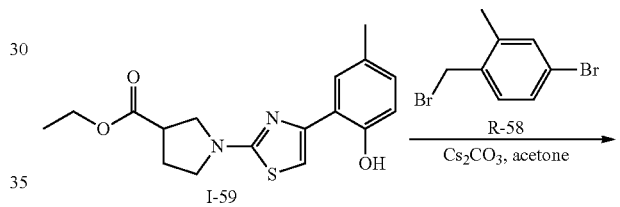

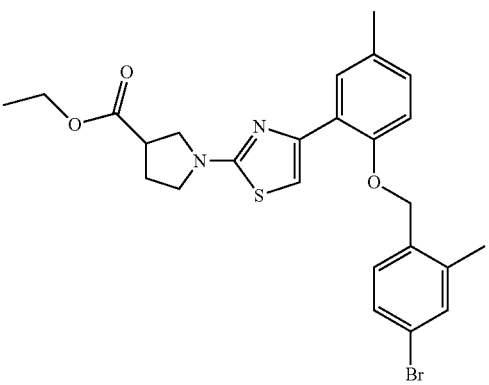

I-107

A mixture of I-59 (1.3 mmol, 0.44-g), R-58 (1.6 mmol, 0.42 g), and Cs$_2$CO$_3$ (2.6 mmol, 0.86 g) is dissolved in acetone (10 mL) and stirred at ambient temperature for 16 h. The mixture is filtered and then concentrated under reduced pressure to give title intermediate which is used without further purification.

The following intermediates are synthesized in similar fashion from the appropriate reagents:

I-108
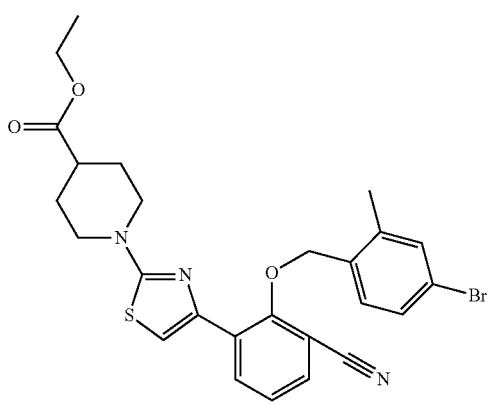 [SMILES: CCOC(=O)C1CCN(c2nc(-c3cccc(C#N)c3OCc3ccc(Br)cc3C)cs2)CC1]
I-109
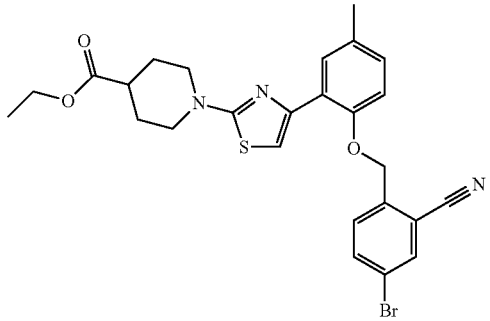 [SMILES: CCOC(=O)C1CCN(c2nc(-c3cc(C)ccc3OCc3ccc(Br)cc3C#N)cs2)CC1]
I-110
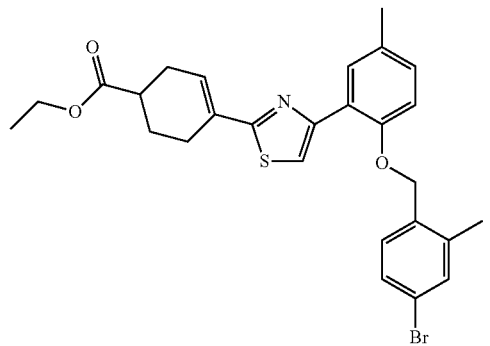 [SMILES: CCOC(=O)C1CC=C(c2nc(-c3cc(C)ccc3OCc3ccc(Br)cc3C)cs2)CC1]
I-111
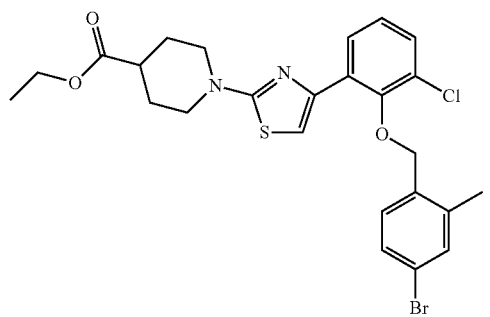 [SMILES: CCOC(=O)C1CCN(c2nc(-c3cccc(Cl)c3OCc3ccc(Br)cc3C)cs2)CC1]
I-112
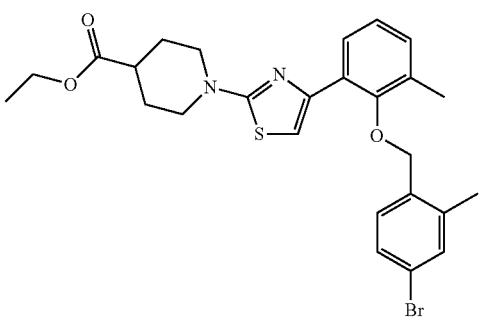 [SMILES: CCOC(=O)C1CCN(c2nc(-c3cccc(C)c3OCc3ccc(Br)cc3C)cs2)CC1]
I-113
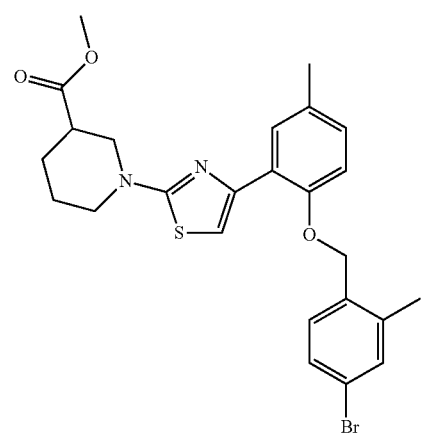 [SMILES: COC(=O)C1CCCN(c2nc(-c3cc(C)ccc3OCc3ccc(Br)cc3C)cs2)C1]
I-114
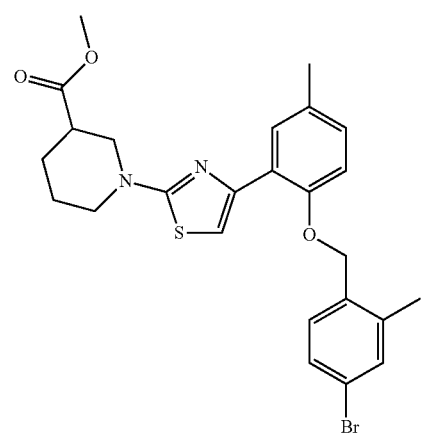 [SMILES: COC(=O)C1CCCN(c2nc(-c3cc(C)ccc3OCc3ccc(Br)cc3C)cs2)C1]
I-115
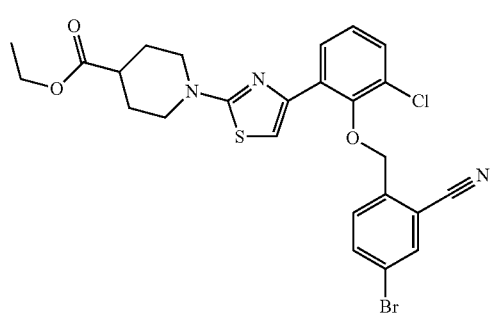 [SMILES: CCOC(=O)C1CCN(c2nc(-c3cccc(Cl)c3OCc3ccc(Br)cc3C#N)cs2)CC1]

I-116 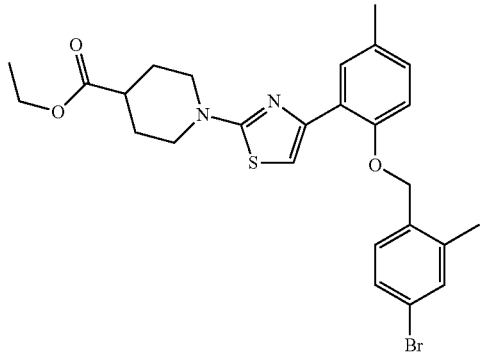 [SMILES: CCOC(=O)C1CCN(c2nc(-c3cc(C)ccc3OCc3ccc(Br)cc3C)cs2)CC1]
I-117 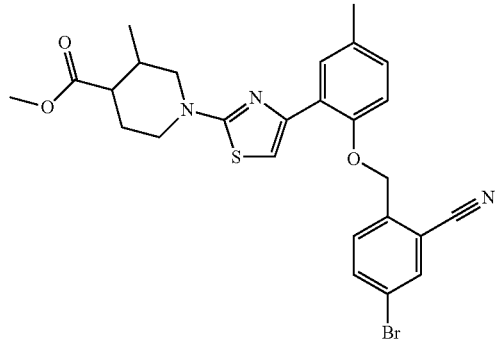 [SMILES: COC(=O)C1CCN(c2nc(-c3cc(C)ccc3OCc3ccc(Br)cc3C#N)cs2)CC1C]
I-118 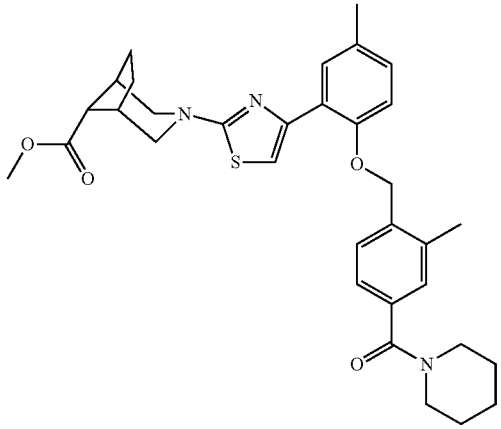 [SMILES: COC(=O)C1C2CCC1CN(c1nc(-c3cc(C)ccc3OCc3ccc(C(=O)N4CCCCC4)cc3C)cs1)C2]
I-119 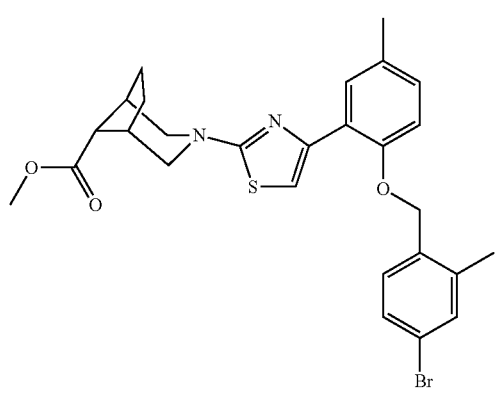
I-120 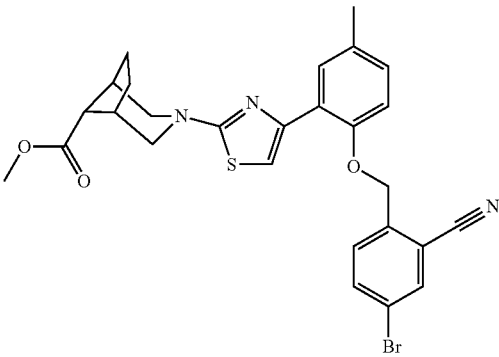 [SMILES: COC(=O)C1C2CCC1CN(c1nc(-c3cc(C)ccc3OCc3ccc(Br)cc3C#N)cs1)C2]
I-121 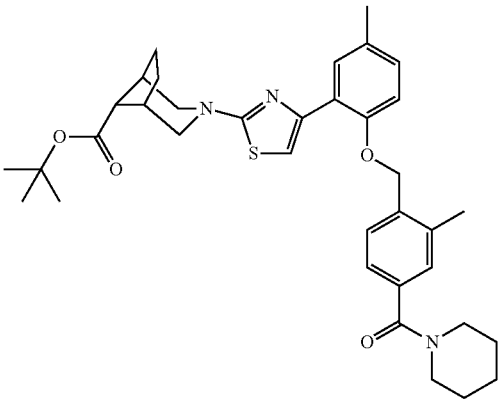 [SMILES: Cc1ccc(OCc2ccc(C(=O)N3CCCCC3)cc2C)c(-c2csc(N3CC4CCC(C3)C4C(=O)OC(C)(C)C)n2)c1]
I-122 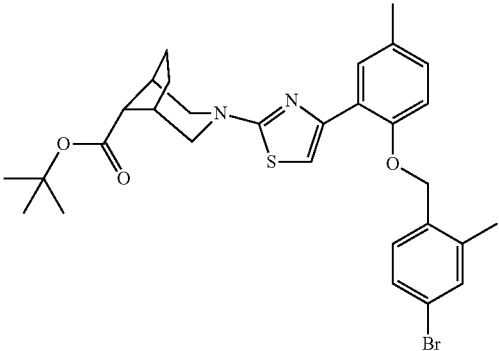 [SMILES: Cc1ccc(OCc2ccc(Br)cc2C)c(-c2csc(N3CC4CCC(C3)C4C(=O)OC(C)(C)C)n2)c1]
I-123 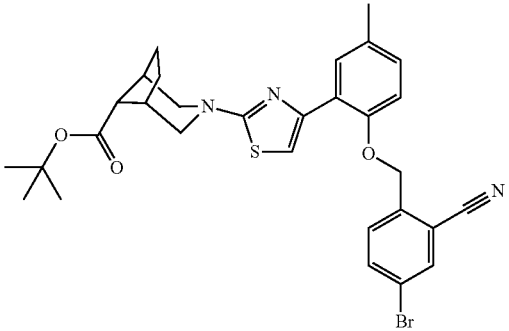 [SMILES: Cc1ccc(OCc2ccc(Br)cc2C#N)c(-c2csc(N3CC4CCC(C3)C4C(=O)OC(C)(C)C)n2)c1]

I-124

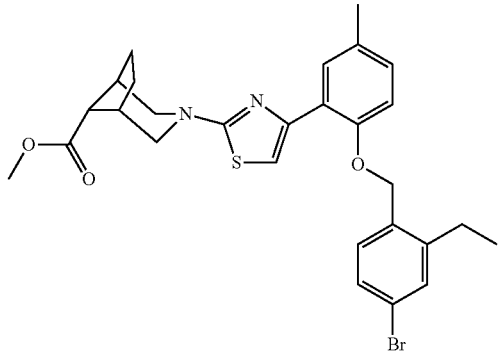 [SMILES: CCc1cc(Br)ccc1COc1ccc(C)cc1-c1csc(N2CC3CCC(C2)C3C(=O)OC)n1]

I-125

I-126

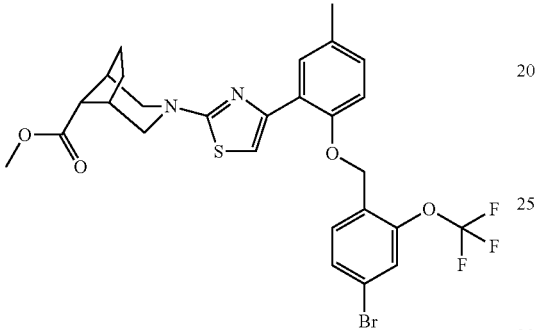

I-127

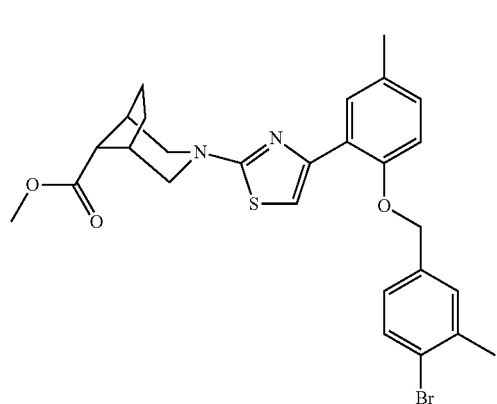

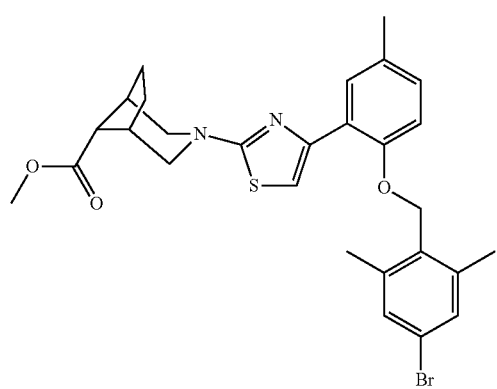

Preparation of ethyl 1-[4-[2-[(4-bromo-2-methoxy-phenyl)methoxy]-5-methyl-phenyl]thiazol-2-yl]piperidine-4-carboxylate (I-128)

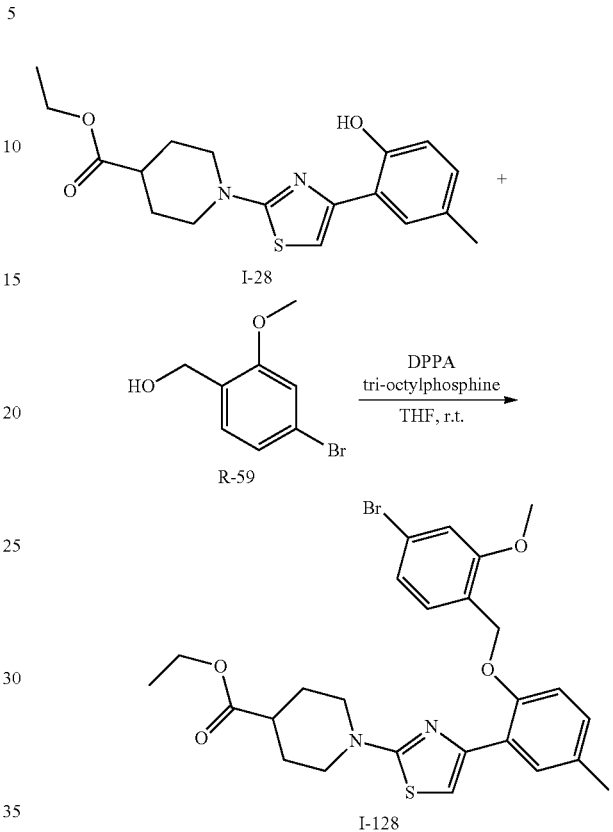

To a solution of I-28 (1.7 mmol, 0.60 g) in toluene (30 mL) is added R-59 (2.6 mmol, 0.56 g) followed by trioctylphosphine (3.5 mmol, 1.5 mL). To this is added ADDP (2.6 mmol, 0.65 g). The mixture is heated at 95° C. overnight then cooled to room temperature and concentrated under reduced pressure. The residue is purified by flash silica gel chromatography to provide the title compound (0.21 g, 22%).

The following intermediate is synthesized in similar fashion using the appropriate reagents:

I-129

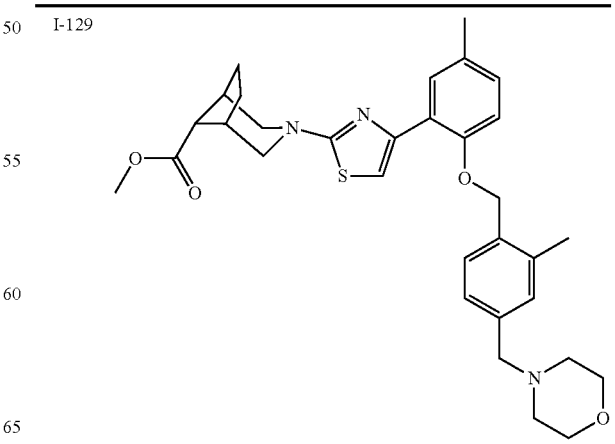

Synthesis of 3-[4-(2-hydroxy-5-methyl-phenyl)-thiazol-2-yl]-3-aza-bicyclo[3.2.1]octane-8(syn)-carboxylic acid methyl ester (I-130)

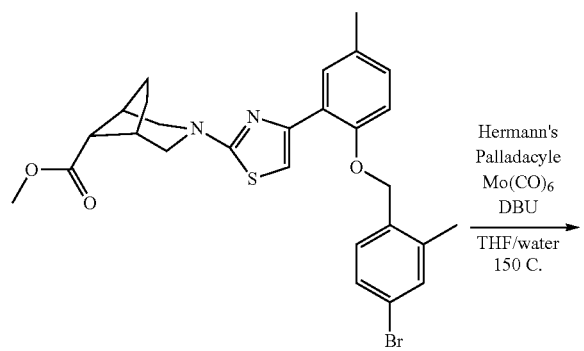

I-119

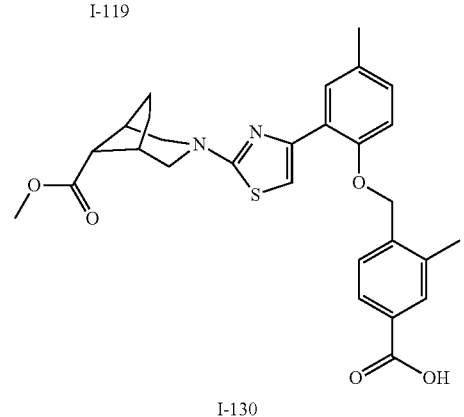

I-130

To a solution of I-119 (1.68 mmol, 0.91 g) in a 1:1 mixture of water:THF (15 mL) is added molybdenum hexacarbonyl (1.0 mmol, 0.27 g), followed by DBU (5.4 mmol, 0.80 mL) and Hermann's palladacycle (1.34 mmol, 1.26 g). The mixture is heated in the microwave at 150° C. for 15 min then concentrated down under reduced pressure. The residue is purified by flash silica gel chromatography to afford the tile compound as a white powder (0.40 g, 48%).

The following intermediate is synthesized in similar fashion from the appropriate reagents:

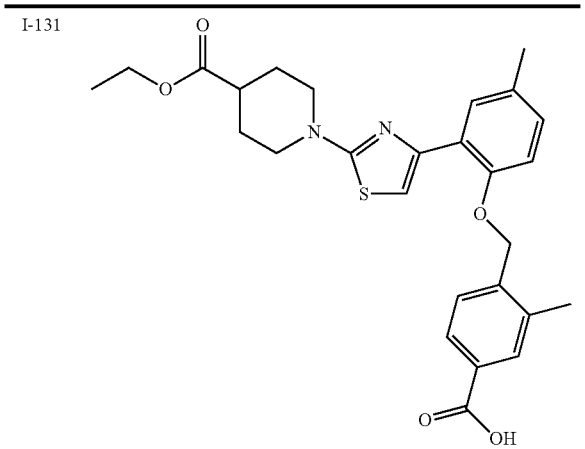

I-131

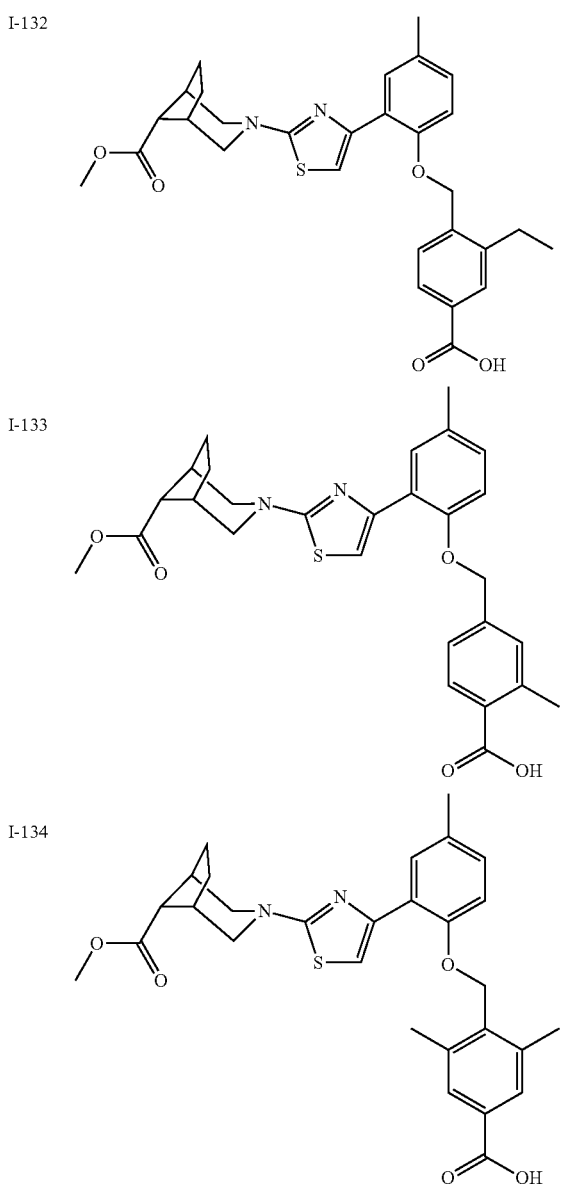

I-132

I-133

I-134

Synthesis of (I-135)

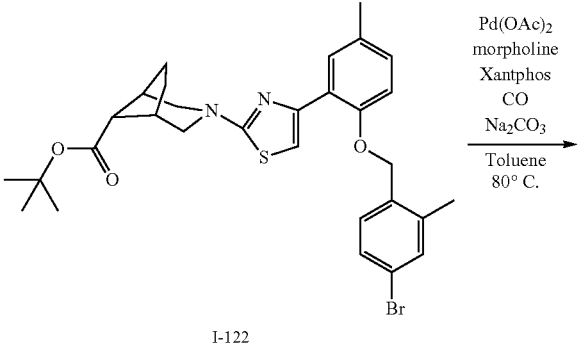

I-122

I-135

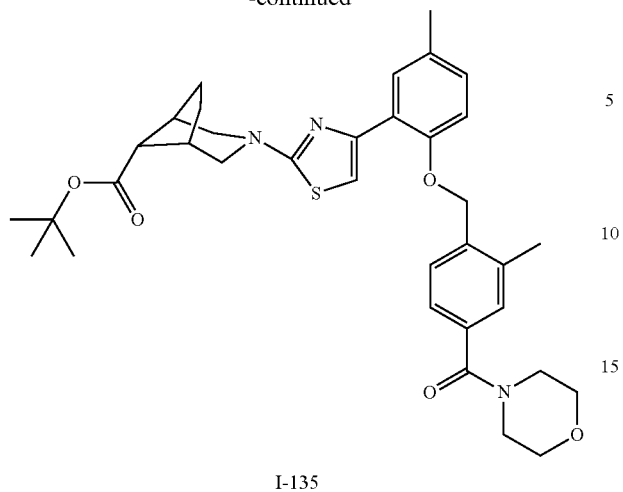

To a solution of I-122 (0.18 mmol, 0.11 g) in toluene (2 mL) is added morpholine (0.55 mmol, 0.056 mL), Pd(OAc)$_2$ (0.02 mmol, 0.004 g), Xantphos (0.037 mmol, 0.021 g), and Na$_2$CO$_3$ (0.55 mmol, 0.058 g). The reaction mixture is heated overnight at 80° C. under an atmosphere of CO. The mixture is cooled to ambient temperature and diluted with EtOAc then washed with an aqueous solution of NaHCO$_3$ followed by brine. The organic phase is dried over anhydrous Na$_2$SO$_4$, concentrated under reduced pressure, and the residue purified by flash silica gel chromatography to provide the title compound (0.075 g, 64%).

The following intermediate is synthesized in similar fashion from the appropriate reagents:

I-136

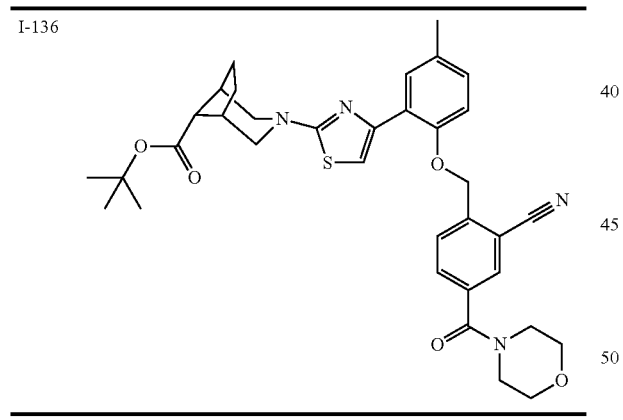

Preparation of 1-{4-[2-(4-Formyl-2-methyl-benzyloxy)-5-methyl-phenyl]-thiazol-2-yl}-piperidine-4-carboxylic acid ethyl ester (I-137)

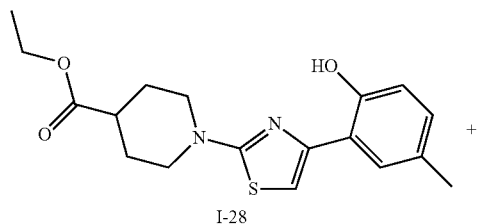

I-28

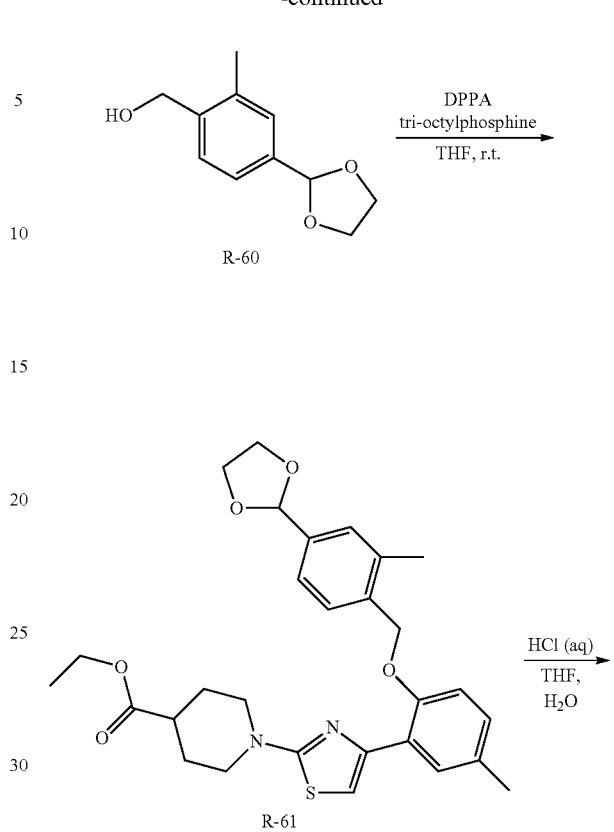

To a solution of I-28 (2.2 mmol, 0.75 g) in THF (6 mL) is added R-60 (3.2 mmol, 0.63 g) and trioctylphosphine (4.3 mmol, 2.0 mL). To this is added ADDP (3.2 mmol, 0.82 g). The mixture is stirred at ambient temperature for 3 h then is diluted with DCM and concentrated under reduced pressure. The residue is purified by flash silica gel chromatography to provide R-61 (1.0 g, 93%) as a clear oil. To a solution of R-61 (0.12 g, 0.23 mmol) in THF (2 mL) is added HCl (2N, 1 mmol, 0.5 mL). The mixture is stirred at room temperature for 30 min then neutralized by the addition of an aqueous solution of NaHCO$_3$. The mixture is diluted with water and extracted with EtOAc. The combined organic phase is dried over anhydrous sodium sulfate and concentrated under reduced pressure to provide the title compound (0.10 g, 91%) as a yellow oil.

The following intermediates are synthesized in similar fashion from the appropriate reagents:

I-138

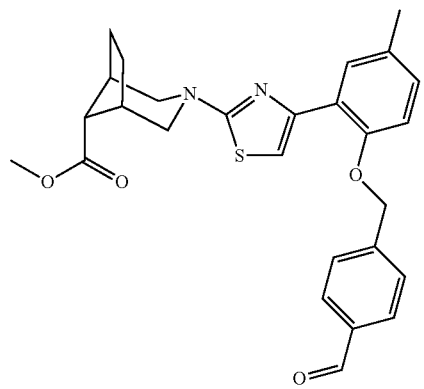 [SMILES: COC(=O)C1C2CCC1CN(c1nc(-c3cc(C)ccc3OCc3ccc(C=O)cc3)cs1)C2]

I-139

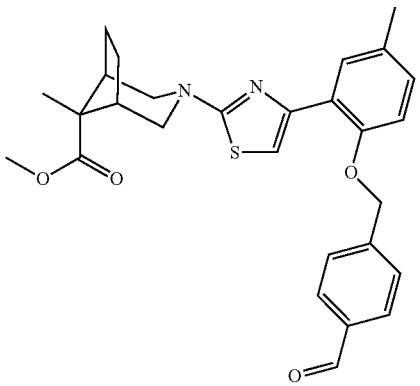 [SMILES: COC(=O)C1(C)C2CCC1CN(c1nc(-c3cc(C)ccc3OCc3ccc(C=O)cc3)cs1)C2]

Synthesis of Final Compounds

Example 1

Synthesis of 3-(4-{5-methyl-2-[2-methyl-4-(piperidine-1-carbonyl)-benzyloxy]-phenyl}-thiazol-2-yl)-3-aza-bicyclo[3.2.1]octane-8-carboxylic acid (89)

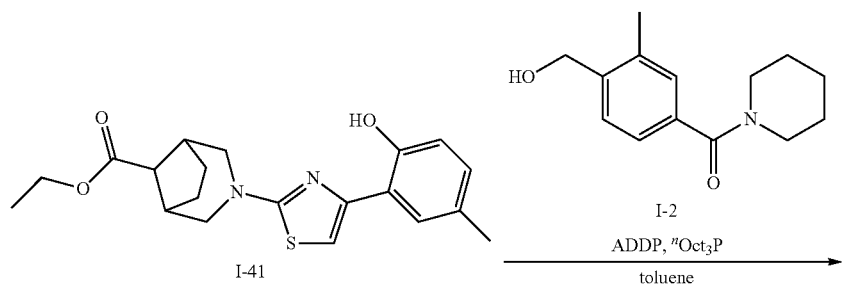

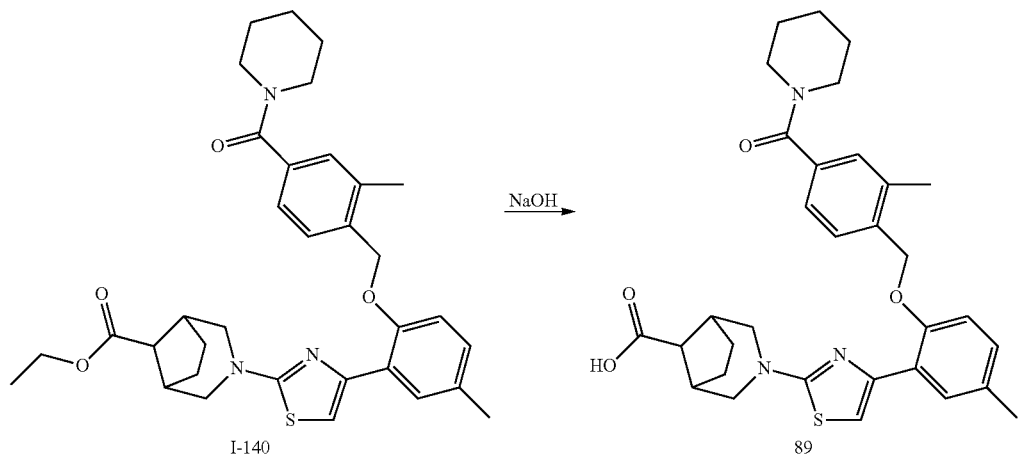

A solution of I-41 (0.38 mmol, 0.14 g) in toluene (8 mL) is treated with I-2 (0.75 mmol, 0.17 m), trioctylphosphine (0.60 mmol, 0.30 mL) and ADDP (0.75 mmol, 0.190 g). The resulting mixture is heated at 80° C. for 16 h. Additional trioctylphosphine (0.60 mmol, 0.30 mL) and ADDP (0.75 mmol, 0.190 g) are added and the mixture is stirred at 80° C. for 16 h. The solution is cooled to ambient temperature and concentrated to dryness. Purification of the crude by flash chromatography gave I-140 that is dissolved in 1:1:1 (v/v/v) MeOH:THF:5M aqueous NaOH (3 mL). The mixture is heated at 60° C. for 15 min then concentrated to dryness. Purification of the crude by HPLC afforded the title compound (33 mg, 16%).

The following compounds from Table 1 are also obtained in a similar manner to the title compound:

Compounds 1, 8, 9, 11-12, 17, 32, 34, 37-38, 41-42, 48, 55-57, 59, 64, 67-68, 72-73, 76, 78-79, 85, 88, 97-98, 102-103, 109, 117-118, 127, 130, 141-142, 145, 148-149, 182-184, 208, 209, 226, 229, 236, 240, 243, 248, 260, 274.

The following compounds are also obtained in a similar manner described for the title compound utilizing I-3:

Compound 224, 241, 247, 256, 268.

The following compound is also obtained in a similar manner described for the title compound utilizing I-4:

Compound 294.

The following compounds are also obtained in a similar manner described for the title compound utilizing I-11:

Compounds 2, 14, 24, 28, 33, 43-44, 58, 61, 71, 74, 77, 80, 83-84, 86-87, 99, 100, 114, 132, 185-193, 206, 210, 213, 218, 220, 231, 233, 237, 242, 246, 254, 257, 261.

The following compounds are also obtained in a similar manner described for the title compound utilizing I-12:

Compounds 82, 101, 107, 108, 110-111, 116, 120-121, 124, 128-129, 131, 133, 135-137, 139, 143-144, 146-147, 150, 152-157, 203, 205, 207, 217, 222, 223, 230, 234, 235, 244, 245, 252, 253, 259, 275.

The following compound is also obtained in a similar manner described for the title compound utilizing I-13:

Compound 351.

The following compounds are also obtained in a similar manner described for the title compound utilizing I-14:

Compound 225, 228, 255

The following compound is also obtained in a similar manner described for the title compound utilizing I-15:

Compound 277.

The following compound is also obtained in a similar manner described for the title compound utilizing I-16:

Compound 276.

The following compounds are also obtained in a similar manner described for the title compound utilizing triphenylphosphine:

Compounds 21, 63, 113, 126, 151, 166, 173-174, 177

Example 2

Preparation of 1-{4-[5-methyl-2-(2-methyl-4-morpholin-4-ylmethyl-benzyloxy)-phenyl]-thiazol-2-yl}-piperidine-4-carboxylic acid (20)

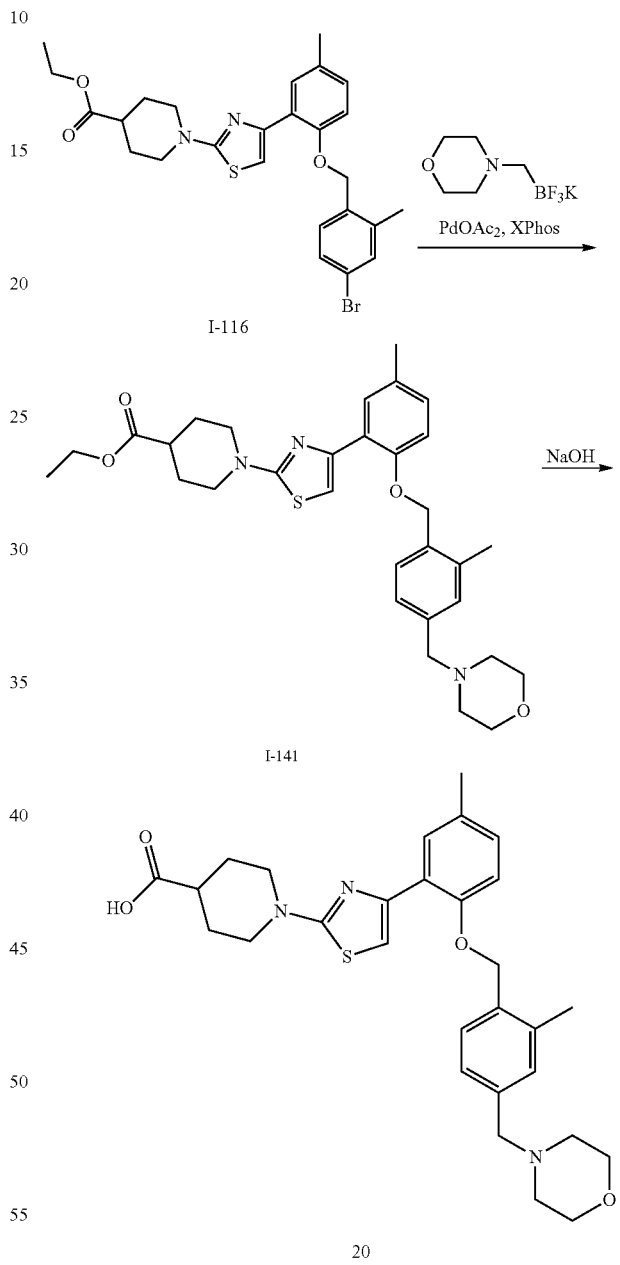

To a vessel is added I-116 (6.3 mmol, 3.3 g), potassium trifluoro(morpholinomethyl)boron (9.4 mmol, 1.95 g), Pd(OAc)$_2$ (0.63 mmol, 0.14 g), Xphos (1.3 mmol, 0.60 g), and Cs$_2$CO$_3$ (19 mmol, 6.1 g) in a 9:1 mixture of THF:water (86 mL). The vessel is sealed then heated at 95° C. for 18 h. The mixture is concentrated in vacuo and the residue is dissolved in EtOAc. Organics are washed with water, then brine, dried over sodium sulfate and concentrated in vacuo to afford a residue that is purified by flash chromatography to give I-141

(2.98 g, 78%). I-141 (4.9 mmol, 3.0 g) is dissolved in THF (12 mL), MeOH (12 mL), and 5N aqueous NaOH (2.5 mL) and stirred at 60° C. for 15 min. The mixture is concentrated in vacuo then purified by flash chromatography to give the title compound (1.6 g, 63%).

The following compounds are prepared in a similar manner to the title compound:

Compounds 3, 4, 6, 10, 22-23, 35-36, 51-52, 60, 62, 81, 167, 179, 181, 201, 278, 280.

Example 3

Preparation of (1R,3S)-3-[[4-[5-methyl-2-[[2-methyl-4-(piperidine-1-carbonyl)phenyl]methoxy]phenyl]thiazol-2-yl]amino]cyclopentanecarboxylic acid (40)

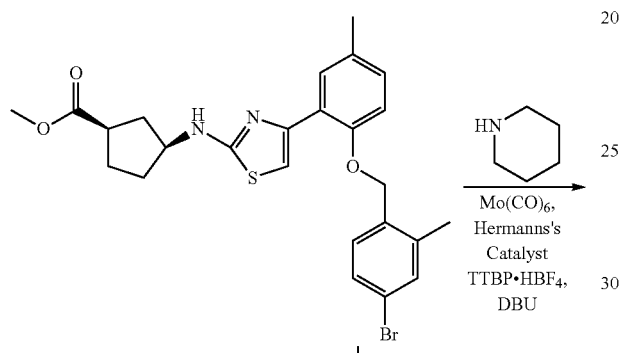

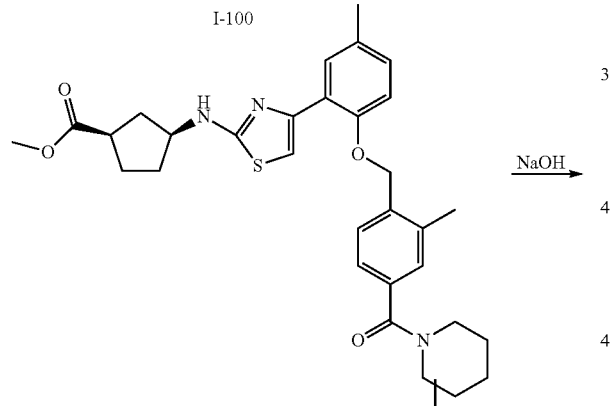

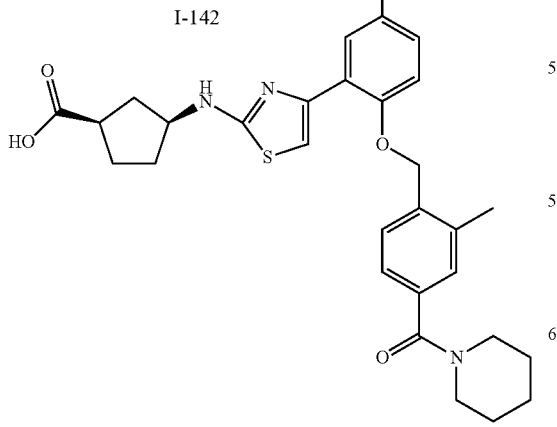

To a microwave vial is added I-100 (0.20 mmol, 0.10 g), molybdenum hexacarbonyl (2.0 mmol, 0.51 g), acetoxy-[[2-(bis-o-tolylphosphanyl)phenyl]methyl]palladium (0.02 mmol, 0.02 g), tri-tert-butyl-phosphonium tetrafluoroborate (0.04 mmol, 0.01 g), and piperidine (2.3 mmol, 0.22 mL) in 2 mL THF followed by DBU (2.00 mmol, 0.30 mL). The tube is sealed and the reaction is heated in a microwave reactor at 150° C. for 20 min. The mixture is filtered through diatomaceous earth and concentrated in vacuo. The residue is purified by flash silica gel chromatography to give I-142 that is dissolved in 1:1:1 (v/v/v) solution of THF:MeOH:5N aqueous NaOH and stirred at 60° C. for 15 min. The mixture is concentrated in vacuo then purified by HPLC to give the title compound (0.03 g, 50%).

The following compounds are prepared in a similar manner to the title compound:

Compounds 15, 31, 39, 49, 66, 106, 122, 239, 279.

Example 4

Preparation of cis-1-[4-[2-[[2-cyano-4-(morpholinomethyl)phenyl]methoxy]-5-methyl-phenyl]thiazol-2-yl]-3-methyl-piperidine-4-carboxylic acid (69)

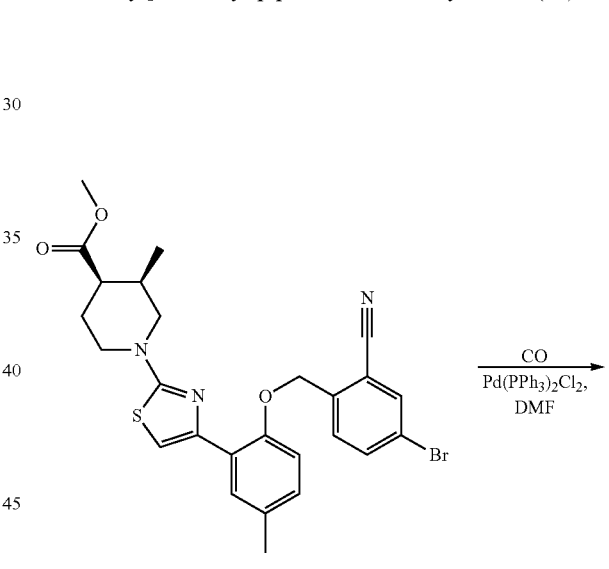

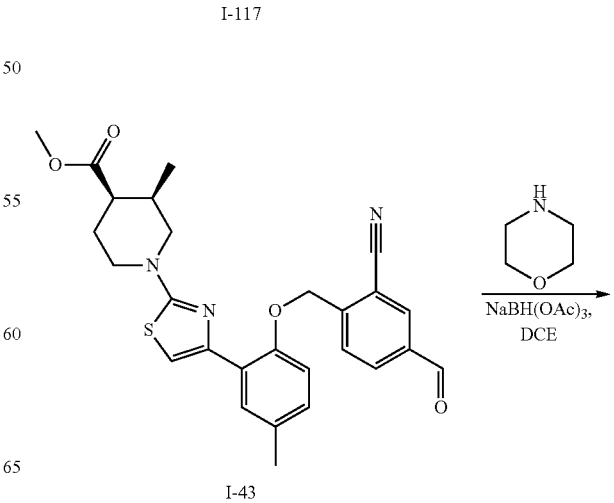

Example 5

Preparation of 1-[4-[2-[[2-cyano-4-(pyrrolidine-1-carbonyl)phenyl]methoxy]-5-methyl-phenyl]thiazol-2-yl]piperidine-4-carboxylic acid (30)

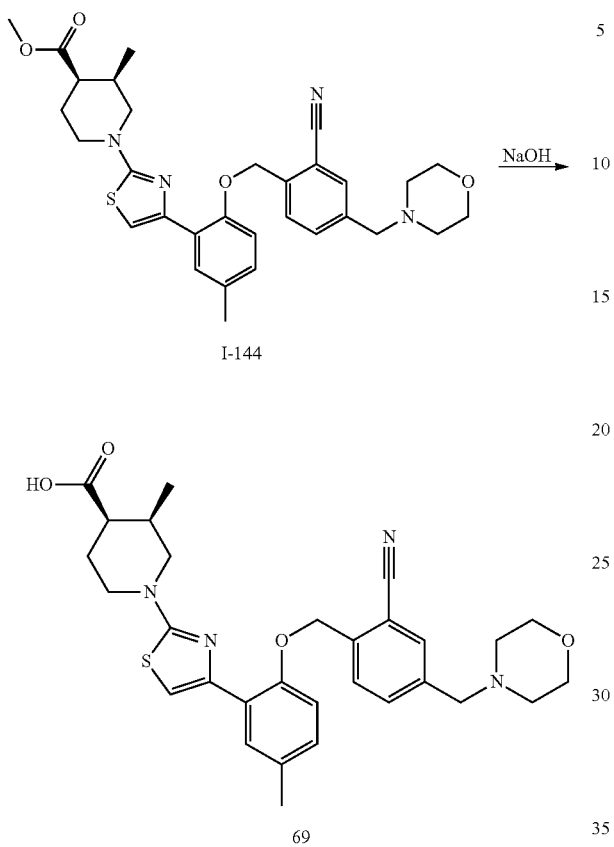

A solution of I-117 (0.65 mmol, 0.35 g), sodium formate (1 mmol, 0.07 g), and palladium(II) bis-triphenylphosphine chloride (0.3 mmol, 0.14 g) in DMF (15 mL) is placed under a CO atmosphere. The reaction is heated to 105° C. with CO being bubbled into the suspension throughout the reaction. The mixture is concentrated under a stream of $N_2$ then directly purified by flash chromatography to give I-143 (0.07 g, 22%). To a solution of I-143 (0.07 mmol, 0.04 g) and morpholine (0.36 mmol, 0.031 mL) in DCE (3 mL) is added NaBH(OAc)$_3$ (0.71 mmol, 0.15 g). The mixture is heated at 60° C. for 1 h then cooled to ambient temperature. The reaction is then partitioned between 5% MeOH in DCM and brine. The mixture is filtered through a phase separator then concentrated in vacuo to afford I-144 that is dissolved in 1:1:1 (V/V/V) THF:MeOH:5 N aqueous NaOH (2 mL) and stirred at 60° C. for 15 min. The mixture is concentrated in vacuo then purified via HPLC to give the title compound (0.01 g, 33%).

The following compounds are prepared in a similar manner to the title compound:
Compounds 7, 16, 18, 25-29, 45-47, 53-54, 75, 91, 93-96, 104-105, 112, 115, 119, 123, 134, 138, 140, 168-172, 175, 212, 227, 232, 238, 264, 265, 267, 352, 354, 355, 356, 357, 358, 359.

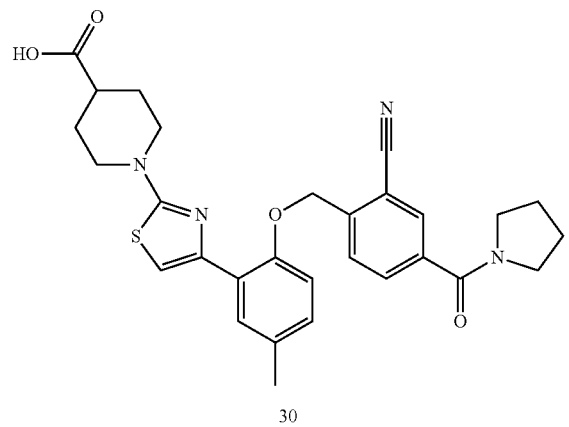

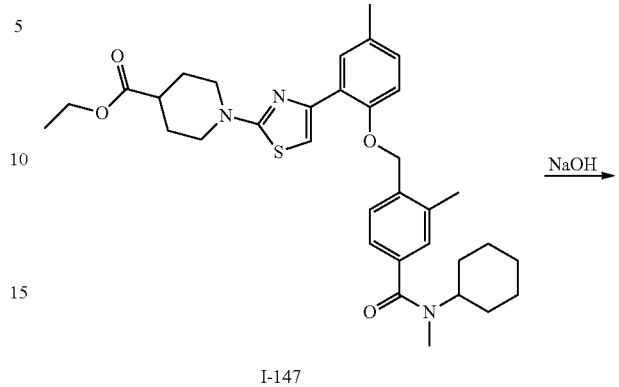

A solution of I-109 (1.3 mmol, 0.70 g) in dioxane (14 mL) is added to three Endeavor reactors. [1,1'-Bis(diphenylphosphino)ferrocene]dichloro palladium(II) dichloromethane adduct (0.07 mmol, 0.05 g), triethylamine (2.6 mmol, 0.36 mL) and water (0.15 mL) are added to each reactor. The reaction mixture is stirred at 100° C. under CO atmosphere at 100 psi for 15 h to yield I-145 (0.47 g, 72%). I-145 (0.1 mmol, 0.05 g) and pyrrolidine (0.25 mmol, 0.020 mL) in DMF (2 mL) is treated with TBTU (0.05 g, 0.16 mmol) followed by Hunig's base (0.20 mL, 1.15 mmol) and the mixture is stirred at 40° C. for 2 h. Water (10 mL) is added and the organics are extracted with DCM (2×5 mL). Organics are combined and concentrated to give I-146 that is dissolved in THF (1 mL), methanol (1 mL) and aqueous 5M NaOH (0.25 mL) and heated at 60° C. for 5 min and then stirred at ambient temperature for 5 min. The mixture is concentrated and diluted with DCM, then acidified to pH=5-6 with 1N HCl. The mixture is concentrated in vacuo and purified by HPLC to give the title compound (0.010 g, 57%).

The following compounds are prepared in a similar manner to the title compound:

Compounds 65, 70, 90, 92, 125, 178.

Example 6

Preparation of 1-(4-{5-methyl-2-[2-methyl-4-(piperidine-1-carbonyl)-benzyloxy]-phenyl}-thiazol-2-yl)-piperidine-4-carboxylic acid (164)

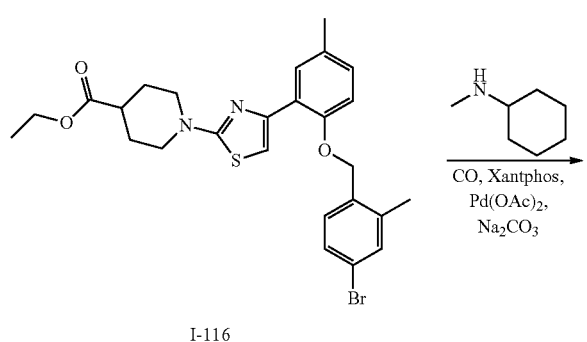

A vessel is charged with Pd(OAc)$_2$ (0.001 g), Xantphos (0.003 g), Na$_2$CO$_3$ (0.18 mmol, 0.021 g) and N-methylcyclohexylamine (0.14 mmol, 0.015 g) and is flushed with N$_2$. To this is added a solution of I-116 (0.09 mmol, 0.048 g) in toluene (3 mL) dropwise. The solution is flushed for 30 seconds with CO then a CO atmosphere is maintained by passing a stream of CO through the vessel while heating at 80° C. overnight. Additional Pd(OAc)$_2$ (0.001 g), Xantphos (0.003 g), and Na$_2$CO$_3$ (0.18 mmol, 0.021 g), is added and the solution is heated at 80° C. overnight. The mixture is cooled to room temperature and filtered, concentrated in vacuo, and purified by HPLC to give I-147 that is dissolved in 3:1:1 mixture of dioxane:MeOH:water (2 mL) and treated with LiOH (0.022 g, 0.090). The mixture is heated at 50° C. for 2 h then concentrated in vacuo and purified by HPLC to afford 164 (0.001 g, 2%).

The following compounds are prepared in a similar manner to the title compound:

Compounds 13, 158-163, 165, 263.

Example 7

Preparation of R-1-{4-[5-methyl-2-(2-methyl-4-morpholin-4-ylmethyl-benzyloxy)-phenyl]-thiazol-2-yl}-pyrrolidine-3-carboxylic acid and S-1-{4-[5-methyl-2-(2-methyl-4-morpholin-4-ylmethyl-benzyloxy)-phenyl]-thiazol-2-yl}-pyrrolidine-3-carboxylic acid (5 and 180)

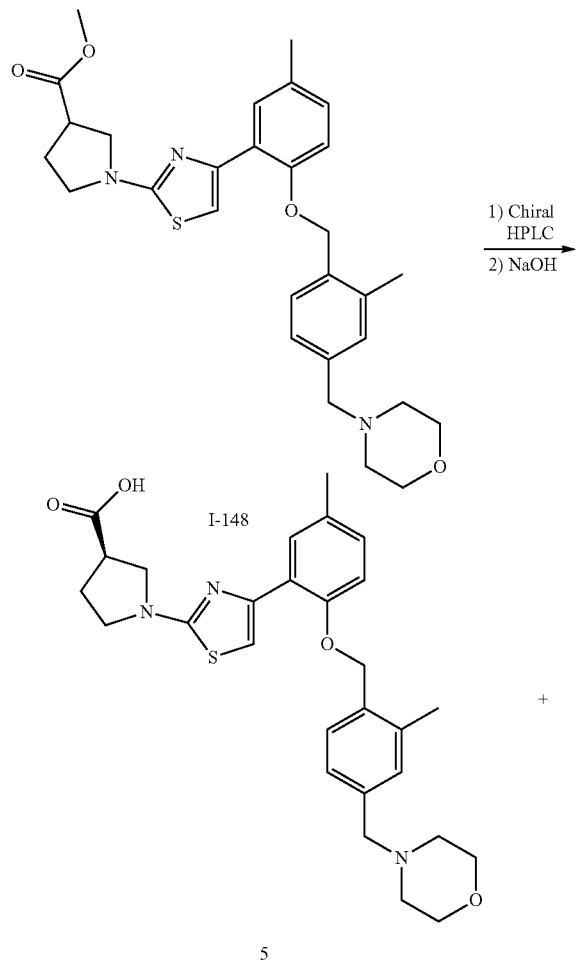

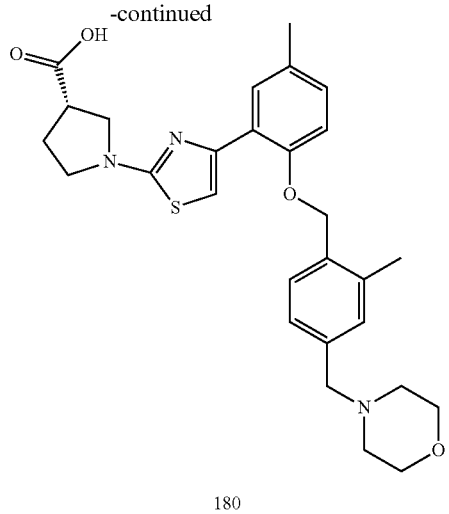

Compound I-148 (0.150 g) is resolved by preparatory HPLC (chiralpak AD-H, 20×2500 mm, 20% isopropanol in heptane (0.1% diethylamine)) to give entantiomer-1 (>98% ee, $t_R$=24 min) and enantiomer-2 (>98% ee, $t_R$=27 min). The individual samples are concentrated, and dissolved in 1:1:1 (V/V/V) solution of THF:MeOH:5 N aqueous NaOH (3 mL) and stirred at 60° C. for 15 min. The mixtures are concentrated in vacuo and then purified by HPLC to give the title compounds 5 (0.013 g, 9%, derived from enantiomer-1) and 180 (0.005 g, 4%, derived from enantiomer-2).

The following compounds are prepared in a similar manner to the title compounds:

Compound 19: isolated in >98% ee
Compound 50: isolated in >98% ee
Compound 176: isolated in >98% ee

Example 8

Preparation of 1-[4-[2-[[4-[[4-(dimethylcarbamoyl)piperazin-1-yl]methyl]-2-methyl-phenyl]methoxy]-5-methyl-phenyl]thiazol-2-yl]piperidine-4-carboxylic acid (198)

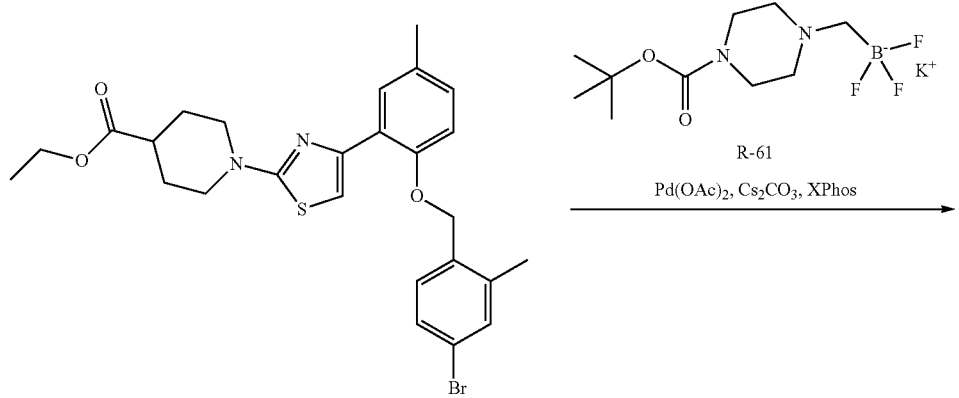

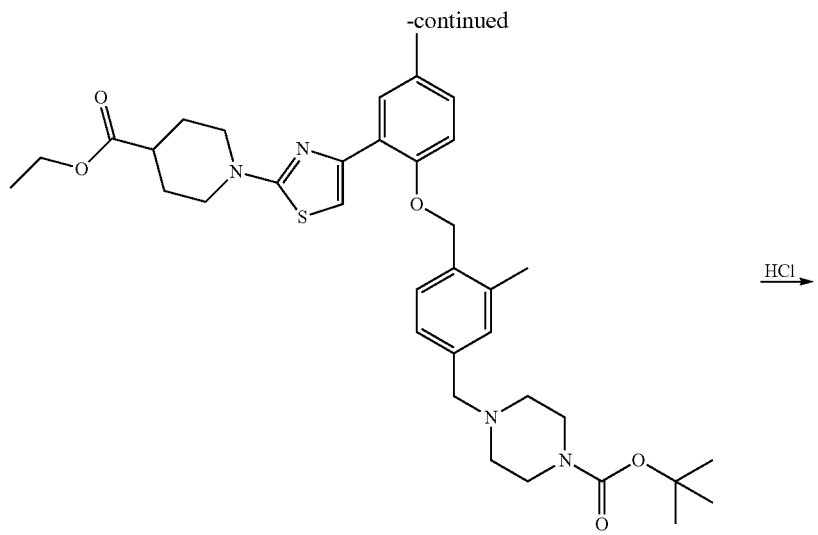
I-149
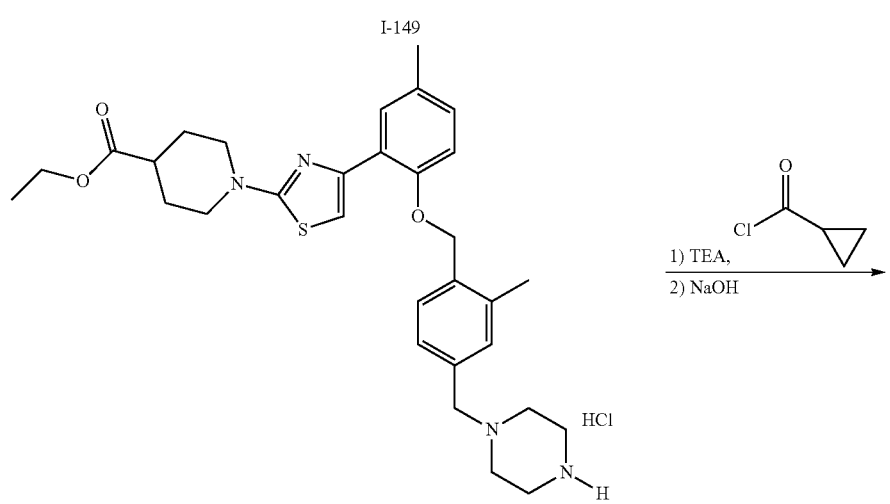
I-150
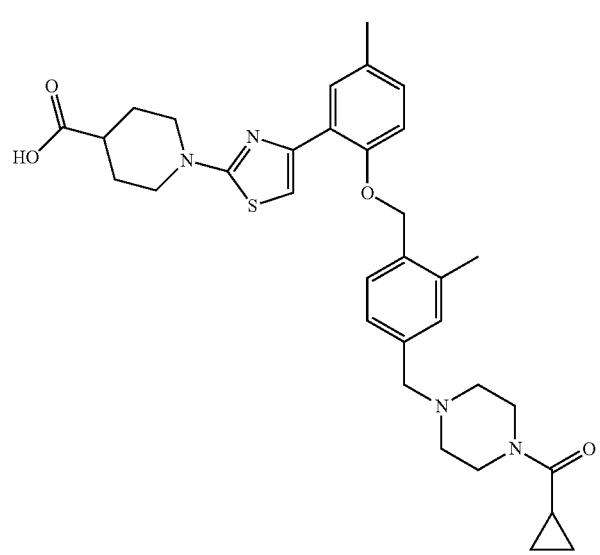

A pressure flask is charged with I-116 (830 mg, 0.94 mmol), R-61 (720 mg, 2.4 mmol), Pd(OAc)$_2$ (35 mg), Cs$_2$CO$_3$ (1.54 g, 4.7 mmol), Xphos (150 mg) and 9:1 (v/v) THF:water (21 mL). The suspension is purged with Ar for 2 min and then the flask is sealed and heated at 95° C. for 4 h. The mixture is cooled, filtered through diatomaceous earth, and concentrated in vacuo. The residue is purified by flash chromatography to afford I-149 (0.25 g, 44%). To a solution of I-149 (0.54 mmol, 0.35 g) in Et$_2$O (10 mL) is added HCl in dioxane (4.0 M, 4 mmol, 1 mL). The reaction is stirred at ambient temperature overnight then concentrated in vacuo to afford I-150 (0.290 g, 92%). To a suspension of I-150 (0.07 mmol, 0.040 g) in DCM (2 ml) is added cyclopropionyl chloride (0.22 mmol, 0.020 mL), followed by TEA (0.22 mmol, 0.030 mL). The mixture is stirred at ambient temperature for 0.5 h then treated with methanol and continued stirring for 10 min. The volatiles are removed in vacuo to afford a residue that is dissolved in MeOH (1 mL), THF (1 mL), and aqueous 5M NaOH (0.25 mL) and heated at 60° C. for 15 min. The mixture is concentrated in vacuo, diluted with CH$_2$Cl$_2$, and acidified to pH=5-6 with 1N formic acid. The mixture is concentrated in vacuo then purified by HPLC to afford the title compound (27 mg, 71%).

The following compounds are prepared in a similar manner to the title compound:

Compounds 194-197, 199-200

Example 9

Preparation of 3-(4-{2-[4-(azetidine-1-carbonyl)-2-methyl-benzyloxy]-5-methyl-phenyl}-thiazol-2-yl)-3-aza-bicyclo[3.2.1]octane-8(syn)-carboxylic acid (361)

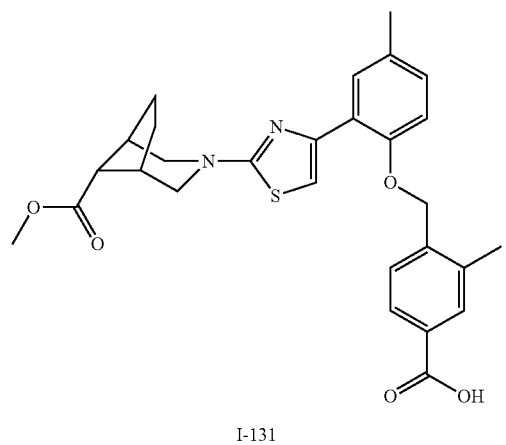

I-131

+

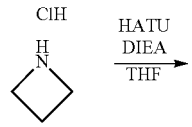

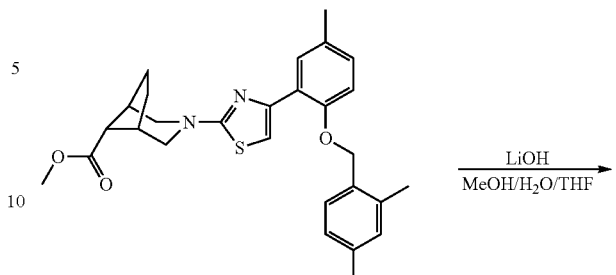

I-151

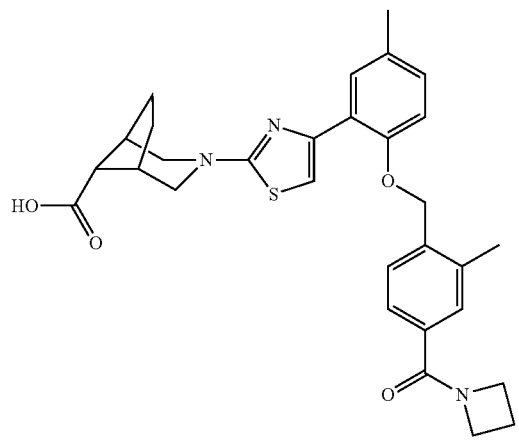

361

To a solution of I-130 (0.099 mmol, 0.050 g) and azetadine hydrochloride (0.12 mmol, 0.010 g) in THF (1 mL) is added HATU (0.12 mmol, 0.045 g) followed by Hunig's base (0.30 mmol, 0.051 mL). The mixture is stirred overnight at ambient temperature then purified by flash silica gel chromatography to provide I-151 (30 mg, 55%). To a solution of I-151 (0.040 mmol, 0.022 g) in a 2:1:1 mixture of methanol:water:THF (2 mL) is added lithium hydroxide monohydrate (0.2 mmol, 0.004 g). The mixture is stirred overnight at room temperature then purified by flash reverse phase chromatography to afford the title compound (15 mg, 70%).

The following compounds are prepared in a similar manner to the title compound:

Compounds: 296 to 348 and 360.

The following compound is prepared from I-131 in a similar manner to the title compound:

Compound: 349.

The following compounds are prepared from I-132 in a similar manner to the title compound:

Compounds: 287, 288, 295.

The following compounds are prepared from I-133 in a similar manner to the title compound:

Compounds: 281, 283, 286.

The following compounds are prepared from I-134 in a similar manner to the title compound:

Compounds: 282, 284, 285.

Example 10

Preparation of (1S,5R,8S)-3-(4-{2-[4-(azetidine-1-carbonyl)-2-methyl-benzyloxy]-5-methyl-phenyl}-thiazol-2-yl)-3-aza-bicyclo[3.2.1]octane-8-carboxylic acid (292)

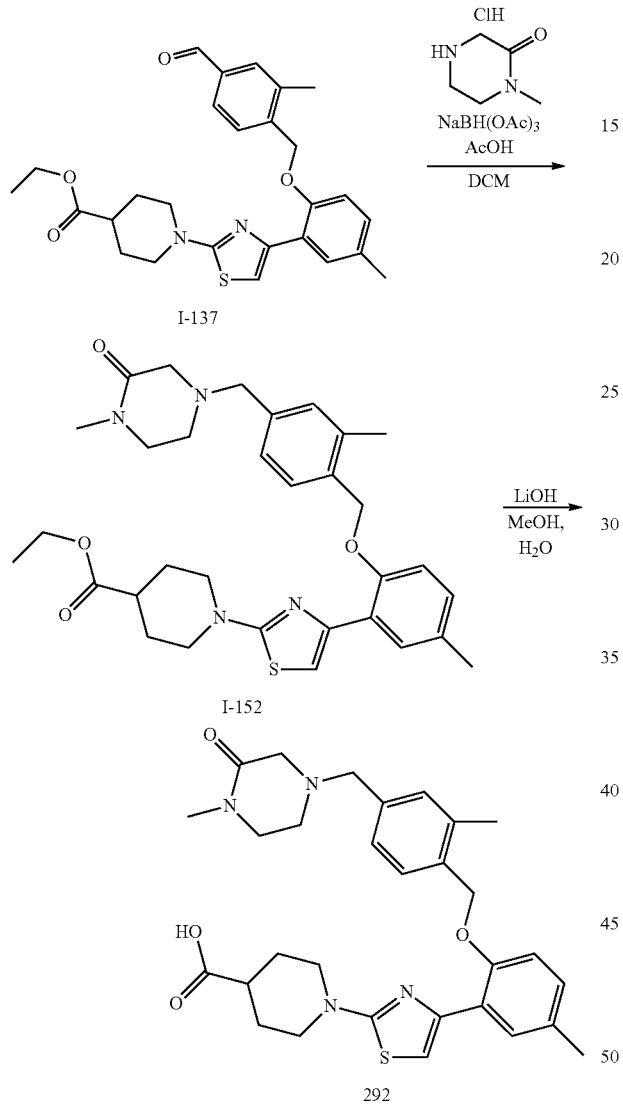

To a solution of I-137 (0.21 mmol, 0.10 g) in DCM (2 mL) is added 1-methyl-piperazin-2-one hydrochloride (0.030 g, 0.26 mmol) followed by NaBH(OAc)₃ (0.47 mmol, 0.10 g) and acetic acid (0.60 mmol, 0.035 mL). The mixture is stirred at room temperature for 6 days then concentrated under reduced pressure. The residue is purified by C18 reverse phase flash chromatography to provide I-152 (0.044 g, 36%) as a clear film. To a suspension of I-152 (0.076 mmol, 0.044 g) in a 1:1 mixture of methanol:water (10 mL) is added LiOH (1.2 mmol, 0.050 g). The mixture is stirred at room temperature for 3 days during which time all of the solids went into solution. The pH of the mixture is then adjusted to approximately pH 5 by the addition of a 2N solution of hydrochloric acid and the mixture is concentrated under reduced pressure. The residue is purified by flash C18 reverse phase chromatography to provide the title compound (0.007 g, 16%) as a white powder.

The following compounds are prepared in a similar manner to the title compound:

Compounds 269, 289, 290, 291, 293, 350, 353

Example 11

Preparation of 8-fluoro-3-(4-{5-methyl-2-[2-methyl-4-(piperidine-1-carbonyl)-benzyloxy]-phenyl}-thiazol-2-yl)-3-aza-bicyclo[3.2.1]octane-8(syn)-carboxylic acid (221)

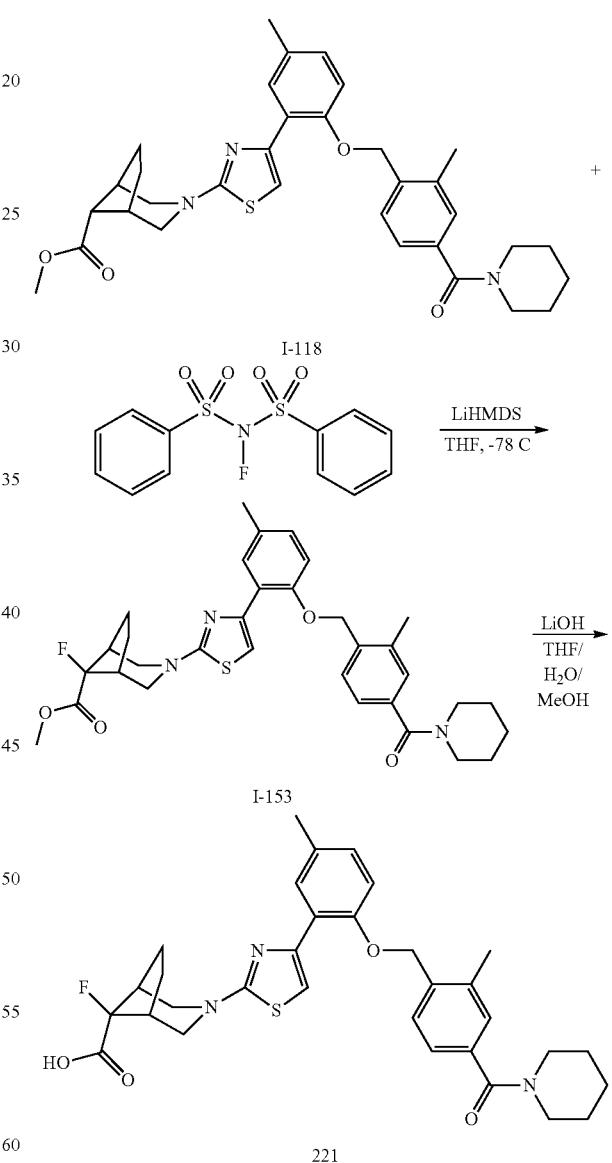

To a solution of I-118 (0.87 mmol, 0.50 g) in THF (10 mL), cooled to −78° C., is added a solution of LiHMDS in THF (1M, 2.5 mmol, 2.5 mL). The mixture is stirred at −78° C. for 1 h then N-fluorobenzenesulfinimide (1.4 mmol, 0.45 g) is added as a solution in THF (3 mL). The mixture is allowed to slowly warm to room temperature and stirred for three h. The mixture is diluted with water and extracted with ethyl acetate. The combined organic phase is washed with saturated sodium bicarbonate, dried over anhydrous sodium sulfate, and concentrated under reduced pressure to provide I-153 which was used directly. The crude I-153 is dissolved in a 1:1:1 mixture of MeOH:THF:water (9 mL) and to this is added LiOH (2.4 mmol, 0.10 g). The mixture is stirred at room temperature overnight then washed with diethyl ether. The pH of the aqueous phase is adjusted to acidic by the addition of a 1N solution of HCl. The mixture is extracted with ethyl acetate and the combined organic phase is dried over anhydrous sodium sulfate then concentrated under reduced pressure. The residue is purified by C18 flash reverse phase chromatography to provide the title compound (0.052 g, 10%) as a white powder.

Example 12

Preparation of 8-hydroxy-3-(4-{5-methyl-2-[2-methyl-4-(piperidine-1-carbonyl)-benzyloxy]-phenyl}-thiazol-2-yl)-3-aza-bicyclo[3.2.1]octane-8(syn)-carboxylic acid (216)

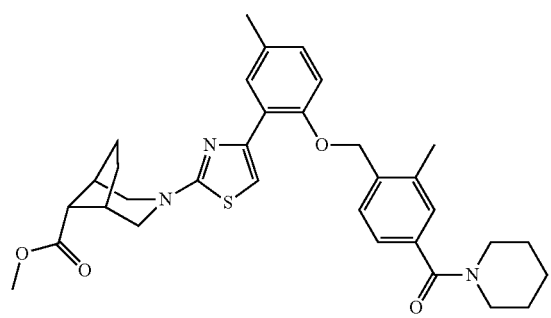

I-118

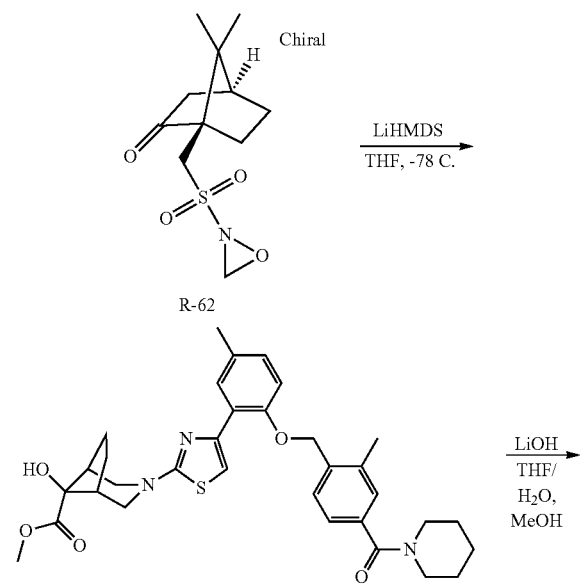

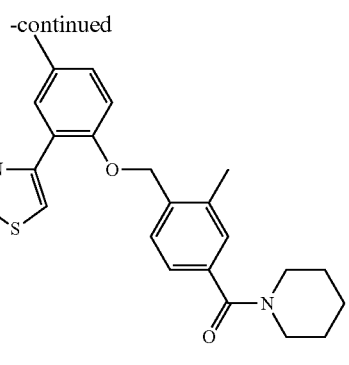

216

To a solution of I-118 (0.87 mmol, 0.50 g) in THF (10 mL), cooled to −78° C., is added a solution of LiHMDS in THF (1M, 2.6 mmol, 2.6 mL). The mixture is stirred at −78° C. for 1 h then R-62 (0.45 g, 1.7 mmol) is added as a solution in THF (5 mL). The mixture is slowly warmed to ambient temperature and is stirred overnight. The mixture is diluted with water and the pH adjusted to slightly acidic by the addition of a 1N solution of HCl. The mixture is extracted with EtOAc and the combined organic phase is dried over anhydrous sodium sulfate then concentrated under reduced pressure. The residue is purified by flash silica gel chromatography to provide I-154 (0.022 g, 4.3%) as a clear film. To a solution of I-154 (0.037 mmol, 0.022 g) in a 1:1:1 mixture of water:THF:MeOH (3 mL) is added LiOH (1.2 mmol, 0.050 g). The mixture is stirred overnight at room temperature then washed with ether and the aqueous phase acidified to approximately pH 4 by the addition of 1 N HCl. The mixture is extracted with ethyl acetate and the combined organic phase is dried over anhydrous sodium sulfate then concentrated under reduced pressure. The residue is purified by C18 flash reverse phase chromatography to provide the title compound (0.012 g, 56%) as a white powder.

Example 13

Preparation of 8-ethyl-3-(4-{5-methyl-2-[2-methyl-4-(piperidine-1-carbonyl)-benzyloxy]-phenyl}-thiazole-2-yl)-3-aza-bicyclo[3.2.1]octane-8(syn)-carboxylic acid (250)

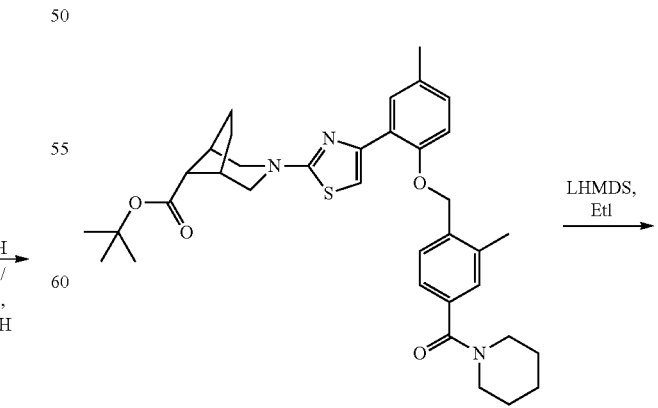

I-121

315
-continued

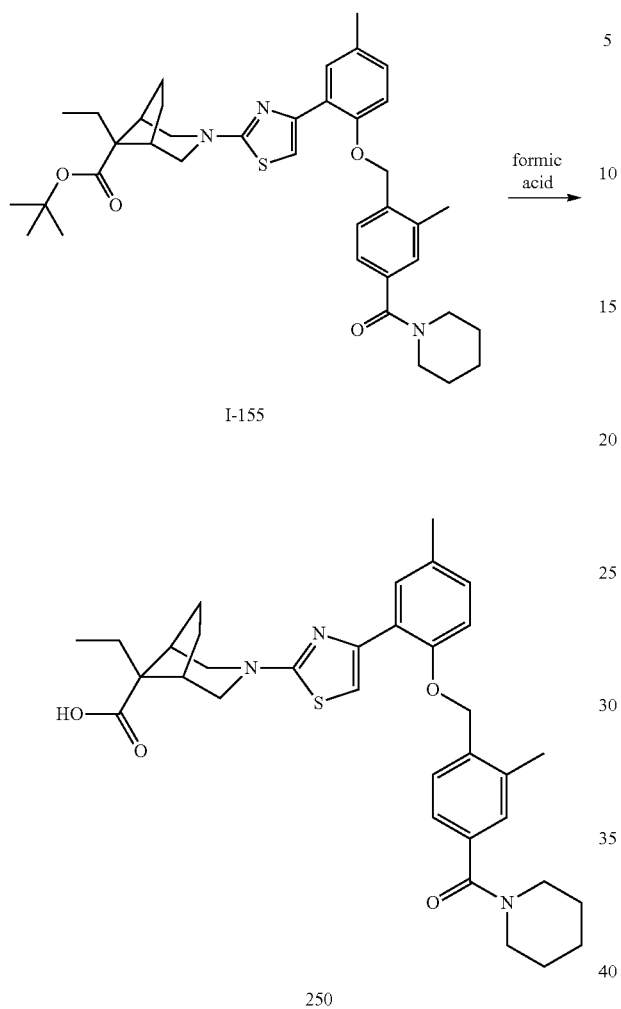

To a solution of I-121 (0.23 mmol, 0.140 g) in THF (4 mL), cooled to −78° C., is added a solution of LiHMDS in THF (1M, 0.45 mmol, 0.45 mL). The mixture is stirred at −78° C. for 30 min, then treated with ethyl iodide (0.037 mL, 0.46 mmol) and allowed to warm to ambient temperature. The mixture is stirred overnight then diluted with DCM and excess reactants are consumed by the addition of an aqueous solution of NH$_4$Cl. The organic layer is separated, washed with brine, and then concentrated under reduced pressure. The residue is purified on by flash silica gel chromatography to provide I-155 (0.089 g, 61%). A solution of I-155 (0.13 mmol, 0.081 g) in formic acid (2 mL) is heated to 90° C. for 30 min then cooled down to ambient temperature. The solvent is removed under reduced pressure and the residue is purified by flash silica gel chromatography to provide the title compound (0.043 g, 58%).

The following compounds are prepared in a similar manner to the title compound:

Compounds 214, 262.

316

Example 14

Preparation of 8-hydroxymethyl-3-(4-{5-methyl-2-[2-methyl-4-(piperidine-1-carbonyl)-benzyloxy]-phenyl}-thiazole-2-yl)-3-aza-bicyclo[3.2.1]octane-8 (syn)-carboxylic acid (258)

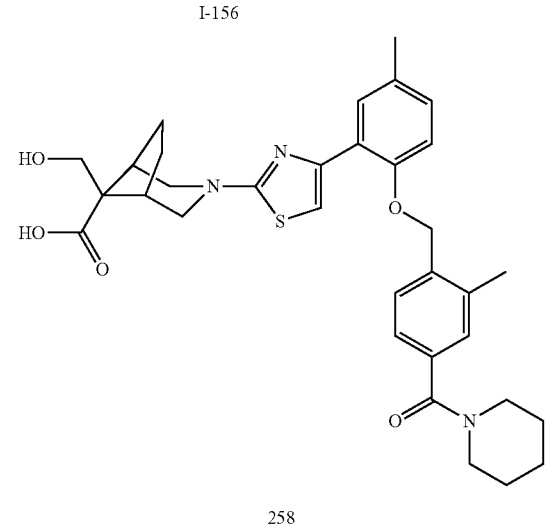

To a solution of I-121 (0.16 mmol, 0.10 g) in THF (4 mL), cooled to (−78° C.), is added a solution of LiHMDS in THF (1M, 0.49 mmol, 0.49 mL). The mixture is stirred at −78° C. for 30 min then treated with SEMCl (0.11 mL, 0.58 mmol).

After the addition is complete the mixture is stirred at −78° C. for an additional 2 h then warmed to ambient temperature and stirred overnight. The solution is diluted with DCM and excess reactants are consumed by the addition of a saturated aqueous solution of $NH_4Cl$. The organic layer is separated, washed with brine, and concentrated under reduced pressure. The residue is purified by flash silica gel chromatography to provide I-156 (0.70 g, 58%). A solution of I-156 (mmol, 0.070 g) in DCM (1 mL) is treated with TFA (1.4 mmol, 0.16 mL). The reaction mixture is stirred at ambient temperature for 5 h then purified by flash silica gel chromatography to provide the title compound (25 mg, 61%) as an off-white solid.

Example 15

Preparation of 3-(4-{2-[2-cyano-4-(morpholine-4-carbonyl)-benzyloxy]-5-methyl-phenyl}-thiazole-2-yl)-3-aza-bicyclo[3.2.1]octane-8(syn)-carboxylic acid (266)

residue is purified by flash silica gel chromatography to provide the title compound (0.45 g, 66%).

Example 16

Preparation of 3-[5-fluoro-4-[5-methyl-2-[[2-methyl-4-(piperidine-1-carbonyl)phenyl]methoxy]phenyl] thiazol-2-yl]-3-azabicyclo[3.2.1]octane-8(syn)-carboxylic acid (202)

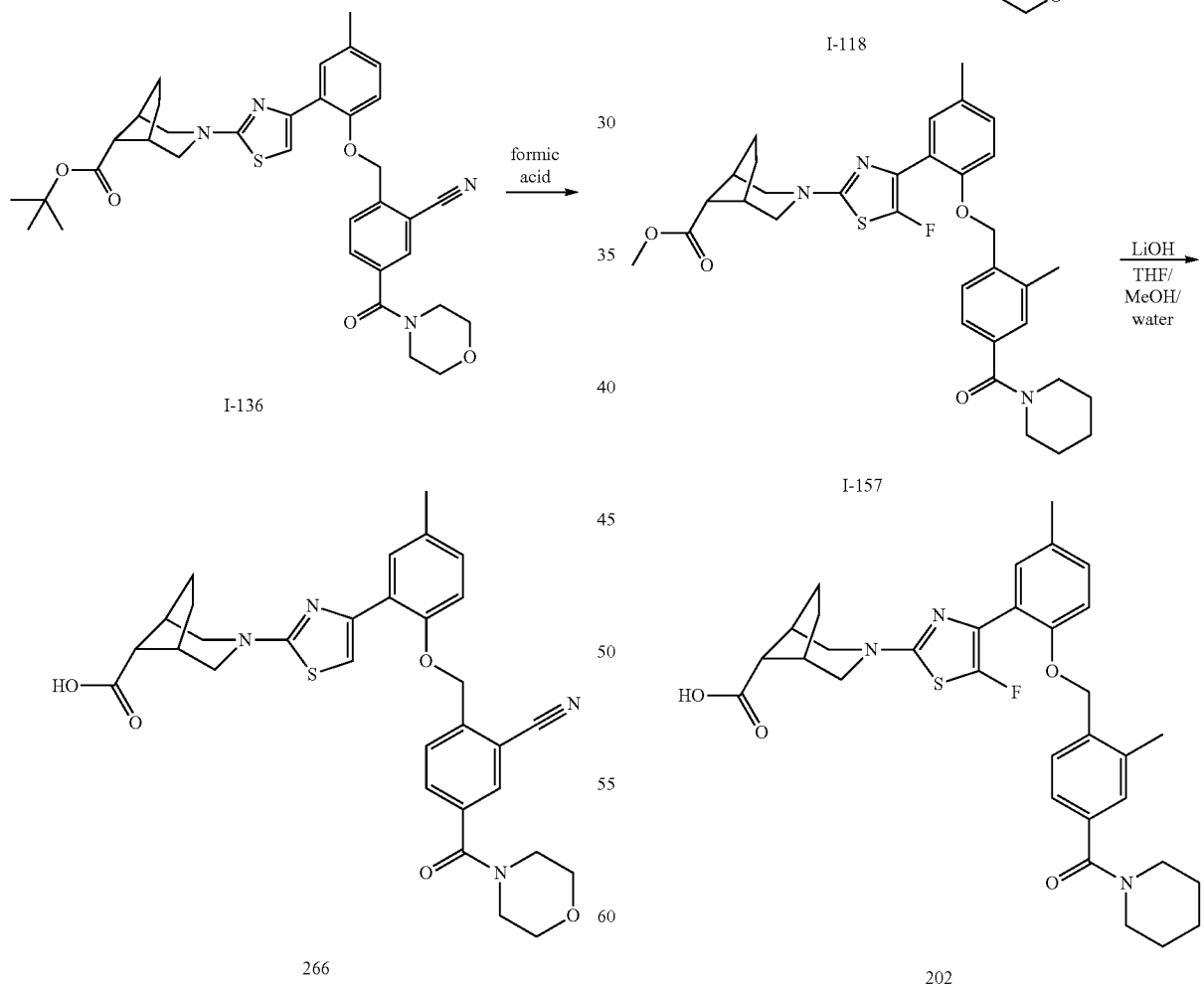

A solution of I-136 (0.12 mmol, 0.75 g) dissolved in formic acid (2 mL) is heated to 60° C. for 1 h then cooled to ambient temperature and concentrated under reduced pressure. The To a suspension of I-118 (0.17 mmol, 0.10 mg) in MeCN (6.8 mL), cooled to 0° C., is added Selectfluor® (0.26 mmol, 0.93 g). The mixture is stirred at 0° C. for 10 min then diluted with water and extracted with EtOAc. The organic layer is washed with brine, concentrated under reduced pressure, and the residue is purified by flash silica gel chromatography to give I-157 (0.25 g, 25%). To a solution of I-157 (0.043 mmol, 0.025 g) in a 2:1:1 mixture of methanol:THF:water (2 mL) is added LiOH (0.09 mmol, 0.002 g). The mixture is stirred overnight at ambient temperature then purified by C18 reverse phase flash chromatography to provide the title compound (0.020 g, 79%).

Example 17

Preparation of 8-methyl-3-{4-[5-methyl-2-(2-methyl-4-morpholin-4-ylmethyl-benzyloxy)-phenyl]-thiazol-2-yl}-3-aza-bicyclo[3.2.1]octane-8(syn)-carboxylic acid (270)

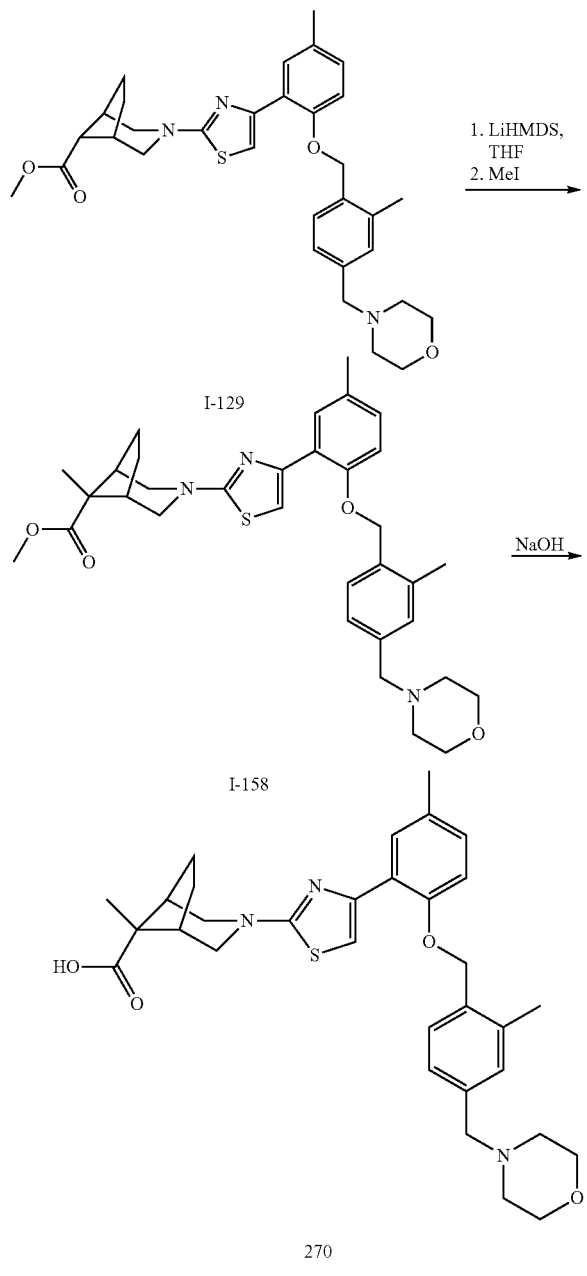

To a solution of I-129 (0.14 mmol, 0.080 g) in THF (1.4 mL), cooled to −78° C., is added a solution of LiHMDS in THF (1M, 0.28 mmol, 0.28 mL). The mixture is stirred at −78° C. for 0.5 h and treated with MeI (0.28 mmol, 0.017 mL). The mixture is allowed to warm to room temperature and is stirred overnight. It is then diluted with DCM and excess reactants are consumed by the addition of a saturated aqueous solution of $NH_4Cl$. The organic layer is separated, washed with brine, and concentrated under reduced pressure. The residue is purified by flash silica gel chromatography to provide I-158 (0.40 g, 49%). To a solution of I-158 (0.070 mmol, 0.040 g) in a 2:1:1 mixture of MeOH:THF:water (2 mL) is added NaOH (2.5 mmol, 0.10 g). The mixture is heated at 80° C. overnight. Additional NaOH (10 mmol, 0.40 g), THF (0.5 mL) and water (0.5 mL) are added and the mixture is refluxed for an additional 2 h. The mixture is purified by flash silica gel chromatography to provide the title compound (0.013 g, 33%).

The retention times and molecular ions found for the final compounds from Table 1 and the LCMS method described under the Analytical Methods section that was used for each compound are shown below in Table 2.

TABLE 2

| Compound Number | Mol Ion | RT (min) | LCMS Method |
|---|---|---|---|
| 1 | 551.9 | 1.13 | A |
| 2 | 522.1 | 0.71 | A |
| 3 | 482.4 | 2.6 | B |
| 4 | 496.2 | 2.6 | B |
| 5 | 508.2 | 2.49 | B |
| 6 | 508.3 | 2.61 | B |
| 7 | 510.3 | 2.74 | B |
| 8 | 517.2 | 3.32 | B |
| 9 | 518.2 | 3.05 | B |
| 10 | 519.2 | 3.11 | B |
| 11 | 519.3 | 3.24 | B |
| 12 | 519.3 | 3.25 | B |
| 13 | 520.3 | 3.05 | B |
| 14 | 520.3 | 2.66 | B |
| 15 | 520.3 | 3.16 | B |
| 16 | 520.3 | 2.97 | B |
| 17 | 520.3 | 3.13 | B |
| 18 | 520.4 | 2.8 | B |
| 19 | 522.2 | 2.87 | B |
| 20 | 522.3 | 2.77 | B |
| 21 | 522.3 | 2.66 | B |
| 22 | 522.3 | 2.7 | B |
| 23 | 522.3 | 0.29 | B |
| 24 | 522.3 | 2.58 | B |
| 25 | 524.3 | 3.04 | B |
| 26 | 524.3 | 3.05 | B |
| 27 | 524.3 | 3.085 | B |
| 28 | 526.3 | 2.64 | B |
| 29 | 531.3 | 2.66 | B |
| 30 | 531.3 | 3 | B |
| 31 | 531.3 | 3.02 | B |
| 32 | 531.3 | 3.41 | B |
| 33 | 531.3 | 2.57 | B |
| 34 | 532.3 | 3.13 | B |
| 35 | 533.2 | 2.61 | B |
| 36 | 533.3 | 2.64 | B |
| 37 | 533.3 | 3.32 | B |
| 38 | 533.3 | 3.28 | B |
| 39 | 534.3 | 3.24 | B |
| 40 | 534.3 | 2.83 | B |
| 41 | 534.3 | 3.16 | B |
| 42 | 534.3 | 3.19 | B |
| 43 | 534.3 | 2.57 | B |
| 44 | 534.3 | 2.53 | B |
| 45 | 534.4 | 2.86 | B |
| 46 | 535.3 | 2.65 | B |
| 47 | 535.3 | 2.59 | B |
| 48 | 535.3 | 3.38 | B |

TABLE 2-continued

| Compound Number | Mol Ion | RT (min) | LCMS Method |
|---|---|---|---|
| 49 | 536.3 | 2.9 | B |
| 50 | 536.3 | 2.7 | B |
| 51 | 536.2 | 0.79 | A |
| 52 | 536.3 | 2.75 | B |
| 53 | 536.3 | 2.8 | B |
| 54 | 536.3 | 2.77 | B |
| 55 | 536.3 | 3.18 | B |
| 56 | 537.4 | 3.28 | B |
| 57 | 537.4 | 3.25 | B |
| 58 | 538.2 | 2.74 | B |
| 59 | 538.3 | 3.24 | B |
| 60 | 540.2 | 2.7 | B |
| 61 | 540.3 | 2.68 | B |
| 62 | 542.2 | 2.845 | B |
| 63 | 542.3 | 2.73 | B |
| 64 | 543.3 | 3.11 | B |
| 65 | 545.3 | 3.01 | B |
| 66 | 545.3 | 3.14 | B |
| 67 | 546.3 | 3.23 | B |
| 68 | 546.3 | 3.14 | B |
| 69 | 547.3 | 2.65 | B |
| 70 | 547.3 | 2.8 | B |
| 71 | 547.3 | 2.64 | B |
| 72 | 548.3 | 3.23 | B |
| 73 | 548.3 | 3.27 | B |
| 74 | 548.3 | 2.63 | B |
| 75 | 549.3 | 2.68 | B |
| 76 | 551.3 | 3.49 | B |
| 77 | 551.9 | 2.95 | B |
| 78 | 552.3 | 3.29 | B |
| 79 | 552.3 | 3.29 | B |
| 80 | 552.2 | 0.78 | A |
| 81 | 553.2 | 2.67 | B |
| 82 | 554.3 | 2.87 | B |
| 83 | 556.2 | 2.76 | B |
| 84 | 556.2 | 2.75 | B |
| 85 | 559.3 | 3.22 | B |
| 86 | 559.3 | 2.66 | B |
| 87 | 559.3 | 2.64 | B |
| 88 | 560.3 | 3.13 | B |
| 89 | 560.3 | 3.34 | B |
| 90 | 561.4 | 2.77 | B |
| 91 | 562.5 | 2.97 | B |
| 92 | 563.2 | 2.9 | B |
| 93 | 563.3 | 2.75 | B |
| 94 | 563.3 | 2.53 | B |
| 95 | 563.3 | 2.77 | B |
| 96 | 564.3 | 2.77 | B |
| 97 | 564.3 | 3.25 | B |
| 98 | 564 | 1.14 | A |
| 99 | 568.2 | 2.78 | B |
| 100 | 568.1 | 0.81 | A |
| 101 | 568.2 | 2.78 | B |
| 102 | 568.3 | 3.4 | B |
| 103 | 568.3 | 3.39 | B |
| 104 | 570.3 | 2.97 | B |
| 105 | 570.3 | 3 | B |
| 106 | 570.3 | 3.01 | B |
| 107 | 570.3 | 2.85 | B |
| 108 | 570.3 | 2.82 | B |
| 109 | 571.3 | 3.19 | B |
| 110 | 572.3 | 2.88 | B |
| 111 | 574.3 | 2.94 | B |
| 112 | 575.3 | 2.675 | B |
| 113 | 576.3 | 2.99 | B |
| 114 | 576.4 | 2.73 | B |
| 115 | 577.3 | 2.78 | B |
| 116 | 579.4 | 2.96 | B |
| 117 | 580.3 | 3.36 | B |
| 118 | 580.3 | 3.47 | B |
| 119 | 581.3 | 2.84 | B |
| 120 | 582.3 | 2.98 | B |
| 121 | 582.3 | 2.76 | B |
| 122 | 584.3 | 2.81 | B |
| 123 | 584.4 | 2.84 | B |
| 124 | 584.4 | 3.04 | B |
| 125 | 587.3 | 3.26 | B |
| 126 | 588.3 | 3.3 | B |
| 127 | 588.3 | 3.22 | B |
| 128 | 588.3 | 2.97 | B |
| 129 | 588.4 | 2.98 | B |
| 130 | 588.4 | 3.17 | B |
| 131 | 588.4 | 2.98 | B |
| 132 | 590.3 | 2.77 | B |
| 133 | 590.3 | 3.03 | B |
| 134 | 591.5 | 2.61 | B |
| 135 | 595.3 | 2.93 | B |
| 136 | 596.3 | 2.89 | B |
| 137 | 596.3 | 2.82 | B |
| 138 | 598.3 | 2.72 | B |
| 139 | 600.4 | 2.94 | B |
| 140 | 601.3 | 2.93 | B |
| 141 | 602.3 | 3.23 | B |
| 142 | 602.4 | 3.3 | B |
| 143 | 604.2 | 3.07 | B |
| 144 | 604.4 | 3.19 | B |
| 145 | 606.3 | 3.26 | B |
| 146 | 607.3 | 2.96 | B |
| 147 | 607.4 | 3.01 | B |
| 148 | 613.3 | 3.2 | B |
| 149 | 622.3 | 3.32 | B |
| 150 | 624.3 | 3.09 | B |
| 151 | 624.4 | 2.98 | B |
| 152 | 624.4 | 2.99 | B |
| 153 | 638.3 | 3.04 | B |
| 154 | 638.3 | 3.04 | B |
| 155 | 642.3 | 3.02 | B |
| 156 | 649.3 | 2.95 | B |
| 157 | 658.3 | 3.11 | B |
| 158 | 524 | 0.94 | A |
| 159 | 536 | 0.96 | A |
| 160 | 549 | 0.7 | A |
| 161 | 574 | 1.26 | A |
| 162 | 552 | 1.02 | A |
| 163 | 548 | 1.13 | A |
| 164 | 560 | 1.2 | A |
| 165 | 550 | 0.89 | A |
| 166 | 508.3 | 1.24 | A |
| 167 | 533.3 | 0.69 | A |
| 168 | 533.3 | 0.65 | A |
| 169 | 531.3 | 0.69 | A |
| 170 | 547.3 | 0.63 | A |
| 171 | 535.5 | 0.68 | A |
| 172 | 521.3 | 0.66 | A |
| 173 | 534.4 | 0.79 | A |
| 174 | 548.3 | 0.78 | A |
| 175 | 536.3 | 0.75 | A |
| 176 | 536.3 | 0.7 | A |
| 177 | 536.3 | 0.78 | A |
| 178 | 549.1 | 1.08 | A |
| 179 | 510.1 | 0.64 | A |
| 180 | 508.2 | 0.55 | A |
| 181 | 522.3 | 0.63 | A |
| 182 | 553.2 | 1.19 | A |
| 183 | 554.2 | 1.05 | A |
| 184 | 542.2 | 1.07 | A |
| 185 | 576.1 | 0.8 | A |
| 186 | 541.1 | 0.82/0.85 - mixture of diastereomers | A |
| 187 | 540.1 | 0.76 | A |
| 188 | 539.1 | 0.83 | A |
| 189 | 529.9 | 0.73 | A |
| 190 | 525.2 | 0.77/0.80 - mixture of diastereomers | A |
| 191 | 523.3 | 0.79 | A |
| 192 | 521.1 | 0.79/0.82 - mixture of diastereomers | A |
| 193 | 505.1 | 0.77 | A |
| 194 | 577.3 | 0.74 | A |
| 195 | 605.3 | 0.79 | A |
| 196 | 599.4 | 2.87 | B |

TABLE 2-continued

| Compound Number | Mol Ion | RT (min) | LCMS Method |
|---|---|---|---|
| 197 | 619.3 | 2.81 | B |
| 198 | 589.4 | 2.87 | B |
| 199 | 592.4 | 2.85 | B |
| 200 | 628.3 | 2.95 | B |
| 201 | 536.4 | 2.66 | B |
| 202 | 578.7 | 1.21 | A |
| 203 | 596.2 | 1.03 | A |
| 204 | 584.2 | 1.08 | A |
| 205 | 596.3 | 0.96 | A |
| 206 | 548.3 | 0.76 | A |
| 207 | 616.2 | 1.08 | A |
| 208 | 560.0 | 1.18 | A |
| 209 | 560.1 | 1.09 | A |
| 210 | 548.3 | 0.73 | A |
| 211 | 616.2 | 1.10 | A |
| 212 | 603.7 | 0.77 | A |
| 213 | 590.2 | 0.82 | A |
| 214 | 574.4 | 2.91 |   |
| 215 | 494.4 | 0.67 | A |
| 216 | 576.7 | 1.01 | A |
| 217 | 582.4 | 0.96 | A |
| 218 | 534.4 | 0.70 | A |
| 219 | 584.4 | 0.96 | A |
| 220 | 534.6 | 0.71 | A |
| 221 | 578.5 | 1.17 | A |
| 222 | 582.6 | 0.96 | A |
| 223 | 582.1 | 0.96 | A |
| 224 | 601.2 | 0.77 | A |
| 225 | 548.2 | 0.94 | A |
| 226 | 546.2 | 1.08 | A |
| 227 | 589.7 | 0.69 | A |
| 228 | 615.2 | 0.78 | A |
| 229 | 562.3 | 1.03 | A |
| 230 | 598.2 | 0.94 | A |
| 231 | 548.2 | 0.72 | A |
| 232 | 571.7 | 0.70 | A |
| 233 | 550.3 | 1.49 | B |
| 234 | 582.3 | 2.07 | A |
| 235 | 550.4 | 1.98 | A |
| 236 | 546.2 | 2.37 | A |
| 237 | 534.3 | 1.00 | A |
| 238 | 573.6 | 0.76 | A |
| 239 | 534.3 | 0.90 | A |
| 240 | 534.2 | 2.34 | A |
| 241 | 536.2 | 1.86 | A |
| 242 | 520.3 | 1.24 | A |
| 243 | 532.1 | 1.99 | A |
| 244 | 568.3 | 1.60 | A |
| 245 | 570.2 | 2.00 | A |
| 246 | 520.2 | 1.01 | A |
| 247 | 534.2 | 1.54 | A |
| 248 | 532.3 | 1.00 | A |
| 249 | 575.6 | 0.65 | A |
| 250 | 588.4 | 1.19 | A |
| 251 | 520.9 | 0.92 | A |
| 252 | 568.3 | 0.90 | A |
| 253 | 556.6 | 0.82 | A |
| 254 | 508.6 | 0.62 | A |
| 255 | 601.6 | 0.70 | A |
| 256 | 534.3 | 0.86 | A |
| 257 | 520.6 | 0.66 | A |
| 258 | 604.5 | 1.12 | A |
| 259 | 582.6 | 0.89 | A |
| 260 | 546.3 | 0.99 | A |
| 261 | 534.6 | 0.69 | A |
| 262 | 602.8 | 1.25 | A |
| 263 | 571.6 | 1.10 | A |
| 264 | 559.6 | 0.76 | A |
| 265 | 626.6 | 0.81 | A |
| 266 | 573.3 | 0.90 | A |
| 267 | 607.6 | 1.02 | A |
| 268 | 562.6 | 1.30 | A |
| 269 | 589.6 | 0.88 | A |
| 270 | 562.6 | 0.77 | A |
| 271 | 554.1 | 1.14 | A |
| 272 | 556.1 | 1.00 | A |
| 273 | 582.2 | 0.99 | A |
| 274 | 545.0 | 1.01 | A |
| 275 | 600.2 | 1.03 | A |
| 276 | 562.7 | 0.76 | A |
| 277 | 590.28M- | 0.78 | A |
| 278 | 538.2 | 0.66 | A |
| 279 | 630.6 | 1.19 | A |
| 280 | 618.6 | 0.85 | A |
| 281 | 562.6 | 0.94 | A |
| 282 | 574.7 | 1.12 | A |
| 283 | 560.7 | 1.08 | A |
| 284 | 603.7 | 0.90 | A |
| 285 | 576.7 | 0.99 | A |
| 286 | 589.6 | 0.86 | A |
| 287 | 574.7 | 1.14 | A |
| 288 | 576.4 | 1.00 | A |
| 289 | 577.0 | 0.89 | A |
| 290 | 589.6 | 0.86 | A |
| 291 | 589.7 | 0.87 | A |
| 292 | 549.6 | 0.78 | A |
| 293 | 601.6 | 0.91 | A |
| 294 | 494.6 | 1.00 | A |
| 295 | 603.7 | 0.92 | A |
| 296 | 559.3 | 1.11 | A |
| 297 | 550.3 | 1.01 | A |
| 298 | 564.3 | 1.07 | A |
| 299 | 546.2 | 1.19 | A |
| 300 | 575.3 | 0.72 | A |
| 301 | 576.3 | 1.02 | A |
| 302 | 574.3 | 1.32 | A |
| 303 | 534.2 | 1.19 | A |
| 304 | 520.0 | 1.12 | A |
| 305 | 577.4 | 0.74 | A |
| 306 | 590.3 | 1.19 | A |
| 307 | 573.3 | 1.14 | A |
| 308 | 589.3 | 1.00 | A |
| 309 | 590.3 | 1.04 | A |
| 310 | 589.4 | 0.71 | A |
| 311 | 589.4 | 0.71 | A |
| 312 | 576.3 | 1.04 | A |
| 313 | 562.3 | 0.98 | A |
| 314 | 575.3 | 0.94 | A |
| 315 | 600.4 | 1.07 | A |
| 316 | 576.3 | 1.11 | A |
| 317 | 596.3 | 1.23 | A |
| 318 | 600.3 | 1.10 | A |
| 319 | 576.3 | 1.04 | A |
| 320 | 582.3 | 1.19 | A |
| 321 | 590.4 | 1.17 | A |
| 322 | 590.4 | 1.19 | A |
| 323 | 585.3 | 1.12 | A |
| 324 | 564.3 | 1.02 | A |
| 325 | 576.3 | 1.00 | A |
| 326 | 576.3 | 0.99 | A |
| 327 | 599.3 | 0.97 | A |
| 328 | 576.3 | 1.08 | A |
| 329 | 576.3 | 1.08 | A |
| 330 | 545.3 | 1.07 | A |
| 331 | 600.4 | 0.78 | A |
| 332 | 590.4 | 1.24 | A |
| 333 | 599.4 | 0.97 | A |
| 334 | 586.4 | 0.77 | A |
| 335 | 578.4 | 1.25 | A |
| 336 | 590.4 | 1.14 | A |
| 337 | 585.4 | 1.17 | A |
| 338 | 578.4 | 1.21 | A |
| 339 | 600.4 | 0.78 | A |
| 340 | 588.4 | 1.19 | A |
| 341 | 562.3 | 1.01 | A |
| 342 | 590.4 | 1.16 | A |
| 343 | 600.4 | 1.13 | A |
| 344 | 564.3 | 1.18 | A |
| 345 | 591.4 | 1.06 | A |
| 346 | 592.4 | 1.23 | A |
| 347 | 577.4 | 1.01 | A |
| 348 | 592.4 | 1.14 | A |
| 349 | 563.6 | 0.84 | A |
| 350 | 561.3 | 0.78 | A |

TABLE 2-continued

| Compound Number | Mol Ion | RT (min) | LCMS Method |
|---|---|---|---|
| 351 | 610.2 | 0.80 | A |
| 352 | 600.3 | 0.70 | A |
| 353 | 538.3 | 0.74 | A |
| 354 | 586.6 | 0.93 | A |
| 355 | 584.7 | 1.02 | A |
| 356 | 587.6 | 0.79 | A |
| 357 | 573.7 | 0.76 | A |
| 358 | 587.6 | 0.87 | A |
| 359 | 573.6 | 0.75 | A |
| 360 | 568.6 | 1.83 | A |
| 361 | 532.6 | 0.97 | A |

Assessment of Biological Activity

The biological activity of the compounds of the invention may be evaluated using the following assays:

Molecular Assay

Recombinant human soluble guanylate cyclase (sGC) is purified from Sf9 insect cells coinfected with baculoviruses expressing the alpha 1 or beta 1 subunit of sGC, both with a C-terminal histidine tag. Heme-free sGC is prepared by treating cell lysate with a final concentration of 0.5% Tween 20 prior to purification on a nickel affinity column.

sGC catalyzes the conversion of guanosine-5'-triphosphate (GTP) to cyclic guanosine monophosphate (cGMP). The activity of sGC is measured in vitro using the commercially available CisBio cGMP detection kit (catalog # 62GM2PEB) in a 384 well format. In brief, 300 pM heme-free sGC is incubated in reaction buffer (50 mM MOPS pH 6.8, 0.2 N KOH, 50 mM NaCl, 2 mM $MgCl_2$, 0.1% BSA, 1.25 mM IBMX, 0.25 mM TCEP, 50 nM GTP) in the presence or absence of dilutions of test compounds diluted in DMSO (final concentration of 1%) in a volume of 10 microL at 37° C. for 60 min. Undiluted reaction products or an 80-fold dilution of reaction products (10 microL of either) prepared in reaction buffer containing 0.2 mM TCEP and 10 mM EDTA is mixed with 5 microL of d2-cGMP plus 5 microL of $Eu^{3+}$ cryptate-labeled anti-cGMP, each diluted in buffer containing 0.1 M $KPO_4$ pH 7.5, 0.4 M KF, 20 mM EDTA, 0.2% BSA. After a one h incubation at room temperature in the dark, the mixtures are quantified on an EnVision plate reader (PerkinElmer) according to manufacturer instructions (laser excitation 337 nm, emission 620 and 665 nm). The ratio at each compound concentration is converted to nM cGMP using the linear portion of a calibration curve. Log compound concentration is plotted against combined undiluted and diluted nM cGMP values to determine the $EC_{50}$ for each curve.

Cellular Assay

The sGC cellular activator assay is performed in the presence and absence of 50% human serum (HS) using Chinese hamster ovary cells that have been stably transfected to express the human soluble guanylate cyclase alpha 1 and beta 1 subunits (sGC). Cells are preincubated with 40 microM 1H-[1,2,4]oxadiazolo[4,3-a]quinoxalin-1-one (ODQ), an sGC inhibitor, for one hour in buffer containing 0.1% bovine serum albumin and 3-isobutyl-1-methylxanthine (IBMX). Concentration response curves are prepared for test compounds in DMSO. An intermediate dilution of the compounds is performed in either buffer containing IBMX or type AB HS containing IBMX. Diluted compounds are added to cells and they are incubated at room temperature for thirty minutes. cGMP is measured using a CisBio homogeneous time resolved fluorescence kit and the $EC_{50}$ is calculated for each compound.

Representative compounds of the present invention were tested for activity in one or both of the above assays. Preferred compounds have an $EC_{50}$<5,000 nM and more preferred compounds have an $EC_{50}$<200 nM in the molecular assay. Preferred compounds have an $EC_{50}$ of <1,000 nM in the cellular activator assay and more preferred compounds have an $EC_{50}$<200 nM. As examples, data for representative compounds from Table 1 are shown in Table 3.

TABLE 3

Activity of Compounds in Molecular Assay

| Compound Number | EC50 nM |
|---|---|
| 1 | 60 |
| 2 | 320 |
| 3 | 1300 |
| 4 | 760 |
| 5 | 2000 |
| 6 | 610 |
| 8 | 330 |
| 9 | 680 |
| 10 | 4900 |
| 11 | 2300 |
| 12 | 4000 |
| 13 | 120 |
| 14 | 4700 |
| 15 | 190 |
| 17 | 79 |
| 20 | 140 |
| 21 | 70 |
| 22 | 1600 |
| 23 | 3200 |
| 24 | 510 |
| 25 | 1300 |
| 26 | 2000 |
| 28 | 200 |
| 29 | 440 |
| 30 | 61 |
| 31 | 250 |
| 32 | 310 |
| 33 | 7800 |
| 34 | 390 |
| 35 | 280 |
| 36 | 140 |
| 37 | 2100 |
| 38 | 1700 |
| 39 | 27 |
| 40 | 2600 |
| 41 | 70 |
| 42 | 51 |
| 43 | 63 |
| 44 | 760 |
| 45 | 730 |
| 46 | 260 |
| 47 | 4000 |
| 48 | 360 |
| 49 | 130 |
| 50 | 520 |
| 51 | 1100 |
| 52 | 39 |
| 53 | 640 |
| 54 | 2000 |
| 55 | 360 |
| 56 | 1600 |
| 57 | 1800 |
| 58 | 480 |
| 59 | 39 |
| 60 | 1200 |
| 61 | 440 |
| 62 | 22 |
| 63 | 110 |
| 64 | 1800 |
| 65 | 58 |
| 66 | 450 |
| 67 | 2.5 |
| 68 | 43 |
| 69 | 72 |

TABLE 3-continued

Activity of Compounds in Molecular Assay

| Compound Number | EC50 nM |
|---|---|
| 70 | 180 |
| 71 | 12000 |
| 72 | 4.8 |
| 73 | 7.6 |
| 74 | 27 |
| 75 | 600 |
| 76 | 600 |
| 77 | 4400 |
| 78 | 550 |
| 79 | 50 |
| 80 | 740 |
| 81 | 70 |
| 82 | 3100 |
| 83 | 210 |
| 84 | 180 |
| 85 | 1100 |
| 86 | 7100 |
| 87 | 800 |
| 88 | 15 |
| 89 | 2.5 |
| 90 | 150 |
| 91 | 730 |
| 92 | 78 |
| 94 | 770 |
| 95 | 35 |
| 96 | 550 |
| 97 | 59 |
| 98 | 780 |
| 99 | 690 |
| 100 | 440 |
| 101 | 1700 |
| 102 | 30 |
| 103 | 17 |
| 104 | 19 |
| 105 | 37 |
| 106 | 100 |
| 107 | 71 |
| 108 | 100 |
| 109 | 1500 |
| 110 | 1200 |
| 111 | 74 |
| 112 | 400 |
| 113 | 56 |
| 114 | 470 |
| 115 | 2700 |
| 116 | 1100 |
| 117 | 30 |
| 118 | 85 |
| 119 | 39 |
| 120 | 18 |
| 121 | 280 |
| 122 | 81 |
| 123 | 17 |
| 124 | 30 |
| 125 | 74 |
| 126 | 46 |
| 127 | 400 |
| 129 | 89 |
| 130 | 30 |
| 131 | 88 |
| 132 | 160 |
| 133 | 45 |
| 134 | 1800 |
| 135 | 2700 |
| 136 | 6.1 |
| 137 | 64 |
| 138 | 180 |
| 139 | 380 |
| 140 | 79 |
| 141 | 3.9 |
| 142 | 160 |
| 143 | 38 |
| 144 | 54 |
| 145 | 650 |
| 146 | 2000 |
| 147 | 1200 |
| 148 | 4100 |
| 149 | 380 |
| 150 | 1200 |
| 151 | 9.9 |
| 152 | 170 |
| 153 | 43 |
| 154 | 530 |
| 156 | 3100 |
| 157 | 940 |
| 159 | 1900 |
| 160 | 2800 |
| 161 | 91 |
| 162 | 71 |
| 163 | 750 |
| 164 | 55 |
| 166 | 520 |
| 167 | 52 |
| 168 | 730 |
| 171 | 2400 |
| 172 | 5600 |
| 173 | 140 |
| 174 | 320 |
| 176 | 160 |
| 177 | 170 |
| 178 | 270 |
| 179 | 990 |
| 181 | 3100 |
| 182 | 1600 |
| 183 | 4400 |
| 184 | 1800 |
| 185 | 2700 |
| 187 | 390 |
| 188 | 830 |
| 189 | 9000 |
| 190 | 2500 |
| 191 | 530 |
| 193 | 2400 |
| 194 | 150 |
| 195 | 83 |
| 196 | 110 |
| 197 | 230 |
| 198 | 20 |
| 199 | 140 |
| 200 | 80 |
| 201 | 960 |
| 203 | 23 |
| 204 | 28 |
| 205 | 80 |
| 206 | 170 |
| 207 | 170 |
| 208 | 250 |
| 209 | 270 |
| 210 | 350 |
| 211 | 370 |
| 214 | 22 |
| 215 | 1000 |
| 217 | 49 |
| 218 | 170 |
| 219 | 1000 |
| 234 | 6.0 |
| 235 | 47 |
| 236 | 190 |
| 237 | 240 |
| 239 | 2900 |
| 271 | 45 |
| 272 | 120 |
| 273 | 320 |
| 274 | 1600 |
| 275 | 1800 |
| 277 | 74 |
| 294 | 290 |
| 350 | 260 |

TABLE 3-continued

Activity of Compounds in Molecular Assay

| Compound Number | EC50 nM |
|---|---|
| 352 | 14 |
| 353 | 470 |

TABLE 4

Activity of Compounds in Cellular Assay

| Compound Number | EC50 nM |
|---|---|
| 202 | 310 |
| 203 | 68 |
| 204 | 17 |
| 205 | 200 |
| 206 | 88 |
| 207 | 93 |
| 208 | 39 |
| 209 | 96 |
| 210 | 430 |
| 211 | 190 |
| 212 | 100 |
| 214 | 15 |
| 216 | 390 |
| 217 | 8.7 |
| 218 | 18 |
| 219 | 300 |
| 220 | 42 |
| 221 | 75 |
| 222 | 110 |
| 223 | 5.2 |
| 224 | 5.8 |
| 225 | 7.3 |
| 226 | 13 |
| 227 | 99 |
| 228 | 39 |
| 229 | 76 |
| 230 | 120 |
| 231 | 150 |
| 232 | 44 |
| 233 | 310 |
| 234 | 7.9 |
| 235 | 57 |
| 236 | 79 |
| 237 | 130 |
| 238 | 39 |
| 239 | 650 |
| 240 | 36 |
| 241 | 41 |
| 242 | 90 |
| 243 | 180 |
| 244 | 180 |
| 245 | 290 |
| 246 | 340 |
| 247 | 720 |
| 248 | 110 |
| 249 | 140 |
| 250 | 140 |
| 251 | 240 |
| 252 | 260 |
| 253 | 380 |
| 254 | 450 |
| 255 | 480 |
| 256 | 500 |
| 257 | 540 |
| 258 | 550 |
| 259 | 580 |
| 260 | 590 |
| 261 | 710 |
| 262 | 980 |
| 263 | 13 |
| 264 | 21 |
| 265 | 42 |

TABLE 4-continued

Activity of Compounds in Cellular Assay

| Compound Number | EC50 nM |
|---|---|
| 266 | 42 |
| 267 | 44 |
| 268 | 7.3 |
| 269 | 9.5 |
| 270 | 96 |
| 271 | 19 |
| 272 | 110 |
| 273 | 570 |
| 274 | 600 |
| 275 | 670 |
| 276 | 45 |
| 277 | 16 |
| 278 | 51 |
| 279 | 11 |
| 280 | 16 |
| 281 | 28 |
| 282 | 39 |
| 283 | 60 |
| 284 | 100 |
| 285 | 120 |
| 286 | 37 |
| 287 | 6.2 |
| 288 | 9.7 |
| 289 | 3.4 |
| 290 | 4.3 |
| 291 | 7.6 |
| 292 | 10 |
| 293 | 29 |
| 296 | 50 |
| 297 | 100 |
| 298 | 59 |
| 299 | 8.4 |
| 300 | 44 |
| 301 | 57 |
| 302 | 35 |
| 303 | 11 |
| 304 | 23 |
| 305 | 140 |
| 306 | 21 |
| 307 | 24 |
| 308 | 20 |
| 309 | 42 |
| 310 | 99 |
| 311 | 29 |
| 312 | 35 |
| 313 | 120 |
| 314 | 63 |
| 315 | 57 |
| 316 | 15 |
| 317 | 20 |
| 318 | 66 |
| 319 | 70 |
| 320 | 15 |
| 321 | 55 |
| 322 | 19 |
| 323 | 51 |
| 324 | 66 |
| 325 | 29 |
| 326 | 61 |
| 327 | 14 |
| 328 | 29 |
| 329 | 23 |
| 330 | 52 |
| 331 | 140 |
| 332 | 30 |
| 333 | 110 |
| 334 | 160 |
| 335 | 70 |
| 336 | 79 |
| 337 | 14 |
| 338 | 43 |
| 339 | 41 |
| 340 | 19 |
| 341 | 110 |
| 342 | 110 |

TABLE 4-continued

Activity of Compounds in Cellular Assay

| Compound Number | EC50 nM |
|---|---|
| 343 | 46 |
| 344 | 23 |
| 345 | 130 |
| 346 | 67 |
| 347 | 260 |
| 348 | 41 |
| 349 | 40 |
| 350 | 170 |
| 351 | 10 |
| 352 | 76 |
| 353 | 140 |
| 354 | 3.8 |
| 355 | 9.2 |
| 356 | 24 |
| 357 | 24 |
| 358 | 30 |
| 359 | 36 |
| 360 | 21 |
| 361 | 17 |

Assessment of Solubility

Solubility is measured by the following method.
1. Sample Preparation:
DMSO stock samples at 10 mM concentration are prepared. 100 ul of 95 compds+1 DMSO (blank) are prepared in a 96 Remp tube plate for HT solubility analysis (2×95 plates). The samples are pierced and 100 ul of thawed samples are transferred into the PCR plate for analysis. Each sample is run in duplicate at each pH (pH 4.5 and 7.4). Up to 95 samples can be run in replicate at 2 pH's+1 DMSO (blank).
2. Preparation of pH 4.5 and 7.4 Buffers:
pH 4.5 buffer:—To 12.5 of system solution (pION)qs to 500 mL of distilled water (pH 2.85-2.90); adjust the pH to pH 4.5 with 0.5 N NaOH.
pH 7.4 buffer: To 12.5 of system solution (pION)qs to 500 mL of distilled water (pH 2.85-2.90); adjust the pH to pH 7.4 with 0.5N NaOH.
3. Procedure:
Preparation of UV Blank Plate:
75 ul of buffer (pH 7.4 or pH 4.5) is added to UV plate followed by addition of 70 ul of N-propanol. The solution is mixed and the blank spectrum is read using spectrophotometer.
Preparation of Reference UV Plate:
10 ul of each stock sample (including DMSO control) is added to 190 ul of N-propanol to prepare the reference stock plate. Reference stock samples are mixed and 5 ul of each stock sample is added to UV blank plate after it is read spectrophotometrically. The reference stock sample is mixed with blank solution in UV plate and the reference spectrum is read using UV spectrophotometer.
Preparation of Sample for Incubation:
Solubility at pH 7.4:6 ul of each stock sample (including DMSO control) is added to the storage plate containing 600 ul of pH 7.4 buffer, mixed and incubated for 16-19 h. The plate is sealed well during the incubation process. The DMSO content in the sample is 1.0%. The concentration in deep well plates is 100 uM
Solubility at pH 4.5:
6 ul of each stock sample (including DMSO control) is added to the deep well plate containing 600 ul of pH 4.5 buffer, mixed and incubated for 16-19 h. The plate is sealed well during the incubation process. The DMSO content in the sample is 1.0%. The concentration in deep well plates is 100 uM Preparation of Sample UV Plate:
At the end of the incubation period, 100 uL of sample from the storage plate is vacuum filtered using a filter plate. This step wets the filters and the filtrate is discarded. Another 200 ul of the sample from the deep well plate is vacuum filtered using the same filter block but a clean filter plate. 75 ul of the filtrate from the filter plate is transferred to a UV sample plate. 75 ul of N-propanol is added to this UV plate. The solution is mixed and the spectrum is read using the UV spectrophotometer.

Data Analysis:
The spectra collected for blank, reference and sample from 250-498 nm is analyzed using pION software. If the sample precipitates out, the solubility is reported as XX µg/ml. If there is no precipitation and the sample is soluble, solubility is reported as >40 µg/mL (YY being the initial concentration of the compound in the sample).

Solubility data (µg/mL) for representative compounds from Table 1 at pH 4.5, 6.8 and 7.4 is shown Table 4 below.

TABLE 4

| Cpd Number | (pH 4.5) | (pH 7.4) | Cpd Number | (pH 4.5) | (pH 6.8) | (pH 7.4) |
|---|---|---|---|---|---|---|
| 1 | 0.85 | >100 | 181 | >52 | | >52 |
| 2 | >71 | >71 | 182 | | | |
| 3 | >52 | >52 | 183 | | | |
| 4 | >54 | >54 | 184 | | | |
| 5 | 37 | 40 | 185 | | | |
| 6 | >62 | >62 | 186 | | | |
| 7 | >62 | 42 | 187 | | | |
| 8 | 0.15 | >51 | 188 | | | |
| 9 | 5.6 | >51 | 189 | | | |
| 10 | 14 | 22 | 190 | | | |
| 11 | 0.1 | >51 | 191 | | | |
| 12 | 0.1 | >51 | 192 | | | |
| 13 | 17 | >51 | 193 | | | |
| 14 | >63 | >63 | 194 | | | |
| 15 | 13 | >51 | 195 | | | |
| 16 | >51 | 33 | 196 | 16 | | 37 |
| 17 | 0.7 | >51 | 197 | 51 | | >71 |
| 18 | >63 | >63 | 198 | 37 | | >58 |
| 19 | >52 | >52 | 199 | >59 | | >59 |
| 20 | 33 | 36 | 200 | 8.5 | | 30 |
| 21 | >52 | >52 | 201 | 36 | | >53 |
| 22 | >63 | >63 | 202 | 97 | 91 | >59 |
| 23 | >56 | >56 | 203 | 3 | | >59 |
| 24 | >59 | >59 | 204 | 0.35 | | 54 |
| 25 | >63 | >63 | 205 | 9.5 | | >59 |
| 26 | >63 | >63 | 206 | >58 | | >58 |
| 27 | >63 | >63 | 207 | 0.95 | | 30 |
| 28 | >52 | >52 | 208 | 0.3 | | >55 |
| 29 | >64 | 5.2 | 209 | 5.1 | | >55 |
| 30 | 3.1 | >53 | 210 | >58 | | >58 |
| 31 | 25 | >53 | 211 | 1.4 | | 17 |
| 32 | 0.15 | 29 | 212 | 11 | 32 | |
| 33 | >60 | >60 | 213 | 32 | | 41 |
| 34 | 0.9 | >53 | 214 | <0.1 | 51 | 21 |
| 35 | >53 | >53 | 215 | >60 | | >60 |
| 36 | >64 | >64 | 216 | <0.1 | 0.17 | |
| 37 | 0.15 | >53 | 217 | 0.95 | | 34 |
| 38 | 0.25 | >53 | 218 | >64 | | 39 |
| 39 | 0.95 | >53 | 219 | 2.4 | | 41 |
| 40 | 2.3 | >53 | 220 | 42 | 4.8 | 4.0 |
| 41 | 1.1 | >53 | 221 | <0.1 | 0.45 | |
| 42 | 0.45 | >53 | 222 | <0.1 | 3.3 | 30 |
| 43 | >60 | >60 | 223 | <0.1 | 2.5 | |
| 44 | >60 | >60 | 224 | <0.1 | 54 | |
| 45 | >64 | 35 | 225 | 4.6 | 0.3 | |
| 46 | >64 | >64 | 226 | <0.1 | 15 | |
| 47 | >64 | >64 | 227 | 54 | 62 | |
| 48 | 0.1 | 27 | 228 | 6.1 | 0.42 | |

TABLE 4-continued

| Cpd Number | (pH 4.5) | (pH 7.4) | Cpd Number | (pH 4.5) | (pH 6.8) | (pH 7.4) | Cpd Number | (pH 4.5) | (pH 7.4) | Cpd Number | (pH 4.5) | (pH 6.8) | (pH 7.4) |
|---|---|---|---|---|---|---|---|---|---|---|---|---|---|
| 49 | 13 | >53 | 229 | 0.4 | 21 | | 126 | 0.15 | >58 | 306 | 0.13 | 50 | 5.2 |
| 50 | 18 | >53 | 230 | <0.1 | 0.95 | | 127 | 0.2 | >58 | 307 | 0.15 | 37 | |
| 51 | >58 | 31 | 231 | | | | 128 | 0.45 | >58 | 308 | 0.88 | 66 | |
| 52 | >58 | >58 | 232 | 46 | 26 | >54 | 129 | 0.15 | >58 | 309 | <0.1 | 63 | |
| 53 | >53 | >53 | 233 | 47 | 0.6 | | 130 | 0.3 | >58 | 310 | 59 | 61 | |
| 54 | 16 | 16 | 234 | 3.3 | | >58 | 131 | 0.15 | >58 | 311 | 58 | 63 | |
| 55 | 0.3 | >53 | 235 | 8.1 | | >58 | 132 | 15 | >58 | 312 | 0.26 | 13 | |
| 56 | 0.2 | 29 | 236 | 6.6 | | >54 | 133 | 0.2 | >58 | 313 | 1.3 | 78 | |
| 57 | 0.1 | >53 | 237 | >53 | | >53 | 134 | >68 | >68 | 314 | 2.4 | 68 | |
| 58 | 44 | >61 | 238 | 4.9 | 5.2 | | 135 | 0.45 | >59 | 315 | <0.1 | 54 | >60 |
| 59 | 0.5 | >53 | 239 | 2.7 | | >53 | 136 | 0.45 | >59 | 316 | <0.1 | 64 | |
| 60 | >58 | >58 | 240 | | | | 137 | 0.95 | >59 | 317 | <0.1 | 41 | |
| 61 | 44 | >61 | 241 | 9.2 | 72 | | 138 | >70 | >70 | 318 | <0.1 | 34 | >53 |
| 62 | 30 | >65 | 242 | 53 | 37 | | 139 | 0.6 | >59 | 319 | 0.23 | 12 | |
| 63 | 30 | 32 | 243 | 1.2 | 61 | | 140 | 1.8 | >60 | 320 | <0.1 | 36 | |
| 64 | 0.1 | >54 | 244 | 2.6 | 65 | | 141 | 0.2 | >60 | 321 | 0.13 | 41 | |
| 65 | 0.1 | 23 | 245 | 3.6 | 48 | | 142 | 2 | >60 | 322 | 0.15 | 42 | |
| 66 | 1 | >54 | 246 | 62 | 54 | | 143 | 0.2 | 36 | 323 | <0.1 | 39 | |
| 67 | 0.2 | >54 | 247 | 46 | 70 | | 144 | | | 324 | 0.92 | 73 | |
| 68 | 1.2 | >54 | 248 | <0.1 | 47 | | 145 | 0.25 | >60 | 325 | 0.17 | 59 | |
| 69 | >65 | >65 | 249 | 45 | 51 | | 146 | 0.75 | >60 | 326 | 0.21 | 65 | |
| 70 | 0.45 | >54 | 250 | <0.1 | 13 | | 147 | 1 | >60 | 327 | <0.1 | 71 | |
| 71 | 42 | >62 | 251 | 0.15 | 56 | | 148 | 0.3 | >61 | 328 | <0.1 | 62 | |
| 72 | 0.5 | >54 | 252 | <0.1 | 0.2 | | 149 | 0.1 | >62 | 329 | <0.1 | 56 | |
| 73 | 1.9 | >54 | 253 | 0.5 | 0.29 | | 150 | 1.4 | >62 | 330 | <0.1 | 40 | |
| 74 | 40 | 42 | 254 | 40 | 51 | | 151 | 0.15 | >62 | 331 | 42 | 47 | |
| 75 | >66 | >66 | 255 | 6 | 0.94 | | 152 | 0.3 | >62 | 332 | 0.14 | 35 | |
| 76 | 0.1 | 4.1 | 256 | 0.69 | 82 | | 153 | 0.2 | >63 | 333 | 1.1 | 59 | |
| 77 | 22 | 16 | 257 | 56 | 45 | | 154 | 0.8 | >63 | 334 | 11 | 24 | |
| 78 | 0.2 | >55 | 258 | <0.1 | 8.2 | | 155 | 0.3 | >63 | 335 | 0.4 | 49 | |
| 79 | 0.25 | >55 | 259 | <0.1 | 19 | | 156 | 0.45 | >64 | 336 | 0.16 | 6.1 | |
| 80 | >62 | >62 | 260 | <0.1 | 14 | | 157 | 0.15 | >65 | 337 | <0.1 | 1.5 | |
| 81 | 36 | 38 | 261 | 17 | 6.4 | | 158 | | | 338 | 0.13 | 58 | |
| 82 | 12 | >55 | 262 | <0.1 | 12 | | 159 | | | 339 | 32 | 48 | |
| 83 | 11 | 25 | 263 | 0.3 | 58 | | 160 | | | 340 | <0.1 | 0.26 | |
| 84 | 14 | 21 | 264 | 21 | 12 | | 161 | | | 341 | 1.1 | 63 | |
| 85 | 0.35 | >55 | 265 | 0.79 | 1.9 | | 162 | | | 342 | <0.1 | 55 | |
| 86 | 3.5 | 5.7 | 266 | 0.48 | 70 | | 163 | | | 343 | <0.1 | 52 | |
| 87 | >63 | >63 | 267 | <0.1 | 13 | | 164 | | | 344 | 0.1 | 61 | >58 |
| 88 | 0.45 | >55 | 268 | <0.1 | 70 | 38 | 165 | | | 345 | 4 | 66 | >58 |
| 89 | 0.35 | 32 | 269 | 0.28 | 16 | | 166 | >55 | >55 | 346 | 0.46 | 36 | >54 |
| 90 | 35 | >56 | 270 | 17 | | >56 | 167 | 41 | >64 | 347 | 5.8 | 70 | >53 |
| 91 | 31 | 12 | 271 | 3.7 | | 21 | 168 | 36 | >57 | 348 | 0.27 | 71 | 37 |
| 92 | 20 | 12 | 272 | 14 | | >160 | 169 | >57 | >57 | 349 | 6.5 | 69 | |
| 93 | >56 | >56 | 273 | 7.3 | | >82 | 170 | 37 | 24 | 350 | >56 | | >56 |
| 94 | >56 | >56 | 274 | 0.95 | | >54 | 171 | 34 | 36 | 351 | 0.21 | 1.3 | |
| 95 | >56 | >56 | 275 | 0.6 | | 4 | 172 | 41 | >63 | 352 | 22 | | >59 |
| 96 | >67 | >67 | 276 | 32 | 1.9 | 41 | 173 | >64 | >64 | 353 | >53 | | 38 |
| 97 | 0.45 | >56 | 277 | 21 | | 41 | 174 | >66 | >66 | 354 | 0.42 | 57 | |
| 98 | 0.2 | >56 | 278 | >53 | | 30 | 175 | >55 | >55 | 355 | 0.77 | 7 | |
| 99 | 4.7 | 13 | 279 | | | | 176 | | | 356 | 2.7 | 1.6 | |
| 100 | 20 | 27 | 280 | 0.72 | 0.9 | | 177 | | | 357 | 2.3 | 11 | |
| 101 | 3 | >56 | 281 | <0.1 | 4.6 | | 178 | | | 358 | 0.14 | 8.1 | |
| 102 | 0.25 | 26 | 282 | <0.1 | 0.89 | | 179 | >55 | >55 | 359 | 12 | 5.8 | |
| 103 | 0.3 | 35 | 283 | <0.1 | 0.1 | | 180 | | | 360 | | 33 | |
| 104 | 0.35 | >68 | 284 | 0.65 | 66 | | | | | 361 | | 34 | |
| 105 | 8.9 | >56 | 285 | <0.1 | 54 | | | | | | | | |
| 106 | 0.3 | >56 | 286 | 1 | 83 | | | | | | | | |
| 107 | 0.65 | >56 | 287 | <0.1 | 21 | | | | | | | | |
| 108 | 2.3 | >56 | 288 | <0.1 | 29 | | | | | | | | |
| 109 | 0.65 | >56 | 289 | 1.5 | 35 | | | | | | | | |
| 110 | 0.35 | >57 | 290 | 0.69 | 21 | | | | | | | | |
| 111 | 0.25 | >57 | 291 | 0.18 | 13 | | | | | | | | |
| 112 | >68 | >68 | 292 | 16 | | >54 | | | | | | | |
| 113 | >57 | >57 | 293 | <0.1 | 3.4 | | | | | | | | |
| 114 | 30 | >57 | 294 | | | | | | | | | | |
| 115 | >57 | >57 | 295 | 0.45 | 60 | | | | | | | | |
| 116 | | | 296 | <0.1 | 10 | | | | | | | | |
| 117 | 0.25 | >57 | 297 | 1.7 | 63 | | | | | | | | |
| 118 | 0.3 | 21 | 298 | 0.32 | 66 | | | | | | | | |
| 119 | 1.6 | >69 | 299 | 0.17 | 36 | | | | | | | | |
| 120 | | | 300 | 53 | 60 | | | | | | | | |
| 121 | 3.3 | >58 | 301 | 0.24 | 65 | | | | | | | | |
| 122 | 4.3 | >58 | 302 | <0.1 | 4.6 | | | | | | | | |
| 123 | 31 | >58 | 303 | 0.13 | 36 | | | | | | | | |
| 124 | | | 304 | <0.1 | 60 | | | | | | | | |
| 125 | 0.1 | 14 | 305 | 62 | 67 | | | | | | | | |

Methods of Therapeutic Use

The compounds disclosed herein effectively activate soluble guanylate cyclase. The activation or potentiation of soluble guanylate cyclase is an attractive means for preventing and treating a variety of diseases or conditions associated with deficient sGC activation. Thus, in one embodiment of the invention, there are provided methods of treating diseases that can be alleviated by sGC activation or potentiation. These include:

Cardiovascular and related diseases including hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina and thromboembolic disorders;

Inflammatory diseases including psoriasis, multiple sclerosis, arthritis, asthma, and chronic obstructive pulmonary disease;

Hepatic fibrotic disorders including but not limited to cirrhosis of any etiology or fibrosis of specific areas of the liver such as periportal fibrosis which may be caused by immunologic injury, hemodynamic effects and/or other causes;

Renal fibrotic disorders including but not limited to glomerulosclerosis, focal glomerulosclerosis, mesangial fibrosis, interstitial fibrosis due to immunologic injury, hemodynamic effects, diabetes (types 1 and 2), IgA nephropathy, lupus nephropathy, membranous nephropathy, hypertension, hemolytic uremic syndrome, multiple glomerulonephritides, interstitial nephritis, tubulointerstitial nephritis again of immunologic and non-immunologic causes;

Pulmonary fibrotic disorders, both diffuse and localized, due to immunologic and non-immunologic causes, including but not limited to idiopathic pulmonary fibrosis, pulmonary fibrosis due to exposure to toxins, chemicals, drugs, and cystic fibrosis;

Cardiac fibrotic disorders due to immunologic and non-immunologic causes including ischemic heart disease (coronary artery disease) and transient and/or sustained decreased blood flow in one or more coronary vessels including possibly related to interventions on coronary arteries or veins, associated with cardiac surgery and/or the use of cardiopulmonary bypass procedures and myocarditis due to viral and non-viral causes, as well as immunologically related myocardial injury potentially due to cross-reactivity to other antigens to which the human body is exposed;

Other diseases mediated at least partially by diminished or decreased soluble guanylate cyclase activity, such as renal disease, diabetes, urologic disorders including overactive bladder, benign prostatic hyperplasia, and erectile dysfunction, and neurological disorders including Alzheimer's disease, Parkinson's disease and neuropathic pain.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:
1. A compound of formula I

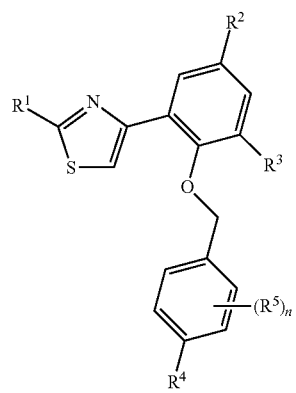

wherein:
$R^1$ is selected from pyrrolidin-1-yl, piperidin-1-yl, azetidin-1-yl, 5-azaspiro[2.3]hexan-5-yl, azepan-1-yl, 3-azabicyclo[3.1.0.]hexan-3-yl, cyclohexyl, cyclohexen-1-yl, cyclohexylamino and cyclopentylamino, wherein each $R^1$ is substituted with —$CO_2H$ or —$CH_2CO_2H$ and optionally further substituted by a group selected from $C_{1-3}$alkyl, OH, —$CH_2OMe$, —$CF_3$ and —F, and wherein two different carbons in said pyrrolidin-1-yl, piperidin-1-yl, azetidin-1-yl or azepan-1-yl may optionally be joined by a $C_{1-3}$alkylene bridge;

or $R^1$ is —N($R^6$)(CH$_2$)$_{2-3}$CO$_2$H;

$R^2$ and $R^3$ are independently selected from H, $C_{1-6}$alkyl, halogen, —CN and —CF$_3$, provided that at least one of $R^2$ or $R^3$ is H;

$R^4$ is selected from —C(O)N($R^6$)($R^7$), —C(O)$R^8$ and —CH($R^6$)$R^9$;

$R^5$ is selected from H, $C_{1-4}$alkyl, halogen, —CF$_3$, —OC$_{1-4}$alkyl, —OCF$_3$ and —CN;

$R^6$ is H, —CH$_3$ or CH$_2$CH$_3$;

$R^7$ is selected from —CH$_3$, —CH$_2$CH$_3$, —(CH$_2$)$_{2-3}$OCH$_3$, —(CH$_2$)$_2$N(CH$_3$)$_2$, $C_{1-3}$alkyl, —(CH$_2$)$_{1-2}$CN, —(CH$_2$)$_{2-3}$OH, —CH$_2$C(O)NHCH$_3$, —CH$_2$C(O)N(CH$_3$)$_2$, —CH$_2$-tetrahydrofuranyl, —CH$_2$-1-methylpyrrazol-3-yl, —CH$_2$-1-methylpyrrazol-4-yl, —CH$_2$-1-methylpyrrazol-5-yl, —CH$_2$-imidazol-2-yl and —(CH$_2$)$_{0-1}$cyclohexyl;

$R^8$ is selected from azepan-1-yl, azetidin-1-yl, 1,1-dioxothiomorpholin-4-yl, morpholin-4-yl, piperidin-1-yl, piperazin-1-yl, pyrrolidin-1-yl, [1,4]oxazepan-4-yl, 5,6,7,8-tetrahydro[1,2,4]triazolo[1,5-a]pyrazin-7-yl and 5,6,7,8-[1,2,4]triazolo[4,3-a]pyrazine-7-yl and is optionally substituted with one to three groups independently selected from $C_{1-3}$alkyl, —CH$_2$OH, —OCH$_3$, —N(CH$_3$)$_2$, —OH, oxo, —CN and halogen;

$R^9$ is a heterocyclyl selected from morpholin-4-yl, 1,1-dioxothiomorpholin-4-yl, pyrrolidin-1-yl, piperidin-1-yl, octahydropyrrolo[1,2-a]pyrazin-2-yl and piperazin-1-yl, wherein said heterocyclyl is optionally substituted with one to three groups independently selected from $C_{1-3}$alkyl, —CH$_2$OH, —CH$_2$OCH$_3$, halogen, —CN, oxo, —OH, —SO$_2$C$_{1-6}$alkyl, —SO$_2$N(C$_{1-6}$alkyl)$_2$, —C(O)NH$_2$, —C(O)NHCH$_3$, —C(O)N(CH$_3$)$_2$, C(O)C$_{1-6}$alkyl, —C(O)C$_{3-6}$cycloalkyl, and —C(O)tetrahydrofuran-3-yl; or $R^9$ is —N($R^6$)($R^{10}$);

$R^{10}$ is tetrahydropyran-4-ylmethyl, $C_{3-6}$cycloalkyl, $C_{3-6}$cycloalkylmethyl, 1,1-dioxotetrahydrothiophen-3-yl, —CH$_2$C(CH$_3$)$_2$OH, —CH$_2$C(CH$_3$)$_2$CH$_2$OH, —C(CH$_3$)$_2$CH$_2$OH, —CH$_2$(CH$_2$)$_{1-2}$OCH$_3$ or —CH$_2$CH$_2$CO$_2$H; and n is 1 or 2;

or a salt thereof.

2. The compound of claim 1, wherein $R^1$ is selected from the group consisting of

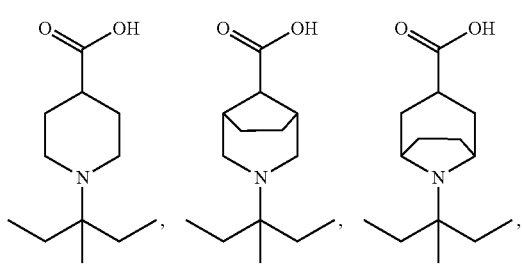

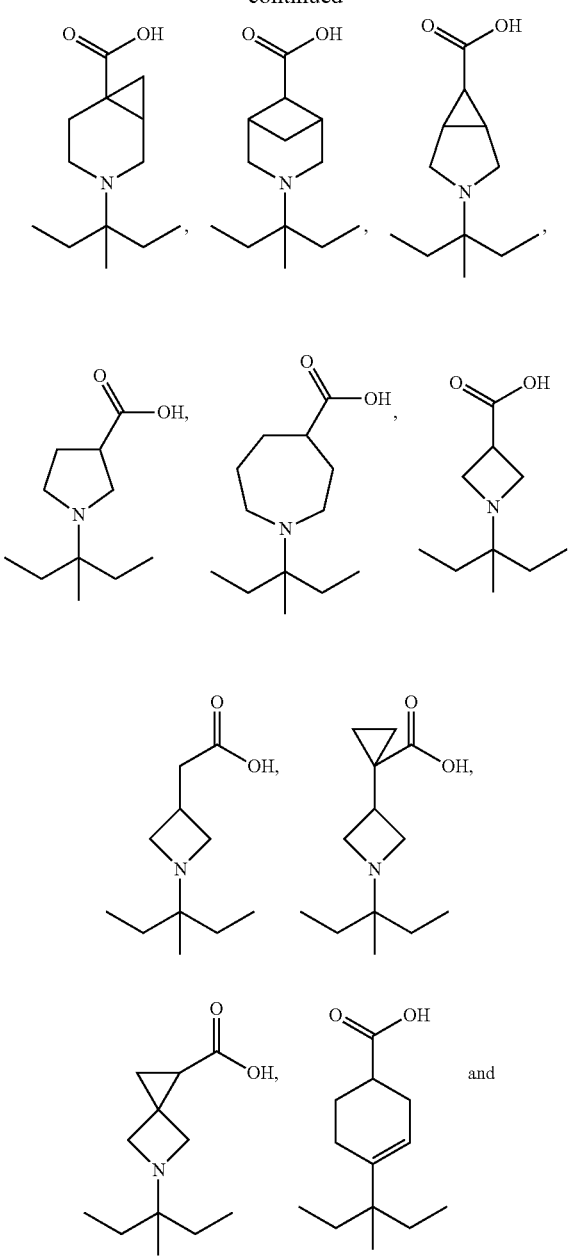

wherein each $R^1$ is optionally substituted by a group selected from $C_{1-3}$alkyl, OH, —CH$_2$OMe, —CF$_3$ and —F;

or a salt thereof.

3. The compound of claim 1, wherein R$^1$ is selected from the group consisting of

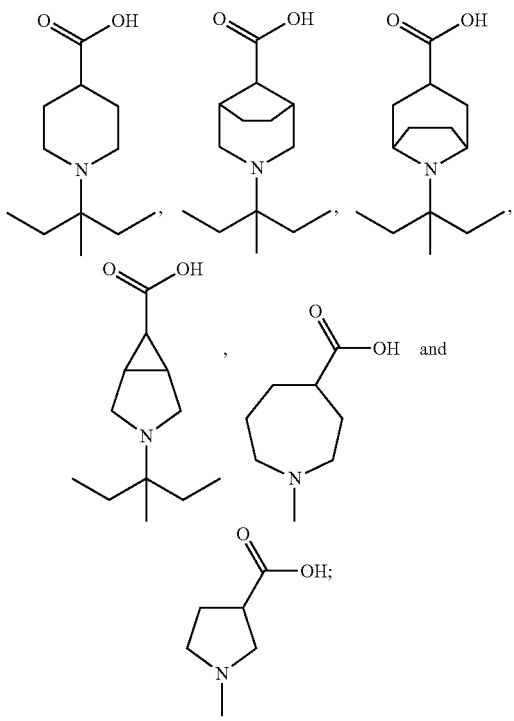

wherein each R$^1$ is optionally substituted by a group selected from —CH$_3$, —CF$_3$ and —F;
n is 1;
R$^4$ is selected from —C(O)N(R$^6$)(R$^7$), —C(O)R$^8$ and —CH$_2$R$^9$;
R$^5$ is selected from H, C$_{1-4}$alkyl, halogen, —CF$_3$, —OC$_{1-4}$alkyl, —OCF$_3$ and —CN and is bonded to a position on the phenyl ring meta to R$^4$;
R$^7$ is selected from —(CH$_2$)$_{2-3}$OCH$_3$, —(CH$_2$)$_2$N(CH$_3$)$_2$ and —(CH$_2$)$_{0-1}$cyclohexyl;
R$^9$ is a heterocyclyl selected from morpholin-4-yl, 1,1-dioxothiomorpholin-4-yl, pyrrolidin-1-yl, piperidin-1-yl and piperazin-1-yl, wherein said heterocyclyl is optionally substituted with one to two groups selected from halogen, —OH, —SO$_2$C$_{1-6}$alkyl, —SO$_2$N(C$_{1-6}$alkyl)$_2$, —C(O)NH$_2$, —C(O)NHCH$_3$, —C(O)N(CH$_3$)$_2$, C(O)C$_{1-6}$alkyl, —C(O)C$_{3-6}$cycloalkyl, and —C(O)tetrahydrofuran-3-yl; or
R$^9$ is —N(R$^6$)(R$^{10}$);
or a salt thereof.

4. The compound of claim 1, wherein R$^1$ is

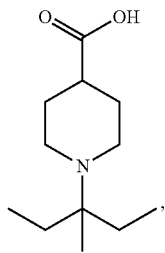

or a salt thereof.

5. The compound of claim 1, wherein R$^1$ is selected from the group consisting of

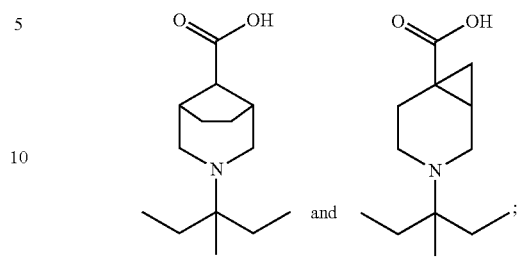

or a salt thereof.

6. The compound of claim 5, wherein R$^1$ is selected from the group consisting of

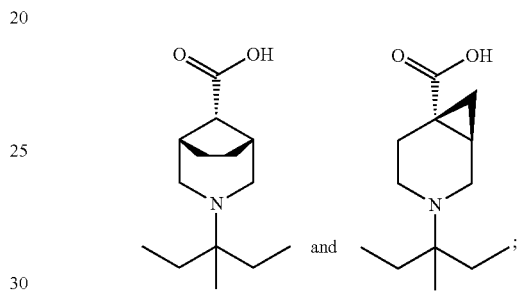

or a salt thereof.

7. The compound of claim 1, wherein
n is 1;
R$^2$ and R$^3$ are independently selected from H, —CH$_3$, —Cl, —F, —CN and —CF$_3$, provided that at least one of R$^2$ or R$^3$ is H;
R$^5$ is selected from —CH$_3$, —CH$_2$CH$_3$, —OCF$_3$ and —CN and is bonded to a position on the phenyl ring meta to R$^4$;
R$^8$ is selected from azepan-1-yl, azetidin-1-yl, morpholin-4-yl, 1,1-dioxothiomorpholin-4-yl, pyrrolidin-1-yl, piperazin-1-yl, [1,4]oxazepan-4-yl, and piperidin-1-yl, wherein each R$^8$ is optionally substituted with one to three groups independently selected from —CH$_3$, —OCH$_3$, —CH$_2$OH, —OCH$_3$, —N(CH$_3$)$_2$, —OH, oxo, —CN and halogen;
R$^9$ is a heterocyclyl selected from morpholin-4-yl, 1,1-dioxothiomorpholin-4-yl, pyrrolidin-1-yl, piperidin-1-yl and piperazin-1-yl, wherein said heterocyclyl is optionally substituted with one to three groups independently selected from —CH$_3$, —CH$_2$CH$_3$, Cl, F, oxo, —OH, —C(O)CH$_3$, —C(O)cyclopropyl and —C(O)tetrahydrofuran-3-yl;
or a salt thereof.

8. The compound of claim 1, wherein
R$^4$ is —C(O)R$^8$;
or a salt thereof.

9. The compound of claim 1, wherein
R$^4$ is —CH$_2$R$^9$;
or a salt thereof.

10. A compound selected from the group consisting of
| Cpd No. | |
|---|---|
| 1 | 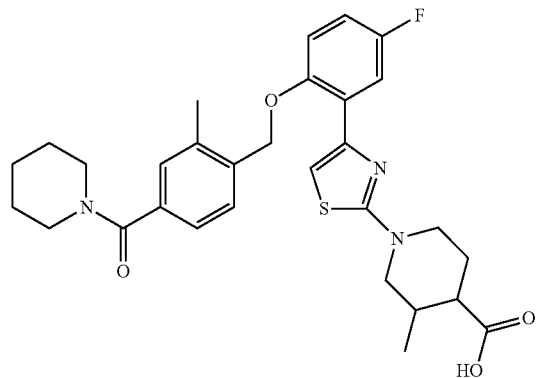 [SMILES: Cc1cc(C(=O)N2CCCCC2)ccc1COc1ccc(F)cc1-c1csc(N2CCC(C(=O)O)C(C)C2)n1] |
| 2 | 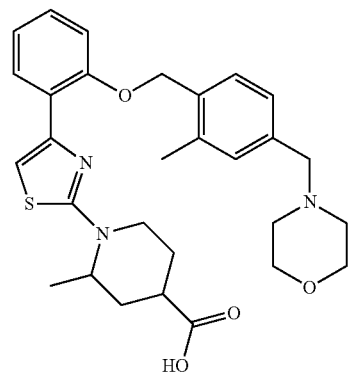 [SMILES: Cc1cc(CN2CCOCC2)ccc1COc1ccccc1-c1csc(N2CCC(C(=O)O)CC2C)n1] |
| 3 | 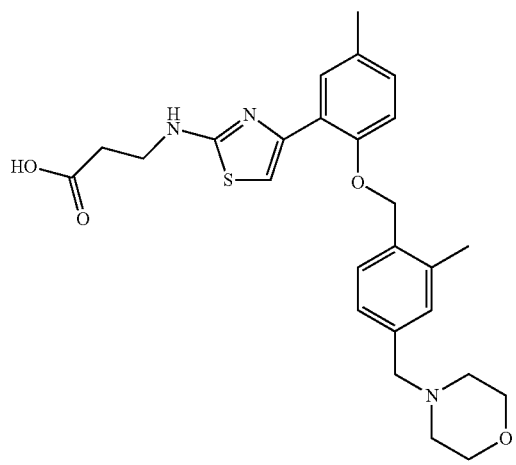 [SMILES: Cc1ccc(OCc2ccc(CN3CCOCC3)cc2C)c(-c2csc(NCCC(=O)O)n2)c1] |

| Cpd No. | |
|---|---|
| 4 | 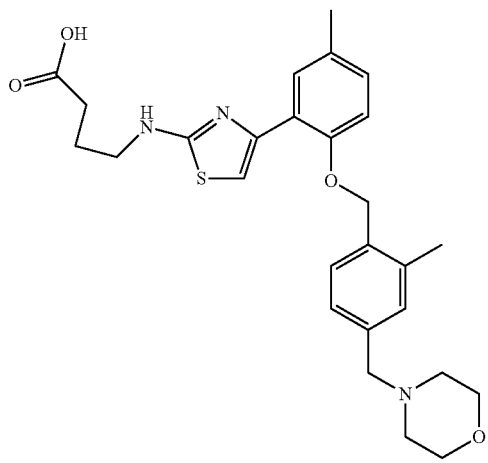 [SMILES: Cc1ccc(OCc2ccc(CN3CCOCC3)cc2C)c(-c2csc(NCCCC(=O)O)n2)c1] |
| 5 | 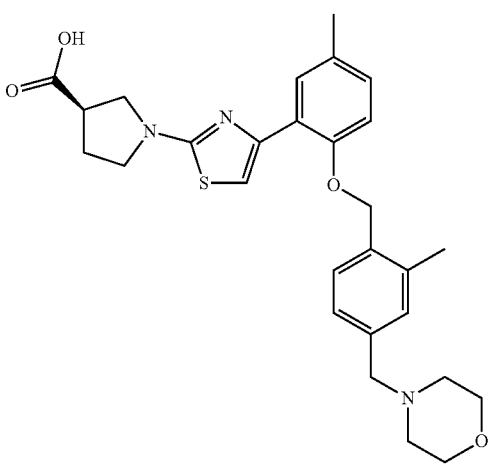 [SMILES: Cc1ccc(OCc2ccc(CN3CCOCC3)cc2C)c(-c2csc(N3CC[C@@H](C(=O)O)C3)n2)c1] |
| 6 | 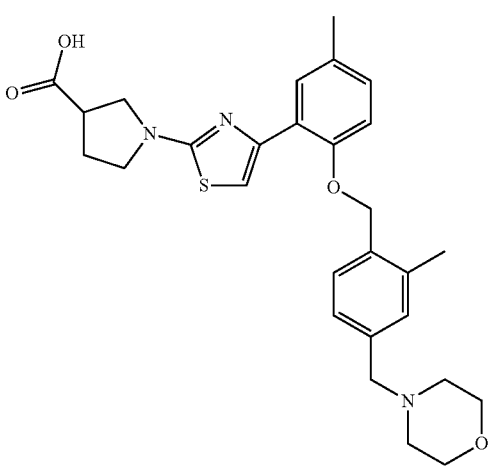 [SMILES: Cc1ccc(OCc2ccc(CN3CCOCC3)cc2C)c(-c2csc(N3CCC(C(=O)O)C3)n2)c1] |

-continued
| Cpd No. | |
|---|---|
| 7 | 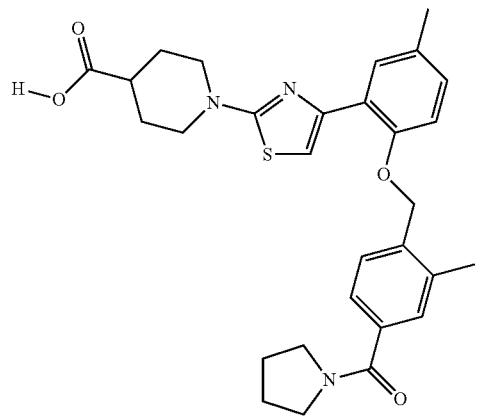 [SMILES: Cc1ccc(OCc2ccc(C(=O)N3CCCC3)cc2C)c(-c2csc(N3CCC(C(=O)O)CC3)n2)c1] |
| 8 | 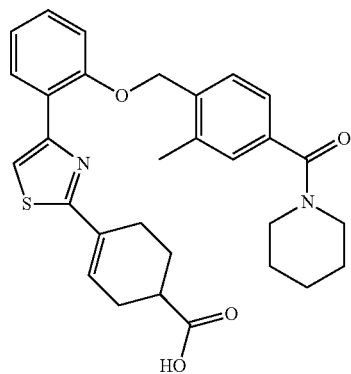 [SMILES: Cc1cc(C(=O)N2CCCCC2)ccc1COc1ccccc1-c1csc(C2=CCC(C(=O)O)CC2)n1] |
| 9 | 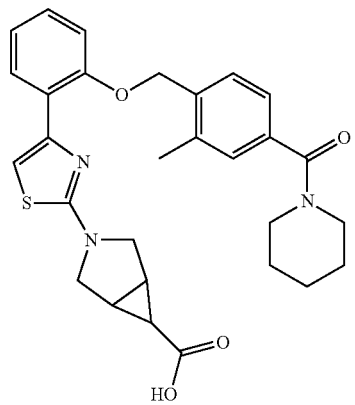 [SMILES: Cc1cc(C(=O)N2CCCCC2)ccc1COc1ccccc1-c1csc(N2CC3C(C2)C3C(=O)O)n1] |

-continued
| Cpd No. |
|---|
| 10 |
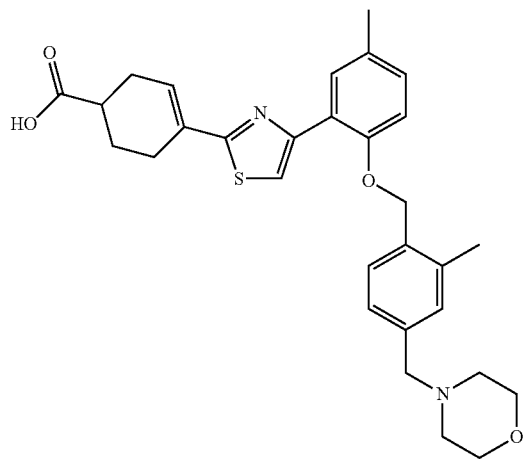 [SMILES: Cc1ccc(OCc2ccc(CN3CCOCC3)cc2C)c(-c2csc(C3=CCC(C(=O)O)CC3)n2)c1]
| 11 |
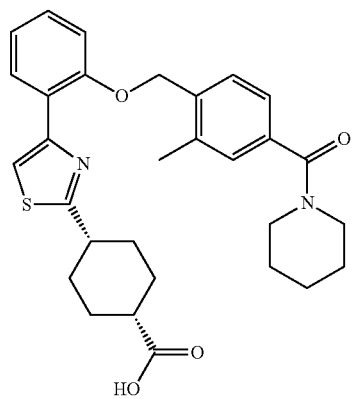 [SMILES: Cc1cc(C(=O)N2CCCCC2)ccc1COc1ccccc1-c1csc([C@H]2CC[C@@H](C(=O)O)CC2)n1]
| 12 |
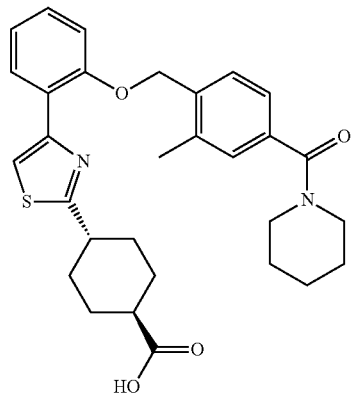 [SMILES: Cc1cc(C(=O)N2CCCCC2)ccc1COc1ccccc1-c1csc([C@H]2CC[C@H](C(=O)O)CC2)n1]

-continued
| Cpd No. | |
|---|---|
| 13 | 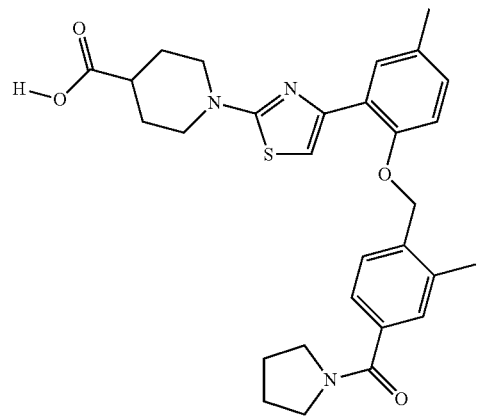 [SMILES: Cc1ccc(OCc2ccc(C(=O)N3CCCC3)cc2C)c(-c2csc(N3CCC(C(=O)O)CC3)n2)c1] |
| 14 | 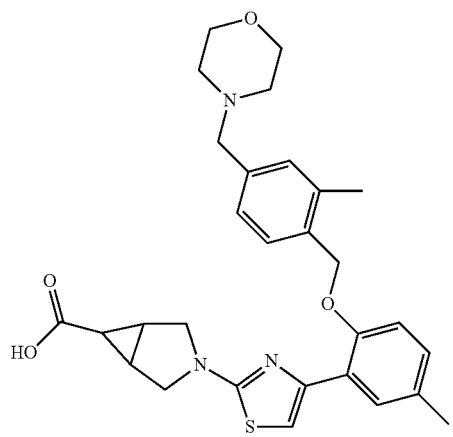 [SMILES: Cc1ccc(OCc2ccc(CN3CCOCC3)cc2C)c(-c2csc(N3CC4C(C3)C4C(=O)O)n2)c1] |
| 15 | 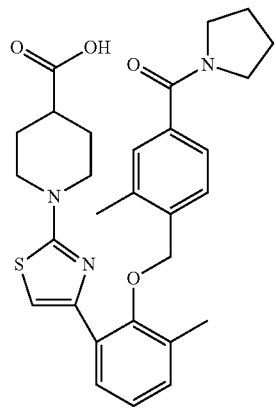 [SMILES: Cc1cc(C(=O)N2CCCC2)ccc1COc1c(C)cccc1-c1csc(N2CCC(C(=O)O)CC2)n1] |

-continued
| Cpd No. |
|---|
| 16 |
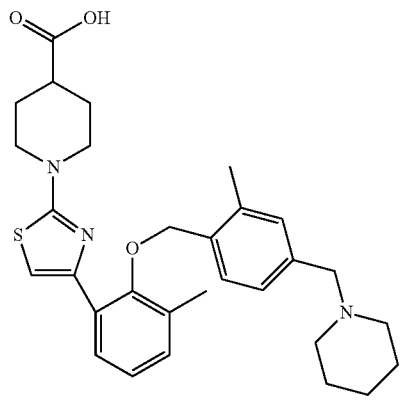 [SMILES: Cc1cc(CN2CCCCC2)ccc1COc1c(C)cccc1-c1csc(N2CCC(C(=O)O)CC2)n1]
| 17 |
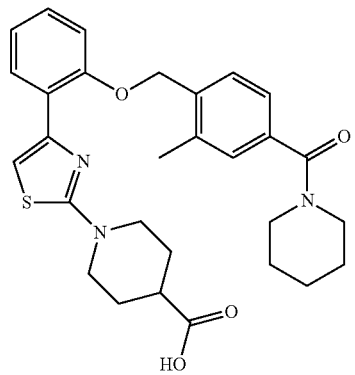 [SMILES: Cc1cc(C(=O)N2CCCCC2)ccc1COc1ccccc1-c1csc(N2CCC(C(=O)O)CC2)n1]
| 18 |
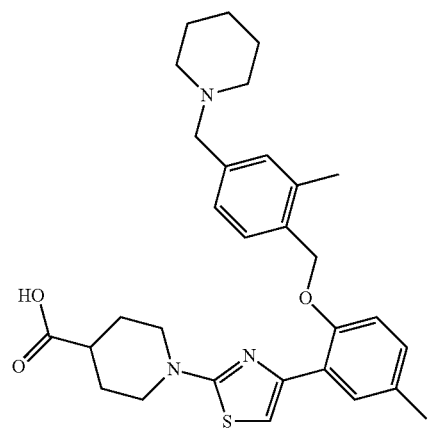 [SMILES: Cc1ccc(OCc2ccc(CN3CCCCC3)cc2C)c(-c2csc(N3CCC(C(=O)O)CC3)n2)c1]

| Cpd No. | |
|---|---|
| 19 | 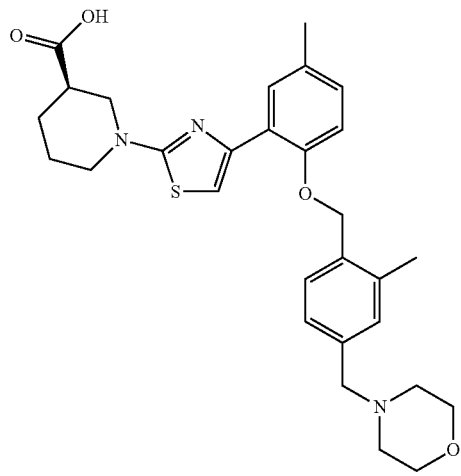 [SMILES: Cc1ccc(OCc2ccc(CN3CCOCC3)cc2C)c(-c2csc(N3CCC[C@@H](C(=O)O)C3)n2)c1] |
| 20 | 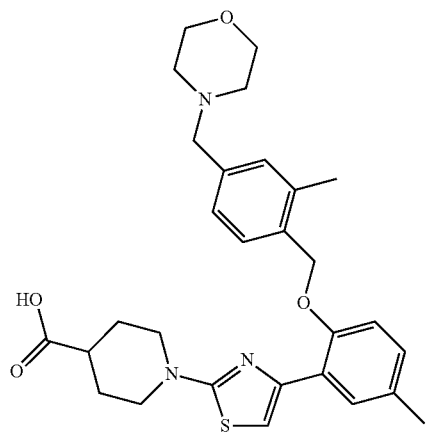 [SMILES: Cc1ccc(OCc2ccc(CN3CCOCC3)cc2C)c(-c2csc(N3CCC(C(=O)O)CC3)n2)c1] |
| 21 | 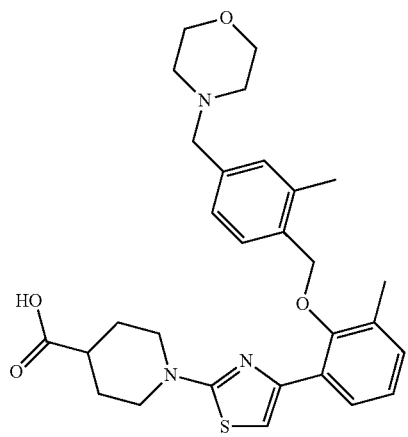 [SMILES: Cc1cc(CN2CCOCC2)ccc1COc1c(C)cccc1-c1csc(N2CCC(C(=O)O)CC2)n1] |

-continued
| Cpd No. |
|---|
| 22 |
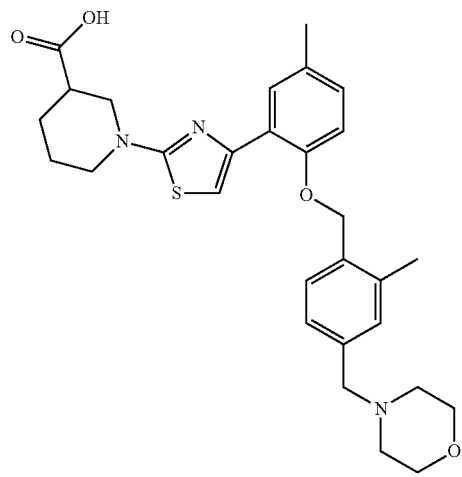 [SMILES: Cc1ccc(OCc2ccc(CN3CCOCC3)cc2C)c(-c2csc(N3CCCC(C(=O)O)C3)n2)c1]
23
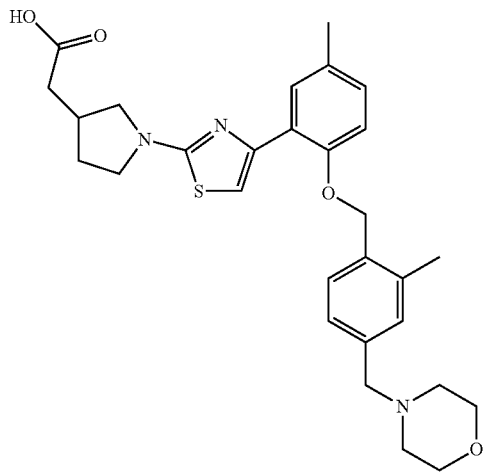 [SMILES: Cc1ccc(OCc2ccc(CN3CCOCC3)cc2C)c(-c2csc(N3CCC(CC(=O)O)C3)n2)c1]
24
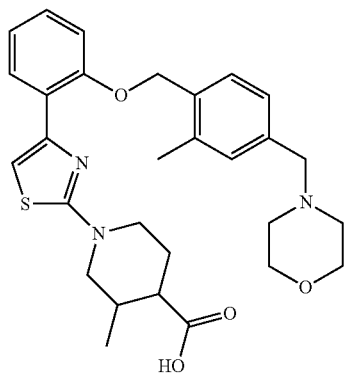 [SMILES: Cc1cc(CN2CCOCC2)ccc1COc1ccccc1-c1csc(N2CCC(C(=O)O)C(C)C2)n1]

| Cpd No. | |
|---|---|
| 25 | 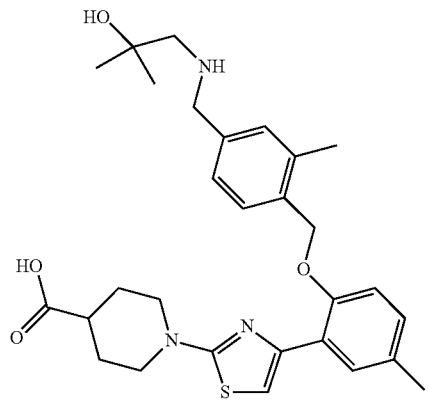 [SMILES: Cc1ccc(OCc2ccc(CNCC(C)(C)O)cc2C)c(-c2csc(N3CCC(C(=O)O)CC3)n2)c1] |
| 26 | 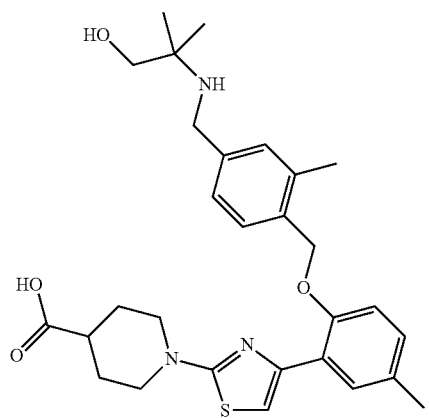 [SMILES: Cc1ccc(OCc2ccc(CNC(C)(C)CO)cc2C)c(-c2csc(N3CCC(C(=O)O)CC3)n2)c1] |
| 27 | 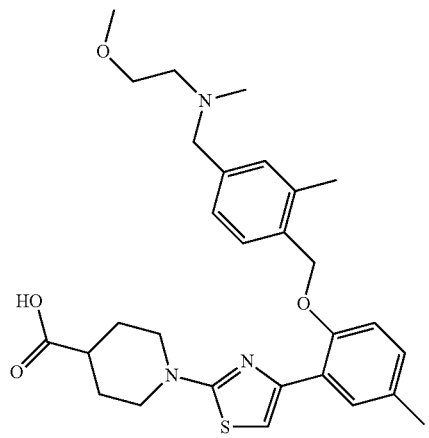 [SMILES: COCCN(C)Cc1ccc(COc2ccc(C)cc2-c2csc(N3CCC(C(=O)O)CC3)n2)c(C)c1] |

| Cpd No. | |
|---|---|
| 28 | 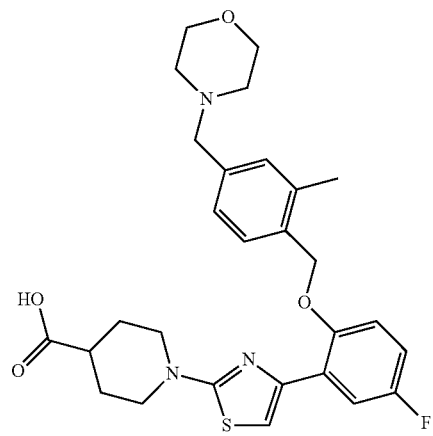 [SMILES: Cc1cc(CN2CCOCC2)ccc1COc1ccc(F)cc1-c1csc(N2CCC(C(=O)O)CC2)n1] |
| 29 | 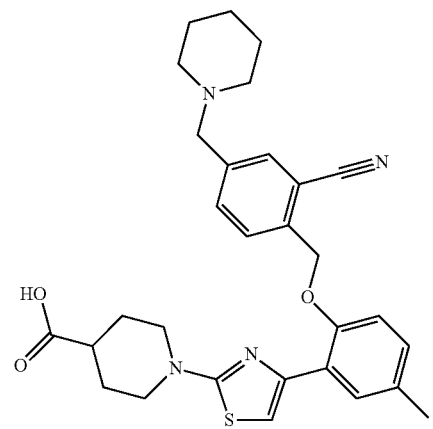 [SMILES: Cc1ccc(OCc2ccc(CN3CCCCC3)cc2C#N)c(-c2csc(N3CCC(C(=O)O)CC3)n2)c1] |
| 30 | 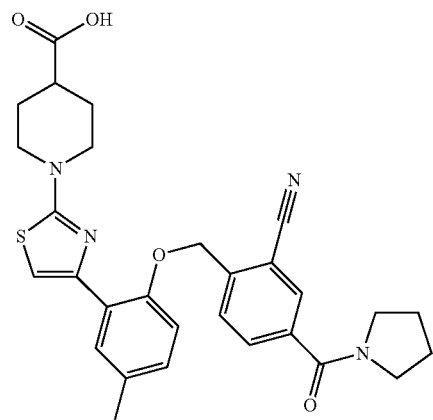 [SMILES: Cc1ccc(OCc2ccc(C(=O)N3CCCC3)cc2C#N)c(-c2csc(N3CCC(C(=O)O)CC3)n2)c1] |

-continued
| Cpd No. | |
|---|---|
| 31 | 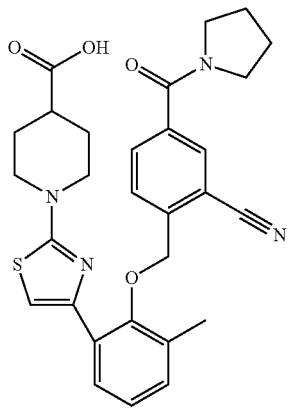 [SMILES: Cc1cccc(-c2csc(N3CCC(C(=O)O)CC3)n2)c1OCc1ccc(C(=O)N2CCCC2)cc1C#N] |
| 32 | 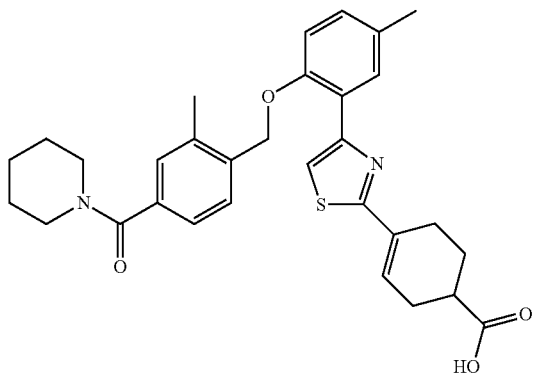 [SMILES: Cc1ccc(OCc2ccc(C(=O)N3CCCCC3)cc2C)c(-c2csc(C3=CCC(C(=O)O)CC3)n2)c1] |
| 33 | 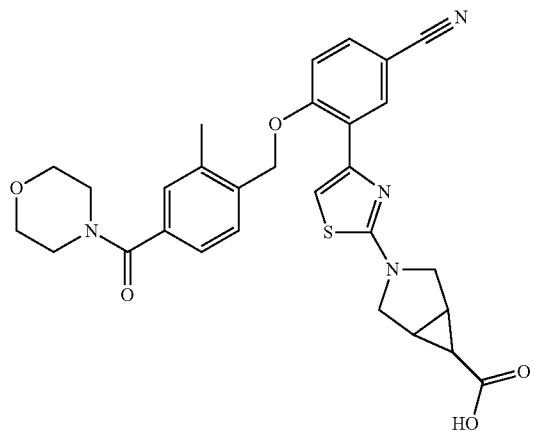 [SMILES: Cc1cc(C(=O)N2CCOCC2)ccc1COc1ccc(C#N)cc1-c1csc(N2CC3C(C2)C3C(=O)O)n1] |

-continued
| Cpd No. | |
|---|---|
| 34 | 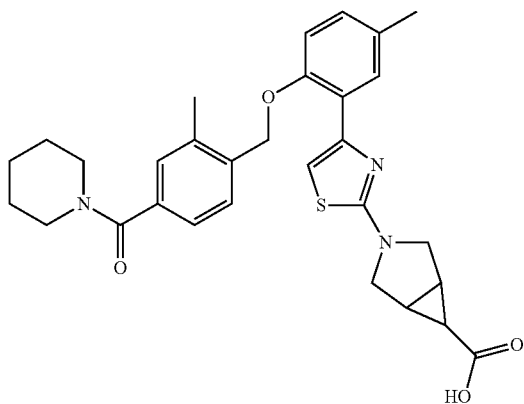 [SMILES: Cc1ccc(OCc2ccc(C(=O)N3CCCCC3)cc2C)c(-c2csc(N3CC4C(C3)C4C(=O)O)n2)c1] |
| 35 | 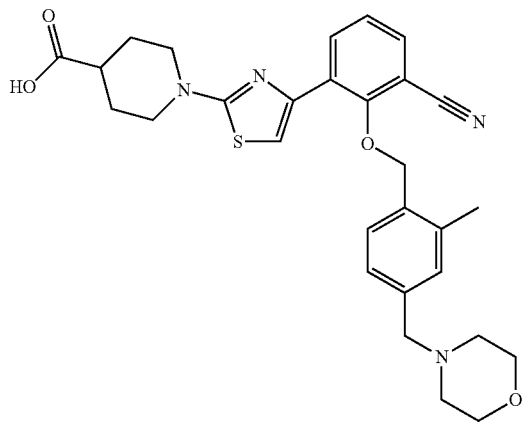 [SMILES: Cc1cc(CN2CCOCC2)ccc1COc1c(C#N)cccc1-c1csc(N2CCC(C(=O)O)CC2)n1] |
| 36 | 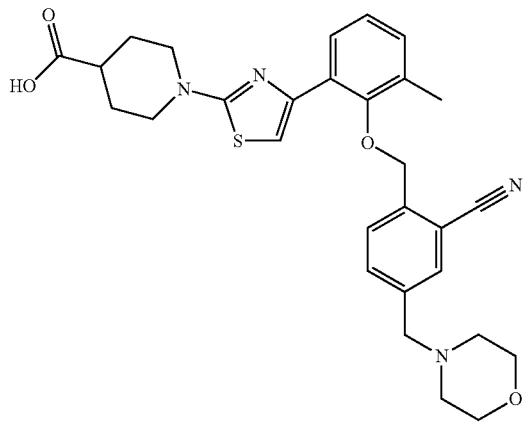 [SMILES: Cc1cccc(-c2csc(N3CCC(C(=O)O)CC3)n2)c1OCc1ccc(CN2CCOCC2)cc1C#N] |

| Cpd No. | |
|---|---|
| 37 | 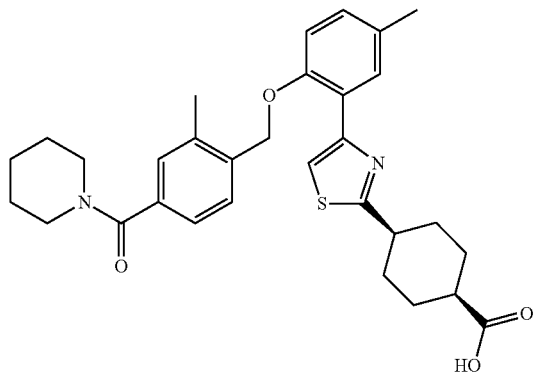 [SMILES: Cc1ccc(OCc2ccc(C(=O)N3CCCCC3)cc2C)c(-c2csc([C@H]3CC[C@@H](C(=O)O)CC3)n2)c1] |
| 38 | 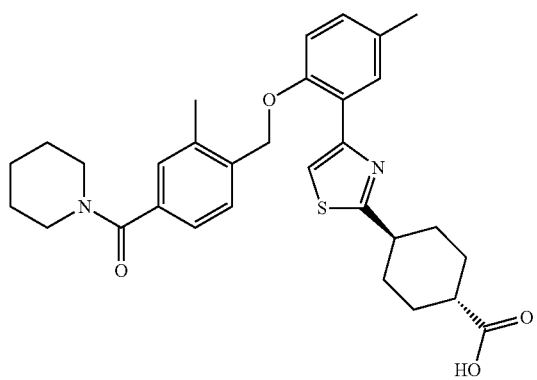 [SMILES: Cc1ccc(OCc2ccc(C(=O)N3CCCCC3)cc2C)c(-c2csc([C@H]3CC[C@H](C(=O)O)CC3)n2)c1] |
| 39 | 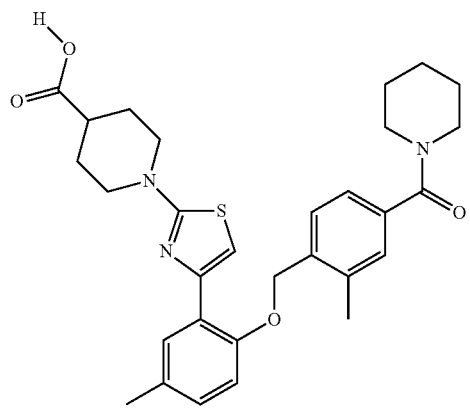 [SMILES: Cc1ccc(OCc2ccc(C(=O)N3CCCCC3)cc2C)c(-c2csc(N3CCC(C(=O)O)CC3)n2)c1] |
| 40 | 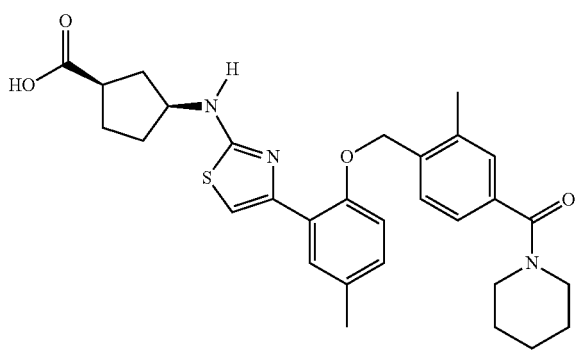 [SMILES: Cc1ccc(OCc2ccc(C(=O)N3CCCCC3)cc2C)c(-c2csc(N[C@H]3CC[C@@H](C(=O)O)C3)n2)c1] |

| Cpd No. | |
|---|---|
| 41 | 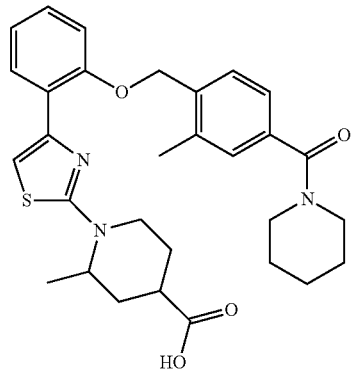 [SMILES: Cc1cc(C(=O)N2CCCCC2)ccc1COc1ccccc1-c1csc(N2CCC(C(=O)O)CC2C)n1] |
| 42 | 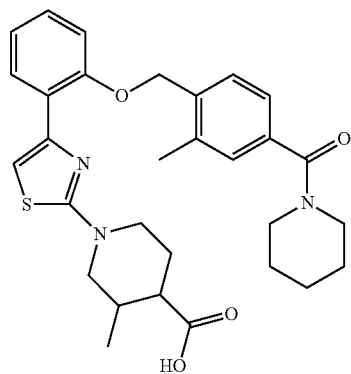 [SMILES: Cc1cc(C(=O)N2CCCCC2)ccc1COc1ccccc1-c1csc(N2CCC(C(=O)O)C(C)C2)n1] |
| 43 | 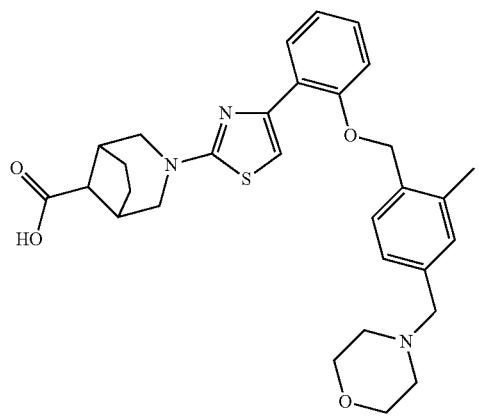 [SMILES: Cc1cc(CN2CCOCC2)ccc1COc1ccccc1-c1csc(N2CC3CCC(C2)C3C(=O)O)n1] |
| 44 | 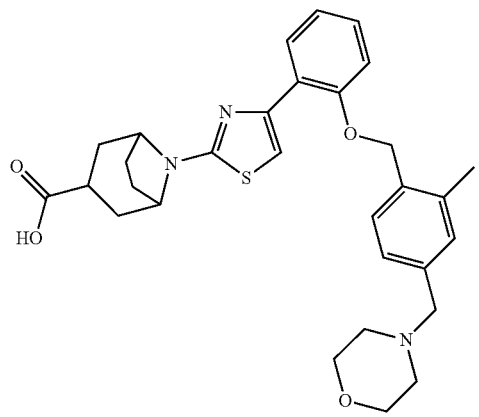 [SMILES: Cc1cc(CN2CCOCC2)ccc1COc1ccccc1-c1csc(N2C3CCC2CC(C(=O)O)C3)n1] |

| Cpd No. | |
|---|---|
| 45 | 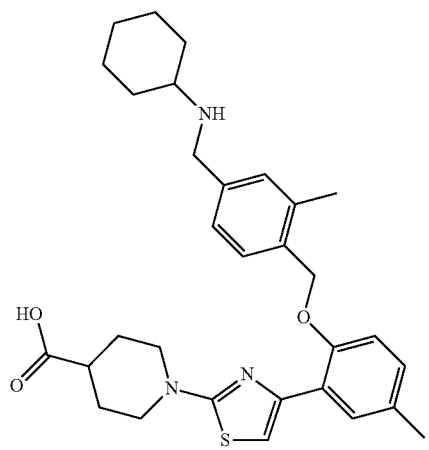 [SMILES: Cc1ccc(OCc2ccc(CNC3CCCCC3)cc2C)c(-c2csc(N3CCC(C(=O)O)CC3)n2)c1] |
| 46 | 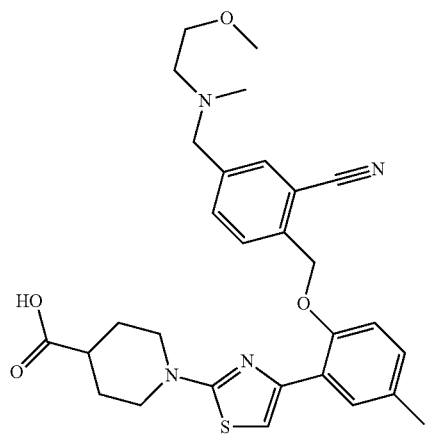 [SMILES: COCCN(C)Cc1ccc(COc2ccc(C)cc2-c2csc(N3CCC(C(=O)O)CC3)n2)c(C#N)c1] |
| 47 | 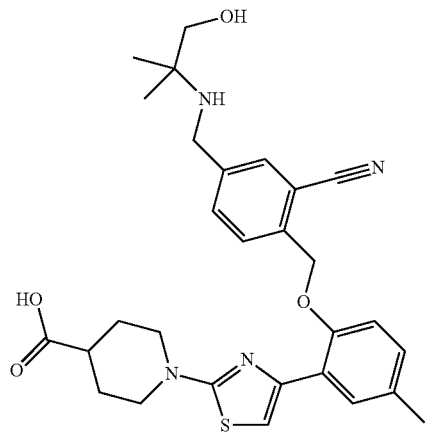 [SMILES: Cc1ccc(OCc2ccc(CNC(C)(C)CO)cc2C#N)c(-c2csc(N3CCC(C(=O)O)CC3)n2)c1] |

| Cpd No. | |
|---|---|
| 48 | 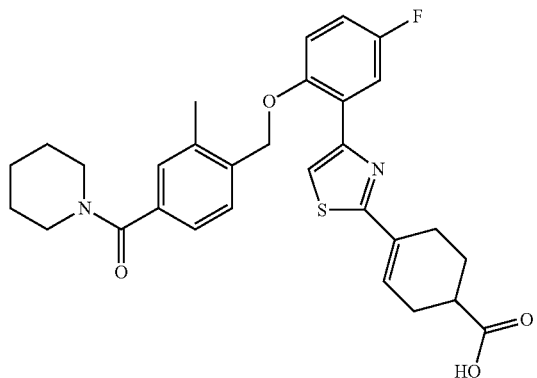 |
| 49 | 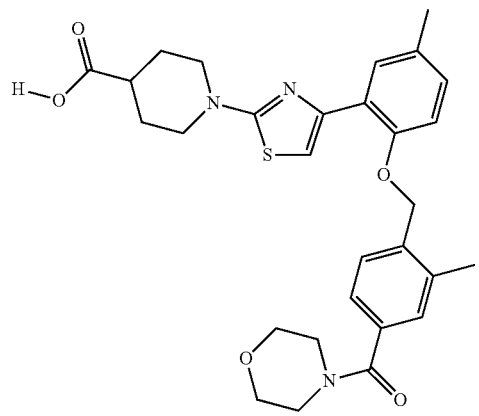 [SMILES: Cc1ccc(OCc2ccc(C(=O)N3CCOCC3)cc2C)c(-c2csc(N3CCC(C(=O)O)CC3)n2)c1] |
| 50 | 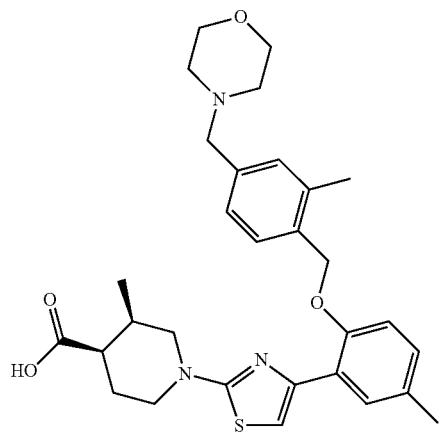 [SMILES: Cc1ccc(OCc2ccc(CN3CCOCC3)cc2C)c(-c2csc(N3CC[C@@H](C(=O)O)[C@@H](C)C3)n2)c1] |

| Cpd No. | |
|---|---|
| 51 | 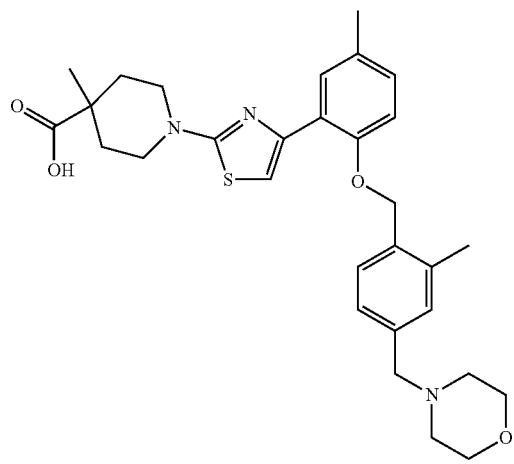 [SMILES: Cc1ccc(OCc2ccc(CN3CCOCC3)cc2C)c(-c2csc(N3CCC(C)(C(=O)O)CC3)n2)c1] |
| 52 | 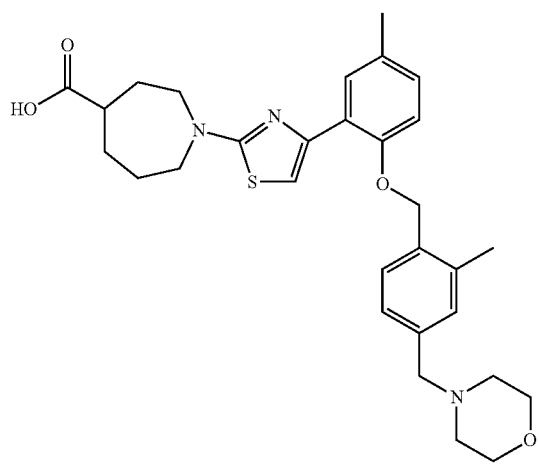 [SMILES: Cc1ccc(OCc2ccc(CN3CCOCC3)cc2C)c(-c2csc(N3CCCC(C(=O)O)CC3)n2)c1] |
| 53 | 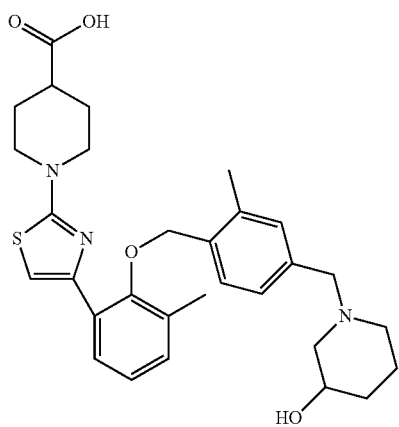 [SMILES: Cc1cc(CN2CCCC(O)C2)ccc1COc1c(C)cccc1-c1csc(N2CCC(C(=O)O)CC2)n1] |

| Cpd No. | |
|---|---|
| 54 | 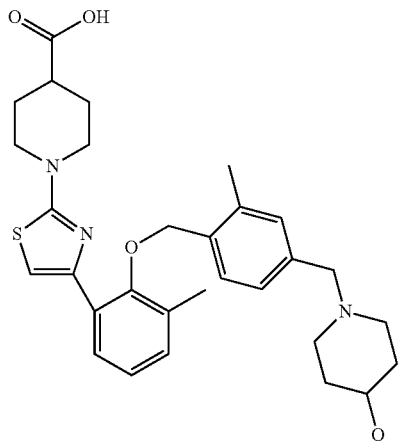 [SMILES: Cc1cc(CN2CCC(O)CC2)ccc1COc1c(C)cccc1-c1csc(N2CCC(C(=O)O)CC2)n1] |
| 55 | 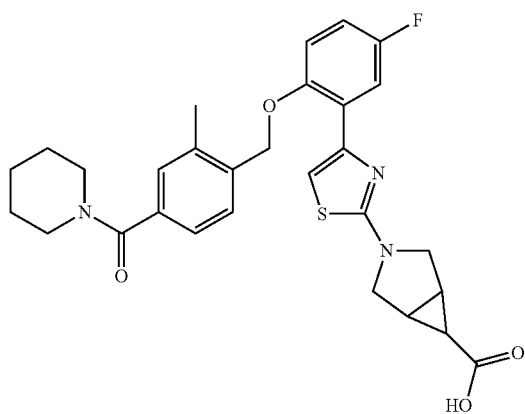 [SMILES: Cc1cc(C(=O)N2CCCCC2)ccc1COc1ccc(F)cc1-c1csc(N2CC3C(C2)C3C(=O)O)n1] |
| 56 | 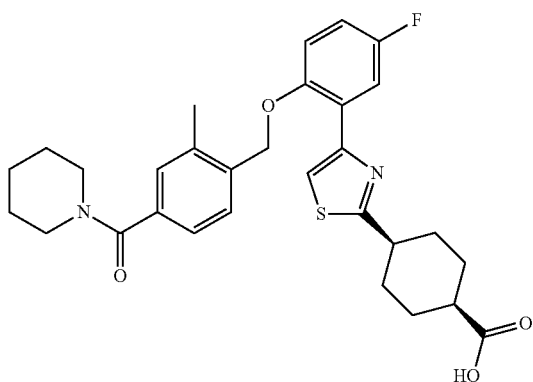 [SMILES: Cc1cc(C(=O)N2CCCCC2)ccc1COc1ccc(F)cc1-c1csc([C@H]2CC[C@@H](C(=O)O)CC2)n1] |

| Cpd No. | |
|---|---|
| 57 | 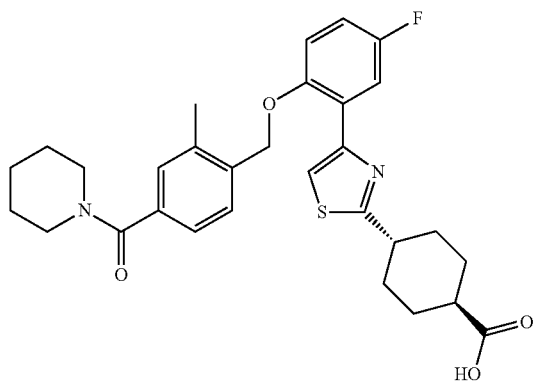 [SMILES: Cc1cc(C(=O)N2CCCCC2)ccc1COc1ccc(F)cc1-c1csc([C@H]2CC[C@H](C(=O)O)CC2)n1] |
| 58 | 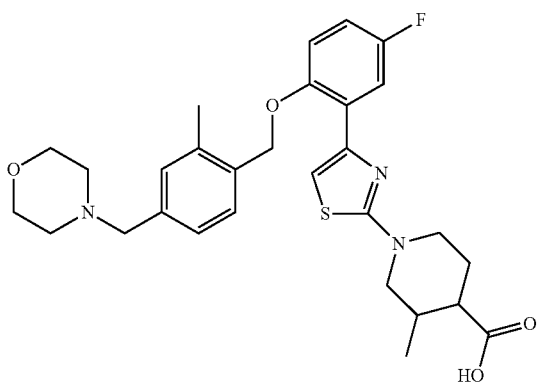 |
| 59 | 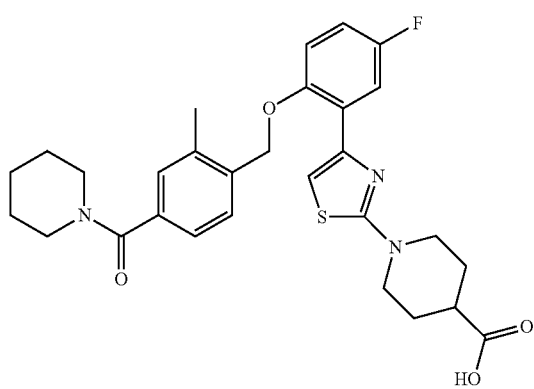 |

| Cpd No. | |
|---|---|
| 60 | 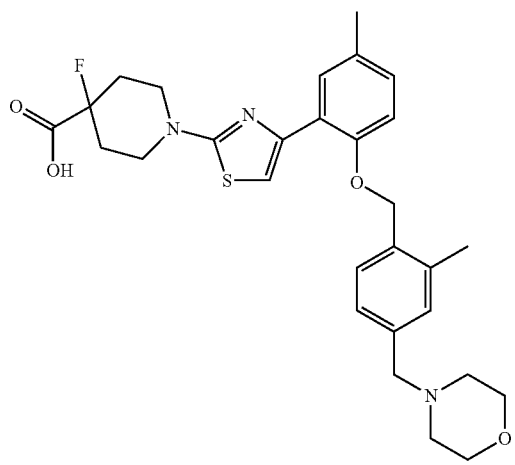 [SMILES: Cc1ccc(OCc2ccc(CN3CCOCC3)cc2C)c(-c2csc(N3CCC(F)(C(=O)O)CC3)n2)c1] |
| 61 | 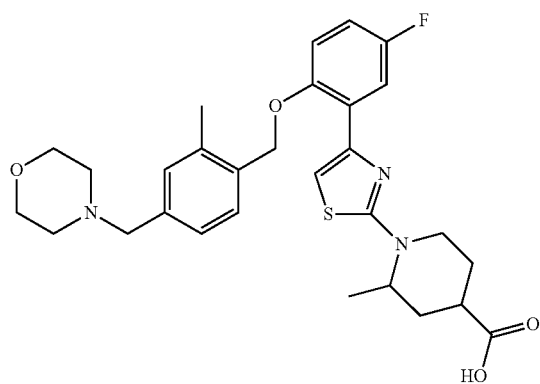 [SMILES: Cc1cc(CN2CCOCC2)ccc1COc1ccc(F)cc1-c1csc(N2CCC(C(=O)O)CC2C)n1] |
| 62 | 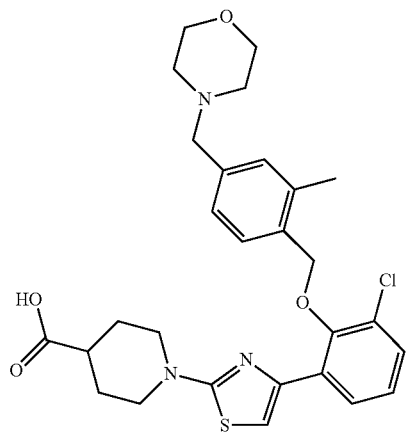 |

| Cpd No. | |
|---|---|
| 63 | 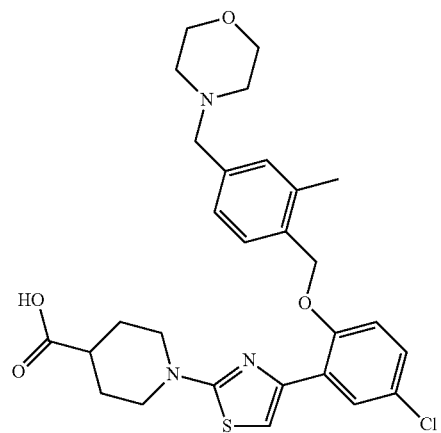 [SMILES: Cc1cc(CN2CCOCC2)ccc1COc1ccc(Cl)cc1-c1csc(N2CCC(C(=O)O)CC2)n1] |
| 64 | 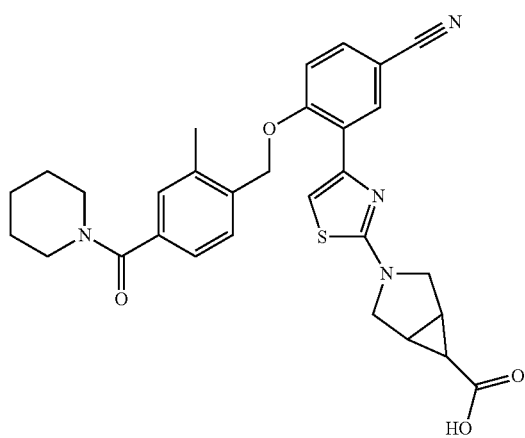 [SMILES: Cc1cc(C(=O)N2CCCCC2)ccc1COc1ccc(C#N)cc1-c1csc(N2CC3C(C2)C3C(=O)O)n1] |
| 65 | 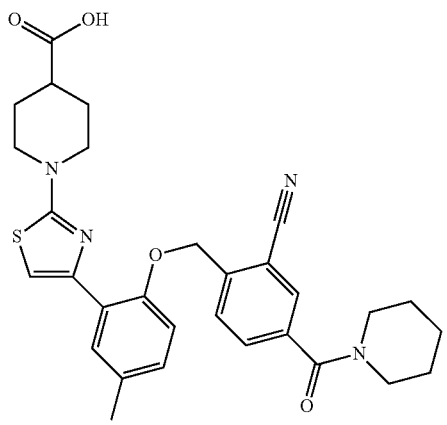 [SMILES: Cc1ccc(OCc2ccc(C(=O)N3CCCCC3)cc2C#N)c(-c2csc(N3CCC(C(=O)O)CC3)n2)c1] |

| Cpd No. | |
|---|---|
| 66 | 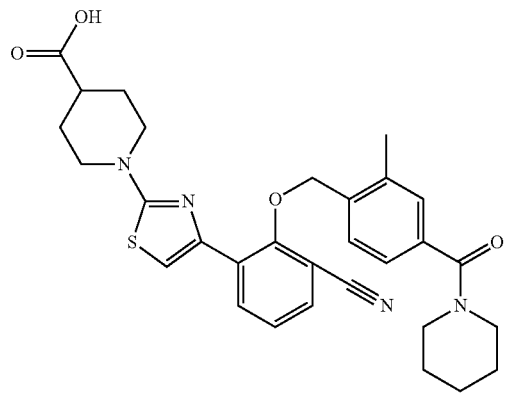 [SMILES: Cc1cc(C(=O)N2CCCCC2)ccc1COc1c(C#N)cccc1-c1csc(N2CCC(C(=O)O)CC2)n1] |
| 67 | 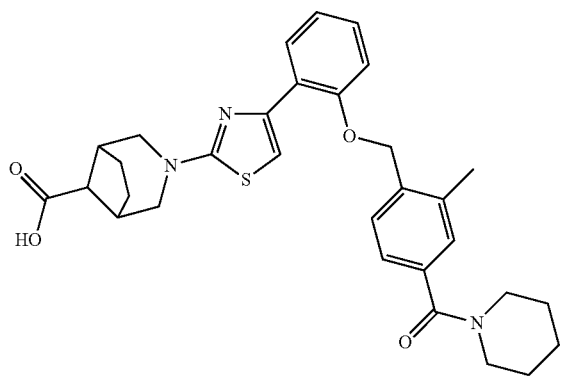 [SMILES: Cc1cc(C(=O)N2CCCCC2)ccc1COc1ccccc1-c1csc(N2CC3CCC(C2)C3C(=O)O)n1] |
| 68 | 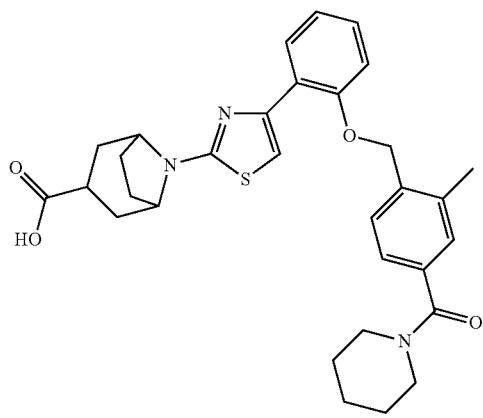 [SMILES: Cc1cc(C(=O)N2CCCCC2)ccc1COc1ccccc1-c1csc(N2C3CCC2CC(C(=O)O)C3)n1] |

-continued
| Cpd No. |
|---|
| 69 |
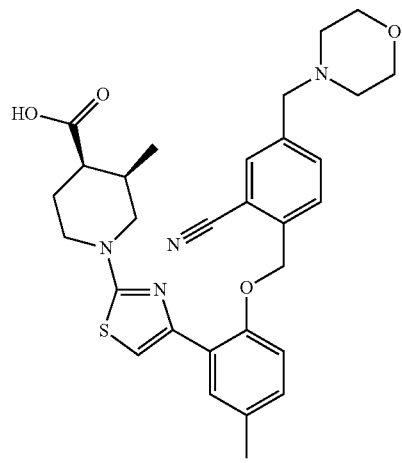 [SMILES: Cc1ccc(OCc2ccc(CN3CCOCC3)cc2C#N)c(-c2csc(N3CC[C@@H](C(=O)O)[C@@H](C)C3)n2)c1]
70
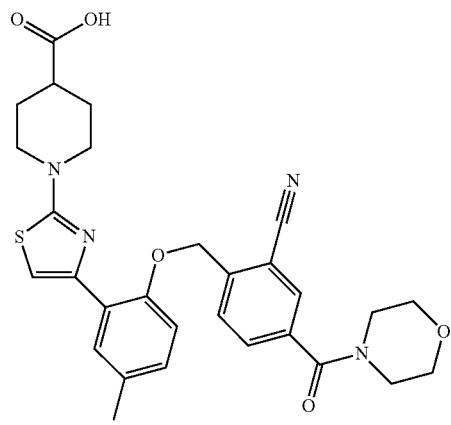 [SMILES: Cc1ccc(OCc2ccc(C(=O)N3CCOCC3)cc2C#N)c(-c2csc(N3CCC(C(=O)O)CC3)n2)c1]
71
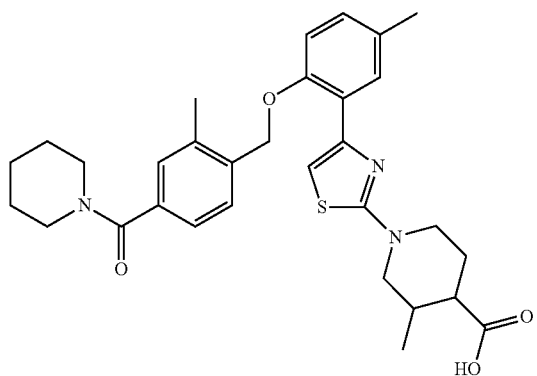 [SMILES: Cc1ccc(OCc2ccc(C(=O)N3CCCCC3)cc2C)c(-c2csc(N3CCC(C(=O)O)C(C)C3)n2)c1]

-continued
| Cpd No. |
| --- |
| 72 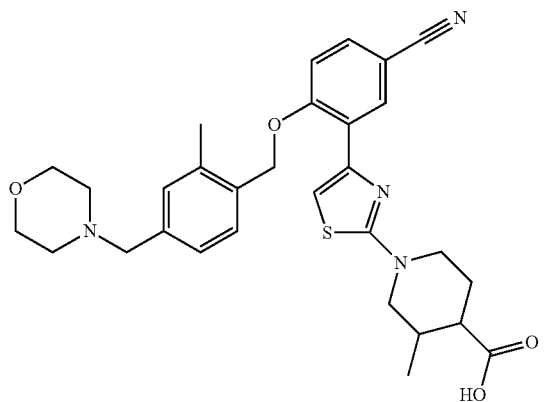 [SMILES: Cc1cc(CN2CCOCC2)ccc1COc1ccc(C#N)cc1-c1csc(N2CCC(C(=O)O)C(C)C2)n1] |
| 73 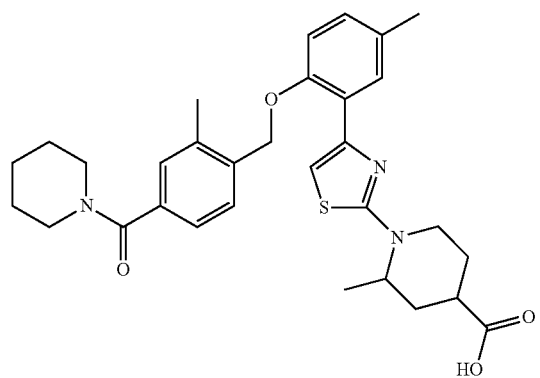 [SMILES: Cc1ccc(OCc2ccc(C(=O)N3CCCCC3)cc2C)c(-c2csc(N3CCC(C(=O)O)CC3C)n2)c1] |
| 74 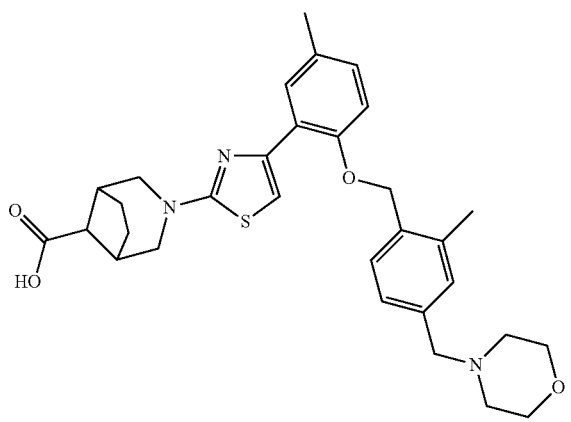 [SMILES: Cc1ccc(OCc2ccc(CN3CCOCC3)cc2C)c(-c2csc(N3CC4CCC(C3)C4C(=O)O)n2)c1] |
| 75 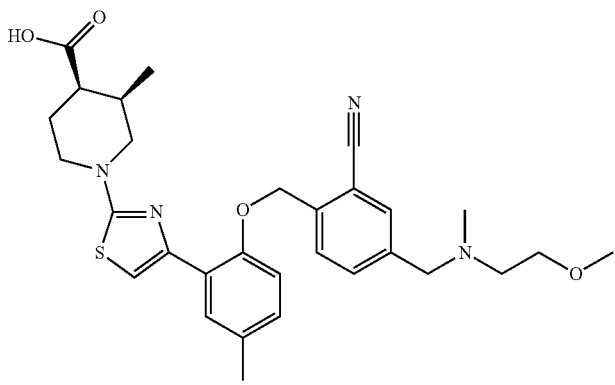 [SMILES: COCCN(C)Cc1ccc(COc2ccc(C)cc2-c2csc(N3CC[C@@H](C(=O)O)[C@@H](C)C3)n2)c(C#N)c1] |

| Cpd No. | |
|---|---|
| 76 | 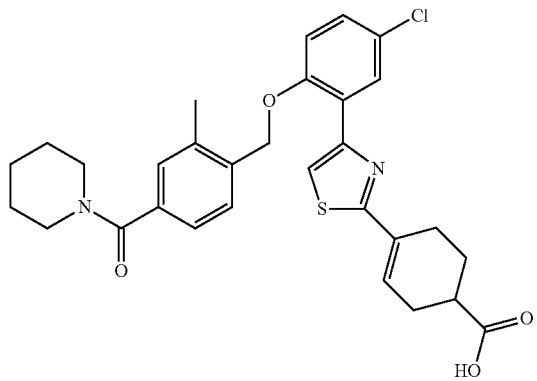 [SMILES: Cc1cc(C(=O)N2CCCCC2)ccc1COc1ccc(Cl)cc1-c1csc(C2=CCC(C(=O)O)CC2)n1] |
| 77 | 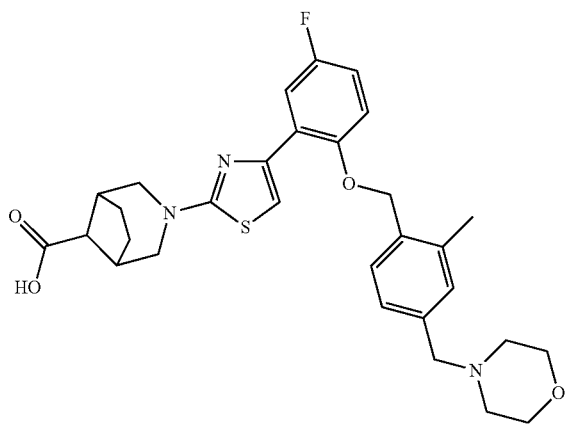 [SMILES: Cc1cc(CN2CCOCC2)ccc1COc1ccc(F)cc1-c1csc(N2CC3CCC(C2)C3C(=O)O)n1] |
| 78 | 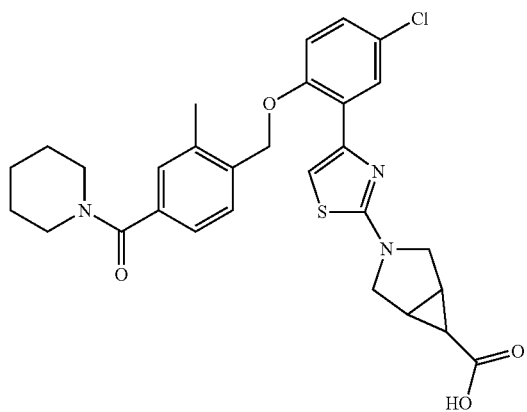 |

| Cpd No. | |
|---|---|
| 79 | 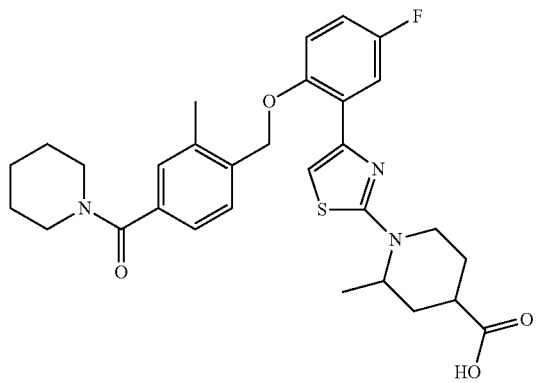 [SMILES: Cc1cc(C(=O)N2CCCCC2)ccc1COc1ccc(F)cc1-c1csc(N2CCC(C(=O)O)CC2C)n1] |
| 80 | 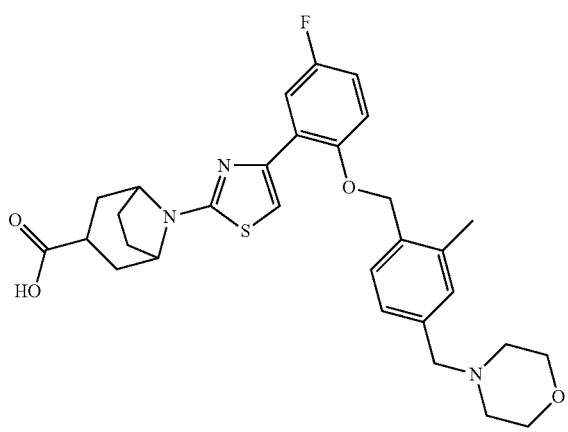 [SMILES: Cc1cc(CN2CCOCC2)ccc1COc1ccc(F)cc1-c1csc(N2C3CCC2CC(C(=O)O)C3)n1] |
| 81 | 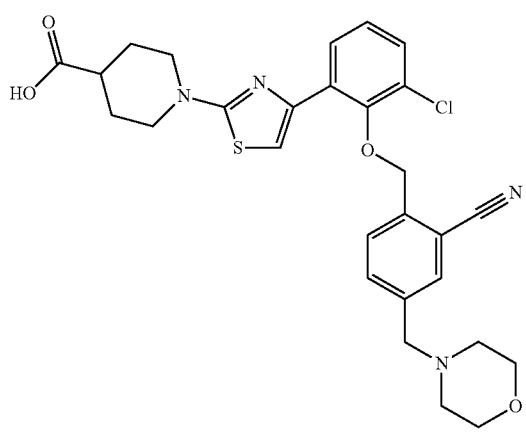 [SMILES: N#Cc1cc(CN2CCOCC2)ccc1COc1c(Cl)cccc1-c1csc(N2CCC(C(=O)O)CC2)n1] |
| 82 | 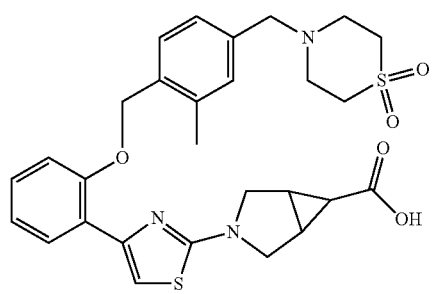 [SMILES: Cc1cc(CN2CCS(=O)(=O)CC2)ccc1COc1ccccc1-c1csc(N2CC3C(C2)C3C(=O)O)n1] |

| Cpd No. | |
|---|---|
| 83 | 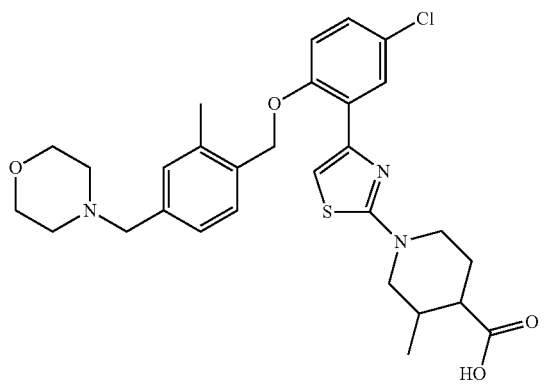 |
| 84 | 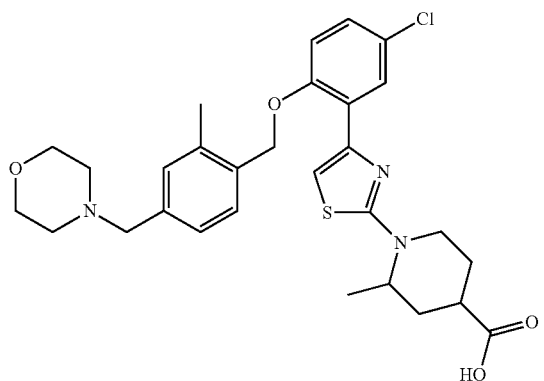 |
| 85 | 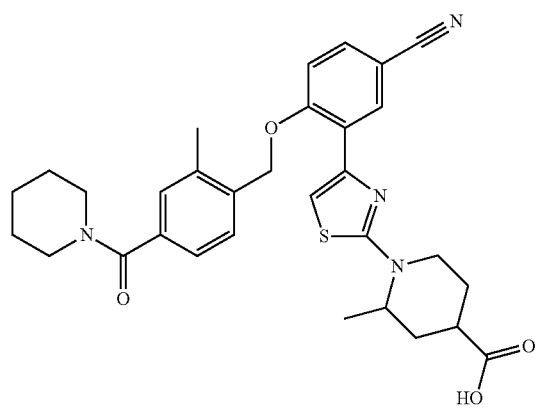 [SMILES: Cc1cc(C(=O)N2CCCCC2)ccc1COc1ccc(C#N)cc1-c1csc(N2CCC(C(=O)O)CC2C)n1] |

| Cpd No. | |
|---|---|
| 86 | 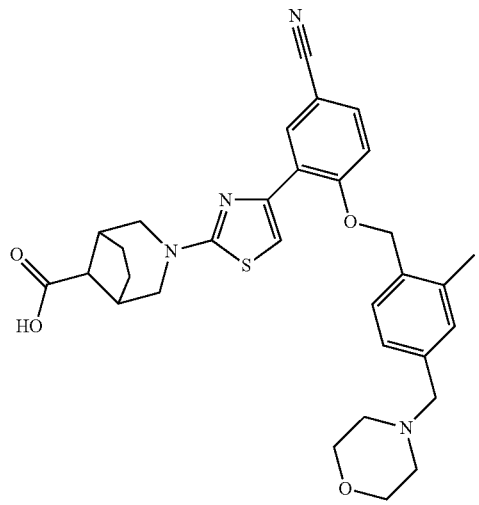 [SMILES: Cc1cc(CN2CCOCC2)ccc1COc1ccc(C#N)cc1-c1csc(N2CC3CCC(C2)C3C(=O)O)n1] |
| 87 | 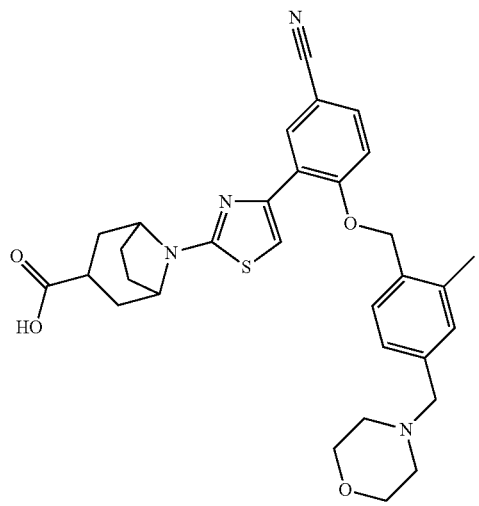 [SMILES: Cc1cc(CN2CCOCC2)ccc1COc1ccc(C#N)cc1-c1csc(N2C3CCC2CC(C(=O)O)C3)n1] |
| 88 | 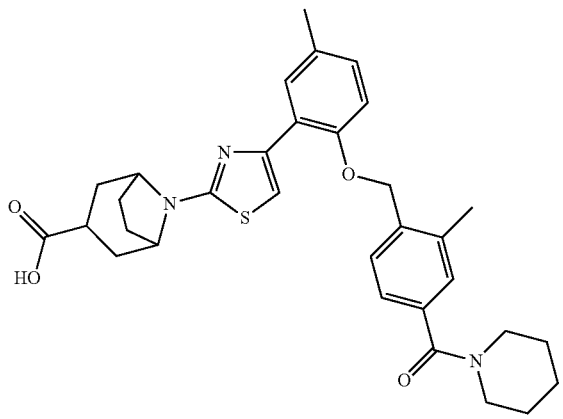 [SMILES: Cc1ccc(OCc2ccc(C(=O)N3CCCCC3)cc2C)c(-c2csc(N3C4CCC3CC(C(=O)O)C4)n2)c1] |

| Cpd No. | |
|---|---|
| 89 | 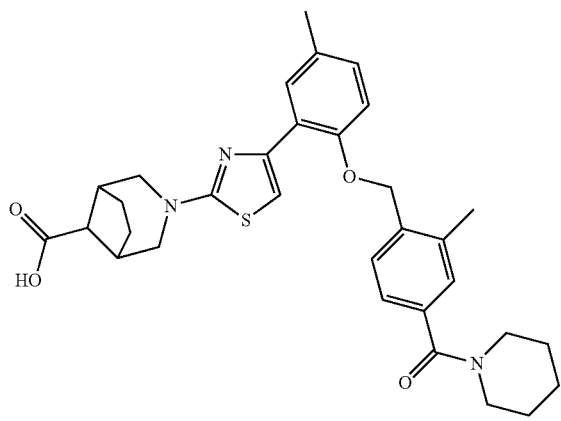 [SMILES: Cc1ccc(OCc2ccc(C(=O)N3CCCCC3)cc2C)c(-c2csc(N3CC4CCC(C3)C4C(=O)O)n2)c1] |
| 90 | 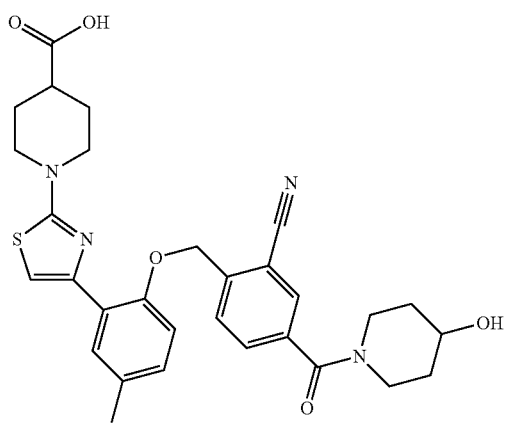 [SMILES: Cc1ccc(OCc2ccc(C(=O)N3CCC(O)CC3)cc2C#N)c(-c2csc(N3CCC(C(=O)O)CC3)n2)c1] |
| 91 | 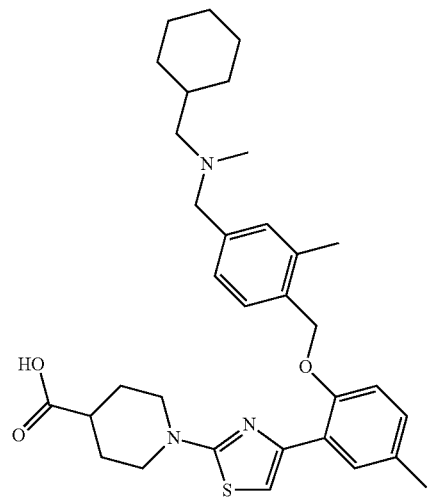 [SMILES: Cc1ccc(OCc2ccc(CN(C)CC3CCCCC3)cc2C)c(-c2csc(N3CCC(C(=O)O)CC3)n2)c1] |

| Cpd No. | |
|---|---|
| 92 | 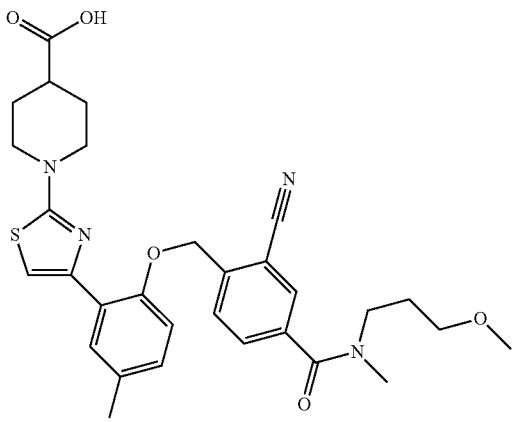 [SMILES: COCCCN(C)C(=O)c1ccc(COc2ccc(C)cc2-c2csc(N3CCC(C(=O)O)CC3)n2)c(C#N)c1] |
| 93 | 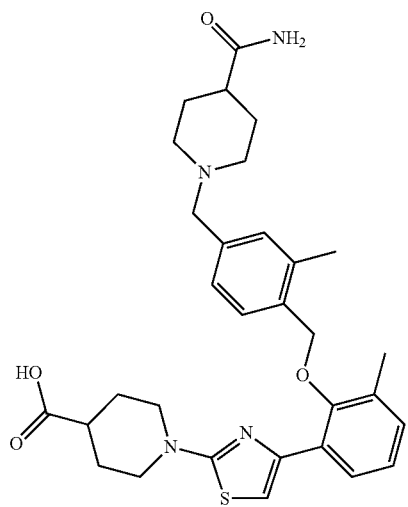 [SMILES: Cc1cc(CN2CCC(C(N)=O)CC2)ccc1COc1c(C)cccc1-c1csc(N2CCC(C(=O)O)CC2)n1] |
| 94 | 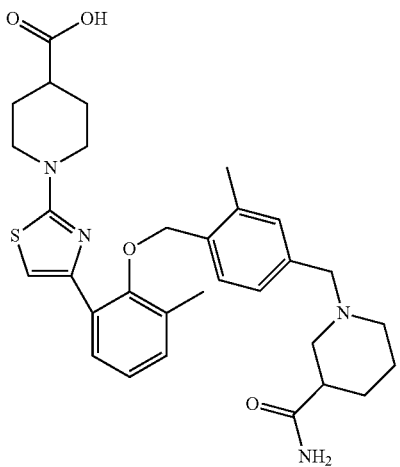 [SMILES: Cc1cc(CN2CCCC(C(N)=O)C2)ccc1COc1c(C)cccc1-c1csc(N2CCC(C(=O)O)CC2)n1] |

-continued
| Cpd No. |
|---|
| 95 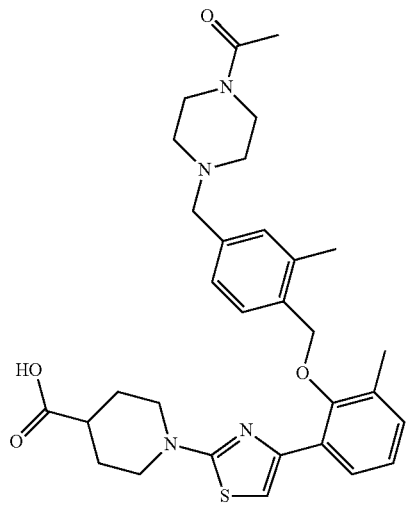 [SMILES: CC(=O)N1CCN(Cc2ccc(COc3c(C)cccc3-c3csc(N4CCC(C(=O)O)CC4)n3)c(C)c2)CC1] |
| 96 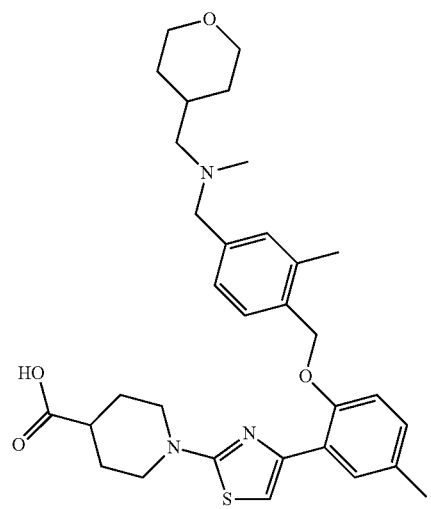 [SMILES: Cc1ccc(OCc2ccc(CN(C)CC3CCOCC3)cc2C)c(-c2csc(N3CCC(C(=O)O)CC3)n2)c1] |
| 97 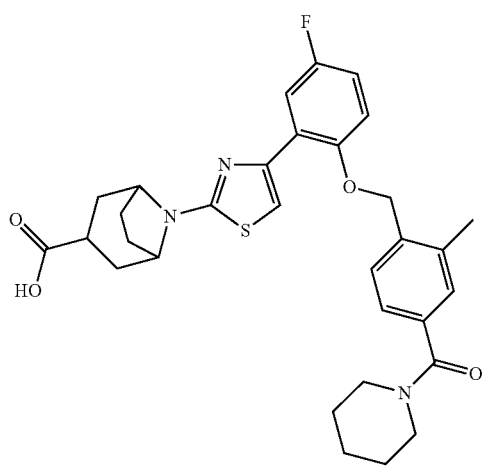 [SMILES: Cc1cc(C(=O)N2CCCCC2)ccc1COc1ccc(F)cc1-c1csc(N2C3CCC2CC(C(=O)O)C3)n1] |

| Cpd No. |
| --- |
| 98 |
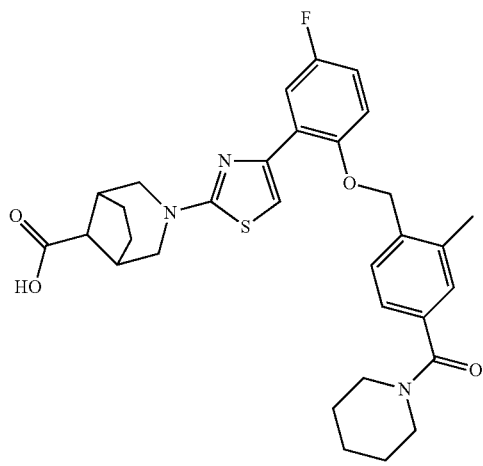 [SMILES: Cc1cc(C(=O)N2CCCCC2)ccc1COc1ccc(F)cc1-c1csc(N2CC3CCC(C2)C3C(=O)O)n1]
| 99 |
| --- |
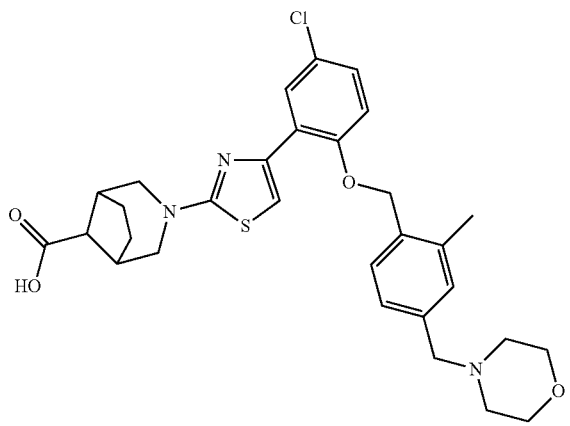 [SMILES: Cc1cc(CN2CCOCC2)ccc1COc1ccc(Cl)cc1-c1csc(N2CC3CCC(C2)C3C(=O)O)n1]
| 100 |
| --- |
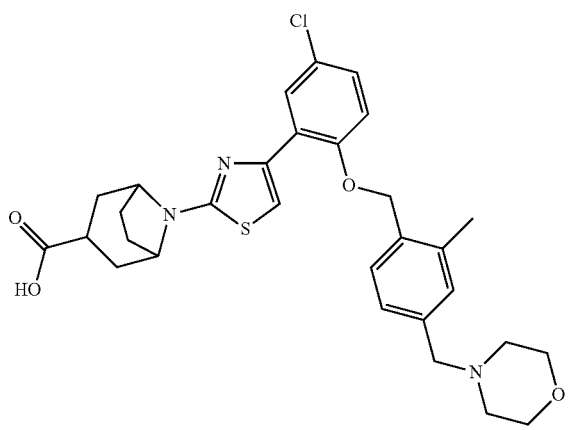 [SMILES: Cc1cc(CN2CCOCC2)ccc1COc1ccc(Cl)cc1-c1csc(N2C3CCC2CC(C(=O)O)C3)n1]

-continued
| Cpd No. |
|---|
| 101 |
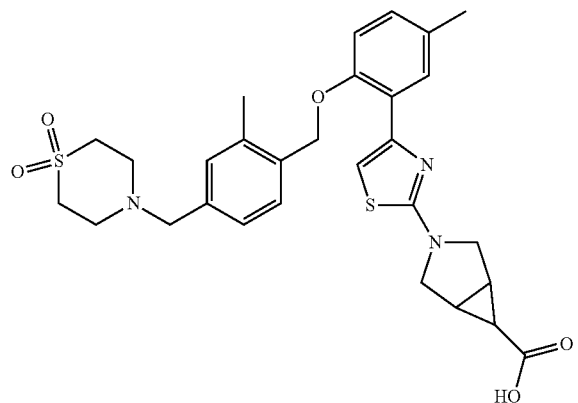 [SMILES: Cc1ccc(OCc2ccc(CN3CCS(=O)(=O)CC3)cc2C)c(-c2csc(N3CC4C(C3)C4C(=O)O)n2)c1]
102
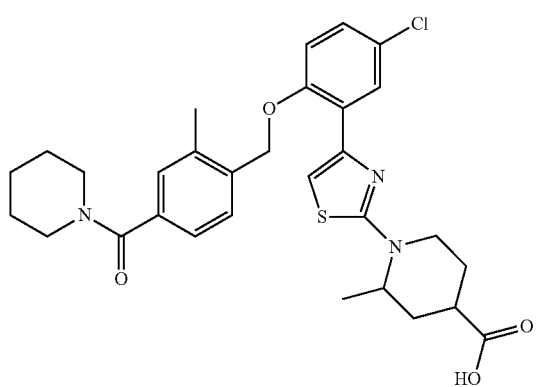 [SMILES: Cc1cc(C(=O)N2CCCCC2)ccc1COc1ccc(Cl)cc1-c1csc(N2CCC(C(=O)O)CC2C)n1]
103
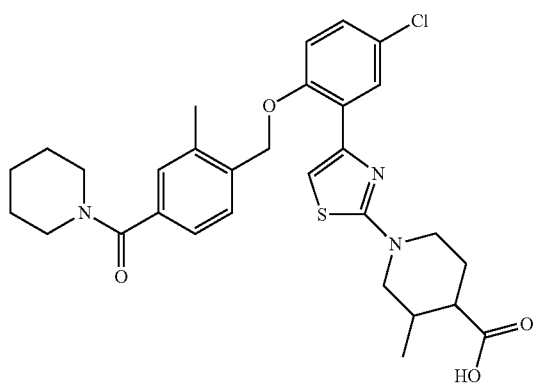 [SMILES: Cc1cc(C(=O)N2CCCCC2)ccc1COc1ccc(Cl)cc1-c1csc(N2CCC(C(=O)O)C(C)C2)n1]

-continued
| Cpd No. | |
|---|---|
| 104 | 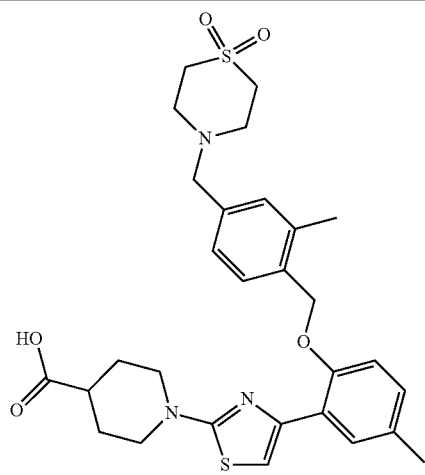 [SMILES: Cc1ccc(OCc2ccc(CN3CCS(=O)(=O)CC3)cc2C)c(-c2csc(N3CCC(C(=O)O)CC3)n2)c1] |
| 105 | 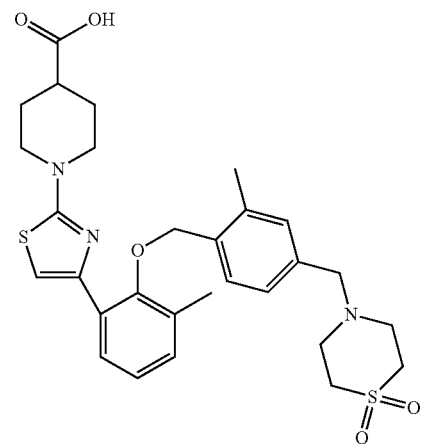 [SMILES: Cc1cc(CN2CCS(=O)(=O)CC2)ccc1COc1c(C)cccc1-c1csc(N2CCC(C(=O)O)CC2)n1] |
| 106 | 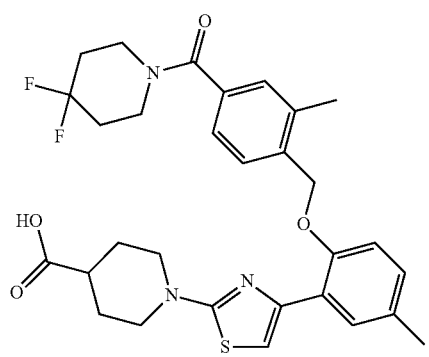 [SMILES: Cc1ccc(OCc2ccc(C(=O)N3CCC(F)(F)CC3)cc2C)c(-c2csc(N3CCC(C(=O)O)CC3)n2)c1] |
| 107 | 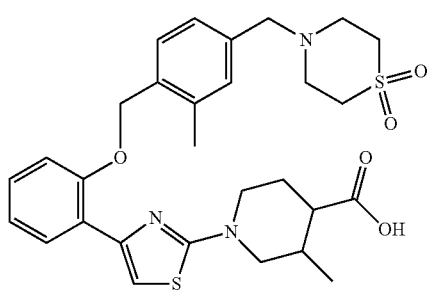 [SMILES: Cc1cc(CN2CCS(=O)(=O)CC2)ccc1COc1ccccc1-c1csc(N2CCC(C(=O)O)C(C)C2)n1] |

-continued
| Cpd No. | |
|---|---|
| 108 | 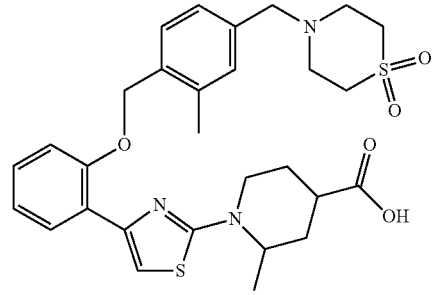 [SMILES: Cc1cc(CN2CCS(=O)(=O)CC2)ccc1COc1ccccc1-c1csc(N2CCC(C(=O)O)CC2C)n1] |
| 109 | 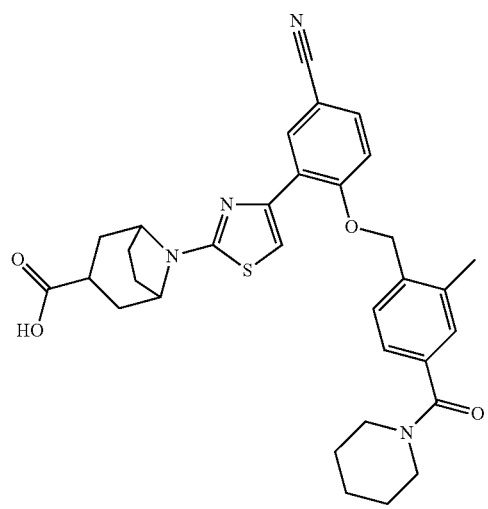 [SMILES: Cc1cc(C(=O)N2CCCCC2)ccc1COc1ccc(C#N)cc1-c1csc(N2C3CCC2CC(C(=O)O)C3)n1] |
| 110 | 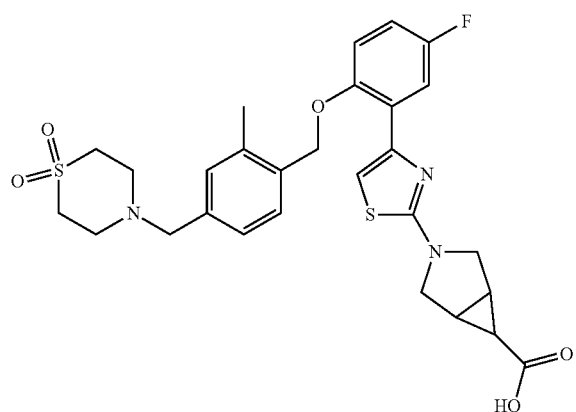 [SMILES: Cc1cc(CN2CCS(=O)(=O)CC2)ccc1COc1ccc(F)cc1-c1csc(N2CC3C(C2)C3C(=O)O)n1] |
| 111 | 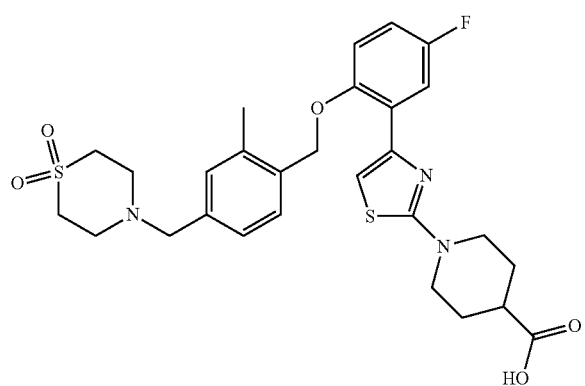 [SMILES: Cc1cc(CN2CCS(=O)(=O)CC2)ccc1COc1ccc(F)cc1-c1csc(N2CCC(C(=O)O)CC2)n1] |

| Cpd No. | |
|---|---|
| 112 | 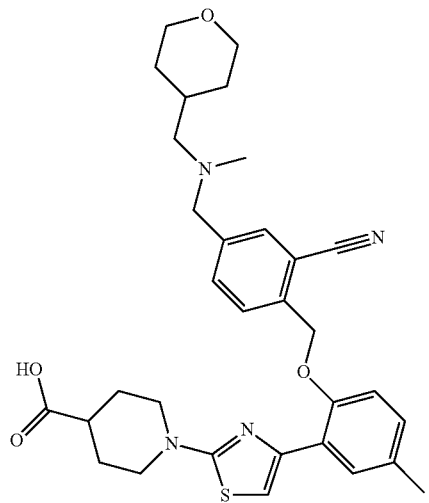 [SMILES: Cc1ccc(OCc2ccc(CN(C)CC3CCOCC3)cc2C#N)c(-c2csc(N3CCC(C(=O)O)CC3)n2)c1] |
| 113 | 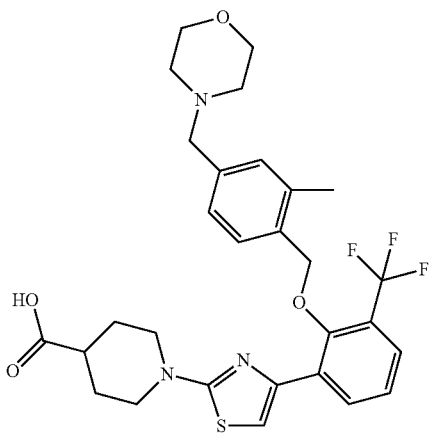 [SMILES: Cc1cc(CN2CCOCC2)ccc1COc1c(-c2csc(N3CCC(C(=O)O)CC3)n2)cccc1C(F)(F)F] |
| 114 | 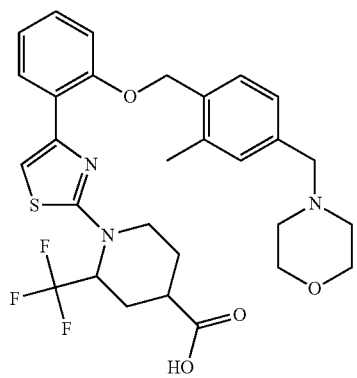 [SMILES: Cc1cc(CN2CCOCC2)ccc1COc1ccccc1-c1csc(N2CCC(C(=O)O)CC2C(F)(F)F)n1] |

-continued
| Cpd No. | |
|---|---|
| 115 | 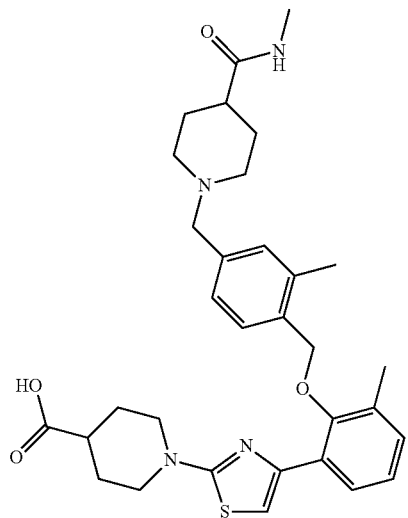 [SMILES: CNC(=O)C1CCN(Cc2ccc(COc3c(C)cccc3-c3csc(N4CCC(C(=O)O)CC4)n3)c(C)c2)CC1] |
| 116 | 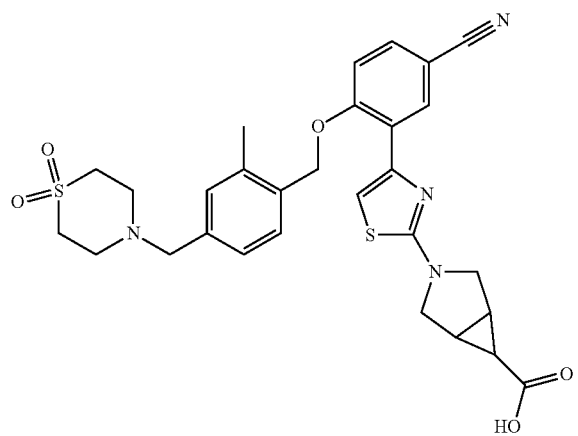 [SMILES: Cc1cc(CN2CCS(=O)(=O)CC2)ccc1COc1ccc(C#N)cc1-c1csc(N2CC3C(C2)C3C(=O)O)n1] |
| 117 | 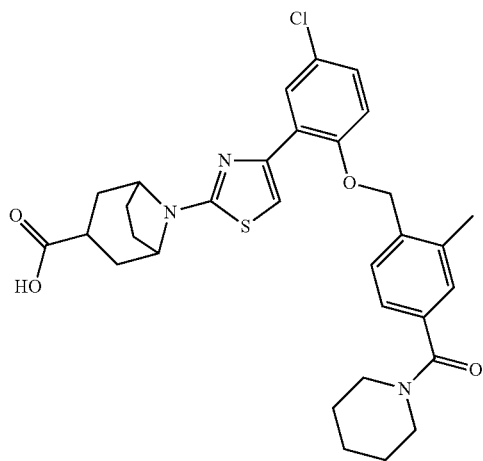 [SMILES: Cc1cc(C(=O)N2CCCCC2)ccc1COc1ccc(Cl)cc1-c1csc(N2C3CCC2CC(C(=O)O)C3)n1] |

| Cpd No. |
| --- |
| 118 |
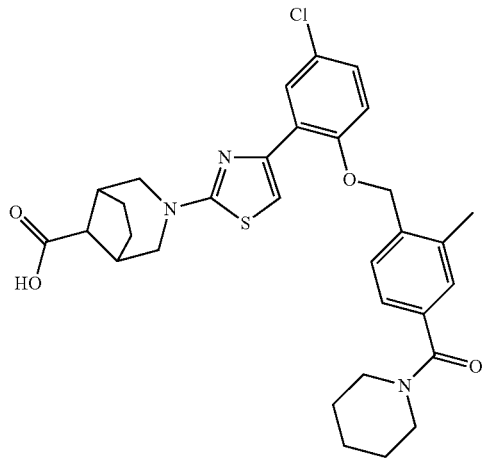 [SMILES: Cc1cc(C(=O)N2CCCCC2)ccc1COc1ccc(Cl)cc1-c1csc(N2CC3CCC(C2)C3C(=O)O)n1]
119
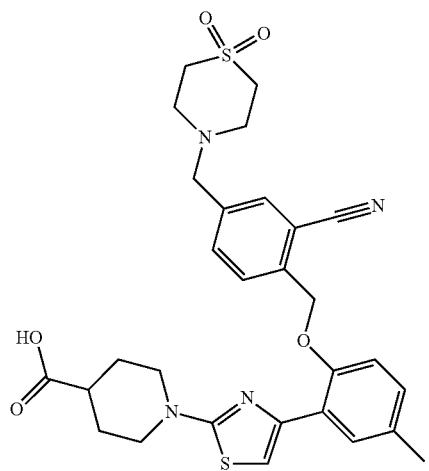 [SMILES: Cc1ccc(OCc2ccc(CN3CCS(=O)(=O)CC3)cc2C#N)c(-c2csc(N3CCC(C(=O)O)CC3)n2)c1]
120
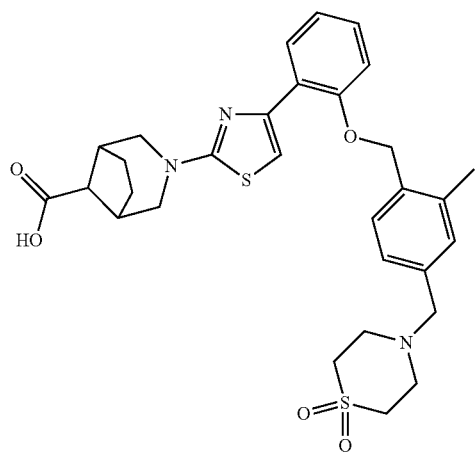 [SMILES: Cc1cc(CN2CCS(=O)(=O)CC2)ccc1COc1ccccc1-c1csc(N2CC3CCC(C2)C3C(=O)O)n1]

-continued
| Cpd No. | |
|---|---|
| 121 | 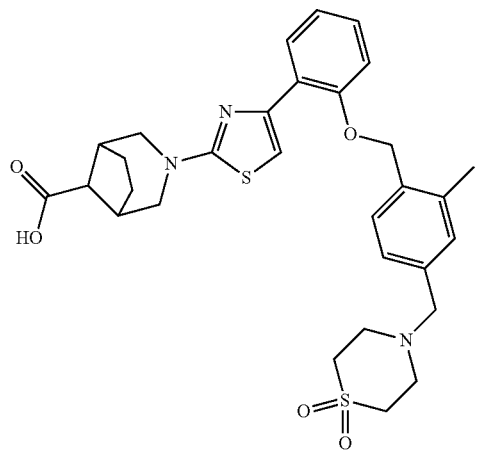 [SMILES: Cc1cc(CN2CCS(=O)(=O)CC2)ccc1COc1ccccc1-c1csc(N2CC3CCC(C2)C3C(=O)O)n1] |
| 122 | 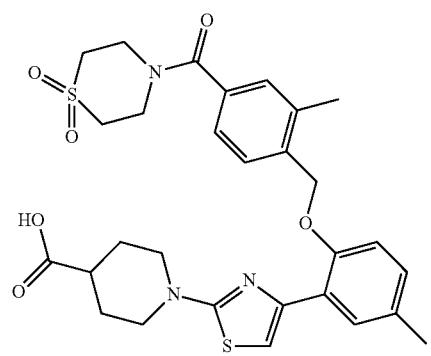 [SMILES: Cc1ccc(OCc2ccc(C(=O)N3CCS(=O)(=O)CC3)cc2C)c(-c2csc(N3CCC(C(=O)O)CC3)n2)c1] |
| 123 | 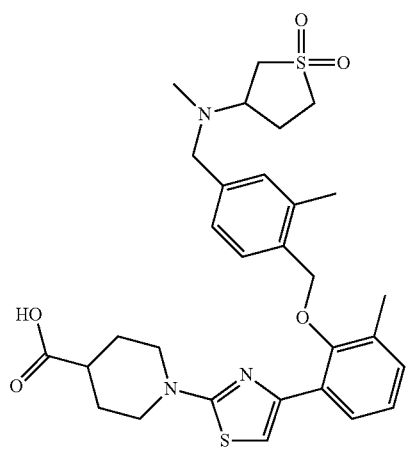 [SMILES: Cc1cc(CN(C)C2CCS(=O)(=O)C2)ccc1COc1c(C)cccc1-c1csc(N2CCC(C(=O)O)CC2)n1] |

-continued
| Cpd No. |
|---|
| 124 |
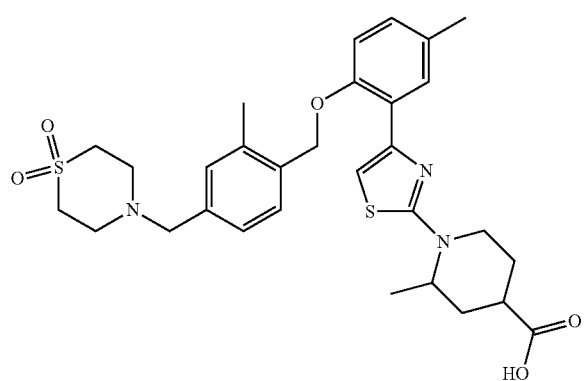 [SMILES: Cc1ccc(OCc2ccc(CN3CCS(=O)(=O)CC3)cc2C)c(-c2csc(N3CCC(C(=O)O)CC3C)n2)c1]
125
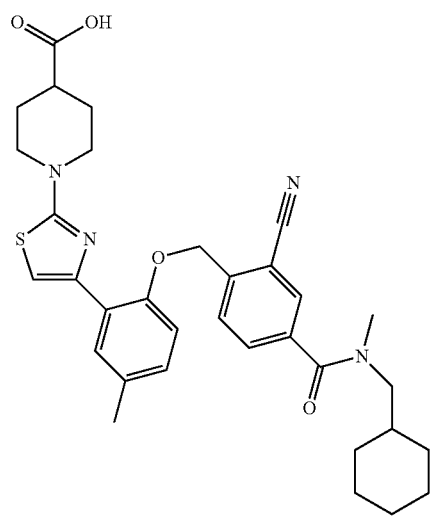 [SMILES: Cc1ccc(OCc2ccc(C(=O)N(C)CC3CCCCC3)cc2C#N)c(-c2csc(N3CCC(C(=O)O)CC3)n2)c1]
126
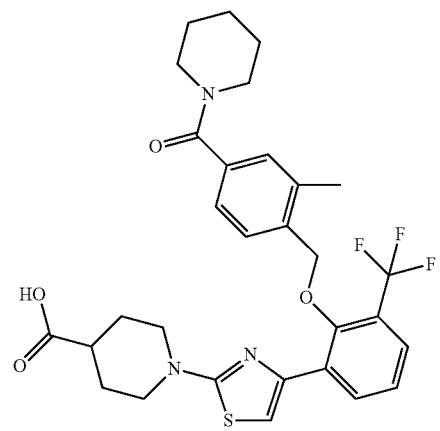 [SMILES: Cc1cc(C(=O)N2CCCCC2)ccc1COc1c(-c2csc(N3CCC(C(=O)O)CC3)n2)cccc1C(F)(F)F]

-continued
| Cpd No. | |
|---|---|
| 127 | 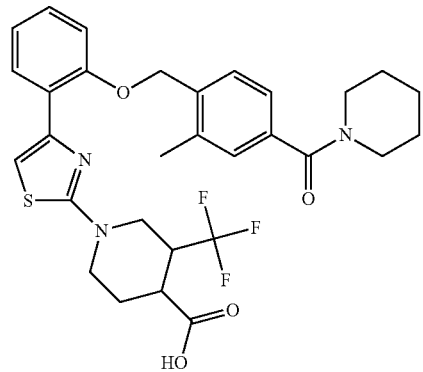 [SMILES: Cc1cc(C(=O)N2CCCCC2)ccc1COc1ccccc1-c1csc(N2CCC(C(=O)O)C(C(F)(F)F)C2)n1] |
| 128 | 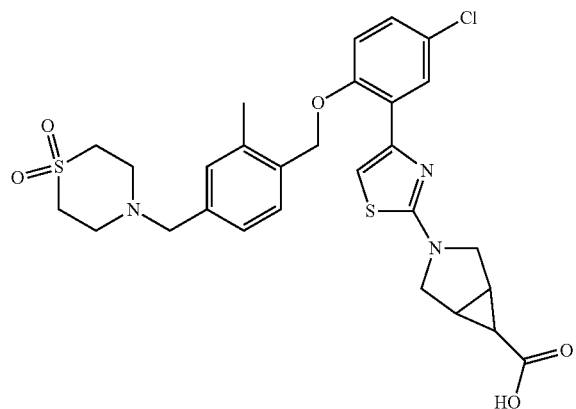 |
| 129 | 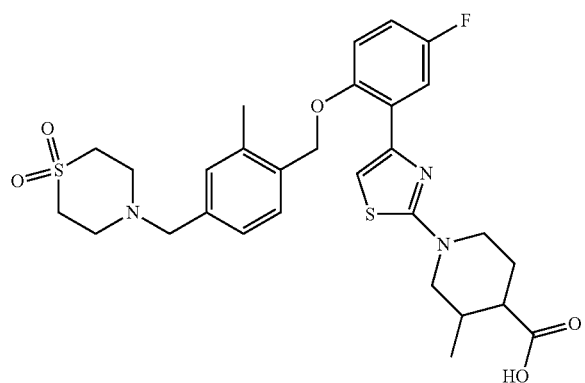 [SMILES: Cc1cc(CN2CCS(=O)(=O)CC2)ccc1COc1ccc(F)cc1-c1csc(N2CCC(C(=O)O)C(C)C2)n1] |
| 130 | 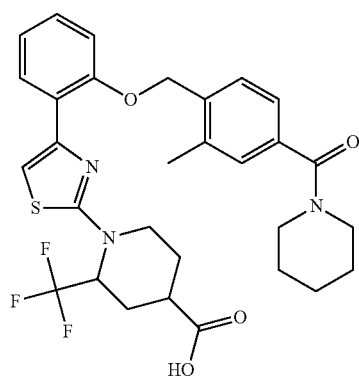 [SMILES: Cc1cc(C(=O)N2CCCCC2)ccc1COc1ccccc1-c1csc(N2CCC(C(=O)O)CC2C(F)(F)F)n1] |

-continued
| Cpd No. |
|---|
| 131 |
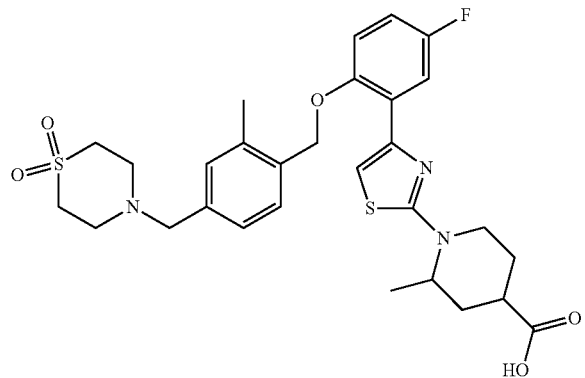 [SMILES: Cc1cc(CN2CCS(=O)(=O)CC2)ccc1COc1ccc(F)cc1-c1csc(N2CCC(C(=O)O)CC2C)n1]
| 132 |
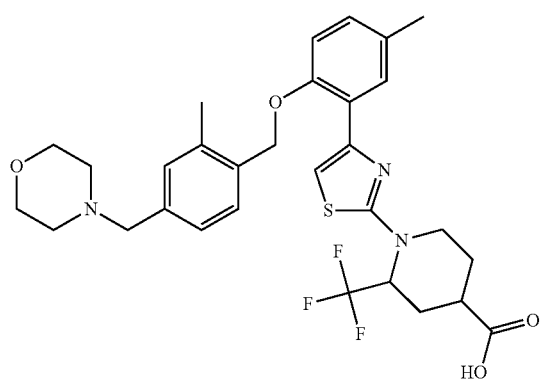 [SMILES: Cc1ccc(OCc2ccc(CN3CCOCC3)cc2C)c(-c2csc(N3CCC(C(=O)O)CC3C(F)(F)F)n2)c1]
| 133 |
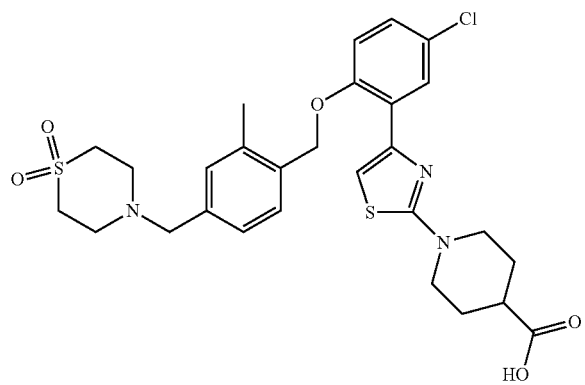

| Cpd No. | |
|---|---|
| 134 | 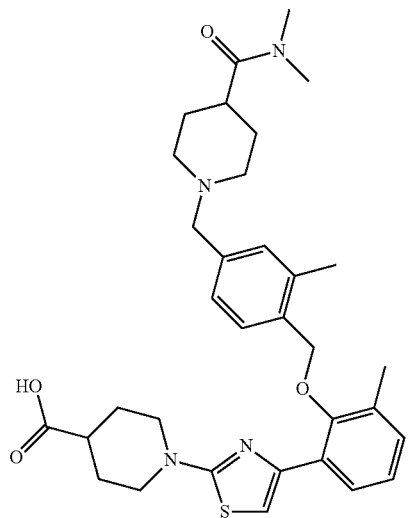 [SMILES: Cc1cc(CN2CCC(C(=O)N(C)C)CC2)ccc1COc1c(C)cccc1-c1csc(N2CCC(C(=O)O)CC2)n1] |
| 135 | 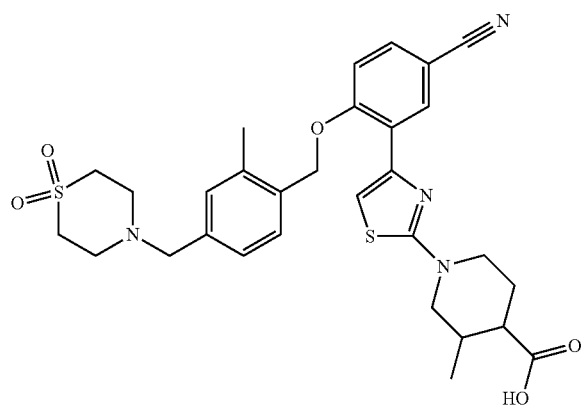 [SMILES: Cc1cc(CN2CCS(=O)(=O)CC2)ccc1COc1ccc(C#N)cc1-c1csc(N2CCC(C(=O)O)C(C)C2)n1] |
| 136 | 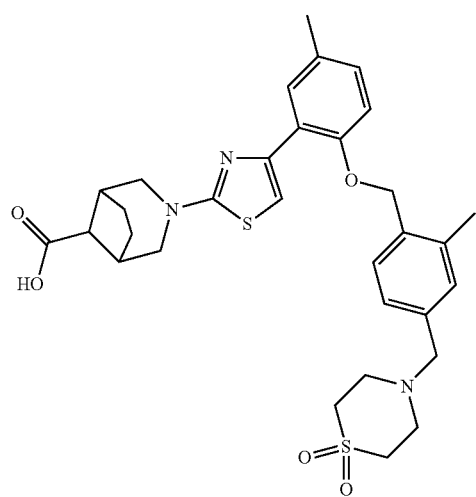 [SMILES: Cc1ccc(OCc2ccc(CN3CCS(=O)(=O)CC3)cc2C)c(-c2csc(N3CC4CCC(C3)C4C(=O)O)n2)c1] |

-continued
| Cpd No. |
|---|
137
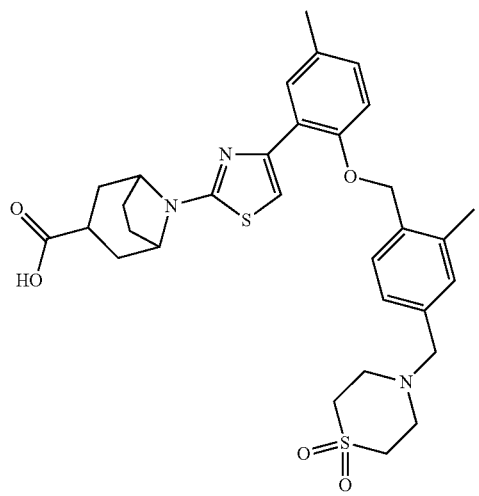 [SMILES: Cc1ccc(OCc2ccc(CN3CCS(=O)(=O)CC3)cc2C)c(-c2csc(N3C4CCC3CC(C(=O)O)C4)n2)c1]
138
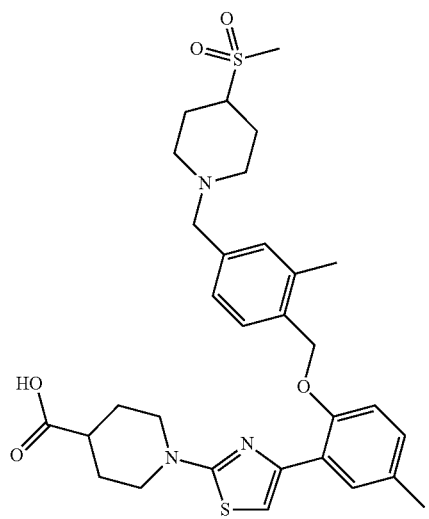 [SMILES: Cc1ccc(OCc2ccc(CN3CCC(S(C)(=O)=O)CC3)cc2C)c(-c2csc(N3CCC(C(=O)O)CC3)n2)c1]
139
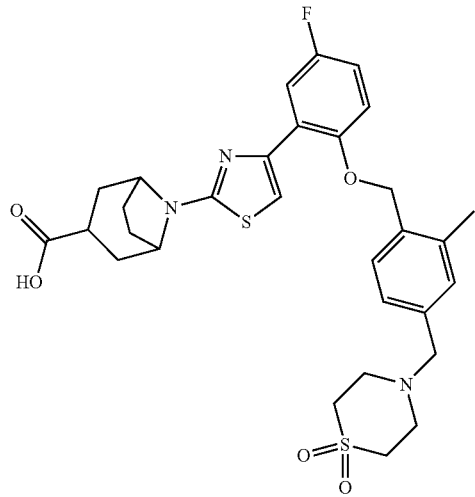 [SMILES: Cc1cc(CN2CCS(=O)(=O)CC2)ccc1COc1ccc(F)cc1-c1csc(N2C3CCC2CC(C(=O)O)C3)n1]

| Cpd No. | |
|---|---|
| 140 | 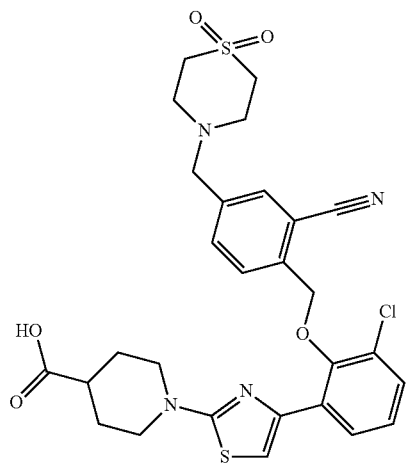 [SMILES: N#Cc1cc(CN2CCS(=O)(=O)CC2)ccc1COc1c(Cl)cccc1-c1csc(N2CCC(C(=O)O)CC2)n1] |
| 141 | 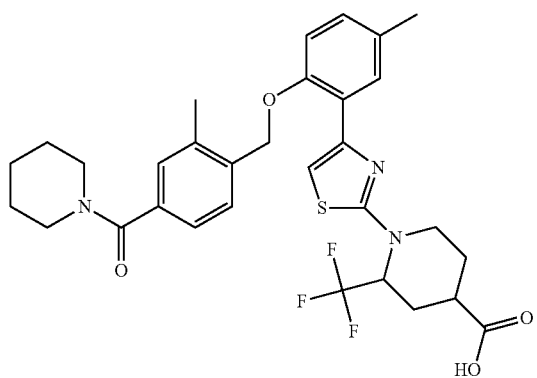 [SMILES: Cc1ccc(OCc2ccc(C(=O)N3CCCCC3)cc2C)c(-c2csc(N3CCC(C(=O)O)CC3C(F)(F)F)n2)c1] |
| 142 | 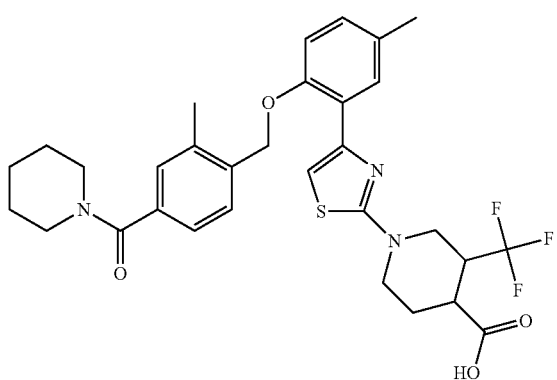 [SMILES: Cc1ccc(OCc2ccc(C(=O)N3CCCCC3)cc2C)c(-c2csc(N3CCC(C(=O)O)C(C(F)(F)F)C3)n2)c1] |

-continued
| Cpd No. |
| --- |
143
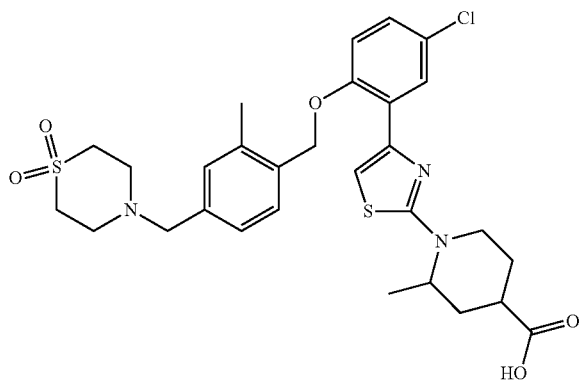
144
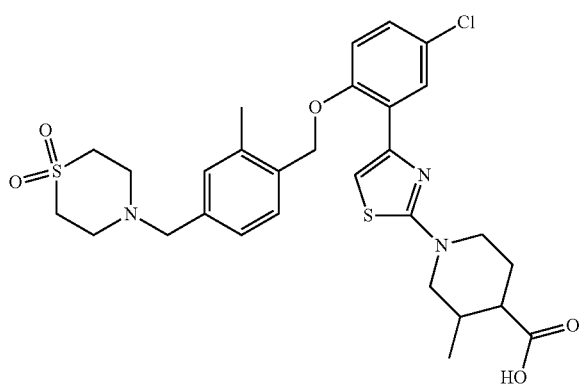
145
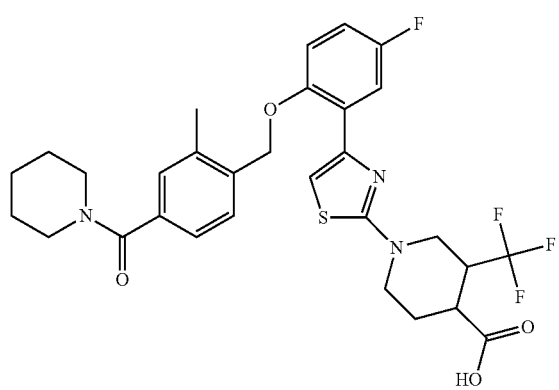 [SMILES: Cc1cc(C(=O)N2CCCCC2)ccc1COc1ccc(F)cc1-c1csc(N2CCC(C(=O)O)C(C(F)(F)F)C2)n1]

-continued
| Cpd No. | |
|---|---|
| 146 | 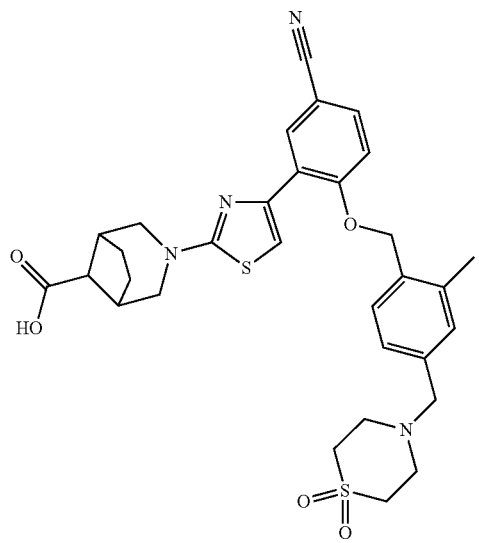 [SMILES: Cc1cc(CN2CCS(=O)(=O)CC2)ccc1COc1ccc(C#N)cc1-c1csc(N2CC3CCC(C2)C3C(=O)O)n1] |
| 147 | 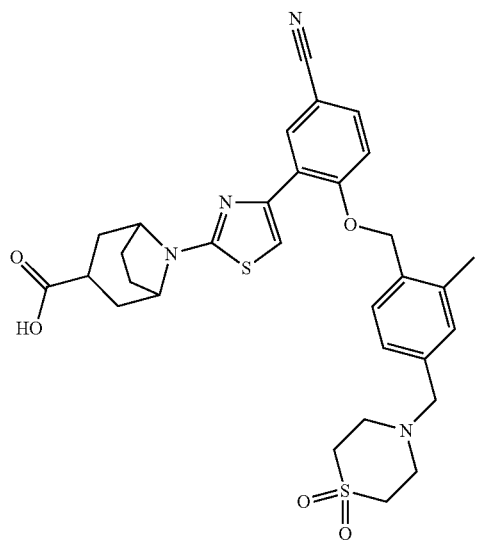 [SMILES: Cc1cc(CN2CCS(=O)(=O)CC2)ccc1COc1ccc(C#N)cc1-c1csc(N2C3CCC2CC(C(=O)O)C3)n1] |
| 148 | 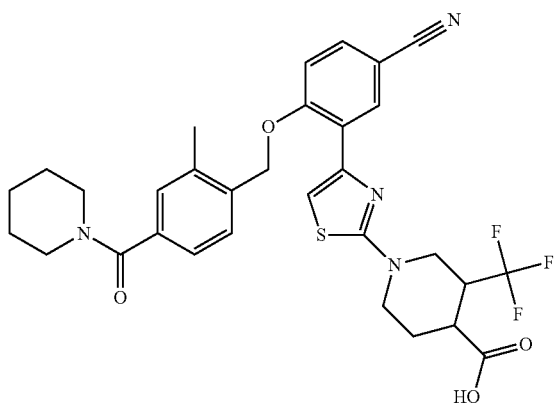 [SMILES: Cc1cc(C(=O)N2CCCCC2)ccc1COc1ccc(C#N)cc1-c1csc(N2CCC(C(=O)O)C(C(F)(F)F)C2)n1] |

-continued
| Cpd No. | |
|---|---|
| 149 | 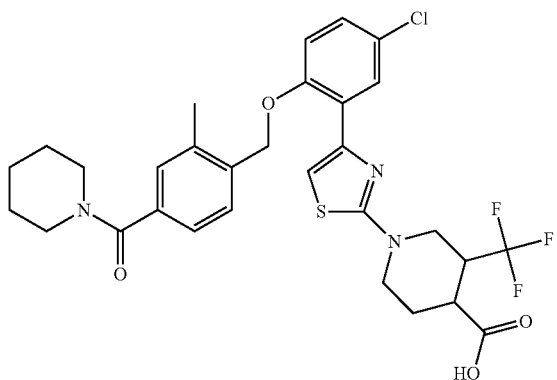 |
| 150 | 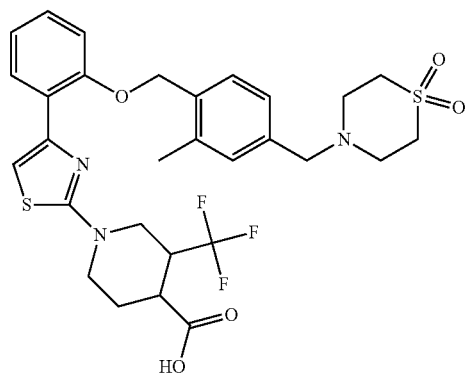 [SMILES: Cc1cc(CN2CCS(=O)(=O)CC2)ccc1COc1ccccc1-c1csc(N2CCC(C(=O)O)C(C(F)(F)F)C2)n1] |
| 151 | 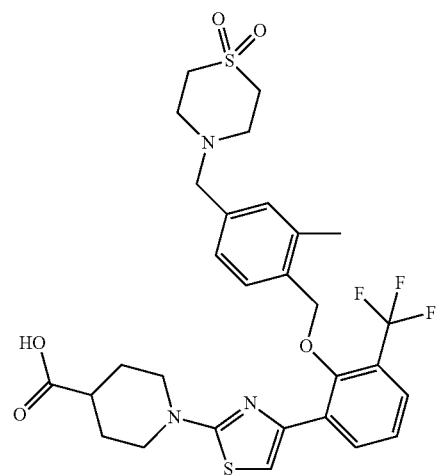 [SMILES: Cc1cc(CN2CCS(=O)(=O)CC2)ccc1COc1c(-c2csc(N3CCC(C(=O)O)CC3)n2)cccc1C(F)(F)F] |

-continued
| Cpd No. | |
|---|---|
| 152 | 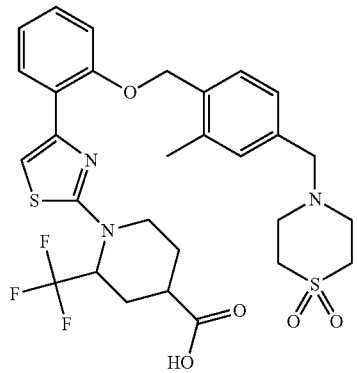 [SMILES: Cc1cc(CN2CCS(=O)(=O)CC2)ccc1COc1ccccc1-c1csc(N2CCC(C(=O)O)CC2C(F)(F)F)n1] |
| 153 | 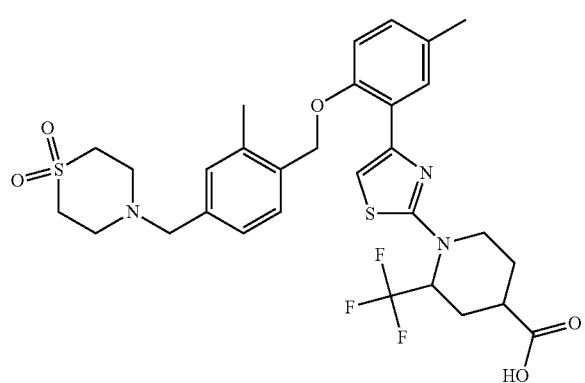 [SMILES: Cc1ccc(OCc2ccc(CN3CCS(=O)(=O)CC3)cc2C)c(-c2csc(N3CCC(C(=O)O)CC3C(F)(F)F)n2)c1] |
| 154 | 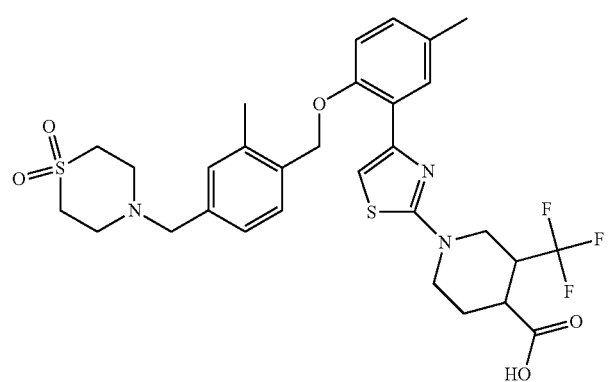 [SMILES: Cc1ccc(OCc2ccc(CN3CCS(=O)(=O)CC3)cc2C)c(-c2csc(N3CCC(C(=O)O)C(C(F)(F)F)C3)n2)c1] |
| 155 | 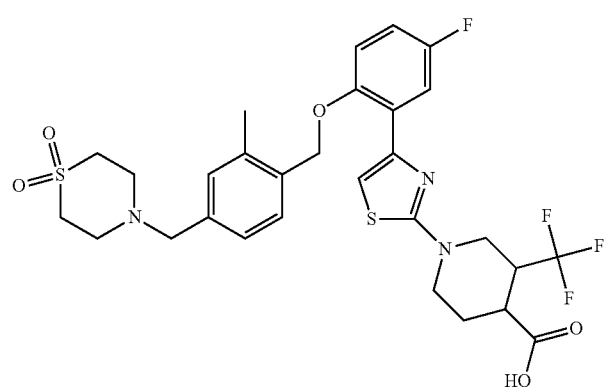 [SMILES: Cc1cc(CN2CCS(=O)(=O)CC2)ccc1COc1ccc(F)cc1-c1csc(N2CCC(C(=O)O)C(C(F)(F)F)C2)n1] |

| Cpd No. | |
|---|---|
| 156 | 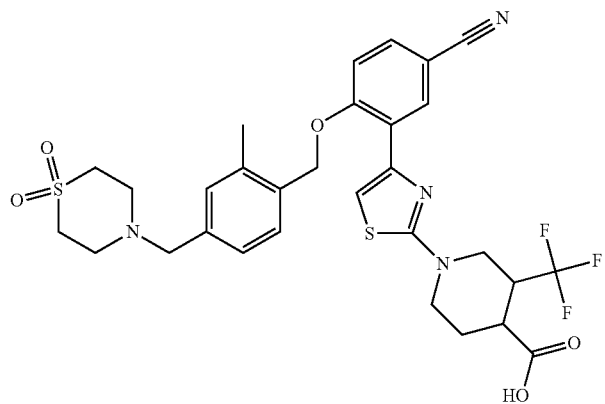 [SMILES: Cc1cc(CN2CCS(=O)(=O)CC2)ccc1COc1ccc(C#N)cc1-c1csc(N2CCC(C(=O)O)C(C(F)(F)F)C2)n1] |
| 157 | 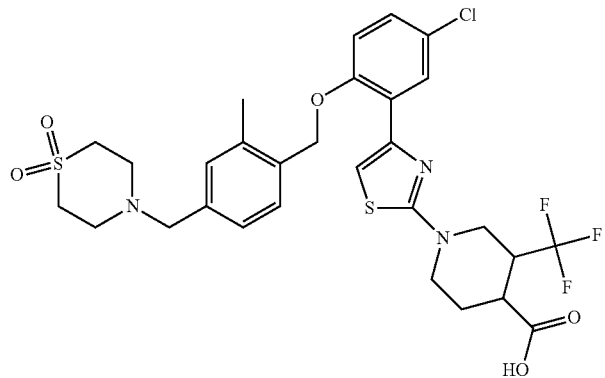 [SMILES: Cc1cc(CN2CCS(=O)(=O)CC2)ccc1COc1ccc(Cl)cc1-c1csc(N2CCC(C(=O)O)C(C(F)(F)F)C2)n1] |
| 158 | 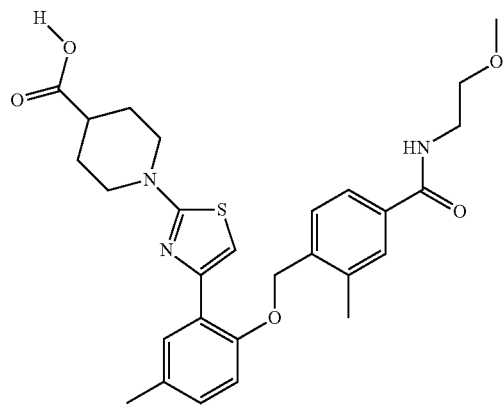 [SMILES: COCCNC(=O)c1ccc(COc2ccc(C)cc2-c2csc(N3CCC(C(=O)O)CC3)n2)c(C)c1] |

| Cpd No. |
| --- |
| 159 |
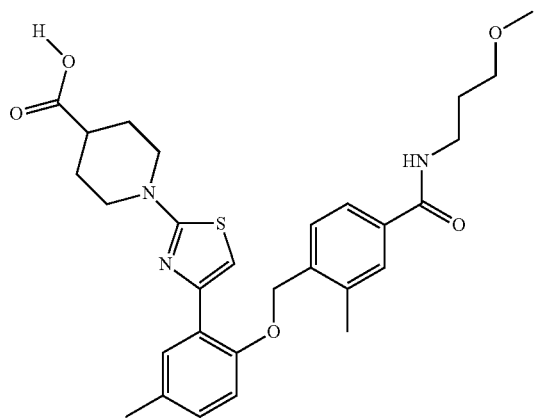 [SMILES: COCCCNC(=O)c1ccc(COc2ccc(C)cc2-c2csc(N3CCC(C(=O)O)CC3)n2)c(C)c1]
160
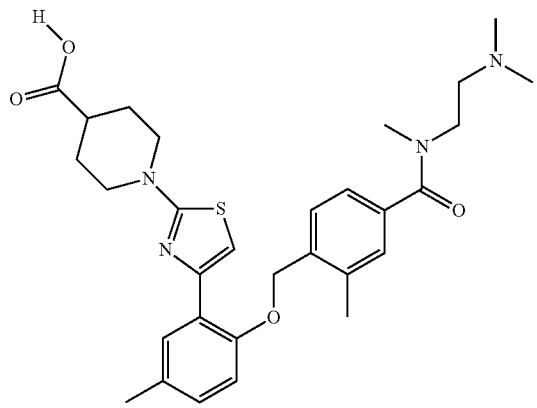 [SMILES: Cc1ccc(OCc2ccc(C(=O)N(C)CCN(C)C)cc2C)c(-c2csc(N3CCC(C(=O)O)CC3)n2)c1]
161
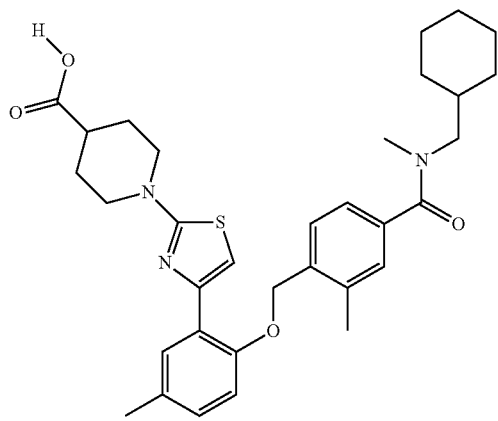 [SMILES: Cc1ccc(OCc2ccc(C(=O)N(C)CC3CCCCC3)cc2C)c(-c2csc(N3CCC(C(=O)O)CC3)n2)c1]

| Cpd No. | |
|---|---|
| 162 | 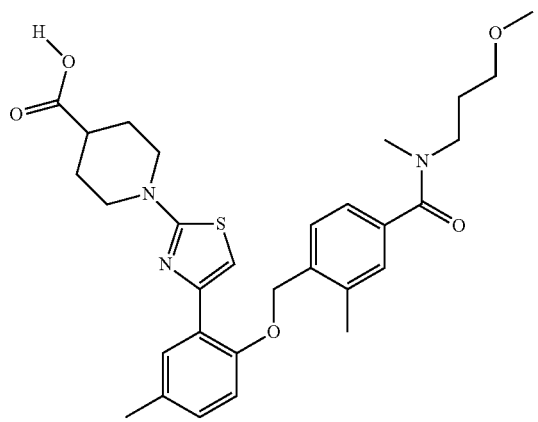 [SMILES: COCCCN(C)C(=O)c1ccc(COc2ccc(C)cc2-c2csc(N3CCC(C(=O)O)CC3)n2)c(C)c1] |
| 163 | 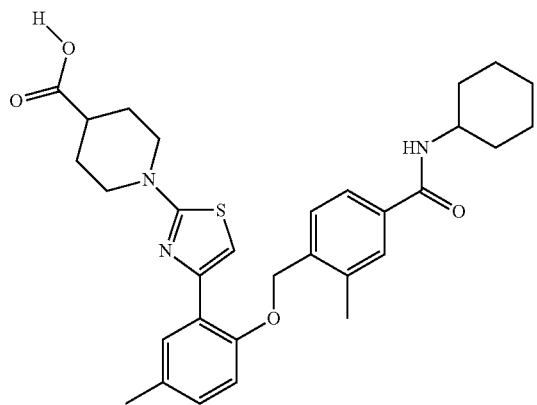 [SMILES: Cc1ccc(OCc2ccc(C(=O)NC3CCCCC3)cc2C)c(-c2csc(N3CCC(C(=O)O)CC3)n2)c1] |
| 164 | 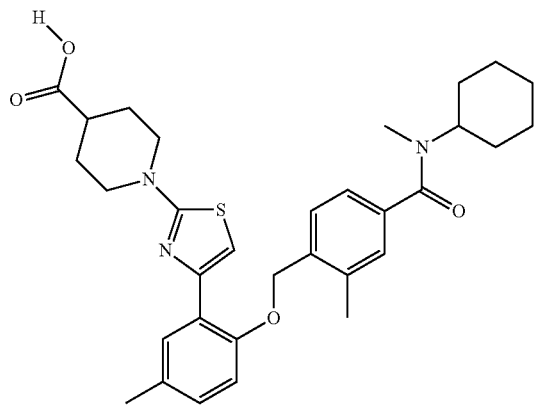 [SMILES: Cc1ccc(OCc2ccc(C(=O)N(C)C3CCCCC3)cc2C)c(-c2csc(N3CCC(C(=O)O)CC3)n2)c1] |

-continued
| Cpd No. |
|---|
| 165 |
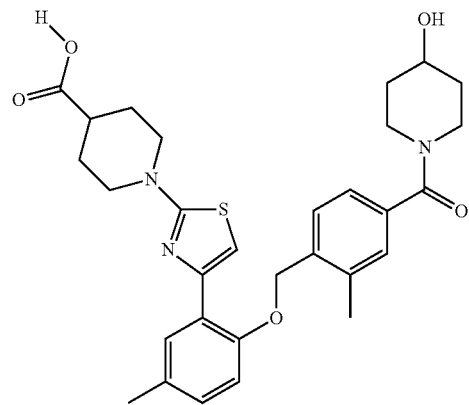 [SMILES: Cc1ccc(OCc2ccc(C(=O)N3CCC(O)CC3)cc2C)c(-c2csc(N3CCC(C(=O)O)CC3)n2)c1]
166
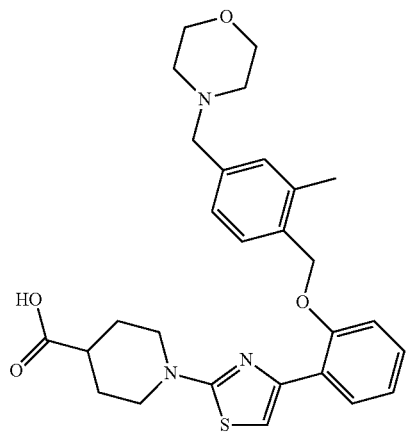 [SMILES: Cc1cc(CN2CCOCC2)ccc1COc1ccccc1-c1csc(N2CCC(C(=O)O)CC2)n1]
167
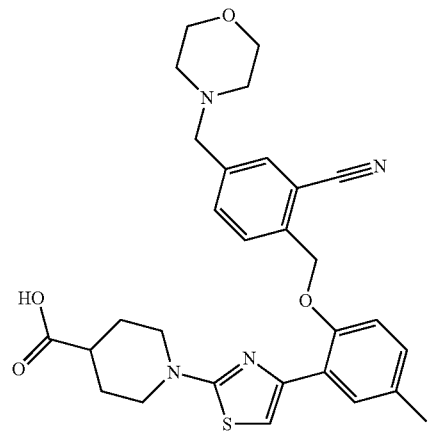 [SMILES: Cc1ccc(OCc2ccc(CN3CCOCC3)cc2C#N)c(-c2csc(N3CCC(C(=O)O)CC3)n2)c1]

-continued
| Cpd No. |
|---|
| 168 |
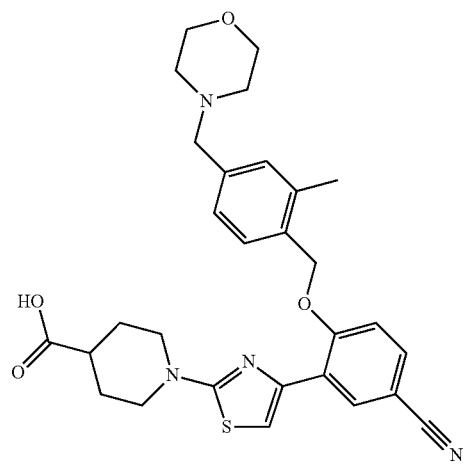 [SMILES: Cc1cc(CN2CCOCC2)ccc1COc1ccc(C#N)cc1-c1csc(N2CCC(C(=O)O)CC2)n1]
169
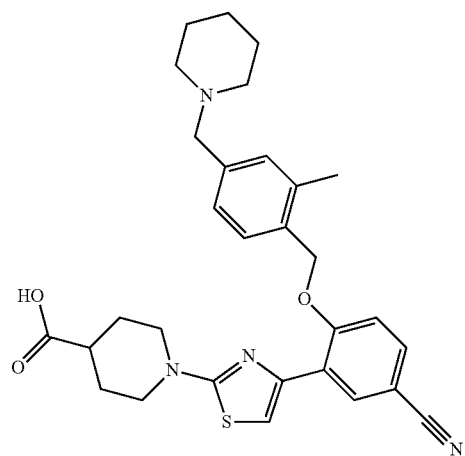 [SMILES: Cc1cc(CN2CCCCC2)ccc1COc1ccc(C#N)cc1-c1csc(N2CCC(C(=O)O)CC2)n1]
170
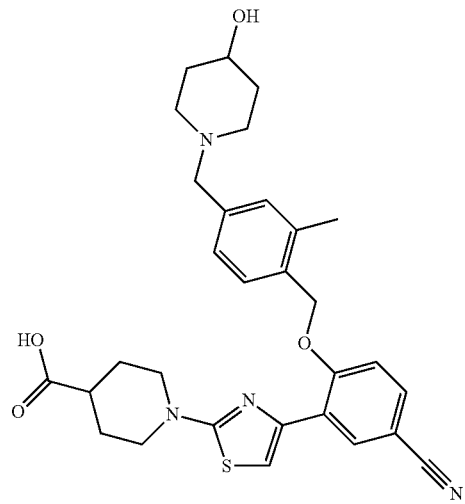 [SMILES: Cc1cc(CN2CCC(O)CC2)ccc1COc1ccc(C#N)cc1-c1csc(N2CCC(C(=O)O)CC2)n1]

| Cpd No. | |
|---|---|
| 171 | 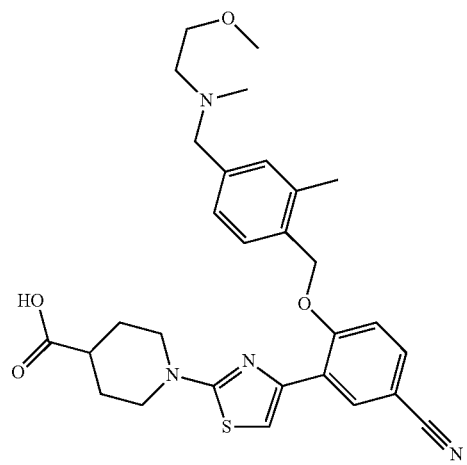 [SMILES: COCCN(C)Cc1ccc(COc2ccc(C#N)cc2-c2csc(N3CCC(C(=O)O)CC3)n2)c(C)c1] |
| 172 | 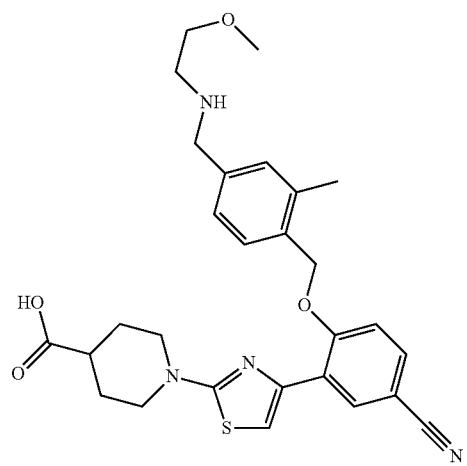 [SMILES: COCCNCc1ccc(COc2ccc(C#N)cc2-c2csc(N3CCC(C(=O)O)CC3)n2)c(C)c1] |
| 173 | 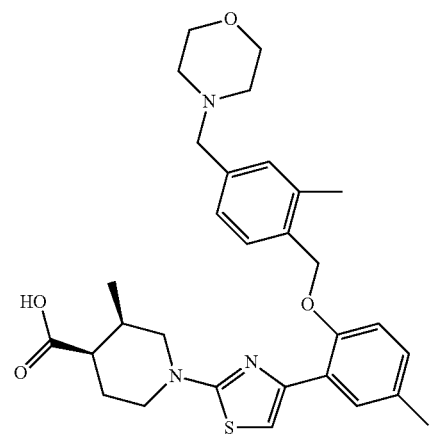 [SMILES: Cc1ccc(OCc2ccc(CN3CCOCC3)cc2C)c(-c2csc(N3CC[C@@H](C(=O)O)[C@@H](C)C3)n2)c1] |

-continued
| Cpd No. |
|---|
| 174 |
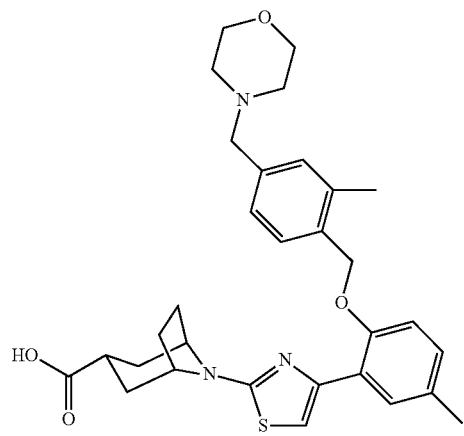 [SMILES: Cc1ccc(OCc2ccc(CN3CCOCC3)cc2C)c(-c2csc(N3C4CCC3CC(C(=O)O)C4)n2)c1]
| 175 |
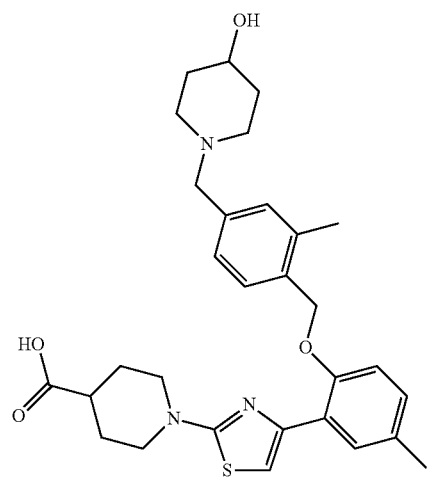 [SMILES: Cc1ccc(OCc2ccc(CN3CCC(O)CC3)cc2C)c(-c2csc(N3CCC(C(=O)O)CC3)n2)c1]
| 176 |
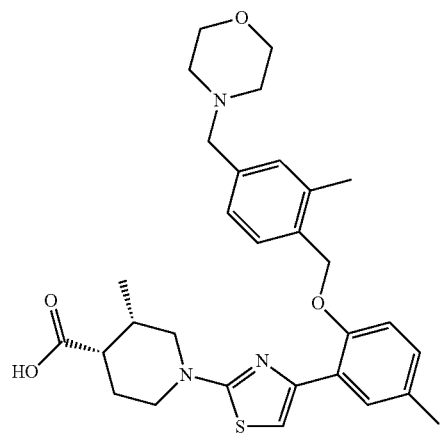 [SMILES: Cc1ccc(OCc2ccc(CN3CCOCC3)cc2C)c(-c2csc(N3CC[C@H](C(=O)O)[C@H](C)C3)n2)c1]

-continued
| Cpd No. | |
|---|---|
| 177 | 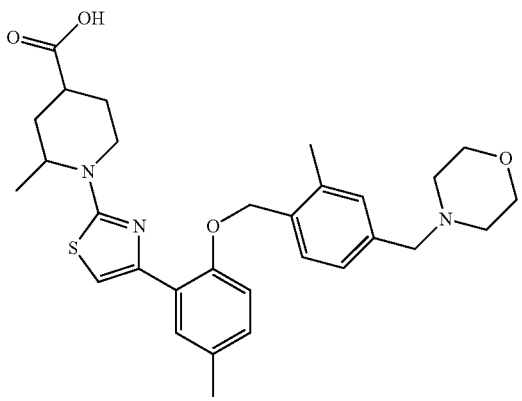 [SMILES: Cc1ccc(OCc2ccc(CN3CCOCC3)cc2C)c(-c2csc(N3CCC(C(=O)O)CC3C)n2)c1] |
| 178 | 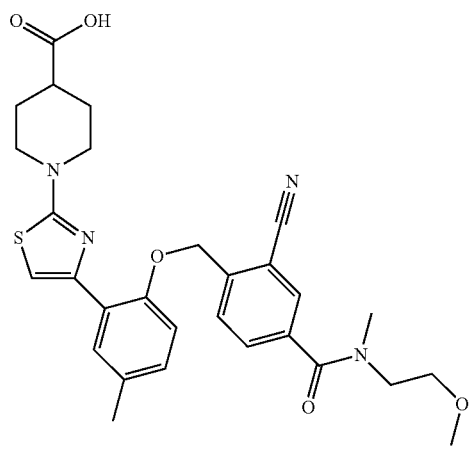 [SMILES: COCCN(C)C(=O)c1ccc(COc2ccc(C)cc2-c2csc(N3CCC(C(=O)O)CC3)n2)c(C#N)c1] |
| 179 | 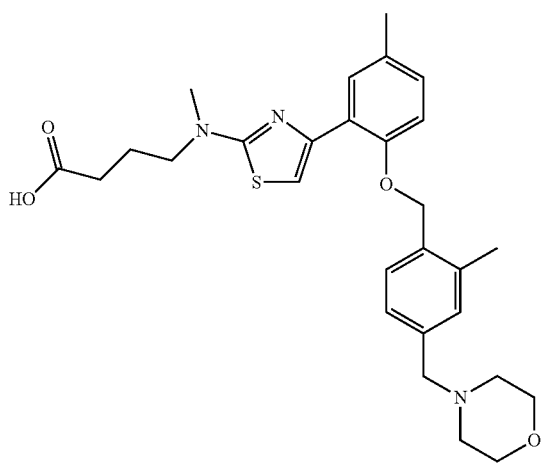 [SMILES: Cc1ccc(OCc2ccc(CN3CCOCC3)cc2C)c(-c2csc(N(C)CCCC(=O)O)n2)c1] |

| Cpd No. | |
|---|---|
| 180 | 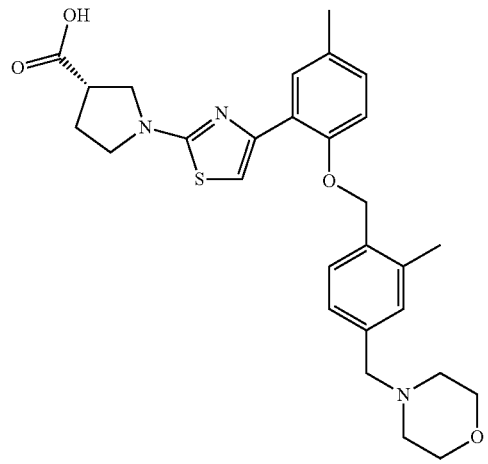 [SMILES: Cc1ccc(OCc2ccc(CN3CCOCC3)cc2C)c(-c2csc(N3CC[C@H](C(=O)O)C3)n2)c1] |
| 181 | 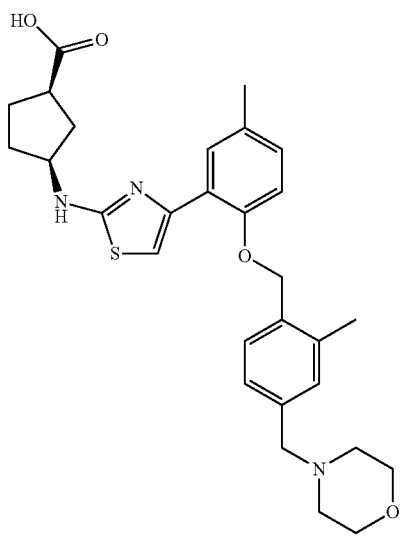 [SMILES: Cc1ccc(OCc2ccc(CN3CCOCC3)cc2C)c(-c2csc(N[C@H]3CC[C@@H](C(=O)O)C3)n2)c1] |
| 182 | 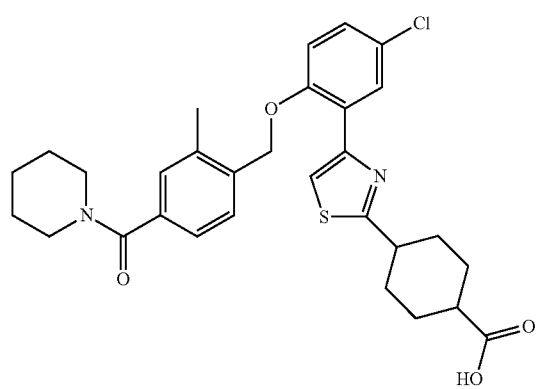 |

-continued
| Cpd No. | |
|---|---|
| 183 | 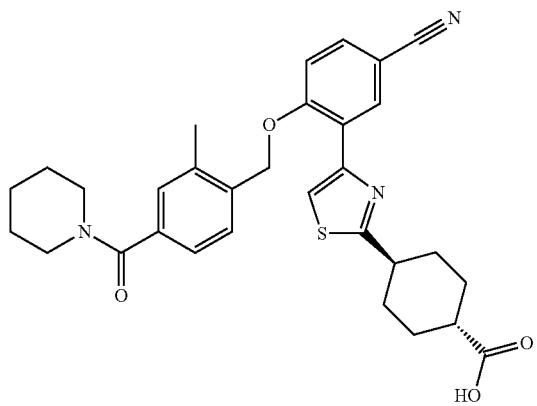 [SMILES: Cc1cc(C(=O)N2CCCCC2)ccc1COc1ccc(C#N)cc1-c1csc([C@H]2CC[C@H](C(=O)O)CC2)n1] |
| 184 | 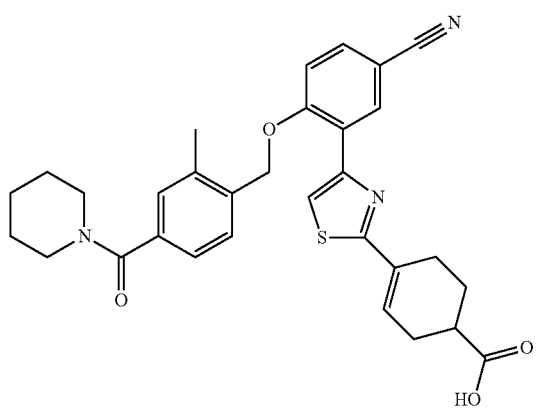 |
| 185 | 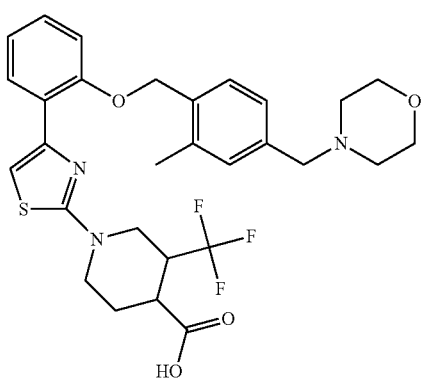 [SMILES: Cc1cc(CN2CCOCC2)ccc1COc1ccccc1-c1csc(N2CCC(C(=O)O)C(C(F)(F)F)C2)n1] |
| 186 | 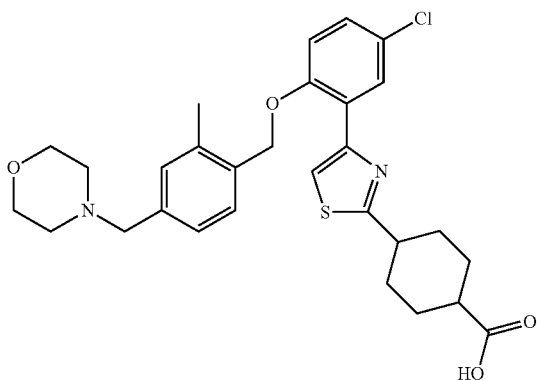 [SMILES: Cc1cc(CN2CCOCC2)ccc1COc1ccc(F)cc1-c1csc(C2CCC(C(=O)O)CC2)n1] |

| Cpd No. | |
|---|---|
| 187 | 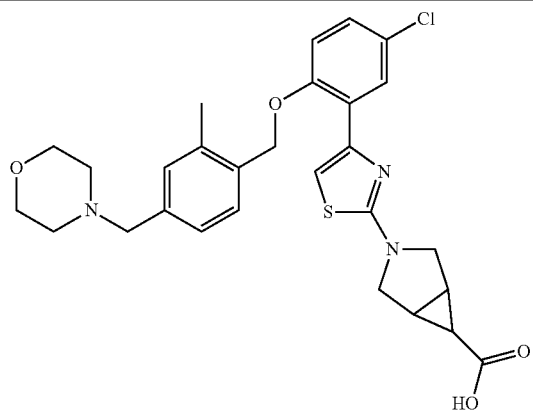 |
| 188 | 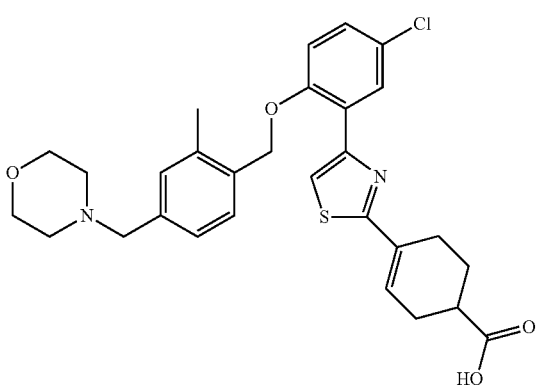 [SMILES: Cc1cc(CN2CCOCC2)ccc1COc1ccc(F)cc1-c1csc(C2=CCC(C(=O)O)CC2)n1] |
| 189 | 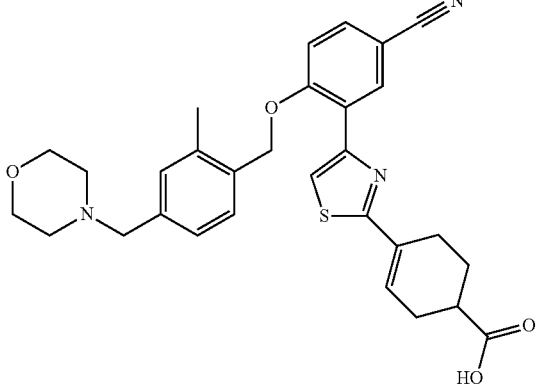 |
| 190 | 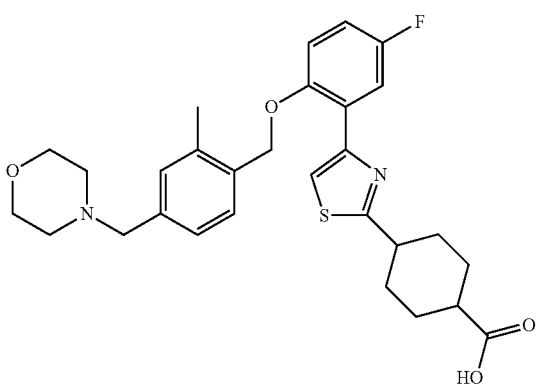 |

-continued
| Cpd No. |
|---|
| 191 |
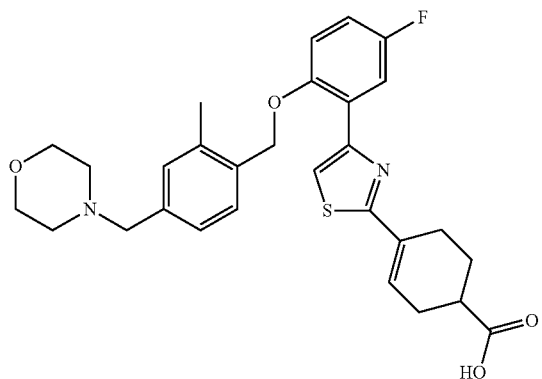
192
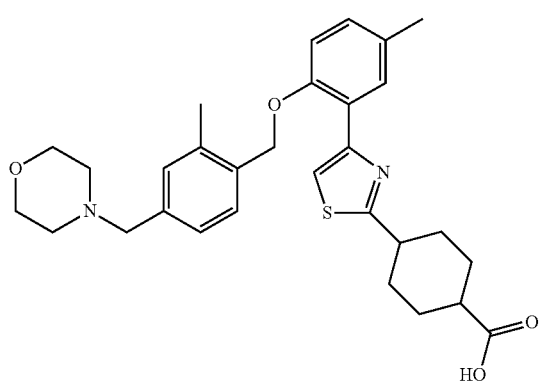 [SMILES: Cc1ccc(OCc2ccc(CN3CCOCC3)cc2C)c(-c2csc(C3CCC(C(=O)O)CC3)n2)c1]
193
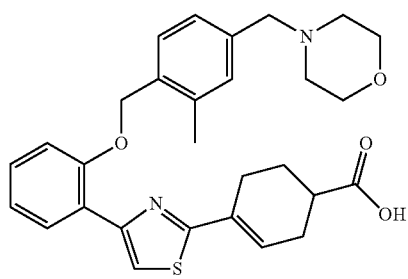 [SMILES: Cc1cc(CN2CCOCC2)ccc1COc1ccccc1-c1csc(C2=CCC(C(=O)O)CC2)n1]

| Cpd No. |
|---|
| 194 |
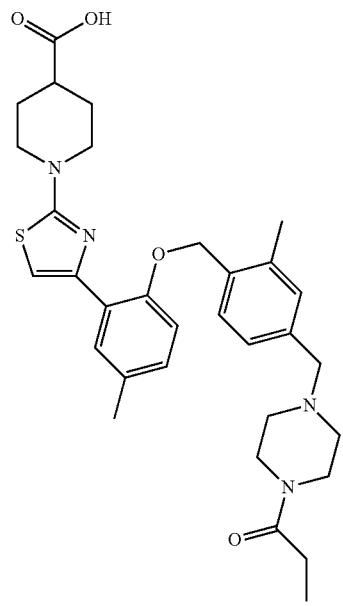 [SMILES: CCC(=O)N1CCN(Cc2ccc(COc3ccc(C)cc3-c3csc(N4CCC(C(=O)O)CC4)n3)c(C)c2)CC1]
| 195 |
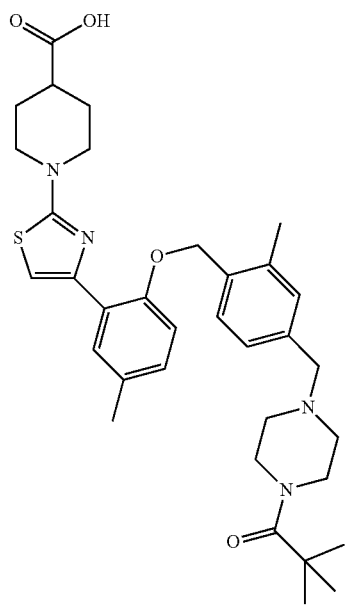 [SMILES: Cc1ccc(OCc2ccc(CN3CCN(C(=O)C(C)(C)C)CC3)cc2C)c(-c2csc(N3CCC(C(=O)O)CC3)n2)c1]

| Cpd No. |
| --- |
| 196 |
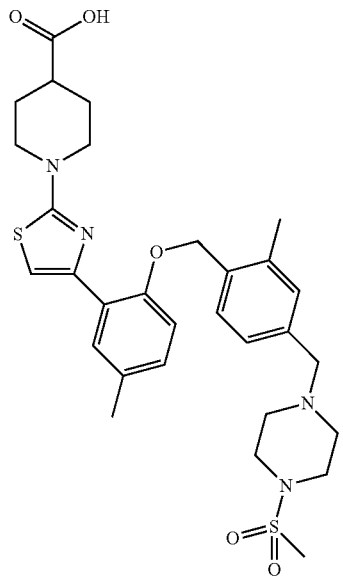 [SMILES: Cc1ccc(OCc2ccc(CN3CCN(S(C)(=O)=O)CC3)cc2C)c(-c2csc(N3CCC(C(=O)O)CC3)n2)c1]
197
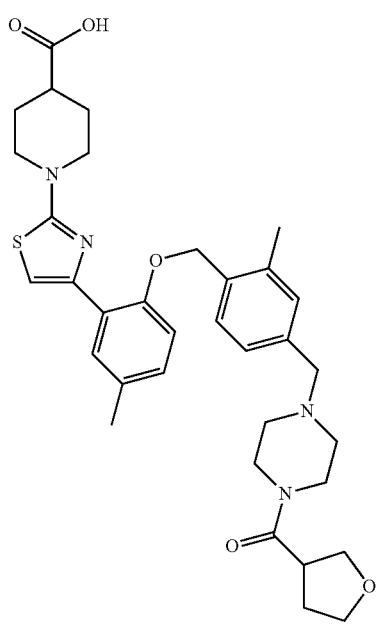 [SMILES: Cc1ccc(OCc2ccc(CN3CCN(C(=O)C4CCOC4)CC3)cc2C)c(-c2csc(N3CCC(C(=O)O)CC3)n2)c1]

| Cpd No. |
|---|
| 198 |
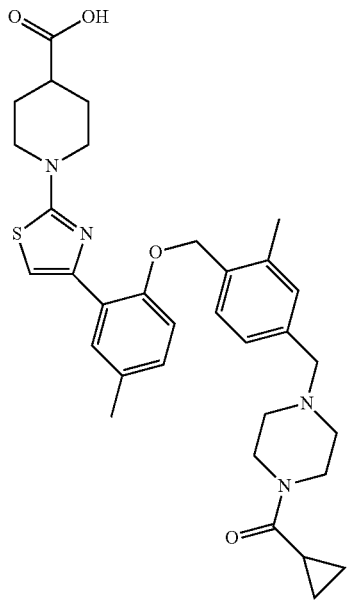 [SMILES: Cc1ccc(OCc2ccc(CN3CCN(C(=O)C4CC4)CC3)cc2C)c(-c2csc(N3CCC(C(=O)O)CC3)n2)c1]
199
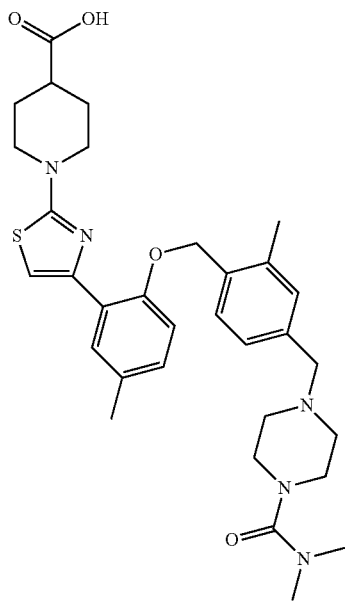 [SMILES: Cc1ccc(OCc2ccc(CN3CCN(C(=O)N(C)C)CC3)cc2C)c(-c2csc(N3CCC(C(=O)O)CC3)n2)c1]

| Cpd No. | |
|---|---|
| 200 | 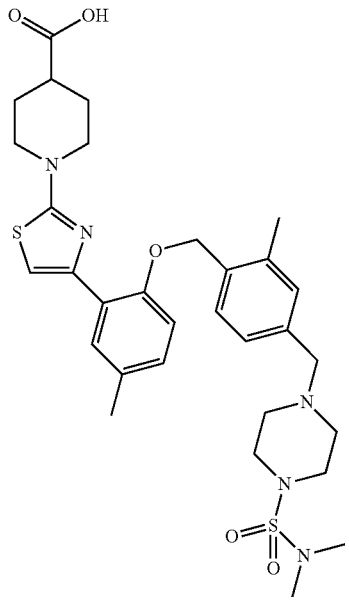 [SMILES: Cc1ccc(OCc2ccc(CN3CCN(S(=O)(=O)N(C)C)CC3)cc2C)c(-c2csc(N3CCC(C(=O)O)CC3)n2)c1] |
| 201 | 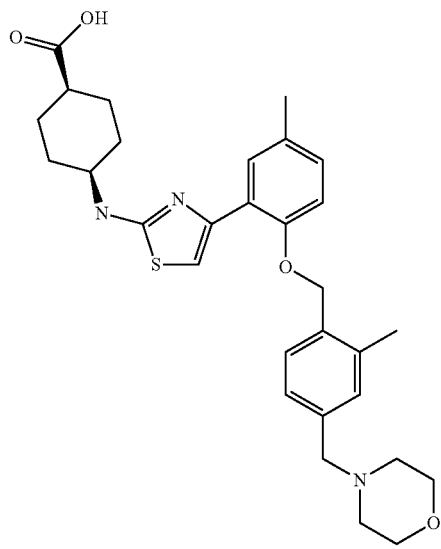 [SMILES: Cc1ccc(OCc2ccc(CN3CCOCC3)cc2C)c(-c2csc(N[C@H]3CC[C@@H](C(=O)O)CC3)n2)c1] |
| 202 | 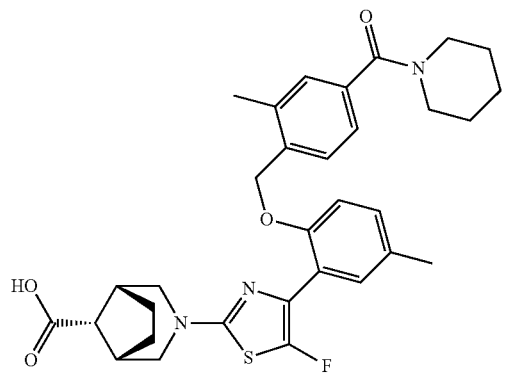 [SMILES: Cc1ccc(OCc2ccc(C(=O)N3CCCCC3)cc2C)c(-c2nc(N3C[C@H]4CC[C@@H](C3)[C@H]4C(=O)O)sc2F)c1] |

| Cpd No. | |
|---|---|
| 203 | 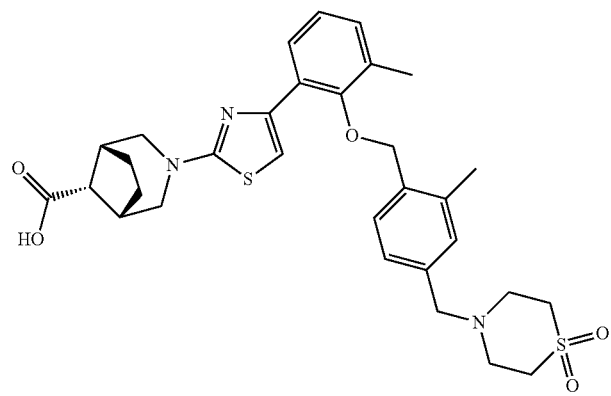 [SMILES: Cc1cc(CN2CCS(=O)(=O)CC2)ccc1COc1c(C)cccc1-c1csc(N2C[C@H]3CC[C@@H](C2)[C@H]3C(=O)O)n1] |
| 204 | 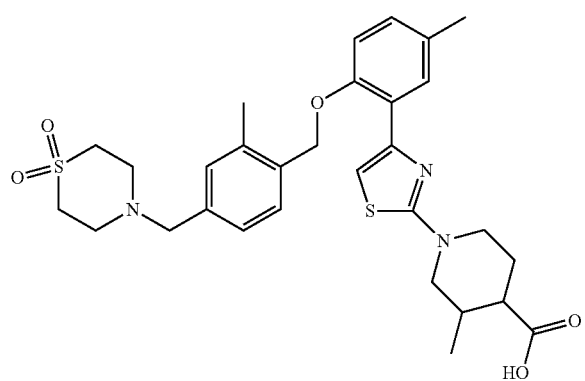 [SMILES: Cc1ccc(OCc2ccc(CN3CCS(=O)(=O)CC3)cc2C)c(-c2csc(N3CCC(C(=O)O)C(C)C3)n2)c1] |
| 205 | 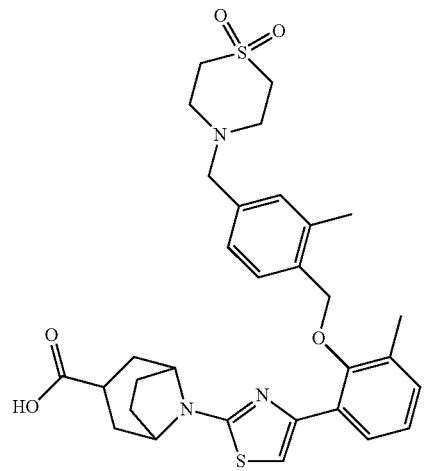 [SMILES: Cc1cc(CN2CCS(=O)(=O)CC2)ccc1COc1c(C)cccc1-c1csc(N2C3CCC2CC(C(=O)O)C3)n1] |

| Cpd No. |
| --- |
| 206 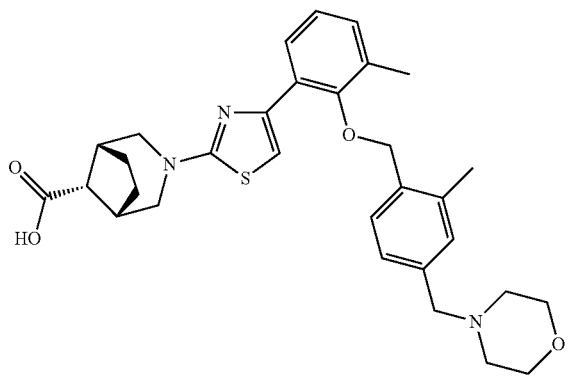 [SMILES: Cc1cc(CN2CCOCC2)ccc1COc1c(C)cccc1-c1csc(N2C[C@H]3CC[C@@H](C2)[C@H]3C(=O)O)n1] |
| 207 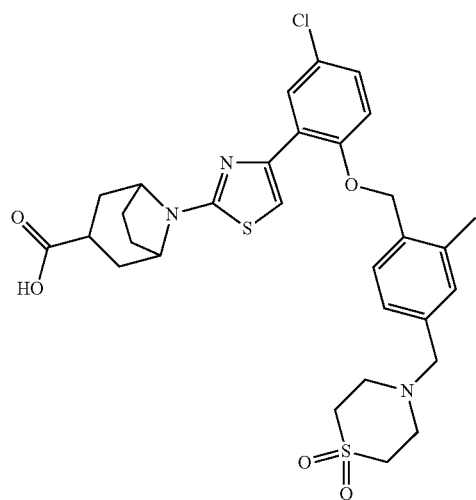 [SMILES: Cc1cc(CN2CCS(=O)(=O)CC2)ccc1COc1ccc(Cl)cc1-c1csc(N2C3CCC2CC(C(=O)O)C3)n1] |
| 208 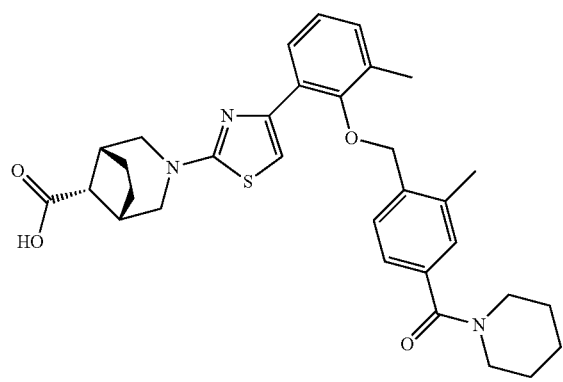 [SMILES: Cc1cc(C(=O)N2CCCCC2)ccc1COc1c(C)cccc1-c1csc(N2C[C@H]3CC[C@@H](C2)[C@H]3C(=O)O)n1] |

-continued
| Cpd No. | |
|---|---|
| 209 | 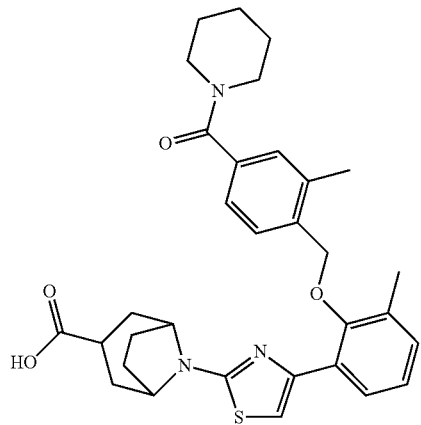 [SMILES: Cc1cc(C(=O)N2CCCCC2)ccc1COc1c(C)cccc1-c1csc(N2C3CCC2CC(C(=O)O)C3)n1] |
| 210 | 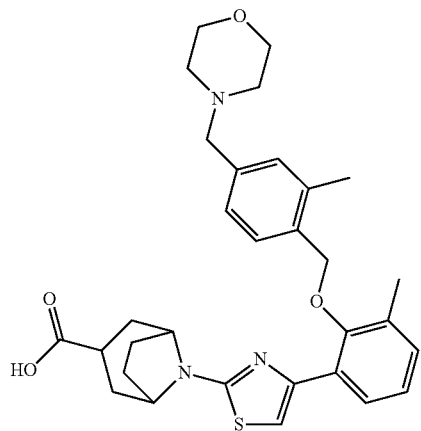 [SMILES: Cc1cc(CN2CCOCC2)ccc1COc1c(C)cccc1-c1csc(N2C3CCC2CC(C(=O)O)C3)n1] |
| 211 | 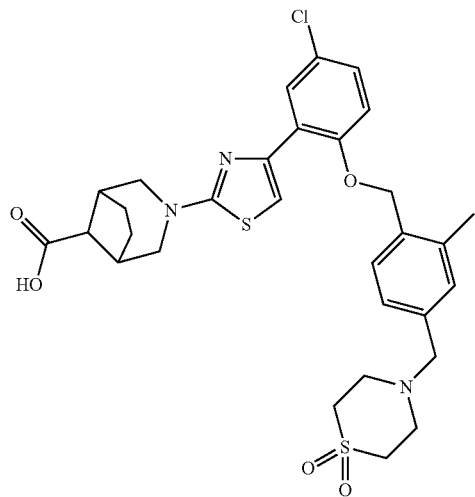 [SMILES: Cc1cc(CN2CCS(=O)(=O)CC2)ccc1COc1ccc(Cl)cc1-c1csc(N2CC3CCC(C2)C3C(=O)O)n1] |

| Cpd No. | |
|---|---|
| 212 | 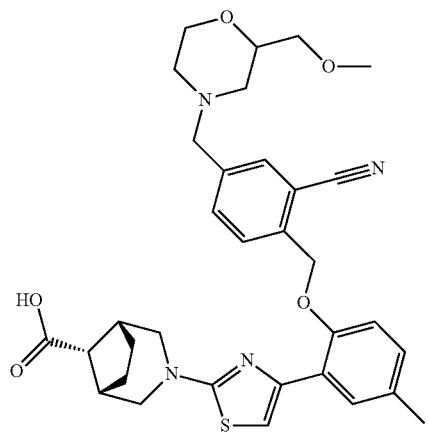 [SMILES: COCC1CN(Cc2ccc(COc3ccc(C)cc3-c3csc(N4C[C@H]5CC[C@@H](C4)[C@H]5C(=O)O)n3)c(C#N)c2)CCO1] |
| 213 | 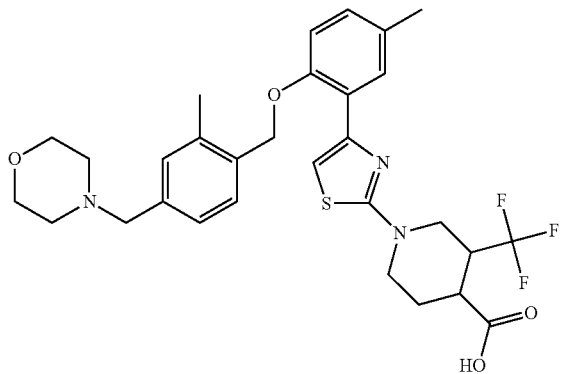 [SMILES: Cc1ccc(OCc2ccc(CN3CCOCC3)cc2C)c(-c2csc(N3CCC(C(=O)O)C(C(F)(F)F)C3)n2)c1] |
| 214 | 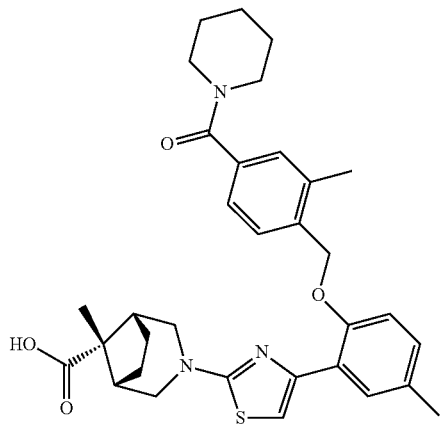 [SMILES: Cc1ccc(OCc2ccc(C(=O)N3CCCCC3)cc2C)c(-c2csc(N3C[C@H]4CC[C@@H](C3)[C@@]4(C)C(=O)O)n2)c1] |

| Cpd No. | |
|---|---|
| 215 | 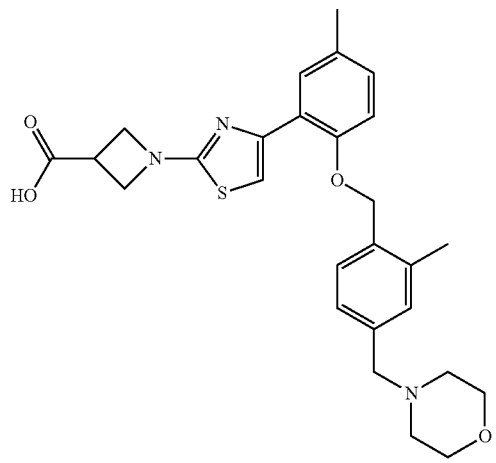 [SMILES: Cc1ccc(OCc2ccc(CN3CCOCC3)cc2C)c(-c2csc(N3CC(C(=O)O)C3)n2)c1] |
| 216 | 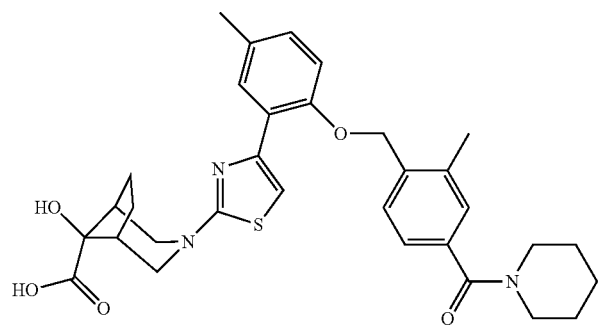 [SMILES: Cc1ccc(OCc2ccc(C(=O)N3CCCCC3)cc2C)c(-c2csc(N3CC4CCC(C3)C4(O)C(=O)O)n2)c1] |
| 217 | 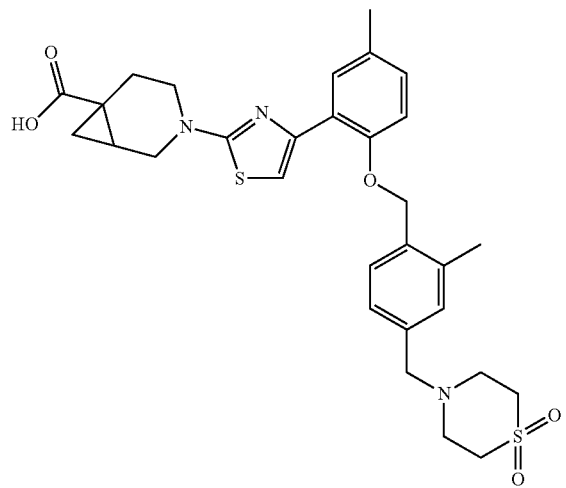 [SMILES: Cc1ccc(OCc2ccc(CN3CCS(=O)(=O)CC3)cc2C)c(-c2csc(N3CCC4(C(=O)O)CC4C3)n2)c1] |

| Cpd No. | |
|---|---|
| 218 | 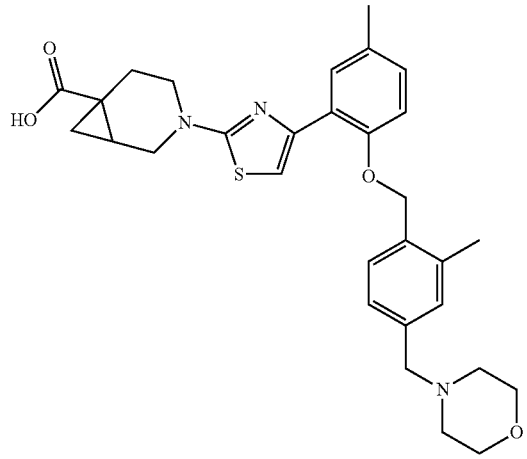 [SMILES: Cc1ccc(OCc2ccc(CN3CCOCC3)cc2C)c(-c2csc(N3CCC4(C(=O)O)CC4C3)n2)c1] |
| 219 | 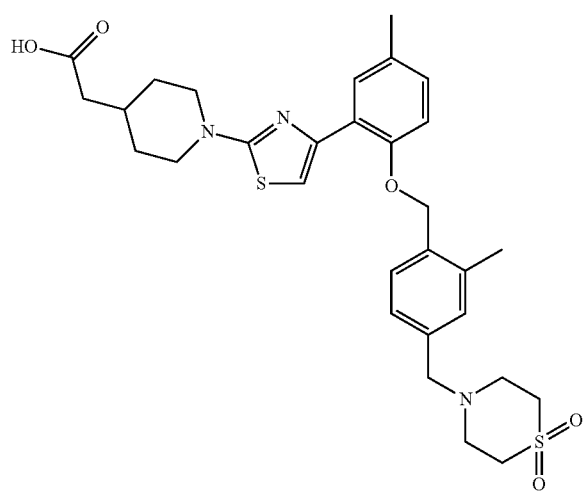 [SMILES: Cc1ccc(OCc2ccc(CN3CCS(=O)(=O)CC3)cc2C)c(-c2csc(N3CCC(CC(=O)O)CC3)n2)c1] |
| 220 | 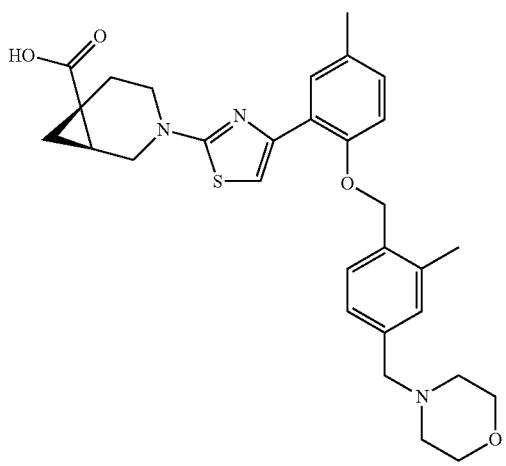 [SMILES: Cc1ccc(OCc2ccc(CN3CCOCC3)cc2C)c(-c2csc(N3CC[C@]4(C(=O)O)C[C@@H]4C3)n2)c1] |

| Cpd No. |
|---|
| 221 |
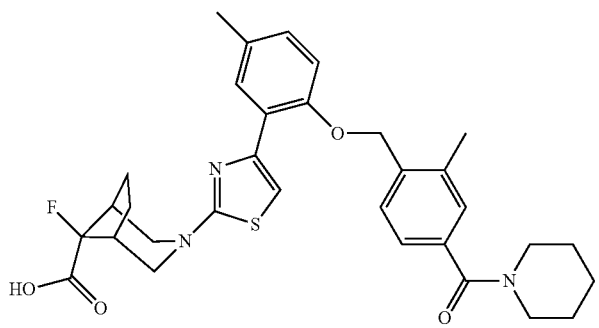 [SMILES: Cc1ccc(OCc2ccc(C(=O)N3CCCCC3)cc2C)c(-c2csc(N3CC4CCC(C3)C4(F)C(=O)O)n2)c1]
222
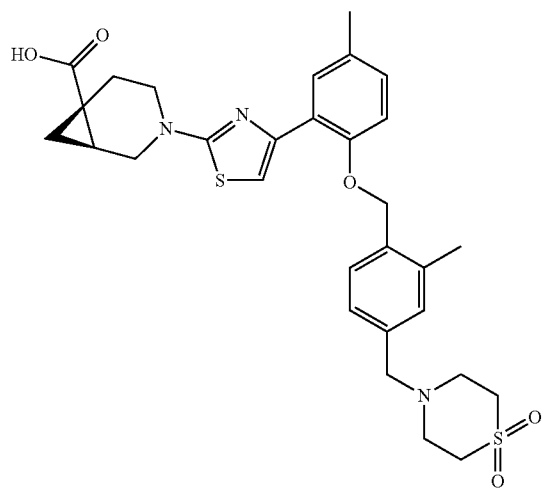 [SMILES: Cc1ccc(OCc2ccc(CN3CCS(=O)(=O)CC3)cc2C)c(-c2csc(N3CC[C@]4(C(=O)O)C[C@@H]4C3)n2)c1]
223
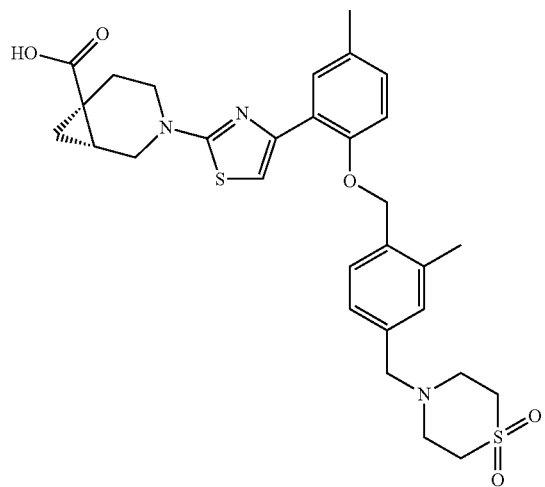 [SMILES: Cc1ccc(OCc2ccc(CN3CCS(=O)(=O)CC3)cc2C)c(-c2csc(N3CC[C@@]4(C(=O)O)C[C@H]4C3)n2)c1]

| Cpd No. | |
|---|---|
| 224 | 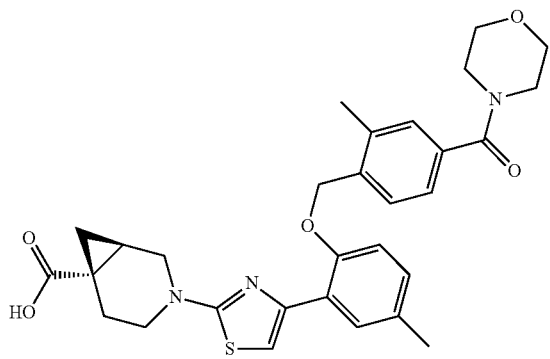 [SMILES: Cc1ccc(OCc2ccc(C(=O)N3CCOCC3)cc2C)c(-c2csc(N3CC[C@@]4(C(=O)O)C[C@H]4C3)n2)c1] |
| 225 | 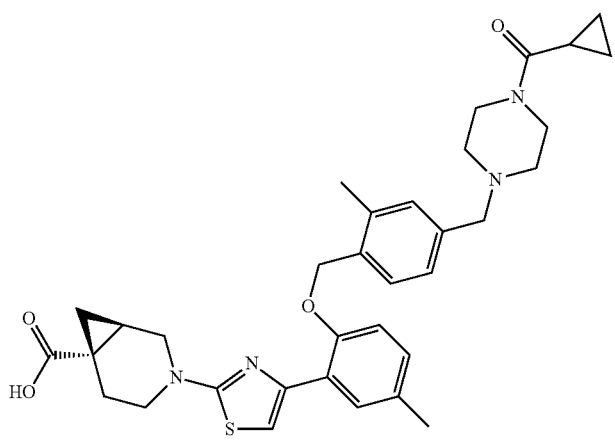 [SMILES: Cc1ccc(OCc2ccc(CN3CCN(C(=O)C4CC4)CC3)cc2C)c(-c2csc(N3CC[C@@]4(C(=O)O)C[C@H]4C3)n2)c1] |
| 226 | 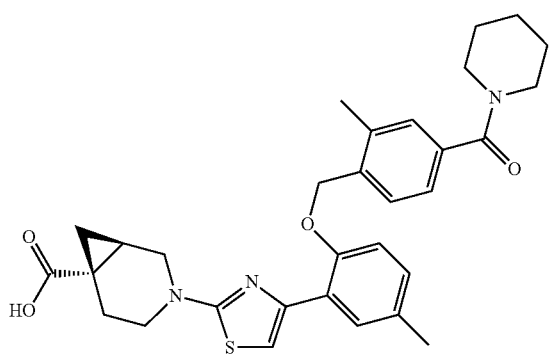 [SMILES: Cc1ccc(OCc2ccc(C(=O)N3CCCCC3)cc2C)c(-c2csc(N3CC[C@@]4(C(=O)O)C[C@H]4C3)n2)c1] |
| 227 | 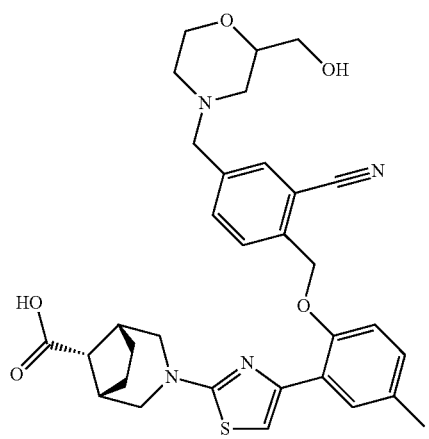 [SMILES: Cc1ccc(OCc2ccc(CN3CCOC(CO)C3)cc2C#N)c(-c2csc(N3C[C@H]4CC[C@@H](C3)[C@H]4C(=O)O)n2)c1] |

| Cpd No. |
|---|
| 228 |
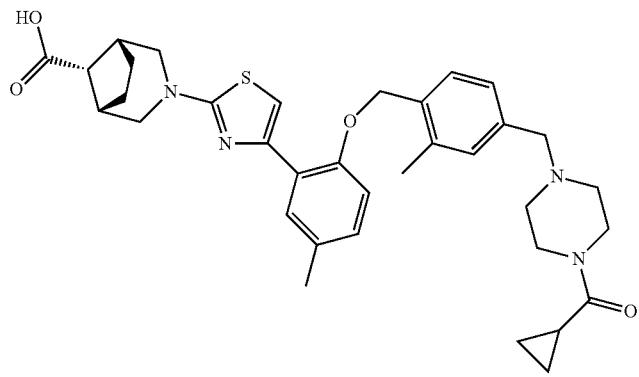 [SMILES: Cc1ccc(OCc2ccc(CN3CCN(C(=O)C4CC4)CC3)cc2C)c(-c2csc(N3C[C@H]4CC[C@@H](C3)[C@H]4C(=O)O)n2)c1]
| 229 |
|---|
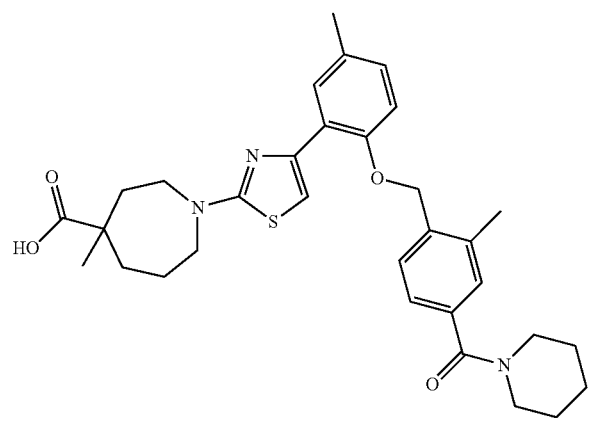 [SMILES: Cc1ccc(OCc2ccc(C(=O)N3CCCCC3)cc2C)c(-c2csc(N3CCCC(C)(C(=O)O)CC3)n2)c1]
| 230 |
|---|
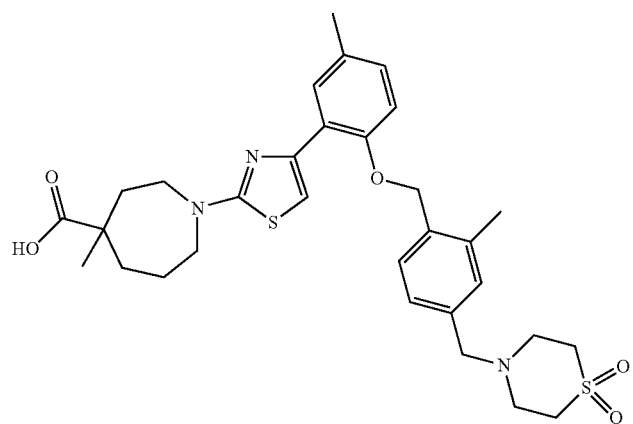 [SMILES: Cc1ccc(OCc2ccc(CN3CCS(=O)(=O)CC3)cc2C)c(-c2csc(N3CCCC(C)(C(=O)O)CC3)n2)c1]

| Cpd No. |
|---|
| 231 |
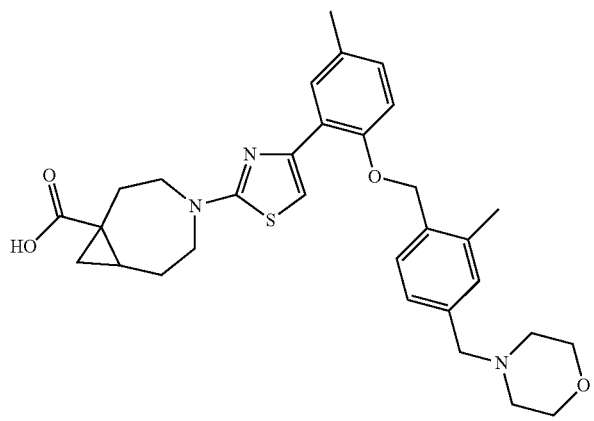 [SMILES: Cc1ccc(OCc2ccc(CN3CCOCC3)cc2C)c(-c2csc(N3CCC4CC4(C(=O)O)CC3)n2)c1]
232
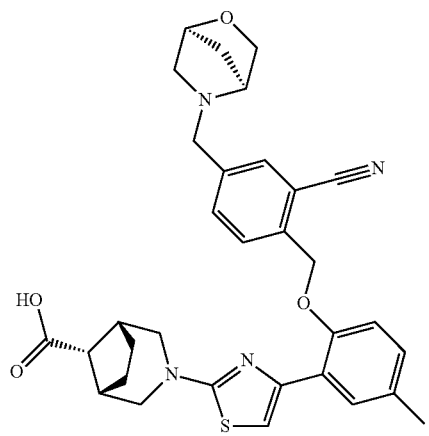 [SMILES: Cc1ccc(OCc2ccc(CN3C[C@@H]4C[C@H]3CO4)cc2C#N)c(-c2csc(N3C[C@H]4CC[C@@H](C3)[C@H]4C(=O)O)n2)c1]
233
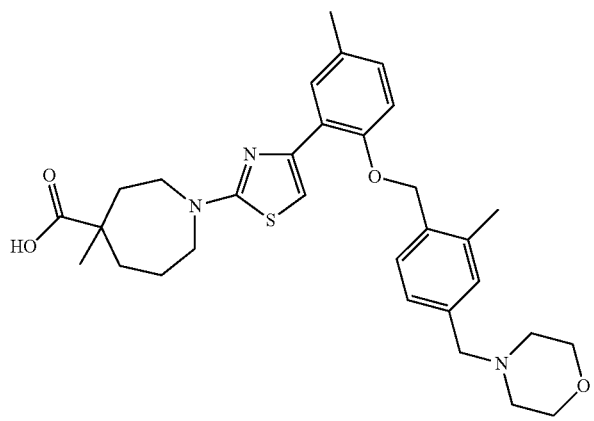 [SMILES: Cc1ccc(OCc2ccc(CN3CCOCC3)cc2C)c(-c2csc(N3CCCC(C)(C(=O)O)CC3)n2)c1]

| Cpd No. | |
|---|---|
| 234 | 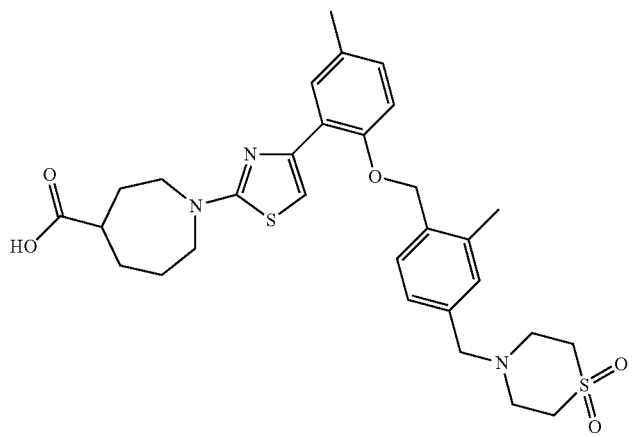 [SMILES: Cc1ccc(OCc2ccc(CN3CCS(=O)(=O)CC3)cc2C)c(-c2csc(N3CCCC(C(=O)O)CC3)n2)c1] |
| 235 | 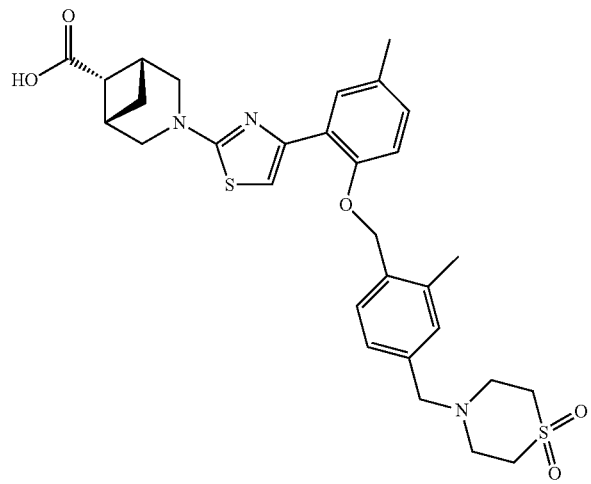 [SMILES: Cc1ccc(OCc2ccc(CN3CCS(=O)(=O)CC3)cc2C)c(-c2csc(N3C[C@H]4C[C@@H](C3)[C@H]4C(=O)O)n2)c1] |
| 236 | 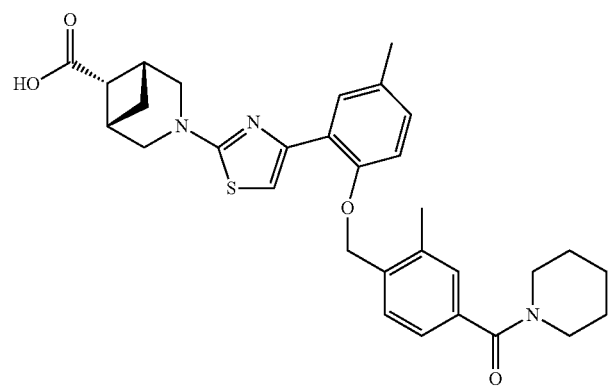 [SMILES: Cc1ccc(OCc2ccc(C(=O)N3CCCCC3)cc2C)c(-c2csc(N3C[C@H]4C[C@@H](C3)[C@H]4C(=O)O)n2)c1] |

| Cpd No. | |
|---|---|
| 237 | 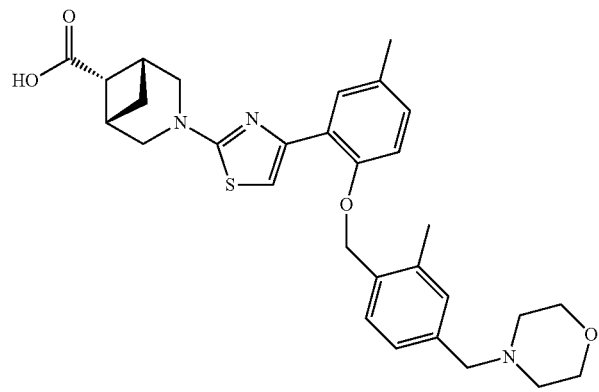 [SMILES: Cc1ccc(OCc2ccc(CN3CCOCC3)cc2C)c(-c2csc(N3C[C@H]4C[C@@H](C3)[C@H]4C(=O)O)n2)c1] |
| 238 | 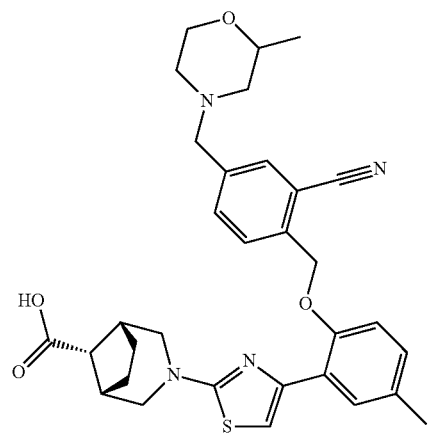 [SMILES: Cc1ccc(OCc2ccc(CN3CCOC(C)C3)cc2C#N)c(-c2csc(N3C[C@H]4CC[C@@H](C3)[C@H]4C(=O)O)n2)c1] |
| 239 | 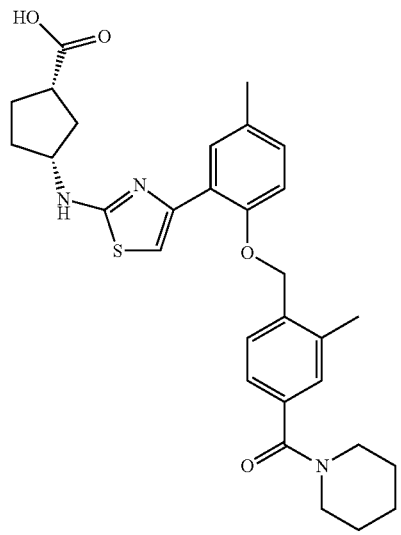 [SMILES: Cc1ccc(OCc2ccc(C(=O)N3CCCCC3)cc2C)c(-c2csc(N[C@@H]3CC[C@H](C(=O)O)C3)n2)c1] |

| Cpd No. |
|---|
| 240 |
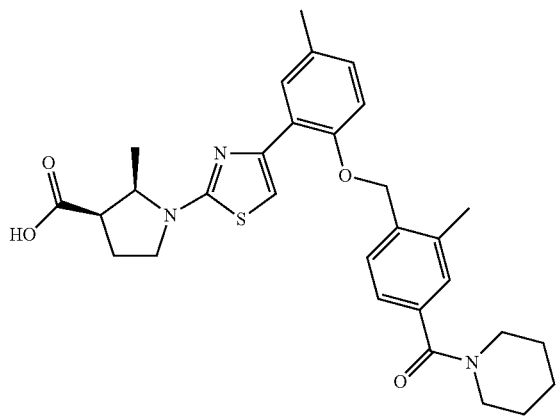 [SMILES: Cc1ccc(OCc2ccc(C(=O)N3CCCCC3)cc2C)c(-c2csc(N3CC[C@@H](C(=O)O)[C@H]3C)n2)c1]
| 241 |
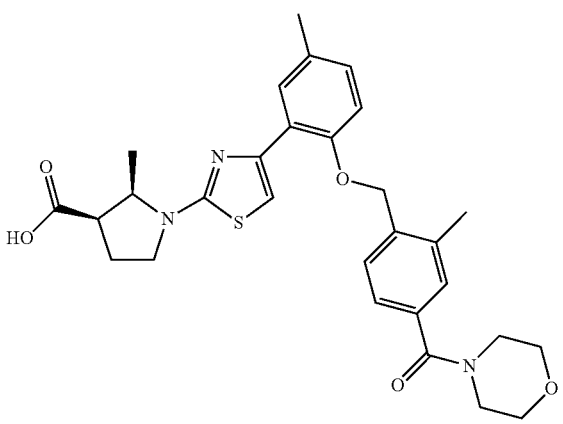 [SMILES: Cc1ccc(OCc2ccc(C(=O)N3CCOCC3)cc2C)c(-c2csc(N3CC[C@@H](C(=O)O)[C@H]3C)n2)c1]
| 242 |
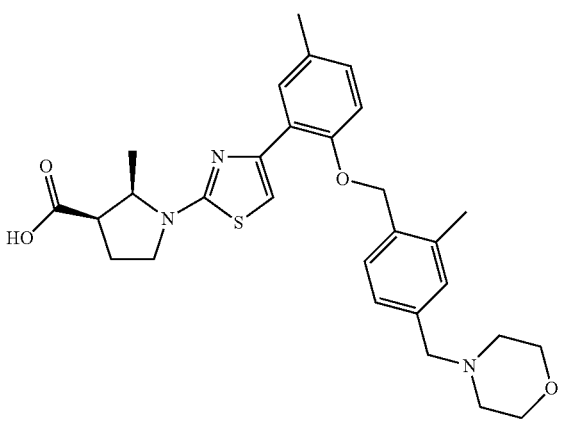 [SMILES: Cc1ccc(OCc2ccc(CN3CCOCC3)cc2C)c(-c2csc(N3CC[C@@H](C(=O)O)[C@H]3C)n2)c1]

| Cpd No. | |
|---|---|
| 243 | 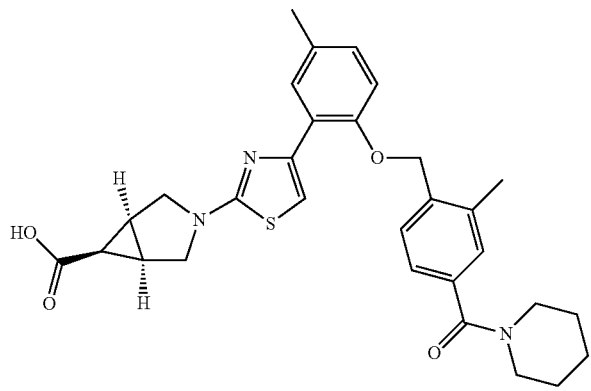 [SMILES: Cc1ccc(OCc2ccc(C(=O)N3CCCCC3)cc2C)c(-c2csc(N3C[C@@H]4[C@H](C3)[C@@H]4C(=O)O)n2)c1] |
| 244 | 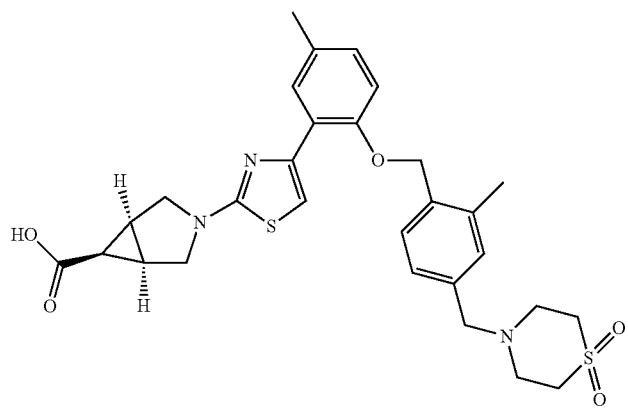 [SMILES: Cc1ccc(OCc2ccc(CN3CCS(=O)(=O)CC3)cc2C)c(-c2csc(N3C[C@@H]4[C@H](C3)[C@@H]4C(=O)O)n2)c1] |
| 245 | 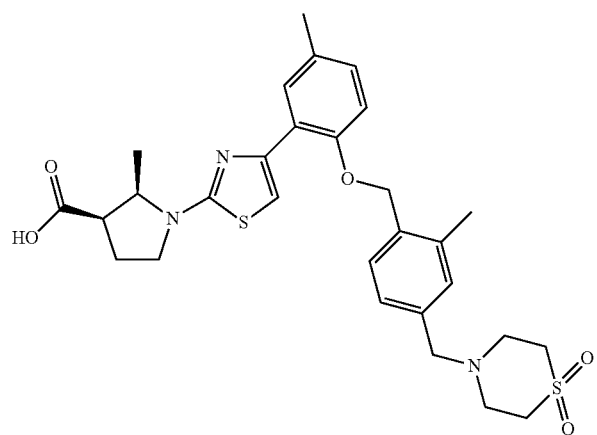 [SMILES: Cc1ccc(OCc2ccc(CN3CCS(=O)(=O)CC3)cc2C)c(-c2csc(N3CC[C@@H](C(=O)O)[C@H]3C)n2)c1] |

| Cpd No. |
| --- |
| 246 |
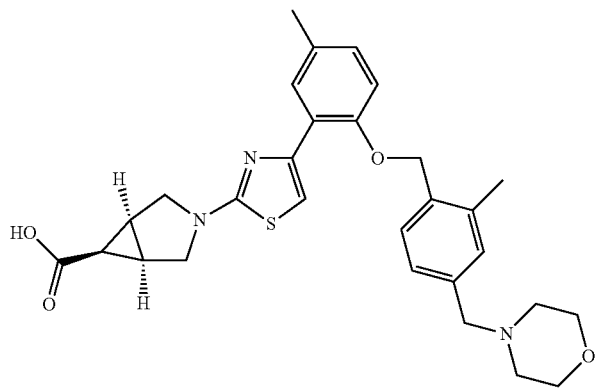 [SMILES: Cc1ccc(OCc2ccc(CN3CCOCC3)cc2C)c(-c2csc(N3C[C@@H]4[C@H](C3)[C@@H]4C(=O)O)n2)c1]
247
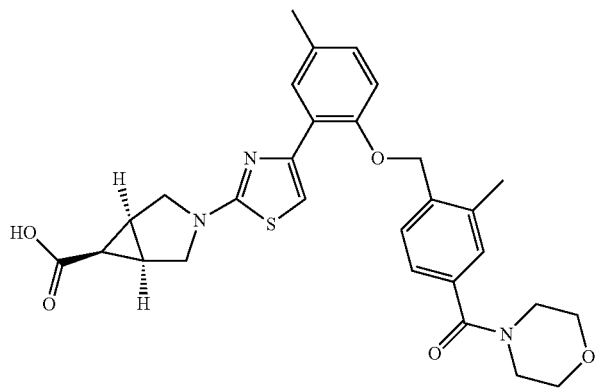 [SMILES: Cc1ccc(OCc2ccc(C(=O)N3CCOCC3)cc2C)c(-c2csc(N3C[C@@H]4[C@H](C3)[C@@H]4C(=O)O)n2)c1]
248
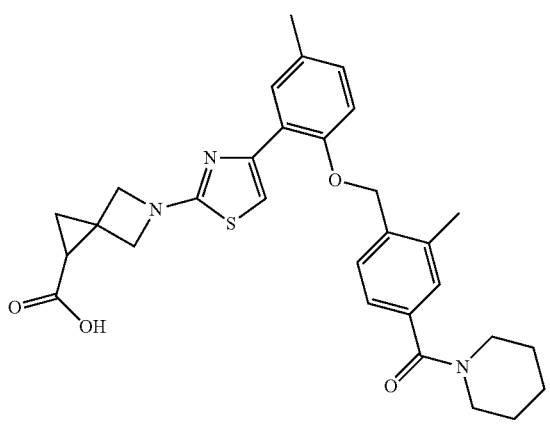 [SMILES: Cc1ccc(OCc2ccc(C(=O)N3CCCCC3)cc2C)c(-c2csc(N3CC4(CC4C(=O)O)C3)n2)c1]

| Cpd No. | |
|---|---|
| 249 | 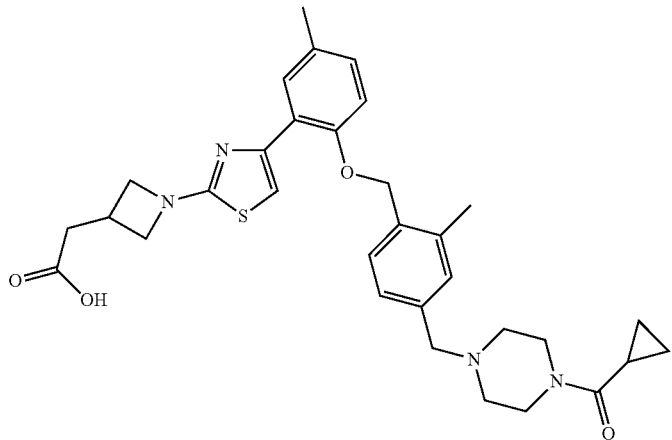 [SMILES: Cc1ccc(OCc2ccc(CN3CCN(C(=O)C4CC4)CC3)cc2C)c(-c2csc(N3CC(CC(=O)O)C3)n2)c1] |
| 250 | 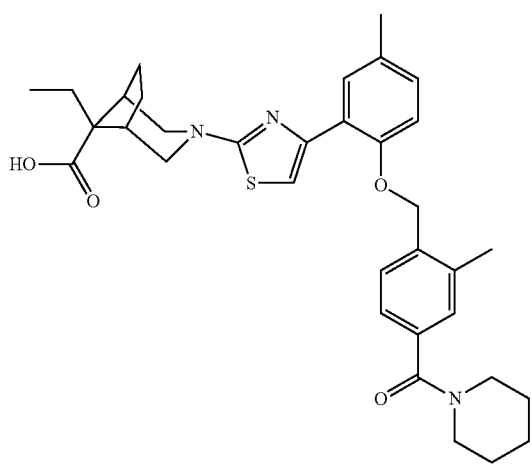 [SMILES: CCC1(C(=O)O)C2CCC1CN(c1nc(-c3cc(C)ccc3OCc3ccc(C(=O)N4CCCCC4)cc3C)cs1)C2] |
| 253 | 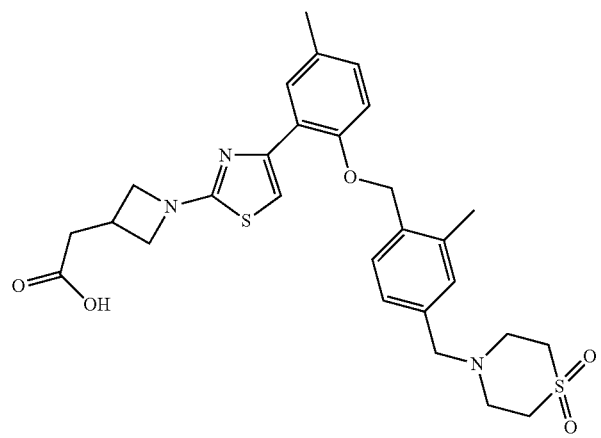 [SMILES: Cc1ccc(OCc2ccc(CN3CCS(=O)(=O)CC3)cc2C)c(-c2csc(N3CC(CC(=O)O)C3)n2)c1] |

| Cpd No. | |
|---|---|
| 254 | 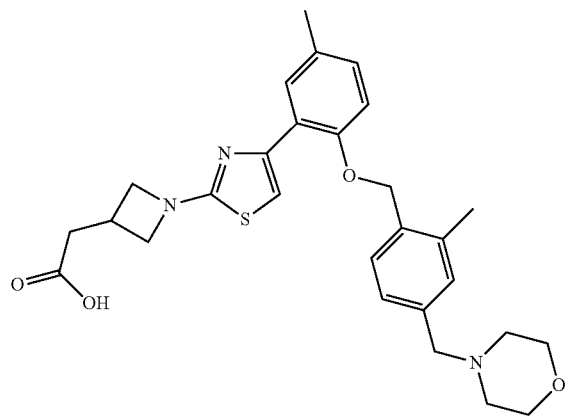 [SMILES: Cc1ccc(OCc2ccc(CN3CCOCC3)cc2C)c(-c2csc(N3CC(CC(=O)O)C3)n2)c1] |
| 255 | 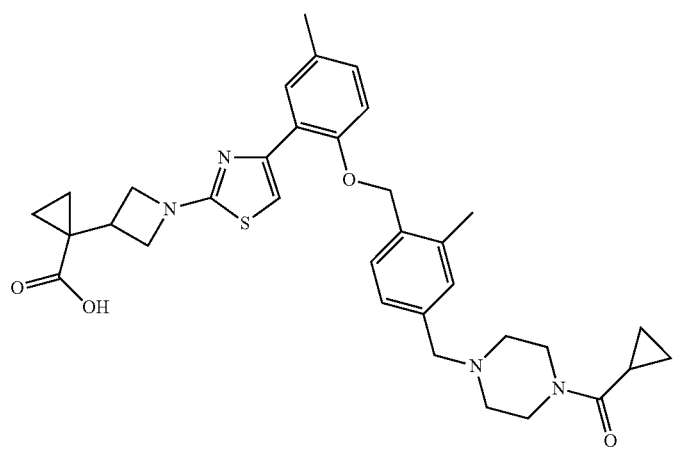 [SMILES: Cc1ccc(OCc2ccc(CN3CCN(C(=O)C4CC4)CC3)cc2C)c(-c2csc(N3CC(C4(C(=O)O)CC4)C3)n2)c1] |
| 256 | 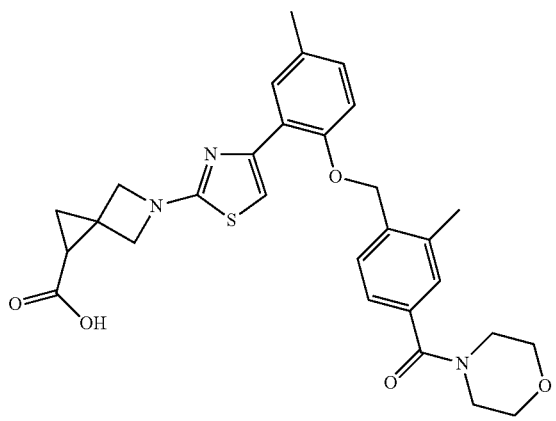 [SMILES: Cc1ccc(OCc2ccc(C(=O)N3CCOCC3)cc2C)c(-c2csc(N3CC4(CC4C(=O)O)C3)n2)c1] |

| Cpd No. | |
|---|---|
| 257 | 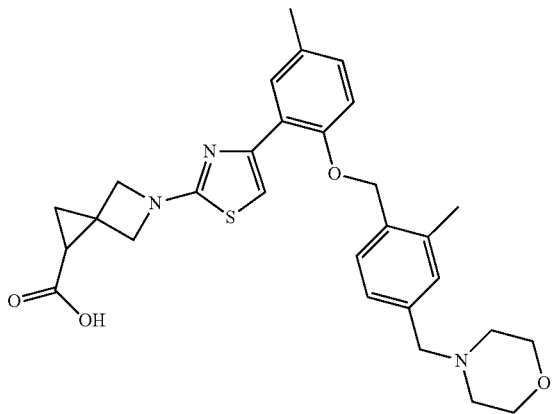 [SMILES: Cc1ccc(OCc2ccc(CN3CCOCC3)cc2C)c(-c2csc(N3CC4(CC4C(=O)O)C3)n2)c1] |
| 258 | 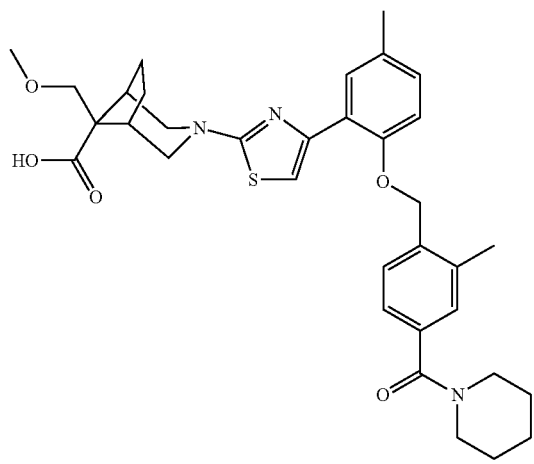 [SMILES: COCC1(C(=O)O)C2CCC1CN(c1nc(-c3cc(C)ccc3OCc3ccc(C(=O)N4CCCCC4)cc3C)cs1)C2] |
| 259 | 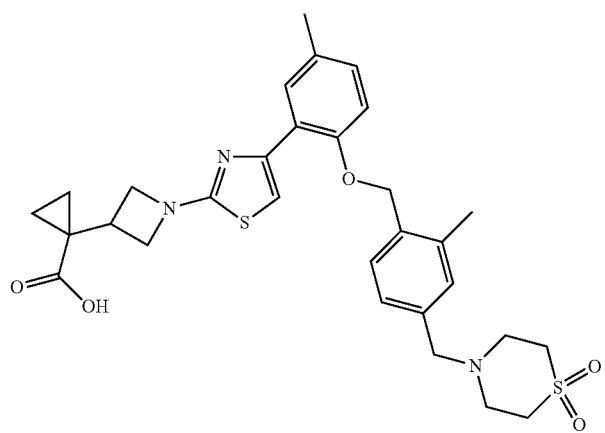 [SMILES: Cc1ccc(OCc2ccc(CN3CCS(=O)(=O)CC3)cc2C)c(-c2csc(N3CC(C4(C(=O)O)CC4)C3)n2)c1] |

| Cpd No. | |
|---|---|
| 260 | 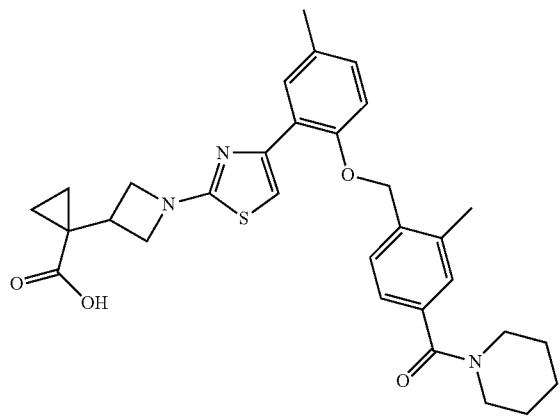 [SMILES: Cc1ccc(OCc2ccc(C(=O)N3CCCCC3)cc2C)c(-c2csc(N3CC(C4(C(=O)O)CC4)C3)n2)c1] |
| 261 | 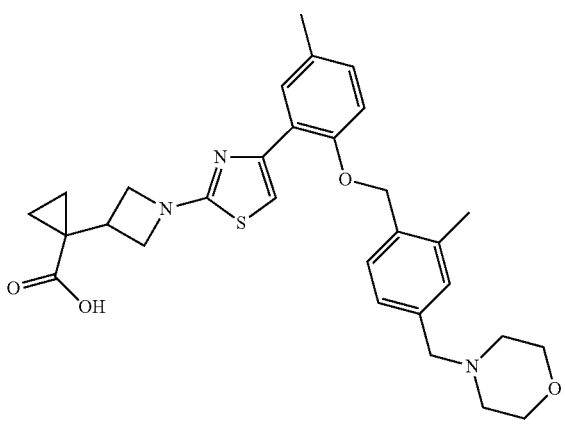 [SMILES: Cc1ccc(OCc2ccc(CN3CCOCC3)cc2C)c(-c2csc(N3CC(C4(C(=O)O)CC4)C3)n2)c1] |
| 262 | 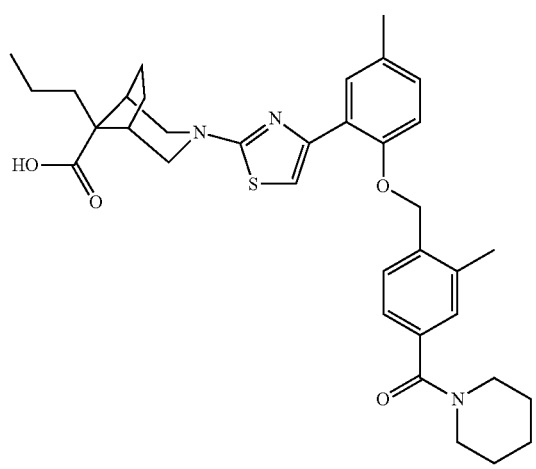 [SMILES: CCCC1(C(=O)O)C2CCC1CN(c1nc(-c3cc(C)ccc3OCc3ccc(C(=O)N4CCCCC4)cc3C)cs1)C2] |

| Cpd No. | |
|---|---|
| 263 | 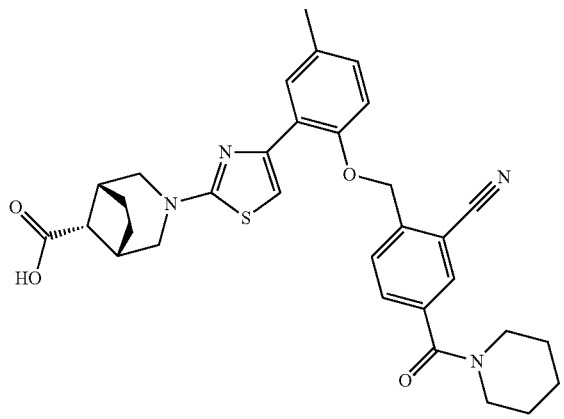 [SMILES: Cc1ccc(OCc2ccc(C(=O)N3CCCCC3)cc2C#N)c(-c2csc(N3C[C@H]4CC[C@@H](C3)[C@H]4C(=O)O)n2)c1] |
| 264 | 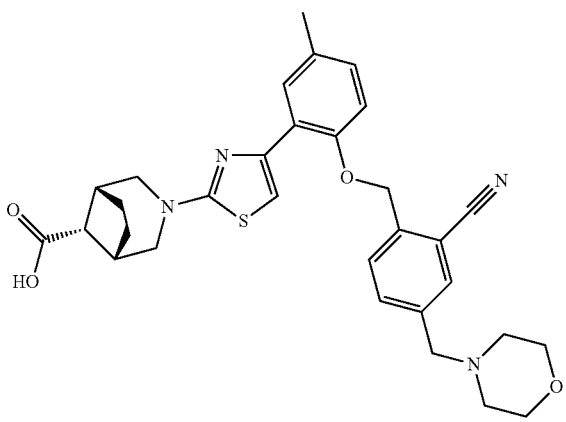 [SMILES: Cc1ccc(OCc2ccc(CN3CCOCC3)cc2C#N)c(-c2csc(N3C[C@H]4CC[C@@H](C3)[C@H]4C(=O)O)n2)c1] |
| 265 | 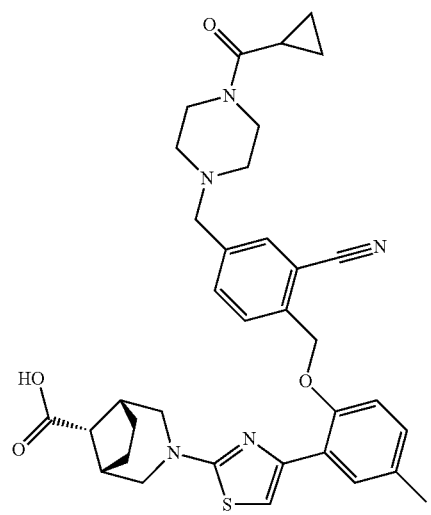 [SMILES: Cc1ccc(OCc2ccc(CN3CCN(C(=O)C4CC4)CC3)cc2C#N)c(-c2csc(N3C[C@H]4CC[C@@H](C3)[C@H]4C(=O)O)n2)c1] |

| Cpd No. | |
|---|---|
| 266 | 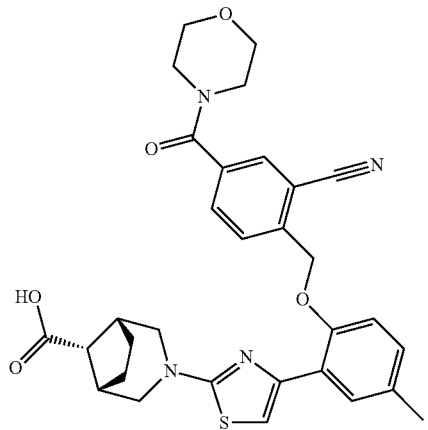 [SMILES: Cc1ccc(OCc2ccc(C(=O)N3CCOCC3)cc2C#N)c(-c2csc(N3C[C@H]4CC[C@@H](C3)[C@H]4C(=O)O)n2)c1] |
| 267 | 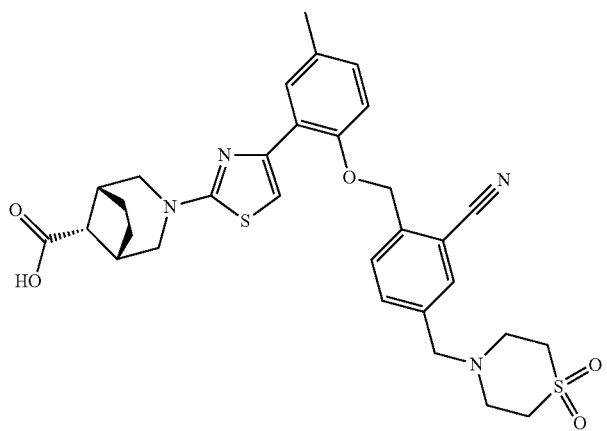 [SMILES: Cc1ccc(OCc2ccc(CN3CCS(=O)(=O)CC3)cc2C#N)c(-c2csc(N3C[C@H]4CC[C@@H](C3)[C@H]4C(=O)O)n2)c1] |
| 268 | 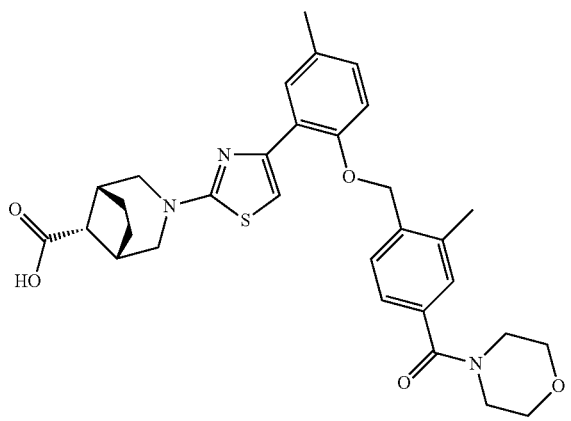 [SMILES: Cc1ccc(OCc2ccc(C(=O)N3CCOCC3)cc2C)c(-c2csc(N3C[C@H]4CC[C@@H](C3)[C@H]4C(=O)O)n2)c1] |

| Cpd No. | |
|---|---|
| 269 | 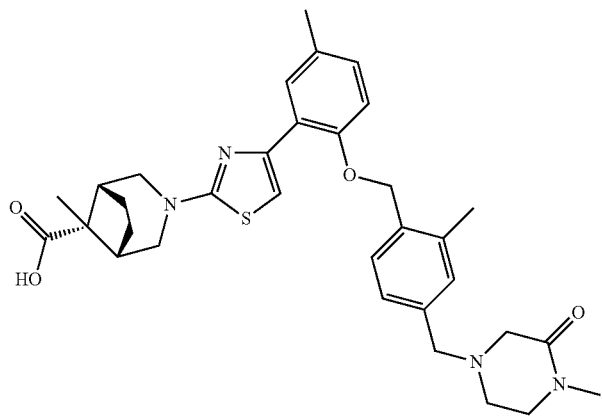 [SMILES: Cc1ccc(OCc2ccc(CN3CCN(C)C(=O)C3)cc2C)c(-c2csc(N3C[C@H]4CC[C@@H](C3)[C@@]4(C)C(=O)O)n2)c1] |
| 270 | 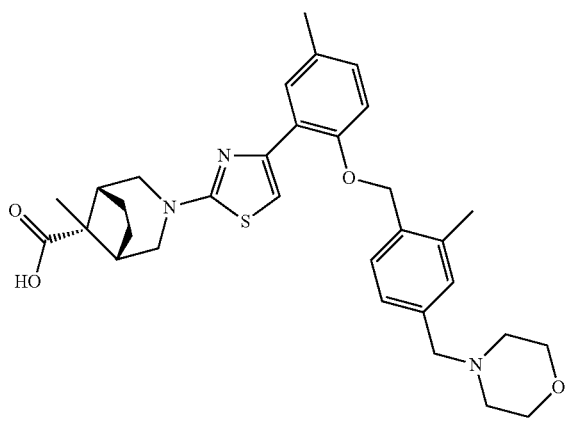 [SMILES: Cc1ccc(OCc2ccc(CN3CCOCC3)cc2C)c(-c2csc(N3C[C@H]4CC[C@@H](C3)[C@@]4(C)C(=O)O)n2)c1] |
| 271 | 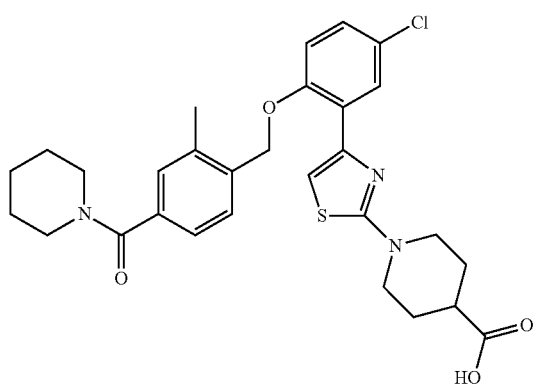 |
| 272 | 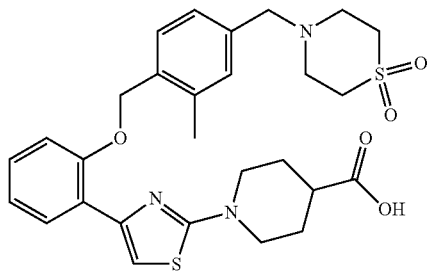 [SMILES: Cc1cc(CN2CCS(=O)(=O)CC2)ccc1COc1ccccc1-c1csc(N2CCC(C(=O)O)CC2)n1] |

| Cpd No. | |
|---|---|
| 273 | 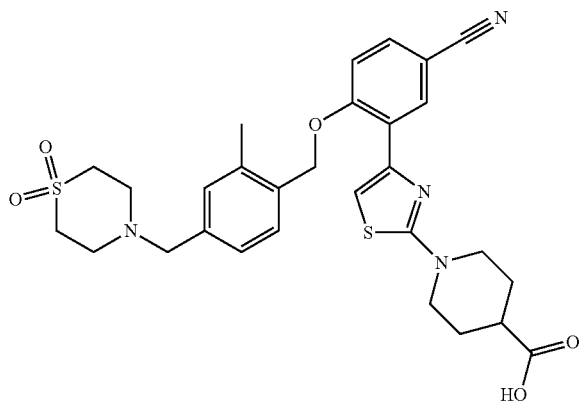 [SMILES: Cc1cc(CN2CCS(=O)(=O)CC2)ccc1COc1ccc(C#N)cc1-c1csc(N2CCC(C(=O)O)CC2)n1] |
| 274 | 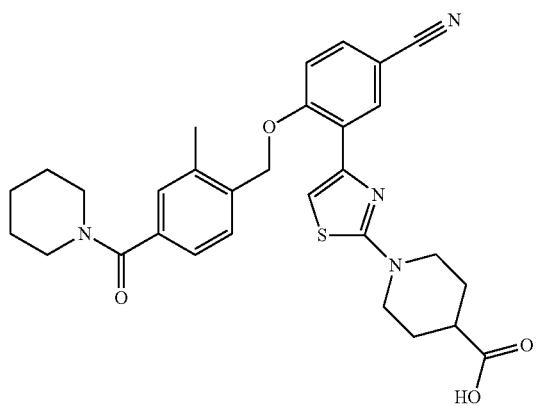 [SMILES: Cc1cc(C(=O)N2CCCCC2)ccc1COc1ccc(C#N)cc1-c1csc(N2CCC(C(=O)O)CC2)n1] |
| 275 | 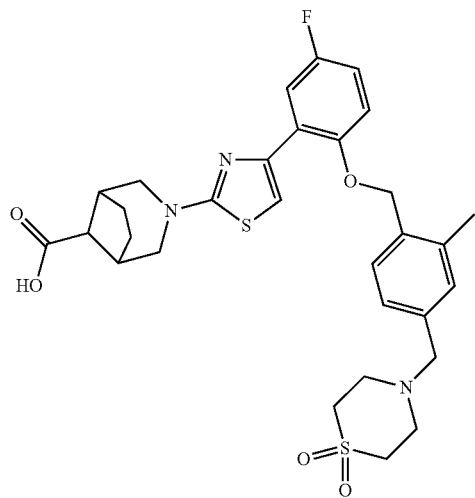 [SMILES: Cc1cc(CN2CCS(=O)(=O)CC2)ccc1COc1ccc(F)cc1-c1csc(N2CC3CCC(C2)C3C(=O)O)n1] |

| Cpd No. | |
|---|---|
| 276 | 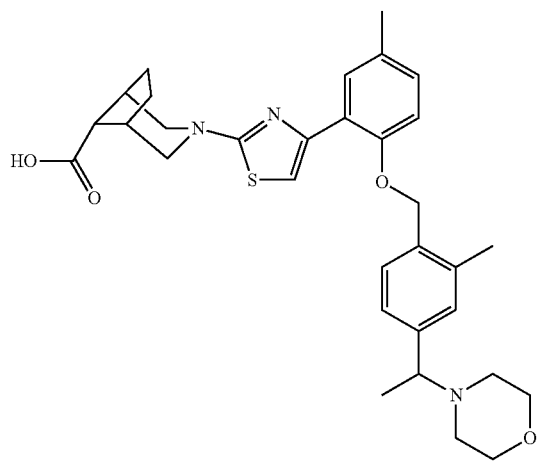 [SMILES: Cc1ccc(OCc2ccc(C(C)N3CCOCC3)cc2C)c(-c2csc(N3CC4CCC(C3)C4C(=O)O)n2)c1] |
| 277 | 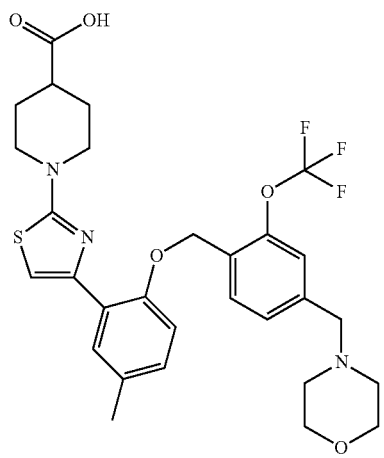 [SMILES: Cc1ccc(OCc2ccc(CN3CCOCC3)cc2OC(F)(F)F)c(-c2csc(N3CCC(C(=O)O)CC3)n2)c1] |
| 278 | 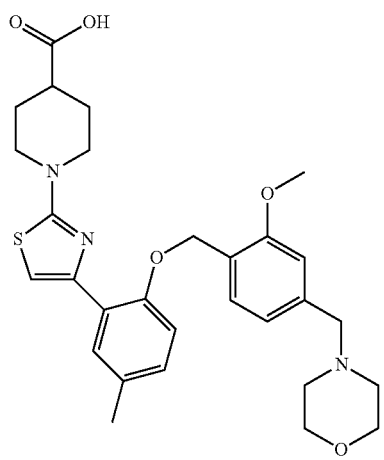 [SMILES: COc1cc(CN2CCOCC2)ccc1COc1ccc(C)cc1-c1csc(N2CCC(C(=O)O)CC2)n1] |

| Cpd No. | |
|---|---|
| 279 | 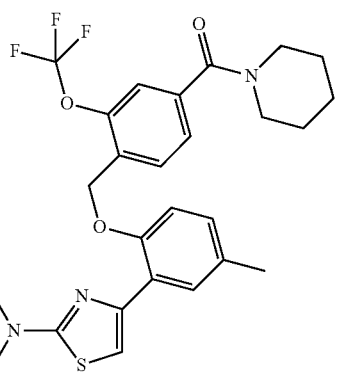 |
| 280 | 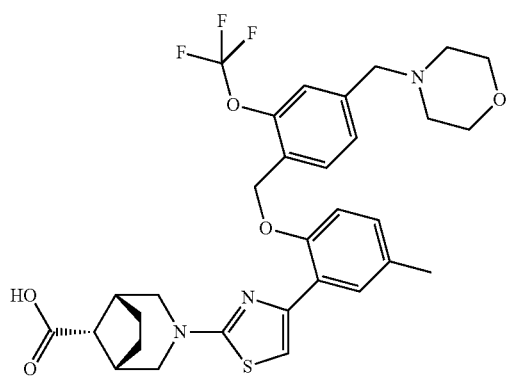 [SMILES: Cc1ccc(OCc2ccc(CN3CCOCC3)cc2OC(F)(F)F)c(-c2csc(N3C[C@H]4CC[C@@H](C3)[C@H]4C(=O)O)n2)c1] |
| 281 | 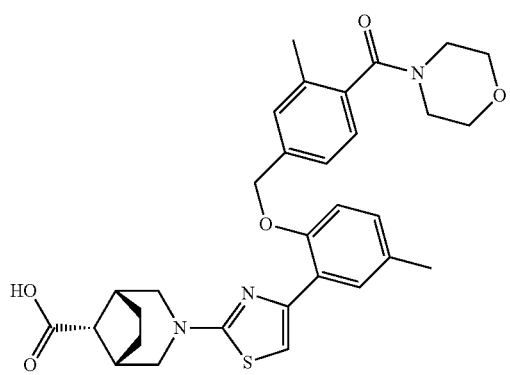 [SMILES: Cc1ccc(OCc2ccc(C(=O)N3CCOCC3)c(C)c2)c(-c2csc(N3C[C@H]4CC[C@@H](C3)[C@H]4C(=O)O)n2)c1] |
| 282 | 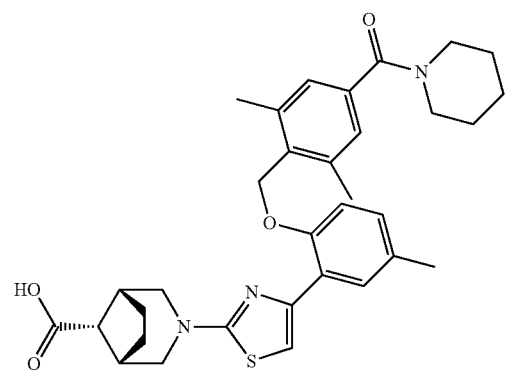 [SMILES: Cc1ccc(OCc2c(C)cc(C(=O)N3CCCCC3)cc2C)c(-c2csc(N3C[C@H]4CC[C@@H](C3)[C@H]4C(=O)O)n2)c1] |

| Cpd No. | |
|---|---|
| 283 | 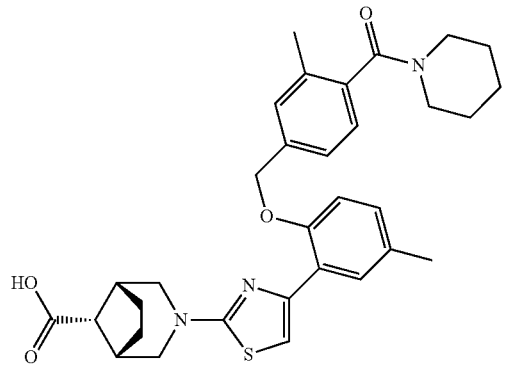 [SMILES: Cc1ccc(OCc2ccc(C(=O)N3CCCCC3)c(C)c2)c(-c2csc(N3C[C@H]4CC[C@@H](C3)[C@H]4C(=O)O)n2)c1] |
| 284 | 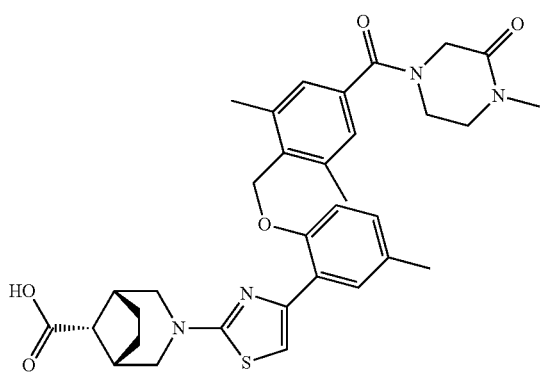 [SMILES: Cc1ccc(OCc2c(C)cc(C(=O)N3CCN(C)C(=O)C3)cc2C)c(-c2csc(N3C[C@H]4CC[C@@H](C3)[C@H]4C(=O)O)n2)c1] |
| 285 | 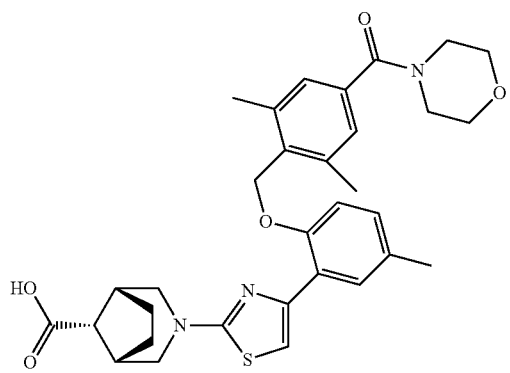 [SMILES: Cc1ccc(OCc2c(C)cc(C(=O)N3CCOCC3)cc2C)c(-c2csc(N3C[C@H]4CC[C@@H](C3)[C@H]4C(=O)O)n2)c1] |
| 286 | 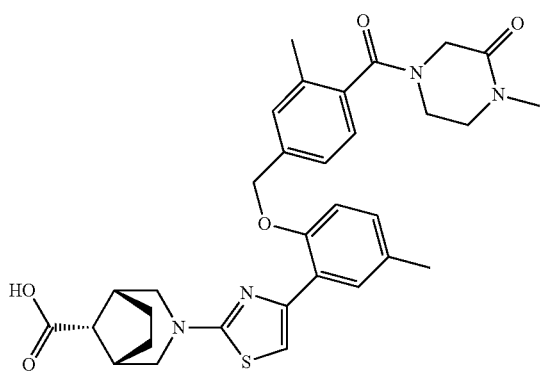 [SMILES: Cc1ccc(OCc2ccc(C(=O)N3CCN(C)C(=O)C3)c(C)c2)c(-c2csc(N3C[C@H]4CC[C@@H](C3)[C@H]4C(=O)O)n2)c1] |

| Cpd No. | |
|---|---|
| 287 | 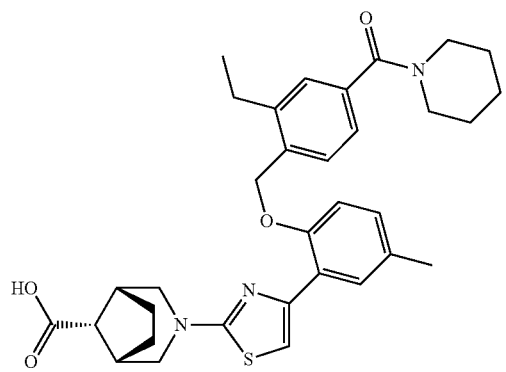 [SMILES: CCc1cc(C(=O)N2CCCCC2)ccc1COc1ccc(C)cc1-c1csc(N2C[C@H]3CC[C@@H](C2)[C@H]3C(=O)O)n1] |
| 288 | 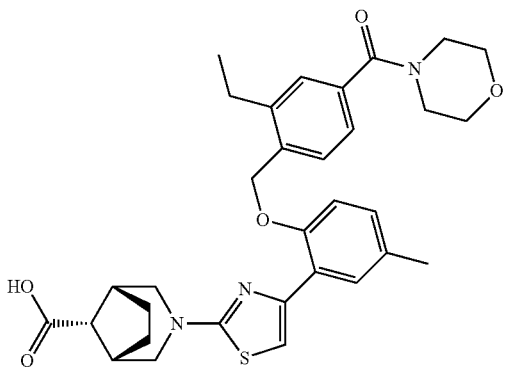 [SMILES: CCc1cc(C(=O)N2CCOCC2)ccc1COc1ccc(C)cc1-c1csc(N2C[C@H]3CC[C@@H](C2)[C@H]3C(=O)O)n1] |
| 289 | 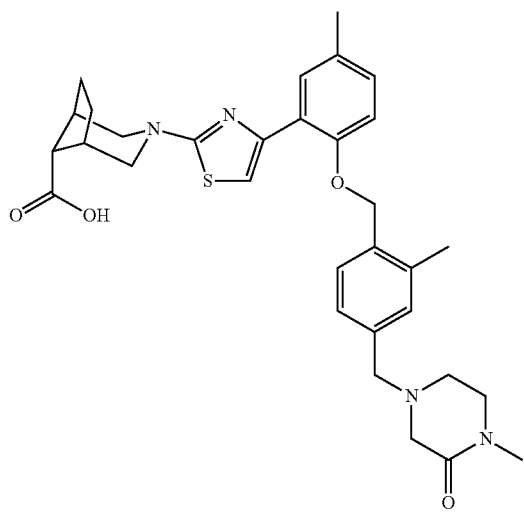 [SMILES: Cc1ccc(OCc2ccc(CN3CCN(C)C(=O)C3)cc2C)c(-c2csc(N3CC4CCC(C3)C4C(=O)O)n2)c1] |

| Cpd No. | |
|---|---|
| 290 | 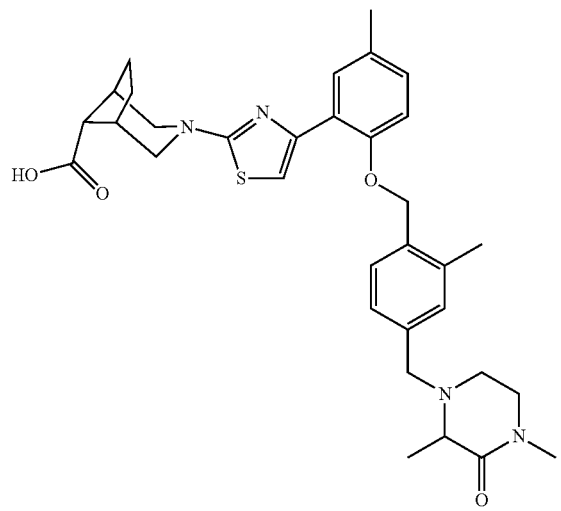 [SMILES: Cc1ccc(OCc2ccc(CN3CCN(C)C(=O)C3C)cc2C)c(-c2csc(N3CC4CCC(C3)C4C(=O)O)n2)c1] |
| 291 | 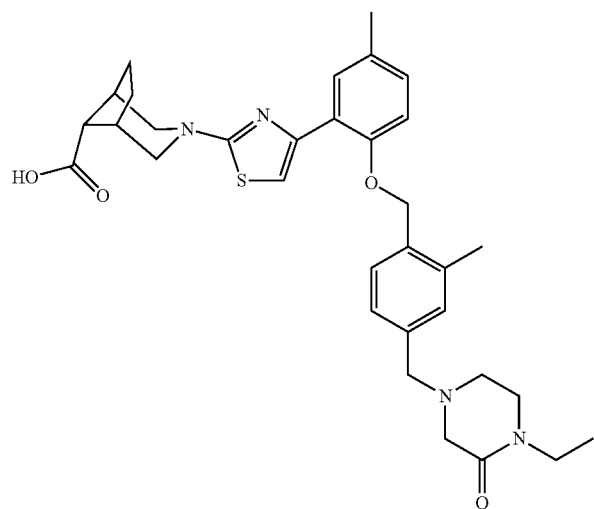 [SMILES: CCN1CCN(Cc2ccc(COc3ccc(C)cc3-c3csc(N4CC5CCC(C4)C5C(=O)O)n3)c(C)c2)CC1=O] |
| 292 | 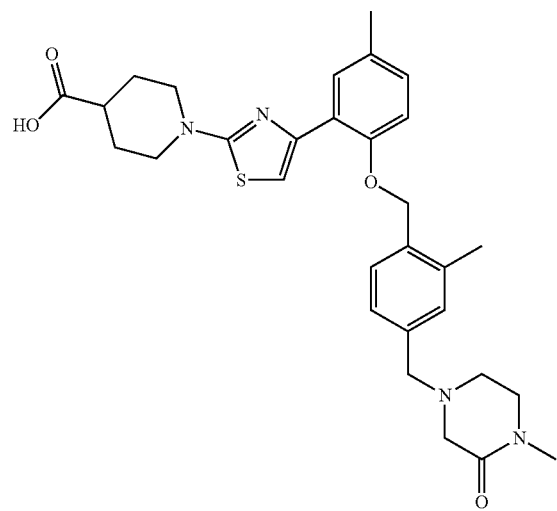 [SMILES: Cc1ccc(OCc2ccc(CN3CCN(C)C(=O)C3)cc2C)c(-c2csc(N3CCC(C(=O)O)CC3)n2)c1] |

-continued
| Cpd No. |
|---|
| 293 |
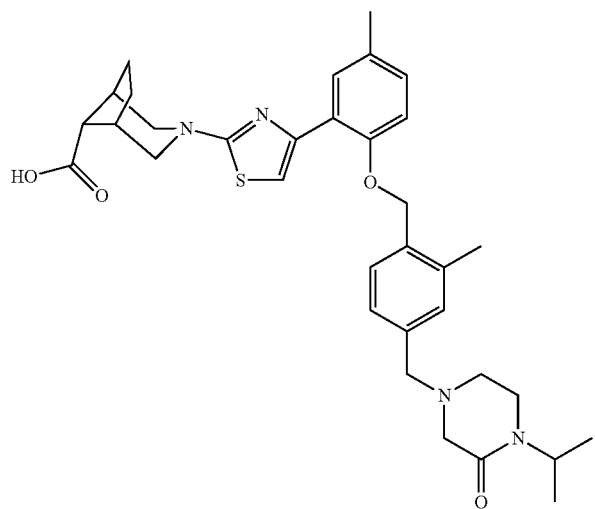 [SMILES: Cc1ccc(OCc2ccc(CN3CCN(C(C)C)C(=O)C3)cc2C)c(-c2csc(N3CC4CCC(C3)C4C(=O)O)n2)c1]
294
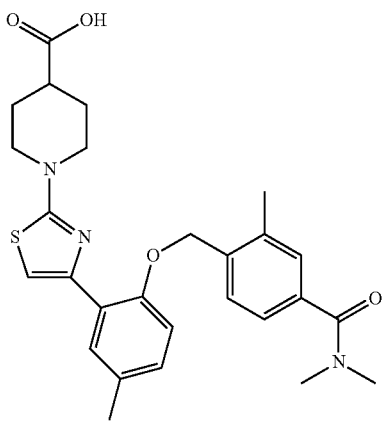 [SMILES: Cc1ccc(OCc2ccc(C(=O)N(C)C)cc2C)c(-c2csc(N3CCC(C(=O)O)CC3)n2)c1]
295
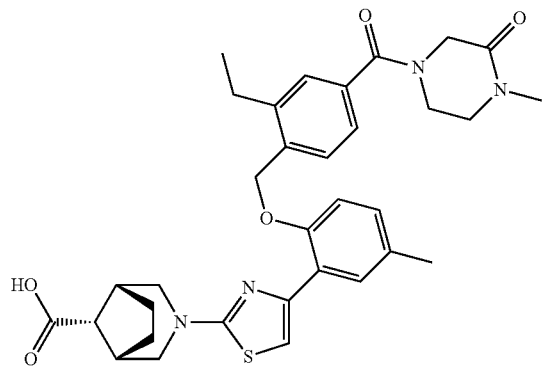 [SMILES: CCc1cc(C(=O)N2CCN(C)C(=O)C2)ccc1COc1ccc(C)cc1-c1csc(N2C[C@H]3CC[C@@H](C2)[C@H]3C(=O)O)n1]

-continued
| Cpd No. | |
|---|---|
| 296 | 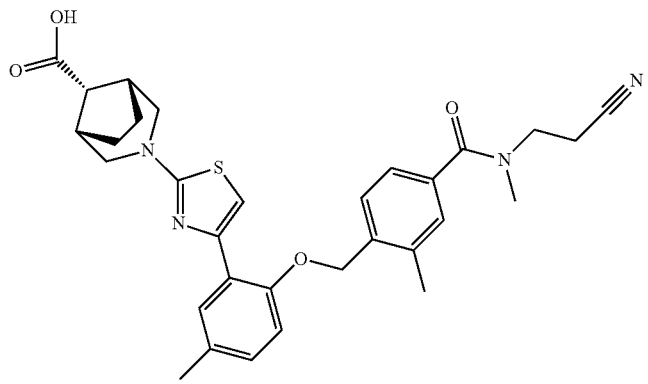 [SMILES: Cc1ccc(OCc2ccc(C(=O)N(C)CCC#N)cc2C)c(-c2csc(N3C[C@H]4CC[C@@H](C3)[C@H]4C(=O)O)n2)c1] |
| 297 | 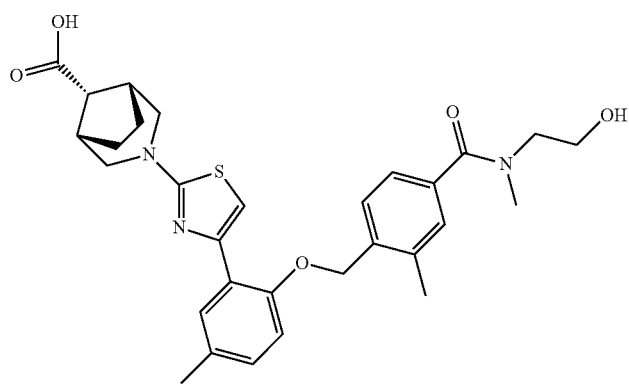 [SMILES: Cc1ccc(OCc2ccc(C(=O)N(C)CCO)cc2C)c(-c2csc(N3C[C@H]4CC[C@@H](C3)[C@H]4C(=O)O)n2)c1] |
| 298 | 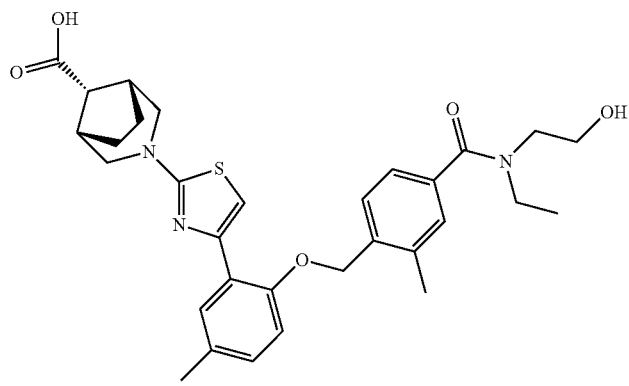 [SMILES: CCN(CCO)C(=O)c1ccc(COc2ccc(C)cc2-c2csc(N3C[C@H]4CC[C@@H](C3)[C@H]4C(=O)O)n2)c(C)c1] |
| 299 | 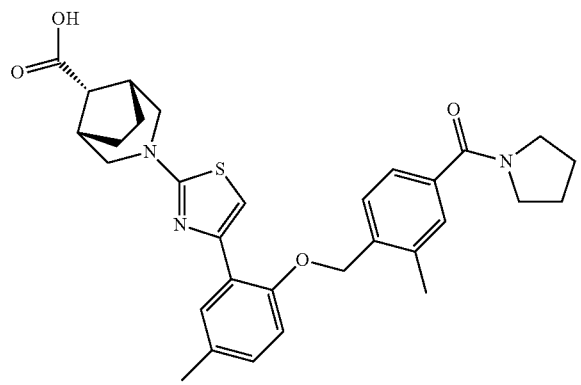 [SMILES: Cc1ccc(OCc2ccc(C(=O)N3CCCC3)cc2C)c(-c2csc(N3C[C@H]4CC[C@@H](C3)[C@H]4C(=O)O)n2)c1] |

| Cpd No. | |
|---|---|
| 300 | 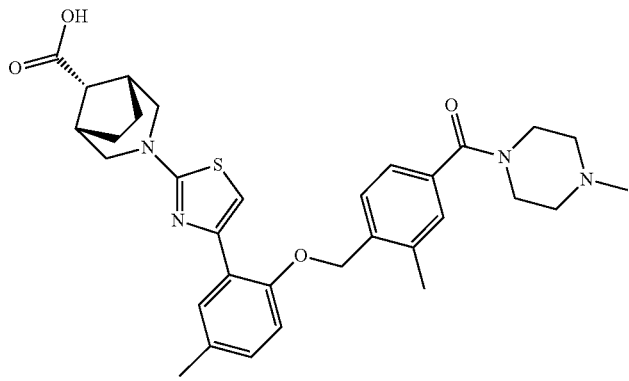 [SMILES: Cc1ccc(OCc2ccc(C(=O)N3CCN(C)CC3)cc2C)c(-c2csc(N3C[C@H]4CC[C@@H](C3)[C@H]4C(=O)O)n2)c1] |
| 301 | 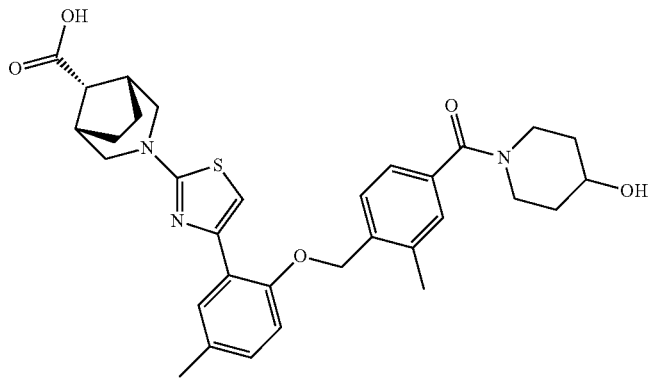 [SMILES: Cc1ccc(OCc2ccc(C(=O)N3CCC(O)CC3)cc2C)c(-c2csc(N3C[C@H]4CC[C@@H](C3)[C@H]4C(=O)O)n2)c1] |
| 302 | 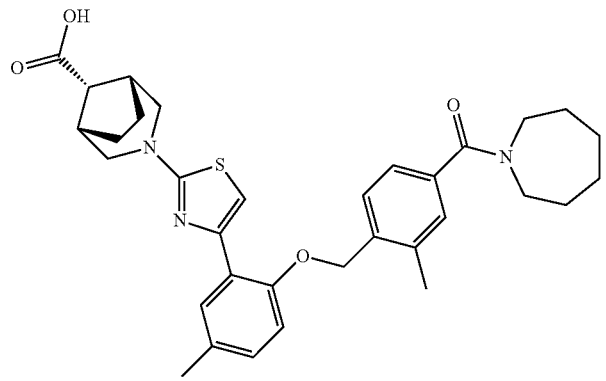 [SMILES: Cc1ccc(OCc2ccc(C(=O)N3CCCCCC3)cc2C)c(-c2csc(N3C[C@H]4CC[C@@H](C3)[C@H]4C(=O)O)n2)c1] |
| 303 | 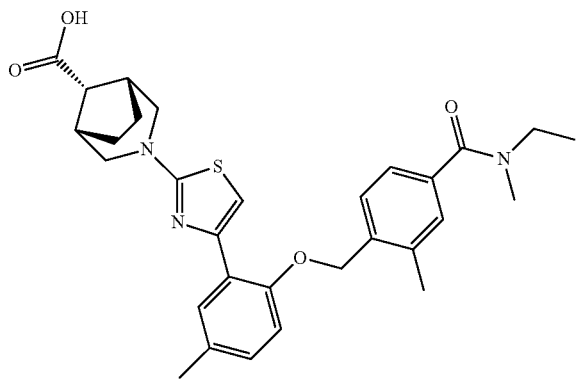 [SMILES: CCN(C)C(=O)c1ccc(COc2ccc(C)cc2-c2csc(N3C[C@H]4CC[C@@H](C3)[C@H]4C(=O)O)n2)c(C)c1] |

| Cpd No. | |
|---|---|
| 304 | 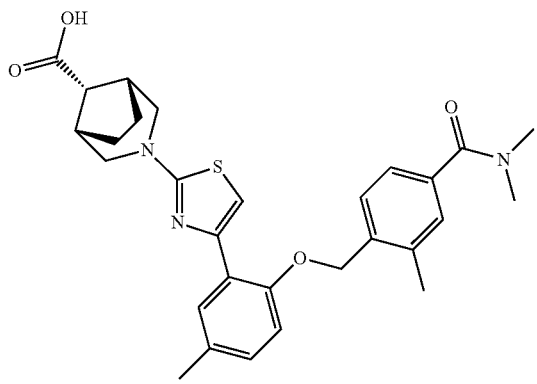 [SMILES: Cc1ccc(OCc2ccc(C(=O)N(C)C)cc2C)c(-c2csc(N3C[C@H]4CC[C@@H](C3)[C@H]4C(=O)O)n2)c1] |
| 305 | 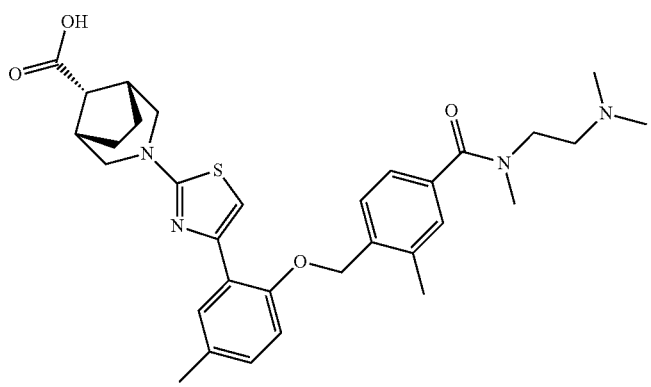 [SMILES: Cc1ccc(OCc2ccc(C(=O)N(C)CCN(C)C)cc2C)c(-c2csc(N3C[C@H]4CC[C@@H](C3)[C@H]4C(=O)O)n2)c1] |
| 306 | 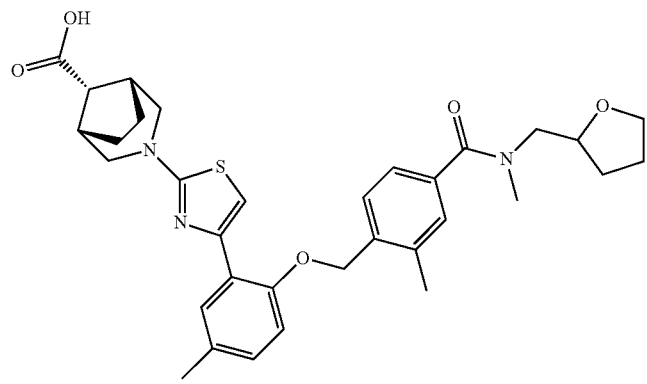 [SMILES: Cc1ccc(OCc2ccc(C(=O)N(C)CC3CCCO3)cc2C)c(-c2csc(N3C[C@H]4CC[C@@H](C3)[C@H]4C(=O)O)n2)c1] |
| 307 | 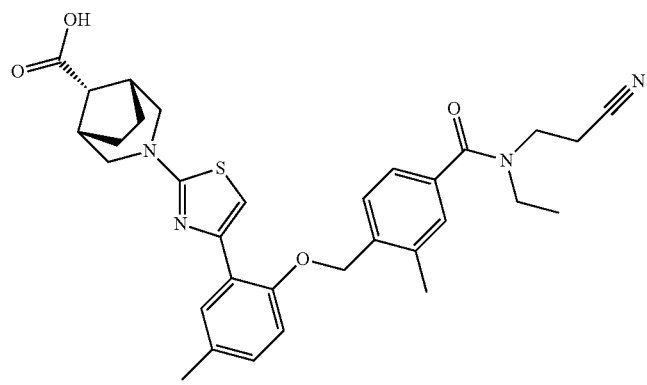 [SMILES: CCN(CCC#N)C(=O)c1ccc(COc2ccc(C)cc2-c2csc(N3C[C@H]4CC[C@@H](C3)[C@H]4C(=O)O)n2)c(C)c1] |

| Cpd No. | |
|---|---|
| 308 | 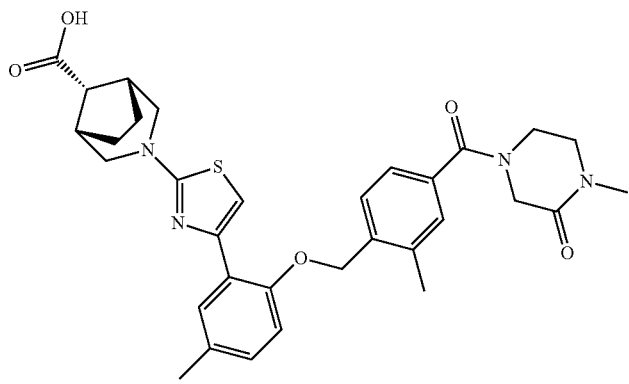 [SMILES: Cc1ccc(OCc2ccc(C(=O)N3CCN(C)C(=O)C3)cc2C)c(-c2csc(N3C[C@H]4CC[C@@H](C3)[C@H]4C(=O)O)n2)c1] |
| 309 | 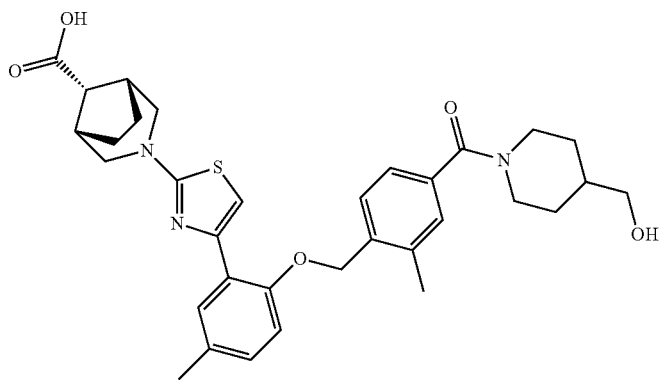 [SMILES: Cc1ccc(OCc2ccc(C(=O)N3CCC(CO)CC3)cc2C)c(-c2csc(N3C[C@H]4CC[C@@H](C3)[C@H]4C(=O)O)n2)c1] |
| 310 | 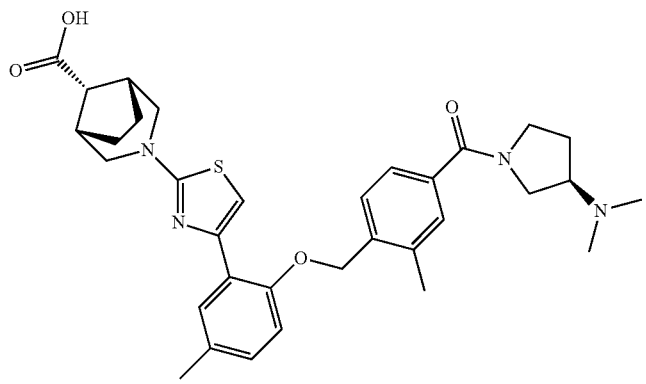 [SMILES: Cc1ccc(OCc2ccc(C(=O)N3CC[C@@H](N(C)C)C3)cc2C)c(-c2csc(N3C[C@H]4CC[C@@H](C3)[C@H]4C(=O)O)n2)c1] |
| 311 | 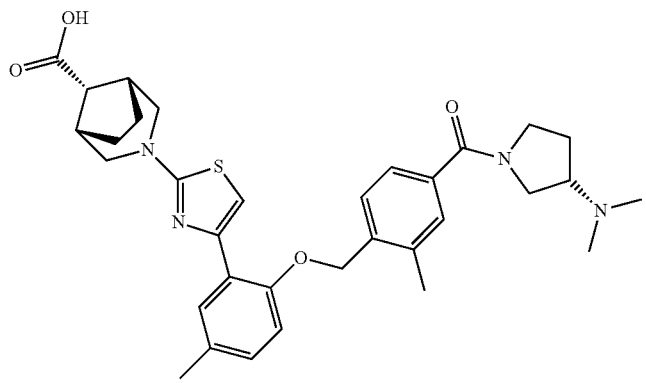 |

-continued
| Cpd No. | |
|---|---|
| 312 | 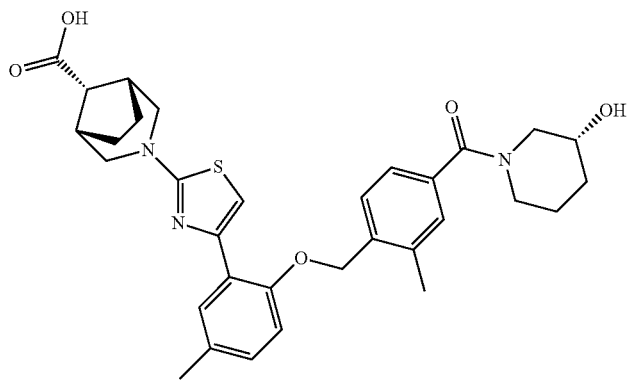 [SMILES: Cc1ccc(OCc2ccc(C(=O)N3CCC[C@@H](O)C3)cc2C)c(-c2csc(N3C[C@H]4CC[C@@H](C3)[C@H]4C(=O)O)n2)c1] |
| 313 | 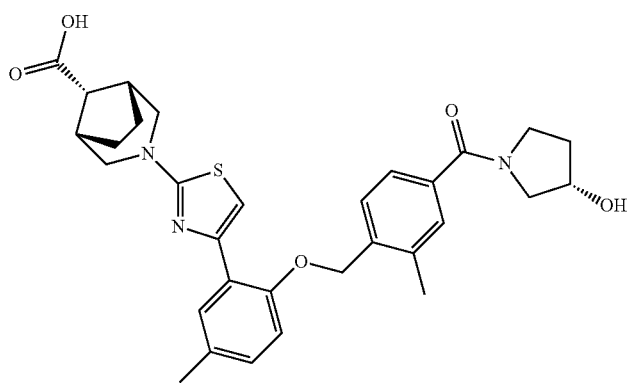 [SMILES: Cc1ccc(OCc2ccc(C(=O)N3CC[C@H](O)C3)cc2C)c(-c2csc(N3C[C@H]4CC[C@@H](C3)[C@H]4C(=O)O)n2)c1] |
| 314 | 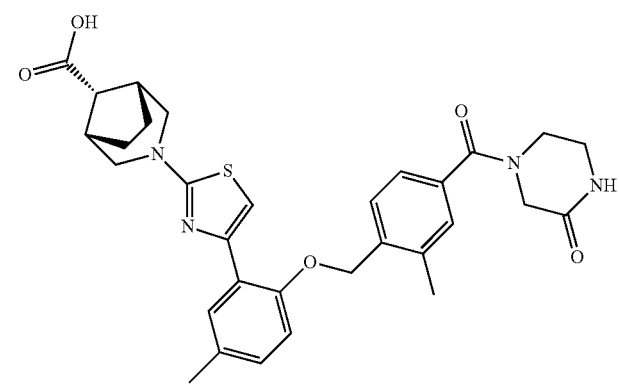 [SMILES: Cc1ccc(OCc2ccc(C(=O)N3CCNC(=O)C3)cc2C)c(-c2csc(N3C[C@H]4CC[C@@H](C3)[C@H]4C(=O)O)n2)c1] |
| 315 | 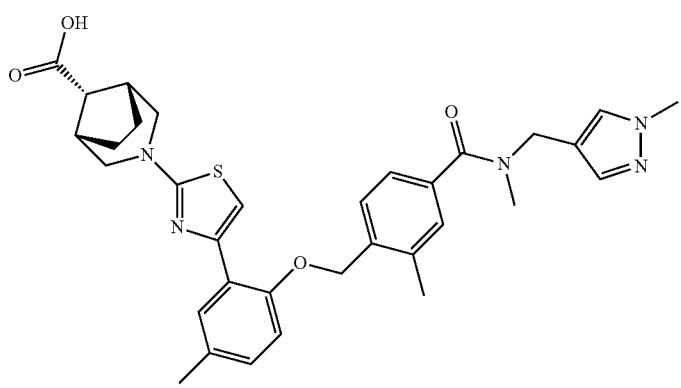 [SMILES: Cc1ccc(OCc2ccc(C(=O)N(C)Cc3cnn(C)c3)cc2C)c(-c2csc(N3C[C@H]4CC[C@@H](C3)[C@H]4C(=O)O)n2)c1] |

| Cpd No. | |
|---|---|
| 316 | 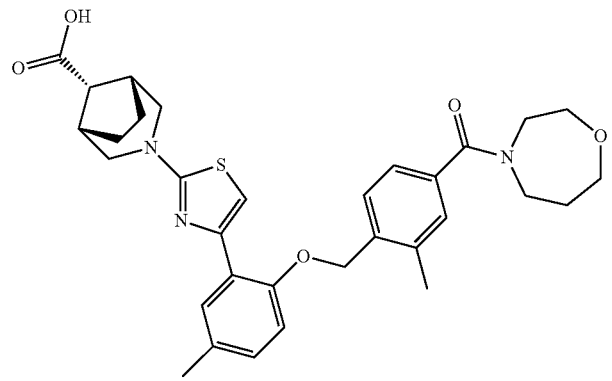 [SMILES: Cc1ccc(OCc2ccc(C(=O)N3CCCOCC3)cc2C)c(-c2csc(N3C[C@H]4CC[C@@H](C3)[C@H]4C(=O)O)n2)c1] |
| 317 | 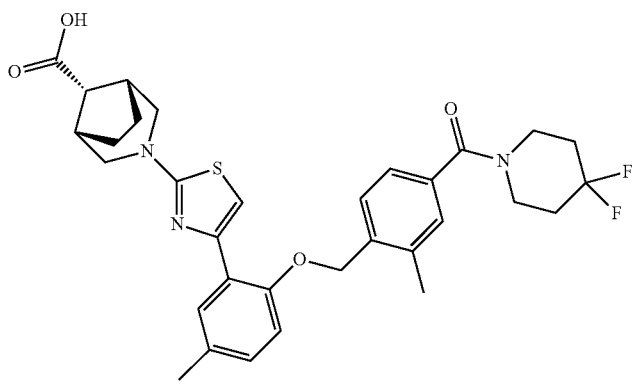 [SMILES: Cc1ccc(OCc2ccc(C(=O)N3CCC(F)(F)CC3)cc2C)c(-c2csc(N3C[C@H]4CC[C@@H](C3)[C@H]4C(=O)O)n2)c1] |
| 318 | 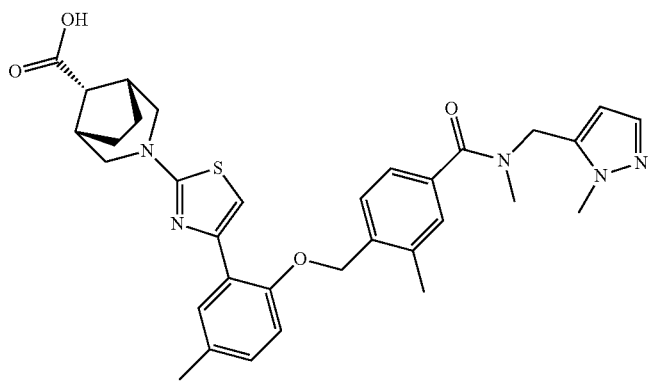 [SMILES: Cc1ccc(OCc2ccc(C(=O)N(C)Cc3ccnn3C)cc2C)c(-c2csc(N3C[C@H]4CC[C@@H](C3)[C@H]4C(=O)O)n2)c1] |
| 319 | 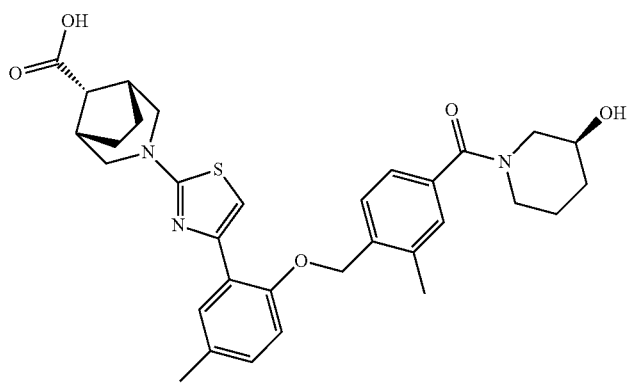 [SMILES: Cc1ccc(OCc2ccc(C(=O)N3CCC[C@H](O)C3)cc2C)c(-c2csc(N3C[C@H]4CC[C@@H](C3)[C@H]4C(=O)O)n2)c1] |

-continued
| Cpd No. |
|---|
| 320 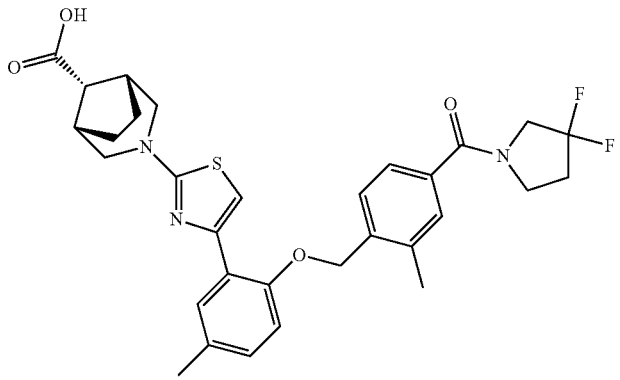 [SMILES: Cc1ccc(OCc2ccc(C(=O)N3CCC(F)(F)C3)cc2C)c(-c2csc(N3C[C@H]4CC[C@@H](C3)[C@H]4C(=O)O)n2)c1] |
| 321 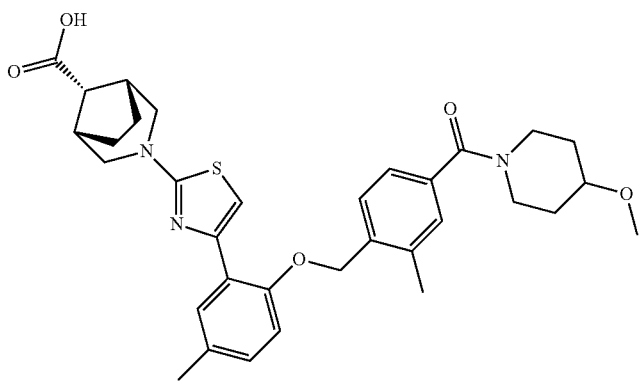 [SMILES: COC1CCN(C(=O)c2ccc(COc3ccc(C)cc3-c3csc(N4C[C@H]5CC[C@@H](C4)[C@H]5C(=O)O)n3)c(C)c2)CC1] |
| 322 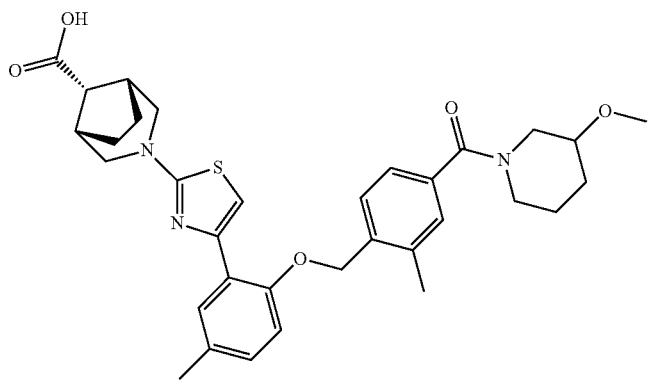 [SMILES: COC1CCCN(C(=O)c2ccc(COc3ccc(C)cc3-c3csc(N4C[C@H]5CC[C@@H](C4)[C@H]5C(=O)O)n3)c(C)c2)C1] |
| 323 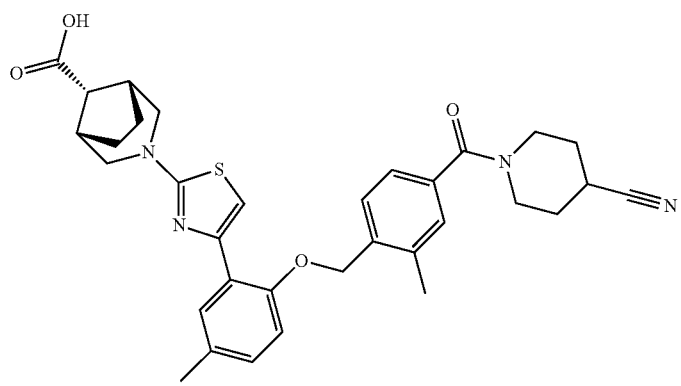 [SMILES: Cc1ccc(OCc2ccc(C(=O)N3CCC(C#N)CC3)cc2C)c(-c2csc(N3C[C@H]4CC[C@@H](C3)[C@H]4C(=O)O)n2)c1] |

| Cpd No. | |
|---|---|
| 324 | 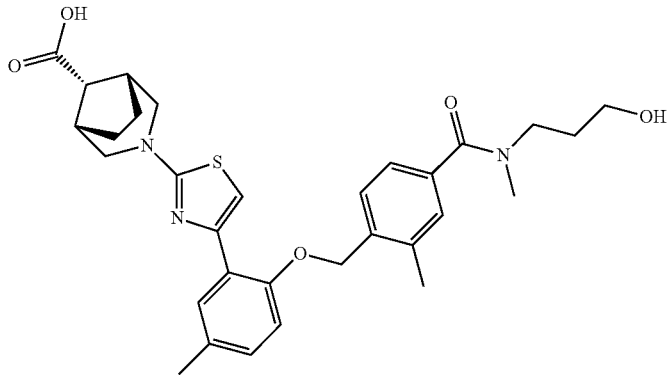 [SMILES: Cc1ccc(OCc2ccc(C(=O)N(C)CCCO)cc2C)c(-c2csc(N3C[C@H]4CC[C@@H](C3)[C@H]4C(=O)O)n2)c1] |
| 325 | 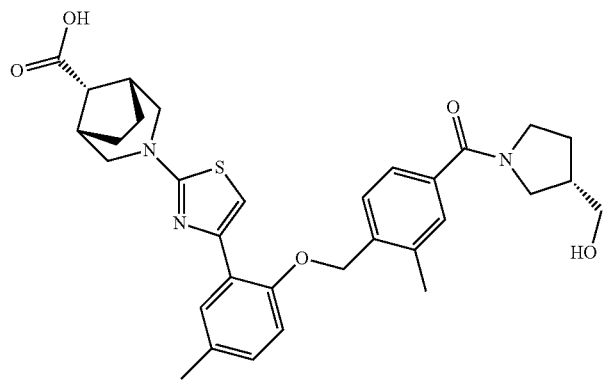 [SMILES: Cc1ccc(OCc2ccc(C(=O)N3CC[C@H](CO)C3)cc2C)c(-c2csc(N3C[C@H]4CC[C@@H](C3)[C@H]4C(=O)O)n2)c1] |
| 326 | 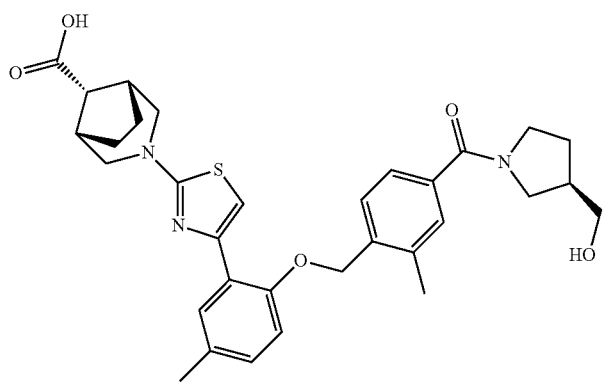 [SMILES: Cc1ccc(OCc2ccc(C(=O)N3CC[C@@H](CO)C3)cc2C)c(-c2csc(N3C[C@H]4CC[C@@H](C3)[C@H]4C(=O)O)n2)c1] |

| Cpd No. | |
|---|---|
| 327 | 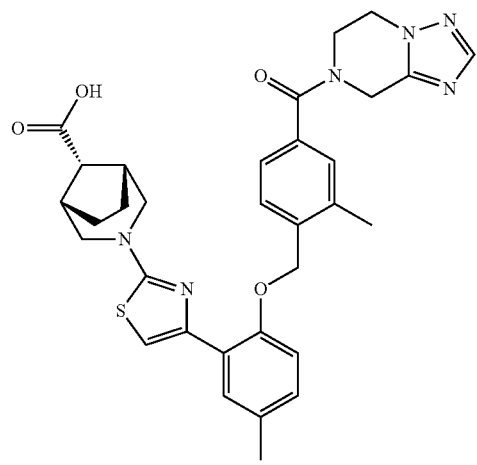 [SMILES: Cc1ccc(OCc2ccc(C(=O)N3CCn4ncnc4C3)cc2C)c(-c2csc(N3C[C@H]4CC[C@@H](C3)[C@H]4C(=O)O)n2)c1] |
| 328 | 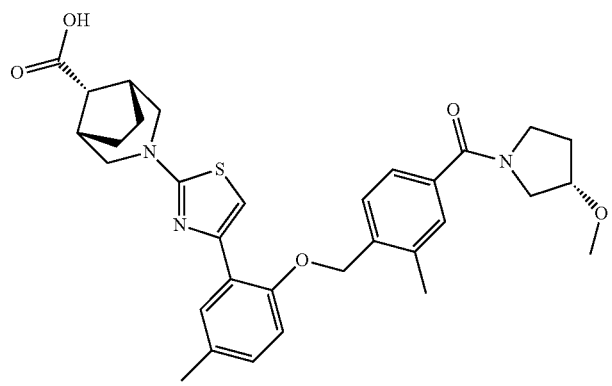 [SMILES: CO[C@H]1CCN(C(=O)c2ccc(COc3ccc(C)cc3-c3csc(N4C[C@H]5CC[C@@H](C4)[C@H]5C(=O)O)n3)c(C)c2)C1] |
| 329 | 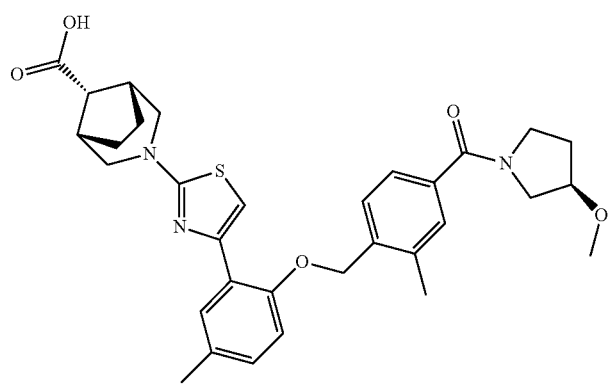 [SMILES: CO[C@@H]1CCN(C(=O)c2ccc(COc3ccc(C)cc3-c3csc(N4C[C@H]5CC[C@@H](C4)[C@H]5C(=O)O)n3)c(C)c2)C1] |

| Cpd No. | |
|---|---|
| 330 | 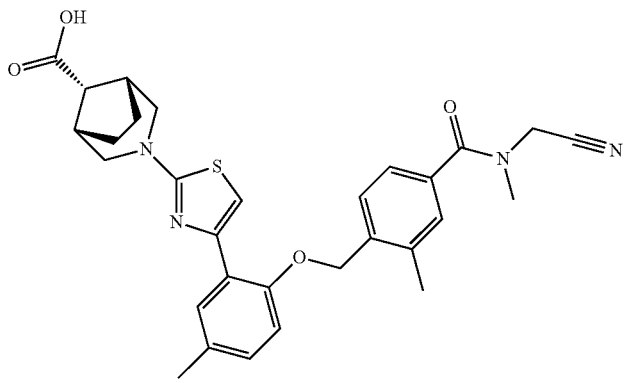 [SMILES: Cc1ccc(OCc2ccc(C(=O)N(C)CC#N)cc2C)c(-c2csc(N3C[C@H]4CC[C@@H](C3)[C@H]4C(=O)O)n2)c1] |
| 331 | 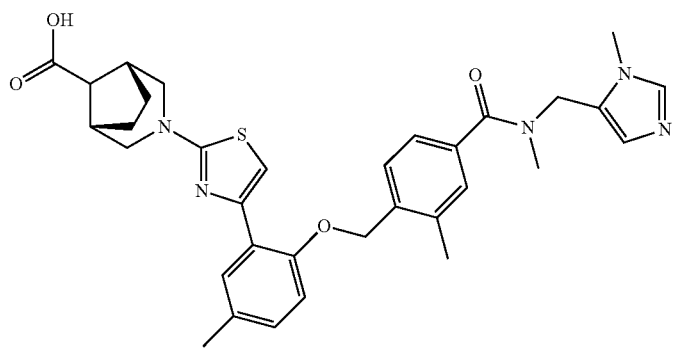 [SMILES: Cc1ccc(OCc2ccc(C(=O)N(C)Cc3cncn3C)cc2C)c(-c2csc(N3C[C@H]4CC[C@@H](C3)C4C(=O)O)n2)c1] |
| 332 | 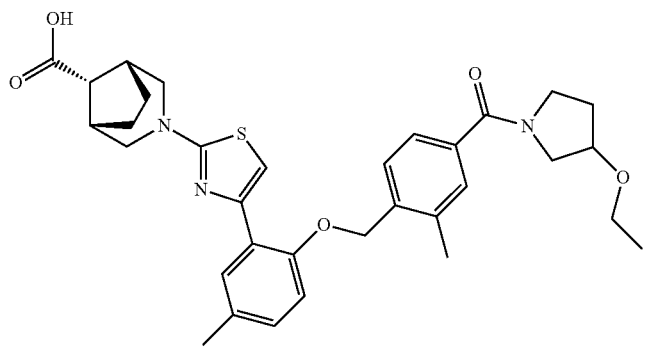 [SMILES: CCOC1CCN(C(=O)c2ccc(COc3ccc(C)cc3-c3csc(N4C[C@H]5CC[C@@H](C4)[C@H]5C(=O)O)n3)c(C)c2)C1] |
| 333 | 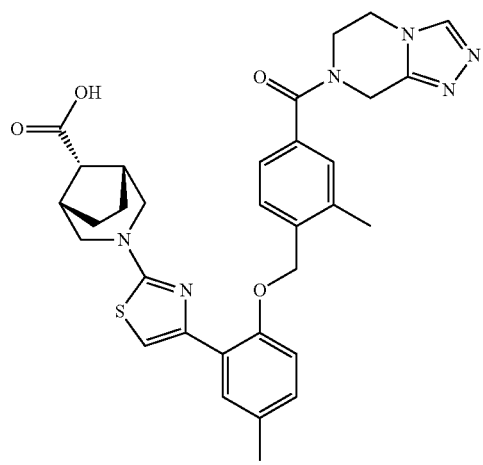 [SMILES: Cc1ccc(OCc2ccc(C(=O)N3CCn4cnnc4C3)cc2C)c(-c2csc(N3C[C@H]4CC[C@@H](C3)[C@H]4C(=O)O)n2)c1] |

| Cpd No. | |
|---|---|
| 334 | 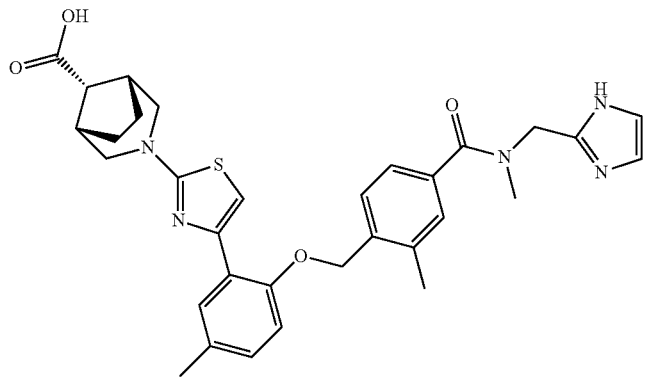 [SMILES: Cc1ccc(OCc2ccc(C(=O)N(C)Cc3ncc[nH]3)cc2C)c(-c2csc(N3C[C@H]4CC[C@@H](C3)[C@H]4C(=O)O)n2)c1] |
| 335 | 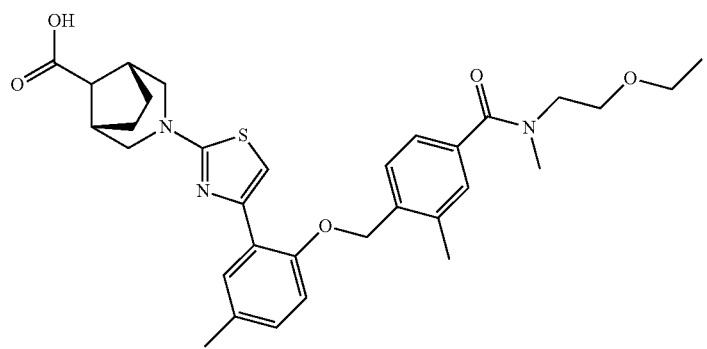 [SMILES: CCOCCN(C)C(=O)c1ccc(COc2ccc(C)cc2-c2csc(N3C[C@H]4CC[C@@H](C3)C4C(=O)O)n2)c(C)c1] |
| 336 | 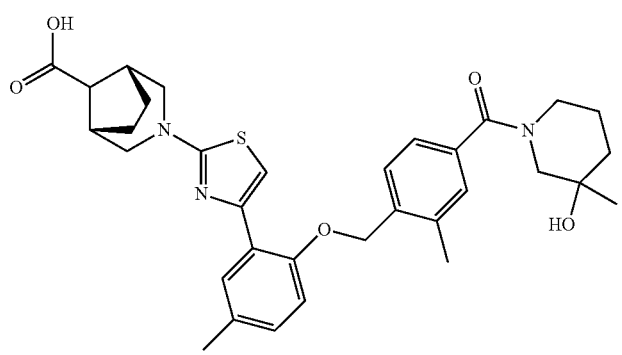 [SMILES: Cc1ccc(OCc2ccc(C(=O)N3CCCC(C)(O)C3)cc2C)c(-c2csc(N3C[C@H]4CC[C@@H](C3)C4C(=O)O)n2)c1] |
| 337 | 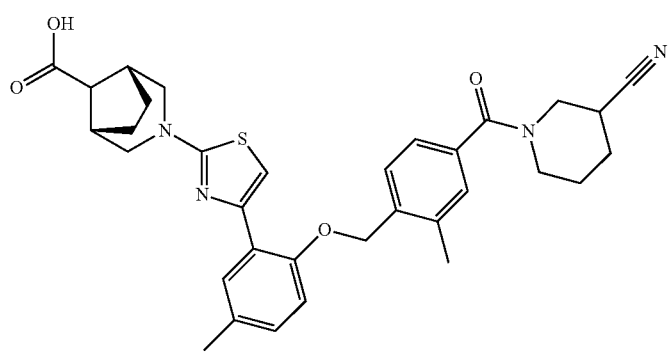 [SMILES: Cc1ccc(OCc2ccc(C(=O)N3CCCC(C#N)C3)cc2C)c(-c2csc(N3C[C@H]4CC[C@@H](C3)C4C(=O)O)n2)c1] |

| Cpd No. | |
|---|---|
| 338 | 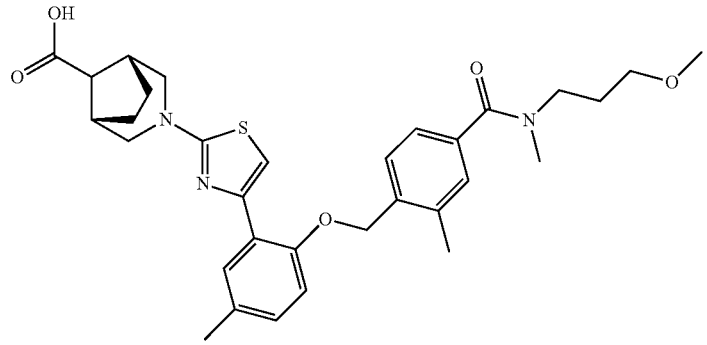 [SMILES: COCCCN(C)C(=O)c1ccc(COc2ccc(C)cc2-c2csc(N3C[C@H]4CC[C@@H](C3)C4C(=O)O)n2)c(C)c1] |
| 339 | 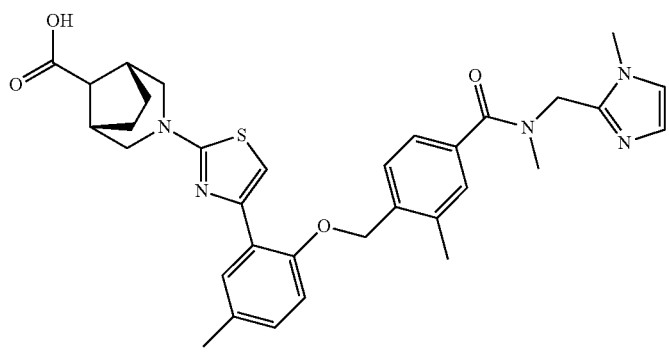 [SMILES: Cc1ccc(OCc2ccc(C(=O)N(C)Cc3nccn3C)cc2C)c(-c2csc(N3C[C@H]4CC[C@@H](C3)C4C(=O)O)n2)c1] |
| 340 | 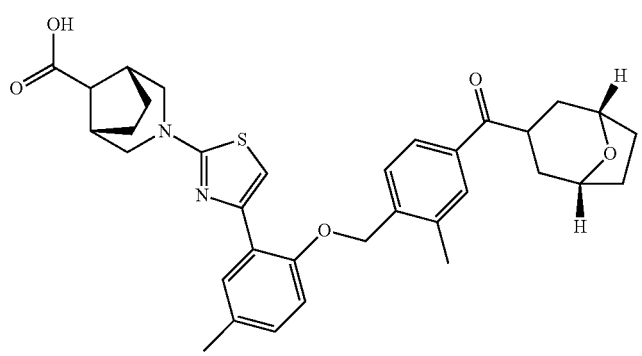 [SMILES: Cc1ccc(OCc2ccc(C(=O)C3C[C@H]4CC[C@@H](C3)O4)cc2C)c(-c2csc(N3C[C@H]4CC[C@@H](C3)C4C(=O)O)n2)c1] |
| 341 | 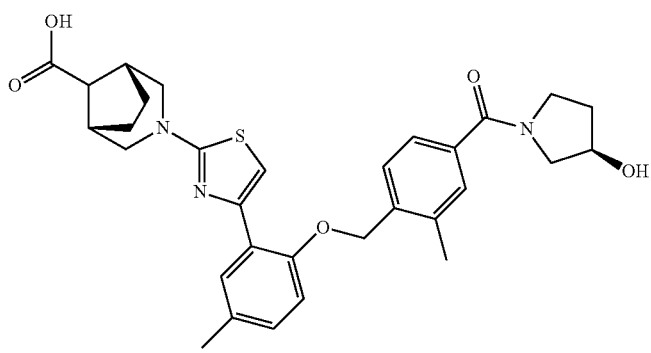 [SMILES: Cc1ccc(OCc2ccc(C(=O)N3CC[C@@H](O)C3)cc2C)c(-c2csc(N3C[C@H]4CC[C@@H](C3)C4C(=O)O)n2)c1] |

| Cpd No. | |
|---|---|
| 342 | 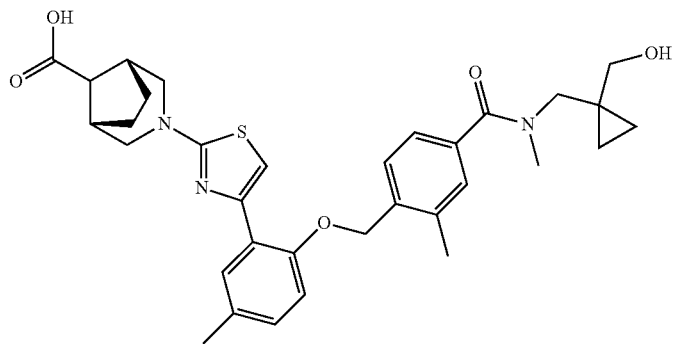 [SMILES: Cc1ccc(OCc2ccc(C(=O)N(C)CC3(CO)CC3)cc2C)c(-c2csc(N3C[C@H]4CC[C@@H](C3)C4C(=O)O)n2)c1] |
| 343 | 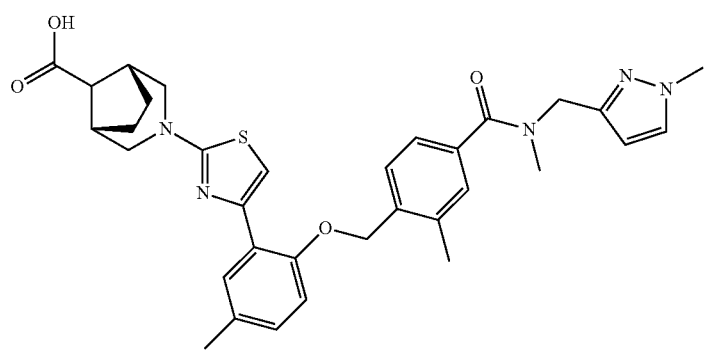 [SMILES: Cc1ccc(OCc2ccc(C(=O)N(C)Cc3ccn(C)n3)cc2C)c(-c2csc(N3C[C@H]4CC[C@@H](C3)C4C(=O)O)n2)c1] |
| 344 | 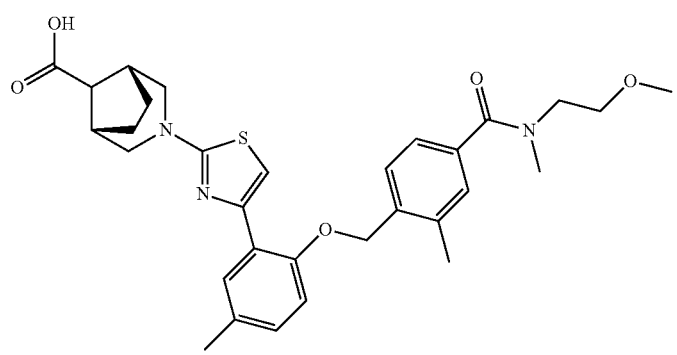 [SMILES: COCCN(C)C(=O)c1ccc(COc2ccc(C)cc2-c2csc(N3C[C@H]4CC[C@@H](C3)C4C(=O)O)n2)c(C)c1] |
| 345 | 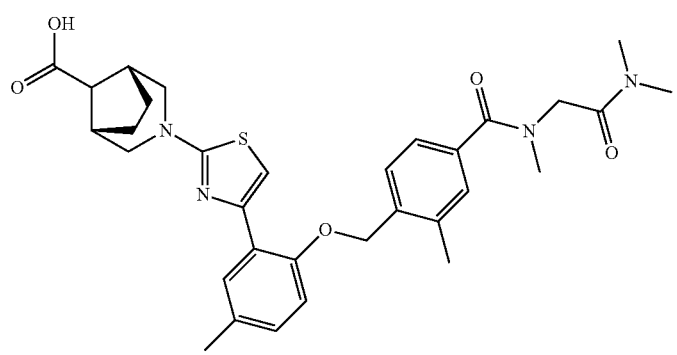 [SMILES: Cc1ccc(OCc2ccc(C(=O)N(C)CC(=O)N(C)C)cc2C)c(-c2csc(N3C[C@H]4CC[C@@H](C3)C4C(=O)O)n2)c1] |

| Cpd No. | |
|---|---|
| 346 | 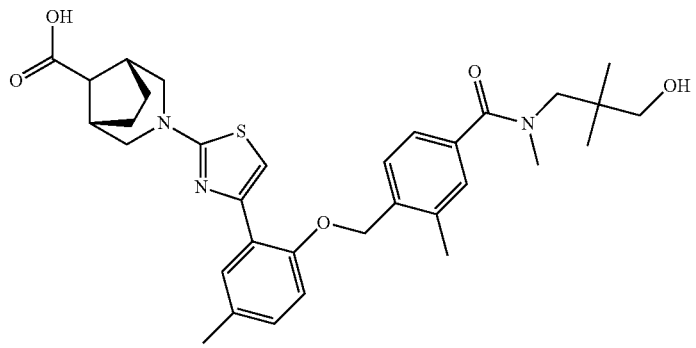 [SMILES: Cc1ccc(OCc2ccc(C(=O)N(C)CC(C)(C)CO)cc2C)c(-c2csc(N3C[C@H]4CC[C@@H](C3)C4C(=O)O)n2)c1] |
| 347 | 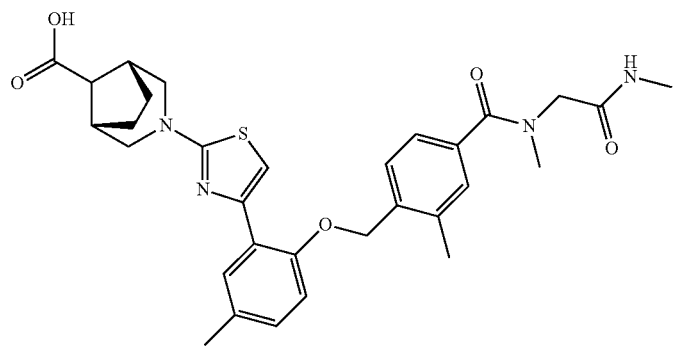 [SMILES: CNC(=O)CN(C)C(=O)c1ccc(COc2ccc(C)cc2-c2csc(N3C[C@H]4CC[C@@H](C3)C4C(=O)O)n2)c(C)c1] |
| 348 | 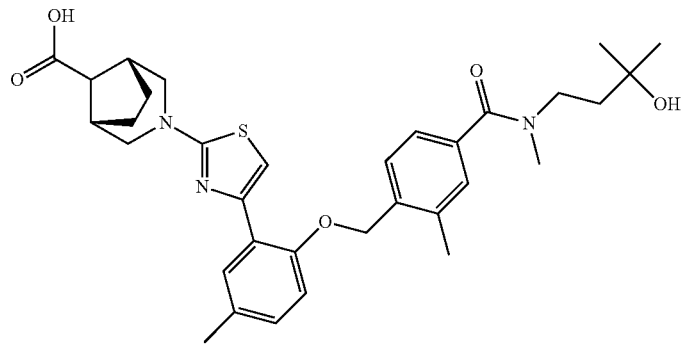 [SMILES: Cc1ccc(OCc2ccc(C(=O)N(C)CCC(C)(C)O)cc2C)c(-c2csc(N3C[C@H]4CC[C@@H](C3)C4C(=O)O)n2)c1] |
| 349 | 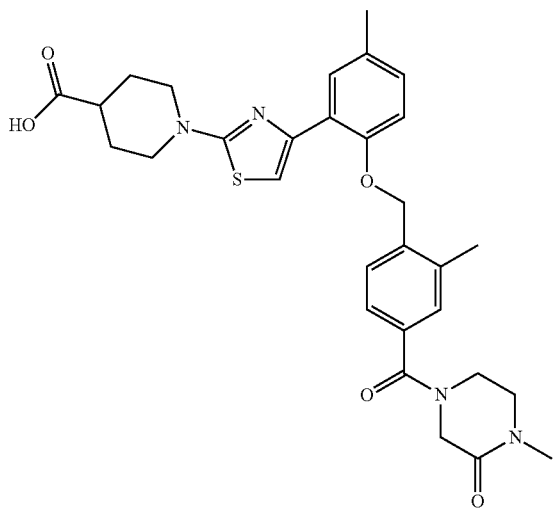 [SMILES: Cc1ccc(OCc2ccc(C(=O)N3CCN(C)C(=O)C3)cc2C)c(-c2csc(N3CCC(C(=O)O)CC3)n2)c1] |

| Cpd No. | |
|---|---|
| 350 | 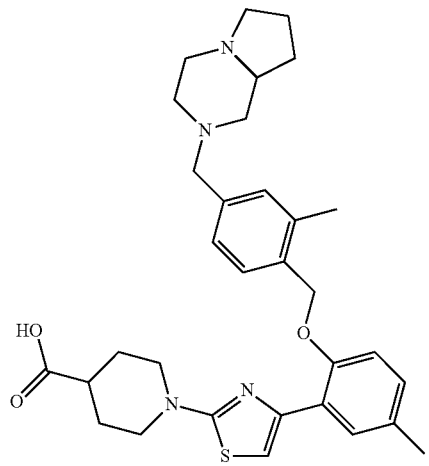 [SMILES: Cc1ccc(OCc2ccc(CN3CCN4CCCC4C3)cc2C)c(-c2csc(N3CCC(C(=O)O)CC3)n2)c1] |
| 351 | 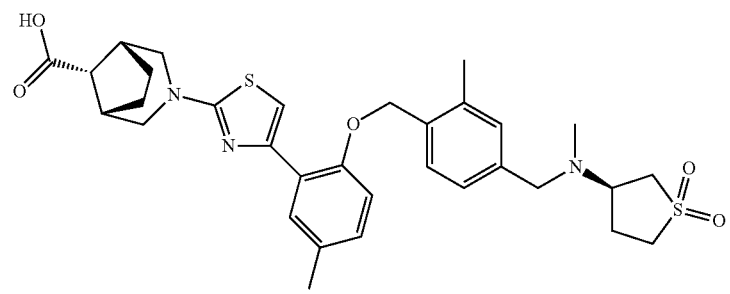 [SMILES: Cc1ccc(OCc2ccc(CN(C)[C@@H]3CCS(=O)(=O)C3)cc2C)c(-c2csc(N3C[C@H]4CC[C@@H](C3)[C@H]4C(=O)O)n2)c1] |
| 352 | 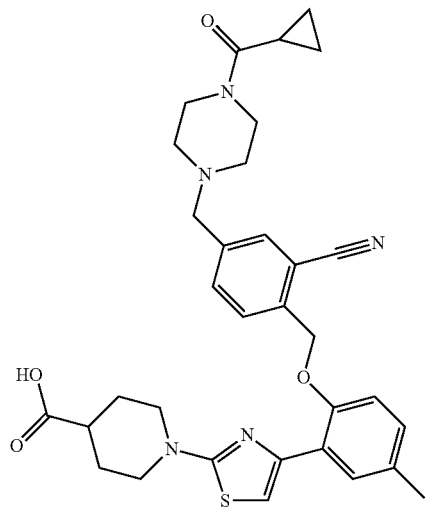 [SMILES: Cc1ccc(OCc2ccc(CN3CCN(C(=O)C4CC4)CC3)cc2C#N)c(-c2csc(N3CCC(C(=O)O)CC3)n2)c1] |

-continued
| Cpd No. |
|---|
| 353 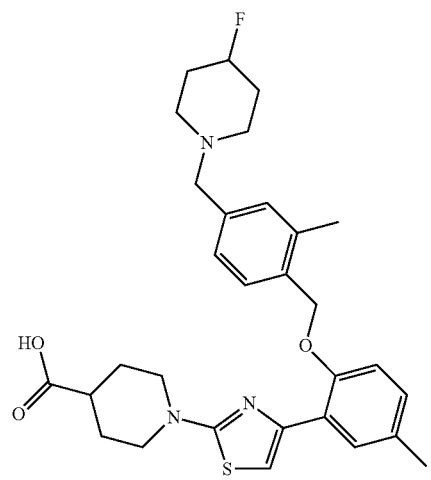 [SMILES: Cc1ccc(OCc2ccc(CN3CCC(F)CC3)cc2C)c(-c2csc(N3CCC(C(=O)O)CC3)n2)c1] |
| 354 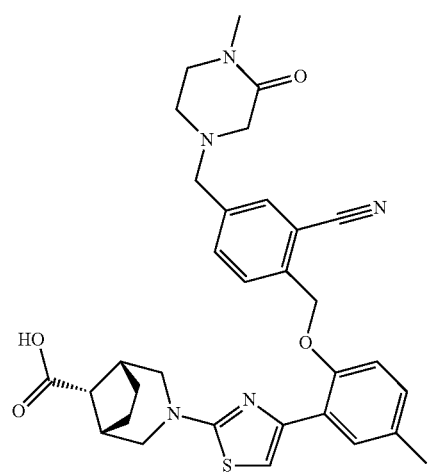 [SMILES: Cc1ccc(OCc2ccc(CN3CCN(C)C(=O)C3)cc2C#N)c(-c2csc(N3C[C@H]4CC[C@@H](C3)[C@H]4C(=O)O)n2)c1] |
| 355 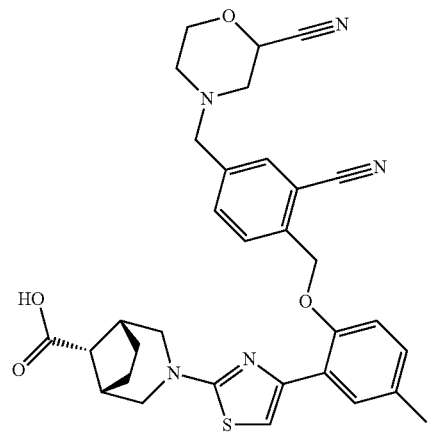 [SMILES: Cc1ccc(OCc2ccc(CN3CCOC(C#N)C3)cc2C#N)c(-c2csc(N3C[C@H]4CC[C@@H](C3)[C@H]4C(=O)O)n2)c1] |

| Cpd No. |
|---|
| 356 |
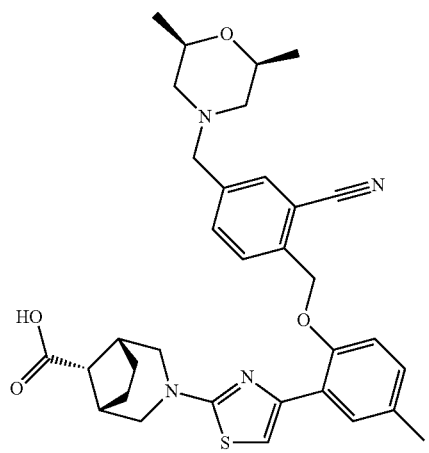 [SMILES: Cc1ccc(OCc2ccc(CN3C[C@@H](C)O[C@@H](C)C3)cc2C#N)c(-c2csc(N3C[C@H]4CC[C@@H](C3)[C@H]4C(=O)O)n2)c1]
357
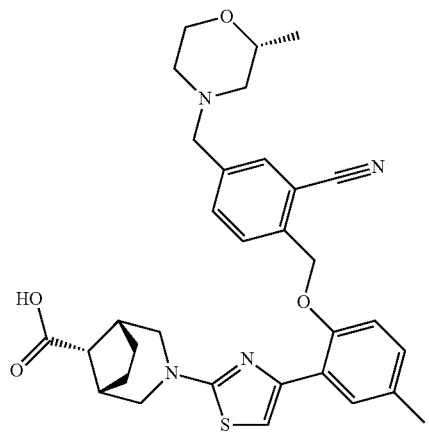 [SMILES: Cc1ccc(OCc2ccc(CN3CCO[C@H](C)C3)cc2C#N)c(-c2csc(N3C[C@H]4CC[C@@H](C3)[C@H]4C(=O)O)n2)c1]
358
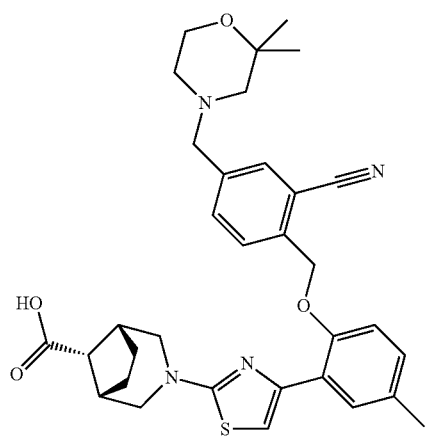 [SMILES: Cc1ccc(OCc2ccc(CN3CCOC(C)(C)C3)cc2C#N)c(-c2csc(N3C[C@H]4CC[C@@H](C3)[C@H]4C(=O)O)n2)c1]

| Cpd No. | |
|---|---|
| 359 | 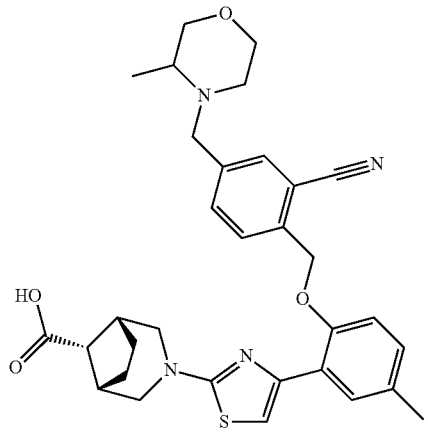 [SMILES: Cc1ccc(OCc2ccc(CN3CCOCC3C)cc2C#N)c(-c2csc(N3C[C@H]4CC[C@@H](C3)[C@H]4C(=O)O)n2)c1] |
| 360 | 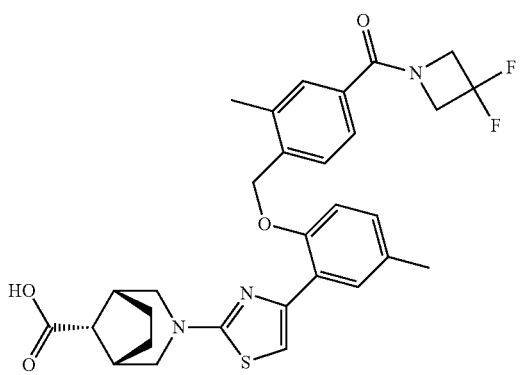 and |
| 361 | 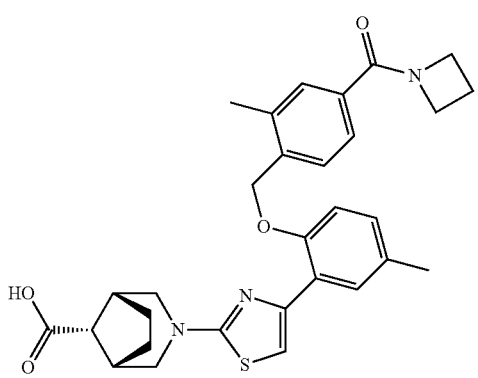 ; | and the pharmaceutically acceptable salts thereof.

11. The compound of claim 10 selected from the group consisting of compound numbers 1, 13, 15, 17, 20, 21, 28, 30, 36, 39, 41-43, 49, 52, 59, 62, 63, 65, 67-70, 72-74, 79, 81, 84, 88-90, 92, 95, 97, 102-108, 111, 113, 117-120, 122-126, 129-133, 136-138, 140-144, 151-153, 161, 162, 164, 167, 173, 176, 177, 194-196, 198-200, 203-209, 211, 212, 214, 217, 218, 220-232, 234-238, 240-244, 248, 249, 250, 263-272, 276-293, 296-346, and 348-361;
and the pharmaceutically acceptable salts thereof.

12. A pharmaceutical composition comprising the compound of claim 1 and a pharmaceutically acceptable excipient or carrier.

13. A method of treating a disease or disorder that can be alleviated by sGC activation or potentiation comprising administering a therapeutically effective amount of a compound of claim 1 to patient in need thereof.

14. The method according to claim 13 wherein the disease or disorder is selected from a cardiovascular disease, inflammatory disease, hepatic fibrotic disorder, renal fibrotic disorder, pulmonary fibrotic disorder and cardiac fibrotic disorder.

15. The method according to claim 13 where the disease is selected from renal disease, overactive bladder, benign prostatic hyperplasia, erectile dysfunction, Alzheimer's disease, Parkinson's disease and neuropathic pain.

* * * * *